(12) United States Patent
Dyckman et al.

(10) Patent No.: US 10,660,877 B2
(45) Date of Patent: May 26, 2020

(54) PYRIDYL SUBSTITUTED INDOLE COMPOUNDS

(71) Applicant: BRISTOL-MYERS SQUIBB COMPANY, Princeton, NJ (US)

(72) Inventors: Alaric J. Dyckman, Lawrenceville, NJ (US); Dharmpal S. Dodd, Monmouth Junction, NJ (US); Tasir Shamsul Haque, Yardley, PA (US); Louis J. Lombardo, Belle Mead, NJ (US); John E. Macor, Washington Crossing, PA (US); Christopher P. Mussari, Princeton, NJ (US); Laxman Pasunoori, Warangal (IN); Michael A. Poss, Lawrenceville, NJ (US); Sreekantha Ratna Kumar, Bangalore (IN); Shoshana L. Posy, Highland Park, NJ (US); David R. Tortolani, Skillman, NJ (US); Brian K. Whiteley, Lebanon, NJ (US); Ramesh Kumar Sistla, Bangalore (IN); Subramanya Hegde, Bangalore (IN); Anupama Kandhi Ramachandra Reddy, Chitradurga (IN)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 16/330,964

(22) PCT Filed: Sep. 8, 2017

(86) PCT No.: PCT/US2017/050577
§ 371 (c)(1),
(2) Date: Mar. 6, 2019

(87) PCT Pub. No.: WO2018/049089
PCT Pub. Date: Mar. 15, 2018

(65) Prior Publication Data
US 2019/0262311 A1    Aug. 29, 2019

(30) Foreign Application Priority Data

Sep. 9, 2016   (IN) .............................. 201611030860

(51) Int. Cl.
| | |
|---|---|
| *A61K 31/404* | (2006.01) |
| *A61P 37/06* | (2006.01) |
| *A61P 29/00* | (2006.01) |
| *A61K 9/00* | (2006.01) |
| *C07D 401/14* | (2006.01) |

(52) U.S. Cl.
CPC .......... *A61K 31/404* (2013.01); *A61K 9/0019* (2013.01); *A61P 29/00* (2018.01); *A61P 37/06* (2018.01); *C07D 401/14* (2013.01)

(58) Field of Classification Search
CPC ........................... C07D 401/14; A61K 31/404
See application file for complete search history.

(56) References Cited

U.S. PATENT DOCUMENTS

| | | | |
|---|---|---|---|
| 6,867,200 | B1 | 3/2005 | Allen et al. |
| 7,410,975 | B2 | 8/2008 | Lipford et al. |
| 8,138,187 | B2 | 3/2012 | Zemolka et al. |
| 8,354,400 | B2 | 1/2013 | Zheng et al. |
| 9,126,996 | B2 | 9/2015 | Lipford et al. |
| 9,126,999 | B2 | 9/2015 | Boivin et al. |
| 9,241,991 | B2 | 1/2016 | Ji et al. |
| 9,353,115 | B2 | 5/2016 | Lipford et al. |
| 9,376,398 | B2 | 6/2016 | Hori et al. |
| 9,428,495 | B2 | 8/2016 | Carlson et al. |
| 9,643,967 | B2 | 5/2017 | Koul et al. |
| 2006/0235037 | A1 | 10/2006 | Purandare et al. |
| 2010/0160314 | A1 | 6/2010 | Lipford et al. |
| 2011/0015219 | A1 | 1/2011 | Trawick et al. |
| 2011/0275631 | A1 | 11/2011 | Abeywardane et al. |
| 2013/0045986 | A1 | 2/2013 | Nagarathnam et al. |
| 2014/0066432 | A1 | 3/2014 | Howbert et al. |
| 2014/0088085 | A1 | 3/2014 | Burgess et al. |
| 2014/0242121 | A1 | 8/2014 | Lipford et al. |

FOREIGN PATENT DOCUMENTS

| | | |
|---|---|---|
| EP | 2738172 A1 | 6/2014 |
| WO | WO2006113458 A1 | 10/2006 |
| WO | WO2007115306 A2 | 10/2007 |
| WO | WO2008065198 A1 | 6/2008 |
| WO | WO2008152471 A1 | 12/2008 |
| WO | WO2009030996 A1 | 3/2009 |
| WO | WO2010149769 A1 | 12/2010 |
| WO | WO2013010904 A1 | 1/2013 |
| WO | WO2013181579 A2 | 12/2013 |

(Continued)

OTHER PUBLICATIONS

International Preliminary Report on Patentability for No. PCT/US2017/050577, dated Mar. 12, 2019.

(Continued)

*Primary Examiner* — Golam M Shameem
(74) *Attorney, Agent, or Firm* — Gary Greenblatt

(57) ABSTRACT

Disclosed are compounds of Formula (I) N-oxide, or salt thereof, wherein $R_1$, $R_2$, $R_3$, $R_4$, $R_5$, m, n, and p are defined herein. Also disclosed are methods of using such compounds as inhibitors of signaling through Toll-like receptor 7, or 8, or 9, and pharmaceutical compositions comprising such compounds. These compounds are useful in treating inflammatory and autoimmune diseases.

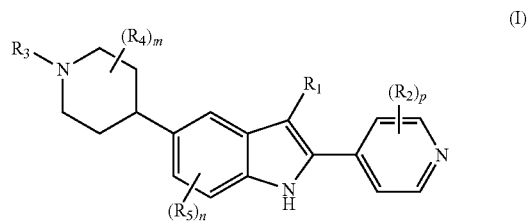

(I)

18 Claims, No Drawings

(56) References Cited

FOREIGN PATENT DOCUMENTS

| WO | WO2015088045 A1 | 6/2015 |
| WO | WO2016029077 A1 | 2/2016 |
| WO | WO2018005586 A1 | 2/2018 |
| WO | WO2018026620 A1 | 2/2018 |
| WO | WO2018049089 A1 | 3/2018 |

OTHER PUBLICATIONS

Kawai, T., et al., "The Role of Pattern-Recognition Receptors in Innate Immunity: Update on Toll-like Receptors", Nature Immunol., 2011, 11, 373-384.
Lamphier, M. et al., "Novel Small Molecule Inhibitors of TLR7 and TLR9: Mechanism of Action and Efficacy in Vivo", Mol Pharmacol, 2014, 85:429-440.
Patra, Mahesh Chandra, et al., "Recent Progress in the Development of Toll-like Receptor (TLR) antagonists", Exp. Opin. On Therapeutic Patents, 2016, vol. 26, No. 6, 719-730.
Roy, et al., "Design and developmen of benzoxazole derivatives with toll-like receptor 9 antagonism", Eur J Med Chem, 2017, vol. 134, 334-347.
Sims, et al., "The IL-1 Family: Regulators of Immunity", Nature Rev. Immunol., 2010, 10, 89-102.

PYRIDYL SUBSTITUTED INDOLE COMPOUNDS

CROSS-REFERENCE TO RELATED APPLICATIONS

This application is a national phase application under 35 U.S.C. § 371 of International Patent Application No. PCT/US2017/050577, filed Sep. 8, 2017, which claims priority to Indian Provisional Application Serial No. 201611030860, filed Sep. 9, 2016, the contents of which are specifically incorporated fully herein by reference.

DESCRIPTION

The present invention generally relates to pyridyl substituted indole compounds useful as inhibitors of signaling through Toll-like receptor 7, 8, or 9 (TLR7, TLR8, TLR9) or combinations thereof. Provided herein are pyridyl substituted indole compounds, compositions comprising such compounds, and methods of their use. The invention further pertains to pharmaceutical compositions containing at least one compound according to the invention that are useful for the treatment of conditions related to TLR modulation, such as inflammatory and autoimmune diseases, and methods of inhibiting the activity of TLRs in a mammal.

Toll/IL-1 receptor family members are important regulators of inflammation and host resistance. The Toll-like receptor family recognizes molecular patterns derived from infectious organisms including bacteria, fungi, parasites, and viruses (reviewed in Kawai, T. et al., *Nature Immunol.*, 11:373-384 (2010)). Ligand binding to the receptor induces dimerization and recruitment of adaptor molecules to a conserved cytoplasmic motif in the receptor termed the Toll/IL-1 receptor (TIR) domain. With the exception of TLR3, all TLRs recruit the adaptor molecule MyD88. The IL-1 receptor family also contains a cytoplasmic TIR motif and recruits MyD88 upon ligand binding (reviewed in Sims, J. E. et al., *Nature Rev. Immunol.*, 10:89-102 (2010)).

Toll-like receptors (TLRs) are a family of evolutionarily conserved, transmembrane innate immune receptors that participate in the first-line defense, as pattern recognition receptors, the TLRs protect against foreign molecules, activated by pathogen associated molecular patterns (PAMPs), or from damaged tissue, activated by danger associated molecular patterns (DAMPs). A total of 13 TLR family members have been identified, 10 in human, that span either the cell surface or the endosomal compartment. TLR7-9 are among the set that are endosomally located and respond to single-stranded RNA (TLR7 and TLR8) or unmethylated single-stranded DNA containing cytosine-phosphate-guanine (CpG) motifs (TLR9).

Activation of TLR7/8/9 can initiate a variety of inflammatory responses (cytokine production, B cell activation and IgG production, Type I interferon response), in the case of autoimmune disorders, the aberrant sustained activation of TLR7/8/9 leads to worsening of disease states. Whereas overexpression of TLR7 in mice has been shown to exacerbate autoimmune disease, knockout of TLR7 in mice was found to be protective against disease in lupus-prone MRL/lpr mice. Dual knockout of TLR7 and 9 showed further enhanced protection.

As numerous conditions may benefit by treatment involving modulation of cytokines, IFN production and B cell activity, it is immediately apparent that new compounds capable of modulating TLR7 and/or TLR8 and/or TLR9 and methods of using these compounds could provide substantial therapeutic benefits to a wide variety of patients.

The present invention relates to a new class of pyridyl substituted indole compounds found to be effective inhibitors of signaling through TLR7/8/9. These compounds are provided to be useful as pharmaceuticals with desirable stability, bioavailability, therapeutic index, and toxicity values that are important to their drugability.

SUMMARY OF THE INVENTION

The present invention provides compounds of Formula (I) that are useful as inhibitors of signaling through Toll-like receptor 7, 8, or 9 and are useful for the treatment of proliferative diseases, allergic diseases, autoimmune diseases and inflammatory diseases, or stereoisomers, tautomers, N-oxides, pharmaceutically acceptable salts, solvates or prodrugs thereof.

The present invention also provides pharmaceutical compositions comprising a pharmaceutically acceptable carrier and at least one of the compounds of the present invention or stereoisomers, tautomers, N-oxides, pharmaceutically acceptable salts, solvates, or prodrugs thereof.

The present invention also provides a method for inhibition of Toll-like receptor 7, 8, or 9 comprising administering to a host in need of such treatment a therapeutically effective amount of at least one of the compounds of the present invention or stereoisomers, tautomers, N-oxides, pharmaceutically acceptable salts, solvates, or prodrugs thereof.

The present invention also provides a method for treating proliferative, metabolic, allergic, autoimmune and inflammatory diseases, comprising administering to a host in need of such treatment a therapeutically effective amount of at least one of the compounds of the present invention or stereoisomers, tautomers, N-oxides, pharmaceutically acceptable salts, solvates, or prodrugs thereof.

The present invention also provides a method of treating a disease or disorder associated with Toll-like receptor 7, 8, or 9 activity, the method comprising administering to a mammal in need thereof, at least one of the compounds of Formula (I) or N-oxides, salts, solvates, and prodrugs thereof.

The present invention also provides processes and intermediates for making the compounds of Formula (I) including N-oxides, salts, solvates, and prodrugs thereof.

The present invention also provides at least one of the compounds of Formula (I) or N-oxides, salts, solvates, and prodrugs thereof, for use in therapy.

The present invention also provides the use of at least one of the compounds of Formula (I) or N-oxides, salts, solvates, and prodrugs thereof, for the manufacture of a medicament for the treatment of prophylaxis of Toll-like receptor 7, 8, or 9 related conditions, such as allergic disease, autoimmune diseases, inflammatory diseases, and proliferative diseases.

The compound of Formula (I) and compositions comprising the compounds of Formula (I) may be used in treating, preventing, or curing various Toll-like receptor 7, 8, or 9 related conditions. Pharmaceutical compositions comprising these compounds are useful for treating, preventing, or slowing the progression of diseases or disorders in a variety of therapeutic areas, such as allergic disease, autoimmune diseases, inflammatory diseases, and proliferative diseases.

These and other features of the invention will be set forth in expanded form as the disclosure continues.

DETAILED DESCRIPTION

The first aspect of the present invention provides at least one compound of Formula (I):

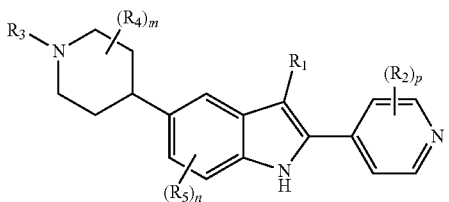

(I)

N-oxide, or salt thereof, wherein:

$R_1$ is H, Cl, —CN, $C_{1-4}$ alkyl, $C_{1-3}$ fluoroalkyl, $C_{1-3}$ hydroxy-fluoroalkyl, —$CR_z$=$CH_2$, $C_{3-6}$ cycloalkyl, —$CH_2(C_{3-6}$ cycloalkyl), —C(O)O($C_{1-3}$ alkyl), or tetrahydropyranyl;

each $R_2$ is independently halo, —CN, —OH, —$NO_2$, $C_{1-3}$ alkyl, $C_{1-2}$ fluoroalkyl, $C_{1-3}$ hydroxyalkyl, $C_{1-3}$ aminoalkyl, —$(CH_2)_{0-4}$O($C_{1-3}$ alkyl), $C_{1-3}$ fluoroalkoxy, $C_{2-4}$ alkoxyalkoxy, —O$(CH_2)_{1-2}NR_xR_x$, —C(O)O($C_{1-3}$ alkyl), —C(O)$NR_yR_y$, —$NR_yR_y$, —$NR_xC(O)(C_{1-3}$ alkyl), —$NR_x(CH_2$-cyclopropyl), $C_{3-6}$ cycloalkyl, methylpiperidinyl, methylpiperazinyl, amino-oxadiazolyl, imidazolyl, triazolyl, or —C(O)(thiazolyl);

$R_3$ is:

(a) -$L_1$-A; or (b) H, $C_{1-6}$ alkyl, $C_{1-3}$ fluoroalkyl, $C_{1-3}$ cyanoalkyl, $C_{1-6}$ hydroxyalkyl, $C_{1-3}$ hydroxy-fluoroalkyl, —$CR_xR_x$-$CR_x$(OH)$CR_x$=$CR_xR_x$, —$(CR_xR_x)_{1-4}$O($C_{1-3}$ alkyl), —$(CR_xR_x)_{1-4}$O$(CR_xR_x)_{1-3}$O($C_{1-3}$ alkyl), —$CR_xR_x$-$CR_x$(OH)$CH_2$O($C_{1-3}$ alkyl), —$(CR_xR_x)_{1-3}$S($C_{1-3}$ alkyl), —$(CH_2)_{1-3}$C(O)OC$(CH_3)_3$, —$(CR_xR_x)_{0-3}NR_yR_y$, —$(CR_xR_x)_{0-3}NR_x$($C_{1-4}$ hydroxyalkyl), —$CR_xR_xCR_x$(OH)$CH_2NR_yR_y$, —C(O)H, —C(O)($C_{1-6}$ alkyl), —C(O)($C_{1-3}$ hydroxyalkyl), —C(O)($C_{1-3}$ fluoroalkyl), —C(O)($C_{1-3}$ chloroalkyl), —C(O)($C_{1-3}$ cyanoalkyl), —$C(O)(CR_xR_x)_{0-3}$C(O)OH, —C(O)$(CH_2)_{0-2}$O($C_{1-4}$ alkyl), —$C(O)(CR_xR_x)_{0-2}$O($CR_xR_x)_{1-2}$O($C_{1-3}$ alkyl), —$C(O)CR_xR_xS(O)_2(C_{1-3}$ alkyl), —$C(O)CR_xR_xNR_xS(O)_2(C_{1-3}$ alkyl), —C(O)$CR_xR_xOC(O)(C_{1-3}$ alkyl), —$C(O)(CR_xR_x)_{0-3}NR_yR_y$, —$C(O)(CR_xR_x)_{0-1}NR_x(C_{1-3}$ cyanoalkyl), —C(O)$(CR_xR_x)_{0-2}NR_x(C_{1-6}$ hydroxyalkyl), —$C(O)(CR_xR_x)_{0-1}NR_x(C_{1-3}$ fluoroalkyl), —$C(O)(CR_xR_x)_{0-1}NR_x$($C_{1-5}$ hydroxy-fluoroalkyl), —$C(O)(CR_xR_x)_{0-1}NR_x$$(CH_2)_{1-2}$O($C_{1-3}$ hydroxyalkyl), —$C(O)(CR_xR_x)_{0-1}NR_x(CH_2)_{1-2}NR_xC(O)(C_{1-2}$ alkyl), —$C(O)(CR_xR_x)_{0-1}NR_x((CR_xR_x)_{1-2}$O$(C_{1-2}$ alkyl)), —C(O)$CR_x(NH_2)(CR_xR_x)_{1-4}NR_xR_x$, —C(O)$CR_x(NH_2)(CR_xR_x)_{1-4}NR_xC(O)NR_xR_x$, —$C(O)(CR_xR_x)_{0-3}NR_x(CH_2)_{0-1}$C(O)($C_{1-3}$ alkyl), —$C(O)(CR_xR_x)_{0-1}NR_x(CH_2)_{0-1}$C(O)($C_{1-3}$ cyanoalkyl), —$C(O)(CR_xR_x)_{0-1}NR_x(CH_2)_{1-2}$C(O)$NR_yR_y$, —$C(O)(CR_xR_x)_{1-3}C(O)NR_yR_y$, —$C(O)(CR_xR_x)_{0-1}NR_x(CHR_x(CH_2OH))$, —$(CR_xR_x)_{1-2}C(O)NR_yR_y$, —$(CR_xR_x)_{1-2}C(O)NR_y(C_{1-3}$ fluoroalkyl), —$(CR_xR_x)_{1-2}C(O)NR_y(C_{1-4}$ hydroxyalkyl), —$(CR_xR_x)_{1-2}C(O)NR_y(C_{1-3}$ cyanoalkyl), —$(CR_xR_x)_{1-2}C(O)NR_x(CH_2)_{1-2}$O($C_{1-3}$ alkyl), —$(CR_xR_x)_{1-2}C(O)NR_xCH(C_{1-4}$ alkyl)($C_{1-3}$ hydroxyalkyl), —$(CH_2)_{1-2}C(O)NR_x(CH_2)_{1-2}C(O)NR_xR_x$, —$(CH_2)_{1-2}C(O)NR_x(CH_2)_{1-2}S(O)_2OH$, —$(CH_2)_{1-2}C(O)NR_x(CH_2)_{1-2}NR_xC(O)(C_{1-3}$ alkyl), —$(CH_2)_{1-2}C(O)NR_x(CH_2)_{1-3}NR_xR_x$, —$(CH_2)_{1-2}C(O)N(CH_2CH_3)(CH_2)_{1-3}NR_xR_x$, —$(CH_2)_{0-2}S(O)_2(C_{1-4}$ alkyl), —$(CH_2)_{0-2}S(O)_2(C_{1-3}$ fluoroalkyl), —$(CH_2)_{0-2}S(O)_2NR_xR_x$, —C(O)C(O)OH, —C(O)C(O)$NR_yR_y$, or —C(O)C(O)$NR_y(CR_xR_x)_{1-2}NR_yR_y$;

$L_1$ is a bond, —$(CR_xR_x)_{1-2}$—, —$(CR_xR_x)_{1-2}CR_x(OH)$—, —$(CR_xR_x)_{1-2}$O—, —$CR_xR_xC(O)$—, —$(CR_xR_x)_2NR_x(CR_xR_x)_{0-1}$—, —$CR_xR_xC(O)NR_x(CR_xR_x)_{0-4}$—, —$C(O)(CR_xR_x)_{0-3}$—, —$C(O)(CR_xR_x)_{0-2}NR_x(CR_xR_x)_{0-2}$—, —$C(O)(CR_xR_x)_{0-2}N(C_{1-2}$ hydroxyalkyl)$(CR_xR_x)_{0-2}$—, —$C(O)(CR_xR_x)_{0-2}NR_x(CR_xR_x)_{1-2}CR_x$(OH)—, —$C(O)(CR_xR_x)_{1-2}C(O)NR_x$—, —$(CR_xR_x)_{0-2}C(O)NR_x(CR_xR_x)_{1-2}CR_x$(OH)—, —$(CR_xR_x)_{0-2}C(O)N(C_{1-2}$ hydroxyalkyl)$(CR_xR_x)_{1-2}$—, —$C(O)(CR_xR_x)_{0-1}$O—, —$C(O)(CR_xR_x)_{1-2}NHS(O)_2$—, —$C(O)CR_x(NH_2)CR_xR_x$—, —$C(O)C(O)(CR_xR_x)_{0-2}$—, —$C(O)C(O)NR_x(CR_xR_x)_{0-2}$—, —$C(O)NR_x(CR_xR_x)_{1-2}$—, or —$S(O)_2$—;

A is 2-oxa-6-azaspiro[3,3]heptanyl, 4-oxaspiro[2.5]octanyl, 7-azaspiro[3.5]nonanyl, 8-azabicyclo[3.2.1]octanyl, 8-oxa-3-azabicyclo[3.2.1]octanyl, 9-azabicyclo[3.3.1]nonanyl, adamantanyl, azepanyl, azetidinyl, $C_{3-6}$ cycloalkyl, diazepanyl, dihydroinonyl, dihydropyrimidinonyl, dioxidoisothiazolidinyl, dioxidothiazinanyl, dioxotetrahydrothiophenyl, dioxotetrahydrothiopyranyl, dioxothiomorpholinyl, furanyl, imidazolyl, imidazolidinonyl, indolyl, isoquinolinyl, isoxazolyl, morpholinyl, morpholinonyl, naphthalenyl, octahydrocyclopenta[b]pyranyl, oxazolidinonyl, oxadiazolyl, oxetanyl, oxazolyl, phenyl, piperidinyl, piperidinonyl, piperazinyl, piperazinonyl, pyrazinyl, pyrazolyl, pyridazinonyl, pyridinonyl, pyridinyl, pyrimidinyl, pyrrolidinonyl, pyrrolidinyl, pyrrolyl, quinolinyl, quinolizinonyl, tetrahydrofuranyl, tetrahydropyranyl, tetrazolyl, thiadiazolyl, thiazolyl, or triazolyl, each substituted with -$L_2$-$R_a$ and zero to 4 $R_b$;

$L_2$ is a bond or —$CR_xR_x$—;

$R_a$ is:

(a) H, F, Cl, —CN, —OH, $C_{1-6}$ alkyl, $C_{1-3}$ fluoroalkyl, $C_{1-5}$ hydroxyalkyl, —$(CH_2)_{0-4}$O($C_{1-3}$ alkyl), —$(CR_xR_x)_{1-3}$S($C_{1-3}$ alkyl), —$(CR_xR_x)_{1-3}$NHC(O)O($C_{1-4}$ alkyl), —$(CR_xR_x)_{1-3}NR_yR_y$, —$(CR_xR_x)_{1-3}C(O)NR_yR_y$, —O($C_{1-3}$ fluoroalkyl), —$S(O)_2NR_xR_x$, —O$(CR_xR_x)_{1-3}NR_xR_x$, —$NHS(O)_2(C_{1-3}$ alkyl), —$NR_yR_x$, —$NR_x(C_{1-4}$ alkyl), —$NR_xC(O)(C_{1-4}$ alkyl), —$(CR_xR_x)_{0-3}$C(O)OH, —C(O)($C_{1-5}$ alkyl), —C(O)($C_{1-3}$ fluoroalkyl), —C(O)O($C_{1-4}$ alkyl), —C(O)NH($C_{1-3}$ cyanoalkyl), —C(O)$NR_yR_y$, —$C(O)NR_xCH_2C(O)NR_xR_x$, or —$C(O)NR_xCH_2CH_2NHC(O)(C_{1-3}$ alkyl);

(b) $C_{3-6}$ cycloalkyl or —C(O)NH($C_{3-6}$ cycloalkyl), wherein each cycloalkyl is substituted with zero to 2 substituents independently selected from —OH, $C_{1-3}$ alkyl, $C_{1-3}$ hydroxyalkyl, $C_{1-3}$ fluoroalkyl, and —C(O)O($C_{1-3}$ alkyl); or (c) $A_1$, —$CH_2A_1$, —C(O)$A_1$, —$NR_xA_1$, or —C(O)$NR_xA_1$, wherein $A_1$ is furanyl, imidazolyl, indolyl, isoxazolyl, morpholinyl, octahydropyrrolo[3,4-c]pyrrolyl, oxazolyl, oxetanyl, phenyl, piperazinyl, piperidinyl, pyrazolyl, pyridinyl, pyrimidinyl, pyrrolidinyl, pyrrolyl, tetrahydrofuranyl, tetrahydropyranyl, thiadiazolyl, thiazolyl, thiophenyl, or triazolyl, each substituted with zero to three substituents independently selected from —OH, $C_{1-3}$ alkyl, $C_{1-3}$ hydroxyalkyl, —C(O)($C_{1-2}$ alkyl), —C(O)O($C_{1-3}$ alkyl), —$NR_xR_x$, phenyl, trifluoromethyl-phenyl, —$CH_2$(bromophenyl), and —$CH_2CH_2$(pyrrolidinyl);

each $R_4$ is independently F, —OH, $C_{1-2}$ alkyl, or —$OCH_3$; or two $R_4$ attached to the same carbon atom form =O;

each $R_5$ is independently F, Cl, —CN, $C_{1-2}$ alkyl, $C_{1-2}$ fluoroalkyl, or —$OCH_3$;

each $R_b$ is independently F, —CH$_3$, —CF$_3$, or —OCH$_3$;
each $R_x$ is independently H or —CH$_3$;
each $R_y$ is independently H or C$_{1-6}$ alkyl;
$R_z$ is H, C$_{1-2}$ alkyl, or C$_{1-2}$ fluoroalkyl;
m is zero, 1, 2, 3, or 4;
n is zero, 1, or 2; and
p is zero, 1, 2, 3, or 4.

One embodiment provides a compound of Formula (I), N-oxide, or salt thereof, wherein:

$R_1$ is H, Cl, —CN, C$_{1-4}$ alkyl, C$_{1-3}$ fluoroalkyl, C$_{1-3}$ hydroxy-fluoroalkyl, —CR$_z$=CH$_2$, C$_{3-6}$ cycloalkyl, —CH$_2$(C$_{3-6}$ cycloalkyl), —C(O)O(C$_{1-3}$ alkyl), or tetrahydropyranyl;

each $R_2$ is independently halo, —CN, —OH, —NO$_2$, C$_{1-3}$ alkyl, C$_{1-2}$ fluoroalkyl, C$_{1-3}$ hydroxyalkyl, C$_{1-3}$ aminoalkyl, —(CH$_2$)$_{0-4}$O(C$_{1-3}$ alkyl), C$_{1-3}$ fluoroalkoxy, C$_{2-4}$ alkoxyalkoxy, —O(CH$_2$)$_{1-2}$NR$_x$R$_x$, —C(O)O(C$_{1-3}$ alkyl), —C(O)NR$_y$R$_y$, —NR$_y$R$_y$, —NR$_x$C(O)(C$_{1-3}$ alkyl), —NR$_x$(CH$_2$-cyclopropyl), C$_{3-6}$ cycloalkyl, methylpiperidinyl, methylpiperazinyl, amino-oxadiazolyl, imidazolyl, triazolyl, or —C(O)(thiazolyl);

$R_3$ is:
(a) -L$_1$-A; or
(b) H, C$_{1-6}$ alkyl, C$_{1-3}$ fluoroalkyl, C$_{1-3}$ cyanoalkyl, C$_{1-6}$ hydroxyalkyl, C$_{1-3}$ hydroxy-fluoroalkyl, —CR$_x$R$_x$-CR$_x$(OH)CR$_x$=CR$_x$R$_x$, —(CR$_x$R$_x$)$_{1-4}$O(C$_{1-3}$ alkyl), —(CR$_x$R$_x$)$_{1-4}$O(CR$_x$R$_x$)$_{1-3}$O(C$_{1-3}$ alkyl), —CH$_2$CH(OH)CH$_2$O(C$_{1-3}$ alkyl), —(CR$_x$R$_x$)$_{1-3}$S(C$_{1-3}$ alkyl), —(CH$_2$)$_{1-3}$C(O)OC(CH$_3$)$_3$, —(CR$_x$R$_x$)$_{0-3}$NR$_y$R$_y$, —(CR$_x$R$_x$)$_{0-3}$NR$_x$(C$_{1-4}$ hydroxyalkyl), —CH$_2$CH(OH)CH$_2$NR$_x$R$_y$, —C(O)H, —C(O)(C$_{1-6}$ alkyl), —C(O)(C$_{1-3}$ hydroxyalkyl), —C(O)(C$_{1-3}$ fluoroalkyl), —C(O)(C$_{1-3}$ chloroalkyl), —C(O)(C$_{1-3}$ cyanoalkyl), —(CR$_x$R$_x$)$_{0-3}$C(O)OH, —C(O)(CH$_2$)$_{0-2}$O(C$_{1-4}$ alkyl), —C(O)(CR$_x$R$_x$)$_{0-2}$O(CR$_x$R$_x$)$_{1-2}$O(C$_{1-3}$ alkyl), —C(O)CR$_x$R$_x$S(O)$_2$(C$_{1-3}$ alkyl), —C(O)CR$_x$R$_x$NR$_x$S(O)$_2$(C$_{1-3}$ alkyl), —C(O)CR$_x$R$_x$OC(O)(C$_{1-3}$ alkyl), —C(O)(CR$_x$R$_x$)$_{0-3}$NR$_y$R$_y$, —C(O)(CR$_x$R$_x$)$_{0-1}$NR$_x$(C$_{1-3}$ cyanoalkyl), —C(O)(CR$_x$R$_x$)$_{0-2}$NR$_y$(C$_{1-6}$ hydroxyalkyl), —C(O)(CR$_x$R$_x$)$_{0-1}$NR$_x$(C$_{1-3}$ fluoroalkyl), —C(O)(CR$_x$R$_x$)$_{0-1}$NR$_x$(C$_{1-5}$ hydroxy-fluoroalkyl), —C(O)(CR$_x$R$_x$)$_{0-1}$NR$_x$(CH$_2$)$_{1-2}$O(C$_{1-3}$ hydroxyalkyl), —C(O)(CR$_x$R$_x$)$_{0-1}$NR$_x$(CH$_2$)$_{1-2}$NR$_x$C(O)(C$_{1-2}$ alkyl), —C(O)(CR$_x$R$_x$)$_{0-1}$NR$_x$(CR$_x$R$_x$)$_{1-2}$O(C$_{1-2}$ alkyl), —C(O)(CR$_x$R$_x$(NH$_2$)(CR$_x$R$_x$)$_{1-4}$NR$_x$R$_x$, —C(O)CR$_x$(NH$_2$)(CR$_x$R$_x$)$_{1-4}$NR$_x$C(O)NR$_x$R$_x$, —C(O)(CR$_x$R$_x$)$_{0-3}$NR$_x$(CH$_2$)$_{0-1}$C(O)(C$_{1-3}$ alkyl), —C(O)(CR$_x$R$_x$)$_{0-1}$NR$_x$(CH$_2$)$_{0-1}$C(O)(C$_{1-3}$ cyanoalkyl), —C(O)(CR$_x$R$_x$)$_{0-1}$NR$_x$CH$_2$C(O)NR$_x$R$_y$, —C(O)(CR$_x$R$_x$)$_{0-1}$NR$_x$(CH$_2$)$_{1-2}$C(O)NR$_y$R$_y$, —C(O)(CR$_x$R$_x$)$_{0-1}$NR$_x$(CHR$_y$(CH$_2$OH)), —(CR$_x$R$_x$)$_{1-2}$C(O)NR$_y$R$_y$, —(CR$_x$R$_x$)$_{1-2}$C(O)NR$_y$(C$_{1-3}$ fluoroalkyl), —(CR$_x$R$_x$)$_{1-2}$C(O)NR$_y$(C$_{1-4}$ hydroxyalkyl), —(CR$_x$R$_x$)$_{1-2}$C(O)NR$_y$(C$_{1-3}$ cyanoalkyl), —(CR$_x$R$_x$)$_{1-2}$C(O)NR$_x$(CH$_2$)$_{1-2}$O(C$_{1-3}$ alkyl), —(CR$_x$R$_x$)$_{1-2}$C(O)NR$_x$CH(C$_{1-4}$ alkyl)C$_{1-3}$ hydroxyalkyl), —(CH$_2$)$_{1-2}$C(O)NR$_x$(CH$_2$)$_{1-2}$C(O)NR$_y$R$_x$, —(CH$_2$)$_{1-2}$C(O)NR$_x$(CH$_2$)$_{1-2}$S(O)$_2$OH, —(CH$_2$)$_{1-2}$C(O)NR$_x$(CH$_2$)$_{1-2}$NR$_x$C(O)(C$_{1-3}$ alkyl), —(CH$_2$)$_{1-2}$C(O)NR$_x$(CH$_2$)$_{1-3}$NR$_x$R$_x$, —(CH$_2$)$_{1-2}$C(O)N(CH$_2$CH$_3$)(CH$_2$)$_{1-3}$NR$_x$R$_x$, —(CH$_2$)$_{0-2}$S(O)$_2$(C$_{1-4}$ alkyl), —(CH$_2$)$_{0-2}$S(O)$_2$(C$_{1-3}$ fluoroalkyl), —(CH$_2$)$_{0-2}$S(O)$_2$NR$_x$R$_x$, —C(O)C(O)OH, —C(O)C(O)NR$_y$R$_y$, or —C(O)C(O)NR$_y$(CR$_x$R$_x$)$_{1-2}$NR$_y$R$_y$;

$L_1$ is a bond, —(CR$_x$R$_x$)$_{1-2}$—, —(CR$_x$R$_x$)$_{1-2}$CR$_x$(OH)—, —(CR$_x$R$_x$)$_{1-2}$O—, —CR$_x$R$_x$C(O)—, —(CR$_x$R$_x$)$_2$NR$_x$(CR$_x$R$_x$)$_{0-1}$—, —CR$_x$R$_x$C(O)NR$_x$(CR$_x$R$_x$)$_{0-4}$—, —C(O)(CR$_x$R$_x$)$_{0-3}$—, —C(O)(CR$_x$R$_x$)$_{0-2}$NR$_x$(CR$_x$R$_x$)$_{0-2}$—, —C(O)(CR$_x$R$_x$)$_{0-2}$N(C$_{1-2}$ hydroxyalkyl)(CR$_x$R$_x$)$_{0-2}$—, —C(O)(CR$_x$R$_x$)$_{0-2}$NR$_x$(CR$_x$R$_x$)$_{1-2}$CR$_x$(OH)—, —C(O)(CR$_x$R$_x$)$_{1-2}$C(O)NR$_x$—, —(CR$_x$R$_x$)$_{0-2}$C(O)NR$_x$(CR$_x$R$_x$)$_{1-2}$CR$_x$(OH)—, —(CR$_x$R$_x$)$_{0-2}$C(O)N(C$_{1-2}$ hydroxyalkyl)(CR$_x$R$_x$)$_{1-2}$—, —C(O)(CR$_x$R$_x$)$_{0-1}$O—, —C(O)(CR$_x$R$_x$)$_{1-2}$NHS(O)$_2$—, —C(O)CR$_x$(NH$_2$)CR$_x$R$_x$—, —C(O)C(O)(CR$_x$R$_x$)$_{0-2}$—, —C(O)C(O)NR$_x$(CR$_x$R$_x$)$_{0-2}$—, —C(O)NR$_x$(CR$_x$R$_x$)$_{0-2}$—, —C(O)NR$_x$(CR$_x$R$_x$)$_{1-2}$—, or —S(O)$_2$—;

A is 2-oxa-6-azaspiro[3.3]heptanyl, 4-oxaspiro[2.5]octanyl, 7-azaspiro[3.5]nonanyl, 8-azabicyclo[3.2.1]octanyl, 8-oxa-3-azabicyclo[3.2.1]octanyl, 9-azabicyclo[3.3.1]nonanyl, adamantanyl, azepanyl, azetidinyl, C$_{3-6}$ cycloalkyl, dihydroinonyl, dihydropyrimidinonyl, dioxidoisothiazolidinyl, dioxidothiazinanyl, dioxotetrahydrothiophenyl, dioxotetrahydrothiopyranyl, dioxothiomorpholinyl, imidazolyl, imidazolidinonyl, isoxazolyl, morpholinyl, morpholinonyl, octahydrocyclopenta[b]pyranyl, oxazolidinonyl, oxadiazolyl, oxetanyl, oxazolyl, phenyl, piperidinyl, piperidinonyl, piperazinyl, piperazinonyl, pyrazolyl, pyridazinonyl, pyridinonyl, pyridinyl, pyrimidinyl, pyrrolidinonyl, pyrrolidinyl, pyrrolyl, quinolizinonyl, tetrahydrofuranyl, tetrahydropyranyl, tetrazolyl, thiazolyl, or triazolyl, each substituted with -L$_2$-R$_a$ and zero to 4 R$_b$;

L$_2$ is a bond or —CR$_x$R$_x$—;

R$_a$ is:
(a) H, F, Cl, —CN, —OH, C$_{1-6}$ alkyl, C$_{1-3}$ fluoroalkyl, C$_{1-5}$ hydroxyalkyl, —(CH$_2$)$_{0-4}$O(C$_{1-3}$ alkyl), —(CR$_x$R$_x$)$_{1-3}$S(C$_{1-3}$ alkyl), —(CR$_x$R$_x$)$_{1-3}$NHC(O)O(C$_{1-4}$ alkyl), —(CR$_x$R$_x$)$_{1-3}$NR$_y$R$_y$, —(CR$_x$R$_x$)$_{1-3}$C(O)NR$_y$R$_y$, —O(C$_{1-3}$ fluoroalkyl), —S(O)$_2$NR$_x$R$_x$, —O(CR$_x$R$_x$)$_{1-3}$NR$_x$R$_x$, —NHS(O)$_2$(C$_{1-3}$ alkyl), —NR$_x$R$_x$, —NR$_x$(C$_{1-4}$ alkyl), —NR$_x$C(O)(C$_{1-4}$ alkyl), —(CR$_x$R$_x$)$_{0-3}$C(O)OH, —C(O)(C$_{1-5}$ alkyl), —C(O)(C$_{1-3}$ fluoroalkyl), —C(O)O(C$_{1-4}$ alkyl), —C(O)NH(C$_{1-3}$ cyanoalkyl), —C(O)NR$_y$R$_y$, —C(O)NR$_x$CH$_2$C(O)NR$_x$R$_x$, or —C(O)NR$_x$CH$_2$CH$_2$NHC(O)(C$_{1-3}$ alkyl);

(b) C$_{3-6}$ cycloalkyl or —C(O)NH(C$_{3-6}$ cycloalkyl), wherein each cycloalkyl is substituted with zero to 2 substituents independently selected from —OH, C$_{1-3}$ alkyl, C$_{1-3}$ hydroxyalkyl, C$_{1-3}$ fluoroalkyl, and —C(O)O(C$_{1-3}$ alkyl); or (c) A$_1$, —CH$_2$A$_1$, —C(O)A$_1$, —NR$_x$A$_1$, or —C(O)NR$_x$A$_1$, wherein A$_1$ is furanyl, imidazolyl, indolyl, isoxazolyl, morpholinyl, octahydropyrrolo[3,4-c]pyrrolyl, oxazolyl, oxetanyl, phenyl, piperazinyl, piperidinyl, pyrazolyl, pyridinyl, pyrimidinyl, pyrrolidinyl, pyrrolyl, tetrahydrofuranyl, tetrahydropyranyl, thiadiazolyl, thiazolyl, thiophenyl, or triazolyl, each substituted with zero to three substituents independently selected from —OH, C$_{1-3}$ alkyl, C$_{1-3}$ hydroxyalkyl, —C(O)(C$_{1-2}$ alkyl), —C(O)O(C$_{1-3}$ alkyl), —NR$_x$R$_x$, phenyl, trifluoromethyl-phenyl, —CH$_2$(bromophenyl), and —CH$_2$CH$_2$(pyrrolidinyl);

R$_z$ is H, C$_{1-2}$ alkyl, or —CF$_3$; and R$_4$, R$_5$, R$_x$, R$_y$, m, n, and p are defined in the first aspect.

One embodiment provides a compound of Formula (I), N-oxide, or salt thereof, wherein:

R$_1$ is H, —CH$_3$, —CH$_2$CH$_3$, —CH(CH$_3$)$_2$, —C(CH$_3$)$_3$, —CHF$_2$, —CH$_2$CHF$_2$, —CH(CH$_3$)CF$_3$, —C(CF$_3$)=CH$_2$, —C(O)OCH$_3$, cyclopropyl, or —CH$_2$(cyclopropyl);

each R₂ is independently F, Cl, Br, —CN, —OH, —CH₃, —CH₂CH₃, —CF₃, —CH₂OH, —C(CH₃)₂OH, —CH₂NH₂, —OCH₃, —OCH₂CH₃, —OCH(CH₃)₂, —OCH₂CH₂OCH₃, —OCH₂CH₂N(CH₃)₂, —OCHF₂, —C(O)OCH₃, —C(O)NH₂, —C(O)NH(CH₂CH₃), —C(O)(thiazolyl), —NH₂, —NH(CH₃), —NH(CH₂CH₃), —N(CH₃)₂, —NHC(O)CH₃, —NHC(O)C(CH₃)₃, —NH(CH₂-cyclopropyl), —NO₂, cyclopropyl, methylpiperidinyl, methylpiperazinyl, aminooxadiazolyl, imidazolyl, or triazolyl;

R₃ is:

(a) -L₁-A; or (b) H, —CH₃, —CH₂CH₃, —CH₂CH₂CH₃, —CH(CH₃)₂, —CH₂CH(CH₃)₂, —CH₂C(CH₃)₃, —CH(CH₂CH₃)₂, —CH₂CHF₂, —CH₂CF₃, —CH₂CH₂CF₃, —CH(CH₃)CH₂F, —CH(CH₂F)₂, —CH₂CH₂OH, —CH₂CH₂CH₂OH, —CH₂CH(CH₃)OH, —CH₂CH(OH)CH₂CH₃, —CH₂C(CH₃)₂OH, —CH₂CH(OH)CH(CH₃)₂, —CH₂CH(OH)C(CH₃)₃, —CH₂CH(OH)CH₂OH, —CH₂CH(OH)CF₃, —CH₂C(CH₃)(OH)CH=CH₂, —CH₂CN, —CH₂CH₂CN, —C(O)H, —C(O)OH, —CH₂C(O)OH, —CH₂C(CH₃)₂C(O)OH, —CH₂CH₂OCH₃, —CH₂CH₂OCH₂CH₃, —CH₂CH(CH₃)OCH₃, —CH₂CH₂OCH₂OCH₃, —CH₂CH₂OCH₂OCH₃, —CH₂CH(OH)CH₂OCH₃, —NH(CH₃), —NH(CH₂C(CH₃)₂OH), —CH₂CH₂NHCH₃, —CH₂CH₂NH(CH₃), —CH₂CH₂CH₂N(CH₃)₂, —CH₂CH(OH)CH₂N(CH₃)CH(CH₃)₂, —S(O)₂CH₃, —S(O)₂CH₂CH₃, —S(O)₂CH₂CH₂CH₃, —S(O)₂CH(CH₃)₂, —S(O)₂CH₂CH(CH₃)₂, —S(O)₂CH₂CF₃, —C(O)CH₃, —C(O)CH₂CH₃, —C(O)CH(CH₃)₂, —C(O)CH₂CH(CH₃)₂, —C(O)C(CH₃)₃, —C(O)CH(CH₂CH₃)₂, —C(O)CHF₂, —C(O)CF₃, —C(O)CH₂CF₃, —C(O)CH₂OH, —C(O)CH₂CH₂OH, —C(O)C(CH₃)₂OH, —C(O)CH₂CH(CH₃)OH, —C(O)CH₂(CH₂CH₂OH)(CH₂CH₂CH₂CH₃), —C(O)CH₂CN, —C(O)C(CH₃)₂CN, —C(O)CH₂OCH₃, —C(O)CH₂CH₂OCH₃, —C(O)CH₂NH₂, —C(O)CH₂NHCH₃, —C(O)CH(CH₃)NHCH₃, —C(O)C(CH₃)₂NH₂, —C(O)C(CH₃)₂NHCH₃, —C(O)CH₂CH₂CH₂N(CH₃)₂, —C(O)CH₂NHCH₂CH₂CH₃, —C(O)CH₂NHC(CH₃)₂, —C(O)CH₂NHC(CH₃)₃, —C(O)CH₂NHCH(CH₃)CH₂CH₃, —C(O)CH₂NHCH₂CH₂CH(CH₃)₂, —C(O)CH₂NHCH₂C(CH₃)₃, —C(O)CH₂NHCH(CH₂CH₃)₂, —C(O)CH₂NHCH₂C(CH₃)₃, —C(O)CH₂NHCH₂CH₂OH, —C(O)CH₂NH(CH₂CH(OH)CH₃), —C(O)CH₂NH(CH₂CH₂CH(OH)CH₃), —C(O)CH₂NH(CH₂C(CH₃)₂OH), —C(O)CH₂NHCH(CH₂OH)CH₂CH(CH₃)₂, —C(O)CH₂NHCH₂CH(OH)CH₂OH, —C(O)CH₂NHCH₂CH₂OCH₃, —C(O)CH₂NHCH₂CH₂OCH₂CH₃, —C(O)CH₂OCH₂CH₂OCH₃, —C(O)CH₂S(O)₂CH₃, —C(O)CH₂NHS(O)₂CH₃, —C(O)CH₂NHC(O)CH₃, —C(O)CH₂N(CH₃)₂, —C(O)CH₂N(CH₃)CH₂CH₃, —C(O)CH₂N(CH₃)CH(CH₃)₂, —C(O)CH₂N(CH₃)C(CH₃)₃, —C(O)CH₂N(CH₃)CH₂CH(CH₃)₂, —C(O)CH₂N(CH₃)CH₂CH₂OH, —C(O)CH₂N(CH₃)CH₂CH₂CH₂OH, —C(O)CH₂N(CH₃)(CH₂C(CH₃)₂OH), —C(O)CH₂N(CH₃)(CH₂CH₂F), —C(O)CH₂N(CH₃)(CH₂CHF₂), —C(O)CH₂N(CH₃)(CH₂CN), —C(O)CH₂N(CH₃)CH₂CH₂CN, —C(O)CH₂N(CH₃)CH₂CH₂OCH₃, —C(O)CH₂N(CH(CH₃)₂)₂, —C(O)CH₂N(CH₂CH₂OH)(CH₃), —C(O)CH₂N(CH₂CH₂OH)(CH₂CH₃), —C(O)CH₂N(CH₂CH₂OH)(CH(CH₃)₂), —C(O)CH₂N(CH₂CH₂OH)(CH₂CH(CH₃)CH₂CH₃), —C(O)CH₂CH₂NH(CH₃), —C(O)CH₂CH₂N(CH₃)₂, —C(O)CH₂CH₂N(CH₃)CH₂CH₂OH, —C(O)CH₂CH₂N(CH₃)C(O)CH₃, —C(O)CH₂N(CH₂CH₃)₂, —C(O)CH(NH₂)CH₂CH₂CH₂NH₂, —C(O)CH(NH₂)CH₂CH₂CH₂CH₂NH₂, —C(O)CH(NH₂)CH₂CH₂CH₂NHC(O)NH₂, —C(O)OCH₃, —C(O)OCH₂CH₃, —C(O)OCH(CH₃)₂, —C(O)OCH₂CH(CH₃)₂, —C(O)OCH₂CH₂OCH₃, —C(O)C(O)OH, —C(O)C(O)NH(CH₃), —C(O)C(O)N(CH₃)₂, —C(O)C(O)N(CH₃)CH₂CH₂N(CH₃)₂, —CH₂C(O)NH₂, —CH₂C(O)NH(CH₃), —CH₂C(O)NH(CH₂CH₃), —CH₂C(O)NH(CH₂CH₂CH₃), —CH₂C(O)NHCH(CH₃)₂, —CH₂C(O)NH(CH(CH₃)CH₂CH₃), —CH₂C(O)NHCH₂CH(CH₃)₂, —CH₂C(O)NHC(CH₃)₃, —CH₂C(O)NH(CH₂CH(CH₃)₂), —CH₂C(O)NHCH(CH₂CH₃)₂, —CH₂C(O)NH(CH₂CH₂C(CH₃)₃), —CH₂C(O)NH(CH₂CF₃), —CH₂C(O)NH(CH(CH₃)CF₃), —CH₂C(O)NHCH₂CH₂OH, —CH₂C(O)NH(CH₂CH(CH₃)OH), —CH₂C(O)NH(CH(CH₃)OH), —CH₂C(O)NH(CH₂CH₂OCH₃), —CH₂C(O)NH(CH₂CH₂OCH₂CH₃), —CH₂C(O)NH(CH₂CN), —CH₂C(O)NHCH(CH₂OH)(CH₂CH(CH₃)₂), —CH₂CH₂C(O)NH₂, —CH₂C(O)N(CH₃)₂, —CH₂C(O)N(CH₃)CH₂CH₃, —CH₂C(O)N(CH₃)CH(CH₃)₂, —CH₂C(O)N(CH₃)CH₂CH(CH₃)₂, —CH₂C(O)N(CH₃)C(CH₃)₃, —CH₂C(O)N(CH₃)CH₂CH₂CH₂OH, —CH₂C(O)N(CH₃)CH₂C(CH₃)₂OH, —CH₂C(O)N(CH₃)CH₂CH₂OCH₃, —CH₂C(O)N(CH₃)CH₂CN, —CH₂C(O)N(CH₂CH₃)₂, —CH₂C(O)N(CH(CH₃)₂)₂, —CH(CH₃)C(O)N(CH₃)₂, —CH₂C(O)N(CH₂CH₂OH)(CH₂CH₃), —CH₂C(O)N(CH₂CH₂OH)(CH₂CH₂CH₃), —CH₂C(O)N(CH₂CH₂OH)(CH₂CH₂CH₂CH₃), —CH₂C(O)N(CH₂CH₂OH)(CH(CH₃)₂), or —CH₂C(O)N(CH₂CH₂OH)(CH₂CH(CH₃)CH₂CH₃);

L₁ is a bond, —(CH₂)₁₋₂—, —CH₂CH(OH)—, —CH₂CH₂O—, —CH₂C(O)—, —CH₂C(O)NH—, —CH₂C(O)N(CH₃)—, —CH₂C(O)NHCH₂—, —CH₂C(O)NRₓCH₂CH₂—, —CH₂C(O)NHCH₂—, —CH₂C(O)N(CH₃)CH₂CH₂—, —CH₂C(O)N(CH₃)CH₂CH(OH)—, —CH₂C(O)NHCH₂C(CH₃)₂—, —CH₂C(O)N(CH₂CH₂OH)CH₂—, —C(O)(CH₂)₀₋₂—, —C(O)CH₂C(O)NRₓ—, —C(O)CH₂CH₂NRₓ—, —C(O)NH—, —C(O)CH₂NRₓ(CH₂)₀₋₂—, —C(O)CH₂NHCH₂C(CH₃)₂—, —C(O)CH₂N(CH₃)CH₂CH(OH)—, —C(O)CH₂N(CH₂CH₂OH)CH₂—, —C(O)CH₂CH₂NHS(O)₂—, —C(O)CH(NH₂)CH₂—, —C(O)O—, —C(O)C(O)—, —C(O)C(O)NH(CH₂)₁₋₂—, or —S(O)₂—;

A is 2-oxa-6-azaspiro[3.3]heptanyl, 4-oxaspiro[2.5]octanyl, 7-azaspiro[3.5]nonanyl, 8-azabicyclo[3.2.1]octanyl, 8-oxa-3-azabicyclo[3.2.1]octanyl, 9-azabicyclo[3.3.1]nonanyl, adamantanyl, azepanyl, azetidinyl, C₃₋₆ cycloalkyl, dihydroinonyl, dihydropyrimidinonyl, dioxidoisothiazolidinyl, dioxidothiazinanyl, dioxotetrahydrothiophenyl, dioxotetrahydrothiopyranyl, dioxothiomorpholinyl, imidazolyl, imidazolidinonyl, isoxazolyl, morpholinyl, morpholinonyl, octahydrocyclopenta[b]pyranyl, oxazolidinonyl, oxadiazolyl, oxetanyl, oxazolyl, phenyl, piperidinyl, piperidinonyl, piperazinyl, piperazinonyl, pyrazolyl, pyridazinonyl, pyridinonyl, pyridinyl, pyrimidinyl, pyrrolidinonyl, pyrrolidinyl, pyrrolyl, quinolizinonyl, tetrahydrofuranyl, tetrahydropyranyl, tetrazolyl, thiazolyl, or triazolyl, each substituted with -$L_2$-$R_a$ and zero to 4 $R_b$;

$L_2$ is bond or —$CH_2$—;

$R_a$ is H, F, Cl, —CN, —OH, —$CH_3$, —$CH_2CH_3$, —CH($CH_3$)$_2$, —C($CH_3$)$_3$, —$CH_2CH(CH_3)_2$, —$CH_2OH$, —$CH_2CH_2OH$, —$CF_3$, —$CH_2OCH_3$, —$CH_2CH_2OCH_3$, —$OCH_3$, —C(O)$CH_3$, —C(O)$CH_2C(CH_3)_3$, —C(O)$CF_3$, —C(O)$OCH_3$, —$CH_2C(O)N(CH_3)_2$, —$CH_2CH_2NH(CH_3)$, cyclopropyl, cyclopentyl, —$NH_2$, —$N(CH_3)_2$, —NH(pyridinyl), —C(O)$NH_2$, —NHC(O)$CH_3$, phenyl, or morpholinyl;

each $R_b$ is independently F, —$CH_3$, —$CF_3$, or —$OCH_3$;

each $R_4$ is independently F, —OH, or —$CH_3$; or two $R_4$ attached to the same carbon atom form =O;

each $R_5$ is independently F, —$CH_3$, or —$CF_3$;

each $R_x$ is independently H or —$CH_3$;

m is zero, 1, 2, 3, or 4;

n is zero, 1, or 2;

p is zero, 1, 2, 3, or 4; and $R_x$ and p are defined in the first aspect.

One embodiment provides a compound of Formula (I), N-oxide, or salt thereof, wherein: $R_3$ is -$L_1$-A; and $R_1$, $R_2$, $R_4$, $R_5$, m, n, and p are defined in the first aspect.

One embodiment provides a compound of Formula (I), N-oxide, or salt thereof, wherein: $R_3$ is H; and $R_1$, $R_2$, $R_4$, $R_5$, m, n, and p are defined in the first aspect.

One embodiment provides a compound of Formula (I), N-oxide, or salt thereof, wherein $R_3$ is H, $C_{1-6}$ alkyl, $C_{1-3}$ fluoroalkyl, $C_{1-3}$ cyanoalkyl, $C_{1-6}$ hydroxyalkyl, $C_{1-3}$ hydroxy-fluoroalkyl, —$CR_xR_xCR_x(OH)CR_x$=$CR_xR_x$, —$(CR_xR_x)_{1-4}O(C_{1-3}$ alkyl), —$(CR_xR_x)_{1-4}O(CR_xR_x)_{1-3}O(C_{1-3}$ alkyl), —$CR_xR_xCR_x(OH)CH_2O(C_{1-3}$ alkyl), —$(CR_xR_x)_{1-3}S(C_{1-3}$ alkyl), —$(CH_2)_{1-3}C(O)OC(CH_3)_3$, —$(CR_xR_x)_{0-3}NR_yR_y$, —$(CR_xR_x)_{0-3}NR_x(C_{1-4}$ hydroxyalkyl), —$CR_xR_xCR_x(OH)CH_2NR_xR_y$, —C(O)H, —C(O)($C_{1-6}$ alkyl), —C(O)($C_{1-3}$ hydroxyalkyl), —C(O)($C_{1-3}$ fluoroalkyl), —C(O)($C_{1-3}$ chloroalkyl), —C(O)($C_{1-3}$ cyanoalkyl), —$(CR_xR_x)_{0-3}C(O)OH$, —C(O)$(CH_2)_{0-2}O(C_{1-4}$ alkyl), —C(O)$(CR_xR_x)_{0-2}O(CR_xR_x)_{1-2}O(C_{1-3}$ alkyl), —C(O)$CR_xR_xS(O)_2(C_{1-3}$ alkyl), —C(O)$CR_xR_xNR_xS(O)_2(C_{1-3}$ alkyl), —C(O)$CR_xR_xOC(O)(C_{1-3}$ alkyl), —C(O)$(CR_xR_x)_{0-3}NR_yR_y$, —C(O)$(CR_xR_x)_{0-1}NR_x(C_{1-3}$ cyanoalkyl), —C(O)$(CR_xR_x)_{0-2}NR_y(C_{1-6}$ hydroxyalkyl), —C(O)$(CR_xR_x)_{0-1}NR_x(C_{1-3}$ fluoroalkyl), —C(O)$(CR_xR_x)_{0-1}NR_x(C_{1-5}$ hydroxyfluoroalkyl), —C(O)$(CR_xR_x)_{0-1}NR_x(CH_2)_{1-2}O(C_{1-3}$ hydroxyalkyl), —C(O)$(CR_xR_x)_{0-1}NR_x(CH_2)_{1-2}NR_xC(O)(C_{1-2}$ alkyl), —C(O)$(CR_xR_x)_{0-1}NR_x((CR_xR_x)_{1-2}O(C_{1-2}$ alkyl)), —C(O)$CR_x(NH_2)(CR_xR_x)_{1-4}NR_xR_x$, —C(O)$CR_x(NH_2)(CR_xR_x)_{1-4}NR_xC(O)NR_xR_x$, —C(O)$(CR_xR_x)_{0-3}NR_x(CH_2)_{0-1}C(O)(C_{1-3}$ alkyl), —C(O)$(CR_xR_x)_{0-1}NR_x(CH_2)_{0-1}C(O)(C_{1-3}$ cyanoalkyl), —C(O)$(CR_xR_x)_{0-1}NR_x(CH_2)_{1-2}C(O)NR_yR_y$, —C(O)$(CR_xR_x)_{1-3}C(O)NR_yR_y$, —C(O)$(CR_xR_x)_{0-1}NR_x(CHR_y(CH_2OH))$, —$(CR_xR_x)_{1-2}C(O)NR_yR_y$, —$(CR_xR_x)_{1-2}C(O)NR_y(C_{1-3}$ fluoroalkyl), —$(CR_xR_x)_{1-2}C(O)NR_y(C_{1-4}$ hydroxyalkyl), —$(CR_xR_x)_{1-2}C(O)NR_y(C_{1-3}$ cyanoalkyl), —$(CR_xR_x)_{1-2}C(O)NR_x(CH_2)_{1-2}O(C_{1-3}$ alkyl), —$(CR_xR_x)_{1-2}C(O)NR_xCH(C_{1-4}$ alkyl)($C_{1-3}$ hydroxyalkyl), —$(CH_2)_{1-2}C(O)NR_x(CH_2)_{1-2}C(O)NR_xR_x$, —$(CH_2)_{1-2}C(O)NR_x(CH_2)_{1-2}S(O)_2OH$, —$(CH_2)_{1-2}C(O)NR_x(CH_2)_{1-2}NR_xC(O)(C_{1-3}$ alkyl), —$(CH_2)_{1-2}C(O)NR_x(CH_2)_{1-3}NR_xR_x$, —$(CH_2)_{1-2}C(O)N(CH_2CH_3)(CH_2)_{1-3}NR_xR_x$, —$(CH_2)_{0-2}S(O)_2(C_{1-4}$ alkyl), —$(CH_2)_{0-2}S(O)_2(C_{1-3}$ fluoroalkyl), —$(CH_2)_{0-2}S(O)_2NR_xR_x$, —C(O)C(O)OH, —C(O)C(O)$NR_yR_y$, or —C(O)C(O)$NR_y(CR_xR_x)_{1-2}NR_yR_y$; and $R_1$, $R_2$, $R_4$, $R_5$, $R_x$, $R_y$, m, n, and p are defined in the first aspect.

One embodiment provides a compound of Formula (I), N-oxide, or salt thereof, wherein $R_3$ is $C_{1-6}$ alkyl, $C_{1-3}$ fluoroalkyl, $C_{1-3}$ cyanoalkyl, $C_{1-6}$ hydroxyalkyl, $C_{1-3}$ hydroxy-fluoroalkyl, —$CR_xR_xCR_x(OH)CR_x$=$CR_xR_x$, —$(CR_xR_x)_{1-4}O(C_{1-3}$ alkyl), —$(CR_xR_x)_{1-4}O(CR_xR_x)_{1-3}O(C_{1-3}$ alkyl), —$CR_xR_xCR_x(OH)CH_2O(C_{1-3}$ alkyl), —$(CR_xR_x)_{1-3}S(C_{1-3}$ alkyl), —$(CH_2)_{1-3}C(O)OC(CH_3)_3$, —$(CR_xR_x)_{0-3}NR_yR_y$, —$(CR_xR_x)_{0-3}NR_x(C_{1-4}$ hydroxyalkyl), —$CR_xR_xCR_x(OH)CH_2NR_xR_y$, —C(O)H, —C(O)($C_{1-6}$ alkyl), —C(O)($C_{1-3}$ hydroxyalkyl), —C(O)($C_{1-3}$ fluoroalkyl), —C(O)($C_{1-3}$ chloroalkyl), —C(O)($C_{1-3}$ cyanoalkyl), —$(CR_xR_x)_{0-3}C(O)OH$, —C(O)$(CH_2)_{0-2}O(C_{1-4}$ alkyl), —C(O)$(CR_xR_x)_{0-2}O(CR_xR_x)_{1-2}O(C_{1-3}$ alkyl), —C(O)$CR_xR_xS(O)_2(C_{1-3}$ alkyl), —C(O)$CR_xR_xNR_xS(O)_2(C_{1-3}$ alkyl), —C(O)$CR_xR_xOC(O)(C_{1-3}$ alkyl), —C(O)$(CR_xR_x)_{0-3}NR_yR_y$, —C(O)$(CR_xR_x)_{0-1}NR_x(C_{1-3}$ cyanoalkyl), —C(O)$(CR_xR_x)_{0-2}NR_y(C_{1-6}$ hydroxyalkyl), —C(O)$(CR_xR_x)_{0-1}NR_x(C_{1-3}$ fluoroalkyl), —C(O)$(CR_xR_x)_{0-1}NR_x(C_{1-5}$ hydroxyfluoroalkyl), —C(O)$(CR_xR_x)_{0-1}NR_x(CH_2)_{1-2}O(C_{1-3}$ hydroxyalkyl), —C(O)$(CR_xR_x)_{0-1}NR_x(CH_2)_{1-2}NR_xC(O)(C_{1-2}$ alkyl), —C(O)$(CR_xR_x)_{0-1}NR_x((CR_xR_x)_{1-2}O(C_{1-2}$ alkyl)), —C(O)$CR_x(NH_2)(CR_xR_x)_{1-4}NR_xR_x$, —C(O)$CR_x(NH_2)(CR_xR_x)_{1-4}NR_xC(O)NR_xR_x$, —C(O)$(CR_xR_x)_{0-3}NR_x(CH_2)_{0-1}C(O)(C_{1-3}$ alkyl), —C(O)$(CR_xR_x)_{0-1}NR_x(CH_2)_{0-1}C(O)(C_{1-3}$ cyanoalkyl), —C(O)$(CR_xR_x)_{0-1}NR_x(CH_2)_{1-2}C(O)NR_yR_y$, —C(O)$(CR_xR_x)_{1-3}C(O)NR_yR_y$, —C(O)$(CR_xR_x)_{0-1}NR_x(CHR_y(CH_2OH))$, —$(CR_xR_x)_{1-2}C(O)NR_yR_y$, —$(CR_xR_x)_{1-2}C(O)NR_y(C_{1-3}$ fluoroalkyl), —$(CR_xR_x)_{1-2}C(O)NR_y(C_{1-4}$ hydroxyalkyl), —$(CR_xR_x)_{1-2}C(O)NR_y(C_{1-3}$ cyanoalkyl), —$(CR_xR_x)_{1-2}C(O)NR_x(CH_2)_{1-2}O(C_{1-3}$ alkyl), —$(CR_xR_x)_{1-2}C(O)NR_xCH(C_{1-4}$ alkyl)($C_{1-3}$ hydroxyalkyl), —$(CH_2)_{1-2}C(O)NR_x(CH_2)_{1-2}C(O)NR_xR_x$, —$(CH_2)_{1-2}C(O)NR_x(CH_2)_{1-2}S(O)_2OH$, —$(CH_2)_{1-2}C(O)NR_x(CH_2)_{1-2}NR_xC(O)(C_{1-3}$ alkyl), —$(CH_2)_{1-2}C(O)NR_x(CH_2)_{1-3}NR_xR_x$, —$(CH_2)_{1-2}C(O)N(CH_2CH_3)(CH_2)_{1-3}NR_xR_x$, —$(CH_2)_{0-2}S(O)_2(C_{1-4}$ alkyl), —$(CH_2)_{0-2}S(O)_2(C_{1-3}$ fluoroalkyl), —$(CH_2)_{0-2}S(O)_2NR_xR_x$, —C(O)C(O)OH, —C(O)C(O)$NR_yR_y$, or —C(O)C(O)$NR_y(CR_xR_x)_{1-2}NR_yR_y$; and $R_1$, $R_2$, $R_4$, $R_5$, $R_x$, $R_y$, m, n, and p are defined in the first aspect.

Included in this embodiment are compounds in which $R_3$ is —$CH_3$, —$CH_2CH_3$, —$CH_2CH_2CH_3$, —CH($CH_3$)$_2$, —$CH_2CH(CH_3)_2$, —$CH_2C(CH_3)_3$, —CH($CH_2CH_3$)$_2$, —$CH_2CHF_2$, —$CH_2CF_3$, —$CH_2CH_2CF_3$, —CH($CH_3$)$CH_2F$, —CH($CH_2F$)$_2$, —$CH_2CH_2OH$, —$CH_2CH_2CH_2OH$, —$CH_2CH(CH_3)OH$, —$CH_2CH(OH)CH_2CH_3$, —$CH_2C(CH_3)_2OH$, —$CH_2CH(OH)CH(CH_3)_2$, —$CH_2CH(OH)C(CH_3)_3$, —$CH_2CH(OH)CH_2OH$, —$CH_2CH(OH)CF_3$, —$CH_2C(CH_3)(OH)CH$=$CH_2$, —$CH_2CN$, —$CH_2CH_2CN$, —C(O)H, —C(O)OH, —$CH_2C(O)OH$, —$CH_2C(CH_3)_2C(O)OH$, —$CH_2CH_2OCH_3$, —$CH_2CH_2OCH_2CH_3$, —$CH_2CH(CH_3)OCH_3$, —$CH_2CH_2OCH_2CH_2OCH_3$, —$CH_2CH_2CH_2OCH_3$, —$CH_2CH(OH)CH_2OCH_3$, —NH($CH_3$), —NH($CH_2C(CH_3)_2OH$), —$CH_2CH_2NHCH_3$, —$CH_2CH_2NH(CH_3)$, —$CH_2CH_2CH_2N(CH_3)_3$, —$CH_2CH(OH)CH_2N(CH_3)CH(CH_3)_2$, —S(O)$_2CH_3$, —S(O)$_2CH_2CH_3$, —S(O)$_2CH_2CH_2CH_3$, —S(O)$_2CH(CH_3)_2$, —S(O)$_2CH_2CH(CH_3)_2$, —S(O)$_2CH_2CF_3$, —C(O)$CH_3$, —C(O)$CH_2CH_3$, —C(O)CH($CH_3$)$_2$, —C(O)$CH_2CH(CH_3)_2$, —C(O)C($CH_3$)$_3$, —C(O)CH($CH_2CH_3$)$_2$, —C(O)$CHF_2$, —C(O)$CF_3$, —C(O)$CH_2CF_3$, —C(O)$CH_2OH$, —C(O)$CH_2CH_2OH$, —C(O)C($CH_3$)$_2OH$, —C(O)$CH_2CH(CH_3)OH$, —C(O)$CH_2(CH_2CH_2OH)(CH_2CH_2CH_3)$, —C(O)$CH_2CN$, —C(O)C($CH_3$)$_2CN$, —C(O)$CH_2OCH_3$, —C(O)$CH_2CH_2OCH_3$, —C(O)$CH_2NH_2$, —C(O)$CH_2NHCH_3$, —C(O)CH($CH_3$)$NHCH_3$, —C(O)C($CH_3$)$_2$ $NH_2$, —C(O)C(CH_3)_2NHCH_3, —C(O)CH_2CH_2CH_2N(CH_3)_2, —C(O)CH_2NHCH_2CH_2CH_3, —C(O)CH_2NHCH(CH_3)_2, —C(O)CH_2NHC(CH_3)_3, —C(O)CH_2NHCH_2CH(CH_3)_2, —C(O)CH_2NHCH(CH_3)CH_2CH_3, —C(O)CH_2NHCH_2CH_2OCH_3, —C(O)CH_2NHCH_2C(CH_3)_3, —C(O)CH_2NHCH(CH_2CH_3)_2, —C(O)CH_2NHCH_2CH_2C(CH_3)_3, —C(O)CH_2NHCH_2CH_2OH, —C(O)CH_2NH(CH_2CH(OH)CH_3), —C(O)CH_2NH(CH_2CH_2CH(OH)CH_3), —C(O)CH_2NH(CH_2C(CH_3)_2OH), —C(O)CH_2NHCH(CH_2OH)CH_2CH(CH_3)_2, —C(O)CH_2NHCH_2CH(OH)CH_2OH, —C(O)CH_2NHCH_2CH_2OCH_3, —C(O)CH_2NHCH_2CH_2OCH_2CH_3, —C(O)CH_2OCH_2CH_2OCH_3, —C(O)CH_2S(O)_2CH_3, —C(O)CH_2NHS(O)_2CH_3, —C(O)CH_2NHC(O)CH_3, —C(O)CH_2N(CH_3)_2, —C(O)CH_2N(CH_3)CH_2CH_3, —C(O)CH_2N(CH_3)CH(CH_3)_2, —C(O)CH_2N(CH_3)C(CH_3)_3, —C(O)CH_2N(CH_3)CH_2CH(CH_3)_2, —C(O)CH_2N(CH_3)CH_2CH_2OH, —C(O)CH_2N(CH_3)CH_2CH_2CH_2OH), —C(O)CH_2N(CH_3)(CH_2C(CH_3)_2OH), —C(O)CH_2N(CH_3)(CH_2CH_2F), —C(O)CH_2N(CH_3)(CH_2CHF_2), —C(O)CH_2N(CH_3)(CH_2CN), —C(O)CH_2N(CH_3)CH_2CH_2CN, —C(O)CH_2N(CH_3)CH_2CH_2OCH_3, —C(O)CH_2N(CH(CH_3)_2)_2, —C(O)CH_2N(CH_2CH_2OH)(CH_3), —C(O)CH_2N(CH_2CH_2OH)(CH_2CH_3), —C(O)CH_2N(CH_2CH_2OH)(CH(CH_3)_2), —C(O)CH_2CH_2N(CH_3)C(O)CH_3, —C(O)CH_2CH_2NH(CH_3), —C(O)CH_2N(CH_2CH_2OH)(CH_2CH(CH_3)CH_2CH_3), —C(O)CH_2CH_2N(CH_3)_2, —C(O)CH_2CH_2N(CH_3)CH_2CH_2OH, —C(O)CH(NH_2)CH_2CH_2CH_2NH_2, —C(O)CH(NH_2)CH_2CH_2CH_2CH_2NH_2, —C(O)CH(NH_2)CH_2CH_2CH_2NHC(O)NH_2, —C(O)OCH_3, —C(O)OCH_2CH_3, —C(O)OCH(CH_3)_2, —C(O)OCH_2CH(CH)_2, —C(O)OCH_2CH_2OCH_3, —C(O)C(O)OH, —C(O)C(O)NH(CH_3), —C(O)C(O)N(CH_3)_2, —C(O)C(O)N(CH_3)CH_2CH_2N(CH_3)_2, —CH_2C(O)NH_2, —CH_2C(O)NH(CH_3), —CH_2C(O)NH(CH_2CH_3), —CH_2C(O)NH(CH_2CH_2CH_3), —CH_2C(O)NHCH(CH_3)_2, —CH_2C(O)NHCH_2CH(CH_3)_2, —CH_2C(O)NH(CH(CH_3)CH_2CH_3), —CH_2C(O)NHC(CH_3)_3, —CH_2C(O)NHCH_2C(CH_3)_3, —CH_2C(O)NH(CH_2CH_2CH(CH_3)_2), —CH_2C(O)NHCH(CH_2CH_3)_2, —CH_2C(O)NH(CH_2CH_2C(CH_3)_3), —CH_2C(O)NH(CH_2CF_3), —CH_2C(O)NH(CH(CH_3)CF_3), —CH_2C(O)NHCH_2CH_2OH, —CH_2C(O)NH(CH_2CH_2CH(CH_3)OH), —CH_2C(O)NH(CH_2CH(CH_3)OH), —CH_2C(O)NH(CH_2CH_2OCH_3), —CH_2C(O)NH(CH_2CH_2OCH_2CH_3), —CH_2C(O)NH(CH_2CN), —CH_2C(O)NHCH(CH_2OH)(CH_2CH(CH_3)_2), —CH_2CH_2C(O)NH_2, —CH_2C(O)N(CH_3)_2, —CH_2C(O)N(CH_3)CH_2CH_3, —CH_2C(O)N(CH_3)CH(CH_3)_2, —CH_2C(O)N(CH_3)CH_2CH(CH_3)_2, —CH_2C(O)N(CH_3)C(CH_3)_3, —CH_2C(O)N(CH_3)CH_2CH_2CH_2OH, —CH_2C(O)N(CH_3)CH_2C(CH_3)_2OH, —CH_2C(O)N(CH_3)CH_2CH_2OCH_3, —CH_2C(O)N(CH_3)CH_2CN, —CH_2C(O)N(CH_2CH_3)_2, —CH_2C(O)N(CH(CH_3)_2)_2, —CH(CH_3)C(O)N(CH_3)_2, —CH_2C(O)N(CH_2CH_2OH)(CH_2CH_3), —CH_2C(O)N(CH_2CH_2OH)(CH_2CH_2CH_3), —CH_2C(O)N(CH_2CH_2OH)(CH(CH_3)_2), or —CH_2C(O)N(CH_2CH_2OH)(CH_2CH(CH_3)CH_2CH_3).

One embodiment provides a compound of Formula (I), N-oxide, or salt thereof, wherein $R_1$ is H, Cl, —CN, $C_{1-4}$ alkyl, $C_{1-3}$ fluoroalkyl, $C_{1-3}$ hydroxy-fluoroalkyl, —CR_z=CH_2, $C_{3-6}$ cycloalkyl, —CH_2($C_{3-6}$ cycloalkyl), —C(O)O($C_{1-3}$ alkyl), or tetrahydropyranyl; and $R_2$, $R_3$, $R_4$, $R_5$, $R_z$, m, n, and p are defined in the first aspect. Included in this embodiment are compounds in which $R_1$ is H, —CH_3, —CH_2CH_3, —CH(CH_3)_2, —C(CH_3)_3, —CHF_2, —CH_2CHF_2, —CH(CH_3)CF_3, —C(CF_3)=CH_2, —C(O)OCH_3, cyclopropyl, or —CH_2(cyclopropyl). Also included in this embodiment are compounds in which $R_1$ is —CH_3, —CH_2CH_3, or —CH(CH_3)_2. Furthermore, included in this embodiment are compounds in which $R_1$ is —CH(CH_3)_2.

One embodiment provides a compound of Formula (I), N-oxide, or salt thereof, wherein each $R_2$ is independently halo, —CN, —OH, —NO_{2+}, $C_{1-3}$ alkyl, $C_{1-2}$ fluoroalkyl, $C_{1-3}$ hydroxyalkyl, $C_{1-3}$ aminoalkyl, —(CH_2)_{0-4}O($C_{1-3}$ alkyl), $C_{1-3}$ fluoroalkoxy, $C_{2-4}$ alkoxyalkoxy, —O(CH_2)_{1-2}NR_xR_x, —C(O)O($C_{1-3}$ alkyl), —C(O)NR_yR_y, —NR_yR_y, —NR_xC(O)($C_{1-3}$ alkyl), —NR_x(CH_2-cyclopropyl), $C_{3-6}$ cycloalkyl, methylpiperidinyl, methylpiperazinyl, amino-oxadiazolyl, imidazolyl, triazolyl, or —C(O)(thiazolyl); and $R_1$, $R_3$, $R_4$, $R_5$, m, n, and p are defined in the first aspect. Included in this embodiment are compounds in which each $R_2$ is independently F, Cl, Br, —CN, —OH, —CH_3, —CH_2CH_3, —CF_3, —CH_2OH, —C(CH_3)_2OH, —CH_2NH_2, —OCH_3, —OCH_2CH_3, —OCH(CH_3)_2, —OCH_2CH_2OCH_3, —OCH_2CH_2N(CH_3)_2, —OCHF_2, —C(O)OCH_3, —C(O)NH_2, —C(O)NH(CH_2CH_3), —C(O)(thiazolyl), —NH_2, —NH(CH_3), —NH(CH_2CH_3), —N(CH_3)_2, —NHC(O)CH_3, —NHC(O)C(CH_3)_3, —NH(CH_2-cyclopropyl), —NO_2, cyclopropyl, methylpiperidinyl, methylpiperazinyl, amino-oxadiazolyl, imidazolyl, or triazolyl. Also included in this embodiment are compounds in which each $R_2$ is independently F, Cl, —CN, —CH_3, —OCH_3, —NH_2, or cyclopropyl. Additionally, included in this embodiment are compounds in which p is 2; one $R_2$ is —CH_3; and the other $R_2$ is F, Cl, —CN, —CH_3, —OCH_3, —NH_2, or cyclopropyl.

One embodiment provides a compound of Formula (I), N-oxide, or salt thereof, wherein p is zero, 1, 2, or 3; and $R_1$, $R_2$, $R_3$, $R_4$, $R_5$, m, and n are defined in the first aspect. Included in this embodiment are compounds in which p is zero, 1, or 2. Also included are compounds in which p is 1 or 2.

One embodiment provides a compound of Formula (I), N-oxide, or salt thereof, wherein $R_3$ is (a) -L_1-A; or (b) H, $C_{1-6}$ alkyl, $C_{1-3}$ fluoroalkyl, $C_{1-3}$ cyanoalkyl, $C_{1-6}$ hydroxyalkyl, $C_{1-3}$ hydroxy-fluoroalkyl, —CR_xR_xCR_x(OH)CR_x=CR_xR_x, —(CR_xR_x)_{1-4}O($C_{1-3}$ alkyl), —(CR_xR_x)_{1-4}O(CR_xR_x)_{1-3}O($C_{1-3}$ alkyl), —CH_2CH(OH)CH_2O($C_{1-3}$ alkyl), —(CR_xR_x)_{1-3}S($C_{1-3}$ alkyl), —(CH_2)_{1-3}C(O)OC(CH_3)_3, —(CR_xR_x)_{0-3}NR_xR_y, —(CR_xR_x)_{0-3}NR_x($C_{1-4}$ hydroxyalkyl), —CH_2CH(OH)CH_2NR_xR_y, —C(O)H, —C(O)($C_{1-6}$ alkyl), —C(O)($C_{1-3}$ hydroxyalkyl), —C(O)($C_{1-3}$ fluoroalkyl), —C(O)($C_{1-3}$ chloroalkyl), —C(O)($C_{1-3}$ cyanoalkyl), —(CR_xR_x)_{0-3}C(O)OH, —C(O)(CH_2)_{0-2}O($C_{1-4}$ alkyl), —C(O)(CR_xR_x)_{0-2}O(CR_xR_x)_{1-2}O($C_{1-3}$ alkyl), —C(O)CR_xR_xS(O)_2($C_{1-3}$ alkyl), —C(O)CR_xR_xNR_xS(O)_2($C_{1-3}$ alkyl), —C(O)CR_xR_xOC(O)($C_{1-3}$ alkyl), —C(O)(CR_xR_x)_{0-3}NR_yR_y, —C(O)(CR_xR_x)_{0-1}NR_x($C_{1-3}$ cyanoalkyl), —C(O)(CR_xR_x)_{0-2}NR_y($C_{1-6}$ hydroxyalkyl), —C(O)(CR_xR_x)_{0-1}NR_x($C_{1-3}$ fluoroalkyl), —C(O)(CR_xR_x)_{0-1}NR_x($C_{1-5}$ hydroxy-fluoroalkyl), —C(O)(CR_xR_x)_{0-1}NR_x(CH_2)_{1-2}O($C_{1-3}$ hydroxyalkyl), —C(O)(CR_xR_x)_{0-1}NR_x(CH_2)_{1-2}NR_xC(O)($C_{1-2}$ alkyl), —C(O)(CR_xR_x)_{0-1}NR_x(CR_xR_x)_{1-2}O($C_{1-2}$ alkyl), —C(O)CR_x(NH_2)(CR_xR_x)_{1-4}NR_xR_x, —C(O)CR_x(NH_2)(CR_xR_x)_{1-4}NR_xC(O)NR_xR_x, —C(O)(CR_xR_x)_{0-3}NR_x(CH_2)_{0-1}C(O)($C_{1-3}$ alkyl), —C(O)(CR_xR_x)_{0-1}NR_x(CH_2)_{0-1}C(O)($C_{1-3}$ cyanoalkyl), —C(O)(CR_xR_x)_{0-1}NR_xCH_2C(O)NR_yR_y, —C(O)(CR_xR_x)_{0-1}NR_x(CH_2)_{1-2}C(O)NR_yR_y, —C(O)(CR_xR_x)_{0-1}NR_x(CHR_y(CH_2OH)), —(CR_xR_x)_{1-2}C(O)NR_yR_y, —(CR_xR_x)_{1-2}C(O)NR_y($C_{1-3}$ fluoroalkyl), —(CR_xR_x)_{1-2}C(O)NR_y($C_{1-4}$ hydroxyalkyl), —(CR_xR_x)_{1-2}C(O)NR_y($C_{1-3}$ cyanoalkyl), —(CR_xR_x)_{1-2}C(O)NR_x(CH_2)_{1-2}O($C_{1-3}$ alkyl), —(CR_xR_x)_{1-2}C(O)NR_xCH(C_{1-4} alkyl)C_{1-3} hydroxyalkyl), —(CH_2)_{1-2}C(O)NR_x(CH_2)_{1-2}C(O)NR_xR_x, —(CH$_2$)$_{1-2}$C(O)NR$_x$(CH$_2$)$_{1-2}$ S(O)$_2$OH, —(CH$_2$)$_{1-2}$C(O)NR$_x$(CH$_2$)$_{1-2}$NR$_x$C(O)(C$_{1-3}$ alkyl), —(CH$_2$)$_{1-2}$C(O)NR$_x$(CH$_2$)$_{1-3}$NR$_x$R$_x$, —(CH$_2$)$_{1-2}$C(O)N(CH$_2$CH$_3$)(CH$_2$)$_{1-3}$NR$_x$R$_x$, —(CH$_2$)$_{0-2}$S(O)$_2$(C$_{1-4}$ alkyl), —(CH$_2$)$_{0-2}$S(O)$_2$(C$_{1-3}$ fluoroalkyl), —(CH$_2$)$_{0-2}$S(O)$_2$NR$_x$R$_x$, —C(O)C(O)OH, —C(O)C(O)NR$_y$R$_y$, or —C(O)C(O)NR$_y$(CR$_x$R$_x$)$_{1-2}$NR$_y$R$_y$; and R$_1$, R$_2$, R$_4$, R$_5$, R$_x$, R$_y$, L$_1$, A, m, n, and p are defined in the first aspect.

One embodiment provides a compound of Formula (I), N-oxide, or salt thereof, wherein R$_3$ is piperidinyl substituted with (i) zero or 1 substituent selected from F, —OH, —CH$_3$, —CH$_2$CH$_3$, —CH(CH$_3$)$_2$, —CH$_2$CH(CH$_3$)$_2$, —CH$_2$CH$_2$NH(CH$_3$), —CH$_2$C(O)N(CH$_3$), —C(O)CH$_3$, —C(O)OCH$_3$, cyclopropyl, and —CH$_2$(cyclopropyl), and (ii) zero to 4 R$_b$; each R$_b$ is independently F, —CH$_3$, —CF$_3$, or —OCH$_3$; and R$_1$, R$_2$, R$_4$, R$_5$, m, n, and p are defined in the first aspect. Included in this embodiment are compounds in which R$_1$ is —CH$_3$, —CH$_2$CH$_3$, or —CH(CH$_3$)$_2$. Also included in this embodiment are compounds in which each R$_1$ is —CH(CH$_3$)$_2$.

One embodiment provides a compound of Formula (I), N-oxide, or salt thereof, wherein R$_3$ is azepanyl, oxetanyl, piperidinyl, pyridinyl, tetrahydrofuranyl, tetrahydropyranyl, dimethyl tetrahydropyranyl, octahydrocyclopenta[b]pyranyl, methyl-4-oxaspiro[2.5]octanyl, methyl-8-azabicyclo[3.2.1]octanyl, or methyl-9-azabicyclo[3.3.1]nonanyl; and R$_1$, R$_2$, R$_4$, R$_5$, m, n, and p are defined in the first aspect.

One embodiment provides a compound of Formula (I), N-oxide, or salt thereof, wherein R$_3$ is —(CH$_2$)$_{0-2}$S(O)$_2$(C$_{1-4}$ alkyl), —(CH$_2$)$_{0-2}$S(O)$_2$(C$_{1-3}$ fluoroalkyl), —(CH$_2$)$_{0-2}$S(O)$_2$NR$_x$R$_x$, or —S(O)$_2$-A; and R$_1$, R$_2$, R$_4$, R$_5$, R$_x$, A, m, n, and p are defined in the first aspect. Included in this embodiment are compounds in which R$_3$ is —S(O)$_2$CH$_3$, —S(O)$_2$CH$_2$CH$_3$, —S(O)$_2$CH$_2$CH$_2$CH$_3$, —S(O)$_2$CH(CH$_3$)$_2$, —S(O)$_2$CH$_2$CH(CH$_3$)$_2$, —S(O)$_2$CH$_2$CF$_3$, —S(O)$_2$(cyclopropyl), —S(O)$_2$(phenyl), —S(O)$_2$(fluorophenyl), —S(O)$_2$(chlorophenyl), —S(O)$_2$(methylphenyl), —S(O)$_2$(acetamidophenyl), —S(O)$_2$(pyridinyl), —S(O)$_2$(dimethylimidazolyl), or —S(O)$_2$CH$_2$(phenyl).

One embodiment provides a compound of Formula (I), N-oxide, or salt thereof, wherein R$_3$ is H; and R$_1$, R$_2$, R$_4$, R$_5$, m, n, and p are defined in the first aspect. Included in this embodiment are compounds in which R$_3$ is H; and R$_1$ is —CH$_3$, —CH$_2$CH$_3$, or —CH(CH$_3$)$_2$. Furthermore, included in this embodiment are compounds in which R$_3$ is H; R$_1$ is —CH$_3$, —CH$_2$CH$_3$, or —CH(CH$_3$)$_2$; m is zero; and n is zero.

One embodiment provides a compound of Formula (I), N-oxide, or salt thereof, wherein R$_3$ is -L$_1$-A; L$_1$ is —C(O)(CH$_2$)$_{0-2}$—; and R$_1$, R$_2$, R$_4$, R$_5$, A, m, n, and p are defined in the first aspect. Included in this embodiment are compounds in which L$_1$ is —C(O)— or —C(O)(CH$_2$)—.

One embodiment provides a compound of Formula (I), N-oxide, or salt thereof, wherein R$_3$ is —C(O)-A; and R$_1$, R$_2$, R$_4$, R$_5$, A, m, n, and p are defined in the first aspect. Included in this embodiment are compounds in which A is 8-azabicyclo[3.2.1]octanyl, azepanyl, azetidinyl, C$_{3-6}$ cycloalkyl, dihydroinonyl, dioxotetrahydrothiopyranyl, isoxazolyl, oxetanyl, piperidinonyl, piperidinyl, pyrazolyl, pyridazinonyl, pyridinonyl, pyridinyl, pyrrolidinonyl, pyrrolidinyl, quinolizinonyl, tetrahydrofuranyl, tetrahydropyranyl, thiazolyl, or 7-azaspiro[3.5]nonanyl, each substituted with -L$_2$-R$_a$ and zero to 4 R$_b$; wherein L$_2$, R$_a$ and R$_b$ are defined in the first aspect. Also included in this embodiment are compounds in which A is 8-azabicyclo[3.2.1]octanyl, azepanyl, azetidinyl, C$_{3-6}$ cycloalkyl, dihydroinonyl, dioxotetrahydrothiopyranyl, isoxazolyl, oxetanyl, piperidinonyl, piperidinyl, pyrazolyl, pyridazinonyl, pyridinonyl, pyridinyl, pyrrolidinonyl, pyrrolidinyl, quinolizinonyl, tetrahydrofuranyl, tetrahydropyranyl, thiazolyl, or 7-azaspiro[3.5]nonanyl, each substituted with -L$_2$-R$_a$ and zero to 4 R$_b$; -L$_2$-R$_a$ is F, —CN, —OH, —CH$_3$, —CH(CH$_3$)$_2$, —C(CH$_3$)$_3$, —CF$_3$, —C(O)NH$_2$, —NH$_2$, —N(CH$_3$)$_2$, cyclopropyl, cyclopentyl, phenyl, or —CH$_2$(phenyl); and each R$_b$ is independently F, —CH$_3$, or —CF$_3$.

One embodiment provides a compound of Formula (I), N-oxide, or salt thereof, wherein R$_3$ is —C(O)C(O)-A, —C(O)C(O)NH(CH$_2$)$_{1-2}$-A, —C(O)C(O)OH, —C(O)C(O)NR$_y$R$_y$, —C(O)C(O)NR$_y$(CR$_x$R$_x$)$_{1-2}$NR$_y$R$_y$, or —C(O)(CR$_x$R$_x$)$_{1-2}$C(O)NR$_x$-A; and R$_1$, R$_2$, R$_4$, R$_5$, A, m, n, and p are defined in the first aspect. Included in this embodiment are compounds in which —C(O)C(O)OH, —C(O)C(O)NH(CH$_3$), —C(O)C(O)N(CH$_3$)$_2$, —C(O)C(O)N(CH$_3$)CH$_2$CH$_2$N(CH$_3$)$_2$, —C(O)C(O)(piperidinyl), —C(O)C(O)(methylpiperidinyl), —C(O)C(O)NHCH$_2$(piperidinyl), —C(O)C(O)NHCH$_2$CH$_2$(pyridinyl), or —C(O)CH$_2$C(O)NH(thiazolyl).

One embodiment provides a compound of Formula (I), N-oxide, or salt thereof, wherein R$_3$ is —C(O)CH$_2$-A or —C(O)CH$_2$CH$_2$-A; and R$_1$, R$_2$, R$_4$, R$_5$, A, m, n, and p are defined in the first aspect. Included in this embodiment are compounds in which R$_3$ is —C(O)CH$_2$-A or —C(O)CH$_2$CH$_2$-A; A is 2-oxa-6-azaspiro[3.3]heptanyl, 8-oxa-3-azabicyclo[3.2.1]octanyl, azetidinyl, dihydropyrimidinonyl, dioxidoisothiazolidinyl, dioxidothiazinanyl, imidazolidinedionyl, imidazolidinonyl, imidazolyl, morpholinonyl, morpholinyl, oxazolidinonyl, piperazinonyl, piperazinyl, piperidinyl, pyrazolyl, pyridinonyl, pyrrolidinonyl, pyrrolidinyl, tetrahydropyranyl, tetrazolyl, or triazolyl, each substituted with -L$_2$-R$_a$ and zero to 4 R$_b$; wherein L$_2$, R$_a$ and R$_b$ are defined in the first aspect. Also included in this embodiment are compounds in which R$_3$ is —C(O)CH$_2$-A or —C(O)CH$_2$CH$_2$-A; A is 2-oxa-6-azaspiro[3.3]heptanyl, 8-oxa-3-azabicyclo[3.2.1]octanyl, azetidinyl, dihydropyrimidinonyl, dioxidoisothiazolidinyl, dioxidothiazinanyl, imidazolidinedionyl, imidazolidinonyl, imidazolyl, morpholinonyl, morpholinyl, oxazolidinonyl, piperazinonyl, piperazinyl, piperidinyl, pyrazolyl, pyridinonyl, pyrrolidinonyl, pyrrolidinyl, tetrahydropyranyl, tetrazolyl, or triazolyl, each substituted with -L$_2$-R$_a$ and zero to 4 R$_b$; L$_2$-R$_a$ is F, —OH, —CH$_3$, —CF$_3$, —CH$_2$OH, —CH$_2$CH$_2$OH, —CH$_2$OCH$_3$, —C(O)CH$_2$C(CH$_3$)$_3$, —NH$_2$, cyclopropyl, or morpholinyl; and each R$_b$ is independently F, —CH$_3$, or —CF$_3$.

One embodiment provides a compound of Formula (I), N-oxide, or salt thereof, wherein R$_3$ is C$_{1-6}$ alkyl, C$_{1-3}$ fluoroalkyl, C$_{1-3}$ cyanoalkyl, C$_{1-6}$ hydroxyalkyl, C$_{1-3}$ hydroxy-fluoroalkyl, —CR$_x$R$_x$CR$_x$(OH)CR$_x$=CR$_x$R$_x$, —(CR$_x$R$_x$)$_{1-4}$O(C$_{1-3}$ alkyl), —(CR$_x$R$_x$)$_{1-4}$O(CR$_x$R$_x$)$_{1-3}$O(C$_{1-3}$ alkyl), —CH$_2$CH(OH)CH$_2$O(C$_{1-3}$ alkyl), or —(CR$_x$R$_x$)$_{0-3}$C(O)OH; and R$_1$, R$_2$, R$_4$, R$_5$, R$_x$, A, m, n, and p are defined in the first aspect. Included in this embodiment are compounds in which R$_3$ is —CH$_3$, —CH$_2$CH$_3$, —CH$_2$CH$_2$CH$_3$, —CH(CH$_3$)$_2$, —CH$_2$CH(CH$_3$)$_2$, —CH$_2$C(CH$_3$)$_3$, —CH(CH$_2$CH$_3$)$_2$, —CH$_2$CN, —CH$_2$CH$_2$CN, —CH$_2$CHF$_2$, —CH$_2$CF$_3$, —CH$_2$CH$_2$CF$_3$, —CH(CH$_2$F)$_2$, —CH(CH$_3$)CH$_2$F, —CH$_2$CH$_2$OH, —CH$_2$CH$_2$CH$_2$OH, —CH$_2$CH(CH$_3$)OH, —CH$_2$C(CH$_3$)$_2$OH, —CH$_2$CH(OH)CH$_2$OH, —CH$_2$CH(OH)C(CH$_3$)$_3$, —CH$_2$CH(OH)CH$_2$OCH$_3$, —CH$_2$CH(OH)CH$_2$CH$_3$, —CH$_2$CH(OH)CH(CH$_3$)$_2$, —CH$_2$C(CH$_3$)(OH)CH=CH$_2$, —CH$_2$CH(OH)CF$_3$, —CH$_2$CH$_2$OCH$_3$, —CH$_2$CH(CH$_3$)OCH$_3$, —CH$_2$CH$_2$OCH$_2$CH$_3$, —CH$_2$CH$_2$CH$_2$OCH$_3$, —CH$_2$CH$_2$OCH$_2$CH$_2$OCH$_3$, or —CH$_2$C(CH$_3$)$_2$C(O)OH.

One embodiment provides a compound of Formula (I), N-oxide, or salt thereof, wherein $R_3$ is —$(CR_xR_x)_{0-3}NR_xR_y$, —$(CR_xR_x)_{0-3}NR_x(C_{1-4}$ hydroxyalkyl), —$CH_2CH(OH)CH_2NR_xR_y$, —$(CR_xR_x)_{1-2}C(O)NR_xR_y$, —$(CR_xR_x)_{1-2}C(O)NR_y(C_{1-3}$ fluoroalkyl), —$(CR_xR_x)_{1-2}C(O)NR_y(C_{1-4}$ hydroxyalkyl), —$(CR_xR_x)_{1-2}C(O)NR_y(C_{1-3}$ cyanoalkyl), —$(CR_xR_x)_{1-2}C(O)NR_x(CH_2)_{1-2}O(C_{1-3}$ alkyl), —$(CR_xR_x)_{1-2}C(O)NR_xCH(C_{1-4}$ alkyl)$(C_{1-3}$ hydroxyalkyl), —$(CH_2)_{1-2}C(O)NR_x(CH_2)_{1-2}C(O)NR_xR_x$, —$(CH_2)_{1-2}C(O)NR_x(CH_2)_{1-2}S(O)_2OH$, —$(CH_2)_{1-2}C(O)NR_x(CH_2)_{1-2}NR_xC(O)(C_{1-3}$ alkyl), —$(CH_2)_{1-2}C(O)NR_x(CH_2)_{1-3}NR_xR_x$, or —$(CH_2)_{1-2}C(O)N(CH_2CH_3)(CH_2)_{1-3}NR_xR_x$; and $R_1$, $R_2$, $R_4$, $R_5$, $R_x$, $R_y$, A, m, n, and p are defined in the first aspect. Included in this embodiment are compounds in which $R_3$ is —$NH(CH_3)$, —$NH(CH_2C(CH_3)_2OH)$, —$CH_2CH_2NH(CH_3)$, —$CH_2CH_2CH_2N(CH_3)_2$, —$CH_2CH_2CH_2N(CH_2CH_3)_2$, —$CH_2C(O)NH_2$, —$CH_2C(O)NH(CH_3)$, —$CH_2C(O)N(CH_3)_2$, —$CH_2C(O)NHC(CH_3)_3$, —$CH_2C(O)N(CH_3)CH_2CH_3$, —$CH_2C(O)N(CH_3)C(CH_3)_3$, —$CH_2C(O)N(CH_3)CH(CH_3)_2$, —$CH_2C(O)N(CH_2CH_3)_2$, —$CH_2C(O)N(CH(CH_3)_2)_2$, —$CH_2C(O)NH(CH_2CN)$, —$CH_2C(O)N(CH_3)CH_2CN$, —$CH_2C(O)N(CH_2CH_2OH)(CH(CH_3)_2)$, —$CH_2C(O)N(CH_2CH_2OH)(CH_2CH(CH_3)CH_2CH_3)$, —$CH_2C(O)N(CH_2CH_2OH)(CH_2CH_2CH_3)$, —$CH_2C(O)N(CH_2CH_2OH)(CH_2CH_3)$, —$CH_2C(O)N(CH_2CH_2OH)(CH_2CH_3)$, —$CH_2C(O)NH(CH_3)$, —$CH_2C(O)NH(CH_2CH_3)$, —$CH_2C(O)NH(CH_2CH_2CH_3)$, —$CH_2C(O)NH(CH(CH_3)_2)$, —$CH_2C(O)NHCH_2C(CH_3)_3$, —$CH_2C(O)NHCH_2CH(CH_3)_2$, —$CH_2C(O)NH(CH_2CH_2OH)$, —$CH_2C(O)NHCH(CH_2CH_3)_2$, —$CH_2C(O)NH(CH(CH_3)CF_3)$, —$CH_2C(O)NH(CH(CH_3)CH_2CH_3)$, —$CH_2C(O)NH(CH_2CF_3)$, —$CH_2C(O)NH(CH_2CH(CH_3)OH)$, —$CH_2C(O)NH(CH_2CH_2C(CH_3)_3)$, —$CH_2C(O)NH(CH_2CH_2CH(CH_3)_2)$, —$CH_2C(O)NH(CH_2CH_2OCH_2CH_3)$, —$CH_2C(O)NH(CH_2CH_2OCH_3)$, —$CH_2C(O)NH(CH_2CH_2CH(CH_3)OH)$, —$CH_2C(O)NHCH(CH_2OH)(CH_2CH(CH_3)_2)$, —$CH_2C(O)N(CH_3)CH_2C(CH_3)_2OH$, —$CH_2C(O)N(CH_3)CH_2CH(CH_3)_2$, —$CH_2C(O)N(CH_3)CH_2CH_2OCH_3$, —$CH_2C(O)N(CH_3)CH_2CH_2CH_2OH$, —$CH(CH_3)C(O)N(CH_3)_2$, —$CH_2CH_2C(O)NH_2$, or —$CH_2CH(OH)CH_2N(CH_3)CH(CH_3)_2$.

One embodiment provides a compound of Formula (I), N-oxide, or salt thereof, wherein $R_3$ is —$CH_2C(O)$-A; and $R_1$, $R_2$, $R_4$, $R_5$, A, m, n, and p are defined in the first aspect. Included in this embodiment are compounds in which A is 2-oxa-6-azaspiro[3.3]heptanyl, 2-oxa-7-azaspiro[3.5]nonanyl, 3-oxa-8-azabicyclo[3.2.1]octanyl, azetidinyl, dioxothiomorpholinyl, morpholinyl, piperazinonyl, piperazinyl, piperidinyl, or pyrrolidinyl, each substituted with zero to 3 substituents independently selected from F, —OH, —$CH_3$, —$CH_2OH$, —$CF_3$, —$OCH_3$, —$CH_2OCH_3$, and —$CH_2CH_2OCH_3$.

One embodiment provides a compound of Formula (I), N-oxide, or salt thereof, wherein $R_3$ is —$C(O)H$, —$C(O)(C_{1-6}$ alkyl), —$C(O)(C_{1-3}$ hydroxyalkyl), —$C(O)(C_{1-3}$ fluoroalkyl), —$C(O)(C_{1-3}$ chloroalkyl), —$C(O)(C_{1-3}$ cyanoalkyl), —$(CR_xR_x)_{0-3}C(O)OH$, —$C(O)(CH_2)_{0-2}O(C_{1-4}$ alkyl), —$C(O)(CR_xR_x)_{0-2}O(CR_xR_x)_{1-2}O(C_{1-3}$ alkyl), —$C(O)CR_xR_xOC(O)(C_{1-3}$ alkyl), —$C(O)(CR_xR_x)_{0-3}NR_yR_y$, —$C(O)(CR_xR_x)_{0-1}NR_x(C_{1-3}$ cyanoalkyl), —$C(O)(CR_xR_x)_{0-2}NR_y(C_{1-6}$ hydroxyalkyl), —$C(O)(CR_xR_x)_{0-1}NR_x(C_{1-3}$ fluoroalkyl), —$C(O)(CR_xR_x)_{0-1}NR_x(C_{1-5}$ hydroxy-fluoroalkyl), —$C(O)(CR_xR_x)_{0-1}NR_x(CH_2)_{1-2}O(C_{1-3}$ hydroxyalkyl), —$C(O)(CR_xR_x)_{0-1}NR_x(CH_2)_{1-2}NR_xC(O)(C_{1-2}$ alkyl), —$C(O)(CR_xR_x)_{0-1}NR_x((CR_xR_x)_{1-2}O(C_{1-2}$ alkyl)), —$C(O)CR_x(NH_2)(CR_xR_x)_{1-4}NR_xR_x$, —$C(O)CR_x(NH_2)(CR_xR_x)_{1-4}NR_xC(O)NR_xR_x$, —$C(O)(CR_xR_x)_{0-3}NR_x(CH_2)_{0-1}C(O)(C_{1-3}$ alkyl), —$C(O)(CR_xR_x)_{0-1}NR_x(CH_2)_{0-1}C(O)(C_{1-3}$ cyanoalkyl), —$C(O)(CR_xR_x)_{0-1}NR_x(CH_2)_{1-2}C(O)NR_yR_y$, —$C(O)(CR_xR_x)_{1-3}C(O)NR_yR_y$, or —$C(O)(CR_xR_x)_{0-1}NR_x(CHR_y(CH_2OH))$; and $R_1$, $R_2$, $R_4$, $R_5$, $R_x$, $R_y$, A, m, n, and p are defined in the first aspect. Included in this embodiment are compounds in which $R_3$ is —$C(O)H$, —$C(O)CH_3$, —$C(O)CHF_2$, —$C(O)CH_2OH$, —$C(O)CH_2OCH_3$, —$C(O)CH_2OCH_2CH_2OCH_3$, —$C(O)CH_2NH_2$, —$C(O)CH_2NH(CH_3)$, —$C(O)CH_2N(CH_3)_2$, —$C(O)CH_2NHC(CH_3)_3$, —$C(O)CH_2NH(CH_2C(CH_3)_2OH)$, —$C(O)CH_2NH(CH_2CH(OH)CH_3)$, —$C(O)CH_2NH(CH_2CH_2CH(OH)CH_3)$, —$C(O)CH_2NH(CH_2CH_2CH_3)$, —$C(O)CH_2NHC(O)CH_3$, —$C(O)CH_2NHCH(CH_2CH_3)_2$, —$C(O)CH_2NHCH(CH_2OH)CH_2CH(CH_3)_2$, —$C(O)CH_2NHCH(CH_3)_2$, —$C(O)CH_2NHCH(CH_3)CH_2CH_3$, —$C(O)CH_2NHCH_2C(CH_3)_3$, —$C(O)CH_2NHCH_2CH(CH_3)_2$, —$C(O)CH_2NHCH_2CH(OH)CH_2OH$, —$C(O)CH_2NHCH_2CH_2C(CH_3)_3$, —$C(O)CH_2NHCH_2CH_2CH(CH_3)_2$, —$C(O)CH_2NHCH_2CH_2OCH_2CH_3$, —$C(O)CH_2NHCH_2CH_2OCH_3$, —$C(O)CH_2NHCH_2CH_2OH$, —$C(O)CH_2N(CH_3)(CH_2C(CH_3)_2OH)$, —$C(O)CH_2N(CH_3)(CH_2CH_2F)$, —$C(O)CH_2N(CH_3)(CH_2CHF_2)$, —$C(O)CH_2N(CH_3)(CH_2CN)$, —$C(O)CH_2N(CH_3)C(CH_3)_3$, —$C(O)CH_2N(CH_3)CH(CH_3)_2$, —$C(O)CH_2N(CH_3)CH_2CH(CH_3)_2$, —$C(O)CH_2N(CH_3)CH_2CH_2OH$, —$C(O)CH_2N(CH_3)CH_2CH_2CN$, —$C(O)CH_2N(CH_3)CH_2CH_2OCH_3$, —$C(O)CH_2N(CH_3)CH_2CH_2OH$, —$C(O)CH_2N(CH_3)CH_2CH_3$, —$C(O)CH_2CH_2NH(CH_3)$, —$C(O)CH_2CH_2OCH_3$, —$C(O)CH_2CH_2OH$, —$C(O)CH_2CH_3$, —$C(O)CH_2CN$, —$C(O)CH_2CF_3$, —$C(O)CH_2CH(CH_3)_2$, —$C(O)CH_2CH(CH_3)OH$, —$C(O)C(CH_3)_2CN$, —$C(O)C(CH_3)_2OH$, —$C(O)C(CH_3)_3$, —$C(O)CF_3$, —$C(O)CH(CH_2CH_3)_2$, —$C(O)CH(CH_3)_2$, —$C(O)C(CH_3)_2NH_2$, —$C(O)C(CH_3)_2NHCH_3$, —$C(O)C(CH_3)NHCH_3$, —$C(O)CH(NH_2)CH_2CH_2CH_2NH_2$, —$C(O)CH(NH_2)CH_2CH_2CH_2NH_2$, —$C(O)CH(NH_2)CH_2CH_2CH_2NHC(O)NH_2$, —$C(O)CH_2CH_2CH_2N(CH_3)_2$, —$C(O)CH_2CH_2N(CH_3)_2$, —$C(O)CH_2CH_2N(CH_3)C(O)CH_3$, —$C(O)CH_2CH_2N(CH_3)CH_2CH_2OH$, —$C(O)CH_2N(CH(CH_3)_2)_2$, —$C(O)CH_2N(CH_2CH_2OH)(CH(CH_3)_2)$, —$C(O)CH_2N(CH_2CH_2OH)(CH_2CH_3)$, —$C(O)CH_2N(CH_2CH_2OH)(CH_2CH(CH_3)CH_2CH_3)$, —$C(O)CH_2N(CH_2CH_3)_2$, —$C(O)CH_2N(CH_2CH_2OH)(CH_2CH_2CH_3)$, —$C(O)CH_2N(CH_2OH)(CH_2CH_3)$, —$C(O)CH_2N(CH_2CH_2OH)(CH_3)$, —$C(O)CH_2S(O)_2CH_3$, —$C(O)CH_2NHS(O)_2CH_3$, —$CH_2C(O)OH$, —$C(O)OCH_3$, —$C(O)OCH_2CH_3$, —$C(O)OCH(CH_3)_2$, —$C(O)OCH_2CH(CH_3)_2$, or —$C(O)OCH_2CH_2OCH_3$.

One embodiment provides a compound of Formula (I), N-oxide, or salt thereof, wherein $R_3$ is -$L_1$-A; $L_1$ is —$CR_xR_xC(O)NR_x(CR_xR_x)_{0-4}$—, —$C(O)(CR_xR_x)_{0-2}NR_x(CR_xR_x)_{0-2}$—, —$C(O)(CR_xR_x)_{0-2}N(C_{1-2}$ hydroxyalkyl)$(CR_xR_x)_{0-2}$—, —$C(O)(CR_xR_x)_{0-2}NR_x(CR_xR_x)_{1-2}CR_x(OH)$—, —$(CR_xR_x)_{0-2}C(O)N(C_{1-2}$ hydroxyalkyl)$(CR_xR_x)_{1-2}$—, or —$C(O)(CR_xR_x)_{1-2}NHS(O)_2$—, —$C(O)CR_x(NH_2)CR_xR_x$—; A is adamantanyl, $C_{3-6}$ cycloalkyl, dioxotetrahydrothiophenyl, imidazolyl, isoxazolyl, morpholinyl, oxetanyl, phenyl, piperidinyl, pyrimidinyl, tetrahydrofuranyl, tetrahydropyranyl or triazolyl, each substituted with zero to 2 substituents independently selected from F, —OH, —$CH_3$, —$OCH_3$, and —$C(O)CF_3$; and $R_1$, $R_2$, $R_4$, $R_5$, $R_x$, m, n, and p are defined in the first aspect. Included in this embodiment are compounds in which —$C(O)CH_2N(CH_2CH_2OH)(CH_2phenyl)$, —$C(O)CH_2N(CH_2CH_2OH)CH_2(fluorophenyl)$, —$C(O)CH_2N(CH_3)(CH_2CH(OH)phenyl)$, —$C(O)CH_2N(CH_3)CH_2CH_2(fluorocyclopentyl)$, —$C(O)CH_2N(CH_3)(cyclohexyl)$, —$C(O)CH_2N(CH_3)(cyclopropyl)$, —$C(O)CH_2N(CH_3)(dioxotetrahydrothiophenyl)$, —$C(O)CH_2N(CH_3)(oxetanyl)$, —$C(O)CH_2N(CH_3)(tetrahydrofuranyl)$, —$C(O)CH_2N(CH_3)CH_2$ (methylisoxazolyl), —C(O)CH$_2$N(CH$_3$)CH$_2$(methoxypyrimidinyl), —C(O)CH$_2$N(CH$_3$)CH$_2$(methyltriazolyl), —C(O)CH$_2$NH(adamantanyl), —C(O)CH$_2$NH(hydroxyadamantanyl), —C(O)CH$_2$NH(cyclobutyl), —C(O)CH$_2$NH(methylcyclobutyl), —C(O)CH$_2$NH(methylcyclopropyl), —C(O)CH$_2$NH(methyloxetanyl), —C(O)CH$_2$NH(tetrahydrofuranyl), —C(O)CH$_2$NH(tetrahydropyranyl), —C(O)CH$_2$NH(methyltetrahydropyranyl), —C(O)CH$_2$NHCH$_2$(cyclopropyl), —C(O)CH$_2$NHCH$_2$(methylcyclopropyl), —C(O)CH$_2$NHCH$_2$(tetrahydrofuranyl), —C(O)CH$_2$NHCH$_2$C(CH$_3$)$_2$(morpholinyl), —C(O)NH(piperidinyl), —C(O)NH(trifluoromethylcarbonylpiperidinyl), —CH$_2$C(O)N(CH$_2$CH$_2$OH)(CH$_2$phenyl), —CH$_2$C(O)N(CH$_2$CH$_2$OH)CH$_2$(fluorophenyl), —CH$_2$C(O)N(CH$_3$)(cyclohexyl), —CH$_2$C(O)N(CH$_3$)(cyclopropyl), —CH$_2$C(O)N(CH$_3$)(tetrahydrofuranyl), —CH$_2$C(O)N(CH$_3$)(tetrahydropyranyl), —CH$_2$C(O)N(CH$_3$)CH$_2$CH(OH)phenyl, —CH$_2$C(O)N(CH$_3$)CH$_2$CH$_2$(hydroxycyclopentyl), —CH$_2$C(O)NH(adamantanyl), —CH$_2$C(O)NH(hydroxyadamantanyl), —CH$_2$C(O)NH(cyclobutyl), —CH$_2$C(O)NH(methylcyclobutyl), —CH$_2$C(O)NH(cyclopropyl), —CH$_2$C(O)NH(methylcyclopropyl), —CH$_2$C(O)NH(methyloxetanyl), —CH$_2$C(O)NH(tetrahydrofuranyl), —CH$_2$C(O)NH(tetrahydropyranyl), —CH$_2$C(O)NH(methyltetrahydropyranyl), —CH$_2$C(O)NHCH$_2$(cyclopropyl), —CH$_2$C(O)NHCH$_2$(methylcyclopropyl), —CH$_2$C(O)NHCH$_2$(tetrahydrofuranyl), —CH$_2$C(O)NHCH$_2$C(CH$_3$)$_2$(morpholinyl), —C(O)CH(NH$_2$)CH$_2$(imidazolyl), —C(O)CH$_2$CH$_2$N(CH$_3$)(oxetanyl), —C(O)CH$_2$CH$_2$NH(pyrimidinyl), or —C(O)CH$_2$CH$_2$NHS(O)$_2$(phenyl).

One embodiment provides a compound of Formula (I), N-oxide, or salt thereof, wherein R$_3$ is —(CH$_2$)$_{1-2}$-A or —CH$_2$CH(OH)-A; A is C$_{3-6}$ cycloalkyl, phenyl, imidazolyl, isoxazolyl, morpholinyl, oxadiazolyl, oxazolyl, oxetanyl, piperidinyl, pyrazolyl, pyridinyl, pyrimidinyl, pyrrolidinyl, pyrrolyl, tetrahydrofuranyl, tetrazolyl, thiazolyl, each substituted with zero to 2 substituents independently selected from —OH, —CH$_3$, —CH(CH$_3$)$_2$, —CH$_2$OH, —OCH$_3$, cyclopropyl, and —NH(pyridinyl); and R$_1$, R$_2$, R$_4$, R$_5$, A, m, n, and p are defined in the first aspect. Included in this embodiment are compounds in which R$_3$ is —CH$_2$(C$_{3-6}$ cycloalkyl), —CH$_2$(imidazolyl), —CH$_2$(methyl imidazolyl), —CH$_2$(isoxazolyl), —CH$_2$(methyl isoxazolyl), —CH$_2$(oxadiazolyl), —CH$_2$(cyclopropyl-oxadiazolyl), —CH$_2$(oxazolyl), —CH$_2$(oxetanyl), —CH$_2$(hydroxymethyl oxetanyl), —CH$_2$(methyl-oxetanyl), —CH$_2$(phenyl), —CH$_2$(isopropyl piperidinyl), —CH$_2$(methyl piperidinyl), —CH$_2$(pyrazolyl), —CH$_2$(methyl pyrazolyl), —CH$_2$(pyridinyl), —CH$_2$(methyl pyridinyl), —CH$_2$(methoxy pyridinyl), —CH$_2$(pyrimidinyl), —CH$_2$(dimethoxy pyrimidinyl), —CH$_2$(methoxypyrimidinyl), —CH$_2$(pyrrolidinyl), —CH$_2$(isopropyl pyrrolidinyl), —CH$_2$(methyl pyrrolyl), —CH$_2$(tetrahydrofuranyl), —CH$_2$(tetrazolyl), —CH$_2$(thiazolyl), —CH$_2$(pyridinylamino thiazolyl), —CH$_2$(triazolyl), —CH$_2$(methyltriazolyl), —CH$_2$CH(OH)(phenyl), or —CH$_2$CH$_2$(morpholinyl).

One embodiment provides a compound of Formula (I), N-oxide, or salt thereof, wherein each R$_4$ is independently F, —OH, —CH$_3$, or —OCH$_3$; or two R$_4$ attached to the same carbon atom form =O; and R$_1$, R$_2$, R$_3$, R$_5$, m, n, and p are defined in the first aspect. Included in this embodiment are compounds in which each R$_4$ is independently F, —OH, or —CH$_3$. Also included in this embodiment are compounds in which m is 1 or 2; and each R$_4$ is independently F or —OH.

One embodiment provides a compound of Formula (I), N-oxide, or salt thereof, wherein m is zero, 1, or 2; and R$_1$, R$_2$, R$_3$, R$_4$, R$_5$, n, and p are defined in the first aspect. Included in this embodiment are compounds in which m is zero or 1. Also included are compounds in which m is zero.

One embodiment provides a compound of Formula (I), N-oxide, or salt thereof, wherein each R$_5$ is independently F, Cl, —CN, —CH$_3$, —CF$_3$, or —OCH$_3$; and R$_1$, R$_2$, R$_3$, R$_4$, m, n, and p are defined in the first aspect. Included in this embodiment are compounds in which each R$_5$ is independently F, —CH$_3$, or —CF$_3$. Also included are compounds in which n is zero or 1; and R$_5$ is F.

One embodiment provides a compound of Formula (I), N-oxide, or salt thereof, wherein n is zero, 1, or 2; and R$_1$, R$_2$, R$_3$, R$_4$, R$_5$, m, and p are defined in the first aspect. Included in this embodiment are compounds in which n is zero or 1. Also included are compounds in which n is zero.

One embodiment provides a compound of Formula (I), N-oxide, or a salt thereof, wherein said compound is selected from: 2-(2,6-dimethylpyridin-4-yl)-3-isopropyl-5-(piperidin-4-yl)-1H-indole hydrochloride (1); 2-(2,6-dimethylpyridin-4-yl)-3-ethyl-5-(piperidin-4-yl)-1H-indole (2); 2-(2-fluoro-6-methylpyridin-4-yl)-3-isopropyl-5-(piperidin-4-yl)-1H-indole (3); 3-isopropyl-2-(2-methylpyridin-4-yl)-5-(piperidin-4-yl)-1H-indole (5); 3-isopropyl-5-(piperidin-4-yl)-2-(2-(trifluoromethyl)pyridin-4-yl)-1H-indole (6); 2-(3-fluoropyridin-4-yl)-3-isopropyl-5-(piperidin-4-yl)-1H-indole (7); 4-(3-isopropyl-5-(piperidin-4-yl)-1H-indol-2-yl)pyridin-2-amine (8); 4-(3-isopropyl-5-(piperidin-4-yl)-1H-indol-2-yl)-5-methylpyridin-2-amine (9); 4-(3-isopropyl-5-(piperidin-4-yl)-1H-indol-2-yl)-6-methylpyridin-3-amine (10); 4-(3-isopropyl-5-(piperidin-4-yl)-1H-indol-2-yl)-3-methylpyridin-2-amine (11); 4-(3-isopropyl-5-(piperidin-4-yl)-1H-indol-2-yl)-6-methylpyridin-2-amine (12); 4-(3-isopropyl-5-(piperidin-4-yl)-1H-indol-2-yl)-2-methylpyridin-3-amine (13); (4-(3-isopropyl-5-(piperidin-4-yl)-1H-indol-2-yl)pyridin-2-yl)methanamine (14); 4-(3-isopropyl-5-(piperidin-4-yl)-1H-indol-2-yl)-6-methylnicotinamide (15); 2-(5-fluoro-2-methylpyridin-4-yl)-3-isopropyl-5-(piperidin-4-yl)-1H-indole (16); 2-(5-chloro-2-fluoropyridin-4-yl)-3-isopropyl-5-(piperidin-4-yl)-1H-indole (18); (4-(3-isopropyl-5-(piperidin-4-yl)-1H-indol-2-yl)pyridin-3-yl)methanol (19); 2-(3,5-dichloropyridin-4-yl)-3-isopropyl-5-(piperidin-4-yl)-1H-indole (20); 2-(2-chloro-3-fluoropyridin-4-yl)-3-isopropyl-5-(piperidin-4-yl)-1H-indole (21); (4-(3-isopropyl-5-(piperidin-4-yl)-1H-indol-2-yl)pyridin-2-yl)methanol (22); 3-isopropyl-2-(3-methylpyridin-4-yl)-5-(piperidin-4-yl)-1H-indole (23); 4-(3-isopropyl-5-(piperidin-4-yl)-1H-indol-2-yl)-N,N-dimethylpyridin-2-amine (24); 6-chloro-4-(3-isopropyl-5-(piperidin-4-yl)-1H-indol-2-yl)nicotinonitrile (26); 2-(2,6-dimethyl-3-nitropyridin-4-yl)-3-isopropyl-5-(piperidin-4-yl)-1H-indole (27); 2-(2-fluoro-5-methylpyridin-4-yl)-3-isopropyl-5-(piperidin-4-yl)-1H-indole (28); 4-(3-isopropyl-5-(piperidin-4-yl)-1H-indol-2-yl)-2,6-dimethylpyridin-3-amine (29); 2-(2,3-dimethylpyridin-4-yl)-3-isopropyl-5-(piperidin-4-yl)-1H-indole (30); 2-(2,5-dimethylpyridin-4-yl)-3-isopropyl-5-(piperidin-4-yl)-1H-indole (31); 2-((cyclopropylmethyl)amino)-4-(3-isopropyl-5-(piperidin-4-yl)-1H-indol-2-yl)-6-methylnicotinonitrile (32); 4-(3-isopropyl-5-(piperidin-4-yl)-1H-indol-2-yl)-3-(trifluoromethyl)picolinonitrile (33); N-(4-(3-isopropyl-5-(piperidin-4-yl)-1H-indol-2-yl)-6-methylpyridin-3-yl)acetamide (34); 2-(2-chloro-3-methyl-pyridin-4-yl)-3-isopropyl-5-(piperidin-4-yl)-1H-indole (35); 2-chloro-4-(3-isopropyl-5-(piperidin-4-yl)-1H-indol-2-yl)nicotinonitrile (36); N-(4-(3-isopropyl-5-(piperidin-4-yl)-1H-indol-2-yl)pyridin-3-yl) pivalamide (37); 3-isopropyl-5-(piperidin-4-yl)-2-(pyridin-4-yl)-1H-indole (38); 3-isopropyl-5-(piperidin-4-yl)-2-(2,3,6-trimethylpyridin-4- yl)-1H-indole (39); 2-(3-bromo-2,6-dimethylpyridin-4-yl)-3-isopropyl-5-(piperidin-4-yl)-1H-indole (40); (4-(3-isopropyl-5-(piperidin-4-yl)-1H-indol-2-yl)-6-methylpyridin-3-yl) methanol (42); 3-isopropyl-5-(piperidin-4-yl)-2-(2,3,5,6-tetramethylpyridin-4-yl)-1H-indole (43); 2-(3-chloro-2-methylpyridin-4-yl)-3-isopropyl-5-(piperidin-4-yl)-1H-indole (44); 3-isopropyl-2-(2-methoxy-6-methylpyridin-4-yl)-5-(piperidin-4-yl)-1H-indole (46); 2-(5-fluoro-2-methoxypyridin-4-yl)-3-isopropyl-5-(piperidin-4-yl)-1H-indole (47); 2-(3-chloro-2,6-dimethylpyridin-4-yl)-3-isopropyl-5-(piperidin-4-yl)-1H-indole (50); 2-(3-fluoro-2,6-dimethylpyridin-4-yl)-3-isopropyl-5-(piperidin-4-yl)-1H-indole (51); 2-(3-fluoro-2-methylpyridin-4-yl)-3-isopropyl-5-(piperidin-4-yl)-1H-indole (53); 2-(2-cyclopropyl-5-fluoropyridin-4-yl)-3-isopropyl-5-(piperidin-4-yl)-1H-indole (54); 2-(2-ethyl-5-fluoropyridin-4-yl)-3-isopropyl-5-(piperidin-4-yl)-1H-indole (55); 2-(2,6-dimethyl-1-(l1-oxidanyl)-1l4-pyridin-4-yl)-3-isopropyl-5-(piperidin-4-yl)-1H-indole (56); 2-(2,6-dimethyl-1-(l1-oxidanyl)-1l4-pyridin-4-yl)-3-isopropyl-5-(piperidin-4-yl)-1H-indole (57); 2-(4-(3-isopropyl-5-(piperidin-4-yl)-1H-indol-2-yl)pyridin-2-yl)propan-2-ol (58); 3-ethyl-5-(piperidin-4-yl)-2-(pyridin-4-yl)-1H-indole (60); 3-ethyl-2-(2-methoxypyridin-4-yl)-5-(piperidin-4-yl)-1H-indole (61); 2-(2-chloropyridin-4-yl)-3-ethyl-5-(piperidin-4-yl)-1H-indole (62); 3-ethyl-2-(2-methylpyridin-4-yl)-5-(piperidin-4-yl)-1H-indole (63); 4-(3-ethyl-5-(piperidin-4-yl)-1H-indol-2-yl) picolinonitrile (64); 3-(4-(3-ethyl-5-(piperidin-4-yl)-1H-indol-2-yl)pyridin-2-yl)-1,2,4-oxadiazol-5-amine (65); 2-(2-(4H-1,2,4-triazol-3-yl)pyridin-4-yl)-3-ethyl-5-(piperidin-4-yl)-1H-indole (66); 2-(2-(1H-imidazol-1-yl) pyridin-4-yl)-3-ethyl-5-(piperidin-4-yl)-1H-indole (67); N-(4-(3-ethyl-5-(piperidin-4-yl)-1H-indol-2-yl)pyridin-2-yl)acetamide (68); 4-(3-ethyl-5-(piperidin-4-yl)-1H-indol-2-yl) pyridin-2-amine (69); 2-(2,3-dimethylpyridin-4-yl)-3-ethyl-5-(piperidin-4-yl)-1H-indole (70); 2-amino-4-(3-ethyl-5-(piperidin-4-yl)-1H-indol-2-yl)pyridin-3-ol (71); 6-fluoro-3-isopropyl-2-(2-methylpyridin-4-yl)-5-(piperidin-4-yl)-1H-indole (73); 3-isopropyl-2-(2-methylpyridin-4-yl)-5-(piperidin-4-yl)-6-(trifluoromethyl)-1H-indole (74); 3-isopropyl-6-methyl-2-(2-methylpyridin-4-yl)-5-(piperidin-4-yl)-1H-indole (75); 4-fluoro-3-isopropyl-2-(2-methylpyridin-4-yl)-5-(piperidin-4-yl)-1H-indole (76); 2-(2,6-dimethylpyridin-4-yl)-4-fluoro-3-isopropyl-5-(piperidin-4-yl)-1H-indole (77); 2-(2,6-dimethylpyridin-4-yl)-6-fluoro-3-isopropyl-5-(piperidin-4-yl)-1H-indole (78); 6-fluoro-2-(5-fluoro-2-methylpyridin-4-yl)-3-isopropyl-5-(piperidin-4-yl)-1H-indole (79); 2-(2,5-dimethylpyridin-4-yl)-6-fluoro-3-isopropyl-5-(piperidin-4-yl)-1H-indole (80); 3-ethyl-7-fluoro-2-(2-methylpyridin-4-yl)-5-(piperidin-4-yl)-1H-indole (81); 3-ethyl-4-methyl-2-(2-methylpyridin-4-yl)-5-(piperidin-4-yl)-1H-indole (82); 3-ethyl-4,6-difluoro-2-(2-methylpyridin-4-yl)-5-(piperidin-4-yl)-1H-indole (83); 3-(2,2-difluoroethyl)-2-(2-methylpyridin-4-yl)-5-(piperidin-4-yl)-1H-indole (84); 3-(tert-butyl)-2-(2-methylpyridin-4-yl)-5-(piperidin-4-yl)-1H-indole (86); 3-cyclopropyl-2-(2-methylpyridin-4-yl)-5-(piperidin-4-yl)-1H-indole (88); 3-(cyclopropylmethyl)-2-(2-methylpyridin-4-yl)-5-(piperidin-4-yl)-1H-indole (89); 2-(2,6-dimethylpyridin-4-yl)-5-(piperidin-4-yl)-3-(3,3,3-trifluoroprop-1-en-2-yl)-1H-indole (91); 2-(2,6-dimethylpyridin-4-yl)-5-(piperidin-4-yl)-3-(1,1,1-trifluoropropan-2-yl)-1H-indole (92); 3-cyclopropyl-2-(2,6-dimethylpyridin-4-yl)-5-(piperidin-4-yl)-1H-indole (93); 2-(2,6-dimethylpyridin-4-yl)-5-(piperidin-4-yl)-1H-indole (94); 3-(tert-butyl)-2-(2,6-dimethylpyridin-4-yl)-5-(piperidin-4-yl)-1H-indole (96); 4-(3-isopropyl-5-(piperidin-4-yl)-1H-indol-2-yl)-N-(2,2,2-trifluoroethyl) picolinamide (476); 4-(3-isopropyl-5-(piperidin-4-yl)-1H-indol-2-yl)-N-(thiazol-2-yl) picolinamide (477); 2-(2-cyclopropyl-6-methylpyridin-4-yl)-3-isopropyl-5-(piperidin-4-yl)-1H-indole (478); 2-(2-ethyl-6-methylpyridin-4-yl)-3-isopropyl-5-(piperidin-4-yl)-1H-indole (479); 3-isopropyl-2-(2-methyl-6-(4-methylpiperazin-1-yl)pyridin-4-yl)-5-(piperidin-4-yl)-1H-indole (480); 2-(2-cyclopropyl-5-fluoropyridin-4-yl)-3-isopropyl-5-(piperidin-4-yl)-1H-indole (481); 2-(2-ethyl-5-fluoropyridin-4-yl)-3-isopropyl-5-(piperidin-4-yl)-1H-indole (482); 2-(2-cyclopropylpyridin-4-yl)-3-isopropyl-5-(piperidin-4-yl)-1H-indole (483); 3-isopropyl-2-(2-methoxypyridin-4-yl)-5-(piperidin-4-yl)-1H-indole (485); 2-(2-cyclopropyl-6-methoxypyridin-4-yl)-3-isopropyl-5-(piperidin-4-yl)-1H-indole (486); 2-(2-ethyl-6-methoxypyridin-4-yl)-3-isopropyl-5-(piperidin-4-yl)-1H-indole (487); 4-(2-(2,6-dimethylpyridin-4-yl)-3-isopropyl-1H-indol-5-yl)piperidin-3-ol (488); 5-(3,3-difluoropiperidin-4-yl)-2-(2,6-dimethylpyridin-4-yl)-3-isopropyl-1H-indole (489); 4-(3-isopropyl-2-(2-methylpyridin-4-yl)-1H-indol-5-yl)piperidin-2-one (490); 4-(3-ethyl-5-(3-fluoropiperidin-4-yl)-1H-indol-2-yl)pyridin-2-amine (491); 3-(2,2-difluoroethyl)-2-(2,6-dimethylpyridin-4-yl)-5-(piperidin-4-yl)-1H-indole (492); 2-(2-chloropyridin-4-yl)-3-(2,2-difluoroethyl)-5-(piperidin-4-yl)-1H-indole (494); and methyl 2-(2,6-dimethylpyridin-4-yl)-5-(piperidin-4-yl)-1H-indole-3-carboxylate (495).

One embodiment provides a compound of Formula (I) or a salt thereof, wherein said compound is selected from: 3-(dimethylamino)-1-(4-(2-(2,6-dimethylpyridin-4-yl)-3-isopropyl-1H-indol-5-yl) piperidin-1-yl)propan-1-one (97); 2-(dimethylamino)-1-(4-(2-(2,6-dimethylpyridin-4-yl)-3-isopropyl-1H-indol-5-yl)piperidin-1-yl)ethan-1-one (98); 2-(diethylamino)-1-(4-(2-(2,6-dimethylpyridin-4-yl)-3-isopropyl-1H-indol-5-yl)piperidin-1-yl)ethan-1-one (99); 1-(4-(2-(2,6-dimethylpyridin-4-yl)-3-isopropyl-1H-indol-5-yl)piperidin-1-yl)-2-ethylbutan-1-one (104); 1-(4-(2-(2,6-dimethylpyridin-4-yl)-3-isopropyl-1H-indol-5-yl)piperidin-1-yl)-2,2-difluoroethan-1-one (105); (S)-1-(4-(2-(2,6-dimethylpyridin-4-yl)-3-isopropyl-1H-indol-5-yl)piperidin-1-yl)-3-hydroxybutan-1-one (109); 4-(dimethylamino)-1-(4-(2-(2,6-dimethylpyridin-4-yl)-3-isopropyl-1H-indol-5-yl) piperidin-1-yl)butan-1-one (111); 1-(4-(2-(2,6-dimethylpyridin-4-yl)-3-isopropyl-1H-indol-5-yl)piperidin-1-yl)-2-(2-methoxyethoxy)ethan-1-one (114); 1-(4-(2-(2,6-dimethylpyridin-4-yl)-3-isopropyl-1H-indol-5-yl)piperidin-1-yl)-2-methoxyethan-1-one (115); 1-(4-(2-(2,6-dimethylpyridin-4-yl)-3-isopropyl-1H-indol-5-yl)piperidin-1-yl)-2-hydroxyethan-1-one (116); 1-(4-(2-(2,6-dimethylpyridin-4-yl)-3-isopropyl-1H-indol-5-yl)piperidin-1-yl)-3-hydroxypropan-1-one (117); 1-(4-(2-(2,6-dimethylpyridin-4-yl)-3-isopropyl-1H-indol-5-yl)piperidin-1-yl)-3-methoxypropan-1-one (118); N-(3-(4-(2-(2,6-dimethylpyridin-4-yl)-3-isopropyl-1H-indol-5-yl)piperidin-1-yl)-3-oxopropyl)-N-methylacetamide (134); 1-(4-(2-(2,6-dimethylpyridin-4-yl)-3-isopropyl-1H-indol-5-yl)piperidin-1-yl)-2-((2-methoxyethyl)(methyl)amino)ethan-1-one (148); N-(2-(4-(2-(2,6-dimethylpyridin-4-yl)-3-isopropyl-1H-indol-5-yl)piperidin-1-yl)-2-oxoethyl) methanesulfonamide (150); 2-(diisopropylamino)-1-(4-(2-(2,6-dimethylpyridin-4-yl)-3-isopropyl-1H-indol-5-yl)piperidin-1-yl) ethan-1-one (153); N-(2-(4-(2-(2,6-dimethylpyridin-4-yl)-3-isopropyl-1H-indol-5-yl)piperidin-1-yl)-2-oxoethyl) acetamide (166); 1-(4-(2-(2,6-dimethylpyridin-4-yl)-3-isopropyl-1H-indol-5-yl)piperidin-1-yl)-2-hydroxy-2-methylpropan-1-one (173); 1-(4-(2-(2,6-dimethylpyridin-4-yl)-3-isopropyl-1H-indol-5-yl)piperidin-1-yl)ethan-1-one (174); 1-(4-(2-(2,6-dimethylpyridin-4-yl)-3-isopropyl-1H- indol-5-yl)piperidin-1-yl)-3-((2-hydroxyethyl)(methyl) amino)propan-1-one (175); 4-(2-(2,6-dimethylpyridin-4-yl)-3-isopropyl-1H-indol-5-yl)-N-methylpiperidine-1-carboxamide (179); 1-(4-(2-(2,6-dimethylpyridin-4-yl)-3-isopropyl-1H-indol-5-yl) piperidin-1-yl)-3-(methylamino) propan-1-one (183); 2-amino-1-(4-(2-(2,6-dimethylpyridin-4-yl)-3-isopropyl-1H-indol-5-yl)piperidin-1-yl)ethan-1-one (184); 1-(4-(2-(2,6-dimethylpyridin-4-yl)-3-isopropyl-1H-indol-5-yl)piperidin-1-yl)-2-methyl-2-(methylamino)propan-1-one (187); (S)-1-(4-(2-(2,6-dimethylpyridin-4-yl)-3-isopropyl-1H-indol-5-yl)piperidin-1-yl)-2-(methylamino) propan-1-one (191); 2-amino-1-(4-(2-(2,6-dimethylpyridin-4-yl)-3-isopropyl-1H-indol-5-yl)piperidin-1-yl)-2-methylpropan-1-one (194); 1-(4-(2-(2,6-dimethylpyridin-4-yl)-3-isopropyl-1H-indol-5-yl)piperidin-1-yl)-2-methylpropan-1-one (202); 2-(4-(2-(2,6-dimethylpyridin-4-yl)-3-isopropyl-1H-indol-5-yl)piperidin-1-yl)-N-methyl-2-oxoacetamide (204); 2-(4-(2-(2,6-dimethylpyridin-4-yl)-3-isopropyl-1H-indol-5-yl)piperidin-1-yl)-N-methyl-2-oxoacetamide (205); 1-(4-(2-(2,6-dimethylpyridin-4-yl)-3-isopropyl-1H-indol-5-yl)piperidin-1-yl)propan-1-one (206); 2-(4-(2-(2,6-dimethylpyridin-4-yl)-3-isopropyl-1H-indol-5-yl)piperidin-1-yl)-N-(2,2,2-trifluoroethyl)acetamide (214); N-(tert-butyl)-2-(4-(2-(2,6-dimethylpyridin-4-yl)-3-isopropyl-1H-indol-5-yl)piperidin-1-yl)acetamide (217); 2-(4-(2-(2,6-dimethylpyridin-4-yl)-3-isopropyl-1H-indol-5-yl)piperidin-1-yl)-N-isopropylacetamide (218); 2-(4-(2-(2,6-dimethylpyridin-4-yl)-3-isopropyl-1H-indol-5-yl)piperidin-1-yl)-N-neopentylacetamide (219); 2-(4-(2-(2,6-dimethylpyridin-4-yl)-3-isopropyl-1H-indol-5-yl)piperidin-1-yl)-N-(pentan-3-yl)acetamide (220); 2-(4-(2-(2,6-dimethylpyridin-4-yl)-3-isopropyl-1H-indol-5-yl)piperidin-1-yl)-N-isobutylacetamide (221); 2-(4-(2-(2,6-dimethylpyridin-4-yl)-3-isopropyl-1H-indol-5-yl)piperidin-1-yl)-N-(2-hydroxyethyl)acetamide (222); 2-(4-(2-(2,6-dimethylpyridin-4-yl)-3-isopropyl-1H-indol-5-yl)piperidin-1-yl)-N,N-diethylacetamide (228); 2-(4-(2-(2,6-dimethylpyridin-4-yl)-3-isopropyl-1H-indol-5-yl) piperidin-1-yl)-N-(2-methoxyethyl)acetamide (231); N-(sec-butyl)-2-(4-(2-(2,6-dimethylpyridin-4-yl)-3-isopropyl-1H-indol-5-yl)piperidin-1-yl)acetamide (234); 2-(4-(2-(2,6-dimethylpyridin-4-yl)-3-isopropyl-1H-indol-5-yl)piperidin-1-yl)-N-ethylacetamide (235); N-(3,3-dimethylbutyl)-2-(4-(2-(2,6-dimethylpyridin-4-yl)-3-isopropyl-1H-indol-5-yl)piperidin-1-yl)acetamide (236); 2-(4-(2-(2,6-dimethylpyridin-4-yl)-3-isopropyl-1H-indol-5-yl)piperidin-1-yl)-N-isopentylacetamide (237); 2-(4-(2-(2,6-dimethylpyridin-4-yl)-3-isopropyl-1H-indol-5-yl)piperidin-1-yl)-N-propylacetamide (238); N-(cyanomethyl)-2-(4-(2-(2,6-dimethylpyridin-4-yl)-3-isopropyl-1H-indol-5-yl) piperidin-1-yl)acetamide (239); 2-(4-(2-(2,6-dimethylpyridin-4-yl)-3-isopropyl-1H-indol-5-yl) piperidin-1-yl)-N-(2-ethoxyethyl)acetamide (240); 2-(4-(2-(2,6-dimethylpyridin-4-yl)-3-isopropyl-1H-indol-5-yl)piperidin-1-yl)-N-isopropyl-N-methylacetamide (244); 2-(4-(2-(2,6-dimethylpyridin-4-yl)-3-isopropyl-1H-indol-5-yl) piperidin-1-yl)-N-isobutyl-N-methylacetamide (245); 2-(4-(2-(2,6-dimethylpyridin-4-yl)-3-isopropyl-1H-indol-5-yl)piperidin-1-yl)-N-ethyl-N-methylacetamide (246); N-(cyanomethyl)-2-(4-(2-(2,6-dimethylpyridin-4-yl)-3-isopropyl-1H-indol-5-yl)piperidin-1-yl)-N-methylacetamide (247); N-(tert-butyl)-2-(4-(2-(2,6-dimethylpyridin-4-yl)-3-isopropyl-1H-indol-5-yl) piperidin-1-yl)-N-methylacetamide (250); (R)-2-(4-(2-(2,6-dimethylpyridin-4-yl)-3-isopropyl-1H-indol-5-yl)piperidin-1-yl)-N-(1,1,1-trifluoropropan-2-yl)acetamide (252); 2-(4-(2-(2,6-dimethylpyridin-4-yl)-3-isopropyl-1H-indol-5-yl)piperidin-1-yl)-N,N-diisopropylacetamide (253); 2-(4-(2-(2,6-dimethylpyridin-4-yl)-3-isopropyl-1H-indol-5-yl)piperidin-1-yl)-N-(2-methoxyethyl)-N-methylacetamide (254); 2-(4-(2-(2,6-dimethylpyridin-4-yl)-3-isopropyl-1H-indol-5-yl)piperidin-1-yl)-N-(2-hydroxypropyl) acetamide (260); 2-(4-(2-(2,6-dimethylpyridin-4-yl)-3-isopropyl-1H-indol-5-yl)piperidin-1-yl)-N-(3-hydroxybutyl)acetamide (262); 2-(4-(2-(2,6-dimethylpyridin-4-yl)-3-isopropyl-1H-indol-5-yl)piperidin-1-yl)-N-(2-hydroxy-2-methylpropyl)acetamide (268); (S)-2-(4-(2-(2,6-dimethylpyridin-4-yl)-3-isopropyl-1H-indol-5-yl)piperidin-1-yl)-N-(1-hydroxy-4-methylpentan-2-yl) acetamide (276); 2-(4-(2-(2,6-dimethylpyridin-4-yl)-3-isopropyl-1H-indol-5-yl)piperidin-1-yl)-N-(3-hydroxypropyl)-N-methylacetamide (288); 2-(4-(2-(2,6-dimethylpyridin-4-yl)-3-isopropyl-1H-indol-5-yl)piperidin-1-yl)-N-ethyl-N-(2-hydroxyethyl)acetamide (294); 2-(4-(2-(2,6-dimethylpyridin-4-yl)-3-isopropyl-1H-indol-5-yl) piperidin-1-yl)-N-(2-hydroxyethyl)-N-propylacetamide (295); 2-(4-(2-(2,6-dimethylpyridin-4-yl)-3-isopropyl-1H-indol-5-yl)piperidin-1-yl)-N-(2-hydroxyethyl)-N-(2-methylbutyl)acetamide (297); N-butyl-2-(4-(2-(2,6-dimethylpyridin-4-yl)-3-isopropyl-1H-indol-5-yl)piperidin-1-yl)-N-(2-hydroxyethyl)acetamide (298); 2-(4-(2-(2,6-dimethylpyridin-4-yl)-3-isopropyl-1H-indol-5-yl)piperidin-1-yl)-N-(2-hydroxyethyl)-N-isopropylacetamide (299); 2-(4-(2-(2,6-dimethylpyridin-4-yl)-3-isopropyl-1H-indol-5-yl)piperidin-1-yl)-N-(2-hydroxy-2-methylpropyl)-N-methylacetamide (305); 2-(4-(2-(2,6-dimethylpyridin-4-yl)-3-isopropyl-1H-indol-5-yl)piperidin-1-yl)-N,N-dimethylacetamide (308); 2-(4-(2-(2,6-dimethylpyridin-4-yl)-3-isopropyl-1H-indol-5-yl) piperidin-1-yl)-N-methylacetamide (309); 2-(2,6-dimethylpyridin-4-yl)-3-isopropyl-5-(1-(2,2,2-trifluoroethyl)piperidin-4-yl)-1H-indole (310); 3-(4-(2-(2,6-dimethylpyridin-4-yl)-3-isopropyl-1H-indol-5-yl)piperidin-1-yl)propan-1-ol (311); 2-(4-(2-(2,6-dimethylpyridin-4-yl)-3-isopropyl-1H-indol-5-yl)piperidin-1-yl)acetonitrile (312); 3-(4-(2-(2,6-dimethylpyridin-4-yl)-3-isopropyl-1H-indol-5-yl)piperidin-1-yl)-1,1,1-trifluoropropan-2-ol (313); 3-(4-(2-(2,6-dimethylpyridin-4-yl)-3-isopropyl-1H-indol-5-yl)piperidin-1-yl)propanamide (314); 3-(4-(2-(2,6-dimethylpyridin-4-yl)-3-isopropyl-1H-indol-5-yl)piperidin-1-yl)propanenitrile (315); 3-(4-(2-(2,6-dimethylpyridin-4-yl)-3-isopropyl-1H-indol-5-yl)piperidin-1-yl)-1,1,1-trifluoropropan-2-ol (316); 3-(4-(2-(2,6-dimethylpyridin-4-yl)-3-isopropyl-1H-indol-5-yl)piperidin-1-yl)-1,1,1-trifluoropropan-2-ol (317); 3-(4-(2-(2,6-dimethylpyridin-4-yl)-3-isopropyl-1H-indol-5-yl)piperidin-1-yl)-2,2-dimethylpropanoic acid (321); 2-(2,6-dimethylpyridin-4-yl)-5-(1-ethylpiperidin-4-yl)-3-isopropyl-1H-indole (322); 2-(2,6-dimethylpyridin-4-yl)-3-isopropyl-5-(1-propylpiperidin-4-yl)-1H-indole (323); 2-(2,6-dimethylpyridin-4-yl)-3-isopropyl-5-(1-(2-(2-methoxyethoxy)ethyl)piperidin-4-yl)-1H-indole (324); 2-(2,6-dimethylpyridin-4-yl)-3-isopropyl-5-(1-(2-methoxyethyl) piperidin-4-yl)-1H-indole (325); 5-(1-(2,2-difluoroethyl) piperidin-4-yl)-2-(2,6-dimethylpyridin-4-yl)-3-isopropyl-1H-indole (327); 2-(4-(2-(2,6-dimethylpyridin-4-yl)-3-isopropyl-1H-indol-5-yl)piperidin-1-yl)ethan-1-ol (329); 2-(2,6-dimethylpyridin-4-yl)-3-isopropyl-5-(1-(3-methoxypropyl)piperidin-4-yl)-1H-indole (330); 1-(4-(2-(2,6-dimethylpyridin-4-yl)-3-isopropyl-1H-indol-5-yl) piperidin-1-yl)propan-2-ol (331); 2-(2,6-dimethylpyridin-4-yl)-3-isopropyl-5-(1-(2-methoxypropyl) piperidin-4-yl)-1H-indole (332); 1-(4-(2-(2,6-dimethylpyridin-4-yl)-3-isopropyl-1H-indol-5-yl)piperidin-1-yl)-2-(isopropylamino) ethan-1-one (335); 1-(4-(2-(2,6-dimethylpyridin-4-yl)-3-isopropyl-1H-indol-5-yl)piperidin-1-yl)-2-((2- hydroxyethyl) amino)ethan-1-one (336); 1-(4-(2-(2,6-dimethylpyridin-4-yl)-3-isopropyl-1H-indol-5-yl)piperidin-1-yl)-2-(neopentylamino)ethan-1-one (337); 1-(4-(2-(2,6-dimethylpyridin-4-yl)-3-isopropyl-1H-indol-5-yl)piperidin-1-yl)-2-(isobutylamino)ethan-1-one (338); 1-(4-(2-(2,6-dimethylpyridin-4-yl)-3-isopropyl-1H-indol-5-yl)piperidin-1-yl)-2-(isopropylamino)ethan-1-one (344); 1-(4-(2-(2,6-dimethylpyridin-4-yl)-3-isopropyl-1H-indol-5-yl)piperidin-1-yl)-2-(pentan-3-ylamino)ethan-1-one (345); 1-(4-(2-(2,6-dimethylpyridin-4-yl)-3-isopropyl-1H-indol-5-yl)piperidin-1-yl)-2-((2-methoxyethyl) amino)ethan-1-one (346); 2-((3,3-dimethylbutyl)amino)-1-(4-(2-(2,6-dimethylpyridin-4-yl)-3-isopropyl-1H-indol-5-yl)piperidin-1-yl) ethan-1-one (347); 1-(4-(2-(2,6-dimethylpyridin-4-yl)-3-isopropyl-1H-indol-5-yl)piperidin-1-yl)-2-(propylamino) ethan-1-one (348); 1-(4-(2-(2,6-dimethylpyridin-4-yl)-3-isopropyl-1H-indol-5-yl)piperidin-1-yl)-2-((2-ethoxyethyl) amino)ethan-1-one (349); 1-(4-(2-(2,6-dimethylpyridin-4-yl)-3-isopropyl-1H-indol-5-yl)piperidin-1-yl)-2-(isopropyl (methyl)amino)ethan-1-one (354); 1-(4-(2-(2,6-dimethylpyridin-4-yl)-3-isopropyl-1H-indol-5-yl)piperidin-1-yl)-2-(isobutyl (methyl)amino)ethan-1-one (355); 1-(4-(2-(2,6-dimethylpyridin-4-yl)-3-isopropyl-1H-indol-5-yl)piperidin-1-yl)-2-(ethyl(methyl)amino)ethan-1-one (356); 2-(tert-butyl (methyl)amino)-1-(4-(2-(2,6-dimethylpyridin-4-yl)-3-isopropyl-1H-indol-5-yl)piperidin-1-yl)ethan-1-one (359); 1-(4-(2-(2,6-dimethylpyridin-4-yl)-3-isopropyl-1H-indol-5-yl) piperidin-1-yl)-2-((2-hydroxypropyl)amino) ethan-1-one (367); 1-(4-(2-(2,6-dimethylpyridin-4-yl)-3-isopropyl-1H-indol-5-yl)piperidin-1-yl)-2-((3-hydroxybutyl) amino)ethan-1-one (369); 1-(4-(2-(2,6-dimethylpyridin-4-yl)-3-isopropyl-1H-indol-5-yl)piperidin-1-yl)-2-((2-hydroxy-2-methylpropyl)amino)ethan-1-one (375); 1-(4-(2-(2,6-dimethylpyridin-4-yl)-3-isopropyl-1H-indol-5-yl)piperidin-1-yl)-2-((1-hydroxy-4-methylpentan-2-yl)amino)ethan-1-one (382); 2-(sec-butylamino)-1-(4-(2-(2,6-dimethylpyridin-4-yl)-3-isopropyl-1H-indol-5-yl)piperidin-1-yl)ethan-1-one (392); 1-(4-(2-(2,6-dimethylpyridin-4-yl)-3-isopropyl-1H-indol-5-yl)piperidin-1-yl)-2-(isopentylamino)ethan-1-one (393); 1-(4-(2-(2,6-dimethylpyridin-4-yl)-3-isopropyl-1H-indol-5-yl)piperidin-1-yl)-2-(ethyl(2-hydroxyethyl)amino)ethan-1-one (397); 1-(4-(2-(2,6-dimethylpyridin-4-yl)-3-isopropyl-1H-indol-5-yl)piperidin-1-yl)-2-((2-hydroxyethyl)(propyl)amino)ethan-1-one (398); 1-(4-(2-(2,6-dimethylpyridin-4-yl)-3-isopropyl-1H-indol-5-yl)piperidin-1-yl)-2-((2-hydroxy-2-methylpropyl)(methyl)amino) ethan-1-one (401); 1-(4-(2-(2,6-dimethylpyridin-4-yl)-3-isopropyl-1H-indol-5-yl) piperidin-1-yl)-2-((2-hydroxyethyl)(2-methylbutyl)amino) ethan-1-one (406); 1-(4-(2-(2,6-dimethylpyridin-4-yl)-3-isopropyl-1H-indol-5-yl)piperidin-1-yl)-2-((3-hydroxypropyl)(methyl)amino)ethan-1-one (411); 2-(butyl(2-hydroxyethyl)amino)-1-(4-(2-(2,6-dimethylpyridin-4-yl)-3-isopropyl-1H-indol-5-yl)piperidin-1-yl)ethan-1-one (414); 1-(4-(2-(2,6-dimethylpyridin-4-yl)-3-isopropyl-1H-indol-5-yl)piperidin-1-yl)-2-((2-hydroxyethyl)(isopropyl)amino) ethan-1-one (415); 1-(4-(2-(2,6-dimethylpyridin-4-yl)-3-isopropyl-1H-indol-5-yl)piperidin-1-yl)-2-((2-hydroxyethyl)(methyl)amino)ethan-1-one (420); 1-(4-(2-(2,6-dimethylpyridin-4-yl)-3-isopropyl-1H-indol-5-yl) piperidin-1-yl)-2-((2-fluoroethyl)(methyl)amino)ethan-1-one (421); 2-((2,2-difluoroethyl)(methyl) amino)-1-(4-(2-(2,6-dimethylpyridin-4-yl)-3-isopropyl-1H-indol-5-yl) piperidin-1-yl) ethan-1-one (422); 2-((2-(4-(2-(2,6-dimethylpyridin-4-yl)-3-isopropyl-1H-indol-5-yl)piperidin-1-yl)-2-oxoethyl)(methyl)amino)acetonitrile (423); 2-(4-(2-(2,6-dimethylpyridin-4-yl)-3-isopropyl-1H-indol-5-yl)piperidin-1-yl)-N-methylethan-1-amine (428); 2-(2,6-dimethylpyridin-4-yl)-3-isopropyl-5-(1-methylpiperidin-4-yl)-1H-indole (429); 2-(2,6-dimethylpyridin-4-yl)-3-isopropyl-5-(1-(pentan-3-yl)piperidin-4-yl)-1H-indole (436); 2-(2,6-dimethylpyridin-4-yl)-3-isopropyl-5-(1-neopentylpiperidin-4-yl)-1H-indole (470); 2-(2,6-dimethylpyridin-4-yl)-5-(1-isobutylpiperidin-4-yl)-3-isopropyl-1H-indole (471); 2-(2,6-dimethylpyridin-4-yl)-5-(1-(1-fluoropropan-2-yl)piperidin-4-yl)-3-isopropyl-1H-indole (472); 5-(1-(1,3-difluoropropan-2-yl)piperidin-4-yl)-2-(2,6-dimethylpyridin-4-yl)-3-isopropyl-1H-indole (473); 2-(4-(3-(2,2-difluoroethyl)-2-(2,6-dimethylpyridin-4-yl)-1H-indol-5-yl)piperidin-1-yl)-N,N-dimethylpropanamide (493); 2-(2,6-dimethylpyridin-4-yl)-3-isopropyl-5-(1,2,2,6,6-pentamethylpiperidin-4-yl)-1H-indole (496); 2-(4-(2-(2-fluoro-6-methylpyridin-4-yl)-3-isopropyl-1H-indol-5-yl) piperidin-1-yl)-N-methylacetamide (498); 1-(4-(2-(2-fluoro-6-methylpyridin-4-yl)-3-isopropyl-1H-indol-5-yl)piperidin-1-yl)ethan-1-one (499); 2-(4-(2-(2-fluoro-6-methylpyridin-4-yl)-3-isopropyl-1H-indol-5-yl)piperidin-1-yl)-N,N-dimethylacetamide (500); 2-(dimethylamino)-1-(4-(2-(2-fluoro-6-methylpyridin-4-yl)-3-isopropyl-1H-indol-5-yl)piperidin-1-yl)ethan-1-one (501); 2-(4-(2-(2-cyclopropyl-6-methylpyridin-4-yl)-3-isopropyl-1H-indol-5-yl)piperidin-1-yl)-N-methylacetamide (503); 1-(4-(2-(2-cyclopropyl-6-methylpyridin-4-yl)-3-isopropyl-1H-indol-5-yl)piperidin-1-yl)ethan-1-one (504); 2-(4-(2-(2-cyclopropyl-6-methylpyridin-4-yl)-3-isopropyl-1H-indol-5-yl) piperidin-1-yl)-N,N-dimethylacetamide (505); 1-(4-(2-(2-cyclopropyl-6-methylpyridin-4-yl)-3-isopropyl-1H-indol-5-yl)piperidin-1-yl)-2-(dimethylamino)ethan-1-one (506); 1-(4-(2-(2-cyclopropyl-6-methylpyridin-4-yl)-3-isopropyl-1H-indol-5-yl)piperidin-1-yl)-2-(methylamino)ethan-1-one (508); 2-(dimethylamino)-1-(4-(3-isopropyl-2-(2-methylpyridin-4-yl)-1H-indol-5-yl)piperidin-1-yl)ethan-1-one (509); 1-(4-(3-isopropyl-2-(2-methylpyridin-4-yl)-1H-indol-5-yl)piperidin-1-yl)-2-(methylamino)ethan-1-one (510); (R)-2-((2,3-dihydroxypropyl)amino)-1-(4-(3-isopropyl-2-(2-methylpyridin-4-yl)-1H-indol-5-yl)piperidin-1-yl)ethan-1-one (511); 2-(4-(3-isopropyl-2-(2-methylpyridin-4-yl)-1H-indol-5-yl)piperidin-1-yl)-N,N-dimethylacetamide (512); 1-(4-(3-isopropyl-2-(2-methylpyridin-4-yl)-1H-indol-5-yl)piperidin-1-yl)-3-(methylamino)propan-2-one (513); 2-(4-(2-(2-cyclopropyl-5-fluoropyridin-4-yl)-3-isopropyl-1H-indol-5-yl)piperidin-1-yl)-N-methylacetamide (514); 2-(4-(2-(2-cyclopropyl-5-fluoropyridin-4-yl)-3-isopropyl-1H-indol-5-yl)piperidin-1-yl)-N,N-dimethylacetamide (515); 1-(4-(2-(2-cyclopropyl-5-fluoropyridin-4-yl)-3-isopropyl-1H-indol-5-yl)piperidin-1-yl)-2-(dimethylamino)ethan-1-one (516); 1-(4-(2-(2-cyclopropyl-5-fluoropyridin-4-yl)-3-isopropyl-1H-indol-5-yl) piperidin-1-yl)-2-(methylamino)ethan-1-one (518); 2-(4-(3-isopropyl-2-(2-methoxypyridin-4-yl)-1H-indol-5-yl)piperidin-1-yl)-N-methylacetamide (519); 2-(dimethylamino)-1-(4-(3-isopropyl-2-(2-methoxypyridin-4-yl)-1H-indol-5-yl) piperidin-1-yl)ethan-1-one (521); 2-(dimethylamino)-1-(4-(2-(2-fluoropyridin-4-yl)-3-isopropyl-1H-indol-5-yl) piperidin-1-yl)ethan-1-one (522); 2-(dimethylamino)-1-(4-(3-isopropyl-2-(pyridin-4-yl)-1H-indol-5-yl)piperidin-1-yl) ethan-1-one (524); 2-(4-(2-(2,6-dimethylpyridin-4-yl)-3-ethyl-1H-indol-5-yl)piperidin-1-yl)-N,N-dimethylacetamide (526); 2-(4-(2-(2,6-dimethylpyridin-4-yl)-3-ethyl-1H-indol-5-yl)piperidin-1-yl)-N-methylacetamide (527); 2-(dimethylamino)-1-(4-(2-(2,6-dimethylpyridin-4-yl)-3-ethyl-1H-indol-5-yl)piperidin-1-yl)ethan-1-one (528); 1-(4-(2-(2,6-dimethylpyridin-4-yl)-3-ethyl-1H-indol-5-yl)piperidin-1-yl)-2-(methylamino)ethan-1-one (529); 2-(4-(3-(2,2- difluoroethyl)-2-(2,6-dimethylpyridin-4-yl)-1H-indol-5-yl)piperidin-1-yl)-N,N-dimethylacetamide (531); 2-(4-(3-(2,2-difluoroethyl)-2-(2,6-dimethylpyridin-4-yl)-1H-indol-5-yl)piperidin-1-yl)-N-methylacetamide (532); 1-(4-(3-(2,2-difluoroethyl)-2-(2,6-dimethylpyridin-4-yl)-1H-indol-5-yl)piperidin-1-yl)-2-(dimethylamino)ethan-1-one (533); 1-(4-(3-(2,2-difluoroethyl)-2-(2,6-dimethylpyridin-4-yl)-1H-indol-5-yl)piperidin-1-yl)-2-(methylamino)ethan-1-one (535); 3-(2,2-difluoroethyl)-2-(2,6-dimethylpyridin-4-yl)-5-(1-isopropylpiperidin-4-yl)-1H-indole (536); 3-(2,2-difluoroethyl)-2-(2,6-dimethylpyridin-4-yl)-5-(1-methylpiperidin-4-yl)-1H-indole (539); 2-(4-(3-(2,2-difluoroethyl)-2-(2,6-dimethylpyridin-4-yl)-1H-indol-5-yl)piperidin-1-yl)-N-methylethan-1-amine (541); 5-(1-((4-chlorophenyl)sulfonyl)piperidin-4-yl)-3-isopropyl-2-(2-methylpyridin-4-yl)-1H-indole (542); 3-isopropyl-2-(2-methylpyridin-4-yl)-5-(1-(pyridin-3-ylsulfonyl)piperidin-4-yl)-1H-indole (543); 3-isopropyl-5-(1-(isopropylsulfonyl)piperidin-4-yl)-2-(2-methylpyridin-4-yl)-1H-indole (544); 3-isopropyl-2-(2-methylpyridin-4-yl)-5-(1-(propylsulfonyl)piperidin-4-yl)-1H-indole (545); 3-isopropyl-2-(2-methylpyridin-4-yl)-5-(1-((2,2,2-trifluoroethyl)sulfonyl)piperidin-4-yl)-1H-indole (546); 5-(1-(isobutylsulfonyl)piperidin-4-yl)-3-isopropyl-2-(2-methylpyridin-4-yl)-1H-indole (548); 5-(1-(ethylsulfonyl)piperidin-4-yl)-3-isopropyl-2-(2-methylpyridin-4-yl)-1H-indole (549); 3-isopropyl-2-(2-methylpyridin-4-yl)-5-(1-(methylsulfonyl)piperidin-4-yl)-1H-indole (550); isobutyl 4-(3-isopropyl-2-(2-methylpyridin-4-yl)-1H-indol-5-yl)piperidine-1-carboxylate (558); isopropyl 4-(3-isopropyl-2-(2-methylpyridin-4-yl)-1H-indol-5-yl)piperidine-1-carboxylate (559); ethyl 4-(3-isopropyl-2-(2-methylpyridin-4-yl)-1H-indol-5-yl)piperidine-1-carboxylate (560); 2-methoxyethyl 4-(3-isopropyl-2-(2-methylpyridin-4-yl)-1H-indol-5-yl)piperidine-1-carboxylate (561); methyl 4-(3-isopropyl-2-(2-methylpyridin-4-yl)-1H-indol-5-yl) piperidine-1-carboxylate (562); (S)-1-(4-amino-5-(4-(3-isopropyl-2-(2-methylpyridin-4-yl)-1H-indol-5-yl)piperidin-1-yl)-5-oxopentyl)urea (564); 1-(4-(3-isopropyl-2-(2-methylpyridin-4-yl)-1H-indol-5-yl)piperidin-1-yl)-3-(methylamino)propan-1-one (570); 1-(4-(3-isopropyl-2-(2-methylpyridin-4-yl)-1H-indol-5-yl)piperidin-1-yl)-3-methoxypropan-1-one (571); (S)-2,5-diamino-1-(4-(3-isopropyl-2-(2-methylpyridin-4-yl)-1H-indol-5-yl)piperidin-1-yl)pentan-1-one (577); 3-(dimethylamino)-1-(4-(3-isopropyl-2-(2-methylpyridin-4-yl)-1H-indol-5-yl)piperidin-1-yl)propan-1-one (578); (S)-2,6-diamino-1-(4-(3-isopropyl-2-(2-methylpyridin-4-yl)-1H-indol-5-yl)piperidin-1-yl)hexan-1-one (579); 1-(4-(2-(2,5-dimethylpyridin-4-yl)-3-isopropyl-1H-indol-5-yl)piperidin-1-yl)ethan-1-one (584); 2-(dimethylamino)-1-(4-(2-(2,5-dimethylpyridin-4-yl)-3-isopropyl-1H-indol-5-yl)piperidin-1-yl)ethan-1-one (585); 2-(dimethylamino)-1-(4-(2-(5-fluoro-2-methylpyridin-4-yl)-3-isopropyl-1H-indol-5-yl)piperidin-1-yl)ethan-1-one (586); 2-(dimethylamino)-1-(4-(2-(3-fluoro-2-methylpyridin-4-yl)-3-isopropyl-1H-indol-5-yl)piperidin-1-yl)ethan-1-one (587); 2-(dimethylamino)-1-(4-(2-(3-fluoro-2,6-dimethylpyridin-4-yl)-3-isopropyl-1H-indol-5-yl)piperidin-1-yl)ethan-1-one (588); 1-(4-(3-cyclopropyl-2-(2,6-dimethylpyridin-4-yl)-1H-indol-5-yl)piperidin-1-yl)-2-(dimethylamino)ethan-1-one (590); 3-(dimethylamino)-1-(4-(3-ethyl-2-(2-methylpyridin-4-yl)-1H-indol-5-yl)piperidin-1-yl)propan-1-one (594); 3,3,3-trifluoro-1-(4-(3-isopropyl-2-(2-methylpyridin-4-yl)-1H-indol-5-yl)piperidin-1-yl)propan-1-one (600); 1-(4-(3-isopropyl-2-(2-methylpyridin-4-yl)-1H-indol-5-yl)piperidin-1-yl)-2,2-dimethylpropan-1-one (601); 1-(4-(3-isopropyl-2-(2-methylpyridin-4-yl)-1H-indol-5-yl)piperidin-1-yl)-2-methylpropan-1-one (602); 1-(4-(3-isopropyl-2-(2-methylpyridin-4-yl)-1H-indol-5-yl) piperidin-1-yl)propan-1-one (603); 1-(4-(3-isopropyl-2-(2-methylpyridin-4-yl)-1H-indol-5-yl)piperidin-1-yl)-2-(methylsulfonyl)ethan-1-one (608); 2,2,2-trifluoro-1-(4-(3-isopropyl-2-(2-methylpyridin-4-yl)-1H-indol-5-yl)piperidin-1-yl)ethan-1-one (614); 3-(4-(3-isopropyl-2-(2-methylpyridin-4-yl)-1H-indol-5-yl)piperidin-1-yl)-2,2-dimethyl-3-oxopropanenitrile (615); 3-(4-(3-isopropyl-2-(2-methylpyridin-4-yl)-1H-indol-5-yl) piperidin-1-yl)-3-oxopropanenitrile (616); 3-(4-(3-isopropyl-2-(2-methylpyridin-4-yl)-1H-indol-5-yl)piperidin-1-yl)-3-oxopropanenitrile (617); 1-(4-(2-(2,5-dimethylpyridin-4-yl)-3-isopropyl-1H-indol-5-yl)piperidin-1-yl)-2-(methylamino)ethan-1-one (620); 1-(4-(2-(5-fluoro-2-methylpyridin-4-yl)-3-isopropyl-1H-indol-5-yl)piperidin-1-yl)-2-(methylamino)ethan-1-one (621); 1-(4-(2-(3-fluoro-2,6-dimethylpyridin-4-yl)-3-isopropyl-1H-indol-5-yl)piperidin-1-yl)-2-(methylamino)ethan-1-one (622); 2-(5-fluoro-2-methylpyridin-4-yl)-3-isopropyl-5-(1-methylpiperidin-4-yl)-1H-indole (635); 2-(2,5-dimethylpyridin-4-yl)-3-isopropyl-5-(1-methylpiperidin-4-yl)-1H-indole (636); 2-(2,3-dimethylpyridin-4-yl)-3-isopropyl-5-(1-methylpiperidin-4-yl)-1H-indole (637); 3-isopropyl-2-(2-methoxypyridin-4-yl)-5-(1-methylpiperidin-4-yl)-1H-indole (638); 3-isopropyl-2-(2-methoxypyridin-4-yl)-5-(1-(2,2,2-trifluoroethyl)piperidin-4-yl)-1H-indole (639); 5-(1-(2-ethoxyethyl)piperidin-4-yl)-3-isopropyl-2-(2-methoxypyridin-4-yl)-1H-indole (640); 2-(2,5-dimethylpyridin-4-yl)-3-isopropyl-5-(1-isopropylpiperidin-4-yl)-1H-indole (641); 2-(4-(2-(2,5-dimethylpyridin-4-yl)-3-isopropyl-1H-indol-5-yl)piperidin-1-yl)-N,N-dimethylacetamide (642); 2-(4-(2-(5-fluoro-2-methylpyridin-4-yl)-3-isopropyl-1H-indol-5-yl)piperidin-1-yl)-N,N-dimethylacetamide (643); 2-(4-(2-(3-chloro-2,6-dimethylpyridin-4-yl)-3-isopropyl-1H-indol-5-yl)piperidin-1-yl)-N,N-dimethylacetamide (644); 2-(4-(2-(3-fluoro-2,6-dimethylpyridin-4-yl)-3-isopropyl-1H-indol-5-yl)piperidin-1-yl)-N,N-dimethylacetamide (645); 2-(4-(2-(5-fluoro-2-methylpyridin-4-yl)-3-isopropyl-1H-indol-5-yl)piperidin-1-yl)ethan-1-ol (647); 2-(4-(2-(3-fluoro-2-methylpyridin-4-yl)-3-isopropyl-1H-indol-5-yl)piperidin-1-yl)-N,N-dimethylacetamide (648); 5-(1-(2,2-difluoroethyl)piperidin-4-yl)-2-(5-fluoro-2-methylpyridin-4-yl)-3-isopropyl-1H-indole (649); 2-(4-(2-(2,5-dimethylpyridin-4-yl)-3-isopropyl-1H-indol-5-yl)piperidin-1-yl)acetamide (651); 2-(4-(2-(5-fluoro-2-methylpyridin-4-yl)-3-isopropyl-1H-indol-5-yl)piperidin-1-yl)acetamide (652); 2-(4-(2-(2,5-dimethylpyridin-4-yl)-3-isopropyl-1H-indol-5-yl)piperidin-1-yl)-N-methylacetamide (653); 2-(4-(2-(5-fluoro-2-methylpyridin-4-yl)-3-isopropyl-1H-indol-5-yl)piperidin-1-yl)-N-methylacetamide (654); 2-(4-(2-(3-fluoro-2,6-dimethylpyridin-4-yl)-3-isopropyl-1H-indol-5-yl)piperidin-1-yl)-N-methylacetamide (655); 3-(4-(2-(5-fluoro-2-methylpyridin-4-yl)-3-isopropyl-1H-indol-5-yl)piperidin-1-yl)propanenitrile (656); 3-isopropyl-2-(2-methylpyridin-4-yl)-5-(1-(2,2,2-trifluoroethyl)piperidin-4-yl)-1H-indole (658); 5-(1-(2-ethoxyethyl)piperidin-4-yl)-3-isopropyl-2-(2-methylpyridin-4-yl)-1H-indole (659); 5-(1-(2,2-difluoroethyl)piperidin-4-yl)-3-isopropyl-2-(2-methylpyridin-4-yl)-1H-indole (660); 1,1,1-trifluoro-3-(4-(3-isopropyl-2-(2-methylpyridin-4-yl)-1H-indol-5-yl)piperidin-1-yl)propan-2-ol (661); 1-(4-(3-isopropyl-2-(2-methylpyridin-4-yl)-1H-indol-5-yl)piperidin-1-yl)butan-2-ol (664); 3-(4-(2-(2,5-dimethylpyridin-4-yl)-3-isopropyl-1H-indol-5-yl)piperidin-1-yl)propanenitrile (665); 2-(2,5-dimethylpyridin-4-yl)-5-(1-isobutylpiperidin-4-yl)-3-isopropyl-1H-indole (666); 1-(4-(3-cyclopropyl-2-(2,6-dimethylpyridin-4-yl)-1H-indol-5-yl)piperidin-1-yl)-2-methylpropan-2-ol (668); 3-(4-(3-isopropyl-2-(2-methylpyridin-4-yl)-1H-indol-5-yl) piperidin-1-yl)-N,N-dimethylpropan-1-amine (669); 3-ethyl-5-(1-methylpiperidin-4-yl)-2-(2-methylpyridin-4-yl)-1H-indole (670); 3-(4-(2-(2,6-dimethylpyridin-4-yl)-3-isopropyl-1H-indol-5-yl)piperidin-1-yl)-N,N-diethylpropan-1-amine (671); 3-ethyl-5-(1-isopropylpiperidin-4-yl)-2-(2-methylpyridin-4-yl)-1H-indole (672); 3-(4-(3-ethyl-2-(2-methylpyridin-4-yl)-1H-indol-5-yl)piperidin-1-yl)-N,N-dimethylpropan-1-amine (673); 3-(4-(2-(2,6-dimethylpyridin-4-yl)-3-isopropyl-1H-indol-5-yl)piperidin-1-yl)-N,N-dimethylpropan-1-amine (674); 3-isopropyl-2-(2-methylpyridin-4-yl)-5-(1-(3,3,3-trifluoropropyl)piperidin-4-yl)-1H-indole (676); 2-(2,6-dimethylpyridin-4-yl)-3-isopropyl-5-(1-(3,3,3-trifluoropropyl)piperidin-4-yl)-1H-indole (677); 3-((2-(4-(2-(5-fluoro-2-methylpyridin-4-yl)-3-isopropyl-1H-indol-5-yl)piperidin-1-yl)-2-oxoethyl)(methyl)amino)propanenitrile (679); 1-(4-(2-(5-fluoro-2-methylpyridin-4-yl)-3-isopropyl-1H-indol-5-yl)piperidin-1-yl)-2-((2-hydroxyethyl)(methyl)amino)ethan-1-one (680); 3-isopropyl-5-(1'-isopropyl-[1,4'-bipiperidin]-4-yl)-2-(2-methylpyridin-4-yl)-1H-indole (701); N-methyl-2-(4-(3-methyl-2-(2-(4-methylpiperazin-1-yl)pyridin-4-yl)-1H-indol-5-yl)piperidin-1-yl)ethan-1-amine (746); N-methyl-2-(4-(3-methyl-2-(2-(trifluoromethyl)pyridin-4-yl)-1H-indol-5-yl)piperidin-1-yl)ethan-1-amine (747); 2-(4-(2-(2-ethylpyridin-4-yl)-3-methyl-1H-indol-5-yl)piperidin-1-yl)-N-methylethan-1-amine (748); 2-(4-(2-(5-fluoro-2-(2-methoxyethoxy)pyridin-4-yl)-3-methyl-1H-indol-5-yl)piperidin-1-yl)-N-methylethan-1-amine (749); 2-(4-(2-(2-fluoropyridin-4-yl)-3-methyl-1H-indol-5-yl)piperidin-1-yl)-N-methylethan-1-amine (750); 2-(4-(2-(2-chloropyridin-4-yl)-3-methyl-1H-indol-5-yl)piperidin-1-yl)-N-methylethan-1-amine (751); methyl 4-(3-methyl-5-(1-(2-(methylamino)ethyl)piperidin-4-yl)-1H-indol-2-yl) picolinate (752); N-(4-(3-methyl-5-(1-(2-(methylamino)ethyl)piperidin-4-yl)-1H-indol-2-yl)pyridin-2-yl)acetamide (753); 2-(4-(2-(3-methoxypyridin-4-yl)-3-methyl-1H-indol-5-yl)piperidin-1-yl)-N-methylethan-1-amine (754); 4-(3-methyl-5-(1-(2-(methylamino) ethyl)piperidin-4-yl)-1H-indol-2-yl) picolinonitrile (755); 2-(4-(2-(5-fluoro-2-methoxypyridin-4-yl)-3-methyl-1H-indol-5-yl)piperidin-1-yl)-N-methylethan-1-amine (756); 2-(4-(2-(2-chloro-5-methoxypyridin-4-yl)-3-methyl-1H-indol-5-yl)piperidin-1-yl)-N-methylethan-1-amine (757); 2-(2-chloropyridin-4-yl)-3-ethyl-5-(1'-isobutyl-[1,4'-bipiperidin]-4-yl)-1H-indole (758); 3-ethyl-2-(2-fluoropyridin-4-yl)-5-(1'-isobutyl-[1,4'-bipiperidin]-4-yl)-1H-indole (759); 2-(2-chloro-5-fluoropyridin-4-yl)-3-ethyl-5-(1'-isobutyl-[1,4'-bipiperidin]-4-yl)-1H-indole (760); 2-(2,6-difluoropyridin-4-yl)-3-ethyl-5-(1'-isobutyl-[1,4'-bipiperidin]-4-yl)-1H-indole (761); methyl 4-(3-ethyl-5-(1'-isobutyl-[1,4'-bipiperidin]-4-yl)-1H-indol-2-yl)picolinate (762); 2-(2-chloro-5-methoxypyridin-4-yl)-3-ethyl-5-(1'-isobutyl-[1,4'-bipiperidin]-4-yl)-1H-indole (763); 4-(3-ethyl-5-(1'-isobutyl-[1,4'-bipiperidin]-4-yl)-1H-indol-2-yl)pyridin-2-ol (765); N-(4-(3-ethyl-5-(1'-isobutyl-[1,4'-bipiperidin]-4-yl)-1H-indol-2-yl)pyridin-2-yl)acetamide (766); N-methyl-2-(4-(3-methyl-2-(pyridin-4-yl)-1H-indol-5-yl)piperidin-1-yl)ethan-1-amine (776); 2-(4-(2-(2-methoxypyridin-4-yl)-3-methyl-1H-indol-5-yl)piperidin-1-yl)-N-methylethan-1-amine (777); 2-(4-(3-ethyl-2-(2-methoxypyridin-4-yl)-1H-indol-5-yl)piperidin-1-yl)-N-methylethan-1-amine (778); 2-(4-(3-ethyl-2-(pyridin-4-yl)-1H-indol-5-yl)piperidin-1-yl)-N-methylethan-1-amine (808); N-methyl-2-(4-(3-methyl-2-(2-methylpyridin-4-yl)-1H-indol-5-yl)piperidin-1-yl)ethan-1-amine (815); 2-(4-(2-(2,5-dimethylpyridin-4-yl)-6-fluoro-3-isopropyl-1H-indol-5-yl)piperidin-1-yl)-N,N-dimethylacetamide (835); 2-(4-(6-fluoro-2-(5-fluoro-2-methylpyridin-4-yl)-3-isopropyl-1H-indol-5-yl)piperidin-1-yl)-N,N-dimethylacetamide (836); 2-(4-(2-(2,6-dimethylpyridin-4-yl)-6-fluoro-3-isopropyl-1H-indol-5-yl)piperidin-1-yl)-N,N-dimethylacetamide (837); 1-(4-(2-(2,6-dimethylpyridin-4-yl)-3-isopropyl-1H-indol-5-yl)piperidin-1-yl)-2-methylpropan-2-ol (848); 1-(4-(2-(2,6-dimethylpyridin-4-yl)-3-isopropyl-1H-indol-5-yl)piperidin-1-yl)-3-methylbutan-2-ol (849); 1-(4-(2-(2,6-dimethylpyridin-4-yl)-3-isopropyl-1H-indol-5-yl)piperidin-1-yl)-3,3-dimethylbutan-2-ol (850); 1-(4-(2-(2,5-dimethylpyridin-4-yl)-3-isopropyl-1H-indol-5-yl)piperidin-1-yl)-2-methylpropan-2-ol (851); (R)-1-(4-(2-(2,6-dimethylpyridin-4-yl)-3-isopropyl-1H-indol-5-yl)piperidin-1-yl)-3-methoxypropan-2-ol (852); 1-(4-(2-(2,6-dimethylpyridin-4-yl)-3-isopropyl-1H-indol-5-yl)piperidin-1-yl)-2-methylbut-3-en-2-ol (853); 3-(4-(2-(2,6-dimethylpyridin-4-yl)-3-isopropyl-1H-indol-5-yl)piperidin-1-yl) propane-1,2-diol (854); 1-(4-(2-(2,6-dimethylpyridin-4-yl)-3-isopropyl-1H-indol-5-yl) piperidin-1-yl)-3-methylbutan-2-ol (855); N-(2-(dimethylamino)ethyl)-2-(4-(2-(2,6-dimethylpyridin-4-yl)-3-isopropyl-1H-indol-5-yl)piperidin-1-yl)-N-methyl-2-oxoacetamide (858); 2-(4-(2-(2,6-dimethylpyridin-4-yl)-3-isopropyl-1H-indol-5-yl)piperidin-1-yl)-2-oxoacetic acid (859); 4-(2-(2,6-dimethylpyridin-4-yl)-3-isopropyl-1H-indol-5-yl)piperidine-1-carbaldehyde (862); 3-ethyl-2-(2-methylpyridin-4-yl)-5-(1-(3,3,3-trifluoropropyl)piperidin-4-yl)-1H-indole (863); 5-(1-(1-fluoropropan-2-yl)piperidin-4-yl)-3-isopropyl-2-(2-methylpyridin-4-yl)-1H-indole (864); 5-(1-(1,3-difluoropropan-2-yl)piperidin-4-yl)-3-isopropyl-2-(2-methylpyridin-4-yl)-1H-indole (865); 3-isopropyl-5-(1-isopropylpiperidin-4-yl)-2-(2-methylpyridin-4-yl)-1H-indole (869); 2-(2,5-dimethylpyridin-4-yl)-5-(1-(1-fluoropropan-2-yl)piperidin-4-yl)-3-isopropyl-1H-indole (870); 2-(4-(2-(2,6-dimethylpyridin-4-yl)-3-isopropyl-1H-indol-5-yl)piperidin-1-yl)acetic acid (875); 2-(4-(3-ethyl-2-(2-methylpyridin-4-yl)-1H-indol-5-yl)piperidin-1-yl)acetic acid (876); 1-(4-(3-ethyl-2-(2-methylpyridin-4-yl)-1H-indol-5-yl)piperidin-1-yl)-3-(isopropyl(methyl)amino)propan-2-ol (877); 2-(4-(3-isopropyl-2-(2-methylpyridin-4-yl)-1H-indol-5-yl)piperidin-1-yl)-N,N-dimethyl-2-oxoacetamide (878); and 2-(4-(3-isopropyl-2-(2-methylpyridin-4-yl)-1H-indol-5-yl)piperidin-1-yl)-N-methyl-2-oxoacetamide (879).

One embodiment provides a compound of Formula (I) or a salt thereof, wherein said compound is selected from: 4-(4-(2-(2,6-dimethylpyridin-4-yl)-3-isopropyl-1H-indol-5-yl)piperidine-1-carbonyl)-1-methylpyrrolidin-2-one (100); 4-(4-(2-(2,6-dimethylpyridin-4-yl)-3-isopropyl-1H-indol-5-yl)piperidine-1-carbonyl)-1-methylpyrrolidin-2-one (101 and 102); (4-(2-(2,6-dimethylpyridin-4-yl)-3-isopropyl-1H-indol-5-yl)piperidin-1-yl)(tetrahydrofuran-2-yl)methanone (103); 1-(4-(2-(2,6-dimethylpyridin-4-yl)-3-isopropyl-1H-indol-5-yl)piperidin-1-yl)-2-(tetrahydro-2H-pyran-4-yl) ethan-1-one (106); (4-(2-(2,6-dimethylpyridin-4-yl)-3-isopropyl-1H-indol-5-yl) piperidin-1-yl)(1-hydroxycyclopropyl)methanone (107); (2,2-difluorocyclopropyl)(4-(2-(2,6-dimethylpyridin-4-yl)-3-isopropyl-1H-indol-5-yl)piperidin-1-yl)methanone (108); (4-(2-(2,6-dimethylpyridin-4-yl)-3-isopropyl-1H-indol-5-yl)piperidin-1-yl)(1-methylpiperidin-4-yl)methanone (110); (4-(2-(2,6-dimethylpyridin-4-yl)-3-isopropyl-1H-indol-5-yl)piperidin-1-yl)(pyridin-3-yl)methanone (112 and 113); (3,5-dimethylisoxazol-4-yl)(4-(2-(2,6-dimethylpyridin-4-yl)-3-isopropyl-1H-indol-5-yl)piperidin-1-yl) methanone (119); N-(3-(4-(2-(2,6-dimethylpyridin-4-yl)-3-isopropyl- 1H-indol-5-yl) piperidin-1-yl)-3-oxopropyl)benzenesulfonamide (120); (3,5-dimethyl-1H-pyrazol-4-yl)(4-(2-(2,6-dimethylpyridin-4-yl)-3-isopropyl-1H-indol-5-yl)piperidin-1-yl)methanone (121); 5-(2-(4-(2-(2,6-dimethylpyridin-4-yl)-3-isopropyl-1H-indol-5-yl)piperidin-1-yl)-2-oxoethyl)-1,3-dimethylimidazolidine-2,4-dione (122); 1-cyclopropyl-3-(4-(2-(2,6-dimethylpyridin-4-yl)-3-isopropyl-1H-indol-5-yl)piperidine-1-carbonyl)pyridin-2(1H)-one (123); 1-(4-(2-(2,6-dimethylpyridin-4-yl)-3-isopropyl-1H-indol-5-yl)piperidin-1-yl)-3-(2-methyl-1H-imidazol-1-yl)propan-1-one (124); 3-(3,5-dimethyl-1H-pyrazol-1-yl)-1-(4-(2-(2,6-dimethylpyridin-4-yl)-3-isopropyl-1H-indol-5-yl)piperidin-1-yl)propan-1-one (125); (4-(2-(2,6-dimethylpyridin-4-yl)-3-isopropyl-1H-indol-5-yl)piperidin-1-yl)(3-methylisoxazol-4-yl)methanone (126); 1-(3-(2-(4-(2-(2,6-dimethylpyridin-4-yl)-3-isopropyl-1H-indol-5-yl)piperidin-1-yl)-2-oxoethyl)morpholino)-3,3-dimethylbutan-1-one (127); 1-(4-(2-(2,6-dimethylpyridin-4-yl)-3-isopropyl-1H-indol-5-yl)piperidin-1-yl)-3-morpholinopropan-1-one (128); 6-(2-(4-(2-(2,6-dimethylpyridin-4-yl)-3-isopropyl-1H-indol-5-yl)piperidin-1-yl)-2-oxoethyl)dihydropyrimidine-2,4(1H,3H)-dione (129); 5-(2-(4-(2-(2,6-dimethylpyridin-4-yl)-3-isopropyl-1H-indol-5-yl)piperidin-1-yl)-2-oxoethyl)-1-methylimidazolidine-2,4-dione (130); (4-(2-(2,6-dimethylpyridin-4-yl)-3-isopropyl-1H-indol-5-yl)piperidin-1-yl)(1,3,5-trimethyl-1H-pyrazol-4-yl)methanone (131); (4-(2-(2,6-dimethylpyridin-4-yl)-3-isopropyl-1H-indol-5-yl)piperidin-1-yl)(1-methyl-1H-pyrazol-4-yl)methanone (132); 1-(4-(2-(2,6-dimethylpyridin-4-yl)-3-isopropyl-1H-indol-5-yl) piperidine-1-carbonyl)cyclopropane-1-carboxamide (133); 4-(4-(2-(2,6-dimethylpyridin-4-yl)-3-isopropyl-1H-indol-5-yl)piperidine-1-carbonyl)-6-methylpyridazin-3 (2H)-one (135); 2-(1,3-dimethyl-1H-pyrazol-5-yl)-1-(4-(2-(2,6-dimethylpyridin-4-yl)-3-isopropyl-1H-indol-5-yl)piperidin-1-yl)ethan-1-one (136); 1-(4-(2-(2,6-dimethylpyridin-4-yl)-3-isopropyl-1H-indol-5-yl)piperidin-1-yl)-2-(1-methyl-1H-imidazol-4-yl)ethan-1-one (137); 3-(4-(2-(2,6-dimethylpyridin-4-yl)-3-isopropyl-1H-indol-5-yl)piperidine-1-carbonyl)-1,6-dimethylpyridin-2(1H)-one (138); 2-(3-amino-1H-pyrazol-5-yl)-1-(4-(2-(2,6-dimethylpyridin-4-yl)-3-isopropyl-1H-indol-5-yl)piperidin-1-yl)ethan-1-one (139); 2-(2-aminothiazol-4-yl)-1-(4-(2-(2,6-dimethylpyridin-4-yl)-3-isopropyl-1H-indol-5-yl) piperidin-1-yl)ethan-1-one (140); (1,3-dimethyl-1H-pyrazol-4-yl)(4-(2-(2,6-dimethylpyridin-4-yl)-3-isopropyl-1H-indol-5-yl)piperidin-1-yl)methanone (141); 3-(4-(2-(2,6-dimethylpyridin-4-yl)-3-isopropyl-1H-indol-5-yl)piperidin-1-yl)-3-oxo-N-(thiazol-2-yl)propanamide (142); 1-(4-(2-(2,6-dimethylpyridin-4-yl)-3-isopropyl-1H-indol-5-yl)piperidin-1-yl)-3-(3-methyl-1H-pyrazol-1-yl)propan-1-one (143); 6-(4-(2-(2,6-dimethylpyridin-4-yl)-3-isopropyl-1H-indol-5-yl)piperidine-1-carbonyl)-2,3-dihydroindolizin-5(1H)-one (144); 3-(4-(2-(2,6-dimethylpyridin-4-yl)-3-isopropyl-1H-indol-5-yl)piperidine-1-carbonyl)-4H-quinolizin-4-one (145); 1-(4-(2-(2,6-dimethylpyridin-4-yl)-3-isopropyl-1H-indol-5-yl)piperidin-1-yl)-3-(pyrimidin-2-ylamino) propan-1-one (146); 1-(4-(2-(2,6-dimethylpyridin-4-yl)-3-isopropyl-1H-indol-5-yl) piperidin-1-yl)-2-((1,1-dioxidotetrahydrothiophen-3-yl)(methyl)amino)ethan-1-one (147); 1-(4-(2-(2,6-dimethylpyridin-4-yl)-3-isopropyl-1H-indol-5-yl)piperidin-1-yl)-2-(5-morpholino-2H-tetrazol-2-yl)ethan-1-one (149); 1-(2-(4-(2-(2,6-dimethylpyridin-4-yl)-3-isopropyl-1H-indol-5-yl)piperidin-1-yl)-2-oxoethyl) imidazolidine-2,4-dione (151); 1-(4-(2-(2,6-dimethylpyridin-4-yl)-3-isopropyl-1H-indol-5-yl)piperidin-1-yl)-2-(1,1-dioxidoisothiazolidin-2-yl)ethan-1-one (152); 1-(2-(4-(2-(2,6-dimethylpyridin-4-yl)-3-isopropyl-1H-indol-5-yl)piperidin-1-yl)-2-oxoethyl)pyrrolidin-2-one (154); 1-(4-(2-(2,6-dimethylpyridin-4-yl)-3-isopropyl-1H-indol-5-yl)piperidin-1-yl)-2-(2H-tetrazol-2-yl) ethan-1-one (155); 1-(4-(2-(2,6-dimethylpyridin-4-yl)-3-isopropyl-1H-indol-5-yl) piperidin-1-yl)-2-(3-(trifluoromethyl)-1H-pyrazol-1-yl) ethan-1-one (156); 1-(2-(4-(2-(2,6-dimethylpyridin-4-yl)-3-isopropyl-1H-indol-5-yl)piperidin-1-yl)-2-oxoethyl) pyridin-2(1H)-one (157); 1-(4-(2-(2,6-dimethylpyridin-4-yl)-3-isopropyl-1H-indol-5-yl) piperidin-1-yl)-2-(1H-1,2,3-triazol-1-yl)ethan-1-one (158); 1-(4-(2-(2,6-dimethylpyridin-4-yl)-3-isopropyl-1H-indol-5-yl)piperidin-1-yl)-2-(5-methyl-1H-tetrazol-1-yl)ethan-1-one (159); 3-(2-(4-(2-(2,6-dimethylpyridin-4-yl)-3-isopropyl-1H-indol-5-yl)piperidin-1-yl)-2-oxoethyl)-1-methylimidazolidine-2,4-dione (160); 4-(2-(4-(2-(2,6-dimethylpyridin-4-yl)-3-isopropyl-1H-indol-5-yl)piperidin-1-yl)-2-oxoethyl) morpholin-3-one (161); 2-(3-cyclopropyl-1H-pyrazol-1-yl)-1-(4-(2-(2,6-dimethylpyridin-4-yl)-3-isopropyl-1H-indol-5-yl)piperidin-1-yl)ethan-1-one (162); 1-(4-(2-(2,6-dimethylpyridin-4-yl)-3-isopropyl-1H-indol-5-yl)piperidin-1-yl)-2-(4-methylpiperazin-1-yl)ethan-1-one (163); 3-(2-(4-(2-(2,6-dimethylpyridin-4-yl)-3-isopropyl-1H-indol-5-yl) piperidin-1-yl)-2-oxoethyl) oxazolidin-2-one (164); 1-(4-(2-(2,6-dimethylpyridin-4-yl)-3-isopropyl-1H-indol-5-yl) piperidin-1-yl)-2-(1H-tetrazol-1-yl)ethan-1-one (165); 1-(4-(2-(2,6-dimethylpyridin-4-yl)-3-isopropyl-1H-indol-5-yl)piperidin-1-yl)-2-(1,1-dioxido-1,2-thiazinan-2-yl)ethan-1-one (167); (R)-3-amino-1-(2-(4-(2-(2,6-dimethylpyridin-4-yl)-3-isopropyl-1H-indol-5-yl) piperidin-1-yl)-2-oxoethyl) pyrrolidin-2-one (168); (S)-1-(2-(4-(2-(2,6-dimethylpyridin-4-yl)-3-isopropyl-1H-indol-5-yl)piperidin-1-yl)-2-oxoethyl)-4-hydroxypyrrolidin-2-one (169); 1-(4-(2-(2,6-dimethylpyridin-4-yl)-3-isopropyl-1H-indol-5-yl) piperidin-1-yl)-2-(1H-1,2,4-triazol-1-yl)ethan-1-one (170); 1-(4-(2-(2,6-dimethylpyridin-4-yl)-3-isopropyl-1H-indol-5-yl)piperidin-1-yl)-2-(4-(2-hydroxyethyl)piperazin-1-yl) ethan-1-one (171); (1-(dimethylamino)cyclopropyl)(4-(2-(2,6-dimethylpyridin-4-yl)-3-isopropyl-1H-indol-5-yl)piperidin-1-yl)methanone (172); (1,4-dimethylpiperidin-4-yl)(4-(2-(2,6-dimethylpyridin-4-yl)-3-isopropyl-1H-indol-5-yl)piperidin-1-yl)methanone (176); (4-(2-(2,6-dimethylpyridin-4-yl)-3-isopropyl-1H-indol-5-yl)piperidin-1-yl)(1-isopropyl-4-methylpiperidin-4-yl)methanone (177); (4-(2-(2,6-dimethylpyridin-4-yl)-3-isopropyl-1H-indol-5-yl)piperidin-1-yl)(piperidin-4-yl)methanone (178); (S)-azetidin-2-yl(4-(2-(2,6-dimethylpyridin-4-yl)-3-isopropyl-1H-indol-5-yl)piperidin-1-yl)methanone (180); (4-(2-(2,6-dimethylpyridin-4-yl)-3-isopropyl-1H-indol-5-yl)piperidin-1-yl)(pyrrolidin-3-yl) methanone (181 and 182); (4-(2-(2,6-dimethylpyridin-4-yl)-3-isopropyl-1H-indol-5-yl) piperidin-1-yl)((2S,3R)-3-hydroxypyrrolidin-2-yl)methanone (185); (4-(2-(2,6-dimethylpyridin-4-yl)-3-isopropyl-1H-indol-5-yl)piperidin-1-yl)(pyrrolidin-3-yl) methanone (186); (S)-3-amino-1-(2-(4-(2-(2,6-dimethylpyridin-4-yl)-3-isopropyl-1H-indol-5-yl)piperidin-1-yl)-2-oxoethyl)pyrrolidin-2-one (188); (S)-(4,4-difluoropyrrolidin-2-yl)(4-(2-(2,6-dimethylpyridin-4-yl)-3-isopropyl-1H-indol-5-yl)piperidin-1-yl) methanone (189); (4-(2-(2,6-dimethylpyridin-4-yl)-3-isopropyl-1H-indol-5-yl)piperidin-1-yl)((2S,4R)-4-fluoropyrrolidin-2-yl)methanone (190); (R)-(4-(2-(2,6-dimethylpyridin-4-yl)-3-isopropyl-1H-indol-5-yl)piperidin-1-yl)(2-methylpyrrolidin-2-yl)methanone (192); (R)-1-(4-(2-(2,6-dimethylpyridin-4-yl)-3-isopropyl-1H-indol-5-yl) piperidin-1-yl)-2-(pyrrolidin-2-yl)ethan-1-one (193); (1-aminocyclopropyl)(4-(2-(2,6-dimethylpyridin-4-yl)-3-isopropyl-1H-indol-5-yl)piperidin-1-yl)methanone (195); (4-(2-(2,6-dimethylpyridin-4-yl)-3-isopropyl-1H-indol-5- yl)piperidin-1-yl)((2S,4S)-4-fluoropyrrolidin-2-yl)methanone (196); (4-(2-(2,6-dimethylpyridin-4-yl)-3-isopropyl-1H-indol-5-yl)piperidin-1-yl)(4-methylpiperidin-4-yl) methanone (197); (4-(2-(2,6-dimethylpyridin-4-yl)-3-isopropyl-1H-indol-5-yl)piperidin-1-yl)(tetrahydro-2H-pyran-4-yl)methanone (198); (4-(2-(2,6-dimethylpyridin-4-yl)-3-isopropyl-1H-indol-5-yl) piperidin-1-yl)(tetrahydrofuran-3-yl)methanone (199); (4-(2-(2,6-dimethylpyridin-4-yl)-3-isopropyl-1H-indol-5-yl)piperidin-1-yl)(2-isopropyltetrahydro-2H-pyran-4-yl) methanone (200); (4-(2-(2,6-dimethylpyridin-4-yl)-3-isopropyl-1H-indol-5-yl)piperidin-1-yl)(thiazol-4-yl)methanone (201); (4-(2-(2,6-dimethylpyridin-4-yl)-3-isopropyl-1H-indol-5-yl) piperidin-1-yl)(isoxazol-3-yl)methanone (203); (4-(2-(2,6-dimethylpyridin-4-yl)-3-isopropyl-1H-indol-5-yl)piperidin-1-yl)(3-methyloxetan-3-yl)methanone (207); 2-(4-(2-(2,6-dimethylpyridin-4-yl)-3-isopropyl-1H-indol-5-yl)piperidin-1-yl)-1-(piperidin-1-yl)ethan-1-one (208); (R)-2-(4-(2-(2,6-dimethylpyridin-4-yl)-3-isopropyl-1H-indol-5-yl)piperidin-1-yl)-1-(3-hydroxypiperidin-1-yl)ethan-1-one (209); (S)-2-(4-(2-(2,6-dimethylpyridin-4-yl)-3-isopropyl-1H-indol-5-yl)piperidin-1-yl)-1-(3-hydroxypiperidin-1-yl)ethan-1-one (210); 2-(4-(2-(2,6-dimethylpyridin-4-yl)-3-isopropyl-1H-indol-5-yl) piperidin-1-yl)-N-((1r,4r)-4-hydroxycyclohexyl) acetamide (211); N-cyclopropyl-2-(4-(2-(2,6-dimethylpyridin-4-yl)-3-isopropyl-1H-indol-5-yl)piperidin-1-yl) acetamide (212); N-cyclobutyl-2-(4-(2-(2,6-dimethylpyridin-4-yl)-3-isopropyl-1H-indol-5-yl)piperidin-1-yl) acetamide (213); 1-(3,3-difluoroazetidin-1-yl)-2-(4-(2-(2,6-dimethylpyridin-4-yl)-3-isopropyl-1H-indol-5-yl) piperidin-1-yl)ethan-1-one (215); 1-(3,3-difluoropyrrolidin-1-yl)-2-(4-(2-(2,6-dimethylpyridin-4-yl)-3-isopropyl-1H-indol-5-yl)piperidin-1-yl)ethan-1-one (216); N-(cyclopropylmethyl)-2-(4-(2-(2,6-dimethylpyridin-4-yl)-3-isopropyl-1H-indol-5-yl)piperidin-1-yl)acetamide (223); N-(adamantan-1-yl)-2-(4-(2-(2,6-dimethylpyridin-4-yl)-3-isopropyl-1H-indol-5-yl)piperidin-1-yl)acetamide (224); 2-(4-(2-(2,6-dimethylpyridin-4-yl)-3-isopropyl-1H-indol-5-yl)piperidin-1-yl)-N-((1r,3 s,5R,7S)-3-hydroxyadamantan-1-yl)acetamide (225); 2-(4-(2-(2,6-dimethylpyridin-4-yl)-3-isopropyl-1H-indol-5-yl)piperidin-1-yl)-1-(3-methoxyazetidin-1-yl)ethan-1-one (226); 1-(azetidin-1-yl)-2-(4-(2-(2,6-dimethylpyridin-4-yl)-3-isopropyl-1H-indol-5-yl)piperidin-1-yl)ethan-1-one (227); 2-(4-(2-(2,6-dimethylpyridin-4-yl)-3-isopropyl-1H-indol-5-yl) piperidin-1-yl)-1-(3-hydroxyazetidin-1-yl)ethan-1-one (229); 2-(4-(2-(2,6-dimethylpyridin-4-yl)-3-isopropyl-1H-indol-5-yl)piperidin-1-yl)-1-(4-hydroxypiperidin-1-yl) ethan-1-one (230); 2-(4-(2-(2,6-dimethylpyridin-4-yl)-3-isopropyl-1H-indol-5-yl) piperidin-1-yl)-1-morpholinoethan-1-one (232); 2-(4-(2-(2,6-dimethylpyridin-4-yl)-3-isopropyl-1H-indol-5-yl)piperidin-1-yl)-N-(3-methyloxetan-3-yl)acetamide (233); 2-(4-(2-(2,6-dimethylpyridin-4-yl)-3-isopropyl-1H-indol-5-yl) piperidin-1-yl)-1-(piperidin-1-yl)ethan-1-one (241); 2-(4-(2-(2,6-dimethylpyridin-4-yl)-3-isopropyl-1H-indol-5-yl) piperidin-1-yl)-1-(pyrrolidin-1-yl)ethan-1-one (242); 2-(4-(2-(2,6-dimethylpyridin-4-yl)-3-isopropyl-1H-indol-5-yl) piperidin-1-yl)-N-(1-methylcyclobutyl)acetamide (243); N-cyclopropyl-2-(4-(2-(2,6-dimethylpyridin-4-yl)-3-isopropyl-1H-indol-5-yl)piperidin-1-yl)-N-methylacetamide (248); 1-(3,3-dimethylpiperidin-1-yl)-2-(4-(2-(2,6-dimethylpyridin-4-yl)-3-isopropyl-1H-indol-5-yl)piperidin-1-yl) ethan-1-one (249); 2-(4-(2-(2,6-dimethylpyridin-4-yl)-3-isopropyl-1H-indol-5-yl)piperidin-1-yl)-N-(1-methylcyclopropyl)acetamide (251); 2-(4-(2-(2,6-dimethylpyridin-4-yl)-3-isopropyl-1H-indol-5-yl)piperidin-1-yl)-N-((1-methylcyclopropyl)methyl)acetamide (255); 2-(4-(2-(2,6-dimethylpyridin-4-yl)-3-isopropyl-1H-indol-5-yl)piperidin-1-yl)-1-(2-oxa-6-azaspiro[3.3]heptan-6-yl) ethan-1-one (256); 1-(4,4-difluoropiperidin-1-yl)-2-(4-(2-(2,6-dimethylpyridin-4-yl)-3-isopropyl-1H-indol-5-yl) piperidin-1-yl)ethan-1-one (257); 2-(4-(2-(2,6-dimethylpyridin-4-yl)-3-isopropyl-1H-indol-5-yl)piperidin-1-yl)-1-(3-fluoropiperidin-1-yl)ethan-1-one (258); 2-(4-(2-(2,6-dimethylpyridin-4-yl)-3-isopropyl-1H-indol-5-yl) piperidin-1-yl)-1-(2-methylpyrrolidin-1-yl)ethan-1-one (259); 2-(4-(2-(2,6-dimethylpyridin-4-yl)-3-isopropyl-1H-indol-5-yl)piperidin-1-yl)-1-(2,5-dimethylpyrrolidin-1-yl) ethan-1-one (261); (S)-2-(4-(2-(2,6-dimethylpyridin-4-yl)-3-isopropyl-1H-indol-5-yl)piperidin-1-yl)-1-(2-(methoxymethyl)pyrrolidin-1-yl)ethan-1-one (263); 2-(4-(2-(2,6-dimethylpyridin-4-yl)-3-isopropyl-1H-indol-5-yl) piperidin-1-yl)-N-(2-methyl-2-morpholinopropyl) acetamide (264); 2-(4-(2-(2,6-dimethylpyridin-4-yl)-3-isopropyl-1H-indol-5-yl)piperidin-1-yl)-1-(4-(2-methoxyethyl)piperazin-1-yl)ethan-1-one (265); 2-(4-(2-(2,6-dimethylpyridin-4-yl)-3-isopropyl-1H-indol-5-yl) piperidin-1-yl)-N-((tetrahydrofuran-2-yl)methyl)acetamide (266); 2-(4-(2-(2,6-dimethylpyridin-4-yl)-3-isopropyl-1H-indol-5-yl)piperidin-1-yl)-N-(4-methyltetrahydro-2H-pyran-4-yl)acetamide (267); 2-(4-(2-(2,6-dimethylpyridin-4-yl)-3-isopropyl-1H-indol-5-yl)piperidin-1-yl)-1-(4-methylpiperidin-1-yl)ethan-1-one (269); 2-(4-(2-(2,6-dimethylpyridin-4-yl)-3-isopropyl-1H-indol-5-yl)piperidin-1-yl)-1-(2-methylpiperidin-1-yl)ethan-1-one (270); 2-(4-(2-(2,6-dimethylpyridin-4-yl)-3-isopropyl-1H-indol-5-yl) piperidin-1-yl)-1-(3-methylpiperidin-1-yl)ethan-1-one (271); 4-(2-(4-(2-(2,6-dimethylpyridin-4-yl)-3-isopropyl-1H-indol-5-yl) piperidin-1-yl)acetyl)piperazin-2-one (272); (S)-2-(4-(2-(2,6-dimethylpyridin-4-yl)-3-isopropyl-1H-indol-5-yl)piperidin-1-yl)-1-(3-hydroxypyrrolidin-1-yl)ethan-1-one (273); (S)-2-(4-(2-(2,6-dimethylpyridin-4-yl)-3-isopropyl-1H-indol-5-yl)piperidin-1-yl)-1-(2-(hydroxymethyl) pyrrolidin-1-yl)ethan-1-one (274); (R)-2-(4-(2-(2,6-dimethylpyridin-4-yl)-3-isopropyl-1H-indol-5-yl)piperidin-1-yl)-1-(3-hydroxypyrrolidin-1-yl)ethan-1-one (275); 2-(4-(2-(2,6-dimethylpyridin-4-yl)-3-isopropyl-1H-indol-5-yl) piperidin-1-yl)-1-(3-hydroxypiperidin-1-yl)ethan-1-one (277); N-cyclohexyl-2-(4-(2-(2,6-dimethylpyridin-4-yl)-3-isopropyl-1H-indol-5-yl)piperidin-1-yl)-N-methylacetamide (278); 2-(4-(2-(2,6-dimethylpyridin-4-yl)-3-isopropyl-1H-indol-5-yl)piperidin-1-yl)-N-(tetrahydro-2H-pyran-3-yl)acetamide (279); 2-(4-(2-(2,6-dimethylpyridin-4-yl)-3-isopropyl-1H-indol-5-yl)piperidin-1-yl)-N-(tetrahydro-2H-pyran-4-yl)acetamide (280); 2-(4-(2-(2,6-dimethylpyridin-4-yl)-3-isopropyl-1H-indol-5-yl)piperidin-1-yl)-1-(1,1-dioxidothiomorpholino)ethan-1-one (281); 2-(4-(2-(2,6-dimethylpyridin-4-yl)-3-isopropyl-1H-indol-5-yl)piperidin-1-yl)-N-(tetrahydrofuran-3-yl)acetamide (282); 2-(4-(2-(2,6-dimethylpyridin-4-yl)-3-isopropyl-1H-indol-5-yl) piperidin-1-yl)-1-(4-fluoropiperidin-1-yl)ethan-1-one (283); 1-(3-oxa-8-azabicyclo[3.2.1]octan-8-yl)-2-(4-(2-(2,6-dimethylpyridin-4-yl)-3-isopropyl-1H-indol-5-yl)piperidin-1-yl)ethan-1-one (284); 1-(3,3-difluoropiperidin-1-yl)-2-(4-(2-(2,6-dimethylpyridin-4-yl)-3-isopropyl-1H-indol-5-yl) piperidin-1-yl)ethan-1-one (285); 2-(4-(2-(2,6-dimethylpyridin-4-yl)-3-isopropyl-1H-indol-5-yl)piperidin-1-yl)-1-(2-oxa-7-azaspiro[3.5]nonan-7-yl)ethan-1-one (286); 2-(4-(2-(2,6-dimethylpyridin-4-yl)-3-isopropyl-1H-indol-5-yl)piperidin-1-yl)-N-methyl-N-(tetrahydro-2H-pyran-4-yl)acetamide (287); 2-(4-(2-(2,6-dimethylpyridin-4-yl)-3-isopropyl-1H-indol-5-yl)piperidin-1-yl)-N-(3-hydroxypropyl)-N-methylacetamide (288); 2-(4-(2-(2,6- dimethylpyridin-4-yl)-3-isopropyl-1H-indol-5-yl)piperidin-1-yl)-N-methyl-N-(tetrahydrofuran-3-yl)acetamide (289); 2-(4-(2-(2,6-dimethylpyridin-4-yl)-3-isopropyl-1H-indol-5-yl)piperidin-1-yl)-1-((2R,4R)-2-(hydroxymethyl)-4-methylpyrrolidin-1-yl) ethan-1-one (290); 2-(4-(2-(2,6-dimethylpyridin-4-yl)-3-isopropyl-1H-indol-5-yl) piperidin-1-yl)-1-((2S,4S)-2-(hydroxymethyl)-4-(trifluoromethyl)pyrrolidin-1-yl)ethan-1-one (291); 2-(4-(2-(2,6-dimethylpyridin-4-yl)-3-isopropyl-1H-indol-5-yl)piperidin-1-yl)-1-((2R,4R)-2-(hydroxymethyl)-4-methoxypyrrolidin-1-yl)ethan-1-one (292); N-benzyl-2-(4-(2-(2,6-dimethylpyridin-4-yl)-3-isopropyl-1H-indol-5-yl)piperidin-1-yl)-N-(2-hydroxyethyl)acetamide (293); 2-(4-(2-(2,6-dimethylpyridin-4-yl)-3-isopropyl-1H-indol-5-yl)piperidin-1-yl)-N-(2-hydroxy-2-phenylethyl)-N-methylacetamide (296); 2-(4-(2-(2,6-dimethylpyridin-4-yl)-3-isopropyl-1H-indol-5-yl)piperidin-1-yl)-N-(4-fluorobenzyl)-N-(2-hydroxyethyl)acetamide (300); 2-(4-(2-(2,6-dimethylpyridin-4-yl)-3-isopropyl-1H-indol-5-yl)piperidin-1-yl)-1-((2R,4R)-2-(hydroxymethyl)-4-(trifluoromethyl)pyrrolidin-1-yl)ethan-1-one (301); (R)-2-(4-(2-(2,6-dimethylpyridin-4-yl)-3-isopropyl-1H-indol-5-yl)piperidin-1-yl)-1-(2-(hydroxymethyl)pyrrolidin-1-yl)ethan-1-one (302); 2-(4-(2-(2,6-dimethylpyridin-4-yl)-3-isopropyl-1H-indol-5-yl) piperidin-1-yl)-N-(2-(1-hydroxycyclopentyl)ethyl)-N-methylacetamide (303); (R)-2-(4-(2-(2,6-dimethylpyridin-4-yl)-3-isopropyl-1H-indol-5-yl)piperidin-1-yl)-1-(3-(hydroxymethyl)morpholino)ethan-1-one (304); (S)-1-(4,4-difluoro-2-(hydroxymethyl)pyrrolidin-1-yl)-2-(4-(2-(2,6-dimethylpyridin-4-yl)-3-isopropyl-1H-indol-5-yl)piperidin-1-yl)ethan-1-one (306); (S)-2-(4-(2-(2,6-dimethylpyridin-4-yl)-3-isopropyl-1H-indol-5-yl)piperidin-1-yl)-N-methyl-N-(tetrahydrofuran-3-yl)acetamide (307); 5-(1-benzylpiperidin-4-yl)-2-(2,6-dimethylpyridin-4-yl)-3-isopropyl-1H-indole (318); (3-((4-(2-(2,6-dimethylpyridin-4-yl)-3-isopropyl-1H-indol-5-yl)piperidin-1-yl)methyl)oxetan-3-yl)methanol (319); 4-benzyl-2-((4-(2-(2,6-dimethylpyridin-4-yl)-3-isopropyl-1H-indol-5-yl)piperidin-1-yl)methyl)morpholine (320); 5-(1-cyclopentylpiperidin-4-yl)-2-(2,6-dimethylpyridin-4-yl)-3-isopropyl-1H-indole (326); 5-(1-(cyclohexylmethyl)piperidin-4-yl)-2-(2,6-dimethylpyridin-4-yl)-3-isopropyl-1H-indole (328); 2-(2,6-dimethylpyridin-4-yl)-3-isopropyl-5-(1-(oxetan-3-ylmethyl)piperidin-4-yl)-1H-indole (333); 2-(cyclobutylamino)-1-(4-(2-(2,6-dimethylpyridin-4-yl)-3-isopropyl-1H-indol-5-yl) piperidin-1-yl)ethan-1-one (334); 2-((cyclopropylmethyl)amino)-1-(4-(2-(2,6-dimethylpyridin-4-yl)-3-isopropyl-1H-indol-5-yl)piperidin-1-yl)ethan-1-one (339); 2-(3,3-difluoroazetidin-1-yl)-1-(4-(2-(2,6-dimethylpyridin-4-yl)-3-isopropyl-1H-indol-5-yl)piperidin-1-yl)ethan-1-one (340); 2-(3,3-difluoropyrrolidin-1-yl)-1-(4-(2-(2,6-dimethylpyridin-4-yl)-3-isopropyl-1H-indol-5-yl)piperidin-1-yl)ethan-1-one (341); 2-(adamantan-1-ylamino)-1-(4-(2-(2,6-dimethylpyridin-4-yl)-3-isopropyl-1H-indol-5-yl) piperidin-1-yl)ethan-1-one (342); 1-(4-(2-(2,6-dimethylpyridin-4-yl)-3-isopropyl-1H-indol-5-yl)piperidin-1-yl)-2-((3-hydroxyadamantan-1-yl)amino)ethan-1-one (343); 1-(4-(2-(2,6-dimethylpyridin-4-yl)-3-isopropyl-1H-indol-5-yl)piperidin-1-yl)-2-morpholinoethan-1-one (350); 1-(4-(2-(2,6-dimethylpyridin-4-yl)-3-isopropyl-1H-indol-5-yl)piperidin-1-yl)-2-(piperidin-1-yl)ethan-1-one (351); 1-(4-(2-(2,6-dimethylpyridin-4-yl)-3-isopropyl-1H-indol-5-yl)piperidin-1-yl)-2-(pyrrolidin-1-yl)ethan-1-one (352); 1-(4-(2-(2,6-dimethylpyridin-4-yl)-3-isopropyl-1H-indol-5-yl)piperidin-1-yl)-2-((1-methylcyclobutyl)amino)ethan-1-one (353); 2-(cyclopropyl(methyl)amino)-1-(4-(2-(2,6-dimethylpyridin-4-yl)-3-isopropyl-1H-indol-5-yl)piperidin-1-yl)ethan-1-one (357); 2-(3,3-dimethylpiperidin-1-yl)-1-(4-(2-(2,6-dimethylpyridin-4-yl)-3-isopropyl-1H-indol-5-yl)piperidin-1-yl)ethan-1-one (358); 1-(4-(2-(2,6-dimethylpyridin-4-yl)-3-isopropyl-1H-indol-5-yl)piperidin-1-yl)-2-((1-methylcyclopropyl)amino)ethan-1-one (360); 1-(4-(2-(2,6-dimethylpyridin-4-yl)-3-isopropyl-1H-indol-5-yl)piperidin-1-yl)-2-((1-methylcyclobutyl)amino)ethan-1-one (361); 2-(4,4-difluoropiperidin-1-yl)-1-(4-(2-(2,6-dimethylpyridin-4-yl)-3-isopropyl-1H-indol-5-yl)piperidin-1-yl)ethan-1-one (362); 1-(4-(2-(2,6-dimethylpyridin-4-yl)-3-isopropyl-1H-indol-5-yl)piperidin-1-yl)-2-(3-fluoropiperidin-1-yl) ethan-1-one (363); 1-(4-(2-(2,6-dimethylpyridin-4-yl)-3-isopropyl-1H-indol-5-yl)piperidin-1-yl)-2-(2-oxa-6-azaspiro[3.3]heptan-6-yl)ethan-1-one (364); 1-(4-(2-(2,6-dimethylpyridin-4-yl)-3-isopropyl-1H-indol-5-yl)piperidin-1-yl)-2-(((1-methylcyclopropyl)methyl)amino)ethan-1-one (365); 1-(4-(2-(2,6-dimethylpyridin-4-yl)-3-isopropyl-1H-indol-5-yl)piperidin-1-yl)-2-(2-methylpyrrolidin-1-yl) ethan-1-one (366); 1-(4-(2-(2,6-dimethylpyridin-4-yl)-3-isopropyl-1H-indol-5-yl)piperidin-1-yl)-2-(2,5-dimethylpyrrolidin-1-yl)ethan-1-one (368); (S)-1-(4-(2-(2,6-dimethylpyridin-4-yl)-3-isopropyl-1H-indol-5-yl)piperidin-1-yl)-2-(2-(methoxymethyl)pyrrolidin-1-yl)ethan-1-one (370); 1-(4-(2-(2,6-dimethylpyridin-4-yl)-3-isopropyl-1H-indol-5-yl)piperidin-1-yl)-2-((2-methyl-2-morpholinopropyl)amino)ethan-1-one (371); 1-(4-(2-(2,6-dimethylpyridin-4-yl)-3-isopropyl-1H-indol-5-yl)piperidin-1-yl)-2-(4-(2-methoxyethyl) piperazin-1-yl)ethan-1-one (372); 1-(4-(2-(2,6-dimethylpyridin-4-yl)-3-isopropyl-1H-indol-5-yl)piperidin-1-yl)-2-(((tetrahydrofuran-2-yl)methyl)amino)ethan-1-one (373); 1-(4-(2-(2,6-dimethylpyridin-4-yl)-3-isopropyl-1H-indol-5-yl)piperidin-1-yl)-2-((4-methyltetrahydro-2H-pyran-4-yl)amino)ethan-1-one (374); 1-(4-(2-(2,6-dimethylpyridin-4-yl)-3-isopropyl-1H-indol-5-yl)piperidin-1-yl)-2-(4-methylpiperidin-1-yl)ethan-1-one (376); 1-(4-(2-(2,6-dimethylpyridin-4-yl)-3-isopropyl-1H-indol-5-yl)piperidin-1-yl)-2-(2-methylpiperidin-1-yl)ethan-1-one (377); 1-(4-(2-(2,6-dimethylpyridin-4-yl)-3-isopropyl-1H-indol-5-yl)piperidin-1-yl)-2-(3-methylpiperidin-1-yl)ethan-1-one (378); 4-(2-(4-(2-(2,6-dimethylpyridin-4-yl)-3-isopropyl-1H-indol-5-yl)piperidin-1-yl)-2-oxoethyl) piperazin-2-one (379); (S)-1-(4-(2-(2,6-dimethylpyridin-4-yl)-3-isopropyl-1H-indol-5-yl)piperidin-1-yl)-2-(3-hydroxypyrrolidin-1-yl)ethan-1-one (380); (S)-1-(4-(2-(2,6-dimethylpyridin-4-yl)-3-isopropyl-1H-indol-5-yl)piperidin-1-yl)-2-(2-(hydroxymethyl) pyrrolidin-1-yl)ethan-1-one (381); 1-(4-(2-(2,6-dimethylpyridin-4-yl)-3-isopropyl-1H-indol-5-yl)piperidin-1-yl)-2-(3-hydroxypiperidin-1-yl) ethan-1-one (383); 2-(cyclohexyl (methyl)amino)-1-(4-(2-(2,6-dimethylpyridin-4-yl)-3-isopropyl-1H-indol-5-yl) piperidin-1-yl)ethan-1-one (384); 1-(4-(2-(2,6-dimethylpyridin-4-yl)-3-isopropyl-1H-indol-5-yl) piperidin-1-yl)-2-((tetrahydro-2H-pyran-3-yl)amino)ethan-1-one (385); 1-(4-(2-(2,6-dimethylpyridin-4-yl)-3-isopropyl-1H-indol-5-yl)piperidin-1-yl)-2-((tetrahydro-2H-pyran-4-yl)amino)ethan-1-one (386); 1-(4-(2-(2,6-dimethylpyridin-4-yl)-3-isopropyl-1H-indol-5-yl)piperidin-1-yl)-2-((tetrahydrofuran-3-yl)amino)ethan-1-one (387); 1-(4-(2-(2,6-dimethylpyridin-4-yl)-3-isopropyl-1H-indol-5-yl)piperidin-1-yl)-2-(4-fluoropiperidin-1-yl)ethan-1-one (388); 2-(8-oxa-3-azabicyclo[3.2.1]octan-3-yl)-1-(4-(2-(2,6-dimethylpyridin-4-yl)-3-isopropyl-1H-indol-5-yl)piperidin-1-yl)ethan-1-one (389); 2-(3,3-difluoropiperidin-1-yl)-1-(4-(2-(2,6-dimethylpyridin-4-yl)-3-isopropyl-1H-indol-5-yl)piperidin-1-yl)ethan-1-one (390); (R)-1-(4-(2-(2,6-dimethylpyridin-4-yl)-3-isopropyl-1H-indol-5-yl)piperidin-1-yl)-2-(3-hydroxypyrrolidin-1-yl)ethan-1-one (391); 1-(4-

(2-(2,6-dimethylpyridin-4-yl)-3-isopropyl-1H-indol-5-yl)piperidin-1-yl)-2-((2S,4S)-2-(hydroxymethyl)-4-(trifluoromethyl)pyrrolidin-1-yl)ethan-1-one (394); 1-(4-(2-(2,6-dimethylpyridin-4-yl)-3-isopropyl-1H-indol-5-yl)piperidin-1-yl)-2-((2R,4R)-2-(hydroxymethyl)-4-methoxypyrrolidin-1-yl)ethan-1-one (395); 2-(benzyl(2-hydroxyethyl)amino)-1-(4-(2-(2,6-dimethylpyridin-4-yl)-3-isopropyl-1H-indol-5-yl) piperidin-1-yl)ethan-1-one (396); 1-(4-(2-(2,6-dimethylpyridin-4-yl)-3-isopropyl-1H-indol-5-yl)piperidin-1-yl)-2-((2-hydroxy-2-phenylethyl)(methyl)amino)ethan-1-one (399); (R)-1-(4-(2-(2,6-dimethylpyridin-4-yl)-3-isopropyl-1H-indol-5-yl)piperidin-1-yl)-2-(3-(hydroxymethyl)morpholino)ethan-1-one (400); (R)-1-(4-(2-(2,6-dimethylpyridin-4-yl)-3-isopropyl-1H-indol-5-yl)piperidin-1-yl)-2-(methyl(tetrahydrofuran-3-yl)amino)ethan-1-one (402); (S)-2-(4,4-difluoro-2-(hydroxymethyl)pyrrolidin-1-yl)-1-(4-(2-(2,6-dimethylpyridin-4-yl)-3-isopropyl-1H-indol-5-yl)piperidin-1-yl)ethan-1-one (403); 1-(4-(2-(2,6-dimethylpyridin-4-yl)-3-isopropyl-1H-indol-5-yl)piperidin-1-yl)-2-((2R)-2-(hydroxymethyl)-4-(trifluoromethyl)pyrrolidin-1-yl)ethan-1-one (404); (S)-1-(4-(2-(2,6-dimethylpyridin-4-yl)-3-isopropyl-1H-indol-5-yl)piperidin-1-yl)-2-(3-(hydroxymethyl) morpholino)ethan-1-one (405); 1-(4-(2-(2,6-dimethylpyridin-4-yl)-3-isopropyl-1H-indol-5-yl)piperidin-1-yl)-2-((4-fluorobenzyl)(2-hydroxyethyl)amino)ethan-1-one (407); 1-(4-(2-(2,6-dimethylpyridin-4-yl)-3-isopropyl-1H-indol-5-yl)piperidin-1-yl)-2-((2-(1-hydroxycyclopentyl)ethyl)(methyl)amino)ethan-1-one (408); 1-(4-(2-(2,6-dimethylpyridin-4-yl)-3-isopropyl-1H-indol-5-yl)piperidin-1-yl)-2-((2S,4S)-4-fluoro-2-(hydroxymethyl)pyrrolidin-1-yl)ethan-1-one (409); 1-(4-(2-(2,6-dimethylpyridin-4-yl)-3-isopropyl-1H-indol-5-yl)piperidin-1-yl)-2-((2R,4R)-2-(hydroxymethyl)-4-methylpyrrolidin-1-yl)ethan-1-one (410); (R)-1-(4-(2-(2,6-dimethylpyridin-4-yl)-3-isopropyl-1H-indol-5-yl)piperidin-1-yl)-2-(2-(hydroxymethyl)pyrrolidin-1-yl)ethan-1-one (412); 1-(4-(2-(2,6-dimethylpyridin-4-yl)-3-isopropyl-1H-indol-5-yl)piperidin-1-yl)-2-(methyl(tetrahydrofuran-3-yl)amino)ethan-1-one (413); 1-(4-(2-(2,6-dimethylpyridin-4-yl)-3-isopropyl-1H-indol-5-yl)piperidin-1-yl)-2-(methyl(oxetan-3-yl)amino)ethan-1-one (416); 1-(4-(2-(2,6-dimethylpyridin-4-yl)-3-isopropyl-1H-indol-5-yl)piperidin-1-yl)-2-(methyl((5-methylisoxazol-3-yl)methyl)amino)ethan-1-one (417); 1-(4-(2-(2,6-dimethylpyridin-4-yl)-3-isopropyl-1H-indol-5-yl)piperidin-1-yl)-2-(((2-methoxypyrimidin-5-yl)methyl)(methyl)amino)ethan-1-one (418); 1-(4-(2-(2,6-dimethylpyridin-4-yl)-3-isopropyl-1H-indol-5-yl)piperidin-1-yl)-2-(methyl((1-methyl-1H-1,2,4-triazol-3-yl)methyl)amino)ethan-1-one (419); 5-(1-((1H-imidazol-4-yl)methyl) piperidin-4-yl)-2-(2,6-dimethylpyridin-4-yl)-3-isopropyl-1H-indole (425); 2-(2,6-dimethylpyridin-4-yl)-3-isopropyl-5-(1-((2-methyl-1H-imidazol-4-yl)methyl)piperidin-4-yl)-1H-indole (426); 2-(2,6-dimethylpyridin-4-yl)-3-isopropyl-5-(1'-isopropyl-[1,4'-bipiperidin]-4-yl)-1H-indole (427); 2-(2,6-dimethyl-pyridin-4-yl)-3-isopropyl-5-(1-((2-methoxypyrimidin-5-yl)methyl)piperidin-4-yl)-1H-indole (430); 2-(2,6-dimethylpyridin-4-yl)-3-isopropyl-5-(1-(pyridin-2-ylmethyl)piperidin-4-yl)-1H-indole (431); 3-((4-(2-(2,6-dimethylpyridin-4-yl)-3-isopropyl-1H-indol-5-yl)piperidin-1-yl)methyl)isoxazole (432); 2-(2,6-dimethylpyridin-4-yl)-3-isopropyl-5-(1-(pyridin-3-ylmethyl)piperidin-4-yl)-1H-indole (433); 2-(2,6-dimethylpyridin-4-yl)-3-isopropyl-5-(1-(pyrimidin-5-ylmethyl) piperidin-4-yl)-1H-indole (434); 2-(2,6-dimethylpyridin-4-yl)-3-isopropyl-5-(1-(pyridin-4-ylmethyl)piperidin-4-yl)-1H-indole (435); 2-(2,6-dimethyl-pyridin-4-yl)-3-isopropyl-5-(1-((6-methylpyridin-3-yl)methyl)piperidin-4-yl)-1H-indole (437); 5-(1-((1H-pyrazol-4-yl)methyl)piperidin-4-yl)-2-(2,6-dimethylpyridin-4-yl)-3-isopropyl-1H-indole (438); 2-(2,6-dimethylpyridin-4-yl)-3-isopropyl-5-(1-((3-methyl-1H-pyrazol-4-yl)methyl) piperidin-4-yl)-1H-indole (439); 2-(2,6-dimethylpyridin-4-yl)-3-isopropyl-5-(1-((1-methyl-1H-pyrazol-4-yl)methyl) piperidin-4-yl)-1H-indole (440); 5-(1-((1H-pyrazol-5-yl)methyl)piperidin-4-yl)-2-(2,6-dimethylpyridin-4-yl)-3-isopropyl-1H-indole (441); 2-(2,6-dimethylpyridin-4-yl)-3-isopropyl-5-(1-((1-methyl-1H-1,2,3-triazol-4-yl)methyl)piperidin-4-yl)-1H-indole (442); 3-((4-(2-(2,6-dimethyl-pyridin-4-yl)-3-isopropyl-1H-indol-5-yl)piperidin-1-yl)methyl)-5-methylisoxazole (443); 5-((4-(2-(2,6-dimethyl-pyridin-4-yl)-3-isopropyl-1H-indol-5-yl)piperidin-1-yl)methyl)thiazole (444); 2-(2,6-dimethylpyridin-4-yl)-3-isopropyl-5-(1-((1-methyl-1H-pyrazol-3-yl)methyl)piperidin-4-yl)-1H-indole (445); 5-(1-((1H-1,2,3-triazol-4-yl)methyl)piperidin-4-yl)-2-(2,6-dimethylpyridin-4-yl)-3-isopropyl-1H-indole (446); 5-(1-((4,6-dimethoxypyrimidin-2-yl)methyl)piperidin-4-yl)-2-(2,6-dimethylpyridin-4-yl)-3-isopropyl-1H-indole (447); 2-cyclopropyl-5-((4-(2-(2,6-dimethylpyridin-4-yl)-3-isopropyl-1H-indol-5-yl)piperidin-1-yl)methyl)-1,3,4-oxadiazole (448); 2-((4-(2-(2,6-dimethylpyridin-4-yl)-3-isopropyl-1H-indol-5-yl)piperidin-1-yl)methyl)oxazole (449); 2-(2,6-dimethylpyridin-4-yl)-3-isopropyl-5-(1-(tetrahydro-2H-pyran-4-yl)piperidin-4-yl)-1H-indole (450); 2-(2,6-dimethylpyridin-4-yl)-3-isopropyl-5-(1-((1-methyl-1H-1,2,4-triazol-3-yl)methyl) piperidin-4-yl)-1H-indole (451); 2-(2,6-dimethylpyridin-4-yl)-3-isopropyl-5-(1-(oxetan-3-yl)piperidin-4-yl)-1H-indole (452); 2-(2,6-dimethylpyridin-4-yl)-5-(1-(2,2-dimethyltetrahydro-2H-pyran-4-yl)piperidin-4-yl)-3-isopropyl-1H-indole (453); 2-(2,6-dimethylpyridin-4-yl)-5-(1-(2,6-dimethyltetrahydro-2H-pyran-4-yl)piperidin-4-yl)-3-isopropyl-1H-indole (454); 2-(2,6-dimethylpyridin-4-yl)-5-(1-(2,6-dimethyltetrahydro-2H-pyran-4-yl)piperidin-4-yl)-3-isopropyl-1H-indole (455); 2-(2,6-dimethylpyridin-4-yl)-3-isopropyl-5-(1-(5-methyl-4-oxaspiro[2.5]octan-7-yl)piperidin-4-yl)-1H-indole (456); 2-(2,6-dimethylpyridin-4-yl)-3-isopropyl-5-(1-(tetrahydro-2H-pyran-3-yl) piperidin-4-yl)-1H-indole (457); 2-(2,6-dimethylpyridin-4-yl)-3-isopropyl-5-(1-(octahydrocyclopenta[b]pyran-4-yl) piperidin-4-yl)-1H-indole (458); 4-(4-(2-(2,6-dimethylpyridin-4-yl)-3-isopropyl-1H-indol-5-yl)piperidin-1-yl)tetrahydro-2H-thiopyran 1,1-dioxide (459); 2-(2,6-dimethylpyridin-4-yl)-3-isopropyl-5-(1-(pyrimidin-2-ylmethyl) piperidin-4-yl)-1H-indole (460); 2-(2,6-dimethylpyridin-4-yl)-3-isopropyl-5-(1-((1-methyl-1H-pyrazol-5-yl)methyl)piperidin-4-yl)-1H-indole (461); 5-(1-((2H-tetrazol-5-yl) methyl)piperidin-4-yl)-2-(2,6-dimethylpyridin-4-yl)-3-isopropyl-1H-indole (462); 3-((4-(2-(2,6-dimethylpyridin-4-yl)-3-isopropyl-1H-indol-5-yl)piperidin-1-yl)methyl)-1,2,4-oxadiazole (463); 2-(2,6-dimethylpyridin-4-yl)-3-isopropyl-5-(1-((4-methyl-4H-1,2,4-triazol-3-yl)methyl)piperidin-4-yl)-1H-indole (464); 2-(2,6-dimethylpyridin-4-yl)-3-isopropyl-5-(1-((1-isopropylpyrrolidin-3-yl)methyl)piperidin-4-yl)-1H-indole (465); 2-(2,6-dimethylpyridin-4-yl)-3-isopropyl-5-(1-(pyrrolidin-3-ylmethyl)piperidin-4-yl)-1H-indole (466); 5-(1-(cyclobutylmethyl)piperidin-4-yl)-2-(2,6-dimethylpyridin-4-yl)-3-isopropyl-1H-indole (467); 5-(1-(cyclopentylmethyl)piperidin-4-yl)-2-(2,6-dimethylpyridin-4-yl)-3-isopropyl-1H-indole (468); 2-(2,6-dimethylpyridin-4-yl)-3-isopropyl-5-(1-((tetrahydrofuran-3-yl)methyl) piperidin-4-yl)-1H-indole (469); 5-(1-(cyclopropylmethyl)piperidin-4-yl)-2-(2,6-dimethylpyridin-4-yl)-3-isopropyl-1H-indole (474); 2-(2,6-dimethylpyridin-4-yl)-3-isopropyl- 5-(1-((3-methyloxetan-3-yl)methyl) piperidin-4-yl)-1H-indole (475); 2-(2-cyclopropylpyridin-4-yl)-3-isopropyl-5-(1-((2-methyl-1H-imidazol-4-yl)methyl) piperidin-4-yl)-1H-indole (484); 2-(4-(3-(2,2-difluoroethyl)-2-(2,6-dimethylpyridin-4-yl)-1H-indol-5-yl)piperidin-1-yl)-N,N-dimethylpropanamide (493); (4-(2-(2,6-dimethylpyridin-4-yl)-3-isopropyl-1H-indol-5-yl)piperidin-1-yl)(1-isopropylpiperidin-4-yl)methanone (497); 4-(4-(2-(2-fluoro-6-methylpyridin-4-yl)-3-isopropyl-1H-indol-5-yl)piperidine-1-carbonyl)-1-methylpyrrolidin-2-one (502); 4-(4-(2-(2-cyclopropyl-6-methylpyridin-4-yl)-3-isopropyl-1H-indol-5-yl)piperidine-1-carbonyl)-1-methylpyrrolidin-2-one (507); 4-(4-(2-(2-cyclopropyl-5-fluoropyridin-4-yl)-3-isopropyl-1H-indol-5-yl)piperidine-1-carbonyl)-1-methylpyrrolidin-2-one (517); 3-isopropyl-2-(2-methoxypyridin-4-yl)-5-(1-((2-methyl-1H-imidazol-4-yl)methyl)piperidin-4-yl)-1H-indole (520); 2-(2-fluoropyridin-4-yl)-3-isopropyl-5-(1'-methyl-[1,4'-bipiperidin]-4-yl)-1H-indole (523); 3-isopropyl-5-(1'-methyl-[1,4'-bipiperidin]-4-yl)-2-(pyridin-4-yl)-1H-indole (525); 4-(4-(2-(2,6-dimethylpyridin-4-yl)-3-ethyl-1H-indol-5-yl)piperidine-1-carbonyl)-1-methylpyrrolidin-2-one (530); 4-(4-(3-(2,2-difluoroethyl)-2-(2,6-dimethylpyridin-4-yl)-1H-indol-5-yl)piperidine-1-carbonyl)-1-methylpyrrolidin-2-one (534); 5-(1-((1H-imidazol-4-yl) methyl)piperidin-4-yl)-3-(2,2-difluoroethyl)-2-(2,6-dimethylpyridin-4-yl)-1H-indole (537); 3-(2,2-difluoroethyl)-2-(2,6-dimethylpyridin-4-yl)-5-(1-((2-methyl-1H-imidazol-4-yl)methyl)piperidin-4-yl)-1H-indole (538); 3-(2,2-difluoroethyl)-2-(2,6-dimethylpyridin-4-yl)-5-(1'-isopropyl-[1,4'-bipiperidin]-4-yl)-1H-indole (540); 3-isopropyl-2-(2-methylpyridin-4-yl)-5-(1-(phenylsulfonyl)piperidin-4-yl)-1H-indole (547); 5-(1-((4-fluorophenyl)sulfonyl)piperidin-4-yl)-3-isopropyl-2-(2-methylpyridin-4-yl)-1H-indole (551); N-(4-((4-(3-isopropyl-2-(2-methylpyridin-4-yl)-1H-indol-5-yl)piperidin-1-yl)sulfonyl)phenyl)acetamide (552); 5-(1-((1,2-dimethyl-1H-imidazol-4-yl)sulfonyl) piperidin-4-yl)-3-isopropyl-2-(2-methylpyridin-4-yl)-1H-indole (553); 5-(1-((4-fluorophenyl)sulfonyl)piperidin-4-yl)-3-isopropyl-2-(2-methylpyridin-4-yl)-1H-indole (554); 5-(1-(cyclopropylsulfonyl)piperidin-4-yl)-3-isopropyl-2-(2-methylpyridin-4-yl)-1H-indole (555); 5-(1-(benzylsulfonyl)piperidin-4-yl)-3-isopropyl-2-(2-methylpyridin-4-yl)-1H-indole (556); p-tolyl 4-(3-isopropyl-2-(2-methylpyridin-4-yl)-1H-indol-5-yl) piperidine-1-carboxylate (557); (4-(3-isopropyl-2-(2-methylpyridin-4-yl)-1H-indol-5-yl) piperidin-1-yl)(1-isopropylpiperidin-4-yl)methanone (563); 4-(4-(3-isopropyl-2-(2-methylpyridin-4-yl)-1H-indol-5-yl)piperidine-1-carbonyl)-1-methylpyrrolidin-2-one (566); (1-benzylpiperidin-4-yl)(4-(3-isopropyl-2-(2-methylpyridin-4-yl)-1H-indol-5-yl) piperidin-1-yl)methanone (567); 1-(4-(3-isopropyl-2-(2-methylpyridin-4-yl)-1H-indol-5-yl)piperidin-1-yl)-3-(piperidin-4-yl)propan-1-one (568); ((1S,2R)-2-amino-2-methylcyclopentyl)(4-(3-isopropyl-2-(2-methylpyridin-4-yl)-1H-indol-5-yl)piperidin-1-yl)methanone (569); (4-(3-isopropyl-2-(2-methylpyridin-4-yl)-1H-indol-5-yl) piperidin-1-yl)(pyrrolidin-3-yl)methanone (572); (4-(3-isopropyl-2-(2-methylpyridin-4-yl)-1H-indol-5-yl) piperidin-1-yl)(piperidin-4-yl)methanone (573); (S)-2-amino-3-(1H-imidazol-4-yl)-1-(4-(3-isopropyl-2-(2-methylpyridin-4-yl)-1H-indol-5-yl)piperidin-1-yl)propan-1-one (574); (1-benzylpyrrolidin-3-yl)(4-(3-isopropyl-2-(2-methylpyridin-4-yl)-1H-indol-5-yl) piperidin-1-yl)methanone (575); ((1R,3S)-3-aminocyclohexyl)(4-(3-isopropyl-2-(2-methylpyridin-4-yl)-1H-indol-5-yl)piperidin-1-yl)methanone (576); ((1R,3r,5S)-8-azabicyclo[3.2.1]octan-3-yl)(4-(3-isopropyl-2-(2-methylpyridin-4-yl)-1H-indol-5-yl) piperidin-1-yl)methanone (580); ((2S,4R)-4-hydroxypiperidin-2-yl)(4-(3-isopropyl-2-(2-methylpyridin-4-yl)-1H-indol-5-yl)piperidin-1-yl)methanone (581); 4-(4-(2-(3-fluoro-2-methylpyridin-4-yl)-3-isopropyl-1H-indol-5-yl)piperidine-1-carbonyl)-1-methylpyrrolidin-2-one (582); 4-(4-(2-(5-fluoro-2-methylpyridin-4-yl)-3-isopropyl-1H-indol-5-yl)piperidine-1-carbonyl)-1-methylpyrrolidin-2-one (583); 1-(4-(2-(2,6-dimethylpyridin-4-yl)-3-isopropyl-1H-indol-5-yl)piperidin-1-yl)-3-(methyl(oxetan-3-yl) amino) propan-1-one (589); (4-(3-ethyl-2-(2-methylpyridin-4-yl)-1H-indol-5-yl)piperidin-1-yl)(pyridin-4-yl)methanone (591); (4-(3-ethyl-2-(2-methylpyridin-4-yl)-1H-indol-5-yl)piperidin-1-yl)(2-fluoropyridin-4-yl)methanone (592); (4-(3-ethyl-2-(2-methylpyridin-4-yl)-1H-indol-5-yl)piperidin-1-yl)(1-methylpiperidin-4-yl)methanone (593); (4-(3-ethyl-2-(2-methylpyridin-4-yl)-1H-indol-5-yl)piperidin-1-yl)(pyrrolidin-3-yl)methanone (595); (4-(3-isopropyl-2-(2-methylpyridin-4-yl)-1H-indol-5-yl)piperidin-1-yl)(3-methyloxetan-3-yl)methanone (596); (4-(3-isopropyl-2-(2-methylpyridin-4-yl)-1H-indol-5-yl)piperidin-1-yl)(tetrahydro-2H-pyran-4-yl)methanone (597); (4-(3-isopropyl-2-(2-methylpyridin-4-yl)-1H-indol-5-yl)piperidin-1-yl)(2-isopropyltetrahydro-2H-pyran-4-yl)methanone (598); (4-(3-isopropyl-2-(2-methylpyridin-4-yl)-1H-indol-5-yl)piperidin-1-yl)(tetrahydrofuran-3-yl)methanone (599); (4-(3-isopropyl-2-(2-methylpyridin-4-yl)-1H-indol-5-yl)piperidin-1-yl)(isoxazol-3-yl)methanone (604); (4-(3-isopropyl-2-(2-methylpyridin-4-yl)-1H-indol-5-yl)piperidin-1-yl)(1-(trifluoromethyl)cyclopropyl)methanone (605); cyclopropyl(4-(3-isopropyl-2-(2-methylpyridin-4-yl)-1H-indol-5-yl)piperidin-1-yl)methanone (606); 4-(4-(3-isopropyl-2-(2-methylpyridin-4-yl)-1H-indol-5-yl)piperidine-1-carbonyl)-1-methylpiperidin-2-one (607); (4-(3-isopropyl-2-(2-methylpyridin-4-yl)-1H-indol-5-yl)piperidin-1-yl)(thiazol-4-yl)methanone (609); (4-(3-isopropyl-2-(2-methylpyridin-4-yl)-1H-indol-5-yl)piperidin-1-yl)(1-methylcyclopropyl)methanone (610); 1-(4-(3-isopropyl-2-(2-methylpyridin-4-yl)-1H-indol-5-yl)piperidine-1-carbonyl)cyclopropane-1-carbonitrile (611); 4-(4-(3-isopropyl-2-(2-methylpyridin-4-yl)-1H-indol-5-yl)piperidine-1-carbonyl)pyrrolidin-2-one (612); 1-(tert-butyl)-4-(4-(3-isopropyl-2-(2-methylpyridin-4-yl)-1H-indol-5-yl)piperidine-1-carbonyl)pyrrolidin-2-one (613); 4-(4-(3-isopropyl-2-(2-methylpyridin-4-yl)-1H-indol-5-yl) piperidine-1-carbonyl)-1-methylpyrrolidin-2-one (618); 4-(4-(3-isopropyl-2-(2-methylpyridin-4-yl)-1H-indol-5-yl) piperidine-1-carbonyl)-1-methylpyrrolidin-2-one (619); (R)-(4,4-difluoropyrrolidin-2-yl)(4-(3-ethyl-2-(2-methylpyridin-4-yl)-1H-indol-5-yl)piperidin-1-yl)methanone (623); (4-(3-ethyl-2-(2-methylpyridin-4-yl)-1H-indol-5-yl)piperidin-1-yl)(piperidin-3-yl)methanone (624); (4-(3-ethyl-2-(2-methylpyridin-4-yl)-1H-indol-5-yl)piperidin-1-yl)(piperidin-4-yl)methanone (625); (4-(3-ethyl-2-(2-methylpyridin-4-yl)-1H-indol-5-yl)piperidin-1-yl)(4-methylpiperidin-4-yl)methanone (626); (4-(3-ethyl-2-(2-methylpyridin-4-yl)-1H-indol-5-yl)piperidin-1-yl)(3-phenylpiperidin-4-yl)methanone (627); (S)-(4-(3-ethyl-2-(2-methylpyridin-4-yl)-1H-indol-5-yl)piperidin-1-yl)(piperidin-2-yl)methanone (628); (S)-3-ethyl-2-(2-methylpyridin-4-yl)-5-(1-propylpiperidin-4-yl)-1H-indole (629); azetidin-3-yl (4-(3-ethyl-2-(2-methylpyridin-4-yl)-1H-indol-5-yl)piperidin-1-yl)methanone (630); (4-(3-ethyl-2-(2-methylpyridin-4-yl)-1H-indol-5-yl)piperidin-1-yl)(7-azaspiro[3.5]nonan-2-yl)methanone (631); 1-(4-(3-ethyl-2-(2-methylpyridin-4-yl)-1H-indol-5-yl)piperidin-1-yl)-3-(piperidin-4-yl)propan-1-one (632); (4-(3-ethyl-2-(2-methylpyridin-4-yl)-1H-indol-5-yl)piperidin-1-yl)

(pyrrolidin-3-yl)methanone (633); (3-aminooxetan-3-yl)(4-(3-isopropyl-2-(2-methylpyridin-4-yl)-1H-indol-5-yl)piperidin-1-yl)methanone (634); 2-(5-fluoro-2-methylpyridin-4-yl)-3-isopropyl-5-(1-(oxetan-3-ylmethyl)piperidin-4-yl)-1H-indole (646); 2-(5-fluoro-2-methylpyridin-4-yl)-3-isopropyl-5-(1-(oxetan-3-ylmethyl)piperidin-4-yl)-1H-indole (650); 1-(4-(2-(5-fluoro-2-methylpyridin-4-yl)-3-isopropyl-1H-indol-5-yl)piperidin-1-yl)-3-morpholinopropan-1-one (657); 2-(4-(3-isopropyl-2-(2-methylpyridin-4-yl)-1H-indol-5-yl)piperidin-1-yl)-1-phenylethan-1-ol (662); 3-isopropyl-2-(2-methylpyridin-4-yl)-5-(1-(2-phenoxyethyl)piperidin-4-yl)-1H-indole (663); 3-cyclopropyl-5-(1-(cyclopropylmethyl)piperidin-4-yl)-2-(2,6-dimethylpyridin-4-yl)-1H-indole (667); 3-ethyl-5-(1-((1-isopropylpiperidin-4-yl)methyl)piperidin-4-yl)-2-(2-methylpyridin-4-yl)-1H-indole (675); 1-(4-(2-(5-fluoro-2-methylpyridin-4-yl)-3-isopropyl-1H-indol-5-yl)piperidin-1-yl)-2-(methyl(oxetan-3-yl)amino)ethan-1-one (678); 5-(1-((1H-pyrazol-5-yl)methyl)piperidin-4-yl)-2-(2,5-dimethylpyridin-4-yl)-3-isopropyl-1H-indole (681); 5-(1-((1H-pyrazol-5-yl)methyl)piperidin-4-yl)-2-(5-fluoro-2-methylpyridin-4-yl)-3-isopropyl-1H-indole (682); 2-(2,5-dimethylpyridin-4-yl)-3-isopropyl-5-(1-((1-methyl-1H-1,2,3-triazol-4-yl)methyl)piperidin-4-yl)-1H-indole (683); 2-(5-fluoro-2-methylpyridin-4-yl)-3-isopropyl-5-(1-((1-methyl-1H-1,2,3-triazol-4-yl) methyl)piperidin-4-yl)-1H-indole (684); 3-((4-(2-(2,5-dimethylpyridin-4-yl)-3-isopropyl-1H-indol-5-yl)piperidin-1-yl)methyl)-5-methylisoxazole (685); 3-((4-(2-(5-fluoro-2-methylpyridin-4-yl)-3-isopropyl-1H-indol-5-yl)piperidin-1-yl)methyl)-5-methylisoxazole (686); 5-((4-(2-(2,5-dimethylpyridin-4-yl)-3-isopropyl-1H-indol-5-yl)piperidin-1-yl) methyl)thiazole (687); 5-((4-(2-(5-fluoro-2-methylpyridin-4-yl)-3-isopropyl-1H-indol-5-yl)piperidin-1-yl)methyl)thiazole (688); 2-(2,5-dimethylpyridin-4-yl)-3-isopropyl-5-(1-((1-methyl-1H-pyrazol-3-yl)methyl)piperidin-4-yl)-1H-indole (689); 5-(1-((1H-1,2,3-triazol-4-yl)methyl)piperidin-4-yl)-2-(2,5-dimethylpyridin-4-yl)-3-isopropyl-1H-indole (690); 5-(1-((1H-1,2,3-triazol-4-yl)methyl)piperidin-4-yl)-2-(2,5-dimethylpyridin-4-yl)-3-isopropyl-1H-indole (691); 2-(2,5-dimethylpyridin-4-yl)-3-isopropyl-5-((1-methyl-1H-pyrazol-3-yl)methyl)piperidin-4-yl)-1H-indole (692); 5-(1-((4,6-dimethoxypyrimidin-2-yl)methyl)piperidin-4-yl)-2-(2,5-dimethylpyridin-4-yl)-3-isopropyl-1H-indole (693); 5-(1-((4,6-dimethoxypyrimidin-2-yl)methyl)piperidin-4-yl)-2-(5-fluoro-2-methylpyridin-4-yl)-3-isopropyl-1H-indole (694); 5-(1-((1H-tetrazol-5-yl)methyl)piperidin-4-yl)-2-(2,5-dimethylpyridin-4-yl)-3-isopropyl-1H-indole (695); 5-(1-((1H-tetrazol-5-yl)methyl)piperidin-4-yl)-2-(5-fluoro-2-methylpyridin-4-yl)-3-isopropyl-1H-indole (696); 2-cyclopropyl-5-((4-(2-(2,5-dimethylpyridin-4-yl)-3-isopropyl-1H-indol-5-yl)piperidin-1-yl)methyl)-1,3,4-oxadiazole (697); 2-cyclopropyl-5-((4-(2-(5-fluoro-2-methylpyridin-4-yl)-3-isopropyl-1H-indol-5-yl)piperidin-1-yl)methyl)-1,3,4-oxadiazole (698); 2-((4-(2-(2,5-dimethylpyridin-4-yl)-3-isopropyl-1H-indol-5-yl)piperidin-1-yl)methyl)oxazole (699); 2-((4-(2-(5-fluoro-2-methylpyridin-4-yl)-3-isopropyl-1H-indol-5-yl)piperidin-1-yl) methyl)oxazole (700); 4-(3-isopropyl-2-(2-methylpyridin-4-yl)-1H-indol-5-yl)-[1,3'-bipiperidin]-2'-ol (702); 5-([1,3'-bipiperidin]-4-yl)-3-isopropyl-2-(2-methylpyridin-4-yl)-1H-indole (703); methyl 4-(3-isopropyl-2-(2-methylpyridin-4-yl)-1H-indol-5-yl)-[1,4'-bipiperidine]-2'-carboxylate (704); 5-(3'-fluoro-[1,4'-bipiperidin]-4-yl)-3-isopropyl-2-(2-methylpyridin-4-yl)-1H-indole (705); 5-(3'-fluoro-1'-isopropyl-[1,4'-bipiperidin]-4-yl)-3-isopropyl-2-(2-methylpyridin-4-yl)-1H-indole (706); 3-isopropyl-5-(1'-isopropyl-[1,3'-bipiperidin]-4-yl)-2-(2-methylpyridin-4-yl)-1H-indole (707); 3-isopropyl-5-(2'-methyl-[1,4'-bipiperidin]-4-yl)-2-(2-methylpyridin-4-yl)-1H-indole (708); 3-isopropyl-5-(3'-methyl-[1,4'-bipiperidin]-4-yl)-2-(2-methylpyridin-4-yl)-1H-indole (709); 3-isopropyl-2-(2-methylpyridin-4-yl)-5-(1-(tetrahydro-2H-pyran-4-yl)piperidin-4-yl)-1H-indole (710); 3-isopropyl-2-(2-methylpyridin-4-yl)-5-(1-(oxetan-3-yl)piperidin-4-yl)-1H-indole (711); 5-(1-(2,6-dimethyltetrahydro-2H-pyran-4-yl)piperidin-4-yl)-3-isopropyl-2-(2-methylpyridin-4-yl)-1H-indole (712); 5-(1-(2,6-dimethyltetrahydro-2H-pyran-4-yl)piperidin-4-yl)-3-isopropyl-2-(2-methylpyridin-4-yl)-1H-indole (713); 2-(2,5-dimethylpyridin-4-yl)-3-isopropyl-5-(1-(tetrahydro-2H-pyran-4-yl)piperidin-4-yl)-1H-indole (714); 2-(5-fluoro-2-methylpyridin-4-yl)-3-isopropyl-5-(1-(tetrahydro-2H-pyran-4-yl)piperidin-4-yl)-1H-indole (715); 2-(2,3-dimethylpyridin-4-yl)-3-isopropyl-5-(1-(tetrahydro-2H-pyran-4-yl)piperidin-4-yl)-1H-indole (716); 3-isopropyl-2-(2-methylpyridin-4-yl)-5-(1-(tetrahydrofuran-3-yl)piperidin-4-yl)-1H-indole (717); 3-isopropyl-2-(2-methylpyridin-4-yl)-5-(1-(tetrahydro-2H-pyran-3-yl)piperidin-4-yl)-1H-indole (718); 5-(1-(2,2-dimethyltetrahydro-2H-pyran-4-yl)piperidin-4-yl)-3-isopropyl-2-(2-methylpyridin-4-yl)-1H-indole (719); 3-isopropyl-2-(2-methoxypyridin-4-yl)-5-(1-(tetrahydro-2H-pyran-4-yl)piperidin-4-yl)-1H-indole (720); 2-(5-fluoro-2-methylpyridin-4-yl)-3-isopropyl-5-(1-(oxetan-3-yl)piperidin-4-yl)-1H-indole (721); 2-(2,5-dimethylpyridin-4-yl)-3-isopropyl-5-(1-(oxetan-3-yl)piperidin-4-yl)-1H-indole (722); 2-(2,5-dimethylpyridin-4-yl)-3-isopropyl-5-(1-((1-methyl-1H-1,2,4-triazol-3-yl)methyl) piperidin-4-yl)-1H-indole (723); 2-(5-fluoro-2-methylpyridin-4-yl)-3-isopropyl-5-(1-((1-methyl-1H-1,2,4-triazol-3-yl)methyl)piperidin-4-yl)-1H-indole (724); 2-(5-fluoro-2-methylpyridin-4-yl)-3-isopropyl-5-(1-(tetrahydrofuran-3-yl)piperidin-4-yl)-1H-indole (725); 2-(2,5-dimethylpyridin-4-yl)-3-isopropyl-5-(1-(tetrahydro-2H-pyran-3-yl) piperidin-4-yl)-1H-indole (726); 2-(5-fluoro-2-methylpyridin-4-yl)-3-isopropyl-5-(1-(tetrahydro-2H-pyran-3-yl)piperidin-4-yl)-1H-indole (727); 2-(2,5-dimethylpyridin-4-yl)-3-isopropyl-5-(1-(tetrahydrofuran-3-yl)piperidin-4-yl)-1H-indole (728); 2-(3-fluoro-2,6-dimethylpyridin-4-yl)-3-isopropyl-5-(1-(oxetan-3-yl)piperidin-4-yl)-1H-indole (729); 2-(3-fluoro-2-methylpyridin-4-yl)-3-isopropyl-5-(1-(oxetan-3-yl)piperidin-4-yl)-1H-indole (730); 2-(3-fluoro-2-methylpyridin-4-yl)-3-isopropyl-5-(1-((2-methoxypyrimidin-5-yl) methyl)piperidin-4-yl)-1H-indole (731); 2-(3-fluoro-2-methylpyridin-4-yl)-3-isopropyl-5-(1-((1-methyl-1H-1,2,4-triazol-3-yl)methyl)piperidin-4-yl)-1H-indole (732); 2-(5-fluoro-2-methylpyridin-4-yl)-3-isopropyl-5-(1-((2-methoxypyrimidin-5-yl)methyl) piperidin-4-yl)-1H-indole (733); 3-((4-(2-(2,5-dimethylpyridin-4-yl)-3-isopropyl-1H-indol-5-yl)piperidin-1-yl)methyl)-1,2,4-oxadiazole (734); 3-((4-(2-(5-fluoro-2-methylpyridin-4-yl)-3-isopropyl-1H-indol-5-yl)piperidin-1-yl)methyl)-1,2,4-oxadiazole (735); 2-(2,5-dimethylpyridin-4-yl)-3-isopropyl-5-(1-((4-methyl-4H-1,2,4-triazol-3-yl)methyl) piperidin-4-yl)-1H-indole (736); 2-(5-fluoro-2-methylpyridin-4-yl)-3-isopropyl-5-(1-((4-methyl-4H-1,2,4-triazol-3-yl)methyl)piperidin-4-yl)-1H-indole (737); (R)-3-isopropyl-2-(2-methylpyridin-4-yl)-5-(1-(pyrrolidin-3-ylmethyl)piperidin-4-yl)-1H-indole (738); (R)-3-ethyl-2-(2-methylpyridin-4-yl)-5-(1-(pyrrolidin-3-ylmethyl) piperidin-4-yl)-1H-indole (739); (S)-3-ethyl-2-(2-methylpyridin-4-yl)-5-(1-(pyrrolidin-2-ylmethyl)piperidin-4-yl)-1H-indole (740); (S)-3-ethyl-5-(1-((1-isopropylpyrrolidin-2-yl)methyl)piperidin-4-yl)-2-(2-methylpyridin-4-yl)-1H-indole (741); 3-isopropyl-5-(1-((1-isopropylpiperidin-4-yl) methyl)piperidin-4-yl)-2-(2- methylpyridin-4-yl)-1H-indole (742); 3-isopropyl-5-(1-((1-methylpiperidin-4-yl)methyl)piperidin-4-yl)-2-(2-methylpyridin-4-yl)-1H-indole (743); 3-isopropyl-5-(1-((4-methyl-1H-imidazol-5-yl)methyl)piperidin-4-yl)-2-(2-methylpyridin-4-yl)-1H-indole (744); 4-(5-(1-((1H-imidazol-5-yl)methyl)piperidin-4-yl)-3-isopropyl-1H-indol-2-yl)-2-methylpyridin-3-amine (745); ((1r,4r)-4-aminocyclohexyl) (4-(3-isopropyl-2-(2-methylpyridin-4-yl)-1H-indol-5-yl)piperidin-1-yl)methanone (764); 4-(3-ethyl-5-(1'-isobutyl-[1,4'-bipiperidin]-4-yl)-1H-indol-2-yl)-N,N-dimethylpyridin-2-amine (767); 2-(2-ethoxypyridin-4-yl)-3-ethyl-5-(1'-isobutyl-[1,4'-bipiperidin]-4-yl)-1H-indole (768); 3-ethyl-5-(1'-isobutyl-[1,4'-bipiperidin]-4-yl)-2-(2-isopropoxypyridin-4-yl)-1H-indole (769); 2-((4-(3-ethyl-5-(1'-isobutyl-[1,4'-bipiperidin]-4-yl)-1H-indol-2-yl) pyridin-2-yl)oxy)-N,N-dimethylethan-1-amine (770); 4-(3-ethyl-5-(1'-isobutyl-[1,4'-bipiperidin]-4-yl)-1H-indol-2-yl)-N-methylpyridin-2-amine (771); N-ethyl-4-(3-ethyl-5-(1'-isobutyl-[1,4'-bipiperidin]-4-yl)-1H-indol-2-yl)pyridin-2-amine (772); 4-(3-ethyl-5-(1'-isobutyl-[1,4'-bipiperidin]-4-yl)-1H-indol-2-yl)pyridin-2-amine (773); 2-(2-(difluoromethoxy)pyridin-4-yl)-3-ethyl-5-(1'-isobutyl-[1,4'-bipiperidin]-4-yl)-1H-indole (774); 2-((difluoromethoxy) pyridin-4-yl)-3-ethyl-5-(1'-isobutyl-[1,4'-bipiperidin]-4-yl)-1H-indole (775); 3-ethyl-5-(1'-isobutyl-[1,4'-bipiperidin]-4-yl)-2-(pyridin-4-yl)-1H-indole (779); 3-ethyl-5-(1'-isobutyl-[1,4'-bipiperidin]-4-yl)-2-(2-methoxypyridin-4-yl)-1H-indole (780); 5-(1'-isobutyl-[1,4'-bipiperidin]-4-yl)-2-(2-methoxypyridin-4-yl)-3-methyl-1H-indole (781); 5-(1'-isobutyl-[1,4'-bipiperidin]-4-yl)-3-methyl-2-(pyridin-4-yl)-1H-indole (782); 2-(4-(3-isopropyl-2-(2-methoxypyridin-4-yl)-1H-indol-5-yl)piperidin-1-yl)-N-methylethan-1-amine (783); 2-(4-(3-(cyclopropylmethyl)-2-(2-methoxypyridin-4-yl)-1H-indol-5-yl)piperidin-1-yl)-N-methylethan-1-amine (784); 5-(1'-cyclopentyl-[1,4'-bipiperidin]-4-yl)-3-ethyl-2-(2-methoxypyridin-4-yl)-1H-indole (785); 3-ethyl-5-(1'-isopropyl-[1,4'-bipiperidin]-4-yl)-2-(2-methoxypyridin-4-yl)-1H-indole (786); 5-([1,4'-bipiperidin]-4-yl)-3-ethyl-2-(2-methoxypyridin-4-yl)-1H-indole (787); 5-(1'-cyclopropyl-[1,4'-bipiperidin]-4-yl)-3-ethyl-2-(2-methoxypyridin-4-yl)-1H-indole (788); 5-(1'-(cyclopropylmethyl)-[1,4'-bipiperidin]-4-yl)-3-ethyl-2-(2-methoxypyridin-4-yl)-1H-indole (789); 3-ethyl-2-(2-methoxypyridin-4-yl)-5-(1'-methyl-[1,4'-bipiperidin]-4-yl)-1H-indole (790); 3-ethyl-2-(2-methoxypyridin-4-yl)-5-(1-((1R,3s,5S)-8-methyl-8-azabicyclo[3.2.1]octan-3-yl)piperidin-4-yl)-1H-indole (791); 3-ethyl-5-(1'-ethyl-[1,4'-bipiperidin]-4-yl)-2-(2-methoxypyridin-4-yl)-1H-indole (792); 5-(1-(1-cyclopentylazepan-4-yl)piperidin-4-yl)-3-ethyl-2-(2-methoxypyridin-4-yl)-1H-indole (793); (S)-5-(1-(azepan-4-yl)piperidin-4-yl)-3-ethyl-2-(2-methoxypyridin-4-yl)-1H-indole (794); 3-isopropyl-2-(2-methoxypyridin-4-yl)-5-(1'-methyl-[1,4'-bipiperidin]-4-yl)-1H-indole (795); 5-(1'-(cyclopropylmethyl)-[1,4'-bipiperidin]-4-yl)-3-isopropyl-2-(2-methoxypyridin-4-yl)-1H-indole (796); 3-isopropyl-5-(1'-isopropyl-[1,4'-bipiperidin]-4-yl)-2-(2-methoxypyridin-4-yl)-1H-indole (797); 3-ethyl-2-(2-methoxypyridin-4-yl)-5-(1-((1R,3r,5S)-9-methyl-9-azabicyclo[3.3.1]nonan-3-yl)piperidin-4-yl)-1H-indole (798); 2-(2,3-dimethoxypyridin-4-yl)-5-(1'-isobutyl-[1,4'-bipiperidin]-4-yl)-3-methyl-1H-indole (799); 5-([1,4'-bipiperidin]-4-yl)-3-isopropyl-2-(2-methoxypyridin-4-yl)-1H-indole (800); 5-(1'-ethyl-[1,4'-bipiperidin]-4-yl)-3-isopropyl-2-(2-methoxypyridin-4-yl)-1H-indole (801); 5-(1'-cyclopentyl-[1,4'-bipiperidin]-4-yl)-3-isopropyl-2-(2-methoxypyridin-4-yl)-1H-indole (802); 5-(1'-isobutyl-[1,4'-bipiperidin]-4-yl)-3-isopropyl-2-(2-methoxypyridin-4-yl)-1H-indole (803); 3-ethyl-5-(1'-isopropyl-[1,4'-bipiperidin]-4-yl)-2-(pyridin-4-yl)-1H-indole (804); 3-ethyl-5-(1-((1-methyl-1H-pyrrol-2-yl)methyl)piperidin-4-yl)-2-(pyridin-4-yl)-1H-indole (805); 3-ethyl-5-(1'-methyl-[1,4'-bipiperidin]-4-yl)-2-(pyridin-4-yl)-1H-indole (806); 3-ethyl-2-(pyridin-4-yl)-5-(2',2',6',6'-tetramethyl-[1,4'-bipiperidin]-4-yl)-1H-indole (807); 3-ethyl-5-(1'-ethyl-[1,4'-bipiperidin]-4-yl)-2-(pyridin-4-yl)-1H-indole (809); 5-(1'-isobutyl-[1,4'-bipiperidin]-4-yl)-3-methyl-2-(2-methylpyridin-4-yl)-1H-indole (810); 5-(1'-isopropyl-[1,4'-bipiperidin]-4-yl)-3-methyl-2-(2-methylpyridin-4-yl)-1H-indole (811); 2-(2,3-dimethylpyridin-4-yl)-5-(1'-isopropyl-[1,4'-bipiperidin]-4-yl)-3-methyl-1H-indole (812); 2-(2,6-dimethylpyridin-4-yl)-5-(1'-isopropyl-[1,4'-bipiperidin]-4-yl)-3-methyl-1H-indole (813); 2-(2,5-dimethylpyridin-4-yl)-5-(1'-isopropyl-[1,4'-bipiperidin]-4-yl)-3-methyl-1H-indole (814); 4-(3-isopropyl-5-(1-((4-methyl-1H-imidazol-5-yl)methyl)piperidin-4-yl)-1H-indol-2-yl)pyridin-2-amine (816); 4-(5-(1-((1H-imidazol-5-yl)methyl)piperidin-4-yl)-3-isopropyl-1H-indol-2-yl)pyridin-2-amine (817); 4-(3-isopropyl-5-(1-((2-methyl-1H-imidazol-5-yl)methyl)piperidin-4-yl)-1H-indol-2-yl)pyridin-2-amine (818); (4-(2-(2-aminopyridin-4-yl)-3-isopropyl-1H-indol-5-yl)piperidin-1-yl)(piperidin-4-yl)methanone (819); 5-(1-((1H-imidazol-5-yl)methyl) piperidin-4-yl)-3-isopropyl-2-(2-methylpyridin-4-yl)-1H-indole (820); 3-isopropyl-5-(1-((2-methyl-1H-imidazol-5-yl)methyl)piperidin-4-yl)-2-(2-methylpyridin-4-yl)-1H-indole (821); 5-((4-(3-ethyl-2-(pyridin-4-yl)-1H-indol-5-yl)piperidin-1-yl)methyl)-N-(pyridin-2-yl)thiazol-2-amine (822); 4-(5-(1-((1H-imidazol-5-yl)methyl) piperidin-4-yl)-3-isopropyl-1H-indol-2-yl)-6-methylpyridin-3-amine (823); 5-(1-((1H-imidazol-5-yl)methyl) piperidin-4-yl)-2-(2,5-dimethylpyridin-4-yl)-3-isopropyl-1H-indole (824); 6-fluoro-3-isopropyl-5-(1'-isopropyl-[1,4'-bipiperidin]-4-yl)-2-(2-methylpyridin-4-yl)-1H-indole (825); 1-(4-(3-isopropyl-2-(2-methylpyridin-4-yl)-1H-indol-5-yl)piperidin-1-yl)ethan-1-one (826); 1-(4-(3-isopropyl-2-(2-methylpyridin-4-yl)-1H-indol-5-yl)-[1,4'-bipiperidin]-1'-yl)ethan-1-one (827); 2-(2,6-dimethylpyridin-4-yl)-6-fluoro-3-isopropyl-5-(1-methylpiperidin-4-yl)-1H-indole (828); 1-(4-(2-(2,6-dimethylpyridin-4-yl)-6-fluoro-3-isopropyl-1H-indol-5-yl)piperidin-1-yl)ethan-1-one (829); 2-(2,6-dimethylpyridin-4-yl)-5-(1-(2,6-dimethyltetrahydro-2H-pyran-4-yl)piperidin-4-yl)-6-fluoro-3-isopropyl-1H-indole (830); 2-(2,6-dimethylpyridin-4-yl)-6-fluoro-3-isopropyl-5-(1-(tetrahydro-2H-pyran-4-yl)piperidin-4-yl)-1H-indole (831); 2-(2,6-dimethylpyridin-4-yl)-6-fluoro-3-isopropyl-5-(1-((1-methyl-1H-1,2,4-triazol-3-yl)methyl)piperidin-4-yl)-1H-indole (832); 2-(2,6-dimethylpyridin-4-yl)-5-(1-(2,6-dimethyltetrahydro-2H-pyran-4-yl)piperidin-4-yl)-6-fluoro-3-isopropyl-1H-indole (833); 2-(2,6-dimethylpyridin-4-yl)-6-fluoro-3-isopropyl-5-(1-(oxetan-3-yl)piperidin-4-yl)-1H-indole (834); 2-(2-methoxypyridin-4-yl)-3-methyl-5-(1'-methyl-[1,4'-bipiperidin]-4-yl)-1H-indole (838); 5-(1'-ethyl-[1,4'-bipiperidin]-4-yl)-2-(2-methoxypyridin-4-yl)-3-methyl-1H-indole (839); 5-(1'-isopropyl-[1,4'-bipiperidin]-4-yl)-2-(2-methoxypyridin-4-yl)-3-methyl-1H-indole (840); 5-(1'-ethyl-[1,4'-bipiperidin]-4-yl)-3-methyl-2-(pyridin-4-yl)-1H-indole (841); 3-methyl-5-(1'-methyl-[1,4'-bipiperidin]-4-yl)-2-(pyridin-4-yl)-1H-indole (842); 5-(1'-isopropyl-[1,4'-bipiperidin]-4-yl)-3-methyl-2-(pyridin-4-yl)-1H-indole (843); 2-(4-(2-(1-hydroxy-2,6-dimethyl-1l4-pyridin-4-yl)-3-isopropyl-1H-indol-5-yl)piperidin-1-yl)-N,N-dimethylacetamide (844); 4-(3-ethyl-2-(2-methylpyridin-4-yl)-1H-indol-5-yl)-N-(piperidin-4-yl)piperidine-1-carboxamide (845); 4-(3-ethyl-2-(2-methylpyridin-4-yl)-1H-indol-5-yl)-N-(1-(2,2,2-trifluoroacetyl)piperidin-4-yl)

piperidine-1-carboxamide (846); 3-isopropyl-2-(2-methylpyridin-4-yl)-5-(1-(pyridin-3-yl)piperidin-4-yl)-1H-indole (847); 1-(4-(2-(2,6-dimethylpyridin-4-yl)-3-isopropyl-1H-indol-5-yl)piperidin-1-yl)-2-(4-methylpiperazin-1-yl)ethane-1,2-dione (856); 1-(4-(2-(2,6-dimethylpyridin-4-yl)-3-isopropyl-1H-indol-5-yl)piperidin-1-yl)-2-(piperazin-1-yl)ethane-1,2-dione (857); 2-(4-(2-(2,6-dimethylpyridin-4-yl)-3-isopropyl-1H-indol-5-yl)piperidin-1-yl)-2-oxo-N-(2-(pyridin-4-yl)ethyl)acetamide (860); 2-(4-(2-(2,6-dimethylpyridin-4-yl)-3-isopropyl-1H-indol-5-yl)piperidin-1-yl)-2-oxo-N-(piperidin-4-ylmethyl)acetamide (861); 5-(1-(cyclopropylmethyl)piperidin-4-yl)-3-isopropyl-2-(2-methylpyridin-4-yl)-1H-indole (866); 3-isopropyl-5-(1-((3-methyloxetan-3-yl)methyl)piperidin-4-yl)-2-(2-methylpyridin-4-yl)-1H-indole (867); 5-(1-(cyclohexylmethyl)piperidin-4-yl)-3-isopropyl-2-(2-methylpyridin-4-yl)-1H-indole (868); 5-(1-(cyclopropylmethyl)piperidin-4-yl)-2-(2,5-dimethylpyridin-4-yl)-3-isopropyl-1H-indole (871); 2-(2,5-dimethylpyridin-4-yl)-3-isopropyl-5-(1-((3-methyloxetan-3-yl)methyl)piperidin-4-yl)-1H-indole (872); 3-isopropyl-2-(2-methylpyridin-4-yl)-5-(1-(pyrrolidin-3-ylmethyl)piperidin-4-yl)-6-(trifluoromethyl)-1H-indole (873); and 4-fluoro-3-isopropyl-5-(1-((1-isopropylpiperidin-4-yl)methyl)piperidin-4-yl)-2-(2-methylpyridin-4-yl)-1H-indole (874).

The present invention may be embodied in other specific forms without departing from the spirit or essential attributes thereof. The invention encompasses all combinations of the aspects and/or embodiments of the invention noted herein. It is understood that any and all embodiments of the present invention may be taken in conjunction with any other embodiment or embodiments to describe additional embodiments. It is also to be understood that each individual element of the embodiments is meant to be combined with any and all other elements from any embodiment to describe an additional embodiment.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phase "compounds" refers to at least one compound. For example, a compound of Formula (I) includes a compound of Formula (I) and two or more compounds of Formula (I).

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art, $\xi$— is used in structural formulas herein to depict the bond that is the point of attachment of the moiety or substituent to the core or backbone structure.

The terms "halo" and "halogen," as used herein, refer to F, Cl, Br, and I.

The term "cyano" refers to the group —CN.

The term "amino" refers to the group —NH$_2$.

The term "oxo" refers to the group =O.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-6}$ alkyl" denotes straight and branched chain alkyl groups with one to six carbon atoms.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, —CF$_3$ and —CH$_2$CF$_3$.

The term "chloroalkyl" as used herein is intended to include both branched and straight-chain saturated aliphatic hydrocarbon groups substituted with one or more chlorine atoms. For example, "$C_{1-4}$ chloroalkyl" is intended to include $C_1$, $C_2$, $C_3$, and $C_4$ alkyl groups substituted with one or more chlorine atoms. Representative examples of fluoroalkyl groups include, but are not limited to, —CCl$_3$ and —CH$_2$CCl$_3$.

The term "cyanoalkyl" includes both branched and straight-chain saturated alkyl groups substituted with one or more cyano groups. For example, "cyanoalkyl" includes —CH$_2$CN, —CH$_2$CH$_2$CN, and $C_{1-4}$ cyanoalkyl.

The term "aminoalkyl" includes both branched and straight-chain saturated alkyl groups substituted with one or more amine groups. For example, "aminoalkyl" includes —CH$_2$NH$_2$, —CH$_2$CH$_2$NH$_2$, and $C_{1-4}$ aminoalkyl.

The term "hydroxyalkyl" includes both branched and straight-chain saturated alkyl groups substituted with one or more hydroxyl groups. For example, "hydroxyalkyl" includes —CH$_2$OH, —CH$_2$CH$_2$OH, and $C_{1-4}$ hydroxyalkyl.

The term "hydroxy-fluoroalkyl" includes both branched and straight-chain saturated alkyl groups substituted with one or more hydroxyl groups and one or more fluorine atoms. For example, "hydroxy-fluoroalkyl" includes —CHFCH$_2$OH, —CH$_2$CHFC(CH$_3$)$_2$OH, and $C_{1-4}$ hydroxyfluoroalkyl.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_3$-$C_6$ cycloalkyl" denotes cycloalkyl groups with three to six carbon atoms.

The term "alkoxy," as used herein, refers to an alkyl group attached to the parent molecular moiety through an oxygen atom, for example, methoxy group (—$OCH_3$). For example, "$C_{1-3}$ alkoxy" denotes alkoxy groups with one to three carbon atoms.

The terms "fluoroalkoxy" and "—O(fluoroalkyl)" represent a fluoroalkyl group as defined above attached through an oxygen linkage (—O—). For example, "$C_{1-4}$ fluoroalkoxy" is intended to include $C_1$, $C_2$, $C_3$, and $C_4$ fluoroalkoxy groups.

The term "alkoxyalkoxy," as used herein, refers to an alkoxy group attached through its oxygen atom to a carbon atom in a second alkoxy group, which is attached to the parent molecular moiety through an oxygen atom, for example, methoxymethoxy group (—$OCH_2OCH_3$). For example, "$C_{2-4}$ alkoxyalkoxy" denotes alkoxyalkoxy groups with two to four carbon atoms, such as —$OCH_2OCH_3$, —$OCH_2CH_2OCH_3$, —$OCH_2OCHCH_3$, and —$OCH_2CH_2OCHCH_3$.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as amorphous solids.

It should further be understood that solvates (e.g., hydrates) of the compounds of Formula (I) are also within the scope of the present invention. The term "solvate" means a physical association of a compound of Formula (I) with one or more solvent molecules, whether organic or inorganic. This physical association includes hydrogen bonding, in certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:
a) *The Practice of Medicinal Chemistry*, Camille G. Wermuth et al., Ch 31, (Academic Press, 1996);
b) *Design of Prodrugs*, edited by H. Bundgaard, (Elsevier, 1985);
c) *A Textbook of Drug Design and Development*, P. Krogsgaard-Larson and H. Bundgaard, eds. Ch 5, pgs 113-191 (Harwood Academic Publishers, 1991); and
d) *Hydrolysis in Drug and Prodrug Metabolism*, Bernard Testa and Joachim M. Mayer, (Wiley-VCH, 2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor to TLR7/8/9, or effective to treat or prevent autoimmune and/or inflammatory disease states, such as SLE, IBD, multiple sclerosis (MS), and Sjögren's syndrome, and rheumatoid arthritis.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—$CH_3$) also includes deuterated methyl groups such as —$CD_3$.

Utility

The human immune system has evolved to defend the body from micro-organisms, viruses, and parasites that can cause infection, disease or death. Complex regulatory mechanisms ensure that the various cellular components of the immune system target the foreign substances or organisms, while not causing permanent or significant damage to the individual. While the initiating events are not well understood at this time, in autoimmune disease states the immune system directs its inflammatory response to target organs in the afflicted individual. Different autoimmune diseases are typically characterized by the predominate or initial target organ or tissues affected; such as the joint in the case of rheumatoid arthritis, the thyroid gland in the case of Hashimoto's thyroiditis, the central nervous system in the case of multiple sclerosis, the pancreas in the case of type I diabetes, and the bowel in the case of inflammatory bowel disease.

The compounds of the invention inhibit signaling through Toll-like receptor 7, or 8, or 9 (TLR7, TLR8, TLR9) or combinations thereof. Accordingly, compounds of Formula (I) have utility in treating conditions associated with the inhibition of signaling through one or more of TLR7, TLR8, or TLR9. Such conditions include TLR7, TLR8, or TLR9 receptor associated diseases in which cytokine levels are modulated as a consequence of intracellular signaling.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as selective inhibitors of TLR7, TLR8, or TLR9, compounds of Formula (I) are useful in treating TLR7, TLR8, or TLR9 family receptor associated diseases, but not limited to, inflammatory diseases such as Crohn's disease, ulcerative colitis, asthma, graft versus host disease, allograft rejection, chronic obstructive pulmonary disease; autoimmune diseases such as Graves' disease, rheumatoid arthritis, systemic lupus erythematosis, lupus nephritis, cutaneous lupus, psoriasis; auto-inflammatory diseases including Cryopyrin-Associated Periodic Syndromes (CAPS), TNF Receptor Associated Periodic Syndrome (TRAPS), Familial Mediterranean Fever (FMF), adult onset stills, systemic onset juvenile idiopathic arthritis, gout, gouty arthritis; metabolic diseases including type 2 diabetes, atherosclerosis, myocardial infarction; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovascularization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoidosis, bone resorption disease, allograft rejections, fever and myalgias due to infection, cachexia secondary to infection, keloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hypoxia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from Crohn's disease, ulcerative colitis, allograft rejection, rheumatoid arthritis, psoriasis, ankylosing spondylitis, psoriatic arthritis, and pemphigus vulgaris. Alternatively preferred methods of treatment are those wherein the condition is selected from ischemia reperfusion injury, including cerebral ischemia reperfusions injury arising from stroke and cardiac ischemia reperfusion injury arising from myocardial infarction. Another preferred method of treatment is one in which the condition is multiple myeloma.

In one embodiment, the compounds of Formula (I) are useful in treating cancer, including Waldenstrom's Macroglobulinemia (WM), diffuse large B cell lymphoma (DLBCL), chronic lymphocytic leukemia (CLL), cutaneous diffuse large B cell lymphoma, and primary CNS lymphoma.

In addition, the TLR7, TLR8, or TLR9 inhibitors of the present invention inhibit the expression of inducible pro-inflammatory proteins such as prostaglandin endoperoxide synthase-2 (PGHS-2), also referred to as cyclooxygenase-2 (COX-2), IL-1, IL-6, IL-18, chemokines. Accordingly, additional TLR7/8/9 associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retrovirus infections, including feline immunodeficiency virus, bovine immunodeficiency virus, and canine immunodeficiency virus.

The present invention thus provides methods for treating such conditions, comprising administering to a subject in need thereof a therapeutically-effective amount of at least one compound of Formula (I) or a salt thereof. "Therapeutically effective amount" is intended to include an amount of a compound of the present invention that is effective when administered alone or in combination to inhibit autoimmune disease or chronic inflammatory disease.

The methods of treating TLR7, TLR8, or TLR9 associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to inhibit TLR7, TLR8, or TLR9 and/or treat diseases associated with TLR7, TLR8, or TLR9.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal anti-inflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); anti-malarials such as hydroxychloroquine; cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the *Physicians' Desk Reference* (PDR) or as otherwise determined by one of ordinary skill in the art, in the methods of the present invention, such other therapeutic agent(s) may be administered prior to, simultaneously with, or following the administration of the inventive compounds. The present invention also provides pharmaceutical compositions capable of treating TLR7/8/9 kinase-associated conditions, including IL-1 family receptor mediated diseases as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th Edition (1985), which is incorporated herein by reference in its entirety.

Compounds in accordance with Formula (I) can be administered by any means suitable for the condition to be treated, which can depend on the need for site-specific treatment or quantity of Formula (I) compound to be delivered.

Also embraced within this invention is a class of pharmaceutical compositions comprising a compound of Formula (I) and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration in order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium croscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, *arachis* oil; olive oil; sesame oil; and coconut oil; or in mineral oil, such as, for example, liquid paraffin. An oily suspension can also contain at least one thickening agent, such as, for example, beeswax; hard paraffin; and cetyl alcohol in order to provide a palatable oily suspension, at least one of the sweetening agents already described hereinabove, and/or at least one flavoring agent can be added to the oily suspension. An oily suspension can further contain at least one preservative, including, but not limited to, for example, an antioxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid in addition, dispersible powders and granules can also contain at least one excipient, including, but not limited to, for example, sweetening agents; flavoring agents; and coloring agents.

An emulsion of at least one compound of Formula (I) thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and *arachis* oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution in addition, sterile, fixed oils are conventionally employed as a solvent or suspending medium. For this purpose any bland fixed oil may be employed, including synthetic mono- or diglycerides, in addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and (c) a package insert stating that the pharmaceutical composition can be used for the treatment of a cardiovascular and/or inflammatory disorder (as defined previously). In another embodiment, the package insert states that the pharmaceutical composition can be used in combination (as defined previously) with a second therapeutic agent to treat cardiovascular and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). In one embodiment, the package insert specifically recites the indications for which the pharmaceutical composition has been approved. The package insert may be made of any material on which a person can read information contained therein or thereon. For example, the package insert is a printable material (e.g., paper, plastic, cardboard, foil, adhesive-backed paper or plastic, etc.) on which the desired information has been formed (e.g., printed or applied).

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Third Edition, Wiley and Sons, 1999).

Compounds of Formula (I) may be prepared by reference to the methods illustrated in the following Schemes. As shown therein the end product is a compound having the same structural formula as Formula (I). It will be understood that any compound of Formula (I) may be produced by the schemes by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification.

As shown in Scheme 1, compounds of Formula I may be produced, starting with the substituted 5-bromoindoles (2). 2 can be prepared from the 3-formyl indoles (via reduction) or from the 3-H indoles, via alkylation. Transition metal catalyzed cross coupling of 2 and boronate 3 followed by olefin reduction and Boc deprotection affords 4, which can then be coupled with pyridyl boronic acids and deprotected to give 6. Alkylation of 6 leads to the production of the compounds of Formula I.

SCHEME 1

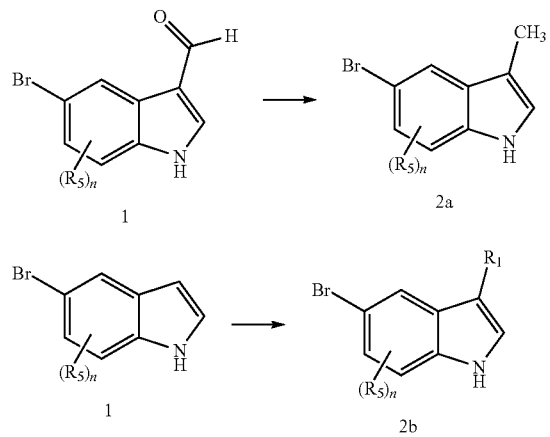

-continued
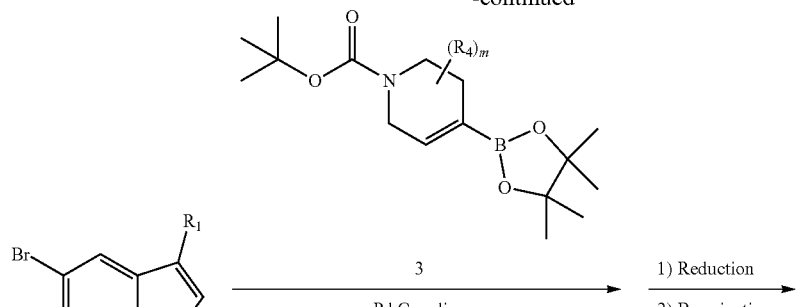
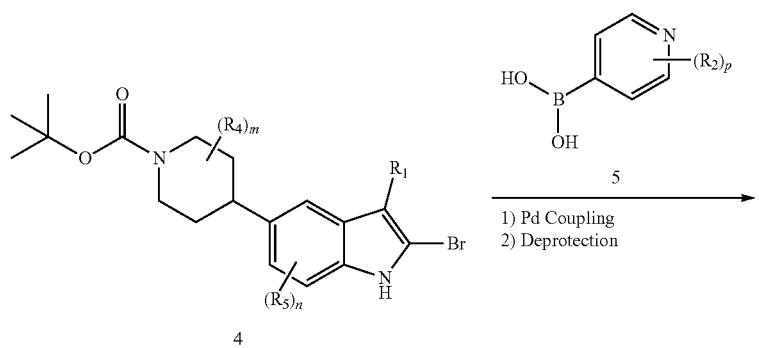
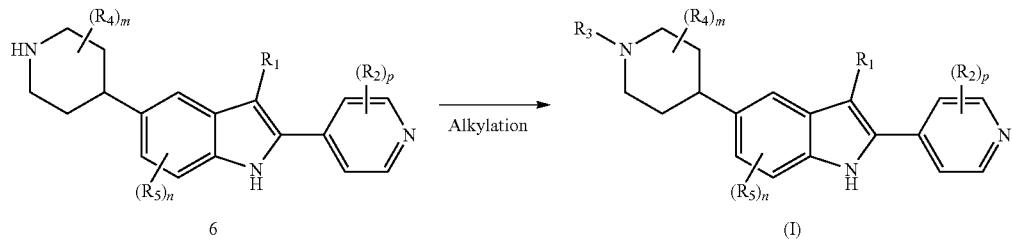
R₁ = H, alkyl, fluoroalkyl, cyclopropyl, —CH₂(cyclopropyl), —C(O)O(alkyl), or —C(CF₃)=CH₂
In an alternative preparation, bromoindole 2b can first be coupled with boronate 3 and reduced. Chlorination proceeds selectively on the 3-position, with bromination then providing the di-halogenated compound 7.
SCHEME 2
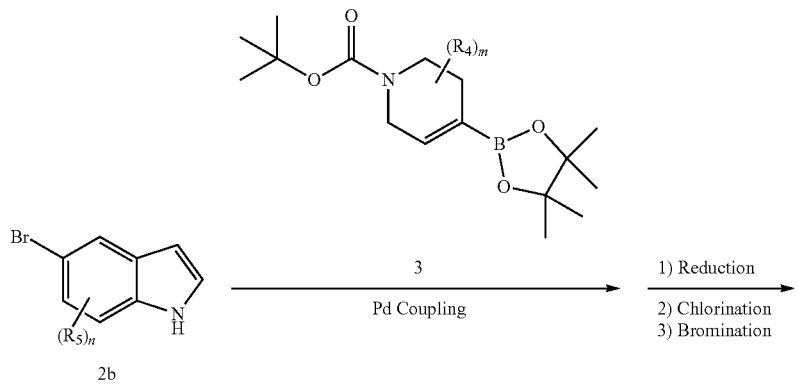

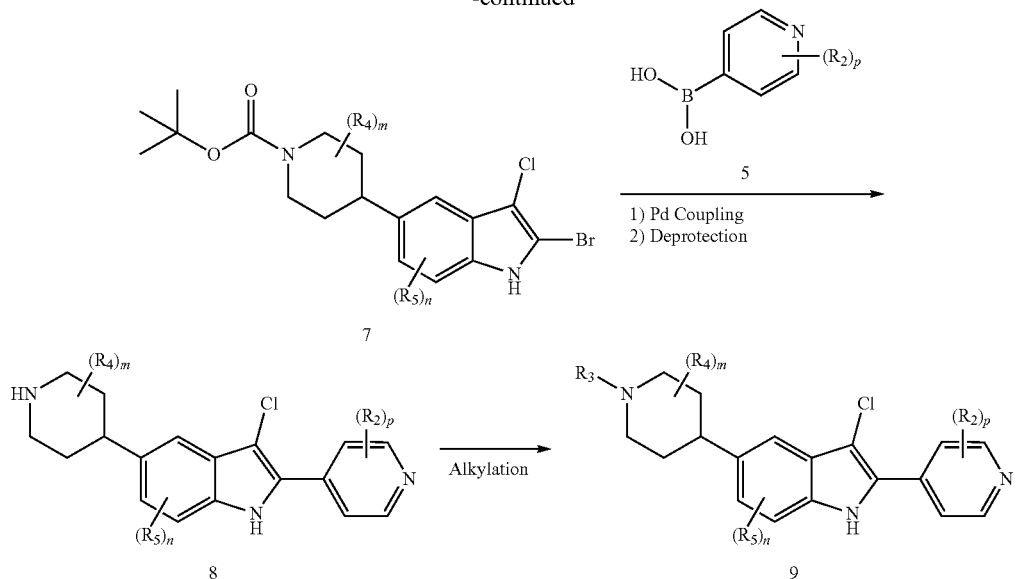

EXAMPLES

Preparation of compounds of Formula (I), and intermediates used in the preparation of compounds of Formula (I), can be prepared using procedures shown in the following Examples and related procedures. The methods and conditions used in these examples, and the actual compounds prepared in these Examples, are not meant to be limiting, but are meant to demonstrate how the compounds of Formula (I) can be prepared. Starting materials and reagents used in these examples, when not prepared by a procedure described herein, are generally either commercially available, or are reported in the chemical literature, or may be prepared by using procedures described in the chemical literature.

ABBREVIATIONS

Ac acetyl
ACN acetonitrile
AcOH acetic acid
anhyd. anhydrous
aq. aqueous
BH$_3$DMS boron dimethylsulfide
BISPIN bis(pinacolato)diboron
Bn benzyl
Bu butyl
Boc or BOC tert-butoxycarbonyl
CV Column Volumes
DAST (diethylamino)sulfur trifluoride
DCE dichloroethane
DCM dichloromethane
DMAP dimethylaminopyridine
DIPEA diisopropylethylamine
DMF dimethylformamide
DMSO dimethylsulfoxide
EtOAc ethyl acetate
Et ethyl
EtOH ethanol
H or H$_2$ hydrogen
h, hr or hrs hour(s)
HATU O-(7-azabenzotriazol-1-yl)-N, N, N', N'-tetramethyluronium hexafluorophosphate
hex hexane
i iso
HCl hydrochloric acid
HPLC high pressure liquid chromatography
LAH lithium aluminum hydride
LC liquid chromatography
LDA lithium diisopropylamide
M molar
mM millimolar
Me methyl
MeOH methanol
MHz megahertz
min. minute(s)
mins minute(s)
M$^{+1}$ (M+H)$^+$
MS mass spectrometry
n or N normal
NBS n-bromosuccinimide
nm nanometer
nM nanomolar
NH$_4$OAc ammonium acetate
Pd/C palladium on carbon
PdCl$_2$(dppf) [1,1'-bis(diphenylphosphino)ferrocene]dichloropalladium(II)
Pd(OAc)$_2$ palladium acetate
Ph phenyl
Pr propyl
PSI pounds per square inch
Ret Time retention time
sat. saturated
SFC supercritical fluid chromatography
TEA triethylamine
TFA trifluoroacetic acid
THF tetrahydrofuran
TsCl 4-toluenesulfonyl chloride Analytical and Preparative HPLC Conditions Gradient Time (min) Flow A % B % Curve Rate: Initial 0.800 98.0 2.0; 1.00 0.800 2.0 98.0 6; 1.50 0.800 2.0 98.0 6; 1.60 0.800 98.0 2.0 11

Method QC-AA: Column: Waters Acquity UPLC BEH C18, 2.1×50 mm, 1.7-µm particles; Mobile Phase A: 5:95 acetonitrile:water with 10 mM ammonium acetate;
Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm.
Method QC-TFA: Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50 OC; Gradient: 0-100% B over 3 minutes, then a 0.75-minute hold at 100% B; Flow: 1.0 mL/min; Detection: UV at 220 nm.
(A) Column-Ascentis Express C18 (50×2.1 mm-2.7 µm) Mphase A: 10 mM $NH_4COOH$ in water:ACN (98:02); Mphase B: 10 mM $NH_4COOH$ in water:ACN (02:98), Gradient: 0-100% B over 3 minutes, Flow=1 mL/min.
(B) Waters Acquity BEH C18 (2.1×50 mm) 1.7 micron; Buffer: 5 mM ammonium acetate pH 5 adjusted with HCOOH, Solvent A: Buffer:ACN (95:5), Solvent B: Buffer:ACN (5:95), Method: % B: 0 min-5%:1.1 min-95%:1.7 min-95%, Flow: 0.8 mL/min.
(C) Column-Ascentis Express C18 (50×2.1 mm-2.7 µm) Mobile phase A: 0.1% HCOOH in water Mobile phase B: ACN. Temperature: 50 OC; Gradient: 0-100% B over 3 minutes; Flow rate: 1.0 mL/min.
(D) Kinetex XB-C18 (75×3 mm) 2.6 micron; Solvent A: 10 mM ammonium formate in water:Acetonitrile (98:02); Mobile Phase B: 10 mM ammonium formate in water:acetonitrile (02:98); Temperature: 50° C.; Gradient: 0-100% B over 3 minutes; Flow rate: 1.1 mL/min; Detection: UV at 220 nm.
(E) Column: Ascentis Express C18 (50×2.1) mm, 2.7 µm; Mobile Phase A: 5:95 acetonitrile:water with 10 mM $NH_4OAc$; Mobile Phase B: 95:5 Acetonitrile:water with 10 mM $NH_4OAc$; Temperature: 50° C.; Gradient: 0-100% B over 3 minutes; Flow: 1.1 ml/min.
(F) Column: Ascentis Express C18 (50×2.1) mm, 2.7 am; Mobile Phase A: 5:95 Acetonitrile:water with 0.1% TFA; Mobile Phase B: 95:5 Acetonitrile:water with 0.1% TFA; Temperature: 50 OC; Gradient: 0-100% B over 3 minutes; Flow: 1.1 mL/min.
(G) Column: Waters Acquity UPLC BEH C18 (2.1×50 mm), 1.7 micron; Solvent A=100% water with 0.05% TFA; Solvent B=100% Acetonitrile with 0.05% TFA; gradient=2-98% B over 1 minute, then a 0.5-minute hold at 98% B; Flow rate: 0.8 mL/min; Detection: UV at 220 nm.
(H) Column: Acentis Express C18 (50×2.1 mm) 1.7 µm, Acentis C8 $NH_4COOH$ 5 MIN·M, Mobile Phase A: –10 mM ammonium formate:ACN (98:2), Mobile Phase B: –10 mM ammonium formate:ACN (2:98), Flow: –1 mL/min.
Preparative HPLC Method:
(I) Column: X Bridge C18 (250×19, 5 µm), Mobile Phase-A: 0.1% TFA in water, Mobile Phase-B: ACN, Solubility: THF+MeOH+DMSO, isocratic 0/10, 10/60, Flow: 17 mL/min.
HPLC Conditions: (J) Column: X Bridge Phenyl (150×4.6 mm) 3.5 micron, A: 0.05% TFA in water:Acetonitrile (95:5) B: Acetonitrile:0.05% TFA in water (95:5), FLOW: 1.0 mL\min, TIME (min)/% B, 0 0, 15 50, 18 100, 23 100; Detection: UV at 254 nm.
(K) SUNFIRE C18 (4.6×150) mm, 3.5 micron, Mobile Phase A: 0.05% TFA in water:Acetonitrile (95:5) Mobile Phase B: Acetonitrile:0.05% TFA in water (95:5), FLOW: 1 mL\min, TIME/B %, 0 0, 15 50, 18 100, 23 100; Detection: UV at 254 nm.

Example 1

2-(2,6-dimethylpyridin-4-yl)-3-isopropyl-5-(piperidin-4-yl)-1H-indole Hydrochloride

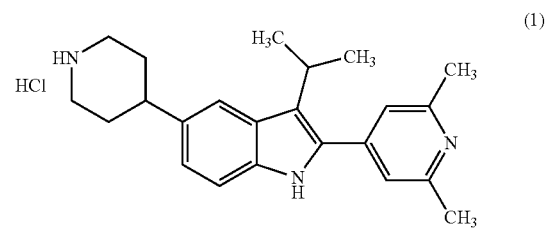 [SMILES: Cl ; Cc1cc(-c2[nH]c3ccc(C4CCNCC4)cc3c2C(C)C)cc(C)n1]

Intermediate 1A: 5-bromo-3-isopropyl-1H-indole

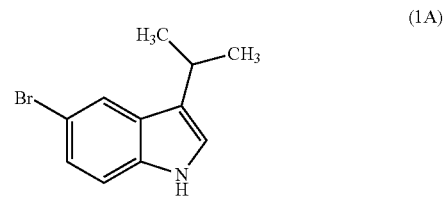

A 250 ml round bottom flask was charged with triethylsilane (8.90 g, 77 mmol), trichloroacetic acid (6.25 g, 38.3 mmol) and toluene (50 mL), the solution was heated to 70° C., then a solution of 5-bromo-1H-indole (5.0 g, 25.5 mmol) and acetone (2.247 mL, 30.6 mmol) in toluene (30 mL) was added drop wise. The resulting brown solution was heated at same temperature for 1.5 h. The solution was cooled to 10° C., quenched with 10% sodium bicarbonate and diluted with diethyl ether. The organic layer was separated, dried and concentrated under vacuum to afford crude compound. The crude was purified using silica gel chromatography eluting with 5% ethyl acetate in hexanes to give 5-bromo-3-isopropyl-1H-indole (5.5 g, 23.10 mmol 95% yield) as an oil. LCMS retention time 1.15 min [B]. MS (E−) m/z: 238.9 (M−H).

Intermediate 1B: Tert-Butyl 4-(3-isopropyl-1H-indol-5-yl)-3,6-dihydropyridine-1(2H)-carboxylate

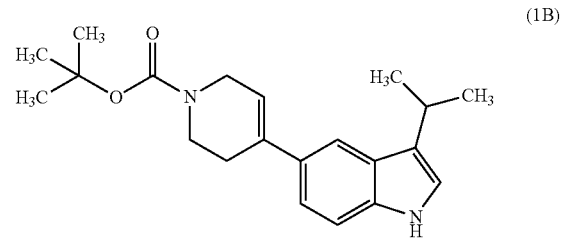 [SMILES: CC(C)c1c[nH]c2ccc(C3=CCN(C(=O)OC(C)(C)C)CC3)cc12]

To a mixture of 5-bromo-3-isopropyl-1H-indole (5.5 g, 23.10 mmol), tert-butyl 4-(4,4,5,5-tetramethyl-1,3,2-dioxaborolan-2-yl)-5,6-dihydropyridine-1 (2H)-carboxylate (7.50 g, 24.25 mmol) in a 250 ml round bottom flask was added THF (50 mL) followed by aqueous solution of potassium phosphate, tribasic (12.07 g, 69.3 mmol, 20 mL). The resulting reaction mixture was degassed for 10 minutes with nitrogen, then PdCl$_2$(dppf)-CH$_2$Cl$_2$ adduct (0.472 g, 0.577 mmol) was added. The reaction mixture was degassed again for 5 min. The resulting reaction mixture was heated at 75° C. for 18 h. The reaction mixture was diluted with ethyl acetate (100 mL), poured into a separate funnel and washed with water (2×50 mL), brine (50 mL), dried over sodium sulfate, and concentrated to afford crude product. The crude material was purified using silica gel chromatography, eluting with 15% ethyl acetate in hexane, the fractions were collected and concentrated to afford tert-butyl 4-(3-isopropyl-1H-indol-5-yl)-5,6-dihydropyridine-1(2H)-carboxylate (6.5 g, 83% yield) as an oil. LCMS retention time 1.21 min [B]. MS (E−) m/z: 339 (M−H).

Intermediate 1C: Tert-Butyl 4-(3-isopropyl-1H-indol-5-yl)piperidine-1-carboxylate

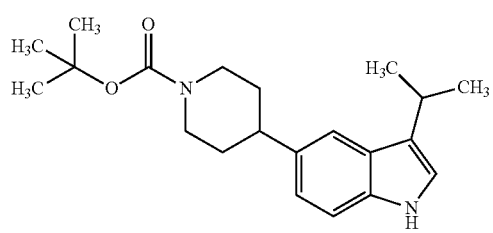

(1C)

A solution of tert-butyl 4-(3-isopropyl-1H-indol-5-yl)-5,6-dihydropyridine-1(2H)-carboxylate (7.9 g, 23.20 mmol) in ethyl acetate (150 mL) was purged with nitrogen (N$_2$), then Palladium on carbon (0.617 g, 0.580 mmol) was added. The solution was purged again with N$_2$ three times. Hydrogen gas was introduced via a balloon to the mixture. The reaction mixture was stirred at room temperature for 5 h. The suspension was filtered through celite, and the filtrate was collected and concentrated to afford crude compound. The crude material was purified by ISCO using 40 g silica column. The compound was eluted in 15% ethyl acetate in hexane, the fractions was collected and concentrated to afford tert-butyl 4-(3-isopropyl-1H-indol-5-yl)piperidine-1-carboxylate (6.5 g, 82% yield) as a white solid. LCMS retention time 2.48 min [C]. MS (E−) m/z: 341 (M−H).

Intermediate 1D: Tert-Butyl 4-(2-bromo-3-isopropyl-1H-indol-5-yl)piperidine-1-carboxylate

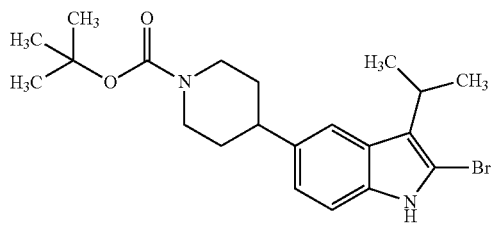

(1D)

To a solution of tert-butyl 4-(3-isopropyl-1H-indol-5-yl)piperidine-1-carboxylate (6.3 g, 18.40 mmol) in DCE (60 mL), NBS (3.27 g, 18.40 mmol) dissolved in DCE (50 mL) was added drop wise via an addition funnel over 10 min at 0° C. The resulting brown solution was stirred at room temperature for 20 min. The reaction was quenched with sodium sulfite solution (15 mL) and the volatiles were removed, the residue was taken up in DCM (50 mL) and the aqueous layer was separated. The organic layer was dried over Na$_2$SO$_4$ and concentrated to afford crude compound. The crude material was purified by ISCO using 40 g silica column, compound was eluted in 15% ethyl acetate in Pet ether, the fractions was collected and concentrated to afford tert-butyl 4-(2-bromo-3-isopropyl-1H-indol-5-yl)piperidine-1-carboxylate (6.4 g, 83% yield) as a white solid. LCMS retention time 2.58 min [H]. MS (E−) m/z: 367.2 (M−H).

Intermediate 1E: Tert-Butyl 4-(3-isopropyl-2-(4,4,5,5-tetramethyl-1,3,2-dioxaborolan-2-yl)-1H-indol-5-yl)piperidine-1-carboxylate

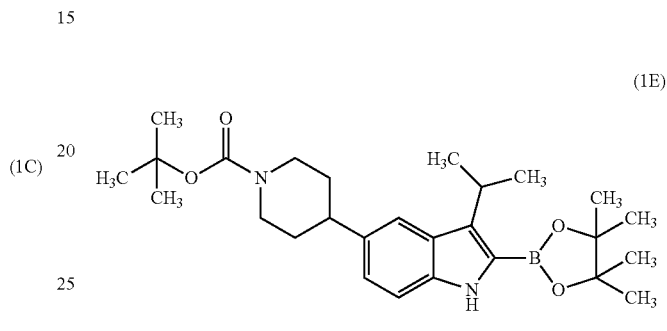

(1E)

To a mixture of tert-butyl 4-(2-bromo-3-isopropyl-1H-indol-5-yl)piperidine-1-carboxylate (1.0 g, 2.373 mmol), 2-dicyclohexyphosphino-2',6'-dimethoxybiphenyl (0.117 g, 0.285 mmol), and bis(benzonitrile)palladium(II) chloride (0.027 g, 0.071 mmol) in a 50 ml sealed tube was added dioxane (10 mL). The resulting reaction mixture was degassed for 10 min and then pinacolborane (0.456 g, 3.56 mmol) was added, followed by the drop wise addition of TEA (0.992 mL, 7.12 mmol). The reaction mixture was degasified again for 5 min. The resulting reaction mixture was heated at 85° C. for 3 h. The reaction mixture was concentrated. The crude material was dissolved in ethyl acetate (100 mL), poured into a separate funnel and was washed thoroughly with water (2×250 mL). The organic layer was dried over Na$_2$SO$_4$, filtered and the filtrate was concentrated in vacuum to give crude product. The residue was taken up in DCM (3 mL). The crude material was purified by a Combiflash system by eluting with 12% EtOAc/Pet ether. Following concentration of fractions, the product was collected as a white gummy product (0.75 g, 67.5% yield). LCMS retention time 4.27 min [H]. MS (E−) m/z: 467.3 (M−H).

Intermediate 1F: Tert-Butyl 4-(2-(2,6-dimethylpyridin-4-yl)-3-isopropyl-1H-indol-5-yl) piperidine-1-carboxylate

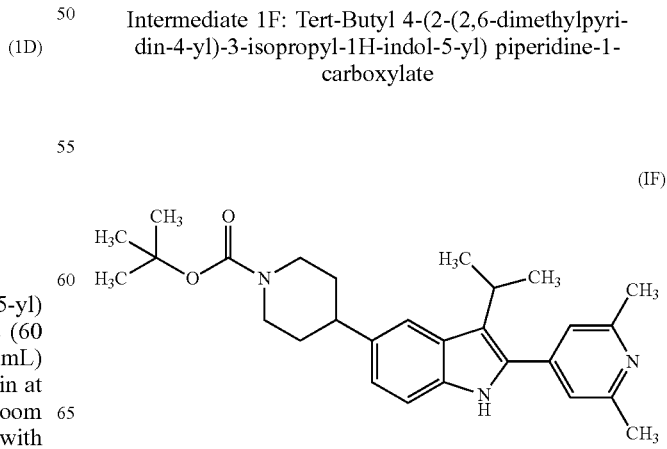

(1F)

A solution of tert-butyl 4-(3-isopropyl-2-(4,4,5,5-tetramethyl-1,3,2-dioxaborolan-2-yl)-1H-indol-5-yl)piperidine-1-carboxylate (3 g, 6.40 mmol), 4-bromo-2,6-dimethylpyridine (1.787 g, 9.61 mmol) and potassium phosphate tribasic (4.08 g, 19.21 mmol)) in dioxane (80 mL) and water (5 mL) was degassed with N₂ for 10 min. Next, PdCl₂(dppf)-CH₂Cl₂ adduct (0.523 g, 0.640 mmol) was added and the solution was degassed again for 5 min. The resulting reaction mixture was heated at 80° C. for 12 h. The reaction mixture was concentrated. The residue was dissolved in ethyl acetate and the solution was washed with water. The organic layer was collected, dried over Na₂SO₄ and concentrated to afford crude compound. The crude material was purified by combiflash, using 24 g silica column, compound was eluted in 65% ethyl acetate in Pet ether. The fractions was combined and concentrated to afford tert-butyl 4-(2-(2,6-dimethylpyridin-4-yl)-3-isopropyl-1H-indol-5-yl) piperidine-1-carboxylate (1.8 g, 4.02 mmol, 62.8% yield) as a light yellow solid. LCMS retention time 1.464 min [B]. MS (E−) m/z: 448.3 (M+H).

Example 1

To a solution of tert-butyl 4-(2-(2,6-dimethylpyridin-4-yl)-3-isopropyl-1H-indol-5-yl)piperidine-1-carboxylate (1.4 g, 2.93 mmol) in DCM (5 mL) was added 4 M HCl in dioxane (3.66 mL, 14.63 mmol) at room temperature. The mixture was stirred at the same temperature for 1 h. Solid material slowly precipitated from the reaction mixture. The slurry was concentrated and the residue was triturated with diethyl ether (2×10 mL) to afford 2-(2,6-dimethylpyridin-4-yl)-3-isopropyl-5-(piperidin-4-yl)-1H-indole (170 mg, 0.489 mmol, 62.6% yield) as a white solid. LCMS retention time 0.62 min [G]. MS (E−) m/z: 348.3 (M+H).

Example 2

2-(2,6-dimethylpyridin-4-yl)-3-ethyl-5-(piperidin-4-yl)-1H-indole

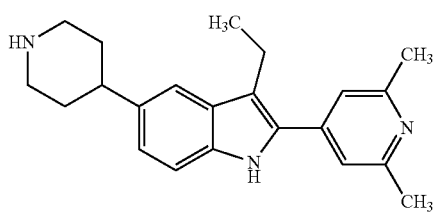

Intermediate 2A:
1-(5-bromo-1H-indol-3-yl)ethan-1-one

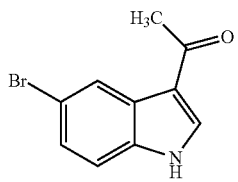

To a solution of 5-bromo-1H-indole (10 g, 51.0 mmol) in toluene (50 mL) were added acetyl chloride (7.25 mL, 102 mmol) at 0° C. followed by tin(IV) chloride (102 mL, 102 mmol) drop wise. The reaction temperature was then raised to 25° C. and the reaction mixture was stirred at the same temperature for 4 h. The reaction mass was quenched with ice cold water (150 mL). Yellow solid precipitated from solution and was collected by filtration. The residue was thoroughly washed with water (100 ml). The solid was air dried under vacuum for 12 h. The solid was further triturated with dry toluene to remove traces of moisture to afford 1-(5-bromo-1H-indol-3-yl)ethanone (11 g, 91%). LCMS retention time 1.80 min [D]. MS (E−) m/z: 239.3 (M+H).

Intermediate 2B: 5-bromo-3-ethyl-1H-indole

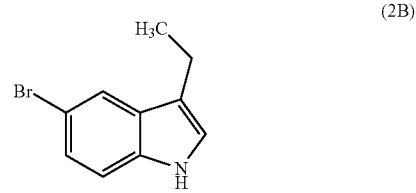

To a solution of 1-(5-bromo-1H-indol-3-yl)ethanone (3 g, 12.60 mmol) in THF (30 mL) was added LAH (6.30 mL, 12.60 mmol) at 25° C. The reaction mixture was heated to 55° C. for 1 h. The reaction was quenched slowly with ice cold water (100 ml) at 0° C. White solid precipitated from the mixture. The reaction mass was diluted with ethyl acetate (150 mL) and filtered through a celite bed. The celite bed was washed thoroughly with ethyl acetate (50 mL). The aqueous layer was separated, and the combined organic layer was dried over sodium sulphate, filtered and concentrated. The crude material was purified by ISCO using silica column, compound was eluted in 6-10% EtOAc in hexane, the fraction was collected and concentrated to afford 5-bromo-3-ethyl-1H-indole (2.8 g, 98%). LCMS retention time 2.45 min [D]. MS (E−) m/z: 226.3 (M+H).

Intermediate 2C: Tert-Butyl 4-(3-ethyl-1H-indol-5-yl)-3,6-dihydropyridine-1(2H)-carboxylate

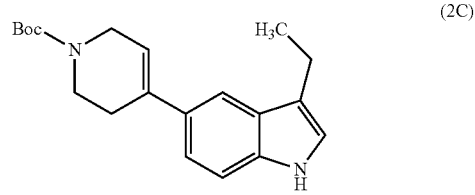 [SMILES: CCc1c[nH]c2ccc(C3=CCN(C(=O)OC(C)(C)C)CC3)cc12]

Tert-butyl 4-(3-ethyl-1H-indol-5-yl)-5,6-dihydropyridine-1 (2H)-carboxylate was prepared according to the general procedure described in Intermediate 1B using 5-bromo-3-ethyl-1H-indole as the starting intermediate (5.0 g, 81% yield). LCMS retention time 3.91 min. [D] MS (E−) m/z: 271.3 (M+H-tBu).

Intermediate 2D: Tert-Butyl 4-(3-ethyl-1H-indol-5-yl)piperidine-1-carboxylate

(2D)

Tert-butyl 4-(3-ethyl-1H-indol-5-yl)piperidine-1-carboxylate was prepared according to the general procedure described in Intermediate 1C using tert-butyl 4-(3-ethyl-1H-indol-5-yl)-5,6-dihydropyridine-1(2H)-carboxylate as the starting intermediate (3.5 g, 71.5% yield). LCMS retention time 3.86 min [D]. MS (E−) m/z: 327.3 (M−H).

Intermediate 2E: Tert-Butyl 4-(2-bromo-3-ethyl-1H-indol-5-yl)piperidine-1-carboxylate

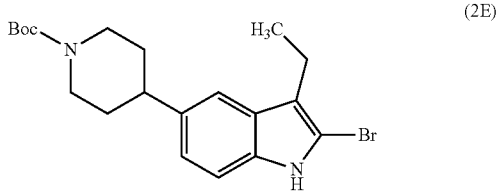 [SMILES: CCc1c(Br)[nH]c2ccc(C3CCN(C(=O)OC(C)(C)C)CC3)cc12]

(2E)

Tert-butyl 4-(2-bromo-3-ethyl-1H-indol-5-yl)piperidine-1-carboxylate was prepared according to the general procedure described in Intermediate 1D using tert-butyl 4-(3-isopropyl-1H-indol-5-yl)piperidine-1-carboxylate as the starting intermediate (0.75 g, 76% yield). LCMS retention time 3.12 min [H]. MS (E−) m/z: 405.3 (M−H).

Intermediate 2F: Tert-Butyl 4-(2-(2,6-dimethylpyridin-4-yl)-3-ethyl-1H-indol-5-yl) piperidine-1-carboxylate

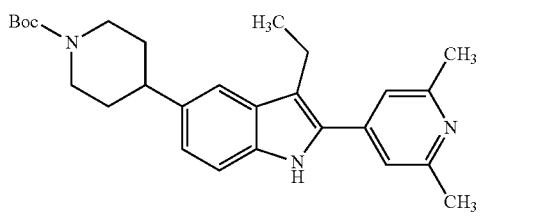

(2F)

Tert-butyl 4-(2-(2,6-dimethylpyridin-4-yl)-3-ethyl-1H-indol-5-yl)piperidine-1-carboxylate was prepared according to the general procedure described in Intermediate 1F using tert-butyl 4-(2-bromo-3-ethyl-1H-indol-5-yl)piperidine-1-carboxylate as the starting intermediate (0.65 g, 98% yield). LCMS retention time 0.89 min [G]. MS (E−) m/z: 434.3 (M+H).

Example 2

2-(2,6-dimethylpyridin-4-yl)-3-ethyl-5-(piperidin-4-yl)-1H-indole was prepared according to the general procedure described in Example 1 using tert-butyl 4-(2-(2,6-dimethylpyridin-4-yl)-3-ethyl-1H-indol-5-yl)piperidine-1-carboxylate as the starting intermediate (0.36 g, 72.7% yield). LCMS retention time 1.019 min [E]. MS (E−) m/z: 334.3 (M+H).

Example 3

2-(2-fluoro-6-methylpyridin-4-yl)-3-isopropyl-5-(piperidin-4-yl)-1H-indole

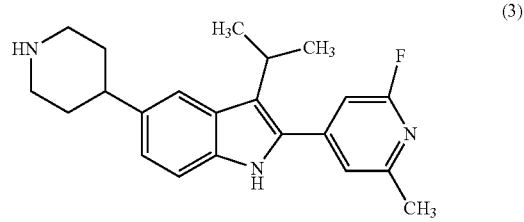 [SMILES: Cc1cc(-c2[nH]c3ccc(C4CCNCC4)cc3c2C(C)C)cc(F)n1]

(3)

Intermediate 3A: 2-fluoro-6-methyl-4-(4,4,5,5-tetramethyl-1,3,2-dioxaborolan-2-yl) Pyridine

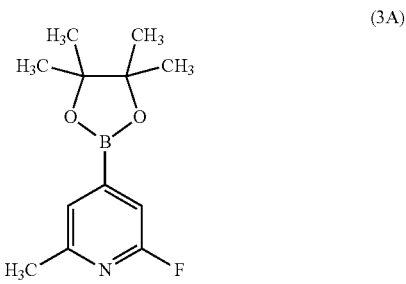 [SMILES: Cc1cc(B2OC(C)(C)C(C)(C)O2)cc(F)n1]

(3A)

To a solution of 2-fluoro-6-methylpyridine (0.5 g, 4.50 mmol) in MTBE (20 mL) were added BISPIN (2.285 g, 9.00 mmol) and 4,4'-di-tert-butyl-2,2'-bipyridine (0.085 g, 0.315 mmol). The mixture was degasified with argon followed by the addition of (1,5-cyclooctadiene)(methoxy)iridium(I) dimer (0.089 g, 0.135 mmol) under an argon atmosphere. The reaction mixture was heated at 80° C. for 14 hours. The resulting black suspension was concentrated under vacuum to afford a black oil which was analyzed by LCMS. The crude product was chromatographed using snap-40g and 9:1 CHCl₃:MeOH. Product spot was isolated at 10% MeOH as white semi solid (0.75 g, 70.3%). White solid was obtained on keeping at 5° C. for a day. LCMS retention time 1.16 min [D]. MS (E−) m/z: 238.1 (M+H).

Intermediate 3B: Tert-Butyl 4-(2-(2-fluoro-6-methylpyridin-4-yl)-3-isopropyl-1H-indol-5-yl)piperidine-1-carboxylate

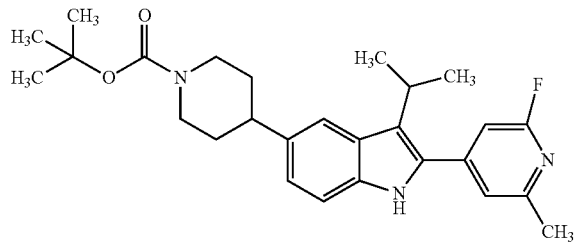

(3B)

Tert-butyl 4-(2-(2-fluoro-6-methylpyridin-4-yl)-3-isopropyl-1H-indol-5-yl) piperidine-1-carboxylate was prepared according to the general procedure described in the last step of Example 1, using tert-butyl 4-(2-bromo-3-isopropyl-1H-indol-5-yl) piperidine-1-carboxylate as the starting intermediate (0.39 g, 91% yield). LCMS retention time 3.74 min [D]. MS (E−) m/z: 453.1 (M+H).

Example 3

To a solution of tert-butyl 4-(2-(2-fluoro-6-methylpyridin-4-yl)-3-isopropyl-1H-indol-5-yl)piperidine-1-carboxylate (0.39 g, 0.864 mmol)) in DCM (2 mL) was added 4M HCl in dioxane (1.295 mL, 5.18 mmol) at room temperature. The mixture was stirred at same temperature for 1 h. The solution was concentrated to provide 2-(2-fluoro-6-methylpyridin-4-yl)-3-isopropyl-5-(piperidin-4-yl)-1H-indole (0.25 g, 95.8% yield). LCMS retention time 1.53 min [E]. MS (E−) m/z: 352.3 (M+H).

The following examples in Table 1 were prepared according to the general procedure described in Example 3.

TABLE 1

| Ex. No. | Structure | LCMS MH+ | Rt (min) | HPLC Method |
|---|---|---|---|---|
| 5 | 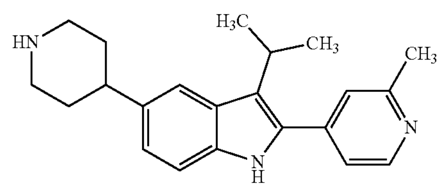 [SMILES: Cc1cc(-c2[nH]c3ccc(C4CCNCC4)cc3c2C(C)C)ccn1] | 334.2 | 2.31 | D |
| 6 | 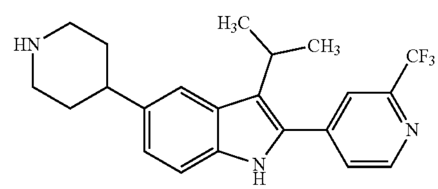 [SMILES: CC(C)c1c(-c2ccnc(C(F)(F)F)c2)[nH]c2ccc(C3CCNCC3)cc12] | 388.4 | 1.34 | E |
| 7 | 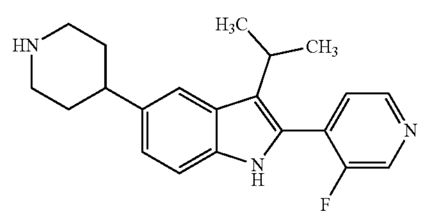 [SMILES: CC(C)c1c(-c2ccncc2F)[nH]c2ccc(C3CCNCC3)cc12] | 338.3 | 0.88 | F |
| 8 | 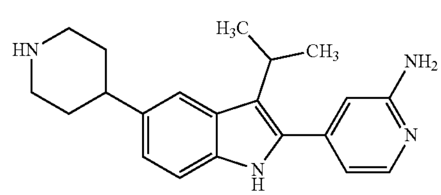 [SMILES: CC(C)c1c(-c2ccnc(N)c2)[nH]c2ccc(C3CCNCC3)cc12] | 335.4 | 0.82 | QC-AA |
| 9 | 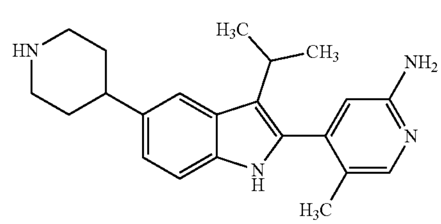 [SMILES: Cc1cnc(N)cc1-c1[nH]c2ccc(C3CCNCC3)cc2c1C(C)C] | 349.2 | 0.75 | QC-TFA |

TABLE 1-continued

| Ex. No. | Structure | LCMS MH+ | Rt (min) | HPLC Method |
|---|---|---|---|---|
| 10 | 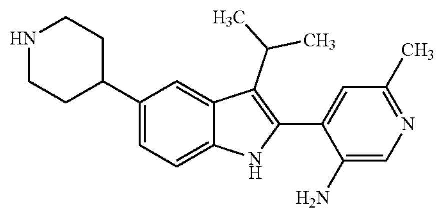 [SMILES: Cc1cc(-c2[nH]c3ccc(C4CCNCC4)cc3c2C(C)C)c(N)cn1] | 349.1 | 0.9 | QC-TFA |
| 11 | 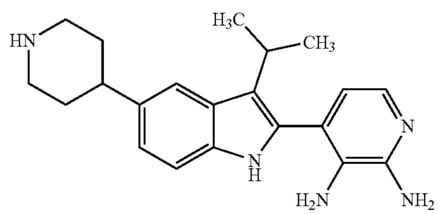 [SMILES: CC(C)c1c(-c2ccnc(N)c2N)[nH]c2ccc(C3CCNCC3)cc12] | 349.3 | 0.89 | QC-AA |
| 12 | 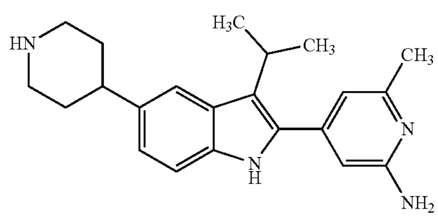 [SMILES: Cc1cc(-c2[nH]c3ccc(C4CCNCC4)cc3c2C(C)C)cc(N)n1] | 349.3 | 0.79 | QC-TFA |
| 13 | 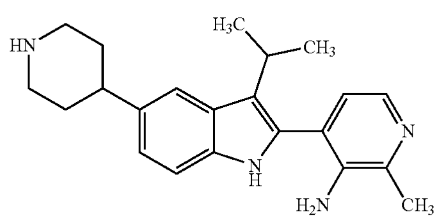 | 349.1 | 0.89 | QC-AA |
| 14 | 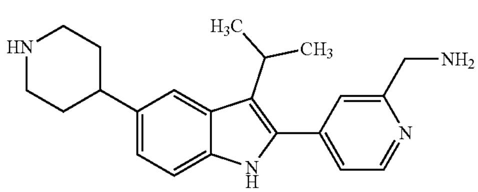 [SMILES: CC(C)c1c(-c2ccnc(CN)c2)[nH]c2ccc(C3CCNCC3)cc12] | 349.3 | 0.63 | QC-AA |
| 15 | 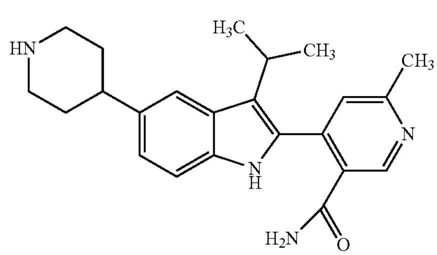 [SMILES: Cc1cc(-c2[nH]c3ccc(C4CCNCC4)cc3c2C(C)C)c(C(N)=O)cn1] | 377.3 | 0.83 | QC-AA |
| 16 | 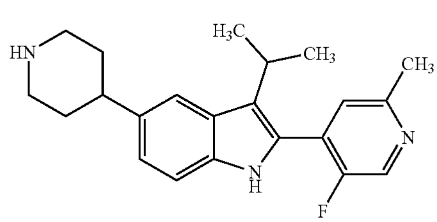 [SMILES: Cc1cc(-c2[nH]c3ccc(C4CCNCC4)cc3c2C(C)C)c(F)cn1] | 352.2 | 1.2 | QC-AA |

TABLE 1-continued

| Ex. No. | Structure | LCMS MH+ | Rt (min) | HPLC Method |
|---|---|---|---|---|
| 18 | 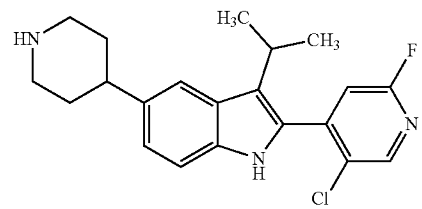 [SMILES: CC(C)c1c(-c2cc(F)ncc2Cl)[nH]c2ccc(C3CCNCC3)cc12] | 372 | 1.42 | QC-TFA |
| 19 | 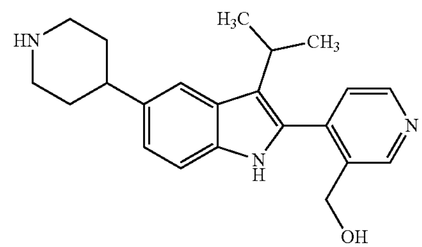 [SMILES: CC(C)c1c(-c2ccncc2CO)[nH]c2ccc(C3CCNCC3)cc12] | 350.1 | 0.56 | QC-TFA |
| 20 | 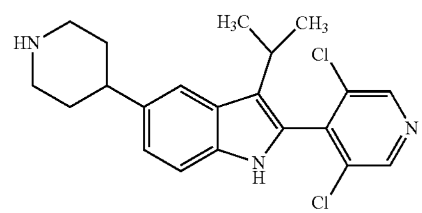 [SMILES: CC(C)c1c(-c2c(Cl)cncc2Cl)[nH]c2ccc(C3CCNCC3)cc12] | 388.2 | 1.37 | QC-AA |
| 21 | 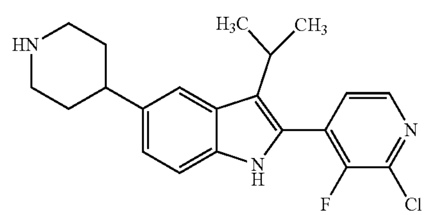 [SMILES: CC(C)c1c(-c2ccnc(Cl)c2F)[nH]c2ccc(C3CCNCC3)cc12] | 372 | 1.42 | QC-TFA |
| 22 | 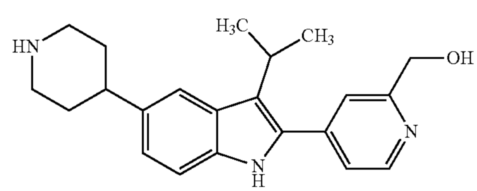 [SMILES: CC(C)c1c(-c2ccnc(CO)c2)[nH]c2ccc(C3CCNCC3)cc12] | 350.4 | 0.64 | QC-TFA |
| 23 | 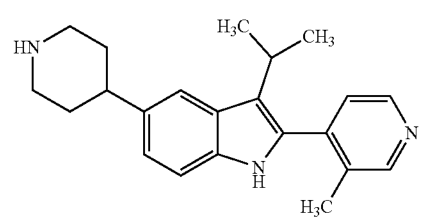 [SMILES: Cc1cnccc1-c1[nH]c2ccc(C3CCNCC3)cc2c1C(C)C] | 334 | 1.42 | QC-AA |
| 24 | 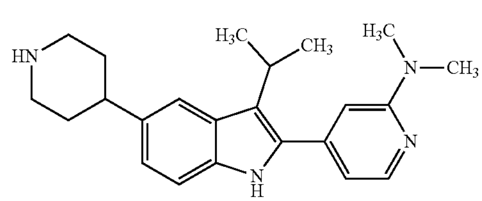 [SMILES: CC(C)c1c(-c2ccnc(N(C)C)c2)[nH]c2ccc(C3CCNCC3)cc12] | 363.4 | 1.31 | QC-AA |

TABLE 1-continued

| Ex. No. | Structure | LCMS MH+ | Rt (min) | HPLC Method |
|---|---|---|---|---|
| 26 | 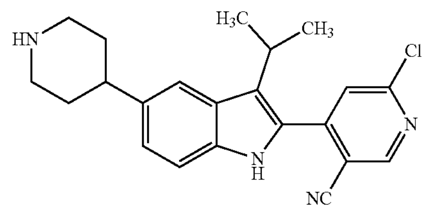 [SMILES: CC(C)c1c(-c2cc(Cl)ncc2C#N)[nH]c2ccc(C3CCNCC3)cc12] | 379.2 | 1.38 | QC-TFA |
| 27 | 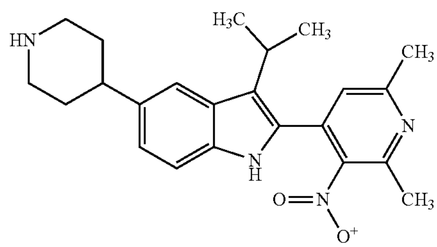 | 393.2 | 1.38 | QC-AA |
| 28 | 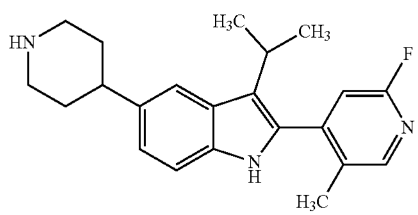 [SMILES: Cc1cnc(F)cc1-c1[nH]c2ccc(C3CCNCC3)cc2c1C(C)C] | 352.1 | 1.35 | QC-TFA |
| 29 | 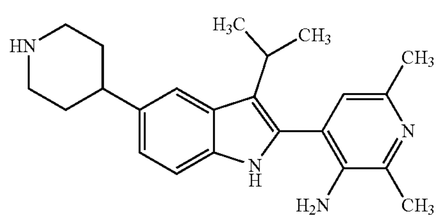 | 363 | 0.75 | QC-TFA |
| 30 | 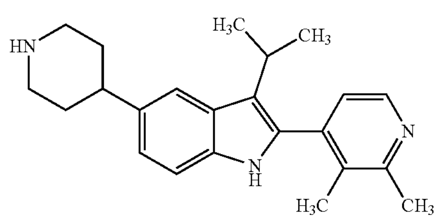 [SMILES: Cc1nccc(-c2[nH]c3ccc(C4CCNCC4)cc3c2C(C)C)c1C] | 348.2 | 1.18 | QC-AA |
| 31 | 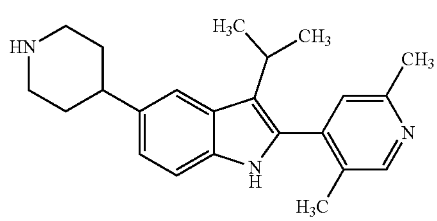 [SMILES: Cc1cc(-c2[nH]c3ccc(C4CCNCC4)cc3c2C(C)C)c(C)cn1] | 348.2 | 0.74 | QC-TFA |
| 32 | 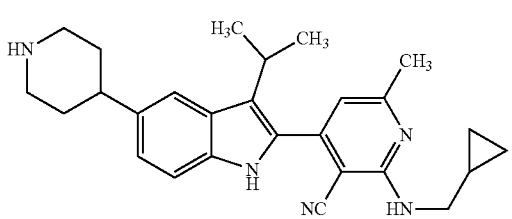 [SMILES: Cc1cc(-c2[nH]c3ccc(C4CCNCC4)cc3c2C(C)C)c(C#N)c(NCC2CC2)n1] | 428.3 | 1.59 | QC-AA |

TABLE 1-continued

| Ex. No. | Structure | LCMS MH+ | Rt (min) | HPLC Method |
|---|---|---|---|---|
| 33 | 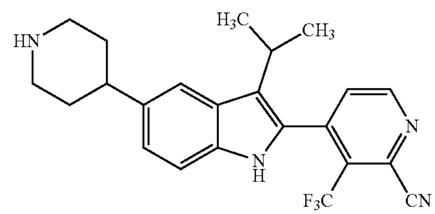 [SMILES: CC(C)c1c(-c2ccnc(C#N)c2C(F)(F)F)[nH]c2ccc(C3CCNCC3)cc12] | 413.2 | 1.69 | QC-AA |
| 34 | 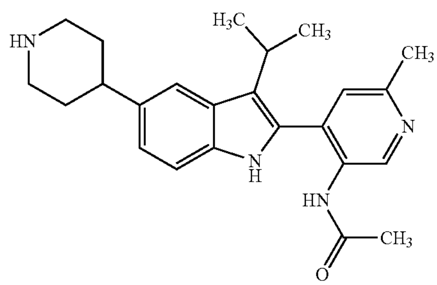 [SMILES: CC(=O)Nc1cnc(C)cc1-c1[nH]c2ccc(C3CCNCC3)cc2c1C(C)C] | 391.2 | 1.29 | QC-TFA |
| 35 | 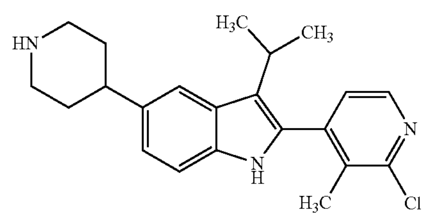 [SMILES: Cc1c(-c2[nH]c3ccc(C4CCNCC4)cc3c2C(C)C)ccnc1Cl] | 368.2 | 1.42 | QC-AA |
| 36 | 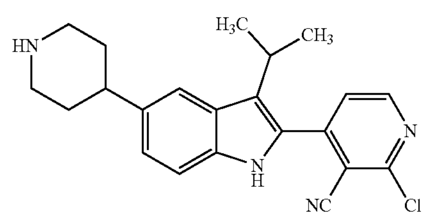 [SMILES: CC(C)c1c(-c2ccnc(Cl)c2C#N)[nH]c2ccc(C3CCNCC3)cc12] | 379.2 | 1.69 | QC-TFA |
| 37 | 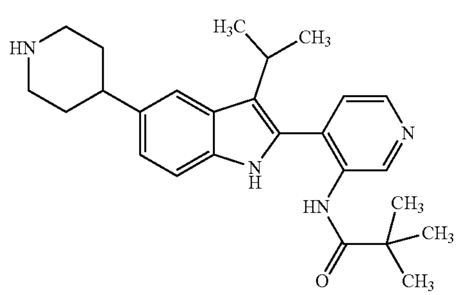 [SMILES: CC(C)c1c(-c2ccncc2NC(=O)C(C)(C)C)[nH]c2ccc(C3CCNCC3)cc12] | 419.4 | 0.92 | QC-AA |
| 38 | 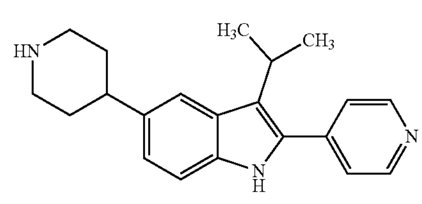 [SMILES: CC(C)c1c(-c2ccncc2)[nH]c2ccc(C3CCNCC3)cc12] | 320.1 | 0.63 | QC-TFA |

TABLE 1-continued

| Ex. No. | Structure | LCMS MH+ | Rt (min) | HPLC Method |
|---|---|---|---|---|
| 39 | 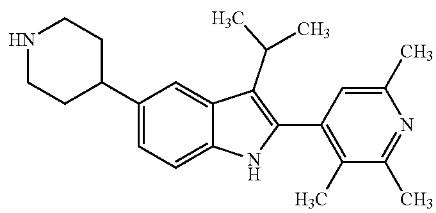 [SMILES: Cc1cc(-c2[nH]c3ccc(C4CCNCC4)cc3c2C(C)C)c(C)c(C)n1] | 362.3 | 0.86 | QC-TFA |
| 40 | 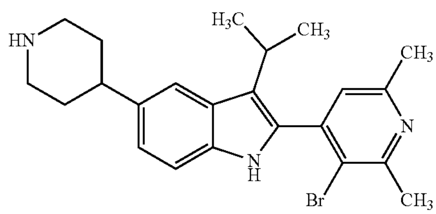 [SMILES: Cc1cc(-c2[nH]c3ccc(C4CCNCC4)cc3c2C(C)C)c(Br)c(C)n1] | 426.2 | 1.89 | QC-AA |
| 42 | 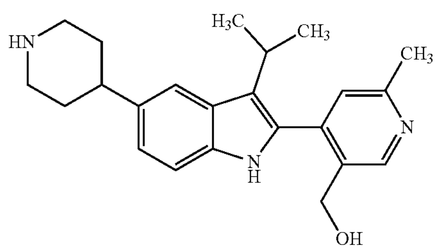 [SMILES: Cc1cc(-c2[nH]c3ccc(C4CCNCC4)cc3c2C(C)C)c(CO)cn1] | 364 | 0.98 | QC-AA |
| 43 | 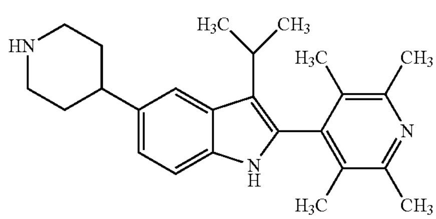 [SMILES: Cc1nc(C)c(C)c(-c2[nH]c3ccc(C4CCNCC4)cc3c2C(C)C)c1C] | 376.3 | 0.89 | QC-TFA |
| 44 | 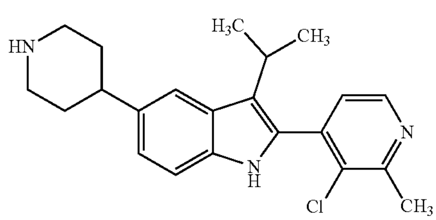 [SMILES: Cc1nccc(-c2[nH]c3ccc(C4CCNCC4)cc3c2C(C)C)c1Cl] | 368.3 | 1.75 | QC-AA |
| 46 | 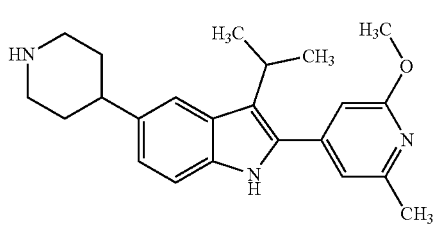 [SMILES: COc1cc(-c2[nH]c3ccc(C4CCNCC4)cc3c2C(C)C)cc(C)n1] | 364 | 1.49 | QC-AA |
| 47 | 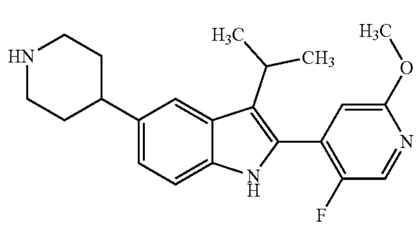 [SMILES: COc1cc(-c2[nH]c3ccc(C4CCNCC4)cc3c2C(C)C)c(F)cn1] | 368.2 | 1.44 | QC-AA |

TABLE 1-continued

| Ex. No. | Structure | LCMS MH+ | Rt (min) | HPLC Method |
|---|---|---|---|---|
| 50 | 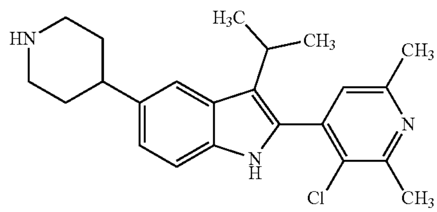 [SMILES: Cc1cc(-c2[nH]c3ccc(C4CCNCC4)cc3c2C(C)C)c(Cl)c(C)n1] | 382.3 | 0.99 | QC-TFA |
| 51 | 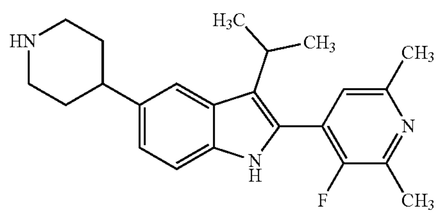 [SMILES: Cc1cc(-c2[nH]c3ccc(C4CCNCC4)cc3c2C(C)C)c(F)c(C)n1] | 366.2 | 0.60 | G |
| 53 | 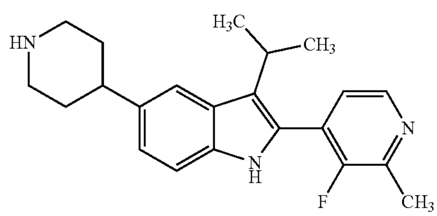 [SMILES: Cc1nccc(-c2[nH]c3ccc(C4CCNCC4)cc3c2C(C)C)c1F] | 352.2 | 0.92 | QC-TFA |
| 56 | 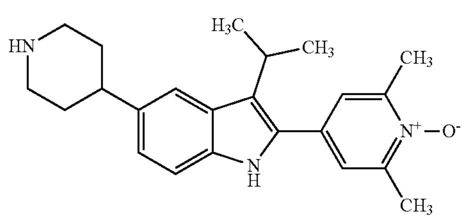 [SMILES: Cc1cc(-c2[nH]c3ccc(C4CCNCC4)cc3c2C(C)C)cc(C)[n+]1[O-]] | 363.9 | 0.89 | QC-TFA |
| 57 | 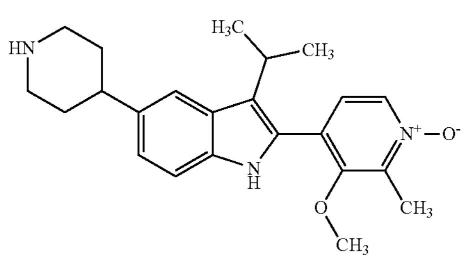 [SMILES: COc1c(-c2[nH]c3ccc(C4CCNCC4)cc3c2C(C)C)cc[n+]([O-])c1C] | 380.2 | 1.14 | QC-TFA |
| 58 | 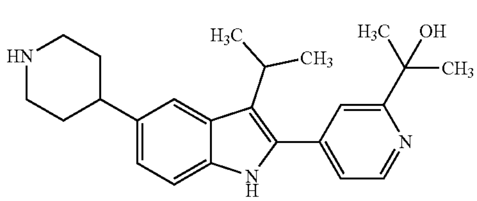 [SMILES: CC(C)c1c(-c2ccnc(C(C)(C)O)c2)[nH]c2ccc(C3CCNCC3)cc12] | 378.3 | 2.09 | D |

The following examples were prepared according to the general procedure described in Example 1.

TABLE 2

| Ex. No. | Structure | LCMS MH+ | Rt (min) | HPLC Method |
|---|---|---|---|---|
| 60 | 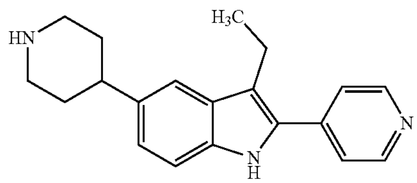 [SMILES: CCc1c(-c2ccncc2)[nH]c2ccc(C3CCNCC3)cc12] | 306.3 | 1.065 | E |
| 61 | 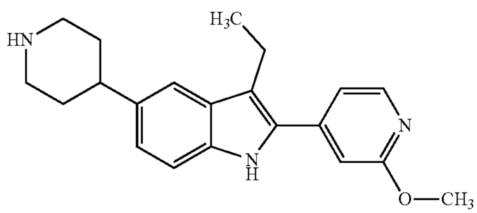 [SMILES: CCc1c(-c2ccnc(OC)c2)[nH]c2ccc(C3CCNCC3)cc12] | 336.2 | 0.95 | QC-TFA |
| 62 | 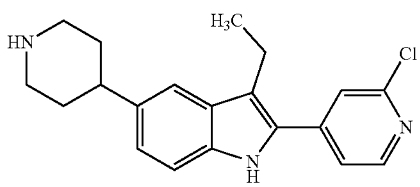 [SMILES: CCc1c(-c2ccnc(Cl)c2)[nH]c2ccc(C3CCNCC3)cc12] | 340.2 | 1.152 | F |
| 63 | 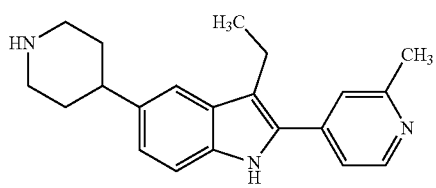 [SMILES: CCc1c(-c2ccnc(C)c2)[nH]c2ccc(C3CCNCC3)cc12] | 320.4 | 1.08 | QC-AA |
| 64 | 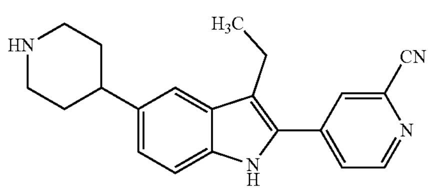 [SMILES: CCc1c(-c2ccnc(C#N)c2)[nH]c2ccc(C3CCNCC3)cc12] | 331.2 | 1.14 | QC-AA |
| 65 | 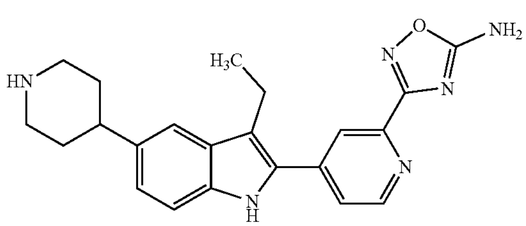 [SMILES: CCc1c(-c2ccnc(-c3noc(N)n3)c2)[nH]c2ccc(C3CCNCC3)cc12] | 389.1 | 0.71 | QC-TFA |
| 66 | 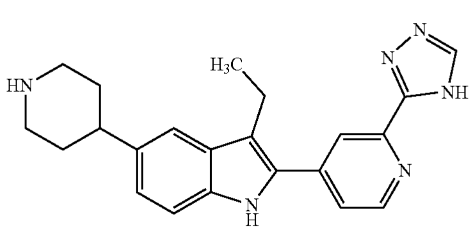 [SMILES: CCc1c(-c2ccnc(-c3nnc[nH]3)c2)[nH]c2ccc(C3CCNCC3)cc12] | 373.3 | 0.83 | QC-AA |

TABLE 2-continued
| Ex. No. | Structure | LCMS MH+ | Rt (min) | HPLC Method |
|---|---|---|---|---|
| 67 | 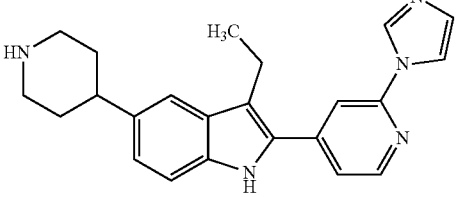 | 372.4 | 1.15 | QC-AA |
| 68 | 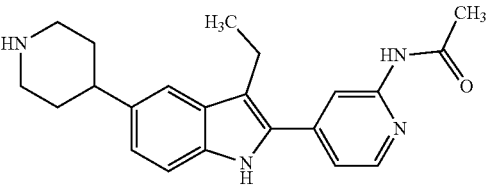 [SMILES: CCc1c(-c2ccnc(NC(C)=O)c2)[nH]c2ccc(C3CCNCC3)cc12] | 363.3 | 0.844 | F |
| 69 | 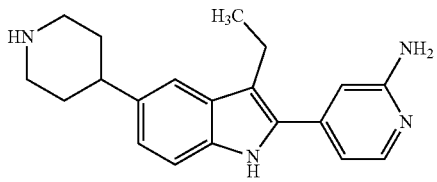 [SMILES: CCc1c(-c2ccnc(N)c2)[nH]c2ccc(C3CCNCC3)cc12] | 321.3 | 0.808 | F |
| 70 | 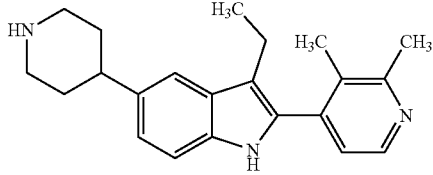 [SMILES: CCc1c(-c2ccnc(C)c2C)[nH]c2ccc(C3CCNCC3)cc12] | 334.2 | 0.62 | QC-TFA |
| 71 | 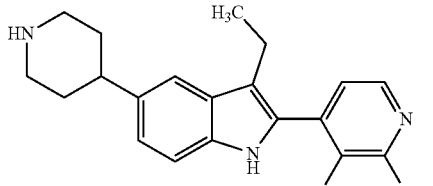 | 337.2 | 0.59 | |
The following examples were prepared according to the general procedure described in Example 1.
TABLE 3
| Ex. No. | Structure | LCMS MH+ | Rt (min) | HPLC Method |
|---|---|---|---|---|
| 73 | 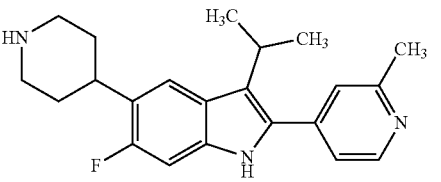 [SMILES: Cc1cc(-c2[nH]c3cc(F)c(C4CCNCC4)cc3c2C(C)C)ccn1] | 352.2 | 1.57 | QC-AA |

TABLE 3-continued

| Ex. No. | Structure | LCMS MH+ | Rt (min) | HPLC Method |
|---|---|---|---|---|
| 74 | 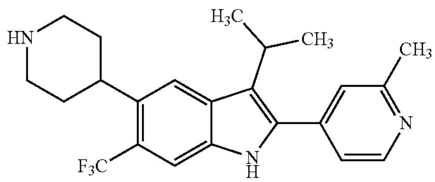 [SMILES: Cc1cc(-c2[nH]c3cc(C(F)(F)F)c(C4CCNCC4)cc3c2C(C)C)ccn1] | 402.4 | 0.63 | G |
| 75 | 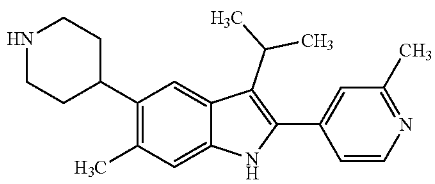 [SMILES: Cc1cc(-c2[nH]c3cc(C)c(C4CCNCC4)cc3c2C(C)C)ccn1] | 348.3 | 0.56 | G |
| 76 | 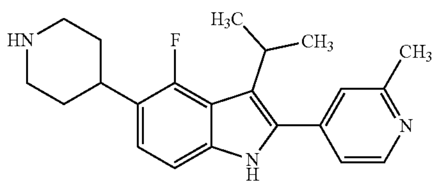 [SMILES: Cc1cc(-c2[nH]c3ccc(C4CCNCC4)c(F)c3c2C(C)C)ccn1] | 352.3 | 0.61 | G |
| 77 | 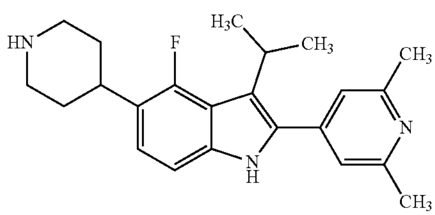 | 366.3 | 0.91 | QC-TFA |
| 78 | 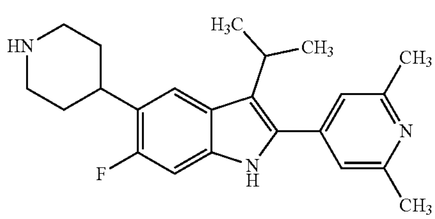 | 366.2 | 0.58 | G |
| 79 | 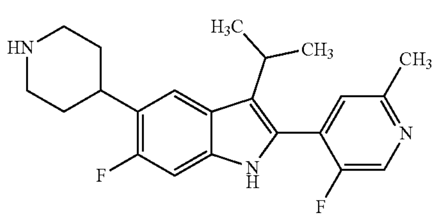 [SMILES: Cc1cc(-c2[nH]c3cc(F)c(C4CCNCC4)cc3c2C(C)C)c(F)cn1] | 370.2 | 0.53 | G |
| 80 | 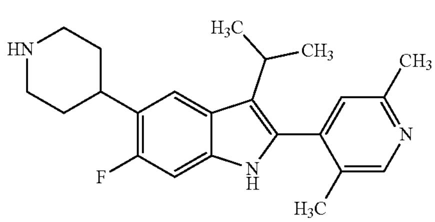 | — | — | — |

TABLE 3-continued

| Ex. No. | Structure | LCMS MH+ | Rt (min) | HPLC Method |
|---|---|---|---|---|
| 81 | 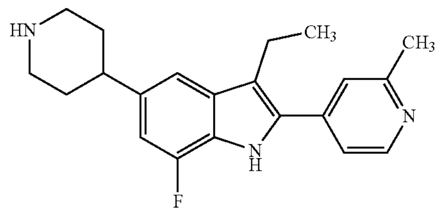 [SMILES: CCc1c(-c2ccnc(C)c2)[nH]c2c(F)cc(C3CCNCC3)cc12] | 338.2 | 1.54 | QC-AA |
| 82 | 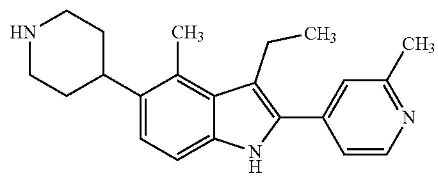 [SMILES: CCc1c(-c2ccnc(C)c2)[nH]c2ccc(C3CCNCC3)c(C)c12] | 334 | 0.8 | QC-TFA |
| 83 | 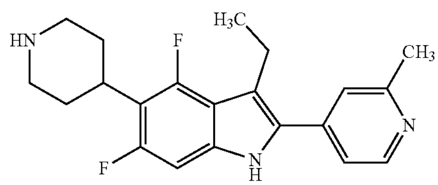 [SMILES: CCc1c(-c2ccnc(C)c2)[nH]c2cc(F)c(C3CCNCC3)c(F)c12] | 356 | 1.15 | QC-AA |

The following examples were prepared according to the general procedure described in Example 1.

TABLE 4

| Ex. No. | Structure | LCMS MH+ | Rt (min) | HPLC Method |
|---|---|---|---|---|
| 84 | 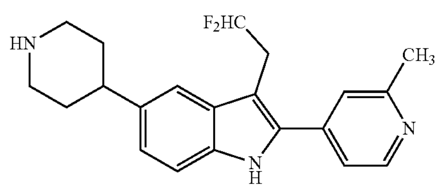 [SMILES: Cc1cc(-c2[nH]c3ccc(C4CCNCC4)cc3c2CC(F)F)ccn1] | 356 | 1.987 | E |
| 85 | 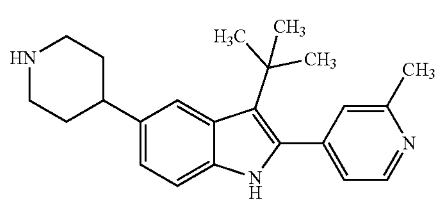 [SMILES: Cc1cc(-c2[nH]c3ccc(C4CCNCC4)cc3c2C(C)(C)C)ccn1] | 348.4 | 1.23 | QC-AA |
| 88 | 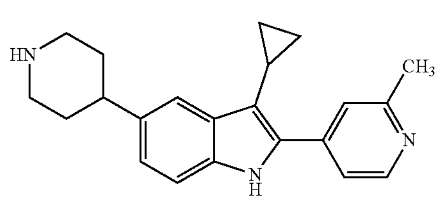 [SMILES: Cc1cc(-c2[nH]c3ccc(C4CCNCC4)cc3c2C2CC2)ccn1] | 332.2 | 1.52 | QC-AA |

TABLE 4-continued

| Ex. No. | Structure | LCMS MH+ | Rt (min) | HPLC Method |
|---|---|---|---|---|
| 89 | 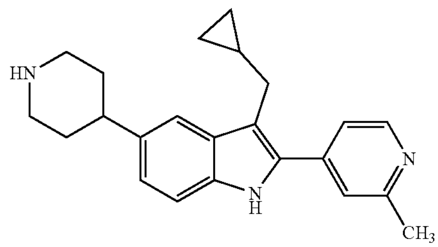 [SMILES: Cc1cc(-c2[nH]c3ccc(C4CCNCC4)cc3c2CC2CC2)ccn1] | 346 | 1.15 | QC-AA |
| 91 | 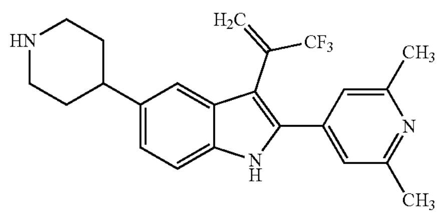 | 400.3 | 0.87 | QC-TFA |
| 92 | 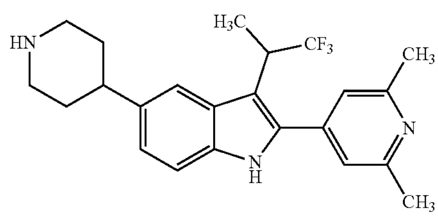 [SMILES: Cc1cc(-c2[nH]c3ccc(C4CCNCC4)cc3c2C(C)C(F)(F)F)cc(C)n1] | 402.1 | 0.86 | QC-TFA |
| 93 | 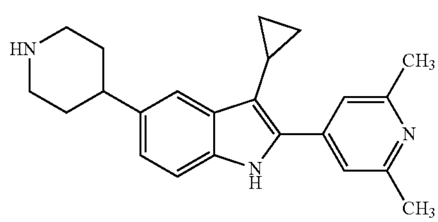 [SMILES: Cc1cc(-c2[nH]c3ccc(C4CCNCC4)cc3c2C2CC2)cc(C)n1] | 346.1 | 1.2 | QC-AA |
| 94 | 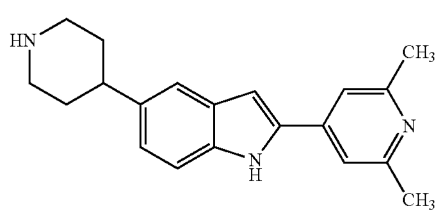 [SMILES: Cc1cc(-c2cc3cc(C4CCNCC4)ccc3[nH]2)cc(C)n1] | 306.2 | 0.991 | E |
| 96 | 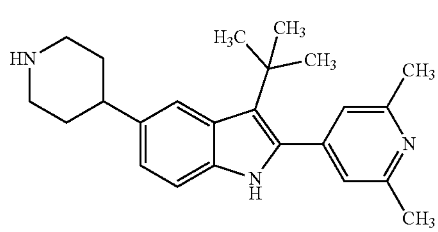 [SMILES: Cc1cc(-c2[nH]c3ccc(C4CCNCC4)cc3c2C(C)(C)C)cc(C)n1] | 362 | 1.4 | QC-AA |

Example 97

3-(dimethylamino)-1-(4-(2-(2,6-dimethylpyridin-4-yl)-3-isopropyl-1H-indol-5-yl) piperidin-1-yl)propan-1-one

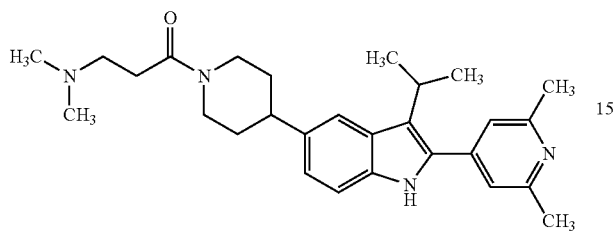
(97)

3-(Dimethylamino)propanoic acid (0.019 g, 0.164 mmol) and HATU (0.083 g, 0.219 mmol) were dissolved in DMF (2 mL). Next, 2-(2,6-dimethylpyridin-4-yl)-3-isopropyl-5-(piperidin-4-yl)-1H-indole, HCl (0.042 g, 0.109 mmol) was added to the reaction mixture followed by TEA (0.2 mL, 1.435 mmol). The resulting reaction mixture was stirred for 3 h at room temperature. DMF was removed under vacuum, the residue was quenched with ice water, and the mixture was extracted with ethyl acetate (3×20) ml. The ethyl acetate layer was dried over $Na_2SO_4$, filtered and the filtrate was concentrated. The crude material was purified by preparative LCMS. The fractions containing the desired product was combined and dried using Genevac centrifugal evaporator to afford 3-(dimethylamino)-1-(4-(2-(2,6-dimethylpyridin-4-yl)-3-isopropyl-1H-indol-5-yl)piperidin-1-yl)propan-1-one (0.023 g, 0.049 mmol, 44.6% yield) as a pale solid. LCMS retention time 1.764 min [E]. MS (E−) m/z: 447.3 (M+H).

The following examples were prepared according to the general procedure used in the preparation of Example 97.

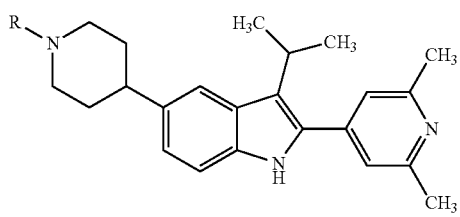

TABLE 5

| Ex. No. | Structure | LCMS [M + H] | Rt (min) | Method |
|---|---|---|---|---|
| 98 | —C(O)CH$_2$N(CH$_3$)$_2$ | 433.4 | 1.37 | E |
| 99 | —C(O)CH$_2$N(CH$_2$CH$_3$)$_2$ | 461.3 | 1.672 | E |
| 100 | 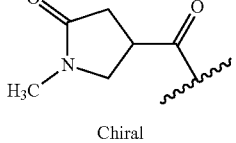 | 473.4 | 2.085 | E |
| 101 | 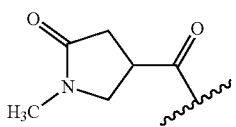<br>Chiral | 473.4 | 2.983 | A |
| 102 | 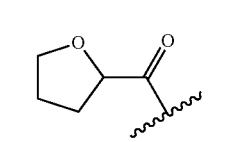 [SMILES: *C(=O)C1CCCO1]<br>Chiral | 473.4 | 2.949 | A |
| 103 | 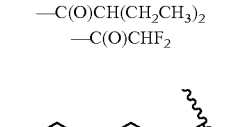 | 446.2 | 2.033 | E |
| 104 | —C(O)CH(CH$_2$CH$_3$)$_2$ | 446.3 | 1.83 | F |
| 105 | —C(O)CHF$_2$ | 426.2 | 2.155 | E |
| 106 | 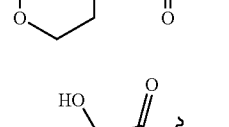 | 474.3 | 2.076 | E |
| 107 | 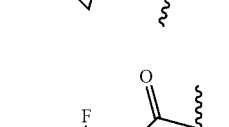 | 432.2 | 1.926 | E |
| 108 | 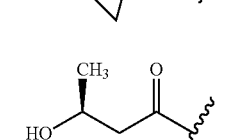 | 452.2 | 1.613 | F |
| 109 | 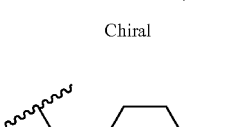<br>Chiral | 434.4 | 1.892 | E |
| 110 | 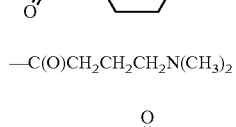 | 473.3 | 1.671 | E |
| 111 | —C(O)CH$_2$CH$_2$CH$_2$N(CH$_3$)$_2$ | 461.3 | 1.807 | E |
| 112 | 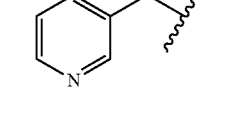 | 453.3 | 1.963 | E |

TABLE 5-continued
| Ex. No. | Structure | LCMS [M + H] | Rt (min) | Method |
|---|---|---|---|---|
| 113 | 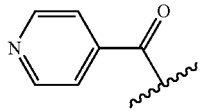 | 453.2 | 1.958 | E |
| 114 | 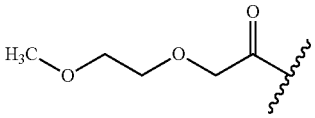 [SMILES: *C(=O)COCCOC] | 464.3 | 1.95 | E |
TABLE 5-continued
| Ex. No. | Structure | LCMS [M + H] | Rt (min) | Method |
|---|---|---|---|---|
| 115 | —C(O)CH$_2$OCH$_3$ | 420.2 | 1.951 | E |
| 116 | —C(O)CH$_2$OH | 406.2 | 1.836 | E |
| 117 | —C(O)CH$_2$CH$_2$OH | 420.3 | 1.778 | E |
| 118 | —C(O)CH$_2$CH$_2$OCH$_3$ | 434.3 | 2.004 | E |
TABLE 6
| Ex. No. | Structure | LCMS MH$^+$ | Rt (min) | HPLC Method |
|---|---|---|---|---|
| 119 | 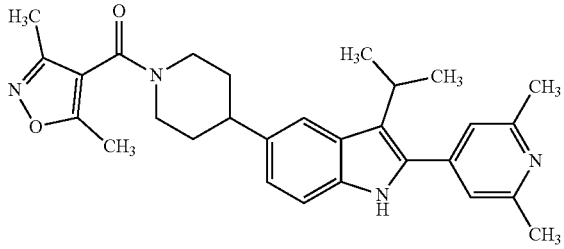 [SMILES: Cc1cc(-c2[nH]c3ccc(C4CCN(C(=O)c5c(C)noc5C)CC4)cc3c2C(C)C)cc(C)n1] | 471.2 | 1.88 | QC-AA |
| 120 | 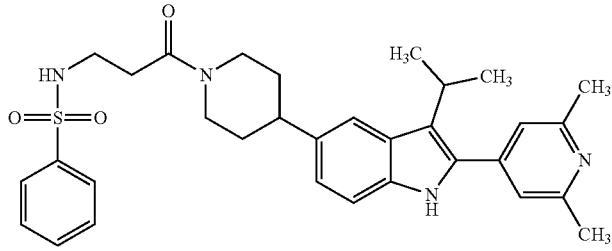 [SMILES: Cc1cc(-c2[nH]c3ccc(C4CCN(C(=O)CCNS(=O)(=O)c5ccccc5)CC4)cc3c2C(C)C)cc(C)n1] | 559.5 | 1.52 | QC-TFA |
| 121 | 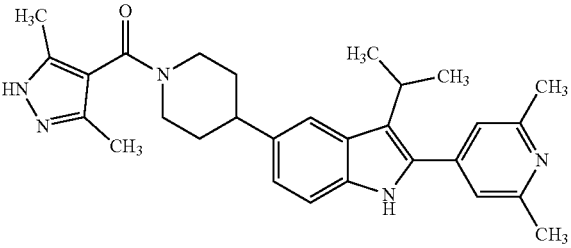 [SMILES: Cc1cc(-c2[nH]c3ccc(C4CCN(C(=O)c5c(C)n[nH]c5C)CC4)cc3c2C(C)C)cc(C)n1] | 470.2 | 1.62 | QC-AA |
| 122 | 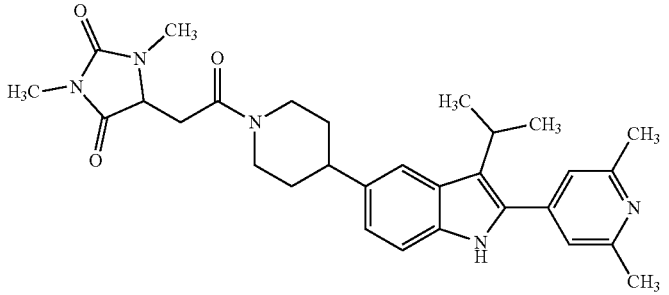 | 516.2 | 1.64 | QC-AA |

TABLE 6-continued

| Ex. No. | Structure | LCMS MH+ | Rt (min) | HPLC Method |
|---|---|---|---|---|
| 123 | 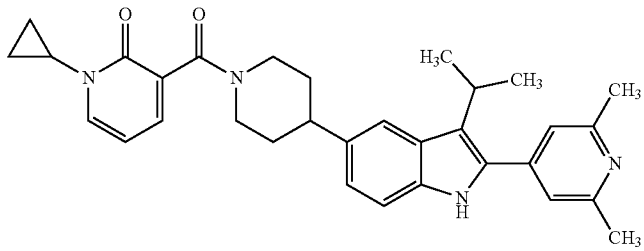 [SMILES: Cc1cc(-c2[nH]c3ccc(C4CCN(C(=O)c5cccn(C6CC6)c5=O)CC4)cc3c2C(C)C)cc(C)n1] | 509.2 | 1.68 | QC-AA |
| 124 | 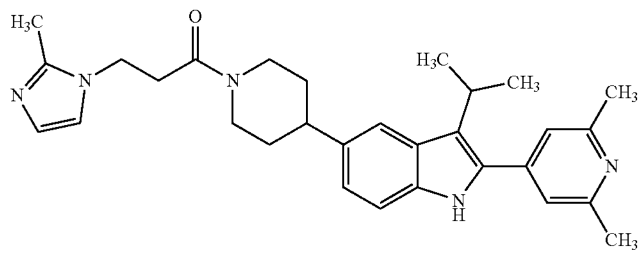 [SMILES: Cc1cc(-c2[nH]c3ccc(C4CCN(C(=O)CCn5ccnc5C)CC4)cc3c2C(C)C)cc(C)n1] | 484.2 | 1.5 | QC-AA |
| 125 | 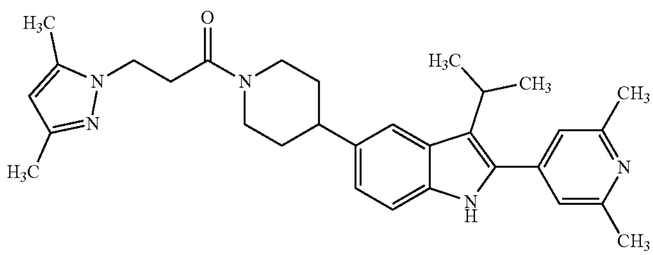 [SMILES: Cc1cc(-c2[nH]c3ccc(C4CCN(C(=O)CCn5nc(C)cc5C)CC4)cc3c2C(C)C)cc(C)n1] | 498.2 | 1.88 | QC-AA |
| 126 | 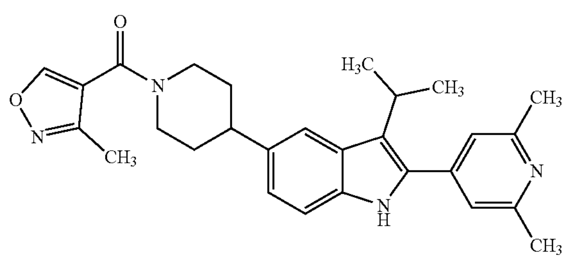 [SMILES: Cc1cc(-c2[nH]c3ccc(C4CCN(C(=O)c5conc5C)CC4)cc3c2C(C)C)cc(C)n1] | 475.2 | 1.85 | QC-AA |
| 127 | 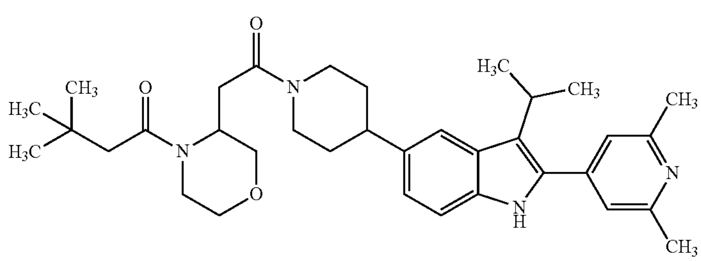 [SMILES: Cc1cc(-c2[nH]c3ccc(C4CCN(C(=O)CC5COCCN5C(=O)CC(C)(C)C)CC4)cc3c2C(C)C)cc(C)n1] | 575.2 | 2.11 | QC-AA |
| 128 | 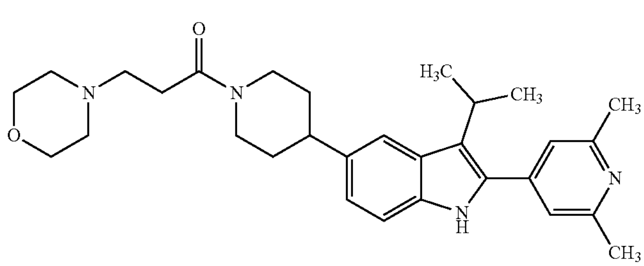 [SMILES: Cc1cc(-c2[nH]c3ccc(C4CCN(C(=O)CCN5CCOCC5)CC4)cc3c2C(C)C)cc(C)n1] | 489.2 | 1.63 | QC-AA |

TABLE 6-continued

| Ex. No. | Structure | LCMS MH+ | Rt (min) | HPLC Method |
|---|---|---|---|---|
| 129 | 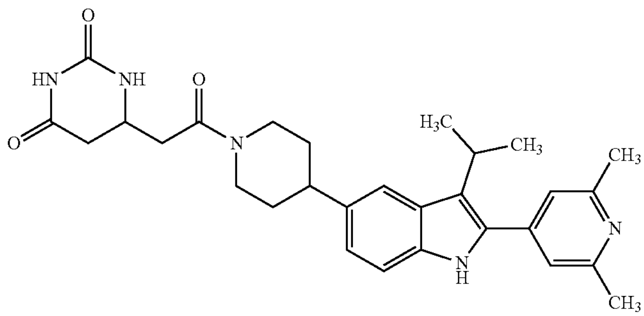 [SMILES: Cc1cc(-c2[nH]c3ccc(C4CCN(C(=O)CC5CC(=O)NC(=O)N5)CC4)cc3c2C(C)C)cc(C)n1] | 502.4 | 1.1 | QC-TFA |
| 130 | 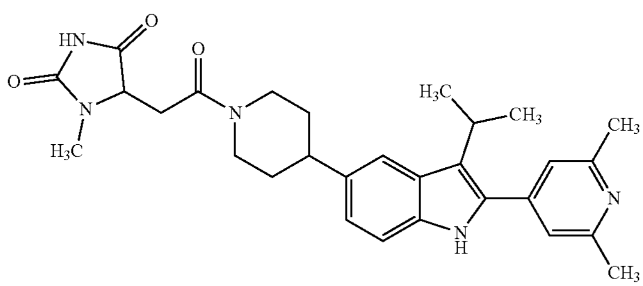 [SMILES: Cc1cc(-c2[nH]c3ccc(C4CCN(C(=O)CC5C(=O)NC(=O)N5C)CC4)cc3c2C(C)C)cc(C)n1] | 502.2 | 1.14 | QC-TFA |
| 131 | 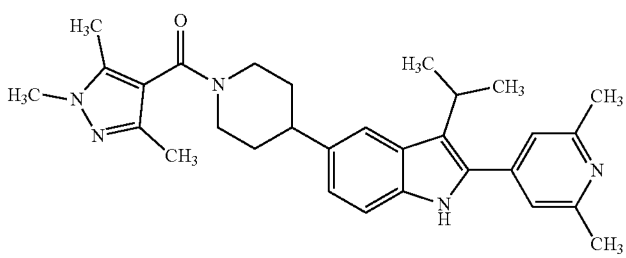 | 484.5 | 1.27 | QC-TFA |
| 132 | 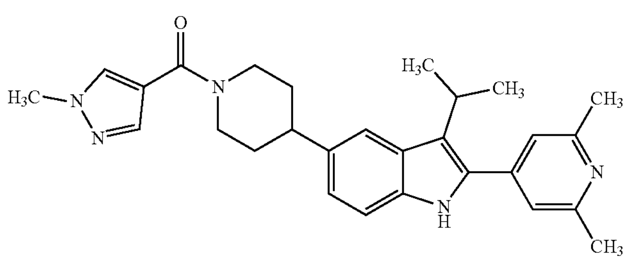 | 456.2 | 1.67 | QC-AA |
| 133 | 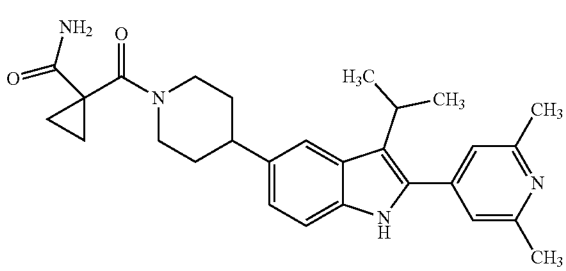 [SMILES: Cc1cc(-c2[nH]c3ccc(C4CCN(C(=O)C5(C(N)=O)CC5)CC4)cc3c2C(C)C)cc(C)n1] | 459.2 | 1.55 | QC-AA |

TABLE 6-continued

| Ex. No. | Structure | LCMS MH+ | Rt (min) | HPLC Method |
|---|---|---|---|---|
| 134 | 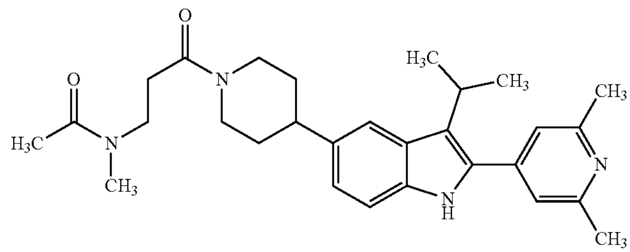 [SMILES: CC(=O)N(C)CCC(=O)N1CCC(c2ccc3[nH]c(-c4cc(C)nc(C)c4)c(C(C)C)c3c2)CC1] | 475.1 | 1.59 | QC-AA |
| 135 | 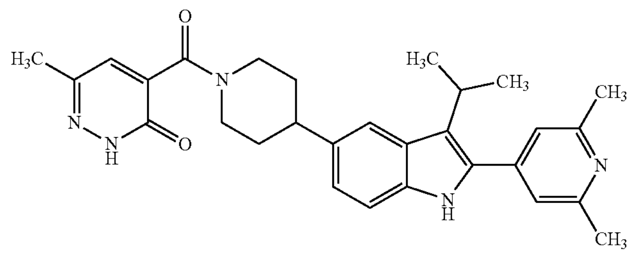 | 484.1 | 1.55 | QC-AA |
| 136 | 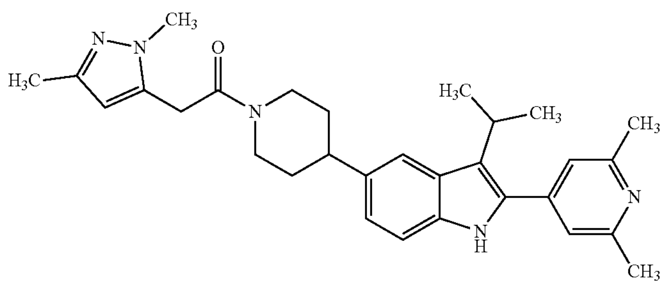 | 484.4 | 1.19 | QC-TFA |
| 137 | 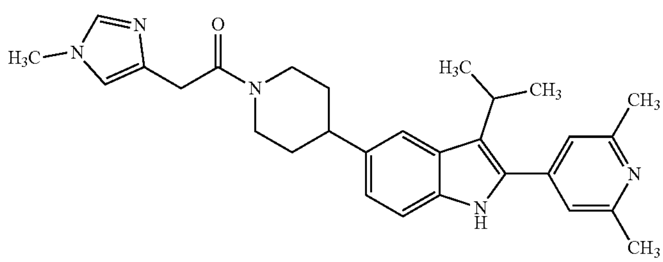 | 470.2 | 1.55 | QC-AA |
| 138 | 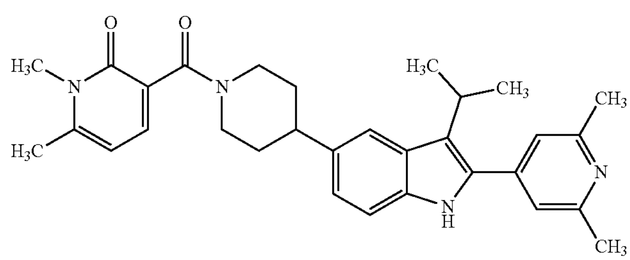 | 497.2 | 1.66 | QC-AA |
| 139 | 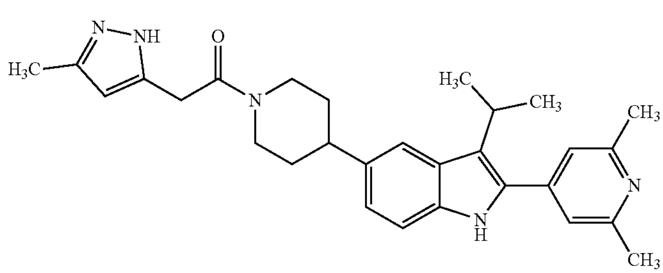 | 471.2 | 1.00 | QC-TFA |

TABLE 6-continued

| Ex. No. | Structure | LCMS MH+ | Rt (min) | HPLC Method |
|---|---|---|---|---|
| 140 | 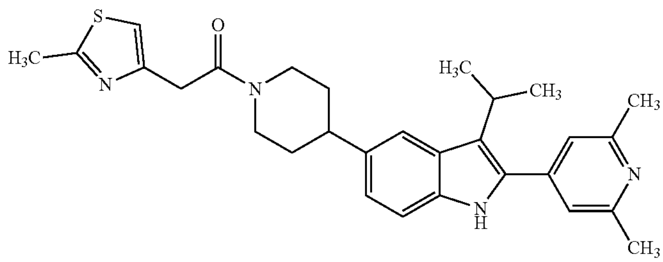 | 487.2 | 1.86 | QC-AA |
| 141 | 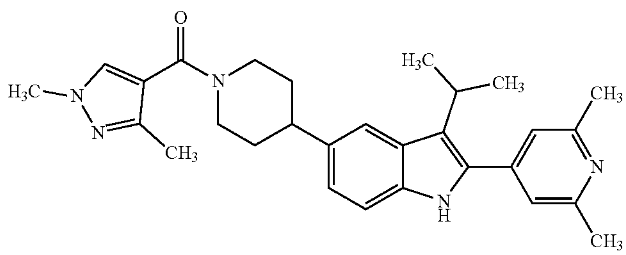 | 470.2 | 1.72 | QC-AA |
| 142 | 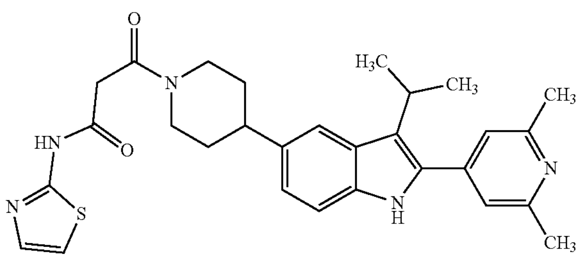 [SMILES: Cc1cc(-c2[nH]c3ccc(C4CCN(C(=O)CC(=O)Nc5nccs5)CC4)cc3c2C(C)C)cc(C)n1] | 516.4 | 1.76 | QC-AA |
| 143 | 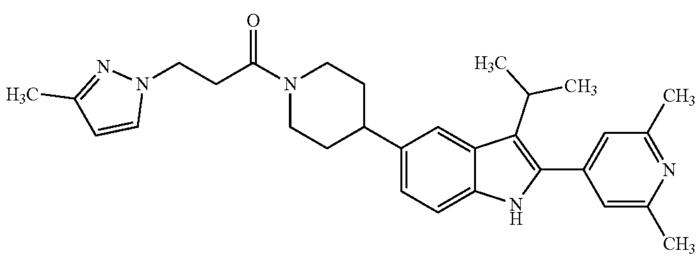 | 484.2 | 1.84 | QC-AA |
| 144 | 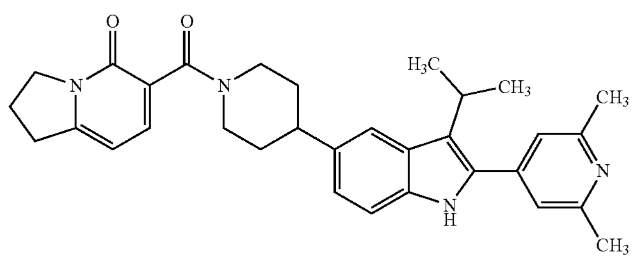 [SMILES: Cc1cc(-c2[nH]c3ccc(C4CCN(C(=O)c5ccc6n(c5=O)CCC6)CC4)cc3c2C(C)C)cc(C)n1] | 509.4 | 1.66 | QC-AA |
| 145 | 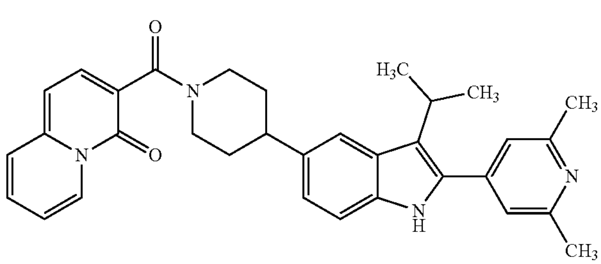 [SMILES: Cc1cc(-c2[nH]c3ccc(C4CCN(C(=O)c5ccc6ccccn6c5=O)CC4)cc3c2C(C)C)cc(C)n1] | 519.2 | 1.77 | QC-AA |

TABLE 6-continued

| Ex. No. | Structure | LCMS MH+ | Rt (min) | HPLC Method |
|---|---|---|---|---|
| 146 | 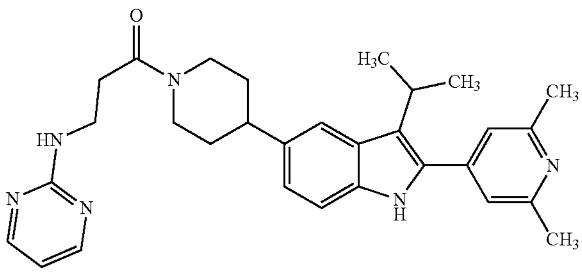 [SMILES: Cc1cc(-c2[nH]c3ccc(C4CCN(C(=O)CCNc5ncccn5)CC4)cc3c2C(C)C)cc(C)n1] | 497.2 | 1.1 | QC-TFA |
| 147 | 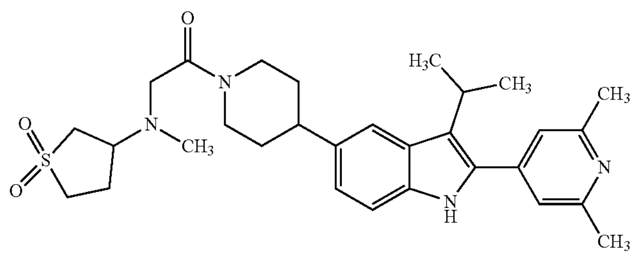 [SMILES: Cc1cc(-c2[nH]c3ccc(C4CCN(C(=O)CN(C)C5CCS(=O)(=O)C5)CC4)cc3c2C(C)C)cc(C)n1] | 537 | 1.7 | QC-AA |
| 148 | 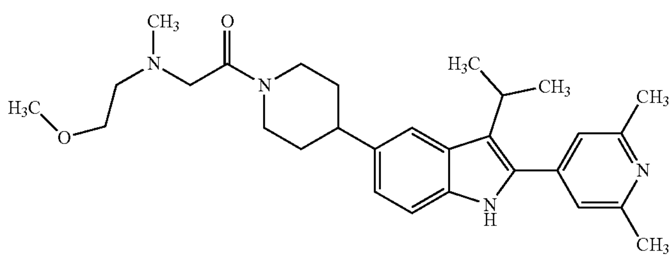 | 477 | 1.7 | QC-AA |
| 149 | 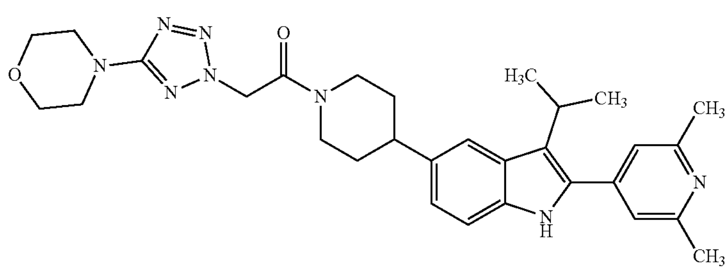 [SMILES: Cc1cc(-c2[nH]c3ccc(C4CCN(C(=O)Cn5nnc(N6CCOCC6)n5)CC4)cc3c2C(C)C)cc(C)n1] | 543 | 1.87 | QC-AA |
| 150 | 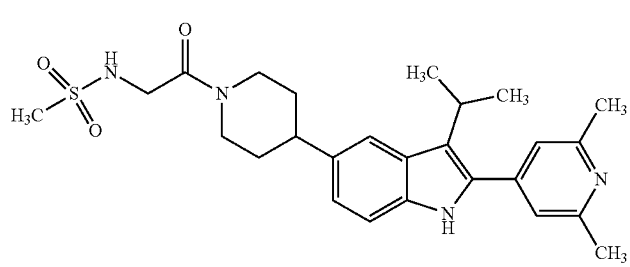 | 483 | 1.62 | QC-AA |

TABLE 6-continued

| Ex. No. | Structure | LCMS MH+ | Rt (min) | HPLC Method |
|---|---|---|---|---|
| 151 | 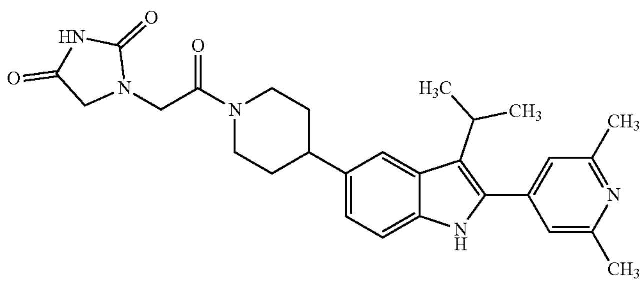 [SMILES: Cc1cc(-c2[nH]c3ccc(C4CCN(C(=O)CN5CC(=O)NC5=O)CC4)cc3c2C(C)C)cc(C)n1] | 488 | 1.5 | QC-AA |
| 152 | 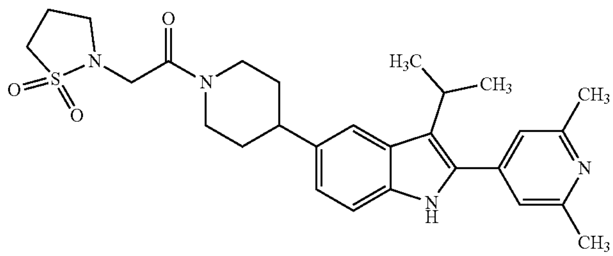 [SMILES: Cc1cc(-c2[nH]c3ccc(C4CCN(C(=O)CN5CCCS5(=O)=O)CC4)cc3c2C(C)C)cc(C)n1] | 509 | 1.61 | QC-AA |
| 153 | 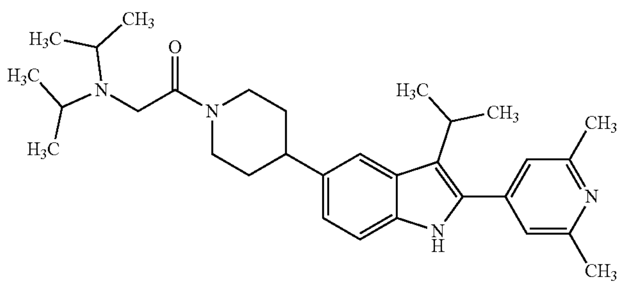 [SMILES: Cc1cc(-c2[nH]c3ccc(C4CCN(C(=O)CN(C(C)C)C(C)C)CC4)cc3c2C(C)C)cc(C)n1] | 489 | 1.58 | QC-AA |
| 154 | 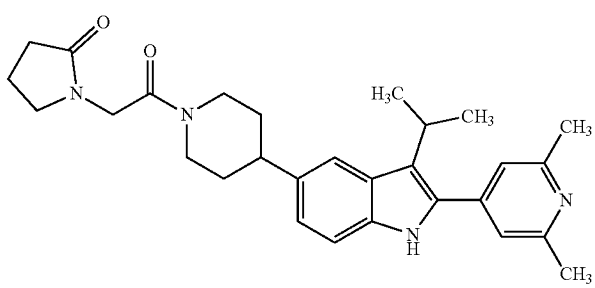 [SMILES: Cc1cc(-c2[nH]c3ccc(C4CCN(C(=O)CN5CCCC5=O)CC4)cc3c2C(C)C)cc(C)n1] | 473 | 1.63 | QC-AA |
| 155 | 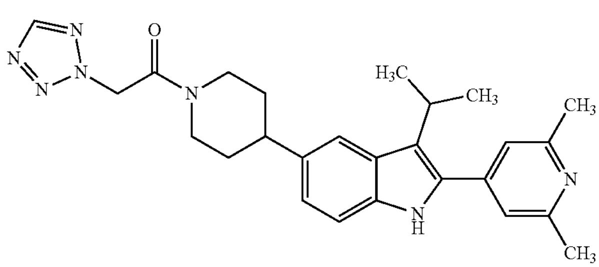 [SMILES: Cc1cc(-c2[nH]c3ccc(C4CCN(C(=O)Cn5ncnn5)CC4)cc3c2C(C)C)cc(C)n1] | 458 | 1.7 | QC-AA |

TABLE 6-continued
| Ex. No. | Structure | LCMS MH+ | Rt (min) | HPLC Method |
|---|---|---|---|---|
| 156 | 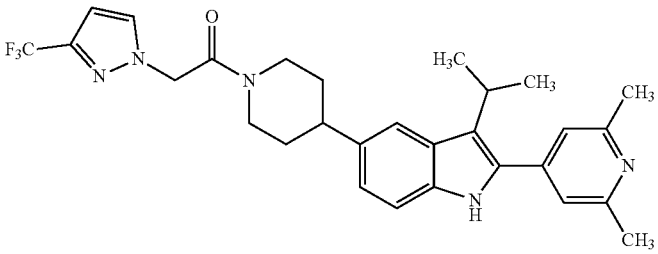 [SMILES: Cc1cc(-c2[nH]c3ccc(C4CCN(C(=O)Cn5ccc(C(F)(F)F)n5)CC4)cc3c2C(C)C)cc(C)n1] | 524 | 2.1 | QC-AA |
| 157 | 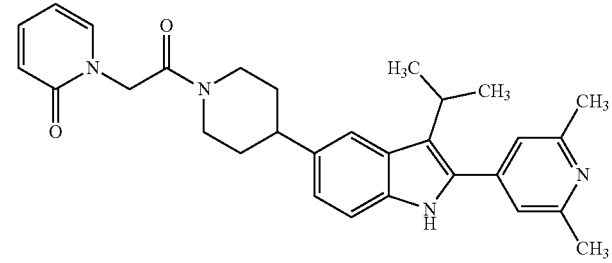 [SMILES: Cc1cc(-c2[nH]c3ccc(C4CCN(C(=O)Cn5ccccc5=O)CC4)cc3c2C(C)C)cc(C)n1] | 483 | 1.6 | QC-AA |
| 158 | 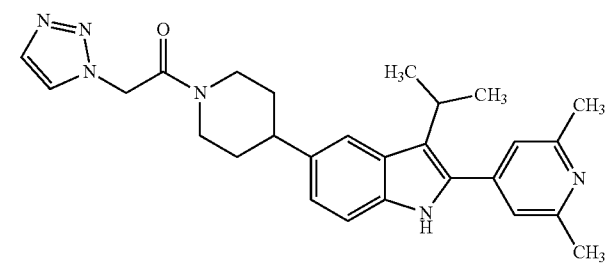 [SMILES: Cc1cc(-c2[nH]c3ccc(C4CCN(C(=O)Cn5ccnn5)CC4)cc3c2C(C)C)cc(C)n1] | 457 | 1.6 | QC-AA |
| 159 | 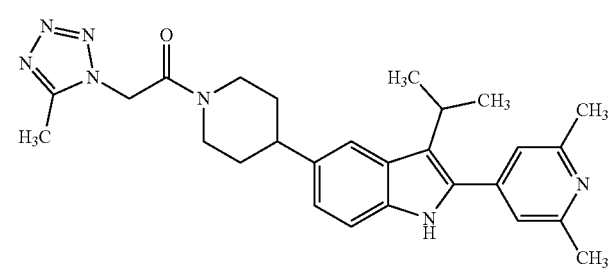 [SMILES: Cc1cc(-c2[nH]c3ccc(C4CCN(C(=O)Cn5nnnc5C)CC4)cc3c2C(C)C)cc(C)n1] | 472 | 1.63 | QC-AA |
| 160 | 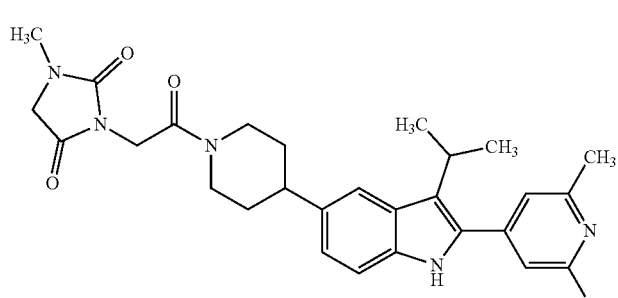 | 502 | 1.6 | QC-AA |

TABLE 6-continued

| Ex. No. | Structure | LCMS MH+ | Rt (min) | HPLC Method |
|---|---|---|---|---|
| 161 | 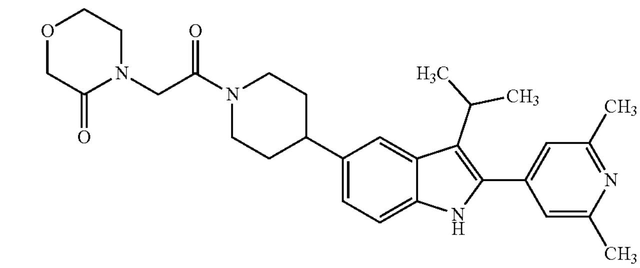 [SMILES: Cc1cc(-c2[nH]c3ccc(C4CCN(C(=O)CN5CCOCC5=O)CC4)cc3c2C(C)C)cc(C)n1] | 489 | 1.6 | QC-AA |
| 162 | 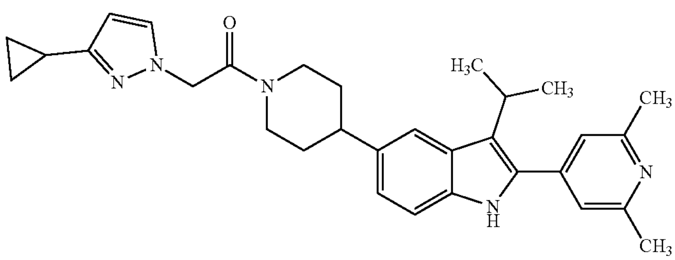 [SMILES: Cc1cc(-c2[nH]c3ccc(C4CCN(C(=O)Cn5ccc(C6CC6)n5)CC4)cc3c2C(C)C)cc(C)n1] | 496 | 1.95 | QC-AA |
| 163 | 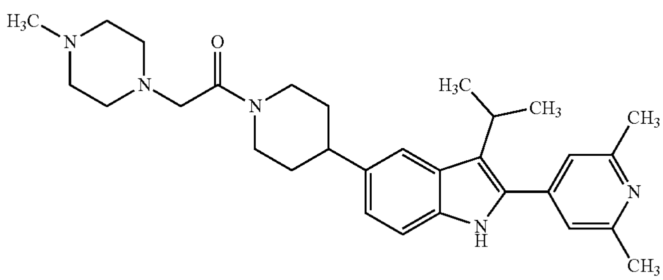 | 488 | 1.45 | QC-AA |
| 164 | 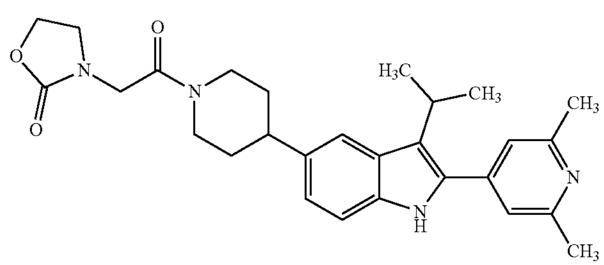 [SMILES: Cc1cc(-c2[nH]c3ccc(C4CCN(C(=O)CN5CCOC5=O)CC4)cc3c2C(C)C)cc(C)n1] | 475 | 1.6 | QC-AA |
| 165 | 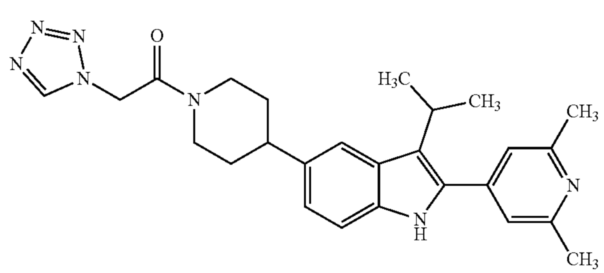 [SMILES: Cc1cc(-c2[nH]c3ccc(C4CCN(C(=O)Cn5cnnn5)CC4)cc3c2C(C)C)cc(C)n1] | 458 | 1.62 | QC-AA |

TABLE 6-continued

| Ex. No. | Structure | LCMS MH+ | Rt (min) | HPLC Method |
|---|---|---|---|---|
| 166 | 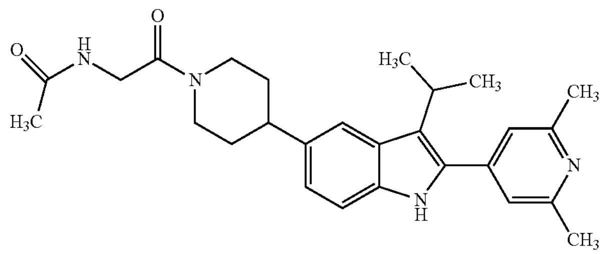 [SMILES: CC(=O)NCC(=O)N1CCC(c2ccc3[nH]c(-c4cc(C)nc(C)c4)c(C(C)C)c3c2)CC1] | 447 | 1.51 | QC-AA |
| 167 | 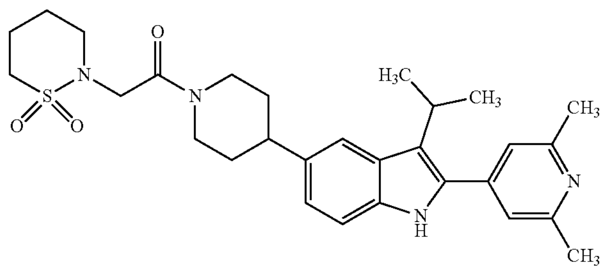 [SMILES: Cc1cc(-c2[nH]c3ccc(C4CCN(C(=O)CN5CCCCS5(=O)=O)CC4)cc3c2C(C)C)cc(C)n1] | 523 | 1.78 | QC-AA |
| 168 | 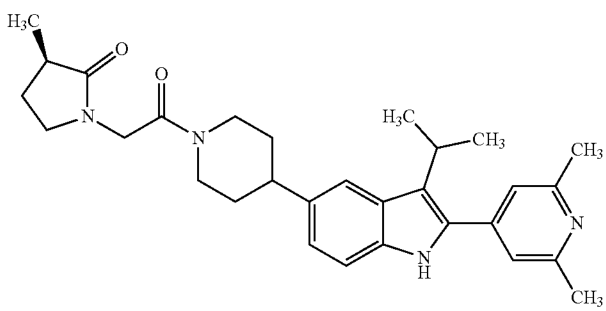 [SMILES: Cc1cc(-c2[nH]c3ccc(C4CCN(C(=O)CN5CC[C@@H](C)C5=O)CC4)cc3c2C(C)C)cc(C)n1] | 488 | 1.42 | QC-AA |
| 169 | 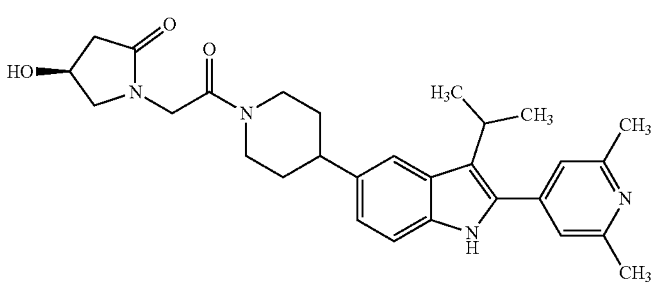 [SMILES: Cc1cc(-c2[nH]c3ccc(C4CCN(C(=O)CN5C[C@@H](O)CC5=O)CC4)cc3c2C(C)C)cc(C)n1] | 489 | 1.42 | QC-AA |
| 170 | 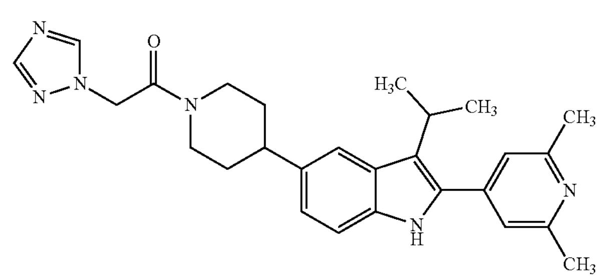 [SMILES: Cc1cc(-c2[nH]c3ccc(C4CCN(C(=O)Cn5cncn5)CC4)cc3c2C(C)C)cc(C)n1] | 457 | 1.57 | QC-AA |

TABLE 6-continued

| Ex. No. | Structure | LCMS MH+ | Rt (min) | HPLC Method |
|---|---|---|---|---|
| 171 | 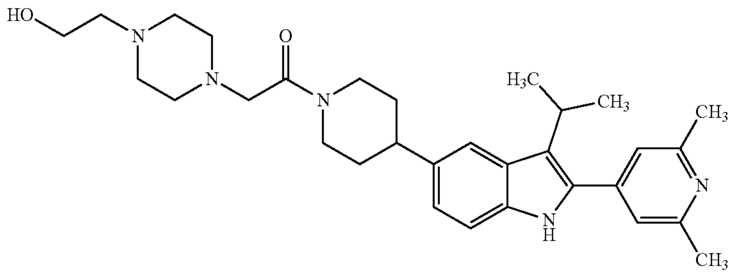 [SMILES: Cc1cc(-c2[nH]c3ccc(C4CCN(C(=O)CN5CCN(CCO)CC5)CC4)cc3c2C(C)C)cc(C)n1] | 518 | 1.39 | QC-AA |
| 172 | 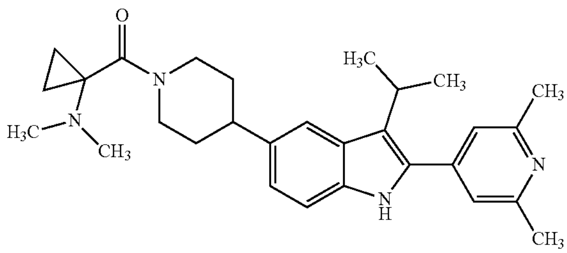 | 459 | 1.91 | QC-AA |
| 173 | 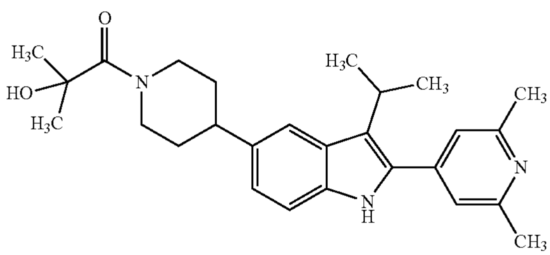 [SMILES: Cc1cc(-c2[nH]c3ccc(C4CCN(C(=O)C(C)(C)O)CC4)cc3c2C(C)C)cc(C)n1] | 434 | 1.78 | QC-AA |
| 174 | 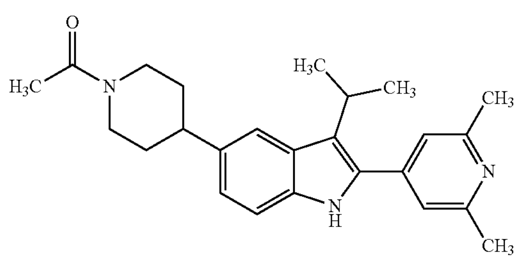 [SMILES: CC(=O)N1CCC(c2ccc3[nH]c(-c4cc(C)nc(C)c4)c(C(C)C)c3c2)CC1] | 390.3 | 1.25 | QC-TFA |
| 175 | 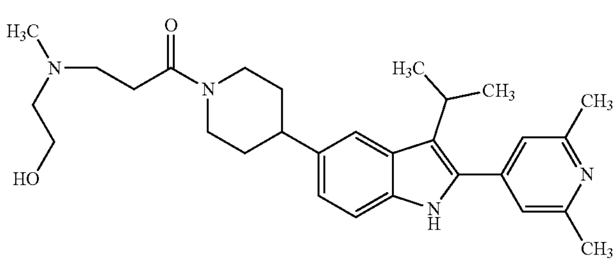 | 477.2 | 1.01 | QC-TFA |
| 176 | 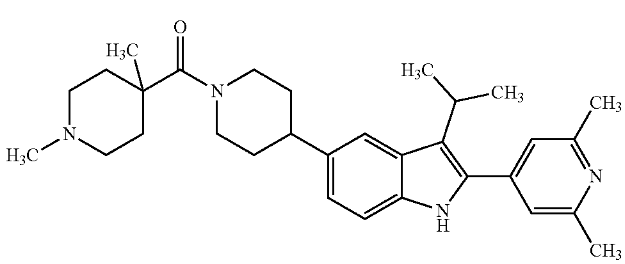 | 487.5 | 1.073 | QC-TFA |

TABLE 6-continued

| Ex. No. | Structure | LCMS MH+ | Rt (min) | HPLC Method |
|---|---|---|---|---|
| 177 | 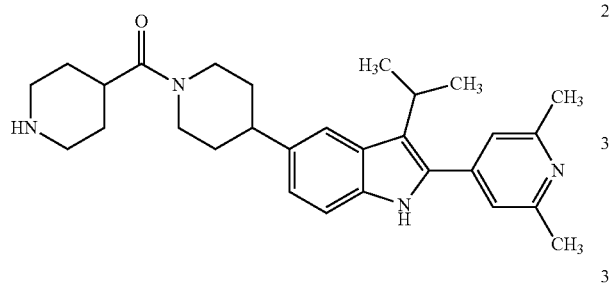 | 515.2 | 1.178 | QC-TFA |

Example 178

(4-(2-(2,6-dimethylpyridin-4-yl)-3-isopropyl-1H-indol-5-yl)piperidin-1-yl)(piperidin-4-yl)methanone (178)

Intermediate 178A: Tert-Butyl 4-(4-(2-(2,6-dimethylpyridin-4-yl)-3-isopropyl-1H-indol-5-yl)piperidine-1-carbonyl)piperidine-1-carboxylate (178A)

Tert-butyl 4-(4-(2-(2,6-dimethylpyridin-4-yl)-3-isopropyl-1H-indol-5-yl) piperidine-1-carbonyl)piperidine-1-carboxylate was prepared according to the general procedure described in Example 1 using 2-(2,6-dimethylpyridin-4-yl)-3-isopropyl-5-(piperidin-4-yl)-1H-indole, HCl as the starting intermediate (0.15 g, 91% yield). LCMS retention time 1.36 min [B]. MS (E−) m/z: 559.4 (M+H).

Example 178

To a solution tert-butyl 4-(4-(2-(2,6-dimethylpyridin-4-yl)-3-isopropyl-1H-indol-5-yl)piperidine-1-carbonyl)piperidine-1-carboxylate (0.145 g, 0.260 mmol) in DCM (2 mL) was added 4M HCl in dioxane (2.00 ml, 8.00 mmol) at room temperature. The mixture was stirred at the same temperature for 1 h. The solution was concentrated to afford crude product. The crude material was purified by prep LCMS to afford (4-(2-(2,6-dimethylpyridin-4-yl)-3-isopropyl-1H-indol-5-yl)piperidin-1-yl)(piperidin-4-yl) methanone, HCl (0.114 g, 0.228 mmol, 88% yield). LCMS retention time 1.51 min [E]. MS (E−) m/z: 459.4 (M+H).

The following examples were prepared according to the general process described in Example 178.

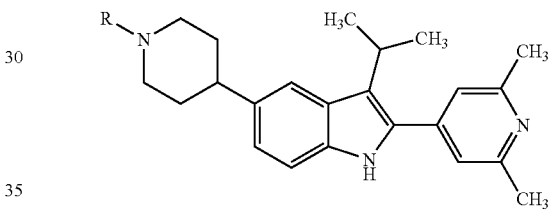

TABLE 7

| Ex. No. | R | LCMS [M + H] | Rt (min) | Method |
|---|---|---|---|---|
| 179 | —C(O)CH₂NHCH₃ | 179 | 419.2 | 1.716 |
| 180 | ![azetidine carbonyl] Chiral | 180 | 431.3 | 1.623 |
| 181 | ![pyrrolidine carbonyl] Homochiral separated By SFC | 181 | 446.4 | 2.13 |
| 182 | ![pyrrolidine carbonyl] Homochiral separated By SFC | 182 | 446.4 | 2.127 |
| 183 | —C(O)CH₂CH₂NH(CH₃) | 183 | 433.3 | 1.544 |
| 184 | —C(O)CH₂NH₂ | 184 | 405.2 | 1.518 |

TABLE 7-continued
| Ex. No. | R | LCMS [M + H] | Rt (min) | Method |
|---|---|---|---|---|
| 185 | ![structure with OH pyrrolidine] | 185 | 461.3 | 1.404 |
| 186 | ![structure pyrrolidine racemate] Racemate | 186 | 445.4 | 1.523 |
TABLE 8
| Ex. No. | Structure | LCMS MH+ | Rt (min) | HPLC Method |
|---|---|---|---|---|
| 187 | 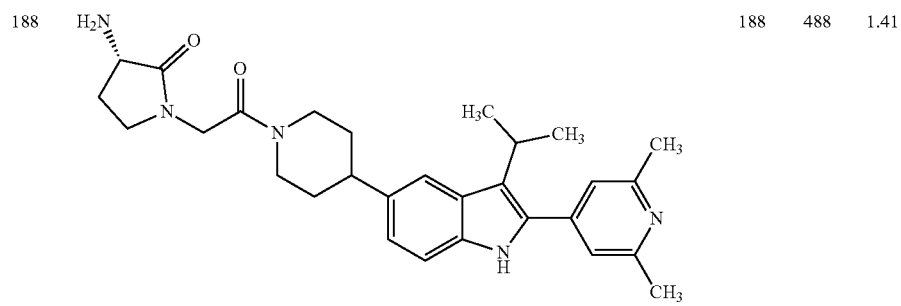 | 187 | 447 | 1.55 |
| 188 | 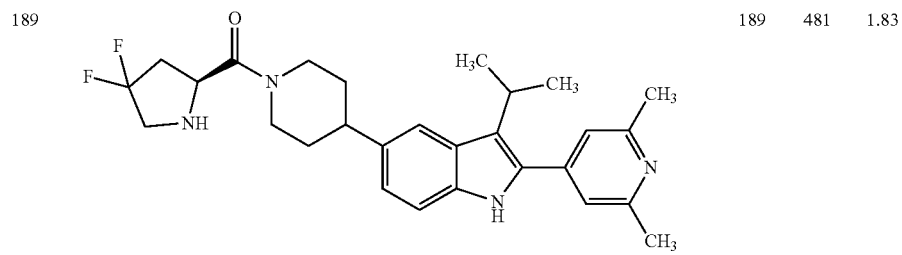 | 188 | 488 | 1.41 |
| 189 | 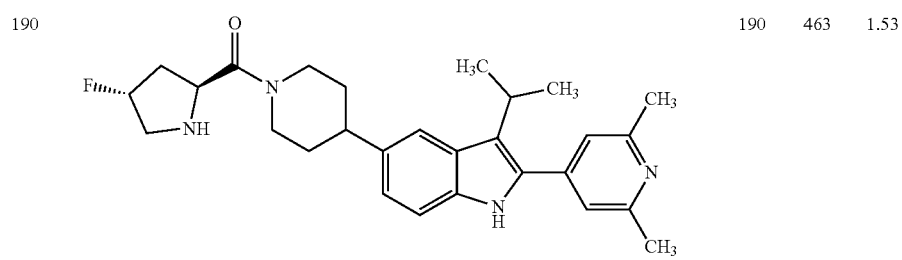 | 189 | 481 | 1.83 |
| 190 | 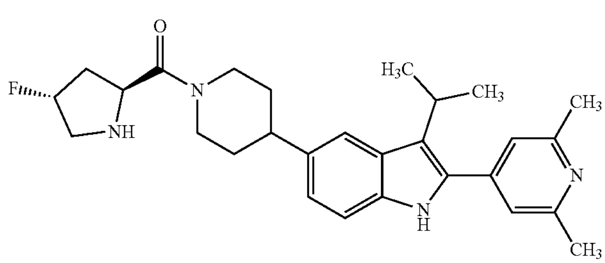 [SMILES: Cc1cc(-c2[nH]c3ccc(C4CCN(C(=O)[C@@H]5C[C@@H](F)CN5)CC4)cc3c2C(C)C)cc(C)n1] | 190 | 463 | 1.53 |

TABLE 8-continued

| Ex. No. | Structure | LCMS MH+ | Rt (min) | HPLC Method |
|---|---|---|---|---|
| 191 | 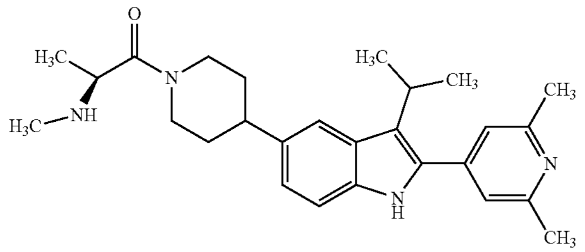 | 191 | 433 | 1.37 |
| 192 | 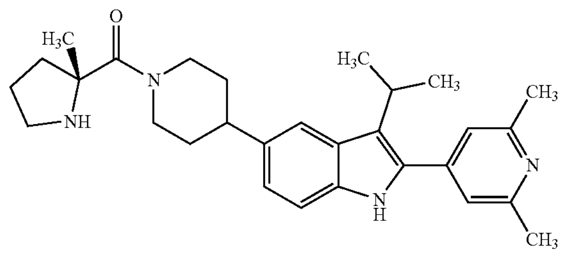 [SMILES: Cc1cc(-c2[nH]c3ccc(C4CCN(C(=O)[C@@]5(C)CCCN5)CC4)cc3c2C(C)C)cc(C)n1] | 192 | 459 | 1.44 |
| 193 | 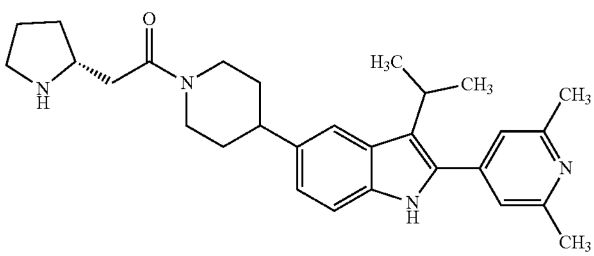 [SMILES: Cc1cc(-c2[nH]c3ccc(C4CCN(C(=O)C[C@H]5CCCN5)CC4)cc3c2C(C)C)cc(C)n1] | 193 | 459 | 1.05 |
| 194 | 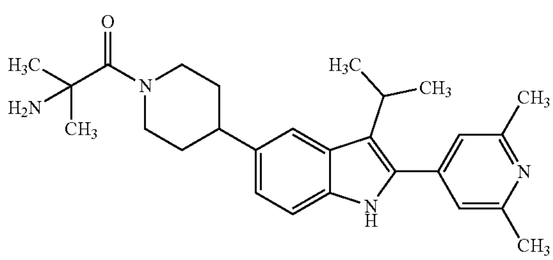 | 194 | 433 | 1.39 |
| 195 | 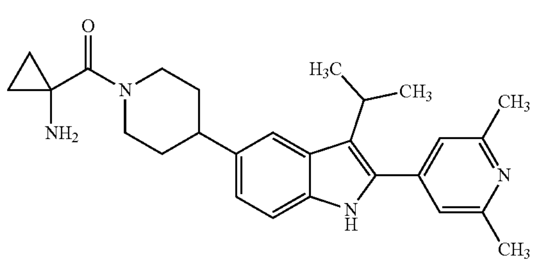 [SMILES: Cc1cc(-c2[nH]c3ccc(C4CCN(C(=O)C5(N)CC5)CC4)cc3c2C(C)C)cc(C)n1] | 195 | 431 | 1.61 |
| 196 | 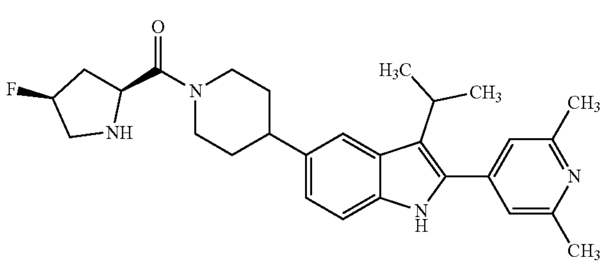 [SMILES: Cc1cc(-c2[nH]c3ccc(C4CCN(C(=O)[C@@H]5C[C@H](F)CN5)CC4)cc3c2C(C)C)cc(C)n1] | 196 | 463 | 1.62 |

TABLE 8-continued
| Ex. No. | Structure | LCMS MH+ | Rt (min) | HPLC Method |
|---|---|---|---|---|
| 197 | 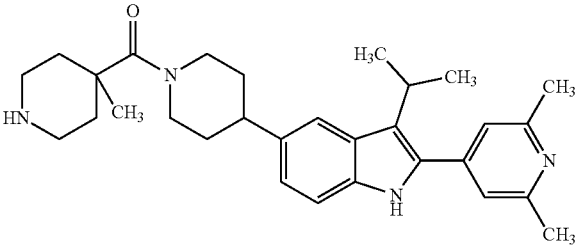 [SMILES: Cc1cc(-c2[nH]c3ccc(C4CCN(C(=O)C5(C)CCNCC5)CC4)cc3c2C(C)C)cc(C)n1] | 197 | 473.3 | 1.071 |
| 198 | 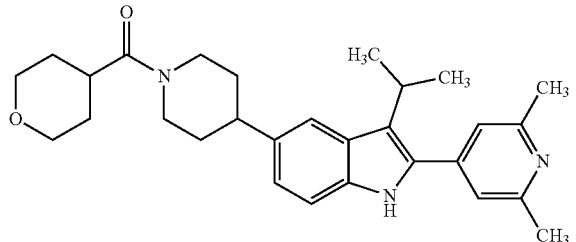 | 198 | 459.9 | 1.395 |
| 199 | 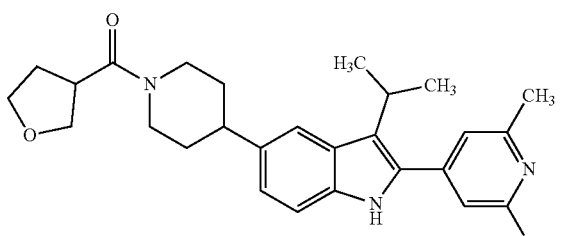 | 199 | 446.4 | 1.295 |
| 200 | 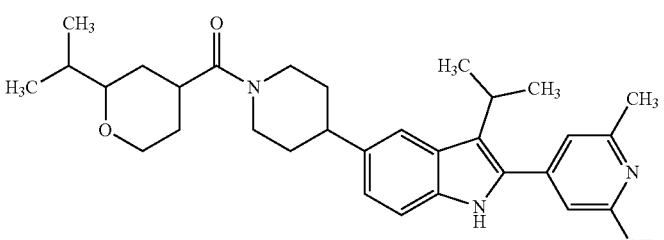 | 200 | 502.5 | 1.681 |
| 201 | 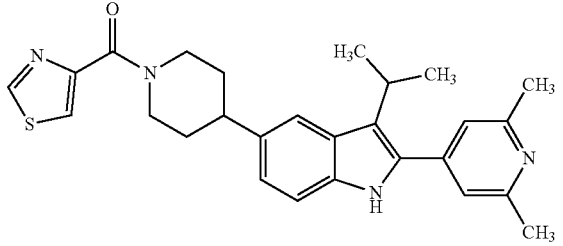 [SMILES: Cc1cc(-c2[nH]c3ccc(C4CCN(C(=O)c5cscn5)CC4)cc3c2C(C)C)cc(C)n1] | 201 | 459.1 | 1.334 |
| 202 | 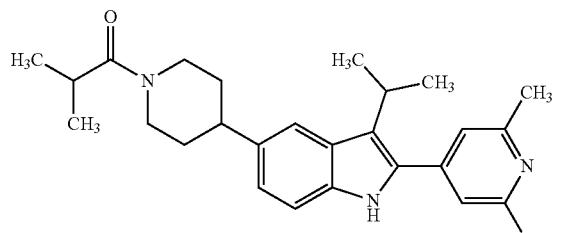 | 202 | 418.4 | 1.54 |

TABLE 8-continued

| Ex. No. | Structure | LCMS MH+ | Rt (min) | HPLC Method |
|---|---|---|---|---|
| 203 | 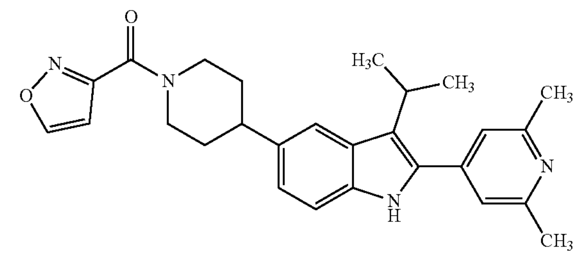 [SMILES: Cc1cc(-c2[nH]c3ccc(C4CCN(C(=O)c5ccon5)CC4)cc3c2C(C)C)cc(C)n1] | 203 | 443.2 | 1.401 |
| 204 | 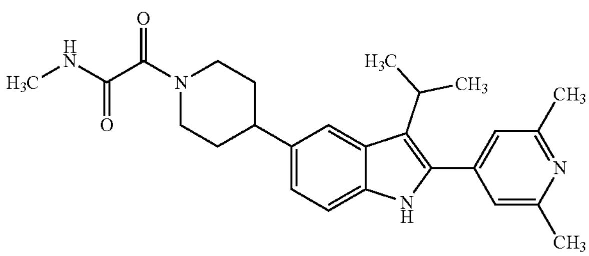 | 204 | 433.4 | 1.157 |
| 205 | 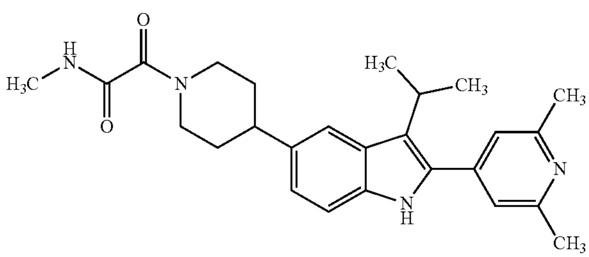 | 205 | 433.4 | 1.157 |
| 206 | 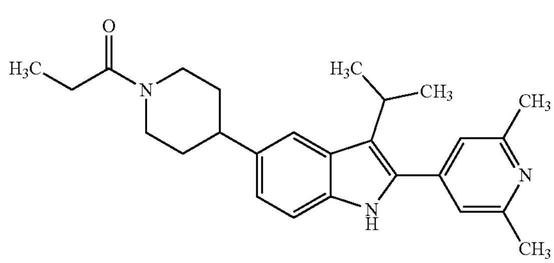 [SMILES: CCC(=O)N1CCC(c2ccc3[nH]c(-c4cc(C)nc(C)c4)c(C(C)C)c3c2)CC1] | 206 | 404.4 | 1.414 |
| 207 | 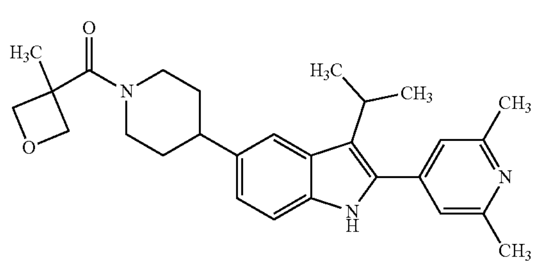 [SMILES: Cc1cc(-c2[nH]c3ccc(C4CCN(C(=O)C5(C)COC5)CC4)cc3c2C(C)C)cc(C)n1] | 207 | 446.1 | 1.268 |

Example 208

2-(4-(2-(2,6-dimethylpyridin-4-yl)-3-isopropyl-1H-indol-5-yl)piperidin-1-yl)-1-(piperidin-1-yl)ethan-1-one

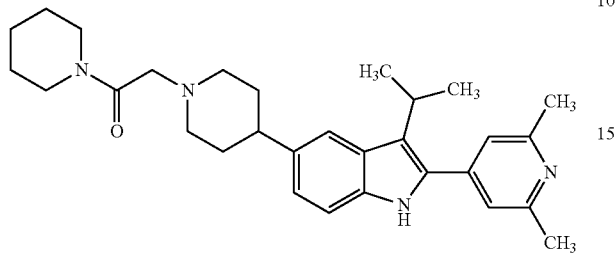

(208)

Intermediate 208A: Tert-Butyl 2-(4-(2-(2,6-dimethylpyridin-4-yl)-3-isopropyl-1H-indol-5-yl)piperidin-1-yl)acetate

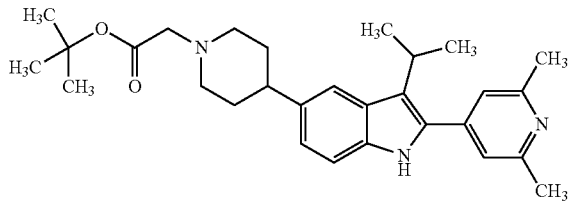

(208A)

To a solution of 2-(2,6-dimethylpyridin-4-yl)-3-isopropyl-5-(piperidin-4-yl)-1H-indole (250 mg, 0.719 mmol) in DCM (2 mL) were added TEA (0.201 mL, 1.439 mmol) and tert-butyl 2-bromoacetate (0.127 mL, 0.863 mmol) at room temperature. The mixture was stirred at same temperature for 16 h. The reaction was quenched with water (10 mL). The reaction mixture was extracted with ethyl acetate (3×30 mL). The combined organic extracts was dried over sodium sulfate, filtered and the filtrate was concentrated under reduced pressure to afford tert-butyl 2-(4-(2-(2,6-dimethylpyridin-4-yl)-3-isopropyl-1H-indol-5-yl)piperidin-1-yl)acetate (200 mg, 60.2% yield) as a pale yellow solid. LCMS retention time 1.43 min [B]. MS (E−) m/z: 462.6 (M+H).

Intermediate 208B: 2-(4-(2-(2,6-dimethylpyridin-4-yl)-3-isopropyl-1H-indol-5-yl) piperidin-1-yl)acetic Acid

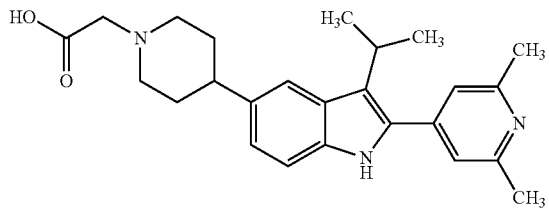

(208B)

To a solution of tert-butyl 2-(4-(2-(2,6-dimethylpyridin-4-yl)-3-isopropyl-1H-indol-5-yl)piperidin-1-yl)acetate (800 mg, 1.733 mmol) in DCM (2 mL) was added 4M HCl in dioxane (0.433 mL, 1.733 mmol) at room temperature. The reaction mixture was stirred at same temperature for 16 h. The reaction was quenched with ice water (50 ml). The reaction mixture was acidified by adding citric acid. White precipitate formed and was filtered through a Buchner funnel and air dried to afford 2-(4-(2-(2,6-dimethylpyridin-4-yl)-3-isopropyl-1H-indol-5-yl)piperidin-1-yl)acetic acid (600 mg, 1.420 mmol, 82% yield) as a white solid. LCMS retention time 1.31 min [D]. MS (E−) m/z: 406.3 (M+H).

Example 208

To a solution of 2-(4-(2-(2,6-dimethylpyridin-4-yl)-3-isopropyl-1H-indol-5-yl) piperidin-1-yl)acetic acid (0.025 g, 0.062 mmol) in DMF (1.00 mL) were added cyclohexanamine (0.012 g, 0.123 mmol), TEA (0.2 mL, 1.435 mmol) and HATU (0.047 g, 0.123 mmol) at room temperature. The reaction mixture was stirred at same temperature for 16 h. DMF was removed under vacuum. The reaction was quenched with ice water. The reaction mixture was extracted with ethyl acetate. The ethyl acetate layer was dried over $Na_2SO_4$ and concentrated to afford an amide. After Preparative LCMS purification, fractions containing the desired product was combined and dried using Genevac centrifugal evaporator to afford N-cyclohexyl-2-(4-(2-(2,6-dimethylpyridin-4-yl)-3-isopropyl-1H-indol-5-yl)piperidin-1-yl)acetamide (0.0146 g, 0.030 mmol, 48.5% yield) as a pale solid. LCMS retention time 2.196 min [E]. MS (E−) m/z: 487.3 (M+H).

The following examples were prepared according to the general procedure described in Example 208.

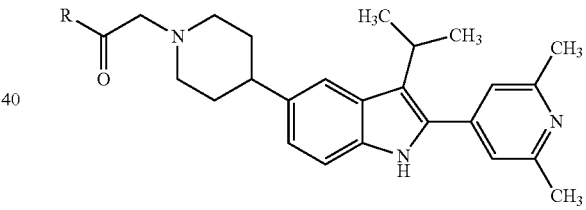

TABLE 9

| Ex. No. | Structure | LCMS (M + H)+ | RT | Method |
|---|---|---|---|---|
| 209 | 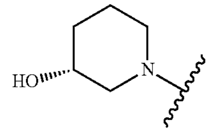 [SMILES: *N1CCC[C@@H](O)C1] | 489.3 | 1.793 | E |
| 210 | 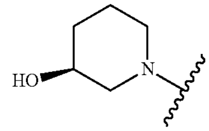 [SMILES: *N1CCC[C@H](O)C1] | 489.3 | 1.794 | E |
| 211 | 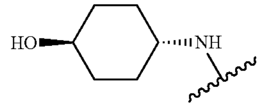 [SMILES: *N[C@H]1CC[C@H](O)CC1] | 503.3 | 1.735 | E |

TABLE 9-continued

| Ex. No. | Structure | LCMS (M + H)+ | RT | Method |
|---|---|---|---|---|
| 212 | —NH(cyclopropyl) | 445.4 | 0.841 | F |
| 213 | —NH(cyclobutyl) | 459.4 | 0.947 | F |
| 214 | —NH(CH₂CF₃) | 487.4 | 0.945 | F |
| 215 | 3,3-difluoroazetidinyl | 481.4 | 0.886 | F |
| 216 | 3,3-difluoropyrrolidinyl | 495.4 | 0.923 | F |
| 217 | —NHC(CH₃)₃ | 461.3 | 2.773 | E |
| 218 | —NHCH(CH₃)₂ | 447.3 | 2.139 | E |
| 219 | —NHCH₂C(CH₃)₃ | 475.3 | 1.324 | F |
| 220 | —NHCH(CH₂CH₃)₂ | 475.3 | 1.339 | F |
| 221 | —NHCH₂CH(CH₃)₂ | 461.3 | 1.264 | F |
| 222 | —NHCH₂CH₂OH | 449.2 | 1.009 | F |
| 223 | —NHCH₂(cyclopropyl) | 459.3 | 1.208 | F |
| 224 | adamantyl-NH | 539.3 | 1.591 | F |
| 225 | bicyclic-OH-NH | 555.3 | 1.232 | F |
| 226 | 3-methoxyazetidinyl | 475.3 | 1.109 | F |
| 227 | azetidinyl | 445.3 | 1.092 | F |
| 228 | —N(CH₂CH₃)₂ | 461.3 | 1.234 | F |
| 229 | 3-hydroxyazetidinyl | 461.3 | 1.721 | E |
| 230 | 4-hydroxypiperidinyl | 489.3 | 1.712 | E |
| 231 | —NH(CH₂CH₂OCH₃) | 463.3 | 1.045 | F |
| 232 | morpholinyl | 475.3 | 1.044 | F |
| 233 | 3-methyloxetanyl-NH | 475.3 | 1.047 | F |
| 234 | —NH(CH(CH₃)CH₂CH₃) | 461.4 | 2.29 | E |
| 235 | —NH(CH₂CH₃) | 433.4 | 1.109 | F |
| 236 | —NH(CH₂CH₂C(CH₃)₃) | 489.4 | 2.56 | E |
| 237 | —NH(CH₂CH₂CH(CH₃)₂) | 475.4 | 2.45 | E |
| 238 | —NH(CH₂CH₂CH₃) | 447.3 | 2.193 | F |
| 239 | —NH(CH₂CN) | 444.3 | 1.06 | F |
| 240 | —NHCH₂CH₂OCH₂CH₃ | 477.3 | 2.136 | E |
| 241 | piperidinyl | 473.3 | 1.25 | F |
| 242 | pyrrolidinyl | 459.3 | 1.921 | E |
| 243 | 1-methylcyclobutyl-NH | 473.3 | 1.296 | F |
| 244 | —N(CH₃)CH(CH₃)₂ | 461.3 | 2.019 | E |
| 245 | —N(CH₃)CH₂CH(CH₃)₂ | 475.3 | 1.322 | F |
| 246 | —N(CH₃)CH₂CH₃ | 447.3 | 1.151 | F |
| 247 | —N(CH₃)CH₂CN | 458.3 | 1.989 | E |
| 248 | —N(CH₃)(cyclopropyl) | 459.3 | 1.909 | E |
| 249 | 3,3-dimethylpiperidinyl | 501.4 | 1.415 | F |
| 250 | —N(CH₃)C(CH₃)₃ | 475.4 | 1.34 | F |
| 251 | 1-methylcyclobutyl-NH | 459.3 | 2.197 | E |
| 252 | CH(CH₃)CF₃-NH | 501.3 | 1.288 | F |
| 253 | —N(CH(CH₃)₂)₂ | 489.4 | 2.333 | E |
| 254 | —N(CH₃)CH₂CH₂OCH₃ | 477.4 | 1.153 | F |
| 255 | 1-methylcyclopropyl-CH₂-NH | 473.3 | 1.298 | F |
| 256 | 2-oxa-6-azaspiro[3.3]heptanyl | 487.3 | 1.065 | F |

TABLE 9-continued

| Ex. No. | Structure | LCMS (M + H)+ | RT | Method |
|---|---|---|---|---|
| 257 | 4,4-difluoropiperidinyl | 509.3 | 2.218 | E |
| 258 | 3-fluoropiperidinyl, Racemate | 491.3 | 1.215 | F |
| 259 | 2-methylpyrrolidinyl, Racemate | 473.3 | 2.077 | E |
| 260 | —NH(CH₂CH(CH₃)OH) Racemate | 463.3 | 1.882 | E |
| 261 | 2,5-dimethylpyrrolidinyl, Diastereomer Mixture | 487.3 | 2.183 | E |
| 262 | HN-CH₂CH(OH)CH₃ | 477.3 | 1.919 | E |
| 263 | 2-(methoxymethyl)pyrrolidinyl | 503.3 | 1.171 | F |
| 264 | NH-CH₂-C(CH₃)₂-morpholinyl | 546.4 | 2.26 | E |
| 265 | 4-(2-methoxyethyl)piperazinyl | 532.4 | 1.872 | E |
| 266 | HN-CH₂-tetrahydrofuranyl, Racemate | 489.3 | 2.099 | E |
| 267 | HN-(4-methyltetrahydropyranyl) | 503.3 | 2.173 | E |
| 268 | —NH(CH₂C(CH₃)₂OH) | 477.3 | 1.032 | F |
| 269 | 4-methylpiperidinyl | 487.3 | 2.267 | E |
| 270 | 2-methylpiperidinyl, Racemate | 487.4 | 2.229 | E |
| 271 | 3-methylpiperidinyl, Racemate | 487.3 | 1.277 | F |
| 272 | 2-oxopiperazinyl | 488.3 | 0.939 | F |
| 273 | (3S)-3-hydroxypyrrolidinyl | 475.3 | 0.977 | F |
| 274 | 2-(hydroxymethyl)pyrrolidinyl | 489.3 | 1.783 | E |
| 275 | (3R)-3-hydroxypyrrolidinyl | 475.3 | 1.646 | E |
| 276 | H₃C-CH(CH₃)-CH₂-CH(CH₂OH)-NH | 505.3 | 1.206 | F |
| 277 | 3-hydroxypiperidinyl, Racemate | 489.3 | 1.766 | E |
| 278 | H₃C-N(cyclohexyl) | 501.4 | 1.359 | F |

TABLE 9-continued

| Ex. No. | Structure | LCMS (M + H)+ | RT | Method |
|---|---|---|---|---|
| 279 | HN-tetrahydropyran-3-yl, Racemate | 489.3 | 2.089 | E |
| 280 | HN-tetrahydropyran-4-yl | 489.3 | 2.016 | E |
| 281 | thiomorpholine 1,1-dioxide | 523.3 | 1.888 | E |
| 282 | HN-tetrahydrofuran-3-yl, Racemate | 475.3 | 1.96 | E |
| 283 | 4-fluoropiperidin-1-yl | 491.3 | 2.059 | E |
| 284 | 2-oxa-5-azabicyclo | 501.3 | 2.008 | E |
| 285 | 3,3-difluoropiperidin-1-yl | 509.2 | 1.233 | F |
| 286 | 2-oxa-6-azaspiro[3.5]nonane | 515.4 | 1.883 | E |

TABLE 10

| Ex. No. | Structure | LCMS MH+ | Rt (min) | HPLC Method |
|---|---|---|---|---|
| 287 | N-methyl-N-(tetrahydropyran-4-yl) acetamide piperidine indole isopropyl dimethylpyridine | 503.2 | 1.1 | QC-TFA |
| 288 | N-methyl-N-(3-hydroxypropyl) acetamide piperidine indole isopropyl dimethylpyridine | 477.3 | 1.5 | QC-AA |
| 289 | N-methyl-N-(tetrahydrofuran-3-yl) acetamide piperidine indole isopropyl dimethylpyridine | 489.2 | 1.67 | QC-AA |

TABLE 10-continued

| Ex. No. | Structure | LCMS MH+ | Rt (min) | HPLC Method |
|---|---|---|---|---|
| 290 | 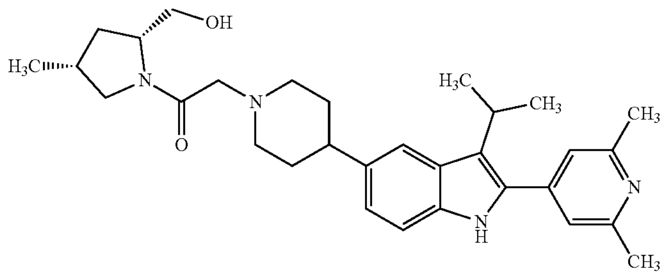 | 503.3 | 1.13 | QC-TFA |
| 291 | 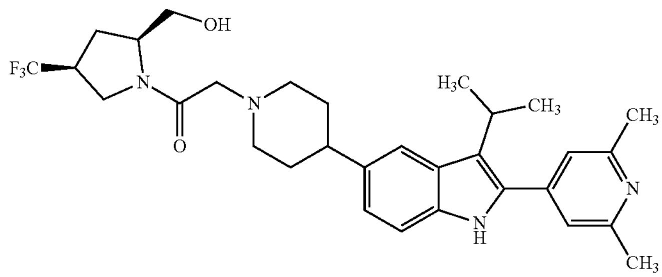 [SMILES: Cc1cc(-c2[nH]c3ccc(C4CCN(CC(=O)N5C[C@@H](C(F)(F)F)C[C@H]5CO)CC4)cc3c2C(C)C)cc(C)n1] | 557.2 | 1.18 | QC-TFA |
| 292 | 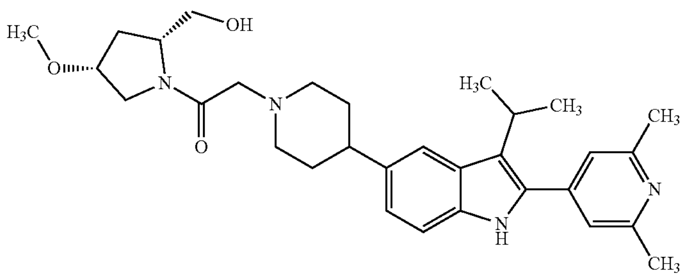 | 519.2 | 1.04 | QC-TFA |
| 293 | 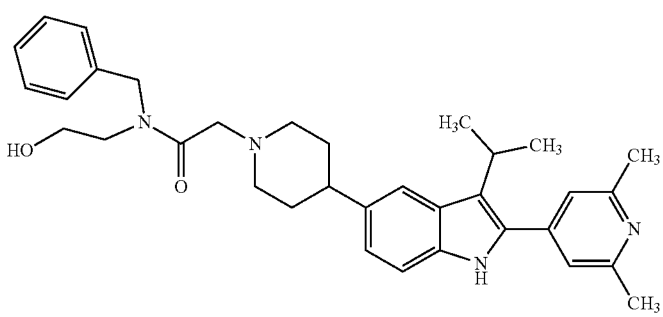 [SMILES: Cc1cc(-c2[nH]c3ccc(C4CCN(CC(=O)N(CCO)Cc5ccccc5)CC4)cc3c2C(C)C)cc(C)n1] | 539.2 | 1.75 | QC-AA |
| 294 | 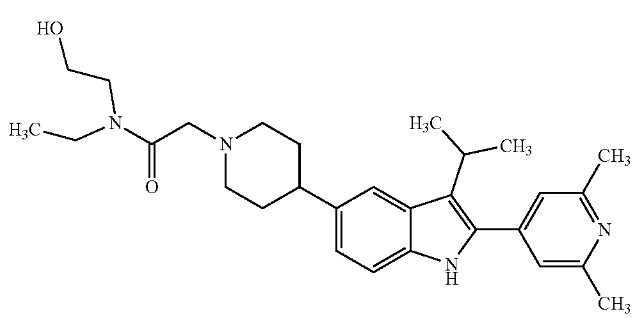 [SMILES: CCN(CCO)C(=O)CN1CCC(c2ccc3[nH]c(-c4cc(C)nc(C)c4)c(C(C)C)c3c2)CC1] | 477.2 | 1.44 | QC-AA |

TABLE 10-continued

| Ex. No. | Structure | LCMS MH+ | Rt (min) | HPLC Method |
|---|---|---|---|---|
| 295 | 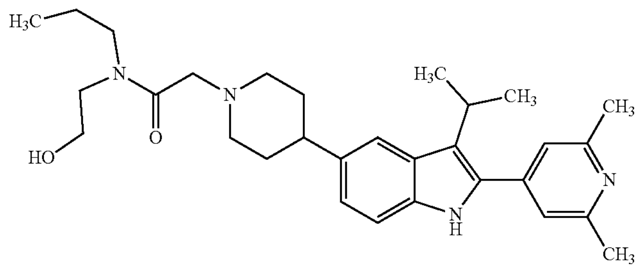 [SMILES: CCCN(CCO)C(=O)CN1CCC(c2ccc3[nH]c(-c4cc(C)nc(C)c4)c(C(C)C)c3c2)CC1] | 491.2 | 1.55 | QC-AA |
| 296 | 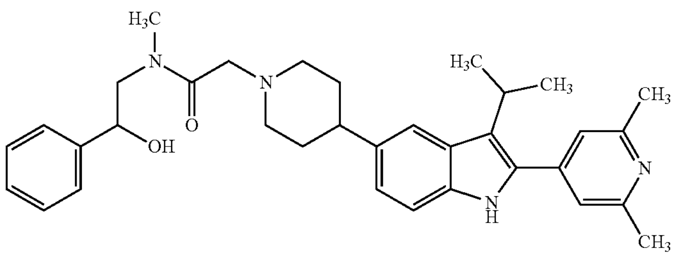 [SMILES: Cc1cc(-c2[nH]c3ccc(C4CCN(CC(=O)N(C)CC(O)c5ccccc5)CC4)cc3c2C(C)C)cc(C)n1] | 539.2 | 1.75 | QC-AA |
| 297 | 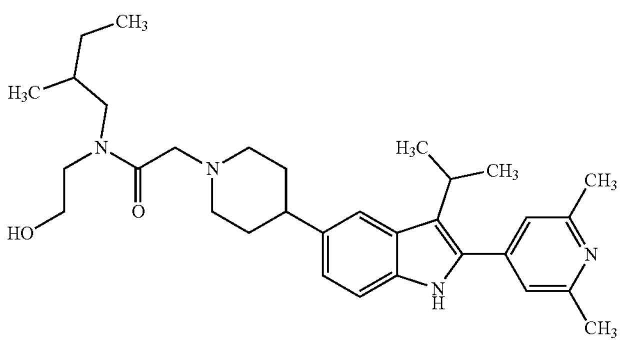 [SMILES: CCC(C)CN(CCO)C(=O)CN1CCC(c2ccc3[nH]c(-c4cc(C)nc(C)c4)c(C(C)C)c3c2)CC1] | 519.2 | 1.27 | QC-TFA |
| 298 | 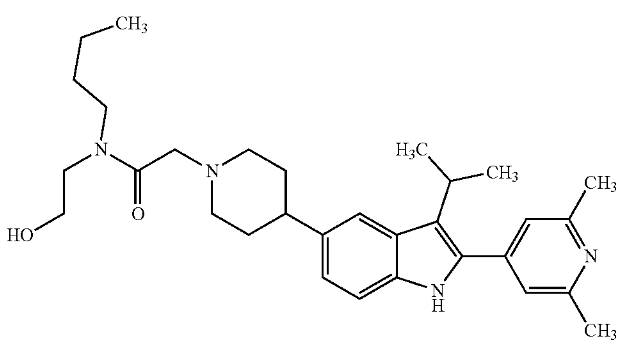 [SMILES: CCCCN(CCO)C(=O)CN1CCC(c2ccc3[nH]c(-c4cc(C)nc(C)c4)c(C(C)C)c3c2)CC1] | 505.2 | 1.2 | QC-TFA |
| 299 | 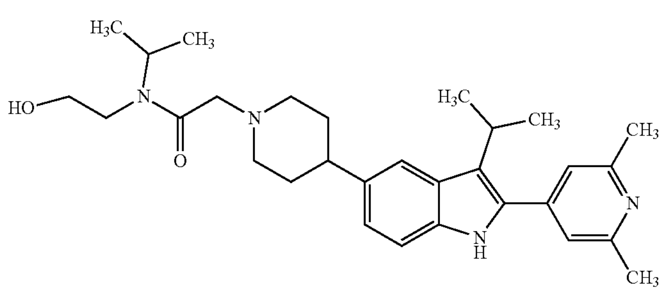 [SMILES: Cc1cc(-c2[nH]c3ccc(C4CCN(CC(=O)N(CCO)C(C)C)CC4)cc3c2C(C)C)cc(C)n1] | 491.2 | 1.52 | QC-AA |

TABLE 10-continued

| Ex. No. | Structure | LCMS MH+ | Rt (min) | HPLC Method |
|---|---|---|---|---|
| 300 | 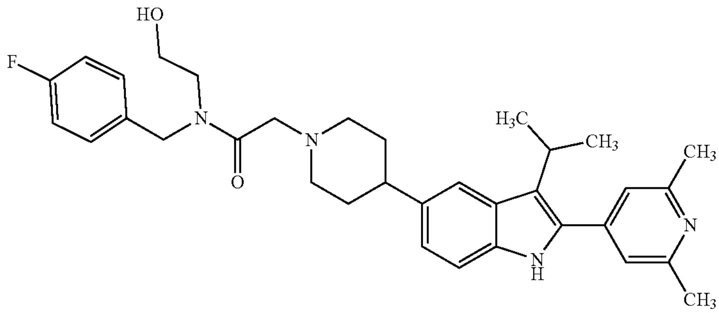 [SMILES: Cc1cc(-c2[nH]c3ccc(C4CCN(CC(=O)N(CCO)Cc5ccc(F)cc5)CC4)cc3c2C(C)C)cc(C)n1] | 557.2 | 1.26 | QC-TFA |
| 301 | 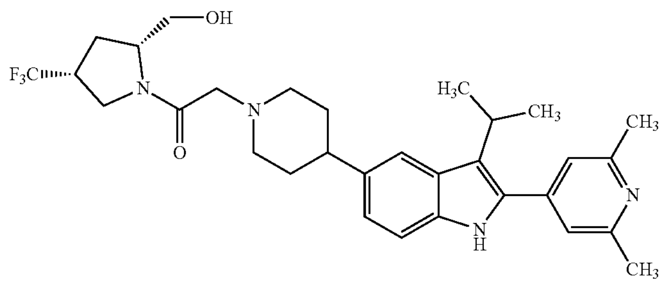 [SMILES: Cc1cc(-c2[nH]c3ccc(C4CCN(CC(=O)N5C[C@H](C(F)(F)F)C[C@@H]5CO)CC4)cc3c2C(C)C)cc(C)n1] | 557.1 | 1.75 | QC-AA |
| 302 | 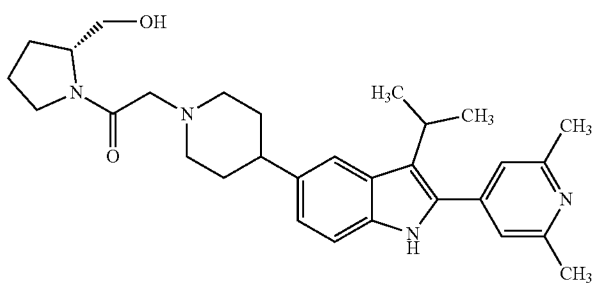 [SMILES: Cc1cc(-c2[nH]c3ccc(C4CCN(CC(=O)N5CCC[C@@H]5CO)CC4)cc3c2C(C)C)cc(C)n1] | 489.2 | 1.46 | QC-AA |
| 303 | 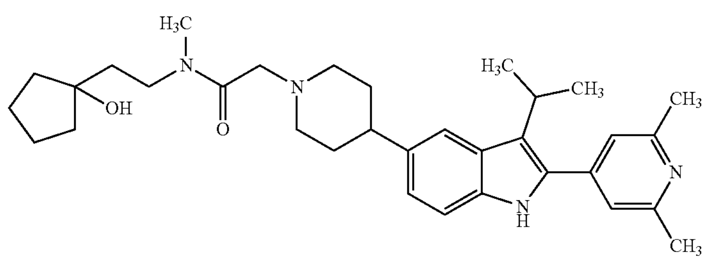 [SMILES: Cc1cc(-c2[nH]c3ccc(C4CCN(CC(=O)N(C)CCC5(O)CCCC5)CC4)cc3c2C(C)C)cc(C)n1] | 531.3 | 1.22 | QC-AA |
| 304 | 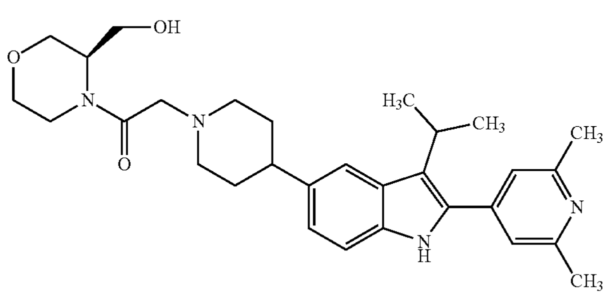 [SMILES: Cc1cc(-c2[nH]c3ccc(C4CCN(CC(=O)N5CCOC[C@H]5CO)CC4)cc3c2C(C)C)cc(C)n1] | 505.2 | 1.01 | QC-AA |

TABLE 10-continued

| Ex. No. | Structure | LCMS MH+ | Rt (min) | HPLC Method |
|---|---|---|---|---|
| 305 | 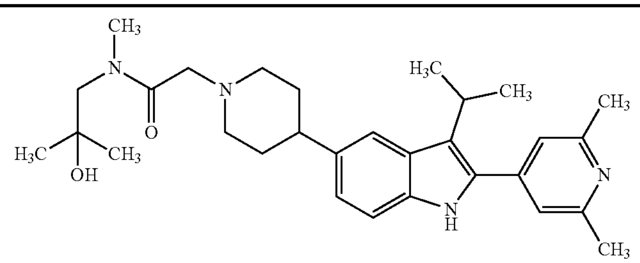 | 491.2 | 1.6 | QC-AA |
| 306 | 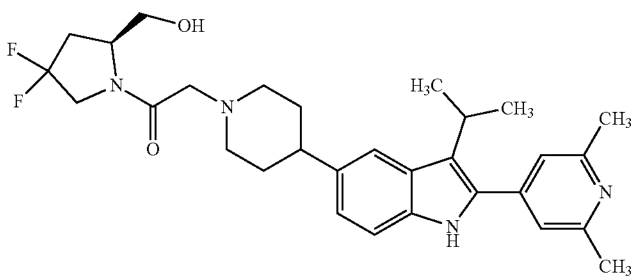 [SMILES: Cc1cc(-c2[nH]c3ccc(C4CCN(CC(=O)N5CC(F)(F)C[C@H]5CO)CC4)cc3c2C(C)C)cc(C)n1] | 525.2 | 1.11 | QC-TFA |
| 307 | 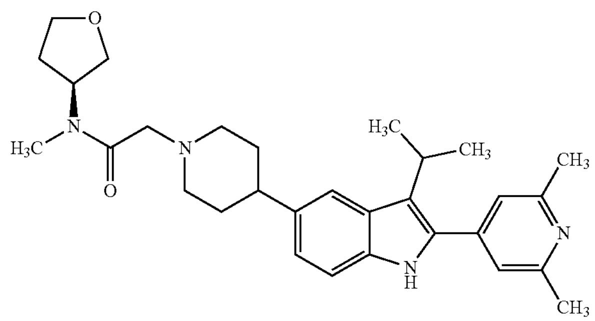 | 489.2 | 1.08 | QC-TFA |

Example 308

2-(4-(2-(2,6-dimethylpyridin-4-yl)-3-isopropyl-1H-indol-5-yl)piperidin-1-yl)-N,N-dimethylacetamide (308)

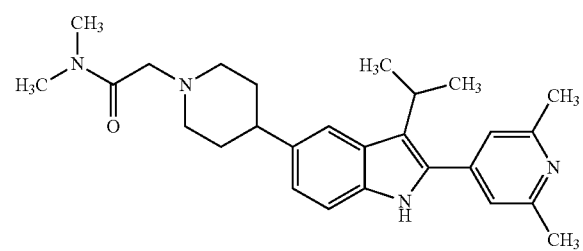

To a stirred solution of 2-(2,6-dimethylpyridin-4-yl)-3-isopropyl-5-(piperidin-4-yl)-1H-indole, HCl (0.030 g, 0.078 mmol) in THF (2.00 mL) and DMF (0.500 mL) solvent mixture were added 2-chloro-N,N-dimethylacetamide (0.014 g, 0.117 mmol) and TEA (0.2 mL, 1.435 mmol) at room temperature. The reaction mixture was stirred at same temperature for 16 h. The reaction mixture was concentrated to afford crude compound. The crude compound was purified by Preparative LCMS purification, the fractions containing desired product was combined and dried using Genevac centrifugal evaporator to afford 2-(4-(2-(2,6-dimethylpyridin-4-yl)-3-isopropyl-1H-indol-5-yl) piperidin-1-yl)-N,N-dimethylacetamide (0.010 g, 0.023 mmol, 29.3% yield) as a pale solid. LCMS retention time 1.42 min [E]. MS (E−) m/z: 433.4 (M+H).

The following examples were prepared according to the general procedure described in Example 308.

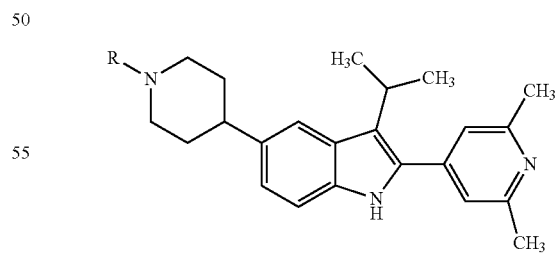

TABLE 11

| Ex. No. | Structure | LCMS [M + H]+ | Rt (min) | Method |
|---|---|---|---|---|
| 309 | —CH₂C(O)NH(CH₃) | 419.4 | 1.608 | E |

TABLE 12

| Ex. No. | Structure | LCMS MH+ | Rt (min) | HPLC Method |
|---|---|---|---|---|
| 310 | 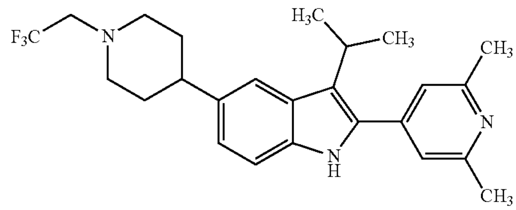 | 430.1 | 2.44 | QC-AA |
| 311 | 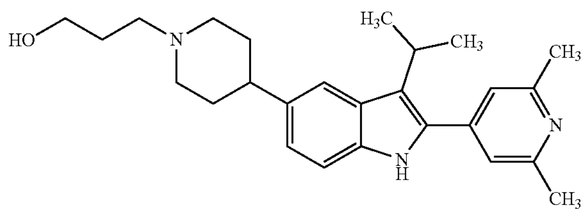 [SMILES: Cc1cc(-c2[nH]c3ccc(C4CCN(CCCO)CC4)cc3c2C(C)C)cc(C)n1] | 406.4 | 1.17 | QC-AA |
| 312 | 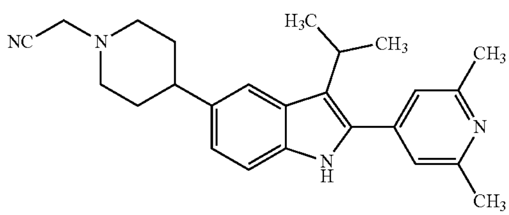 [SMILES: Cc1cc(-c2[nH]c3ccc(C4CCN(CC#N)CC4)cc3c2C(C)C)cc(C)n1] | 387.4 | 1 | QC-TFA |
| 313 | 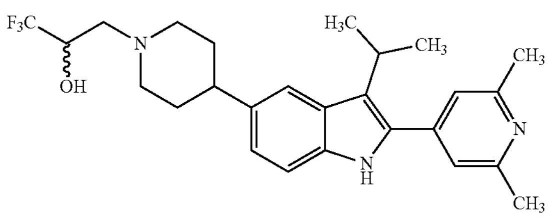 [SMILES: Cc1cc(-c2[nH]c3ccc(C4CCN(CC(O)C(F)(F)F)CC4)cc3c2C(C)C)cc(C)n1] | 460.4 | 1.05 | QC-TFA |
| 314 | 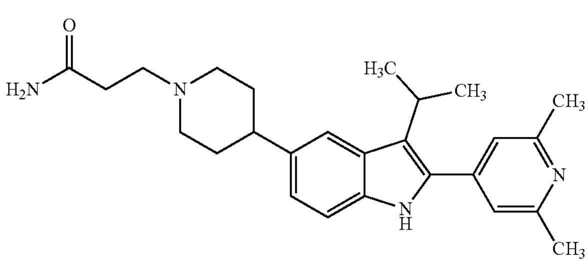 [SMILES: Cc1cc(-c2[nH]c3ccc(C4CCN(CCC(N)=O)CC4)cc3c2C(C)C)cc(C)n1] | 419 | 0.77 | QC-TFA |
| 315 | 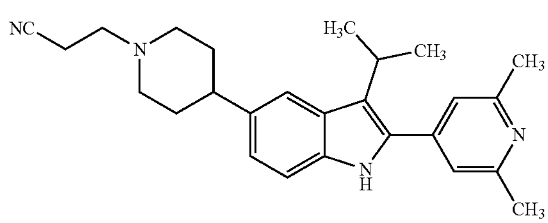 [SMILES: Cc1cc(-c2[nH]c3ccc(C4CCN(CCC#N)CC4)cc3c2C(C)C)cc(C)n1] | 401.4 | 0.9 | QC-TFA |
| 316 | 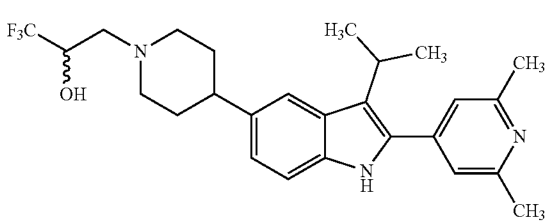 [SMILES: Cc1cc(-c2[nH]c3ccc(C4CCN(CC(O)C(F)(F)F)CC4)cc3c2C(C)C)cc(C)n1] | 460.3 | 0.6 | G |

TABLE 12-continued

| Ex. No. | Structure | LCMS MH+ | Rt (min) | HPLC Method |
|---|---|---|---|---|
| 317 | 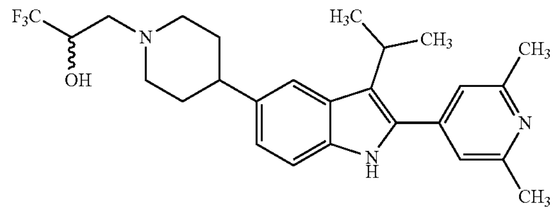 [SMILES: Cc1cc(-c2[nH]c3ccc(C4CCN(CC(O)C(F)(F)F)CC4)cc3c2C(C)C)cc(C)n1] | 460.3 | 0.61 | G |
| 318 | 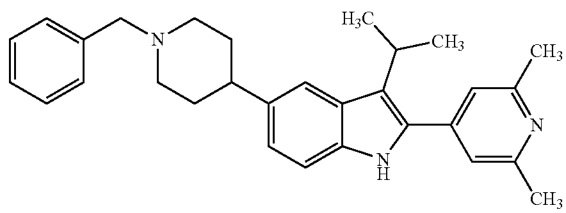 [SMILES: Cc1cc(-c2[nH]c3ccc(C4CCN(Cc5ccccc5)CC4)cc3c2C(C)C)cc(C)n1] | 438.1 | 1.21 | QC-TFA |
| 319 | 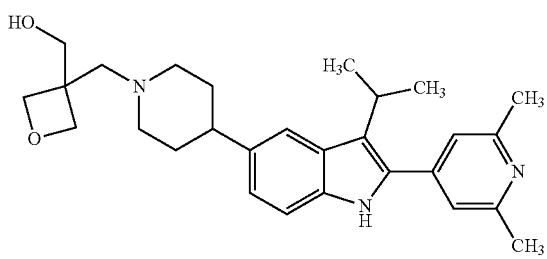 [SMILES: Cc1cc(-c2[nH]c3ccc(C4CCN(CC5(CO)COC5)CC4)cc3c2C(C)C)cc(C)n1] | 448.3 | 1.58 | QC-AA |
| 320 | 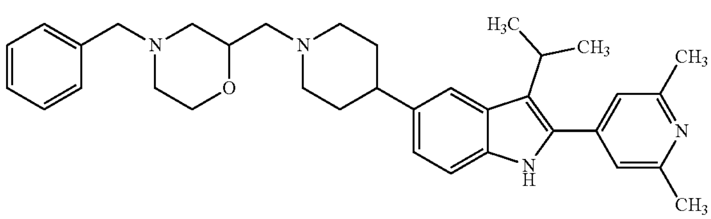 [SMILES: Cc1cc(-c2[nH]c3ccc(C4CCN(CC5CN(Cc6ccccc6)CCO5)CC4)cc3c2C(C)C)cc(C)n1] | 537 | 0.96 | QC-TFA |
| 321 | 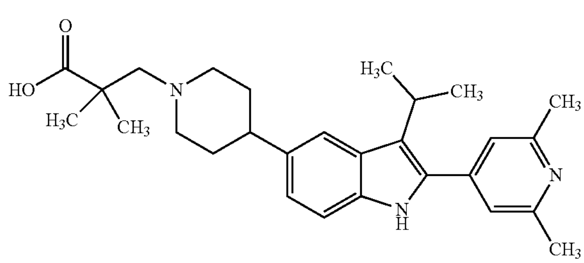 [SMILES: Cc1cc(-c2[nH]c3ccc(C4CCN(CC(C)(C)C(=O)O)CC4)cc3c2C(C)C)cc(C)n1] | 448.4 | 0.98 | QC-TFA |
| 322 | 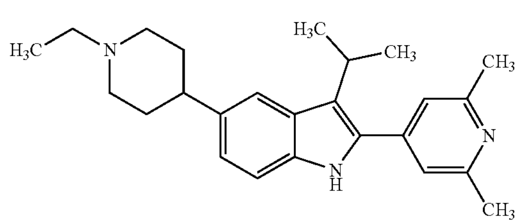 | 376.4 | 0.929 | QC-TFA |

TABLE 12-continued

| Ex. No. | Structure | LCMS MH+ | Rt (min) | HPLC Method |
|---|---|---|---|---|
| 323 | 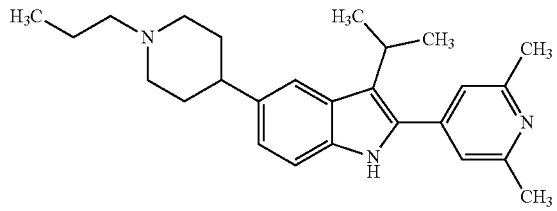 [SMILES: CCCN1CCC(c2ccc3[nH]c(-c4cc(C)nc(C)c4)c(C(C)C)c3c2)CC1] | 390.1 | 1.012 | QC-TFA |
| 324 | 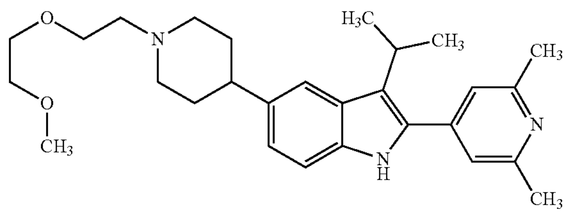 [SMILES: COCCOCCN1CCC(c2ccc3[nH]c(-c4cc(C)nc(C)c4)c(C(C)C)c3c2)CC1] | 450 | 0.985 | QC-TFA |
| 325 | 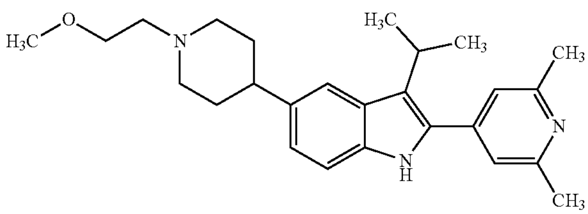 | 406.4 | 0.966 | QC-TFA |
| 326 | 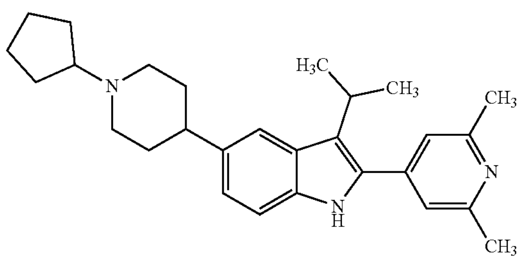 [SMILES: Cc1cc(-c2[nH]c3ccc(C4CCN(C5CCCC5)CC4)cc3c2C(C)C)cc(C)n1] | 416.4 | 1.129 | QC-TFA |
| 327 | 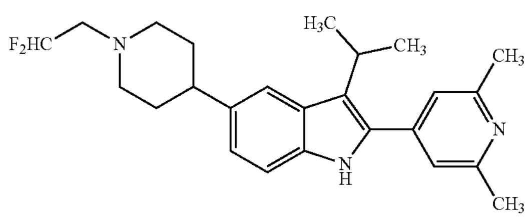 [SMILES: Cc1cc(-c2[nH]c3ccc(C4CCN(CC(F)F)CC4)cc3c2C(C)C)cc(C)n1] | 412.2 | 0.921 | QC-TFA |
| 328 | 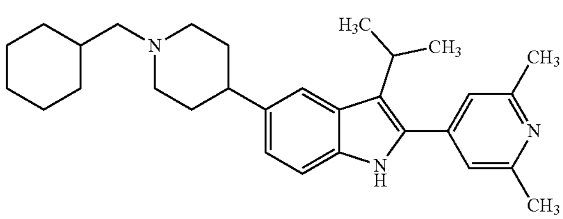 [SMILES: Cc1cc(-c2[nH]c3ccc(C4CCN(CC5CCCCC5)CC4)cc3c2C(C)C)cc(C)n1] | 444.2 | 1.34 | QC-TFA |
| 329 | 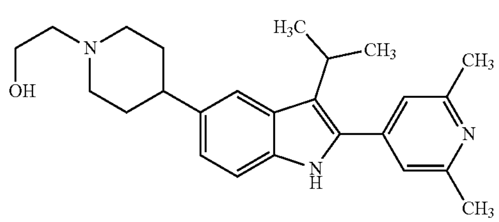 [SMILES: Cc1cc(-c2[nH]c3ccc(C4CCN(CCO)CC4)cc3c2C(C)C)cc(C)n1] | 392.2 | 0.83 | QC-TFA |

TABLE 12-continued
| Ex. No. | Structure | LCMS MH+ | Rt (min) | HPLC Method |
|---|---|---|---|---|
| 330 | 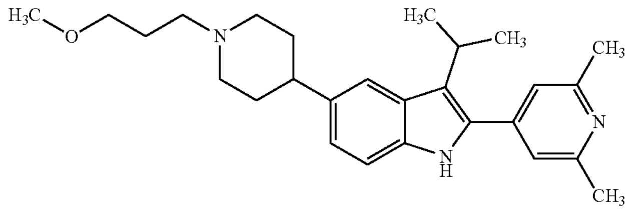 | 420 | 0.991 | QC-TFA |
| 331 | 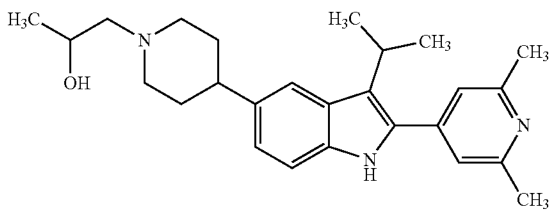 | 406.2 | 0.897 | QC-TFA |
| 332 | 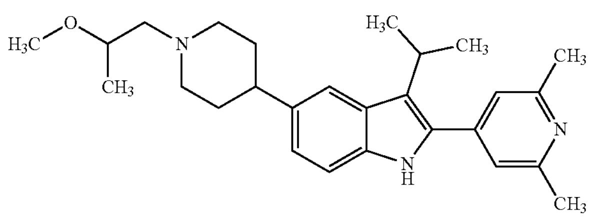 | 420.4 | 1.039 | QC-TFA |
| 333 | 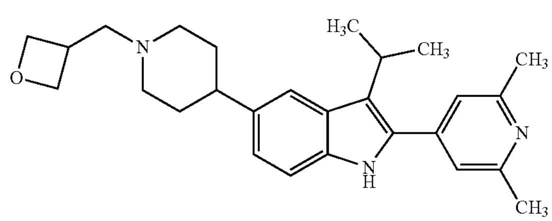 [SMILES: Cc1cc(-c2[nH]c3ccc(C4CCN(CC5COC5)CC4)cc3c2C(C)C)cc(C)n1] | 418.2 | 0.87 | QC-TFA |
Example 334
2-(cyclobutylamino)-1-(4-(2-(2,6-dimethylpyridin-4-yl)-3-isopropyl-1H-indol-5-yl)piperidin-1-yl)ethan-1-one
(334)
Intermediate 334A: 2-chloro-1-(4-(2-(2,6-dimethylpyridin-4-yl)-3-isopropyl-1H-indol-5-yl)piperidin-1-yl)ethan-1-one
(334A)
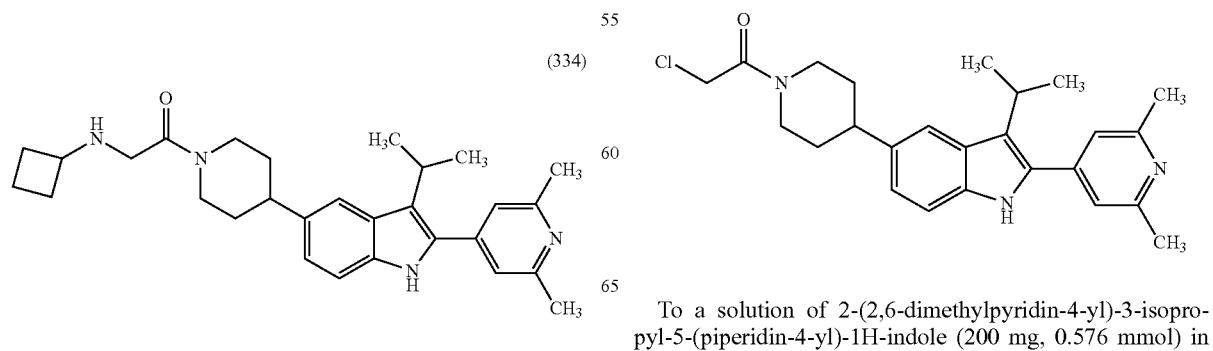
To a solution of 2-(2,6-dimethylpyridin-4-yl)-3-isopropyl-5-(piperidin-4-yl)-1H-indole (200 mg, 0.576 mmol) in DCM (25 mL) were added DIPEA (0.201 mL, 1.151 mmol) and chloroacetyl chloride (0.055 mL, 0.691 mmol) at 0° C. The color of the reaction mixture slowly changed from pale yellow to brown. The reaction mixture was allowed to stir at room temperature for 2 h. The reaction was quenched with water (5 mL). The reaction mixture was extracted with DCM (2×50 mL). The organic layer was collected and dried over Na$_2$SO$_4$ and concentrated to afford crude compound. The crude material was purified by combiflash using 12 g silica column, compound was eluted in 60% ethyl acetate in Pet ether, the fractions was combined and concentrated to afford 2-chloro-1-(4-(2-(2,6-dimethylpyridin-4-yl)-3-isopropyl-1H-indol-5-yl)piperidin-1-yl) ethanone (210 mg, 0.495 mmol, 86% yield) as a dark brown solid. LCMS retention time 1.13 min [B]. MS (E−) m/z: 424.4 (M+H).

Example 334

2-Chloro-1-(4-(2-(2,6-dimethylpyridin-4-yl)-3-isopropyl-1H-indol-5-yl)piperidin-1-yl)ethanone (0.02 g, 0.044 mmol) and DIPEA (0.012 mL, 0.066 mmol) were added to acetonitrile (1 mL). The solution was stirred. Cyclobutylamine (0.053 mmol) was added to the reaction solution. The resulting reaction mixture was stirred at 25° C. for 4 h. The reaction mixture was concentrated. The crude material was dissolved in ethyl acetate. The solution was washed with water. The organic layer was dried over Na$_2$SO$_4$ and concentrated. The crude material was purified using prep LCMS. After Preparative LCMS purification, fractions containing the product were combined and dried using Genevac centrifugal evaporator to afford 2-(cyclobutylamino)-1-(4-(2-(2,6-dimethylpyridin-4-yl)-3-isopropyl-1H-indol-5-yl)piperidin-1-yl)ethan-1-one (0.0011 g) as a solid. LCMS retention time 1.807 min [E]. MS (E−) m/z: 459.3 (M+H).

The following examples were prepared by according to the general procedure described in Example 334.

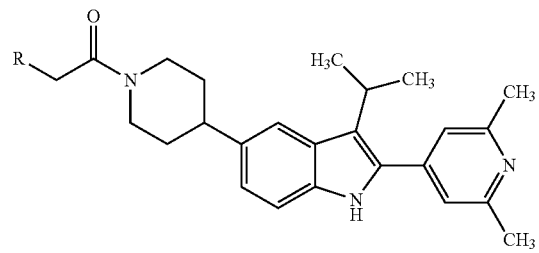

TABLE 13

| Ex. No. | Structure | LCMS [M + H] | Rt (min) | Method |
|---|---|---|---|---|
| 335 | —NHC(CH$_3$)$_3$ | 461.3 | 1.237 | E |
| 336 | —NHCH$_2$CH$_2$OH | 449.4 | 1.452 | E |
| 337 | —NHCH$_2$C(CH$_3$)$_3$ | 475.5 | 1.939 | E |
| 338 | —NHCH$_2$CH(CH$_3$)$_2$ | 461.4 | 0.986 | F |
| 339 | —NHCH$_2$(cyclopropyl) | 459.3 | 1.229 | E |
| 340 | azetidine-3,3-difluoro | 481.2 | 1.179 | E |
| 341 | 3-fluoropyrrolidine derivative | 495.3 | 1.211 | E |
| 342 | adamantyl-NH | 539.3 | 2.074 | E |
| 343 | hydroxyadamantyl-NH | 555.3 | 1.764 | E |
| 344 | —NHCH(CH$_3$)$_2$ | 447.3 | 1.67 | E |
| 345 | —NHCH(CH$_2$CH$_3$)$_2$ | 475.3 | 1.979 | E |
| 346 | —NHCH$_2$CH$_2$OCH$_3$ | 463.3 | 1.15 | E |
| 347 | —NHCH$_2$CH$_2$C(CH$_3$)$_3$ | 489.3 | 1.41 | E |
| 348 | —NH(CH$_2$CH$_2$CH$_3$) | 447.3 | 1.72 | E |
| 349 | —NHCH$_2$CH$_2$OCH$_2$CH$_3$ | 477.3 | 1.23 | E |
| 350 | morpholine | 475.3 | 1.11 | E |
| 351 | piperidine | 473.3 | 1.99 | E |
| 352 | pyrrolidine | 459.3 | 1.68 | E |
| 353 | 1-methylcyclobutyl-NH | 473.3 | 1.97 | E |
| 354 | —N(CH$_3$)CH(CH$_3$)$_2$ | 461.3 | 1.78 | E |
| 355 | —N(CH$_3$)CH$_2$CH(CH$_3$)$_2$ | 475.3 | 1.29 | E |
| 356 | —N(CH$_3$)CH$_2$CH$_3$ | 447.3 | 1.14 | E |
| 357 | —N(CH$_3$)(cyclopropyl) | 459.3 | 1.18 | E |
| 358 | 3,3-dimethylpiperidine | 501.3 | 1.34 | E |
| 359 | —N(CH$_3$)C(CH$_3$)$_3$ | 475.3 | 1.86 | E |
| 360 | 1-methylcyclopropyl-NH | 459.3 | 2.08 | E |
| 361 | 3-methyloxetan-3-yl-NH | 475.3 | 1.83 | E |

TABLE 13-continued

| Ex. No. | Structure | LCMS [M + H] | Rt (min) | Method |
|---|---|---|---|---|
| 362 | N-piperidinyl-4,4-difluoro | 509.3 | 2.29 | E |
| 363 | N-piperidinyl-3-fluoro | 491.3 | 1.2 | E |
| 364 | 2-oxa-6-azaspiro[3.3]heptane | 487.3 | 1.73 | E |
| 365 | —NHCH₂(1-methylcyclopropyl) | 473.3 | 1.97 | E |
| 366 | 2-methylpyrrolidinyl | 473.4 | 1.87 | E |
| 367 | —NH(CH₂CH(OH)CH₃) | 463.3 | 1.66 | B |
| 368 | 2,5-dimethylpyrrolidinyl | 487.4 | 2.08 | E |
| 369 | —NH(CH₂CH₂CH(OH)CH₃) | 477.3 | 1.62 | F |
| 370 | 2-(methoxymethyl)pyrrolidinyl | 503.3 | 2.1 | E |
| 371 | morpholino-neopentyl-NH | 546.3 | 1.89 | E |
| 372 | 4-(2-methoxyethyl)piperazinyl | 532.4 | 1.18 | E |
| 373 | (tetrahydrofuran-2-yl)methyl-NH | 489.3 | 1.9 | E |
| 374 | 4-methyl-4-amino-tetrahydropyran | 503.3 | 1.91 | F |
| 375 | —NH(CH₂C(CH₃)₂OH) | 477.3 | 1.76 | F |
| 376 | 4-methylpiperidinyl | 487.3 | 1.34 | E |
| 377 | 2-methylpiperidinyl | 487.3 | 2.02 | E |
| 378 | 3-methylpiperidinyl | 487.3 | 2.22 | E |
| 379 | 3-oxopiperazinyl | 488.3 | 1.75 | E |
| 380 | 3-hydroxypyrrolidinyl | 475.3 | 1.18 | E |
| 381 | 2-(hydroxymethyl)pyrrolidinyl | 489.3 | 1.79 | F |
| 382 | 4-methyl-1-hydroxy-pentan-2-ylamino | 505.3 | 1.37 | E |
| 383 | 3-hydroxypiperidinyl | 489.3 | 1.87 | E |
| 384 | N-methyl-N-cyclohexylamino | 501.4 | 1.41 | E |

TABLE 13-continued

| Ex. No. | Structure | LCMS [M + H] | Rt (min) | Method |
|---|---|---|---|---|
| 385 | HN-tetrahydropyran-3-yl | 489.3 | 1.93 | E |
| 386 | HN-tetrahydropyran-4-yl | 489.3 | 1.21 | E |
| 387 | HN-tetrahydrofuran-3-yl | 475.3 | 1.18 | E |
| 388 | 4-fluoropiperidin-1-yl | 491.3 | 2.18 | E |
| 389 | 8-oxa-3-azabicyclo[3.2.1]octan-3-yl | 501.3 | 2.04 | E |
| 390 | 3,3-difluoropiperidin-1-yl | 509.3 | 1.37 | E |
| 391 | (3S)-3-hydroxypyrrolidin-1-yl | 475.3 | 1.24 | F |
| 392 | 3-pentan-3-ylamino | 461.3 | 1.24 | F |
| 393 | (3-methylbutyl)amino | 475.3 | 1.35 | F |

TABLE 14

| Ex. No. | Structure | LCMS MH+ | Rt (min) | HPLC Method |
|---|---|---|---|---|
| 394 | (structure with CF3-pyrrolidine, CH2OH, piperidine-indole-dimethylpyridine, isopropyl) | 557.2 | 1.94 | QC-AA |
| 395 | (structure with OMe-pyrrolidine, CH2OH, piperidine-indole-dimethylpyridine, isopropyl) | 519.3 | 1.14 | QC-TFA |

TABLE 14-continued
| Ex. No. | Structure | LCMS MH+ | Rt (min) | HPLC Method |
|---|---|---|---|---|
| 396 | 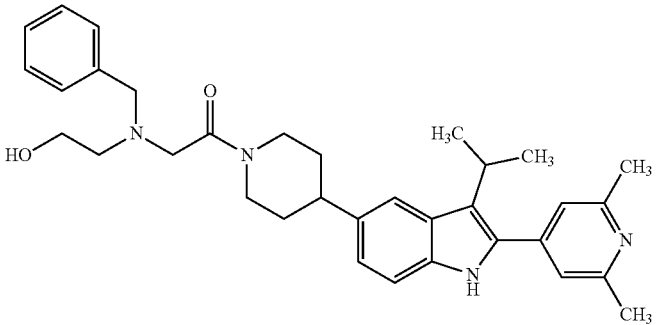 [SMILES: Cc1cc(-c2[nH]c3ccc(C4CCN(C(=O)CN(CCO)Cc5ccccc5)CC4)cc3c2C(C)C)cc(C)n1] | 539.2 | 2.06 | QC-AA |
| 397 | 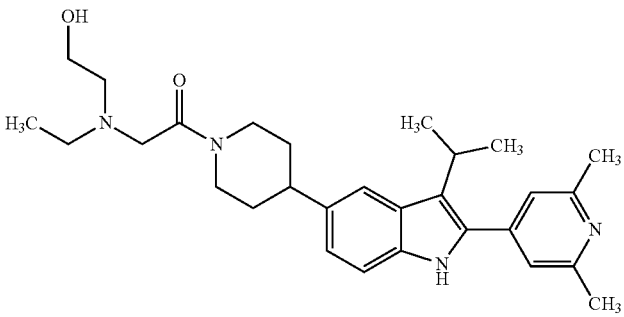 [SMILES: CCN(CCO)CC(=O)N1CCC(c2ccc3[nH]c(-c4cc(C)nc(C)c4)c(C(C)C)c3c2)CC1] | 477.3 | 1.11 | QC-TFA |
| 398 | 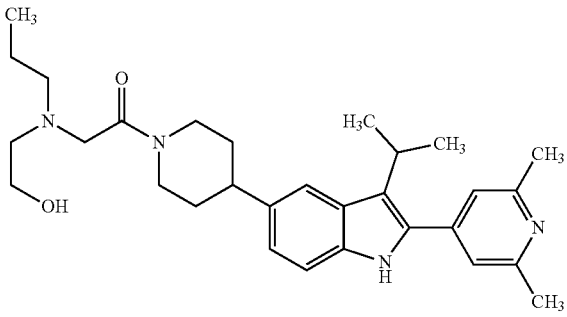 [SMILES: CCCN(CCO)CC(=O)N1CCC(c2ccc3[nH]c(-c4cc(C)nc(C)c4)c(C(C)C)c3c2)CC1] | 491.2 | 1.17 | QC-TFA |
| 399 | 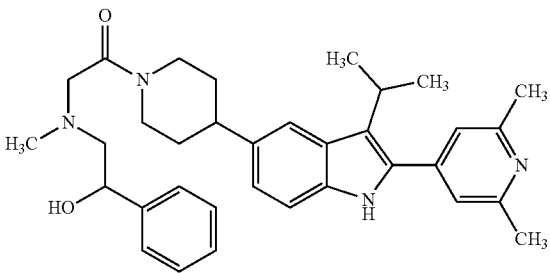 | 539.2 | 1.29 | QC-TFA |
| 400 | 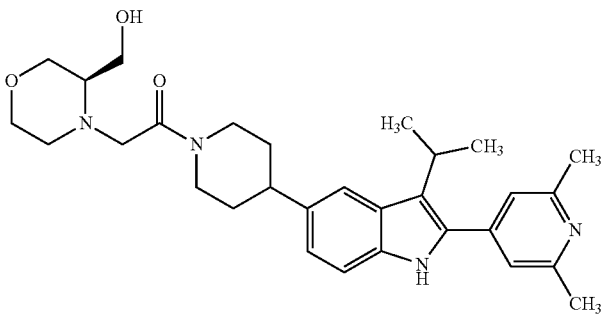 [SMILES: Cc1cc(-c2[nH]c3ccc(C4CCN(C(=O)CN5CCOC[C@H]5CO)CC4)cc3c2C(C)C)cc(C)n1] | 505.2 | 1.63 | QC-AA |

TABLE 14-continued

| Ex. No. | Structure | LCMS MH+ | Rt (min) | HPLC Method |
|---|---|---|---|---|
| 401 | 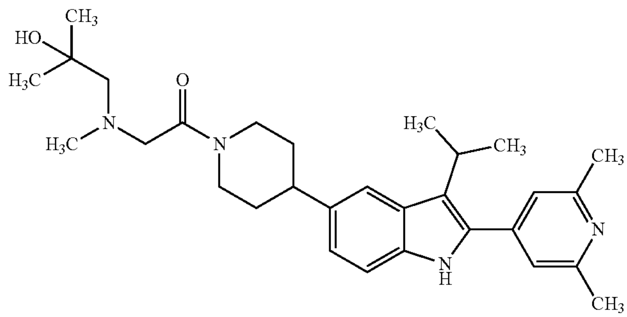 [SMILES: Cc1cc(-c2[nH]c3ccc(C4CCN(C(=O)CN(C)CC(C)(C)O)CC4)cc3c2C(C)C)cc(C)n1] | 491.2 | 1.15 | QC-TFA |
| 402 | 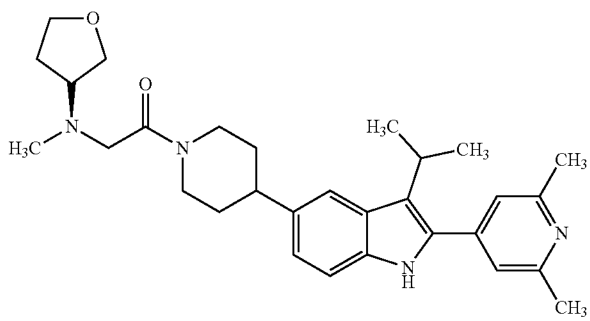 | 489.2 | 1.09 | QC-TFA |
| 403 | 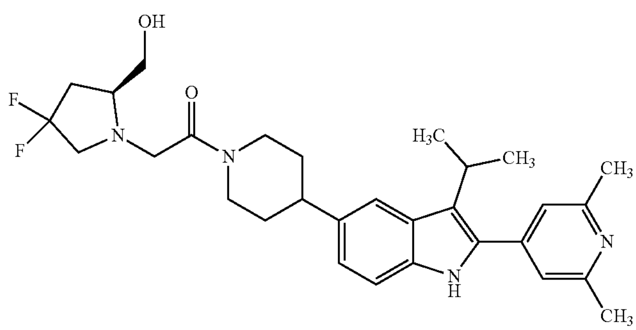 [SMILES: Cc1cc(-c2[nH]c3ccc(C4CCN(C(=O)CN5CC(F)(F)C[C@H]5CO)CC4)cc3c2C(C)C)cc(C)n1] | 525.2 | 1.85 | QC-AA |
| 404 | 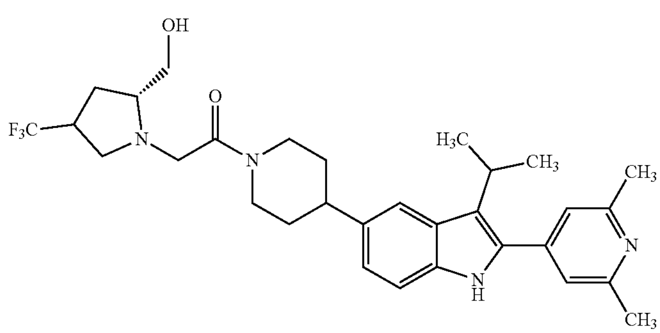 [SMILES: Cc1cc(-c2[nH]c3ccc(C4CCN(C(=O)CN5CC(C(F)(F)F)C[C@@H]5CO)CC4)cc3c2C(C)C)cc(C)n1] | 557.2 | 1.25 | QC-TFA |

TABLE 14-continued

| Ex. No. | Structure | LCMS MH+ | Rt (min) | HPLC Method |
|---|---|---|---|---|
| 405 | 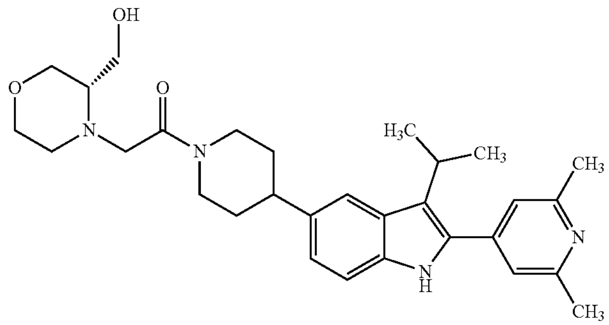 [SMILES: Cc1cc(-c2[nH]c3ccc(C4CCN(C(=O)CN5CCOC[C@@H]5CO)CC4)cc3c2C(C)C)cc(C)n1] | 505.2 | 1.63 | QC-AA |
| 406 | 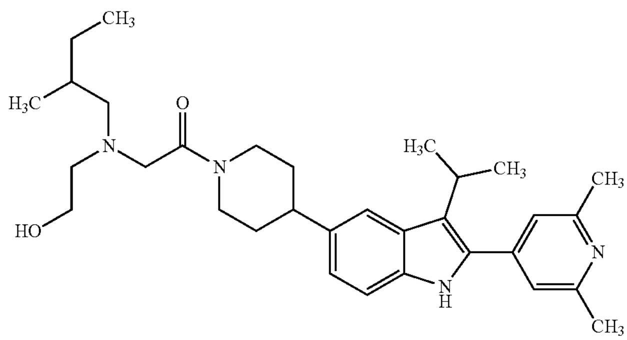 [SMILES: CCC(C)CN(CCO)CC(=O)N1CCC(c2ccc3[nH]c(-c4cc(C)nc(C)c4)c(C(C)C)c3c2)CC1] | 519.2 | 2.11 | QC-AA |
| 407 | 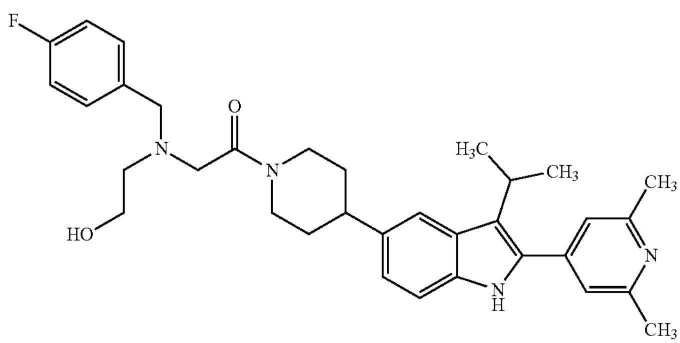 [SMILES: Cc1cc(-c2[nH]c3ccc(C4CCN(C(=O)CN(CCO)Cc5ccc(F)cc5)CC4)cc3c2C(C)C)cc(C)n1] | 557.2 | 1.3 | QC-TFA |
| 408 | 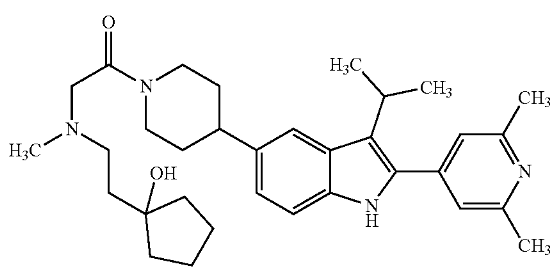 | 531.3 | 1.26 | QC-TFA |
| 409 | 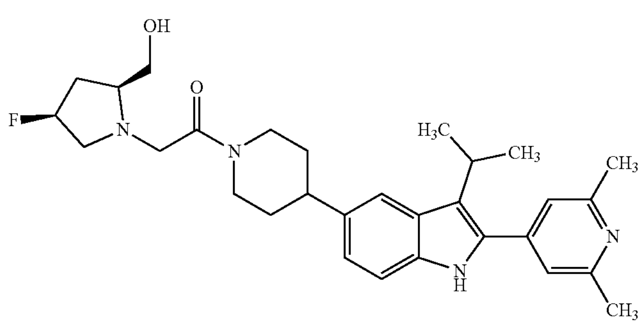 [SMILES: Cc1cc(-c2[nH]c3ccc(C4CCN(C(=O)CN5C[C@@H](F)C[C@H]5CO)CC4)cc3c2C(C)C)cc(C)n1] | 507.2 | 1.12 | QC-TFA |

TABLE 14-continued

| Ex. No. | Structure | LCMS MH+ | Rt (min) | HPLC Method |
|---|---|---|---|---|
| 410 | 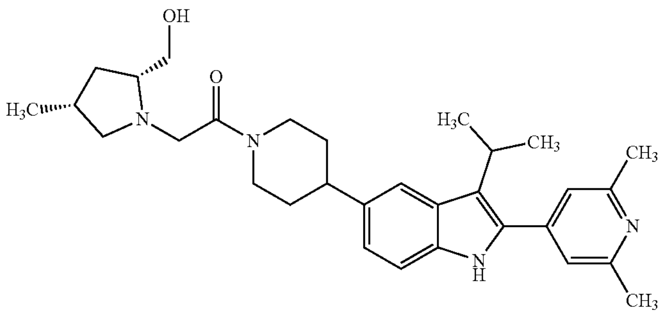 | 503.3 | 1.18 | QC-TFA |
| 411 | 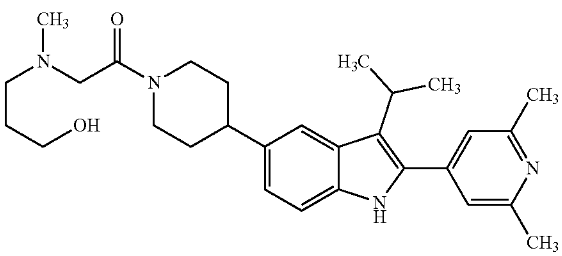 [SMILES: Cc1cc(-c2[nH]c3ccc(C4CCN(C(=O)CN(C)CCCO)CC4)cc3c2C(C)C)cc(C)n1] | 477.2 | 1.08 | QC-TFA |
| 412 | 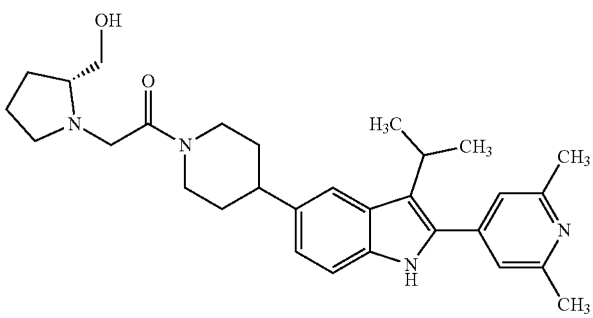 [SMILES: Cc1cc(-c2[nH]c3ccc(C4CCN(C(=O)CN5CCC[C@@H]5CO)CC4)cc3c2C(C)C)cc(C)n1] | 489.2 | 1.58 | QC-AA |
| 413 | 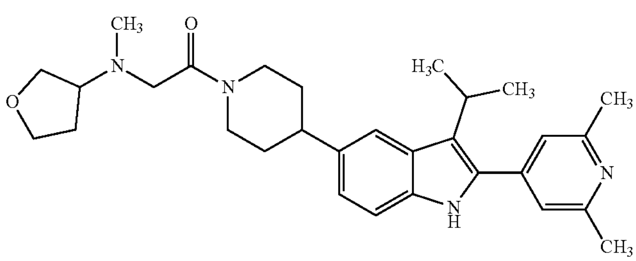 [SMILES: Cc1cc(-c2[nH]c3ccc(C4CCN(C(=O)CN(C)C5CCOC5)CC4)cc3c2C(C)C)cc(C)n1] | 489.2 | 1.13 | QC-TFA |
| 414 | 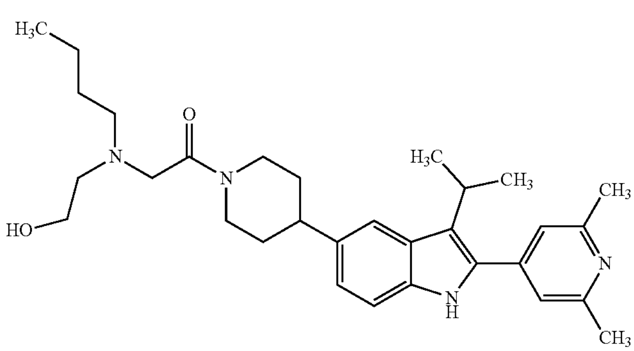 [SMILES: CCCCN(CCO)CC(=O)N1CCC(c2ccc3[nH]c(-c4cc(C)nc(C)c4)c(C(C)C)c3c2)CC1] | 505.3 | 1.96 | QC-AA |

TABLE 14-continued
| Ex. No. | Structure | LCMS MH+ | Rt (min) | HPLC Method |
|---|---|---|---|---|
| 415 | 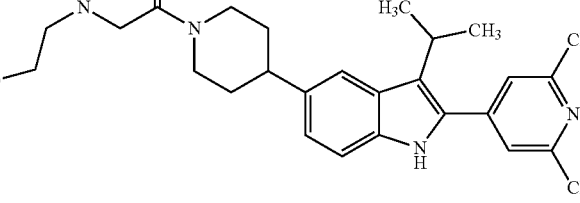 | 491.2 | 1.16 | QC-TFA |
| 416 | 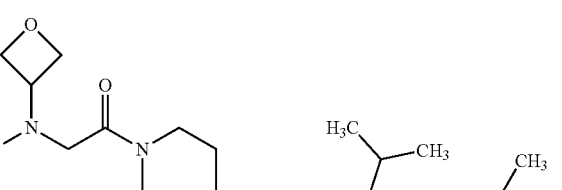 | 475.1 | 1.7 | QC-AA |
| 417 | 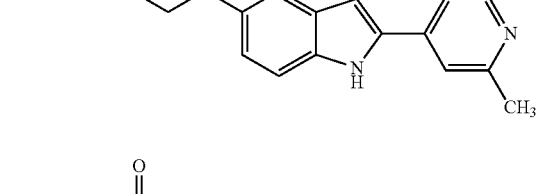 | 514.4 | 1.12 | QC-TFA |
| 418 | 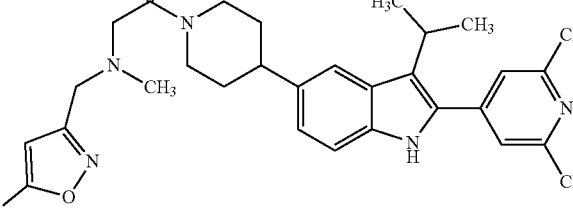 | 541.2 | 1.83 | QC-AA |
| 419 | 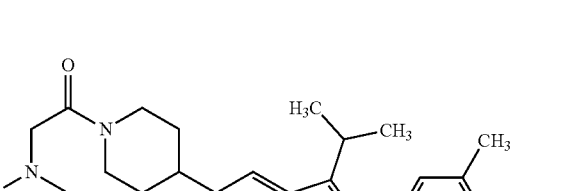 | 514.1 | 1.16 | QC-TFA |

TABLE 14-continued

| Ex. No. | Structure | LCMS MH+ | Rt (min) | HPLC Method |
|---|---|---|---|---|
| 420 | 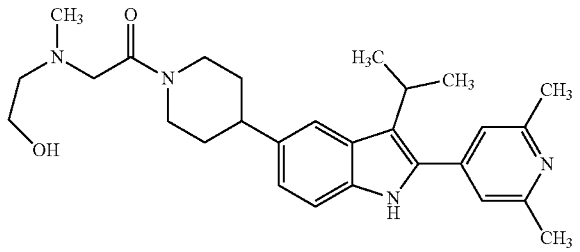 [SMILES: Cc1cc(-c2[nH]c3ccc(C4CCN(C(=O)CN(C)CCO)CC4)cc3c2C(C)C)cc(C)n1] | 463 | 1.48 | QC-AA |
| 421 | 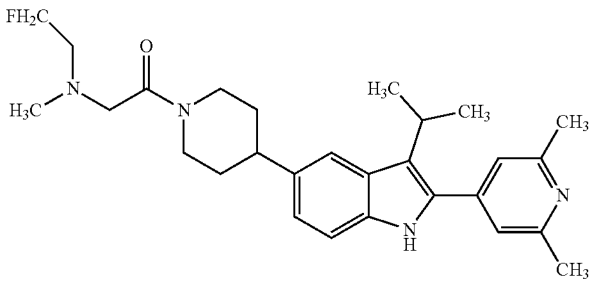 | 465 | 1.87 | QC-AA |
| 422 | 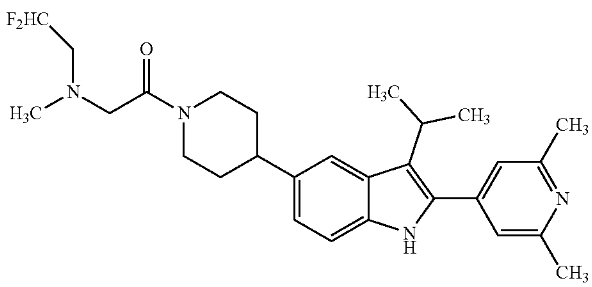 | 483.1 | 1.09 | QC-TFA |
| 423 | 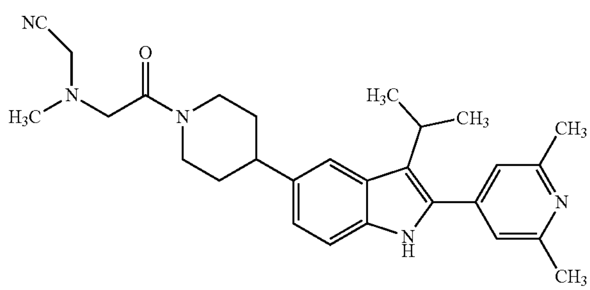 | 458 | 1.8 | QC-AA |

Example 424

2-(2,6-dimethylpyridin-4-yl)-3-isopropyl-5-(1-((6-methoxypyridin-3-yl)methyl)piperidin-4-yl)-1H-indole

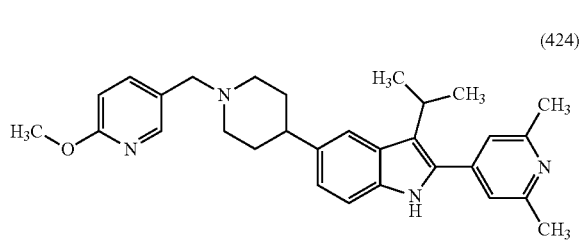

(424)

To a solution of 2-(2,6-dimethylpyridin-4-yl)-3-isopropyl-5-(piperidin-4-yl)-1H-indole, HCl (0.040 g, 0.104 mmol) and 6-methoxynicotinaldehyde (0.029 g, 0.208 mmol) in methanol (3 mL) was added TEA (0.20 mL, 1.435 mmol) at 0° C. The resulting light yellow solution was stirred under nitrogen at 25° C. for 2 h. The reaction mixture was cooled to 0° C. and acetic acid (0.30 ml, 5.24 mmol) was added. The reaction mixture was stirred at 25° C. for 3 h. Again the reaction mixture was cooled to 0° C. and sodium cyanoborohydride (0.033 g, 0.521 mmol) was added, and stirring was continued at the same temperature for 12 h. The reaction mass was diluted with dichloromethane (10 mL). The reaction was quenched with water. The organic layer was dried over sodium sulfate and concentrated. The crude material was purified by Preparative LCMS, the fractions containing desired product was combined and dried using Genevac centrifugal evaporator to afford 2-(2,6-dimethylpyridin-4-yl)-3-isopropyl-5-(1-((6-methoxypyridin-3-yl)methyl) piperidin-4-yl)-1H-indole (0.013 g, 0.027 mmol, 26.2% yield) as a pale solid. LCMS retention time 2.37 min [E]. MS (E−) m/z: 469.3 (M+H).

The following examples were prepared according to the general procedure described in Example 424.

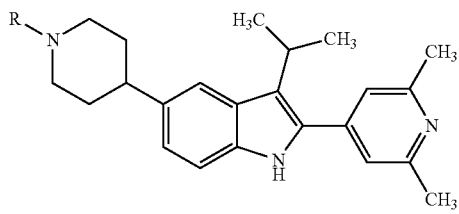

TABLE 15

| Ex. No. | R | LCMS [M + H] | Rt (min) | Method |
|---|---|---|---|---|
| 425 | (imidazol-4-ylmethyl) | 428.4 | 1.187 | E |
| 426 | (2-methyl-imidazol-4-ylmethyl) | 442.4 | 1.205 | E |
| 427 | (1-isopropylpiperidin-4-yl) | 473.3 | 1.767 | E |
| 428 | —CH₂CH₂NHCH₃ | 405.3 | 1.574 | E |
| 429 | —CH₃ | 362.2 | 1.685 | E |
| 430 | (2-methoxypyrimidin-5-ylmethyl) | 470.4 | 2.558 | A |
| 431 | (pyridin-2-ylmethyl) | 439.3 | 2.235 | E |

TABLE 15-continued

| Ex. No. | R | LCMS [M + H] | Rt (min) | Method |
|---|---|---|---|---|
| 432 | (isoxazol-3-ylmethyl) | 429.3 | 2.235 | E |
| 433 | (pyridin-3-ylmethyl) | 439.3 | 2.148 | E |
| 434 | (pyrimidin-5-ylmethyl) | 440.2 | 2.053 | E |
| 435 | (pyridin-4-ylmethyl) | 439.3 | 2.277 | E |
| 436 | —CH(CH₂CH₃)₂ | 418.3 | 1.955 | E |
| 437 | (6-methylpyridin-3-ylmethyl) | 453.3 | 2.07 | E |
| 438 | (1H-pyrazol-4-ylmethyl) | 428.3 | 1.398 | E |
| 439 | (3-methyl-1H-pyrazol-4-ylmethyl) | 442.3 | 1.563 | E |
| 440 | (1-methyl-1H-pyrazol-4-ylmethyl) | 442.3 | 1.652 | E |

TABLE 16

| Ex. No. | Structure | LCMS MH⁺ | Rt (min) | HPLC Method |
|---|---|---|---|---|
| 441 | (1H-pyrazol-5-ylmethyl-piperidinyl indole derivative) | 428.2 | 1.51 | QC-AA |

TABLE 16-continued

| Ex. No. | Structure | LCMS MH+ | Rt (min) | HPLC Method |
|---|---|---|---|---|
| 442 | 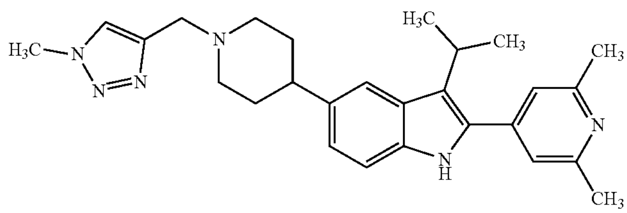 | 443.2 | 1.54 | QC-AA |
| 443 | 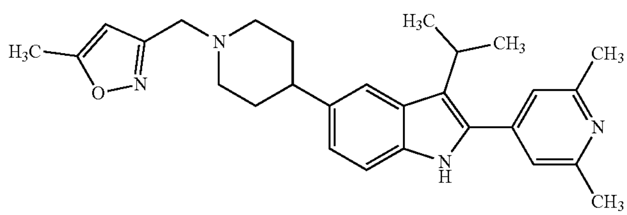 | 443.2 | 1.16 | QC-TFA |
| 444 | 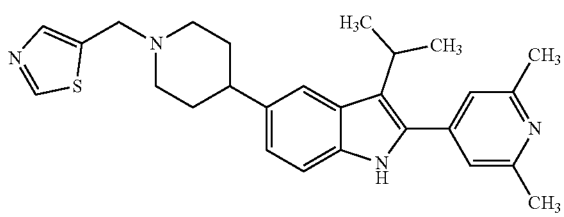 [SMILES: Cc1cc(-c2[nH]c3ccc(C4CCN(Cc5cncs5)CC4)cc3c2C(C)C)cc(C)n1] | 445.2 | 1.04 | QC-TFA |
| 445 | 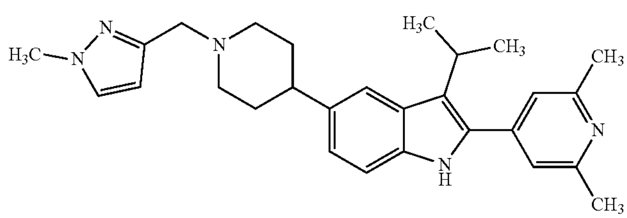 | 442.2 | 1.57 | QC-AA |
| 446 | 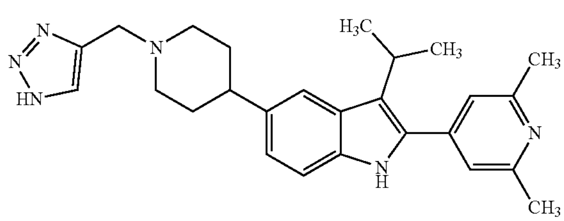 [SMILES: Cc1cc(-c2[nH]c3ccc(C4CCN(Cc5c[nH]nn5)CC4)cc3c2C(C)C)cc(C)n1] | 429.2 | 0.99 | QC-TFA |
| 447 | 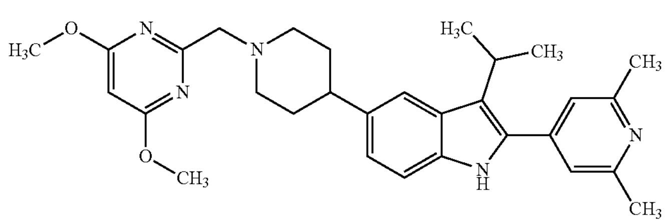 | 500.2 | 1.26 | QC-TFA |
| 448 | 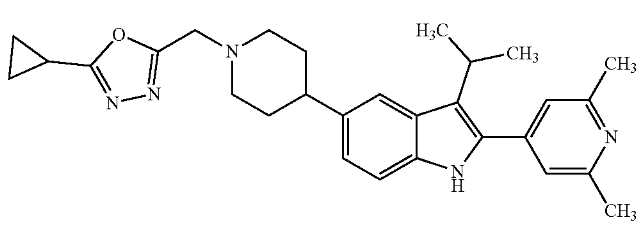 [SMILES: Cc1cc(-c2[nH]c3ccc(C4CCN(Cc5nnc(C6CC6)o5)CC4)cc3c2C(C)C)cc(C)n1] | 470.2 | 1.97 | QC-AA |

TABLE 16-continued

| Ex. No. | Structure | LCMS MH+ | Rt (min) | HPLC Method |
|---|---|---|---|---|
| 449 | 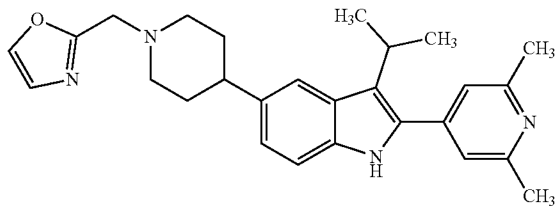 [SMILES: Cc1cc(-c2[nH]c3ccc(C4CCN(Cc5ncco5)CC4)cc3c2C(C)C)cc(C)n1] | 429.2 | 1.03 | QC-TFA |
| 450 | 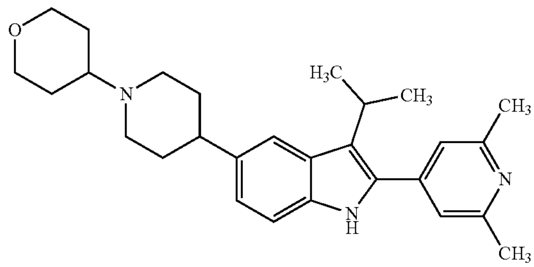 [SMILES: Cc1cc(-c2[nH]c3ccc(C4CCN(C5CCOCC5)CC4)cc3c2C(C)C)cc(C)n1] | 432.1 | 1.41 | QC-AA |
| 451 | 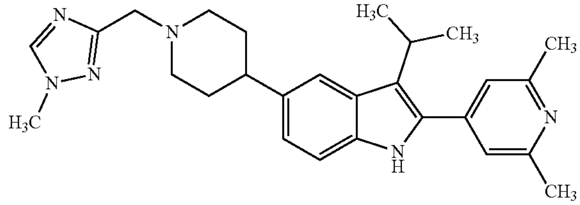 [SMILES: Cc1cc(-c2[nH]c3ccc(C4CCN(Cc5ncn(C)n5)CC4)cc3c2C(C)C)cc(C)n1] | 443.1 | 1.73 | QC-AA |
| 452 | 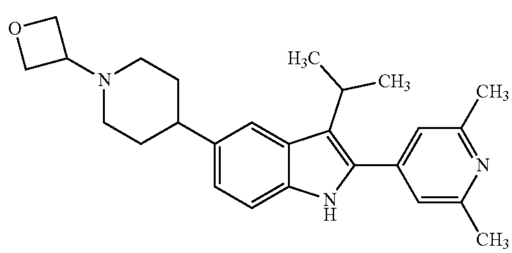 [SMILES: Cc1cc(-c2[nH]c3ccc(C4CCN(C5COC5)CC4)cc3c2C(C)C)cc(C)n1] | 404.2 | 0.83 | QC-TFA |
| 453 | 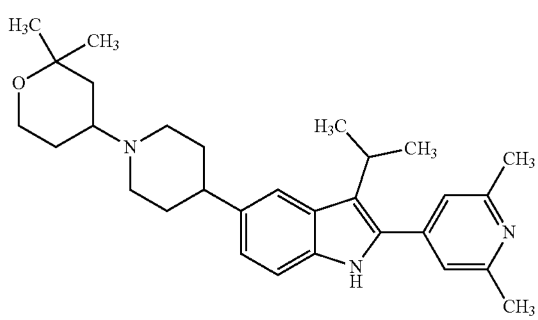 [SMILES: Cc1cc(-c2[nH]c3ccc(C4CCN(C5CCOC(C)(C)C5)CC4)cc3c2C(C)C)cc(C)n1] | 460.4 | 1.05 | QC-TFA |

TABLE 16-continued
| Ex. No. | Structure | LCMS MH+ | Rt (min) | HPLC Method |
|---|---|---|---|---|
| 454 | 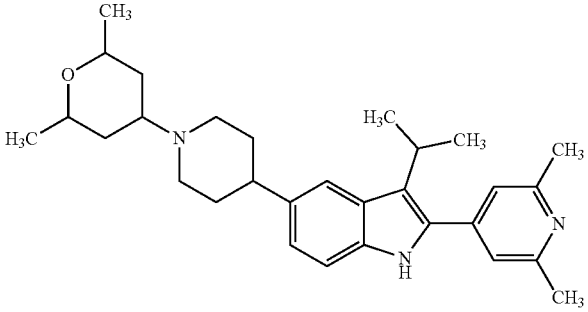 | 460.4 | 1.53 | QC-AA |
| 455 | 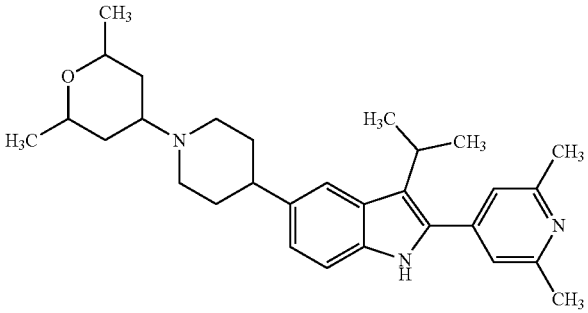 | 460.4 | 1.95 | QC-AA |
| 456 | 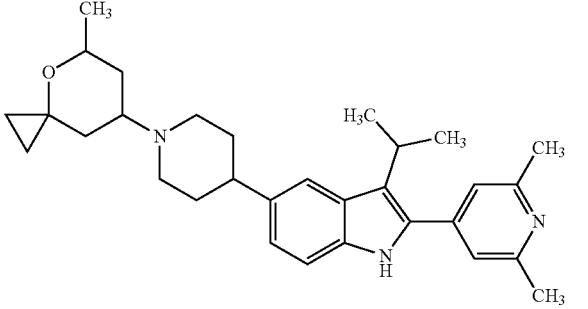 [SMILES: Cc1cc(-c2[nH]c3ccc(C4CCN(C5CC(C)OC6(CC6)C5)CC4)cc3c2C(C)C)cc(C)n1] | 472.4 | 1.76 | QC-AA |
| 457 | 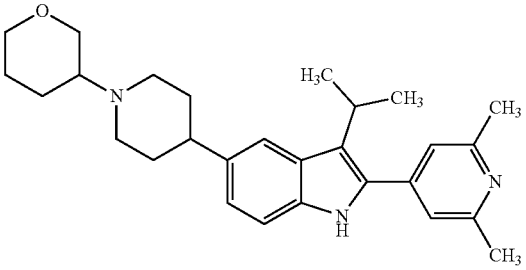 [SMILES: Cc1cc(-c2[nH]c3ccc(C4CCN(C5CCCOC5)CC4)cc3c2C(C)C)cc(C)n1] | 432.1 | 0.92 | QC-TFA |
| 458 | 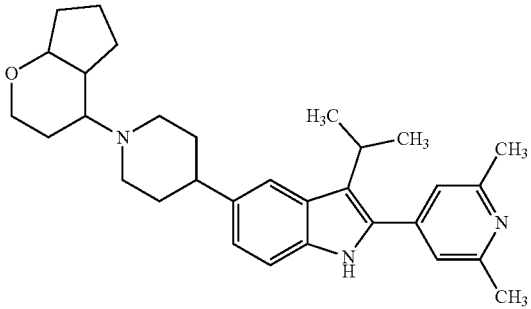 [SMILES: Cc1cc(-c2[nH]c3ccc(C4CCN(C5CCOC6CCCC65)CC4)cc3c2C(C)C)cc(C)n1] | 471.9 | 1.05 | QC-TFA |

TABLE 16-continued

| Ex. No. | Structure | LCMS MH+ | Rt (min) | HPLC Method |
|---|---|---|---|---|
| 459 | 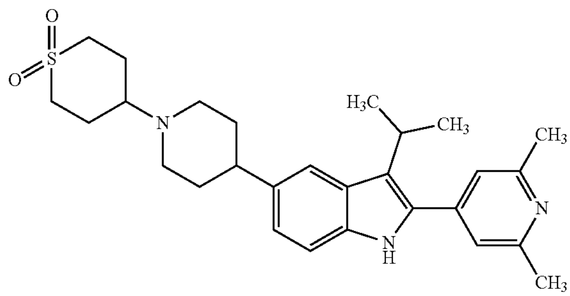 [SMILES: Cc1cc(-c2[nH]c3ccc(C4CCN(C5CCS(=O)(=O)CC5)CC4)cc3c2C(C)C)cc(C)n1] | 480.1 | 1.55 | QC-AA |
| 460 | 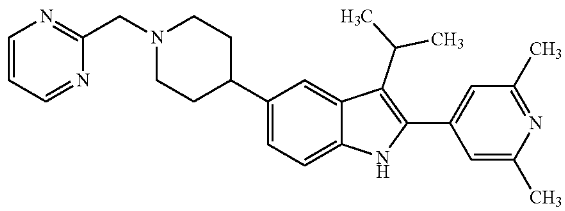 | 440.4 | 1.61 | QC-AA |
| 461 | 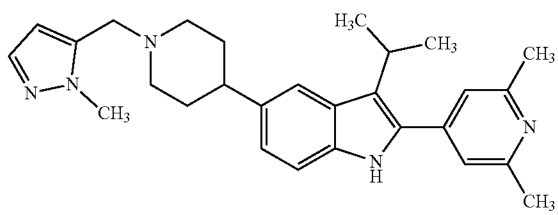 [SMILES: Cc1cc(-c2[nH]c3ccc(C4CCN(Cc5ccnn5C)CC4)cc3c2C(C)C)cc(C)n1] | 442.2 | 2.01 | QC-AA |
| 462 | 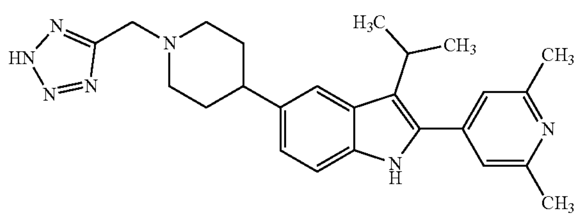 [SMILES: Cc1cc(-c2[nH]c3ccc(C4CCN(Cc5nn[nH]n5)CC4)cc3c2C(C)C)cc(C)n1] | 430 | 1.19 | QC-AA |
| 463 | 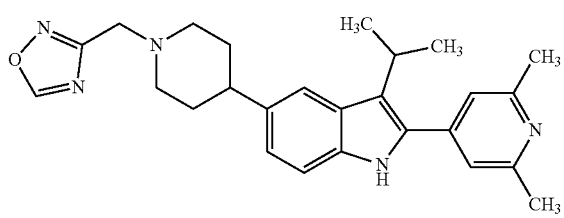 | 430.2 | 1.97 | QC-AA |
| 464 | 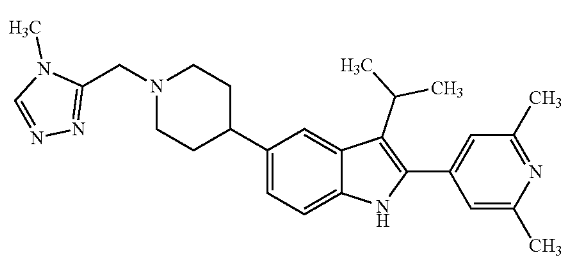 [SMILES: Cc1cc(-c2[nH]c3ccc(C4CCN(Cc5nncn5C)CC4)cc3c2C(C)C)cc(C)n1] | 443 | 1.61 | QC-AA |

TABLE 16-continued

| Ex. No. | Structure | LCMS MH+ | Rt (min) | HPLC Method |
|---|---|---|---|---|
| 465 | 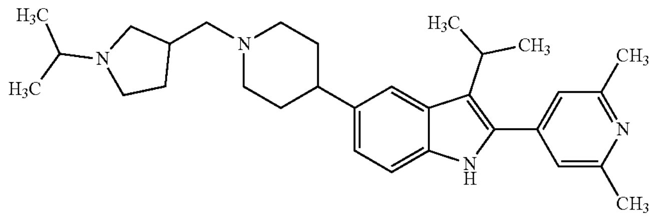 [SMILES: Cc1cc(-c2[nH]c3ccc(C4CCN(CC5CCN(C(C)C)C5)CC4)cc3c2C(C)C)cc(C)n1] | 473.2 | 0.809 | QC-TFA |
| 466 | 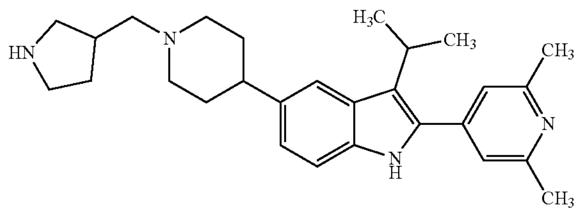 [SMILES: Cc1cc(-c2[nH]c3ccc(C4CCN(CC5CCNC5)CC4)cc3c2C(C)C)cc(C)n1] | 431.3 | 0.744 | QC-TFA |
| 467 | 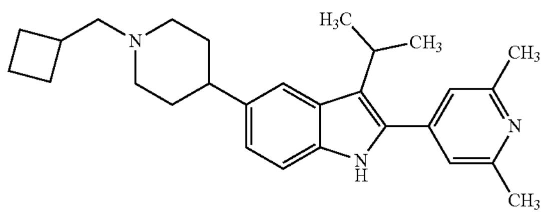 [SMILES: Cc1cc(-c2[nH]c3ccc(C4CCN(CC5CCC5)CC4)cc3c2C(C)C)cc(C)n1] | 416 | 1.154 | QC-TFA |
| 468 | 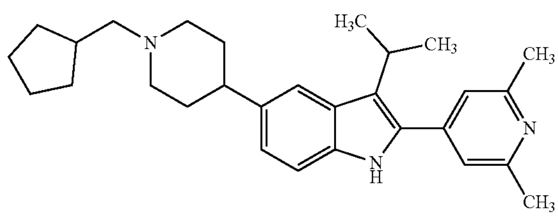 [SMILES: Cc1cc(-c2[nH]c3ccc(C4CCN(CC5CCCC5)CC4)cc3c2C(C)C)cc(C)n1] | 430.5 | 1.252 | QC-TFA |
| 469 | 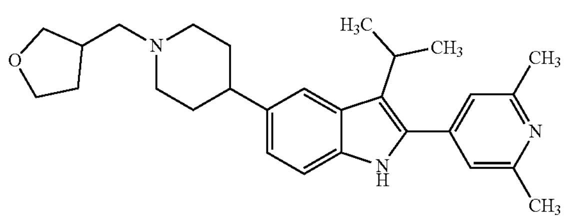 [SMILES: Cc1cc(-c2[nH]c3ccc(C4CCN(CC5CCOC5)CC4)cc3c2C(C)C)cc(C)n1] | 432.5 | 0.949 | QC-TFA |
| 470 | 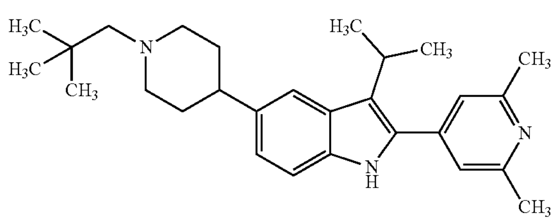 | 418.4 | 1.169 | QC-TFA |
| 471 | 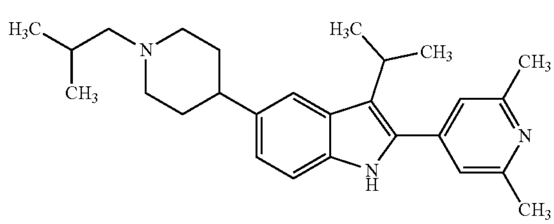 | 404.4 | 1.104 | QC-TFA |

TABLE 16-continued
| Ex. No. | Structure | LCMS MH+ | Rt (min) | HPLC Method |
|---|---|---|---|---|
| 472 | 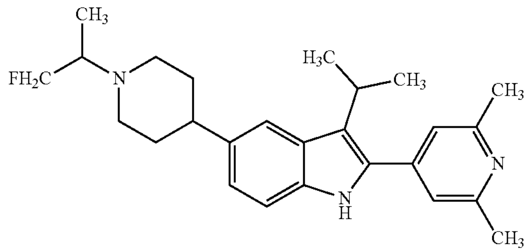 | 408.3 | 0.94 | QC-TFA |
| 473 | 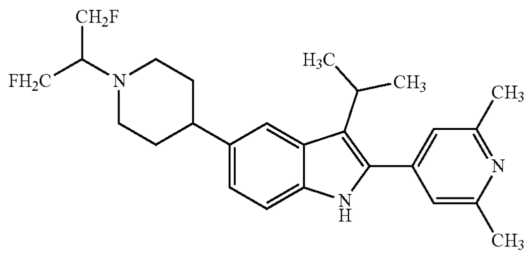 | 426.1 | 0.92 | QC-TFA |
| 474 | 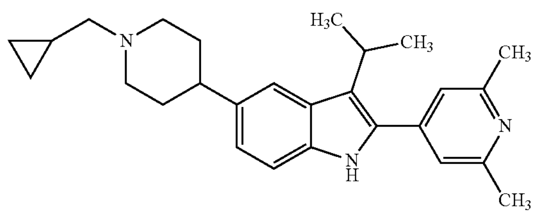 [SMILES: Cc1cc(-c2[nH]c3ccc(C4CCN(CC5CC5)CC4)cc3c2C(C)C)cc(C)n1] | 402.3 | 0.96 | QC-TFA |
| 475 | 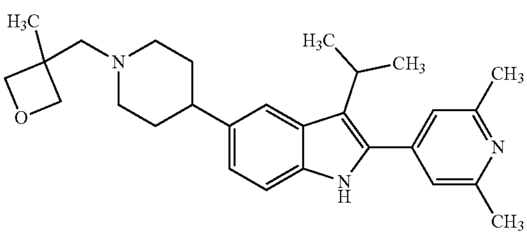 [SMILES: Cc1cc(-c2[nH]c3ccc(C4CCN(CC5(C)COC5)CC4)cc3c2C(C)C)cc(C)n1] | 432.2 | 0.89 | QC-TFA |
Example 476
4-(3-isopropyl-5-(piperidin-4-yl)-1H-indol-2-yl)-N-(2,2,2-trifluoroethyl)picolinamide
Intermediate 476A: Tert-Butyl 4-(2-(2-cyanopyridin-4-yl)-3-isopropyl-1H-indol-5-yl) piperidine-1-carboxylate
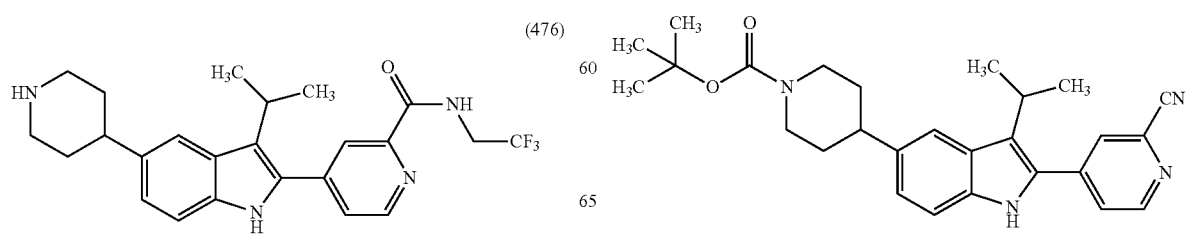
(476)
(476A)

Tert-butyl 4-(2-(2-cyanopyridin-4-yl)-3-isopropyl-1H-indol-5-yl)piperidine-1-carboxylate was prepared according to the general procedure described in Intermediate 1B using tert-butyl 4-(3-isopropyl-2-(4,4,5,5-tetramethyl-1,3,2-dioxaborolan-2-yl)-1H-indol-5-yl)piperidine-1-carboxylate as a starting intermediate (0.45 g, 95% yield). LCMS retention time 3.74 min [B]. MS (E−) m/z: 445.3 (M+H).

Intermediate 476B: 4-(5-(1-(tert-butoxycarbonyl)piperidin-4-yl)-3-isopropyl-1H-indol-2-yl)picolinic Acid

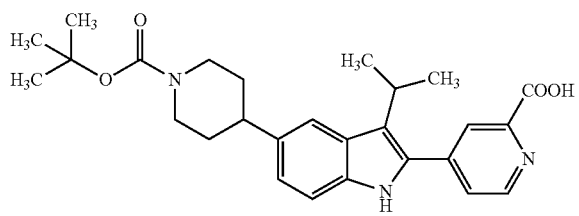

(476B)

To a solution of tert-butyl 4-(2-(2-cyanopyridin-4-yl)-3-isopropyl-1H-indol-5-yl)piperidine-1-carboxylate (0.25 g, 0.562 mmol) in ethanol (5 mL) was added an aqueous solution of NaOH (0.067 g, 1.687 mmol) dropwise. The resulting solution was heated at 90° C. for 12 h. The reaction mass was concentrated under vacuum, then 1.5 N HCL was slowly added to bring the pH to 5 to 6. The solid formed was filtered and dried to afford 4-(5-(1-(tert-butoxycarbonyl)piperidin-4-yl)-3-isopropyl-1H-indol-2-yl) picolinic acid (0.25 g, 95%) as a yellow solid. LCMS retention time 2.80 min [C]. MS (E−) m/z: 464.4 (M+H).

Intermediate 476C: Tert-Butyl 4-(3-isopropyl-2-(2-((2,2,2-trifluoroethyl)carbamoyl) pyridin-4-yl)-1H-indol-5-yl)piperidine-1-carboxylate

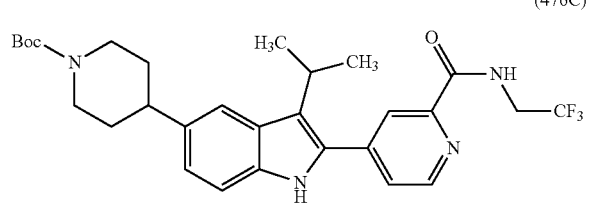

(476C)

To a solution of 4-(5-(1-(tert-butoxycarbonyl)piperidin-4-yl)-3-isopropyl-1H-indol-2-yl)picolinic acid (0.025 g, 0.054 mmol) and 2,2,2-trifluoroethanamine (5.88 mg, 0.059 mmol) in DMF (2 mL) were added DIPEA (0.028 ml, 0.162 mmol) and HATU (0.031 g, 0.081 mmol at room temperature. The mixture was stirred at the same temperature for 4 h. DMF was removed under vacuum. The reaction was quenched with ice water. The reaction mixture was extracted with ethyl acetate. The ethyl acetate layer was dried over $Na_2SO_4$ and concentrated to afford tert-butyl 4-(3-isopropyl-2-(2-((2,2,2-trifluoroethyl) carbamoyl)pyridin-4-yl)-1H-indol-5-yl)piperidine-1-carboxylate (0.024 g, 85% yield) as a yellow solid. LCMS retention time 3.9 min [D]. MS (E−) m/z: 545.1 (M+H).

Example 476

To a solution of tert-butyl 4-(3-isopropyl-2-(2-((2,2,2-trifluoroethyl)carbamoyl) pyridin-4-yl)-1H-indol-5-yl)piperidine-1-carboxylate (0.024 g, 0.044 mmol) in DCM (2 mL) was added 4M HCl in dioxane (0.110 ml, 0.441 mmol) at room temperature. The mixture was stirred at the same temperature for 1 h. The solution was concentrated. The reaction mixture was purified by reverse phase prep LCMS to provide 4-(3-isopropyl-5-(piperidin-4-yl)-1H-indol-2-yl)-N-(2,2,2-trifluoroethyl)picolinamide (5.6 mg, 28.6% yield). LCMS retention time 1.35 min [E]. MS (E−) m/z: 445.2 (M+H).

The following example was prepared according to the general procedure used in Example 476.

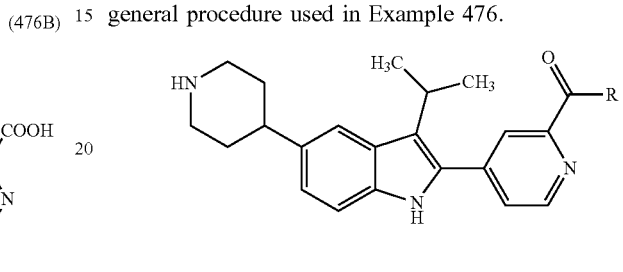

TABLE 17

| Ex. No. | R | LCMS [M + H] | Rt (min) | Method |
|---|---|---|---|---|
| 477 | | 446.3 | 1.37 | E |

Example 478

2-(2-cyclopropyl-6-methylpyridin-4-yl)-3-isopropyl-5-(piperidin-4-yl)-1H-indole

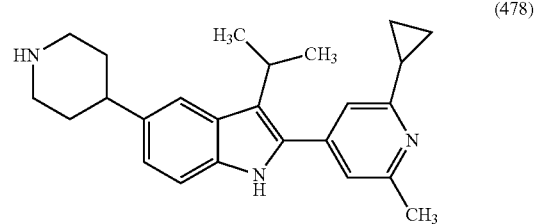 [SMILES: Cc1cc(-c2[nH]c3ccc(C4CCNCC4)cc3c2C(C)C)cc(C2CC2)n1]

(478)

Intermediate 478A: Tert-Butyl 4-(2-(2-chloro-6-methylpyridin-4-yl)-3-isopropyl-1H-indol-5-yl)piperidine-1-carboxylate

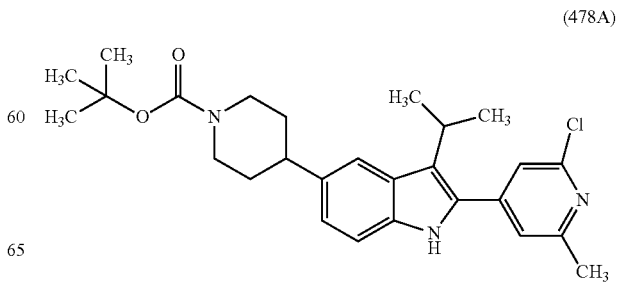

(478A)

Tert-butyl 4-(2-(2-chloro-6-methylpyridin-4-yl)-3-isopropyl-1H-indol-5-yl) piperidine-1-carboxylate was prepared according the general procedure described in Intermediate 1F using tert-butyl 4-(2-bromo-3-isopropyl-1H-indol-5-yl)piperidine-1-carboxylate as the starting intermediate (0.42 g, 76% yield). LCMS retention time 4.29 min [D]. MS (E−) m/z: 469.2 (M+H).

Intermediate 478B: Tert-Butyl 4-(2-(2-cyclopropyl-6-methylpyridin-4-yl)-3-isopropyl-1H-indol-5-yl) piperidine-1-carboxylate (478B)

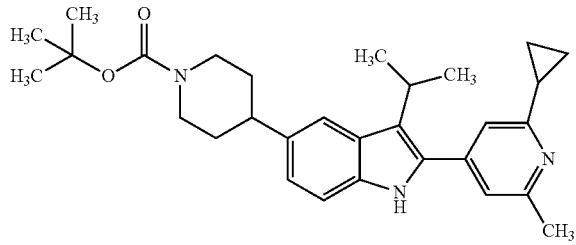

To a mixture of tert-butyl 4-(2-(2-chloro-6-methylpyridin-4-yl)-3-isopropyl-1H-indol-5-yl)piperidine-1-carboxylate (0.4 g, 0.855 mmol) and cyclopropylboronic acid (0.073 g, 0.855 mmol) in a 25 ml round bottom flask were added toluene (10 mL) followed by aqueous solution of potassium phosphate, dibasic (0.372 g, 2.137 mmol. The resulting reaction mixture was degassed for 10 minutes with nitrogen. Next, Pd(OAc)$_2$ (0.019 g, 0.085 mmol) and tricyclohexylphosphine (0.012 g, 0.043 mmol) were added and the reaction mixture was degassed again for 5 min. The reaction mixture was heated at 100° C. for 12 h. The reaction mixture was diluted with ethyl acetate (100 mL), poured into a separate funnel, washed with water (2×50 mL), brine (50 mL), dried over sodium sulfate, and concentrated to afford crude product. The crude product was purified using silica gel chromatography, eluting with 15% ethyl acetate in hexane, the fractions were collected and concentrated to afford tert-butyl 4-(2-(2-cyclopropyl-6-methylpyridin-4-yl)-3-isopropyl-1H-indol-5-yl)piperidine-1-carboxylate (0.38 g, 94% yield) as brown solid. LCMS retention time 4.24 min [D]. MS (E−) m/z: 474.5 (M+H).

Example 478

To a solution of tert-butyl 4-(2-(2-cyclopropyl-6-methylpyridin-4-yl)-3-isopropyl-1H-indol-5-yl)piperidine-1-carboxylate (0.36 g, 0.760 mmol) in DCM (2 mL) was added 4 M HCl in dioxane (0.023 mL, 0.760 mmol) at room temperature. The mixture was stirred at the same temperature for 1 h. The solution was concentrated to afford crude product. The crude sample was purified by prep LCMS to afford 2-(2-cyclopropyl-6-methylpyridin-4-yl)-3-isopropyl-5-(piperidin-4-yl)-1H-indole (0.28 mg, 99% yield). LCMS retention time 2.69 min [D]. MS (E−) m/z: 374.3 (M+H).

Example 479

2-(2-ethyl-6-methylpyridin-4-yl)-3-isopropyl-5-(piperidin-4-yl)-1H-indole (479)

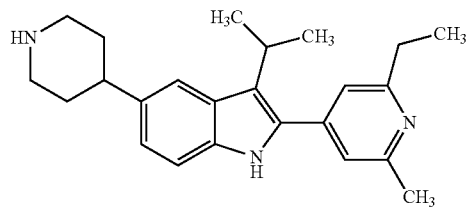

Intermediate 479A: Tert-Butyl 4-(2-(2-ethyl-6-methylpyridin-4-yl)-3-isopropyl-1H-indol-5-yl)piperidine-1-carboxylate (479A)

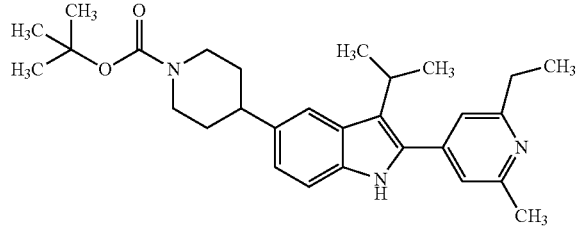

Tert-butyl 4-(2-(2-ethyl-6-methylpyridin-4-yl)-3-isopropyl-1H-indol-5-yl) piperidine-1-carboxylate was prepared according to the general procedure described for Intermediate 478B, using tert-butyl 4-(2-(2-chloro-6-methylpyridin-4-yl)-3-isopropyl-1H-indol-5-yl)piperidine-1-carboxylate as a starting intermediate (0.08 g, 81% yield). LCMS retention time 1.79 min [B]. MS (E−) m/z: 462.5 (M+H).

Example 479

To a solution of tert-butyl 4-(2-(2-ethyl-6-methylpyridin-4-yl)-3-isopropyl-1H-indol-5-yl)piperidine-1-carboxylate (0.08 g, 0.173 mmol) in DCM (2 mL) was added 4 M HCl in dioxane (0.260 mL, 1.040 mmol) at room temperature. The mixture was stirred at the same temperature for 1 h. The solution was concentrated to afford crude product. The crude product was purified by prep LCMS to afford 2-(2-ethyl-6-methylpyridin-4-yl)-3-isopropyl-5-(piperidin-4-yl)-1H-indole (2.3 mg, 3.67% yield). LCMS retention time 1.38 min [E]. MS (E−) m/z: 362.3 (M+H).

Example 480

3-isopropyl-2-(2-methyl-6-(4-methylpiperazin-1-yl) pyridin-4-yl)-5-(piperidin-4-yl)-1H-indole (480)

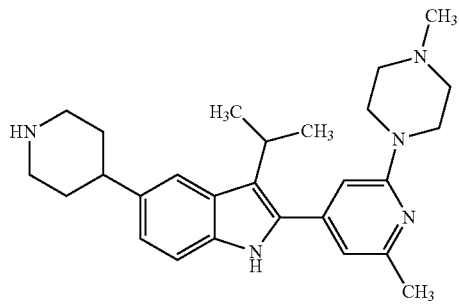

Intermediate 480A: Tert-Butyl 4-(3-isopropyl-2-(2-methyl-6-(4-methylpiperazin-1-yl) pyridin-4-yl)-1H-indol-5-yl) piperidine-1-carboxylate (480A)

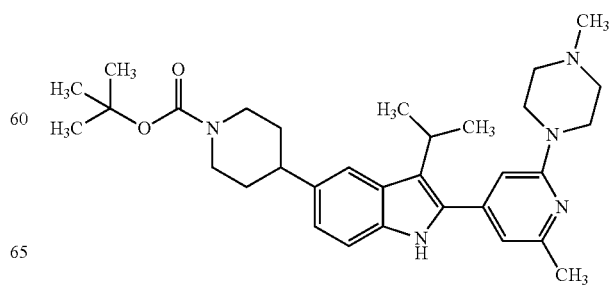

To a mixture of tert-butyl 4-(2-(2-chloro-6-methylpyridin-4-yl)-3-isopropyl-1H-indol-5-yl)piperidine-1-carboxylate (0.02 g, 0.043 mmol) and 1-methylpiperazine (8.56 mg, 0.085 mmol) in dioxane (2 mL) was added potassium t-butoxide (9.59 mg, 0.085 mmol). The resulting reaction mixture was degassed for 10 minutes with nitrogen, then [1,3-bis(2,6-diisopropylphenyl)Imidazol-2-ylidene](3-chloropyridyl) palladium(II) dichloride (2.91 mg, 4.27 μmol) was added. The reaction mixture was degassed again for 5 min. The resulting reaction mixture was heated at 80° C. for 12 h. The reaction mixture was diluted with ethyl acetate (10 mL), poured into a separate funnel and was washed with water (2×10 mL), brine (10 mL), dried over sodium sulfate, and concentrated to afford tert-butyl 4-(3-isopropyl-2-(2-methyl-6-(4-methylpiperazin-1-yl)pyridin-4-yl)-1H-indol-5-yl) piperidine-1-carboxylate (0.022 g, 97% yield) as brown solid. LCMS retention time 1.74 min [B]. MS (E−) m/z: 532.5 (M+H).

Example 480

To a solution of tert-butyl 4-(3-isopropyl-2-(2-methyl-6-(4-methylpiperazin-1-yl) pyridin-4-yl)-1H-indol-5-yl)piperidine-1-carboxylate (0.022 g, 0.041 mmol)) in DCM (2 mL) was added 4M HCl in dioxane (0.062 mL, 0.248 mmol) at room temperature. The mixture was stirred at the same temperature for 1 h. The solution was concentrated. The reaction mixture was purified by reverse phase prep LCMS to provide 3-isopropyl-2-(2-methyl-6-(4-methylpiperazin-1-yl)pyridin-4-yl)-5-(piperidin-4-yl)-1H-indole (5.0 mg, 30.8% yield). LCMS retention time 1.45 min [E]. MS (E−) m/z: 432.3 (M+H).

Example 481

2-(2-cyclopropyl-5-fluoropyridin-4-yl)-3-isopropyl-5-(piperidin-4-yl)-1H-indole

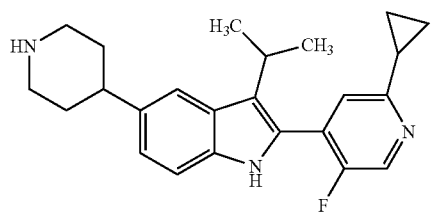

(481)

Intermediate 481A:
2-chloro-5-fluoro-4-iodopyridine

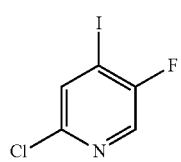

(481A)

Lithium diisopropylamide (6.27 mL, 12.54 mmol) was mixed with THF (80 mL). Next, a solution containing 2-chloro-5-fluoropyridine (1.0 g, 7.60 mmol) in THF (20 mL) was added to the mixture under a nitrogen atmosphere at −75° C., followed by stirring for 3 hours. Subsequently, a solution containing iodine (2.316 g, 9.12 mmol) in THF (20 mL) was added to the reaction mixture, followed by stirring at −75° C. for 1 hour. The reaction was quenched by water/THF (4 ml/16 ml), water (20 ml), and a sodium thiosulfate aqueous solution were added to the reaction solution at the temperatures of −75° C., −50° C., and −35° C., respectively. The reaction solution was adjusted to room temperature, followed by extraction with ethyl acetate (50× 3) ml. The organic layers were washed with saturated saline and dried over anhydrous sodium sulfate. The solvent was distilled away under reduced pressure to afford pale brown solid. LCMS for mol. Formula $C_{25}H_{31}FN_4O$ is 256.89 found 258.2 (M+). LCMS retention time 1.01 min [G].

Intermediate 481B: Tert-Butyl 4-(2-(2-chloro-5-fluoropyridin-4-yl)-3-isopropyl-1H-indol-5-yl)piperidine-1-carboxylate

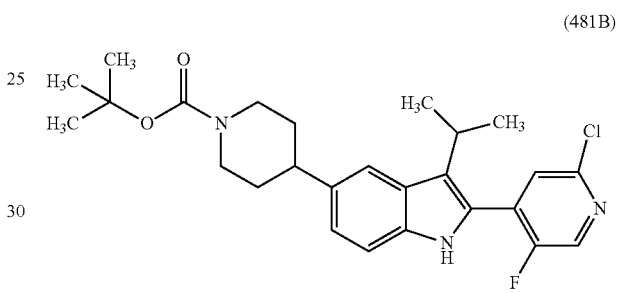

(481B)

Tert-butyl 4-(2-(2-chloro-5-fluoropyridin-4-yl)-3-isopropyl-1H-indol-5-yl) piperidine-1-carboxylate was prepared as described in Intermediate 1F using tert-butyl 4-(3-isopropyl-2-(4,4,5,5-tetramethyl-1,3,2-dioxaborolan-2-yl)-1H-indol-5-yl)piperidine-1-carboxylate as a starting intermediate (0.4 g, 79% yield). LCMS retention time 4.00 min [D]. MS (E−) m/z: 472.2 (M+H).

Intermediate 481C: Tert-Butyl 4-(2-(2-cyclopropyl-5-fluoropyridin-4-yl)-3-isopropyl-1H-indol-5-yl) piperidine-1-carboxylate

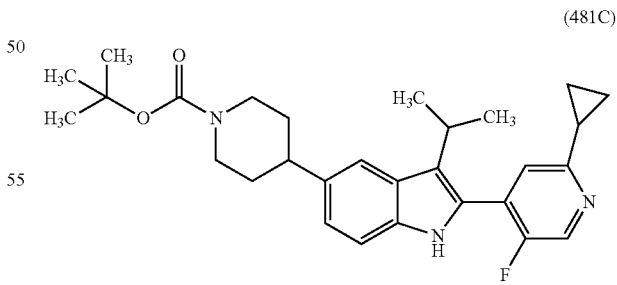

(481C)

Tert-butyl 4-(2-(2-cyclopropyl-5-fluoropyridin-4-yl)-3-isopropyl-1H-indol-5-yl) piperidine-1-carboxylate was prepared as described for Intermediate 478B, using tert-butyl 4-(2-(2-chloro-5-fluoropyridin-4-yl)-3-isopropyl-1H-indol-5-yl)piperidine-1-carboxylate as a starting intermediate (0.25 g, 83% yield). LCMS retention time 4.26 min [D]. MS (E−) m/z: 478.4 (M+H).

Intermediate 481

To a solution of tert-butyl 4-(2-(2-cyclopropyl-5-fluoropyridin-4-yl)-3-isopropyl-1H-indol-5-yl)piperidine-1-carboxylate (0.048 g, 0.100 mmol) in DCM (2 mL) was added 4M HCl in dioxane (3.05 µl, 0.100 mmol at room temperature. The mixture was stirred at same temperature for 1 h. The solution was concentrated to afford crude product. The crude sample was purified by prep LCMS to afford 2-(2-cyclopropyl-5-fluoropyridin-4-yl)-3-isopropyl-5-(piperidin-4-yl)-1H-indole (11.2 mg, 29.5% yield). LCMS retention time 1.63 min [E]. MS (E−) m/z: 378.3 (M+H).

Example 482

2-(2-ethyl-5-fluoropyridin-4-yl)-3-isopropyl-5-(piperidin-4-yl)-1H-indole

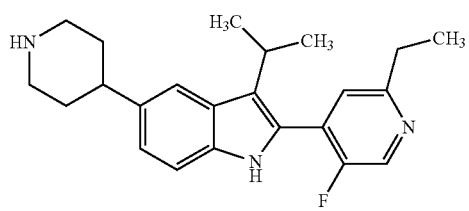

(482)

Intermediate 482A: Isopropyl 4-(2-(2-ethyl-5-fluoropyridin-4-yl)-3-isopropyl-1H-indol-5-yl)piperidine-1-carboxylate

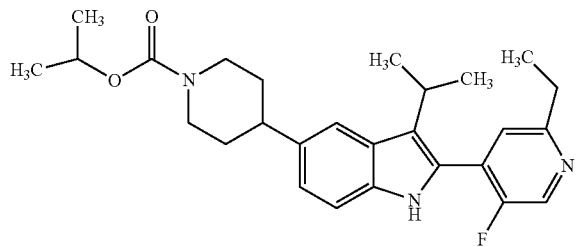

(482A)

Tert-butyl 4-(2-(2-ethyl-5-fluoropyridin-4-yl)-3-isopropyl-1H-indol-5-yl) piperidine-1-carboxylate was prepared as described for Intermediate 478B, using tert-butyl 4-(2-(2-chloro-5-fluoropyridin-4-yl)-3-isopropyl-1H-indol-5-yl) piperidine-1-carboxylate as a starting intermediate (0.09 g, 46% yield). LCMS retention time 4.07 min [D]. MS (E−) m/z: 466.5 (M+H).

Example 482

To a solution of tert-butyl 4-(2-(2-ethyl-5-fluoropyridin-4-yl)-3-isopropyl-1H-indol-5-yl)piperidine-1-carboxylate (0.048 g, 0.103 mmol) in DCM (2 mL) was added 4 M HCl in dioxane (3.13 µl, 0.103 mmol) at room temperature. The mixture was stirred at the same temperature for 1 h. The solution was concentrated to afford crude product. The crude sample was purified by prep LCMS to afford 2-(2-ethyl-5-fluoropyridin-4-yl)-3-isopropyl-5-(piperidin-4-yl)-1H-indole (1.8 mg, 4.78% yield). LCMS retention time 1.53 min [E]. MS (E−) m/z: 366.3 (M+H).

Example 483

2-(2-cyclopropylpyridin-4-yl)-3-isopropyl-5-(piperidin-4-yl)-1H-indole

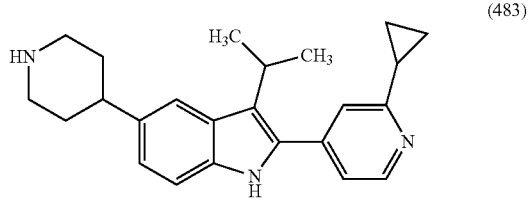 [SMILES: CC(C)c1c(-c2ccnc(C3CC3)c2)[nH]c2ccc(C3CCNCC3)cc12]

(483)

Intermediate 483A: Tert-Butyl 4-(2-(2-chloropyridin-4-yl)-3-isopropyl-1H-indol-5-yl) piperidine-1-carboxylate

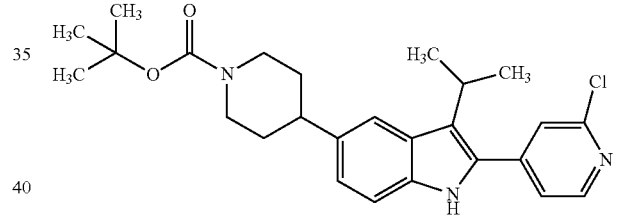

(483A)

To a mixture of tert-butyl 4-(2-bromo-3-isopropyl-1H-indol-5-yl)piperidine-1-carboxylate (0.3 g, 0.712 mmol), 2-chloro-4-(4,4,5,5-tetramethyl-1,3,2-dioxaborolan-2-yl)pyridine (0.188 g, 0.783 mmol) in a 25 ml round bottom flask were added THF (5 mL) followed by aqueous solution of sodium carbonate (0.189 g, 1.780 mmol). The resulting reaction mixture was degassed for 10 minutes with nitrogen. Next, $PdCl_2$(dppf)-$CH_2Cl_2$ adduct (0.015 g, 0.018 mmol) was added followed by the addition of 2-(di-tert-butylphosphino)biphenyl (2.125 mg, 7.12 µmol). The reaction mixture was degassed again for 5 min. The resulting reaction mixture was heated at 85° C. for 4 h. The reaction mixture was diluted with ethyl acetate (100 mL), poured into a separate funnel and was washed with water (2×50 mL), brine (50 mL), dried over sodium sulfate, and concentrated to afford crude product. The crude was purified using silica gel chromatography, eluting with 25% ethyl acetate in hexane, the fractions was collected and concentrated to tert-butyl 4-(2-(2-chloropyridin-4-yl)-3-isopropyl-1H-indol-5-yl) piperidine-1-carboxylate (0.23 g, 72% yield) as off white solid. LCMS retention time 1.21 min [G]. MS (E−) m/z: 456.5 (M+H).

Intermediate 483B: Tert-Butyl 4-(2-(2-cyclopropylpyridin-4-yl)-3-isopropyl-1H-indol-5-yl)piperidine-1-carboxylate

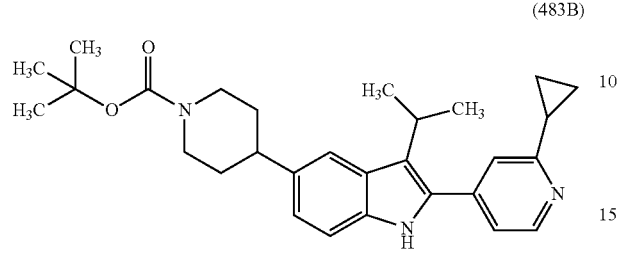

(483B)

Tert-butyl 4-(2-(2-cyclopropylpyridin-4-yl)-3-isopropyl-1H-indol-5-yl)piperidine-1-carboxylate was prepared as described for Intermediate 478B, using tert-butyl 4-(2-(2-chloropyridin-4-yl)-3-isopropyl-1H-indol-5-yl)piperidine-1-carboxylate as a starting intermediate (0.45 g, 89% yield). LCMS retention time 0.95 min [G]. MS (E−) m/z: 460.2 (M+H).

Example 483

To a solution of tert-butyl 4-(2-(2-cyclopropylpyridin-4-yl)-3-isopropyl-1H-indol-5-yl)piperidine-1-carboxylate (0.025 g, 0.054 mmol) in DCM (2 mL) was added 4 M HCl in dioxane (1.653 µl, 0.054 mmol) at room temperature. The reaction mixture was stirred at the same temperature for 1 h. The solution was concentrated to afford crude product. The crude sample was purified by prep LCMS to afford 2-(2-cyclopropylpyridin-4-yl)-3-isopropyl-5-(piperidin-4-yl)-1H-indole (6 mg, 30.5% yield). LCMS retention time 1.60 min [E]. MS (E−) m/z: 360.3 (M+H).

Example 484

2-(2-cyclopropylpyridin-4-yl)-3-isopropyl-5-(1-((2-methyl-1H-imidazol-4-yl)methyl) piperidin-4-yl)-1H-indole

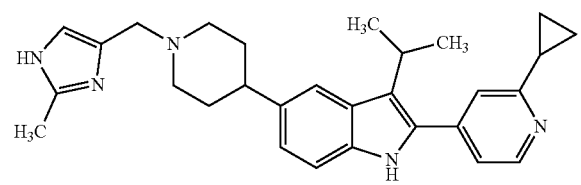

(484)

To a solution of 2-(2-cyclopropylpyridin-4-yl)-3-isopropyl-5-(piperidin-4-yl)-1H-indole (0.04 g, 0.111 mmol) and 2-methyl-1H-imidazole-4-carbaldehyde (0.012 g, 0.111 mmol) in methanol (4 mL) was added titanium(IV) isopropoxide (0.039 mL, 0.134 mmol) dropwise. The resulting light yellow solution was stirred under nitrogen at 25° C. for 4 h. Then sodium cyanoborohydride (8.39 mg, 0.134 mmol) was added. The reaction mixture was stirred at the same temperature for 12 h. The reaction mass was diluted with dichloromethane (10 mL). The reaction was quenched with water. The organic layer was dried over sodium sulfate and concentrated. The crude was purified by prep LCMS to provide 2-(2-cyclopropylpyridin-4-yl)-3-isopropyl-5-(1-((2-methyl-1H-imidazol-4-yl) methyl) piperidin-4-yl)-1H-indole (2.0 mg, 3.96%). LCMS retention time 1.66 min [E]. MS (E−) m/z: 454.3 (M+H).

Example 485

3-isopropyl-2-(2-methoxypyridin-4-yl)-5-(piperidin-4-yl)-1H-indole

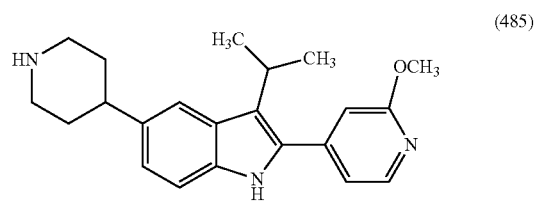 [SMILES: COc1cc(-c2[nH]c3ccc(C4CCNCC4)cc3c2C(C)C)ccn1]

(485)

Intermediate 485A: Tert-Butyl 4-(3-isopropyl-2-(2-methoxypyridin-4-yl)-1H-indol-5-yl) piperidine-1-carboxylate

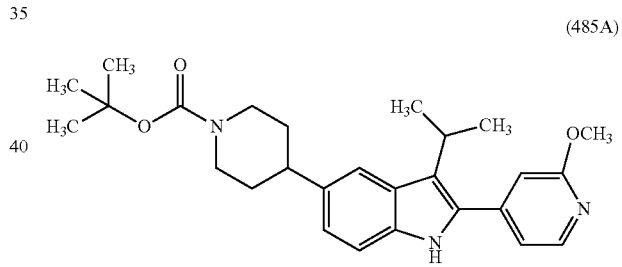

(485A)

Tert-butyl 4-(3-isopropyl-2-(2-methoxypyridin-4-yl)-1H-indol-5-yl)piperidine-1-carboxylate was prepared according to the general procedure described for Intermediate 1E, using tert-butyl 4-(2-bromo-3-isopropyl-1H-indol-5-yl)piperidine-1-carboxylate as a starting intermediate (0.25 g, 78% yield). LCMS retention time 1.59 min [B]. MS (E−) m/z: 450.1 (M+H).

Example 485

To a solution of tert-butyl 4-(3-isopropyl-2-(2-methoxypyridin-4-yl)-1H-indol-5-yl)piperidine-1-carboxylate (0.25 g, 0.556 mmol) in DCM (2 mL) was added 4 M HCl in dioxane (1.295 mL, 5.18 mmol) at room temperature. The mixture was stirred at same temperature for 1 h. The solution was concentrated to afford 3-isopropyl-2-(2-methoxypyridin-4-yl)-5-(piperidin-4-yl)-1H-indole, HCl (0.19 g, 85% yield). LCMS retention time 2.54 min [D]. MS (E−) m/z: 350.4 (M+H).

Example 486

2-(2-cyclopropyl-6-methoxypyridin-4-yl)-3-isopropyl-5-(piperidin-4-yl)-1H-indole

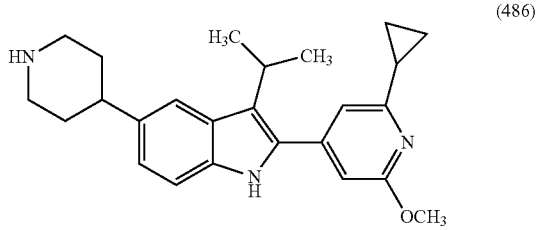 [SMILES: COc1cc(-c2[nH]c3ccc(C4CCNCC4)cc3c2C(C)C)cc(C2CC2)n1]

(486)

Intermediate 486A: Tert-Butyl 4-(2-(2-chloro-6-methoxypyridin-4-yl)-3-isopropyl-1H-indol-5-yl)piperidine-1-carboxylate

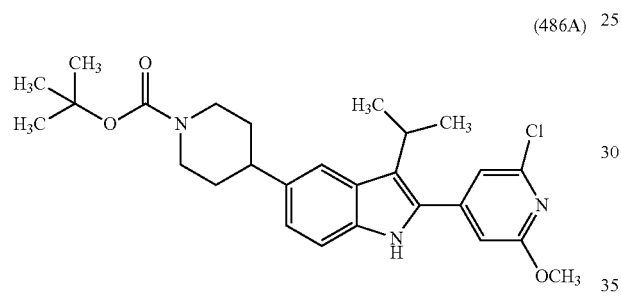

(486A)

Tert-butyl 4-(2-(2-chloro-6-methoxypyridin-4-yl)-3-isopropyl-1H-indol-5-yl) piperidine-1-carboxylate was prepared according to the general procedure described in Example 1 using tert-butyl 4-(2-bromo-3-isopropyl-1H-indol-5-yl)piperidine-1-carboxylate (0.5 g, 1.187 mmol) as a starting intermediate (0.4 g, 70% yield). LCMS retention time 4.31 min [D]. MS (E−) m/z: 484.2 (M+H).

Intermediate 486B: Tert-Butyl 4-(2-(2-cyclopropyl-6-methoxypyridin-4-yl)-3-isopropyl-1H-indol-5-yl)piperidine-1-carboxylate

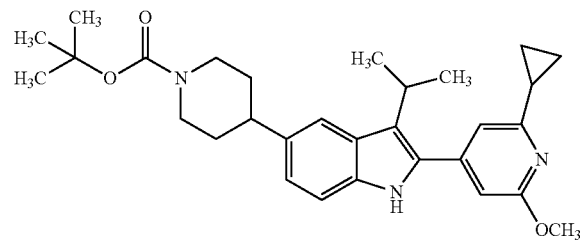

(486B)

Tert-butyl 4-(2-(2-cyclopropyl-6-methoxypyridin-4-yl)-3-isopropyl-1H-indol-5-yl)piperidine-1-carboxylate was prepared as described for Intermediate 478B, using tert-butyl 4-(2-(2-chloro-6-methoxypyridin-4-yl)-3-isopropyl-1H-indol-5-yl)piperidine-1-carboxylate as a starting intermediate (0.048 g, 95% yield). LCMS retention time 1.35 min [G]. MS (E−) m/z: 490.6 (M+H).

Example 486

To a solution of tert-butyl 4-(2-(2-cyclopropyl-6-methoxypyridin-4-yl)-3-isopropyl-1H-indol-5-yl)piperidine-1-carboxylate (0.048 g, 0.098 mmol) in DCM (2 mL) was added hydrochloric acid 4 M in dioxane (2.98 µl, 0.098 mmol) at room temperature. The mixture was stirred at same temperature for 1 h. The solution was concentrated to afford crude product. The crude sample was purified by prep LCMS to afford 2-(2-cyclopropyl-6-methoxypyridin-4-yl)-3-isopropyl-5-(piperidin-4-yl)-1H-indole (12 mg, 33.5% yield). LCMS retention time 1.92 min [E]. MS (E−) m/z: 390.2 (M+H).

Example 487

2-(2-ethyl-6-methoxypyridin-4-yl)-3-isopropyl-5-(piperidin-4-yl)-1H-indole

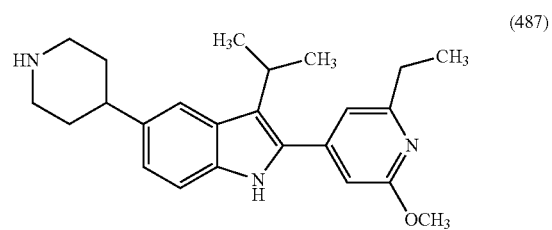 [SMILES: CCc1cc(-c2[nH]c3ccc(C4CCNCC4)cc3c2C(C)C)cc(OC)n1]

(487)

Intermediate 487A: Tert-Butyl 4-(2-(2-ethyl-6-methoxypyridin-4-yl)-3-isopropyl-1H-indol-5-yl)piperidine-1-carboxylate

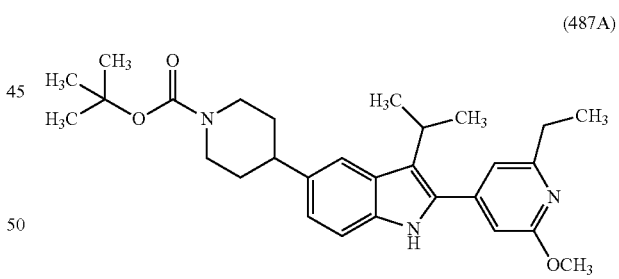

(487A)

Tert-butyl 4-(2-(2-ethyl-6-methoxypyridin-4-yl)-3-isopropyl-1H-indol-5-yl) piperidine-1-carboxylate was prepared as described for Intermediate 478B, using tert-butyl 4-(2-(2-chloro-6-methoxypyridin-4-yl)-3-isopropyl-1H-indol-5-yl)piperidine-1-carboxylate as a starting intermediate (0.052 g, 88% yield). LCMS retention time 1.25 min [G]. MS (E−) m/z: 478.6 (M+H).

Example 487

To a solution of tert-butyl 4-(2-(2-ethyl-6-methoxypyridin-4-yl)-3-isopropyl-1H-indol-5-yl)piperidine-1-carboxylate (0.052 g, 0.109 mmol) in DCM (2 mL) was added hydrochloric acid 4 M in dioxane (3.31 µl, 0.109 mmol) at room temperature. The mixture was stirred at same temperature for 1 h. The solution was concentrated to afford crude product. The crude sample was purified by prep LCMS to afford 2-(2-ethyl-6-methoxypyridin-4-yl)-3-isopropyl-5-(piperidin-4-yl)-1H-indole (12.7 mg, 30.9% yield). LCMS retention time 1.84 min [E]. MS (E−) m/z: 378.3 (M+H).

Examples 488A and 488B 4-(2-(2,6-dimethylpyridin-4-yl)-3-isopropyl-1H-indol-5-yl)piperidin-3-ol

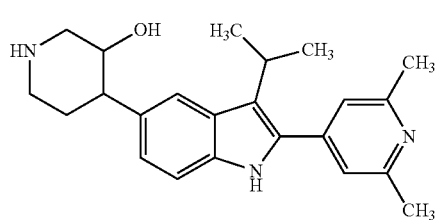

(488)

Intermediate 488A: 5-bromo-2-(2,6-dimethylpyridin-4-yl)-3-isopropyl-1H-indole

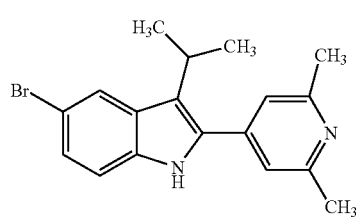

(488A)

5-bromo-2-(2,6-dimethylpyridin-4-yl)-3-isopropyl-1H-indole was prepared according to the procedure described in Intermediate 1F using 5-bromo-2-iodo-3-isopropyl-1H-indole as the starting intermediate (0.7 g, 74% yield). LCMS retention time min 1.29, [B]. MS (E−) m/z: 356.1 (M+H).

Intermediate 488B: Tert-Butyl 5-bromo-2-(2,6-dimethylpyridin-4-yl)-3-isopropyl-1H-indole-1-carboxylate

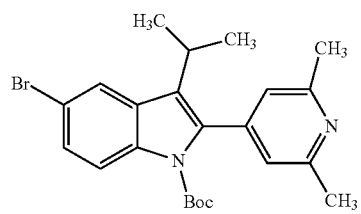

(488B)

To a solution of 5-bromo-2-(2,6-dimethylpyridin-4-yl)-3-isopropyl-1H-indole (1.5 g, 4.37 mmol) in THF (20 ml) were added DMAP (0.534 g, 4.37 mmol) followed by BOC anhydride (1.015 ml, 4.37 mmol). The resulting brown colored solution was stirred at 25° C. for 14 hours. The reaction mass was concentrated under vacuum to afford crude product. The crude product was purified using silica gel chromatography eluting with 70% EtOAc in hexane, the fractions were collected and concentrated to afford tert-butyl 5-bromo-2-(2,6-dimethylpyridin-4-yl)-3-isopropyl-1H-indole-1-carboxylate. Yield (1.1 g, 55.1%). LCMS retention time min 4.41[D]. MS (E−) m/z: 445.0 (M+H).

Intermediate 488C: Tert-Butyl 5-(1-(tert-butoxycarbonyl)-1,2,3,6-tetrahydropyridin-4-yl)-2-(2,6-dimethylpyridin-4-yl)-3-isopropyl-1H-indole-1-carboxylate

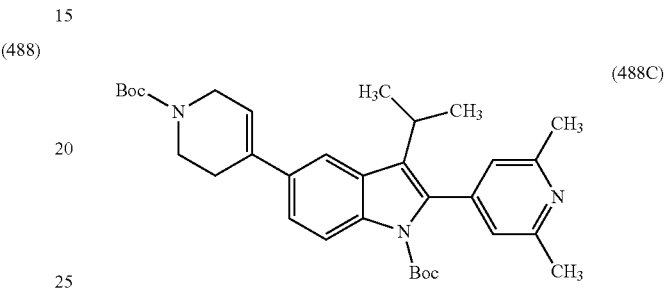

(488C)

Tert-butyl 5-(1-(tert-butoxycarbonyl)-1,2,3,6-tetrahydropyridin-4-yl)-2-(2,6-dimethylpyridin-4-yl)-3-isopropyl-1H-indole-1-carboxylate was prepared according to the procedure described in Intermediate 1F using tert-butyl 5-bromo-2-(2,6-dimethylpyridin-4-yl)-3-isopropyl-1H-indole-1-carboxylate as the starting intermediate (1.3 g, 70.4% yield). LCMS retention time min 4.50 [D]. MS (E−) m/z: 546.1 (M+H).

Intermediate 488D: Tert-Butyl 5-(1-(tert-butoxycarbonyl)-3-hydroxypiperidin-4-yl)-2-(2,6-dimethylpyridin-4-yl)-3-isopropyl-1H-indole-1-carboxylate

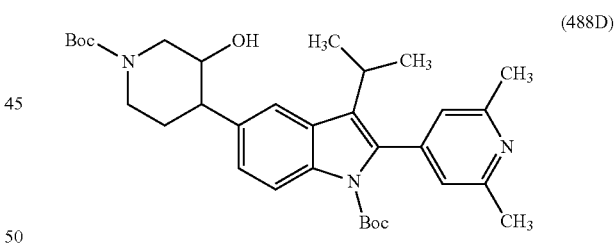

(488D)

Borane-methyl sulfide complex (1.305 ml, 13.74 mmol) was added to a solution of tert-butyl 5-(1-(tert-butoxycarbonyl)-1,2,3,6-tetrahydropyridin-4-yl)-2-(2,6-dimethylpyridin-4-yl)-3-isopropyl-1H-indole-1-carboxylate (1.5 g, 2.75 mmol) in THF (20 ml) at 0° C. The mixture was stirred at the same temperature for 3 h. After complete addition of the starting material, hydrogen peroxide (2.5 ml, 82 mmol) was added drop wise at −10° C. Effervescence were observed during the hydrogen peroxide addition. Next sodium hydroxide (2.5 mL, 2.75 mmol) was added drop wise. The reaction mixture was stirred at room temperature for 10 h. The reaction mass was diluted with ethyl acetate, the organic layer was separated, dried and concentrated to afford crude compound. The crude material was purified by ISCO, using 12 g silica column, the compound was eluted with 80% ethylacetate in hexane, the fractions was collected and concentrated to afford a diastereomeric mixture of tert-butyl 5-(1-(tert-butoxycarbonyl)-3-hydroxypiperidin-4-yl)-2-(2,6-dimethylpyridin-4-yl)-3-isopropyl-1H-indole-1-carboxylate, Yield (1.1 g, 71%). LCMS retention time min 3.93[D]. MS (E−) m/z: 564.4 (M+H).

Examples 488-A and 488-B

Tert-butyl 5-(1-(tert-butoxycarbonyl)-3-hydroxypiperidin-4-yl)-2-(2,6-dimethylpyridin-4-yl)-3-isopropyl-1H-indole-1-carboxylate (0.2 g, 0.355 mmol) was dissolved in DCM (2 mL) to make a solution. Next, 4 M hydrochloric acid in dioxane (5.0 mL, 0.105 mmol) was added to the solution. The reaction mixture was stirred at 25° C. for 60 minutes. The solvent was removed under vacuum and the yellow colored HCl salt obtained was purified by Reverse phase prep HPLC. The collected fractions were concentrated and for the racemic mixtures of diastereomers were separated chromatographically.

Example 488-A: Isomer 1: 4-(2-(2,6-dimethylpyridin-4-yl)-3-isopropyl-1H-indol-5-yl)piperidin-3-ol; (Yield: 27 mg, 20.73%). LCMS retention time 0.91 min [E]. MS (E−) m/z: 364.23 (M+H).

Example 488-B: Isomer 2: 4-(2-(2,6-dimethylpyridin-4-yl)-3-isopropyl-1H-indol-5-yl)piperidin-3-ol; (Yield: 19.3 mg, 14.82%). LCMS retention time 1.01 min [E]. MS (E−) m/z: 364.23 (M+H).

Examples 489A and Example 489B 5-(3,3-difluoropiperidin-4-yl)-2-(2,6-dimethylpyridin-4-yl)-3-isopropyl-1H-indole

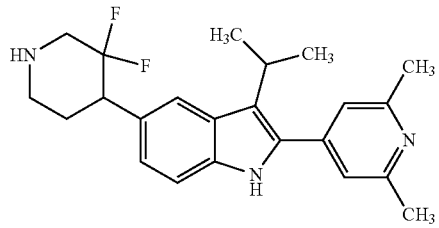

(489)

Intermediate 489A: Tert-Butyl 5-(1-(tert-butoxycarbonyl)-3-oxopiperidin-4-yl)-2-(2,6-dimethylpyridin-4-yl)-3-isopropyl-1H-indole-1-carboxylate

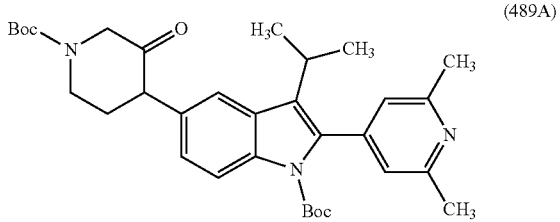 [SMILES: Cc1cc(-c2c(C(C)C)c3cc(C4CCN(C(=O)OC(C)(C)C)CC4=O)ccc3n2C(=O)OC(C)(C)C)cc(C)n1]

(489A)

To a solution of tert-butyl 5-(1-(tert-butoxycarbonyl)-3-hydroxypiperidin-4-yl)-2-(2,6-dimethylpyridin-4-yl)-3-isopropyl-1H-indole-1-carboxylate (1 g, 1.774 mmol) in DCM (15 mL) was added Dess-Martin Periodinane (1.505 g, 3.55 mmol) at 0° C. The mixture was stirred at the same temperature for 3 h. The reaction mixture was diluted with ethyl acetate (250 mL), poured into a separate funnel and washed with water (2×50 mL), brine (50 mL), dried over sodium sulfate, and concentrated to afford crude product. The crude product was purified using silica gel chromatography, eluting with 80% ethyl acetate in hexane, the fractions was collected and concentrated to afford tert-butyl 5-(1-(tert-butoxycarbonyl)-3-oxopiperidin-4-yl)-2-(2,6-dimethylpyridin-4-yl)-3-isopropyl-1H-indole-1-carboxylate (650 mg, 65.2%). LCMS retention time min [4.20]. MS (E−) m/z: 562.2 (M+H).

Intermediate 489B: Tert-Butyl 5-(1-(tert-butoxycarbonyl)-3,3-difluoropiperidin-4-yl)-2-(2,6-dimethylpyridin-4-yl)-3-isopropyl-1H-indole-1-carboxylate

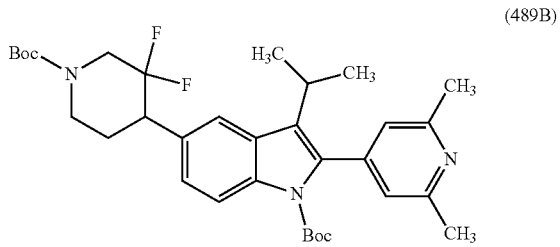 [SMILES: Cc1cc(-c2c(C(C)C)c3cc(C4CCN(C(=O)OC(C)(C)C)CC4(F)F)ccc3n2C(=O)OC(C)(C)C)cc(C)n1]

(489B)

DAST (0.480 mL, 3.63 mmol) was added to a solution of tert-butyl 5-(1-(tert-butoxycarbonyl)-3-oxopiperidin-4-yl)-2-(2,6-dimethylpyridin-4-yl)-3-isopropyl-1H-indole-1-carboxylate (0.68 g, 1.211 mmol) in DCM (15 mL) at 0° C. The mixture was stirred at room temperature for 3 h. The reaction was quenched with ice-cold water. The mixture was extracted with dichloromethane, dried over sodium sulfate, filtered and concentrated to afford tert-butyl 5-(1-(tert-butoxycarbonyl)-3,3-difluoropiperidin-4-yl)-2-(2,6-dimethylpyridin-4-yl)-3-isopropyl-1H-indole-1-carboxylate (450 mg, 63.7%). LCMS retention time min 4.37 [D]. MS (E−) m/z: 584.2 (M+H).

Examples 489-A and 489-B

Tert-butyl 5-(1-(tert-butoxycarbonyl)-3,3-difluoropiperidin-4-yl)-2-(2,6-dimethylpyridin-4-yl)-3-isopropyl-1H-indole-1-carboxylate (0.56 g, 0.959 mmol) was dissolved in DCM (2 mL) to make a solution. Next, 4 M hydrochloric acid in dioxane (5.0 mL, 20 mmol) was added to the solution. The reaction mixture was stirred at 25° C. for 60 minutes. The solvent was removed under vacuum and the resulting yellow colored HCl salt was purified by SFC. The collected fractions were concentrated and diethyl amine impurities were removed by passing through Chiralpak IC (4.6×250) mm column by SFC. The fractions collected from SFC were concentrated and lyophilized using Acetonitrile:water to afford an off white solid.

Example 489A: Isomer 1: (100 mg, 26%). LCMS retention time 1.91 min [E]. MS (E−) m/z: 384.3 (M+H).

Example 489B: Isomer 2: (100 mg, 26%). LCMS retention time 1.91 min [E]. MS (E−) m/z: 384.3 (M+H).

Example 490

4-(3-isopropyl-2-(2-methylpyridin-4-yl)-1H-indol-5-yl)piperidin-2-one

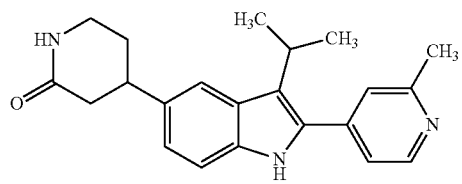
(490)

Intermediate 490A: Tert-Butyl 4-(3-isopropyl-2-(2-methylpyridin-4-yl)-1H-indol-5-yl)-6-oxo-3,6-dihydropyridine-1 (2H)-carboxylate

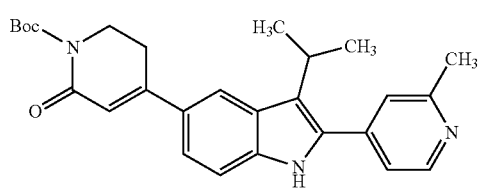
(490A)

Tert-butyl 4-(3-isopropyl-2-(2-methylpyridin-4-yl)-1H-indol-5-yl)-2-oxo-5,6-dihydropyridine-1(2H)-carboxylate was prepared according to the procedure described in Intermediate 1B using 3-isopropyl-2-(2-methylpyridin-4-yl)-5-(4,4,5,5-tetramethyl-1,3,2-dioxaborolan-2-yl)-1H-indole as the starting intermediate (0.4 g, 84% yield). LCMS retention time 1.14 min [B]. MS (E−) m/z: 445 (M+H).

Example 490

A solution of tert-butyl 4-(3-isopropyl-2-(2-methylpyridin-4-yl)-1H-indol-5-yl)-2-oxo-5,6-dihydropyridine-1(2H)-carboxylate (300 mg, 0.673 mmol) in methanol (50 mL) was purged with nitrogen ($N_2$). Next Palladium on carbon (71.7 mg, 0.673 mmol) was added and the solution was purged with $N_2$ three times. Hydrogen gas ($H_2$) was introduced via a balloon to the mixture and the mixture was stirred at room temperature for 16 h. The suspension was filtered through celite, the filtrate was collected, and concentrated to afford crude compound. The crude material was purified via preparative LCMS, the fractions containing the desired product were combined and dried using a Genevac centrifugal evaporator to afford (4-(3-isopropyl-2-(2-methylpyridin-4-yl)-1H-indol-5-yl)piperidin-2-one). LCMS retention time 1.6 min [E]. MS (E−) m/z: 348.2 (M+H).

Examples 491A and 491B 4-(3-ethyl-5-(3-fluoropiperidin-4-yl)-1H-indol-2-yl)pyridin-2-amine

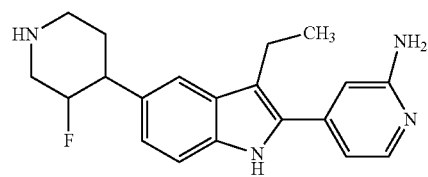
(491)

Intermediate 491A: Tert-Butyl 2-(2-aminopyridin-4-yl)-5-chloro-3-ethyl-1H-indole-1-carboxylate

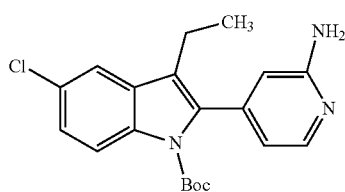
(491A)

Tert-butyl 2-(2-aminopyridin-4-yl)-5-chloro-3-ethyl-1H-indole-1-carboxylate was prepared according to the general procedure described in Intermediate 1B using tert-butyl 2-bromo-5-chloro-3-ethyl-1H-indole-1-carboxylate as the starting intermediate (0.7 g, 58.3% yield). LC retention time 3.89 min [D]. MS (E−) m/z: 587.0 (M+H).

Intermediate 491B: Tert-Butyl 2-(2-((tert-butoxycarbonyl)amino)pyridin-4-yl)-5-chloro-3-ethyl-1H-indole-1-carboxylate

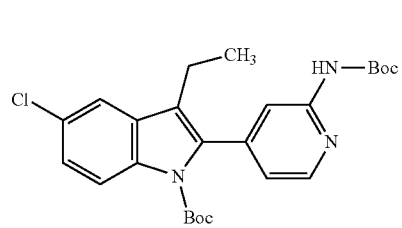
(491B)

Tert-butyl 2-(2-((tert-butoxycarbonyl)amino)pyridin-4-yl)-5-chloro-3-ethyl-1H-indole-1-carboxylate was prepared according to the general procedure described in Intermediate 488B using tert-butyl 2-(2-aminopyridin-4-yl)-5-chloro-3-ethyl-1H-indole-1-carboxylate as the starting intermediate (0.075 g, 60% yield). LC retention time 4.03 min [D]. MS (E−) m/z: 472.2 (M+H).

Intermediate 491C: Tert-Butyl 5-(1-(tert-butoxycarbonyl)-1,2,3,6-tetrahydropyridin-4-yl)-2-(2-((tert-butoxycarbonyl)amino)pyridin-4-yl)-3-ethyl-1H-indole-1-carboxylate

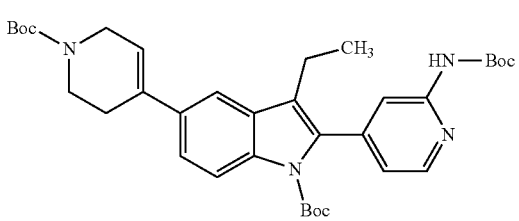
(491C)

To a solution of tert-butyl 2-(2-((tert-butoxycarbonyl)amino)pyridin-4-yl)-5-chloro-3-ethyl-1H-indole-1-carboxylate (0.3 g, 0.636 mmol) and tert-butyl 4-(4,4,5,5-tetramethyl-1,3,2-dioxaborolan-2-yl)-5,6-dihydropyridine-1(2H)-carboxylate (0.275 g, 0.890 mmol) in dioxane (10 mL) were added water (2.500 mL) and potassium carbonate (0.193 g, 1.398 mmol). The mixture was degassed for 10 minutes with nitrogen, then $2^{nd}$ Generation XPHOS precatalyst (0.050 g, 0.064 mmol) was added. The reaction mixture was degassed again for 5 min. The resulting reaction mixture was heated at 85° C. for 12 h. The reaction mixture was diluted with ethyl acetate (100 mL), poured into a separate funnel and was washed with water (2×50 mL), brine (50 mL), dried over sodium sulfate, and concentrated to afford crude product. The crude product was purified using silica gel chromatography, eluting with 40% ethyl acetate in hexane, the fractions was collected and concentrated to afford tert-butyl 5-(1-(tert-butoxycarbonyl)-1,2,3,6-tetrahydropyridin-4-yl)-2-(2-((tert-butoxycarbonyl)amino)pyridin-4-yl)-3-ethyl-1H-indole-1-carboxylate (0.2 g, 59.9%). LCMS retention time min 4.50 [D], m/z: 519.2 (M+H-Boc).

Intermediate 491D: Tert-Butyl 5-(1-(tert-butoxycarbonyl)-3-hydroxypiperidin-4-yl)-2-(2-((tert-butoxycarbonyl)amino)pyridin-4-yl)-3-ethyl-1H-indole-1-carboxylate

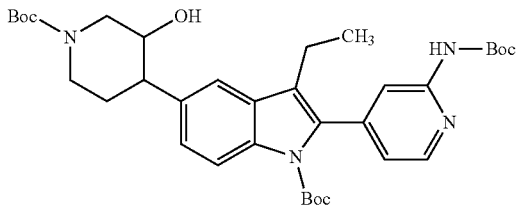

Tert-butyl 5-(1-(tert-butoxycarbonyl)-3-hydroxypiperidin-4-yl)-2-(2-((tert-butoxycarbonyl)amino)pyridin-4-yl)-3-ethyl-1H-indole-1-carboxylate was prepared according to the general procedure described in Intermediate 488D using tert-butyl 5-(1-(tert-butoxycarbonyl)-1,2,3,6-tetrahydropyridin-4-yl)-2-(2-((tert-butoxycarbonyl)amino) pyridin-4-yl)-3-ethyl-1H-indole-1-carboxylate (0.25 g, 81% yield). LCMS retention time 4.20 min [D]. MS (E−) m/z: 637.4 (M+H).

Intermediate 491E: Tert-Butyl 5-(1-(tert-butoxycarbonyl)-3-fluoropiperidin-4-yl)-2-(2-((tert-butoxycarbonyl)amino)pyridin-4-yl)-3-ethyl-1H-indole-1-carboxylate

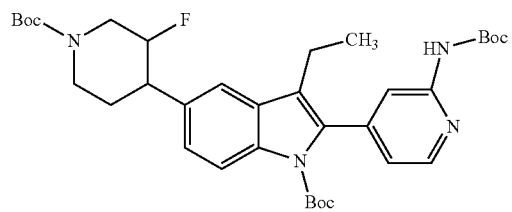

To a solution of tert-butyl 5-(1-(tert-butoxycarbonyl)-3-hydroxypiperidin-4-yl)-2-(2-((tert-butoxycarbonyl)amino) pyridin-4-yl)-3-ethyl-1H-indole-1-carboxylate (0.1 g, 0.157 mmol) in DCM (5 mL) was added DAST (0.062 mL, 0.471 mmol) at −40° C. The resulting reaction mixture was stirred at 25° C. for 12 h. The reaction mass was quenched with ice cold water and concentrated to afford tert-butyl 5-(1-(tert-butoxycarbonyl)-3-fluoropiperidin-4-yl)-2-(2-((tert-butoxycarbonyl)amino)pyridin-4-yl)-3-ethyl-1H-indole-1-carboxylate (80 mg, 80%). As the product was not stable in the column, the crude material was taken for the next step without further purification. LCMS retention time min 1.97 [D]. M/z: 639.2 (M−H).

Examples 491A and 491B

Tert-butyl 5-(1-(tert-butoxycarbonyl)-3-fluoropiperidin-4-yl)-2-(2-((tert-butoxycarbonyl)amino)pyridin-4-yl)-3-ethyl-1H-indole-1-carboxylate (0.1 g, 0.157 mmol) was dissolved in DCM (2 mL) to make a solution. Next, 4 M hydrochloric acid in dioxane (5 mL) was added to the reaction solution. The reaction mixture was stirred at 25° C. for 60 minutes. The solvent was removed under vacuum and the crude material was purified by SFC. The collected fractions were concentrated. The diethyl amine impurities were removed by silica gel chromatography, which also afforded separate isomers.

Example 491A Isomer 1: (3 mg, 5.6%); LCMS retention time 1.12 min [E]. MS (E−) m/z: 339.3 (M+H).

Example 491B Isomer 2: (3 mg, 5.6%). LCMS retention time 1.24 min [E]. MS (E−) m/z: 339.3 (M+H).

Example 492

3-(2,2-difluoroethyl)-2-(2,6-dimethylpyridin-4-yl)-5-(piperidin-4-yl)-1H-indole

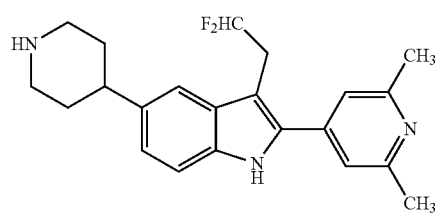

Intermediate 492A: 5-bromo-1-tosyl-1H-indole

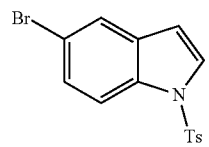

To a stirred solution of 5-bromo-1H-indole (5.0 g, 25.5 mmol), TsCl (6.03 g, 31.6 mmol) and tetrabutylammonium hydrogen sulfate (0.63 g, 1.855 mmol) in toluene (100 mL) was added NaOH (50% solution in water, 10.20 g, 255 mmol) drop wise. The reaction mixture was stirred at room temperature for 16 h. The reaction was quenched with water (20 mL). The two layers were separated. The aqueous layer was extracted with EtOAc (2×50 mL), the combined organic extracts was dried (Na$_2$SO$_4$) and concentrated to afford crude material. The crude material was purified by ISCO using 40 g silica column, compound was eluted in 4% EA in hexanes, the fractions was collected and concentrated to afford 5-bromo-1-tosyl-1H-indole (7.1 g, 20.27 mmol) as white solid. LC retention time=2.23 min [A]. MS (E−) m/z: 393.3 (M−H).

Intermediate 492B: 1-(5-bromo-1-tosyl-1H-indol-3-yl)-2,2-difluoroethan-1-one

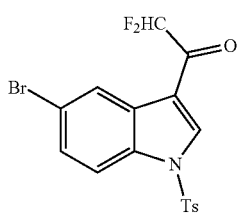

To a suspension of AlCl₃ (6.85 g, 51.4 mmol) in DCM (50 mL) was added difluoroacetic anhydride (4.47 g, 25.7 mmol). The mixture was stirred for 15 min. followed by the addition of a solution of 5-bromo-1-tosyl-1H-indole (3 g, 8.57 mmol) in DCM (30 mL). The reaction mixture was stirred for 1 h at ambient temperature. The reaction was quenched with ice-water. The reaction mixture was extracted with DCM (2×50 mL). The combined extracts was washed with aqueous NaHCO₃, brine, dried over MgSO₄, filtered and concentrated to afford crude product. The crude product was purified by ISCO using silica column. The compound was eluted in 10% EtOAc in hexane, the fraction was collected and concentrated to afford 1-(5-bromo-1-tosyl-1H-indol-3-yl)-2,2-difluoroethanone (2.21 g, 4.1 mmol) as a crystalline solid. LC retention time=2.732 min [A]. MS (E−) m/z: 428.0 (M+H).

Intermediate 492C: 1-(5-bromo-1H-indol-3-yl)-2,2-difluoroethan-1-one

To a solution of 1-(5-bromo-1-tosyl-1H-indol-3-yl)-2,2-difluoroethanone (0.2 g, 0.467 mmol) in THF (4 mL) and MeOH (4.00 mL) was added Cs₂CO₃ (0.45 g, 1.381 mmol) at room temperature. The reaction mixture was stirred at the same temperature for 12 h. The reaction mixture was concentrated, the residue was diluted with minimum amount of water and undissolved solids was filtered and dried under vacuum to afford 1-(5-bromo-1H-indol-3-yl)-2,2-difluoroethanone (105 mg, 0.244 mmol) as a white solid. LC retention time=2.233 min [A]. MS (E−) m/z: 276 (M+2H).

Intermediate 492D: 5-bromo-3-(2,2-difluoroethyl)-1H-indole

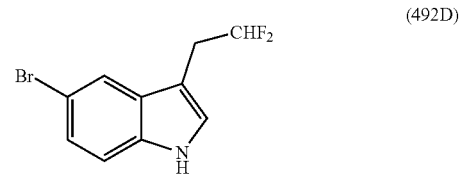 [SMILES: FC(F)Cc1c[nH]c2ccc(Br)cc12]

To the stirred solution of 1-(5-bromo-1H-indol-3-yl)-2,2-difluoroethanone (0.25 g, 0.912 mmol) in THF (10 mL) was added BH₃DMS (1.368 mL, 2.74 mmol) at 0° C. under nitrogen. The mixture was stirred at 80° C. for 20 h. The reaction was quenched with water (2 ml) at 0° C. The reaction mixture was diluted with ethyl acetate (100 ml), washed with sodium bicarbonate (2×25 ml) and water (2×25 ml). The combined organic extracts was dried over anhydrous sodium sulphate, filtered and concentrated to afford crude compound. The crude material was purified on ISCO by using 24 g silica gel column, and the compound was eluted at 8% ethyl acetate/hexane, the fractions was collected and concentrated to afford 5-bromo-3-(2,2-difluoroethyl)-1H-indole (120 mg, 0.438 mmol) as an oil. LC retention time=2.802 min [D]. MS (E−) m/z: 260 (M+H).

Intermediate 492E: Tert-Butyl 4-(3-(2,2-difluoroethyl)-1H-indol-5-yl)-3,6-dihydropyridine-1(2H)-carboxylate

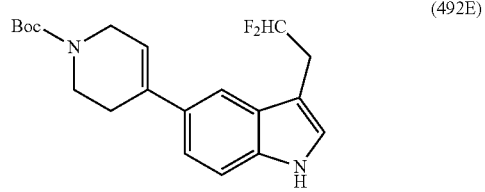

Tert-butyl 4-(3-(2,2-difluoroethyl)-1H-indol-5-yl)-5,6-dihydropyridine-1(2H)-carboxylate was prepared according to the general procedure described in Intermediate 1B using 5-bromo-3-(2,2-difluoroethyl)-1H-indole as the starting intermediate (0.14 g, 80% yield). LC retention time 3.075 min [D]. MS (E−) m/z: 361.2 (M−H).

Intermediate 492F: Tert-Butyl 4-(3-(2,2-difluoroethyl)-1H-indol-5-yl)piperidine-1-carboxylate

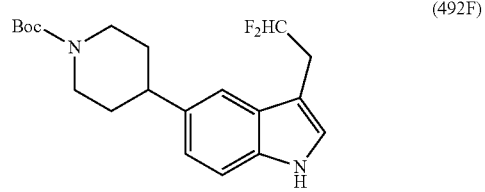 [SMILES: CC(C)(C)OC(=O)N1CC=C(c2ccc3[nH]cc(CC(F)F)c3c2)CC1]

Tert-butyl 4-(3-(2,2-difluoroethyl)-1H-indol-5-yl)piperidine-1-carboxylate was prepared as described in Intermediate 1C using tert-butyl 4-(3-(2,2-difluoroethyl)-1H-indol-5-yl)-5,6-dihydropyridine-1(2H)-carboxylate as the starting intermediate (0.9 g, 88% yield). LC retention time 3.282 min [D]. MS (E−) m/z: 265.0 (M+H-Boc).

Intermediate 492G: Tert-Butyl 4-(2-bromo-3-(2,2-difluoroethyl)-1H-indol-5-yl)piperidine-1-carboxylate

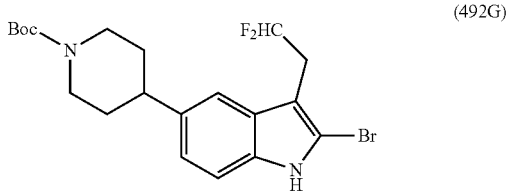 [SMILES: CC(C)(C)OC(=O)N1CCC(c2ccc3[nH]c(Br)c(CC(F)F)c3c2)CC1]

(492G)

Tert-butyl 4-(2-bromo-3-(2,2-difluoroethyl)-1H-indol-5-yl)piperidine-1-carboxylate was prepared as described in Intermediate 1D for tert-butyl 4-(2-bromo-3-(2,2-difluoroethyl)-1H-indol-5-yl)piperidine-1-carboxylate using tert-butyl 4-(3-(2,2-difluoroethyl)-1H-indol-5-yl)piperidine-1-carboxylate as the starting intermediate (0.3 g, 52% yield). LC retention time 1.10 min [G]. MS (E−) m/z: 389.0 (M+2H-tBu).

Intermediate 492H: Tert-Butyl 4-(3-(2,2-difluoroethyl)-2-(4,4,5,5-tetramethyl-1,3,2-dioxaborolan-2-yl)-1H-indol-5-yl)piperidine-1-carboxylate

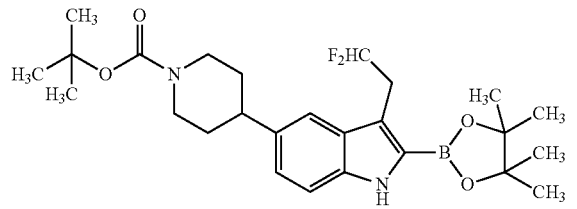

(492H)

Tert-butyl 4-(3-(2,2-difluoroethyl)-2-(4,4,5,5-tetramethyl-1,3,2-dioxaborolan-2-yl)-1H-indol-5-yl)piperidine-1-carboxylate was prepared as described in Intermediate 1E using tert-butyl 4-(2-bromo-3-(2,2-difluoroethyl)-1H-indol-5-yl)piperidine-1-carboxylate as the starting intermediate (0.3 g, 55% yield). LC retention time 1.61 min [B]. MS (E−) m/z: 435.4 (M+H-tBu).

Intermediate 492I: Tert-Butyl 4-(3-(2,2-difluoroethyl)-2-(2,6-dimethylpyridin-4-yl)-1H-indol-5-yl)piperidine-1-carboxylate

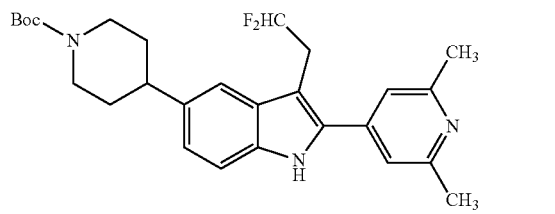

(492I)

Tert-butyl 4-(3-(2,2-difluoroethyl)-2-(2,6-dimethylpyridin-4-yl)-1H-indol-5-yl) piperidine-1-carboxylate was prepared as described in Intermediate 1F using tert-butyl 4-(3-isopropyl-2-(4,4,5,5-tetramethyl-1,3,2-dioxaborolan-2-yl)-1H-indol-5-yl)piperidine-1-carboxylate as the starting intermediate (0.65 g, 67.9% yield). LC retention time 1.37 min [B]. MS (E−) m/z: 470.5 (M+H).

Example 492

3-(2,2-difluoroethyl)-2-(2,6-dimethylpyridin-4-yl)-5-(piperidin-4-yl)-1H-indole was prepared as described in Example 1 using tert-butyl 4-(3-(2,2-difluoroethyl)-2-(2,6-dimethylpyridin-4-yl)-1H-indol-5-yl)piperidine-1-carboxylate as the starting intermediate (0.5 g, 89% yield). LC retention time=2.08 min [D]. MS (E−) m/z: 370.4 (M+H).

Example 493

2-(4-(3-(2,2-difluoroethyl)-2-(2,6-dimethylpyridin-4-yl)-1H-indol-5-yl)piperidin-1-yl)-N,N-dimethylpropanamide

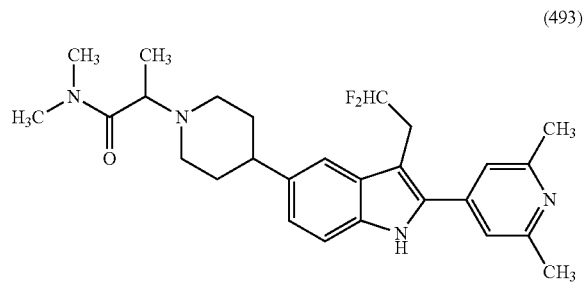

(493)

Intermediate 493A: ethyl 2-(4-(3-(2,2-difluoroethyl)-2-(2,6-dimethylpyridin-4-yl)-1H-indol-5-yl)piperidin-1-yl)propanoate

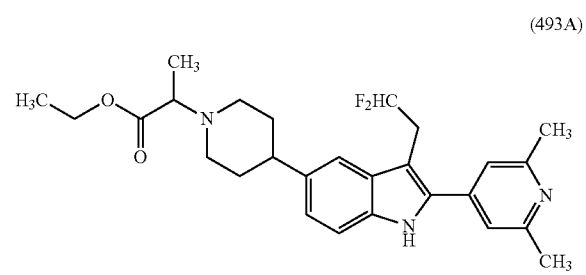 [SMILES: CCOC(=O)C(C)N1CCC(c2ccc3[nH]c(-c4cc(C)nc(C)c4)c(CC(F)F)c3c2)CC1]

(493A)

To a solution of 3-(2,2-difluoroethyl)-2-(2,6-dimethylpyridin-4-yl)-5-(piperidin-4-yl)-1H-indole hydrochloride (0.060 g, 0.148 mmol) in DMF (1 mL) and THF (1.5 mL) were added TEA (0.082 mL, 0.591 mmol) and ethyl 2-bromopropanoate (0.032 g, 0.177 mmol) at room temperature. The mixture was stirred at same temperature for 16 h. Then the reaction was quenched with water (10 mL). The mixture was extracted with ethyl acetate (3×30 mL), the combined organic extracts was dried over sodium sulfate, filtered and the filtrate was concentrated under reduced pressure to afford ethyl 2-(4-(3-(2,2-difluoroethyl)-2-(2,6-dimethylpyridin-4-yl)-1H-indol-5-yl)piperidin-1-yl)propanoate (0.060 g, 0.128 mmol, 86% yield) as a light brown sticky solid. LCMS retention time 1.24 min [B]. MS (E−) m/z: 470.6 (M+H).

Intermediate 493B: 2-(4-(3-(2,2-difluoroethyl)-2-(2,6-dimethylpyridin-4-yl)-1H-indol-5-yl)piperidin-1-yl)propanoic Acid

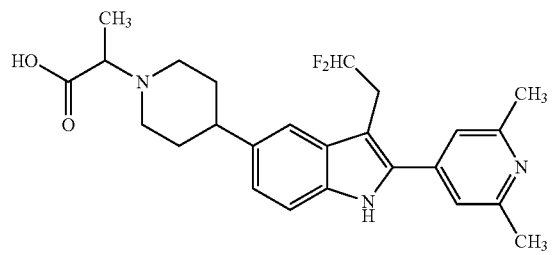

(493B)

To a solution of ethyl 2-(4-(3-(2,2-difluoroethyl)-2-(2,6-dimethylpyridin-4-yl)-1H-indol-5-yl)piperidin-1-yl)propanoate (0.050 g, 0.106 mmol) in EtOH (2.0 mL), THF (2.0 mL), and water (1.0 mL) was added lithium hydroxide (0.026 g, 1.065 mmol) at room temperature, The resulting reaction mixture was heated to 70° C. for 4 h. The volatiles were evaporated under vacuum, the crude material was dissolved in water (10 mL), neutralized with 10% HCl, and stirred for 30 min. The white precipitate formed was filtered through a Buchner funnel and air dried. The solid material was washed thoroughly with pet ether (50 mL) to afford 2-(4-(3-(2,2-difluoroethyl)-2-(2,6-dimethylpyridin-4-yl)-1H-indol-5-yl)piperidin-1-yl)propanoic acid (35 mg, 75%). LCMS retention time 0.79 min [B]. MS (E−) m/z: 442.2 (M+H).

Example 493

2-(4-(3-(2,2-difluoroethyl)-2-(2,6-dimethylpyridin-4-yl)-1H-indol-5-yl)piperidin-1-yl)propanoic acid (0.035 g, 0.079 mmol) and HATU (0.030 g, 0.079 mmol) were dissolved in DMF (2 mL). Dimethylamine (0.991 mL, 1.982 mmol) was added to the reaction mixture followed by TEA (0.033 mL, 0.238 mmol). The resulting reaction mixture was stirred for 3 h at room temperature. DMF was removed under vacuum. The reaction was quenched with ice water. The mixture was extracted with ethyl acetate (3×20) ml. The ethyl acetate layer was dried over Na$_2$SO$_4$, filtered and the filtrate was concentrated. The crude product was purified by Preparative LCMS, the fractions containing desired product was combined and dried using Genevac centrifugal evaporator to afford 2-(4-(3-(2,2-difluoroethyl)-2-(2,6-dimethylpyridin-4-yl)-1H-indol-5-yl) piperidin-1-yl)-N,N-dimethylpropanamide (8 mg, 21.32%). LCMS retention time 1.66 min [E]. MS (E−) m/z: 469.3 (M+H).

Example 494

2-(2-chloropyridin-4-yl)-3-(2,2-difluoroethyl)-5-(piperidin-4-yl)-1H-indole

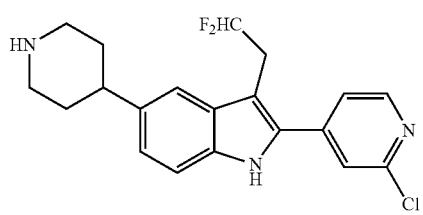

(494)

Intermediate 494A: Tert-Butyl 4-(2-(2-chloropyridin-4-yl)-3-(2,2-difluoroethyl)-1H-indol-5-yl)piperidine-1-carboxylate

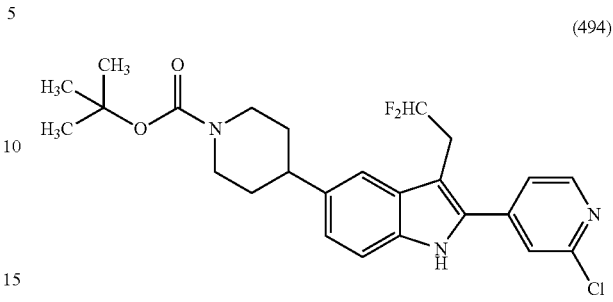

(494)

Tert-butyl 4-(2-(2-chloropyridin-4-yl)-3-(2,2-difluoroethyl)-1H-indol-5-yl) piperidine-1-carboxylate was prepared according to the general procedure described in Intermediate 1F using tert-butyl 4-(2-bromo-3-(2,2-difluoroethyl)-1H-indol-5-yl) piperidine-1-carboxylate as the starting intermediate. The material was used in the next step without further purification.

Example 494

Tert-butyl 4-(2-(2-chloropyridin-4-yl)-3-(2,2-difluoroethyl)-1H-indol-5-yl) piperidine-1-carboxylate (50 mg, 0.105 mmol) was dissolved in DCM (2 mL) to make a solution. Next, 4M hydrochloric acid in dioxane (0.026 mL, 0.105 mmol) was added to the solution. The reaction mixture was stirred at 25° C. for 60 minutes. The solvent was removed under vacuum. The resulting yellow colored solid product was washed with diethyl ether to remove nonpolar impurities to afford 2-(2-chloropyridin-4-yl)-3-(2,2-difluoroethyl)-5-(piperidin-4-yl)-1H-indole (0.005 g, 10% yield). LCMS retention time 1.20 min [F]. MS (E−) m/z: 376.3 (M+H).

Example 495

Methyl 2-(2,6-dimethylpyridin-4-yl)-5-(piperidin-4-yl)-1H-indole-3-carboxylate

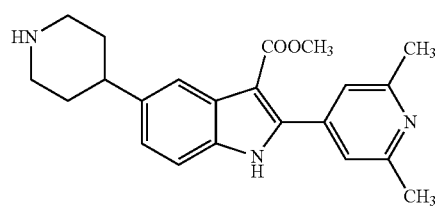

(495)

Intermediate 495 A: Methyl 5-(1-(tert-butoxycarbonyl)-1,2,3,6-tetrahydropyridin-4-yl)-1H-indole-3-carboxylate

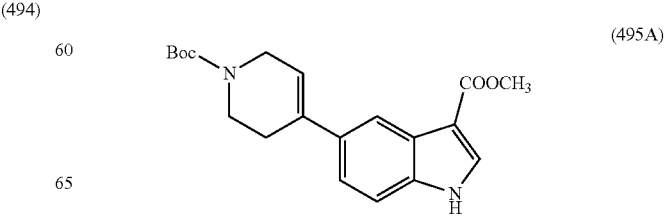

(495A)

Methyl 5-(1-(tert-butoxycarbonyl)-1,2,3,6-tetrahydropyridin-4-yl)-1H-indole-3-carboxylate was prepared according to the general procedure described in Intermediate 1B using methyl 5-bromo-1H-indole-3-carboxylate (3.2 g, 57% yield). LC retention time 2.70 min [D]. MS (E−) m/z: 355.4 (M+H).

Intermediate 495B: Methyl 5-(1-(tert-butoxycarbonyl)piperidin-4-yl)-1H-indole-3-carboxylate

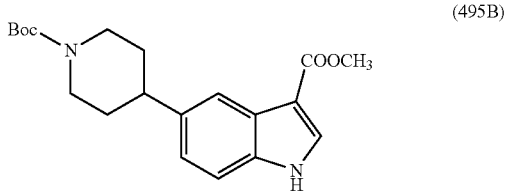 [SMILES: COC(=O)c1c[nH]c2ccc(C3CCN(C(=O)OC(C)(C)C)CC3)cc12]

(495B)

Methyl 5-(1-(tert-butoxycarbonyl)piperidin-4-yl)-1H-indole-3-carboxylate was prepared according to the general procedure described in Intermediate 1C using methyl 5-(1-(tert-butoxycarbonyl)-1,2,3,6-tetrahydropyridin-4-yl)-1H-indole-3-carboxylate (3.1 g, 80% yield). LC retention time 4.49 min [D]. MS (E−) m/z: 357.4 (M−H).

Intermediate 495C: Methyl 2-bromo-5-(1-(tert-butoxycarbonyl)piperidin-4-yl)-1H-indole-3-carboxylate

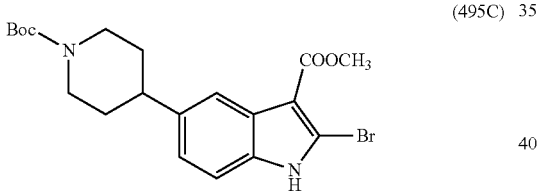

(495C)

Methyl 2-bromo-5-(1-(tert-butoxycarbonyl)piperidin-4-yl)-1H-indole-3-carboxylate was prepared according to the general procedure described in Intermediate 1D using methyl 5-(1-(tert-butoxycarbonyl)piperidin-4-yl)-1H-indole-3-carboxylate (1.8 g, 75% yield). LC retention time 3.21 min [D]. MS (E−) m/z: 435.4 (M−H).

Intermediate 495D: Methyl 5-(1-(tert-butoxycarbonyl)piperidin-4-yl)-2-(2,6-dimethylpyridin-4-yl)-1H-indole-3-carboxylate

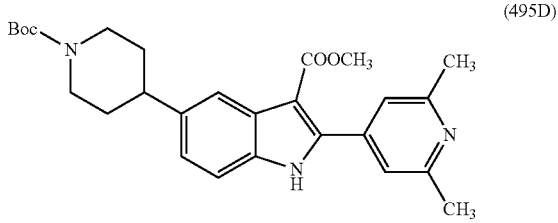 [SMILES: COC(=O)c1c(-c2cc(C)nc(C)c2)[nH]c2ccc(C3CCN(C(=O)OC(C)(C)C)CC3)cc12]

(495D)

Methyl 5-(1-(tert-butoxycarbonyl)piperidin-4-yl)-2-(2,6-dimethylpyridin-4-yl)-1H-indole-3-carboxylate was prepared according to the general procedure described in Intermediate 1F using methyl 2-bromo-5-(1-(tert-butoxycarbonyl)piperidin-4-yl)-1H-indole-3-carboxylate (125 mg, 35% yield). LC retention time 1.22 min [B]. MS (E−) m/z: 464.4 (M+H).

Example 495

Methyl 2-(2,6-dimethylpyridin-4-yl)-5-(piperidin-4-yl)-1H-indole-3-carboxylate was prepared according to the general procedure described in Example 2 using methyl 5-(1-(tert-butoxycarbonyl) piperidin-4-yl)-2-(2,6-dimethylpyridin-4-yl)-1H-indole-3-carboxylate (1 mg, 6% yield). LC retention time 1.22 min [E]. MS (E−) m/z: 364.4 (M+H).

Example 496

2-(2,6-dimethylpyridin-4-yl)-3-isopropyl-5-(1,2,2,6,6-pentamethylpiperidin-4-yl)-1H-indole

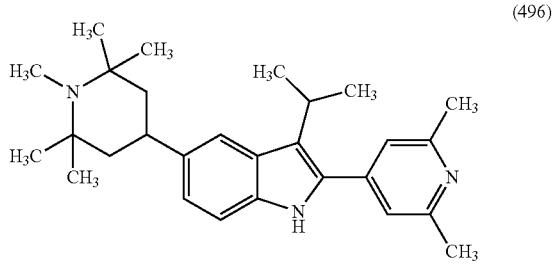

(496)

Intermediate 496A: 1,2,2,6,6-pentamethyl-1,2,3,6-tetrahydropyridin-4-yl trifluoromethanesulfonate

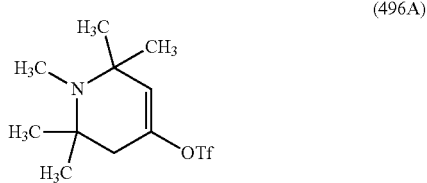 [SMILES: CN1C(C)(C)C=C(OS(=O)(=O)C(F)(F)F)CC1(C)C]

(496A)

To a solution of 1,2,2,6,6-pentamethylpiperidin-4-one (0.200 g, 1.182 mmol) in THF (15.00 mL) was added LDA in THF (0.886 mL, 1.772 mmol) at −78° C. The reaction mixture was stirred at the same temperature for 45 min. Next, N,N-bis(trifluoromethylsulfonyl)aniline (0.633 g, 1.772 mmol) was added at the same temperature. The reaction mixture was maintained at room temperature for 16 h. The reaction was quenched with saturated NH$_4$Cl (10 ml). The mixture was diluted with EtOAc (10 mL), both the layers separated, the aqueous layer was extracted with EtOAc (20 mL), the combined organic extracts was dried (Na$_2$SO$_4$) and concentrated to afford crude compound. The crude material was purified by ISCO using 12 g silica column, compound was eluted in 10% EA in hexanes, the fractions was collected and concentrated to afford 1,2,2,6,6-pentamethyl-1,2,3,6-tetrahydropyridin-4-yl trifluoromethanesulfonate (0.153 g, 0.508 mmol, 43.0% yield) as a liquid. LCMS retention time 1.09 min [B]. MS (E−) m/z: 302.6 (M+H).

Intermediate 496B: 2-(2,6-dimethylpyridin-4-yl)-3-isopropyl-5-(4,4,5,5-tetramethyl-1,3,2-dioxaborolan-2-yl)-1H-indole

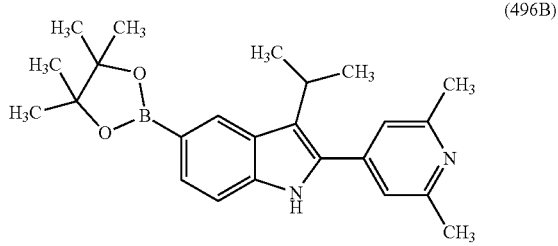

(496B)

To a mixture of 5-bromo-2-(2,6-dimethylpyridin-4-yl)-3-isopropyl-1H-indole (0.6 g, 1.748 mmol), BISPIN (0.710 g, 2.80 mmol) and potassium acetate (0.515 g, 5.24 mmol) in a 50 ml round bottom flask was added dioxane (15 mL). The resulting reaction mixture was degassed for 10 minutes with nitrogen and PdCl$_2$(dppf)-CH$_2$Cl$_2$ adduct (0.143 g, 0.175 mmol) was added. The mixture was degassed again for 5 min. The reaction mixture was heated at 80° C. for 18 h. The reaction mixture was diluted with ethyl acetate (100 mL), poured into a separate funnel and was washed with water (2×50 mL), brine (50 mL), dried over sodium sulfate, and concentrated to afford crude product. The crude material was purified using silica gel chromatography, eluting with 5% MeOH in CHCl$_3$, the fractions was collected and concentrated to afford 2-(2,6-dimethylpyridin-4-yl)-3-isopropyl-5-(4,4,5,5-tetramethyl-1,3,2-dioxaborolan-2-yl)-1H-indole as a pale yellow solid. (0.55 g, 81% yield). LCMS retention time 1.41 min [B]. MS (E−) m/z: 391 (M+H).

Intermediate 496C: 3-isopropyl-2-(2-methylpyridin-4-yl)-5-(1,2,2,6,6-pentamethyl-1,2,3,6-tetrahydropyridin-4-yl)-1H-indole

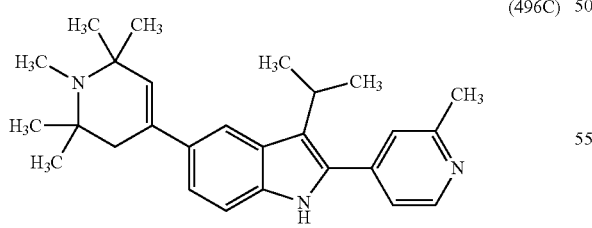

(496C)

To a mixture of 2-(2,6-dimethylpyridin-4-yl)-3-isopropyl-5-(4,4,5,5-tetramethyl-1,3,2-dioxaborolan-2-yl)-1H-indole (0.050 g, 0.128 mmol) and 1,2,2,6,6-pentamethyl-1,2,3,6-tetrahydropyridin-4-yl trifluoromethanesulfonate (0.077 g, 0.256 mmol) in a 25 ml round bottom flask were added THF (2 mL) followed by an aqueous solution of potassium phosphate, tribasic (0.082 g, 0.384 mmol, 0.5 ml). The resulting reaction mixture was degassed for 10 minutes with nitrogen, then was added PdCl$_2$(dppf)-CH$_2$Cl$_2$ adduct (10.46 mg, 0.013 mmol), and the reaction mixture was degassed again for 5 min. The resulting reaction mixture was heated at 80° C. for 16 h. The reaction mixture was diluted with ethyl acetate (100 mL), poured into a separate funnel and was washed with water (2×50 mL), brine (50 mL), dried over sodium sulfate, and concentrated to afford crude product. The crude material was purified using silica gel chromatography, eluting with 80% ethyl acetate in hexane, the fractions was collected and concentrated to 2-(2,6-dimethylpyridin-4-yl)-3-isopropyl-5-(1,2,2,6,6-pentamethyl-1,2,3,6-tetrahydropyridin-4-yl)-1H-indole (0.024 g, 0.058 mmol, 45.1% yield) as a off white solid. LCMS retention time 0.73 min [B]. MS (E−) m/z: 414.6 (M+H).

Example 496

A solution of 2-(2,6-dimethylpyridin-4-yl)-3-isopropyl-5-(1,2,2,6,6-pentamethyl-1,2,3,6-tetrahydropyridin-4-yl)-1H-indole (0.020 g, 0.048 mmol) in methanol (2 mL) was purged with nitrogen (N$_2$). Next, palladium on carbon (0.11 mg, 1.034 μmol) was added and the mixture was purged with N$_2$ three times. Hydrogen gas was introduced via a balloon to the mixture. The reaction mixture was stirred at room temperature for 16 h. The suspension was filtered through celite, the filtrate was collected and concentrated to afford crude compound. The reaction mixture was purified by reverse phase prep LCMS, fractions containing the desired product was combined and dried using Genevac centrifugal evaporator to afford 2-(2,6-dimethylpyridin-4-yl)-3-isopropyl-5-(1,2,2,6,6-pentamethylpiperidin-4-yl)-1H-indole (0.0043 g, 9.83 μmol, 20.43% yield) as a pale solid. LCMS retention time 1.74 min [E]. MS (E−) m/z: 418.3 (M−H).

Example 497

(4-(2-(2,6-dimethylpyridin-4-yl)-3-isopropyl-1H-indol-5-yl)piperidin-1-yl)(1-isopropylpiperidin-4-yl)methanone

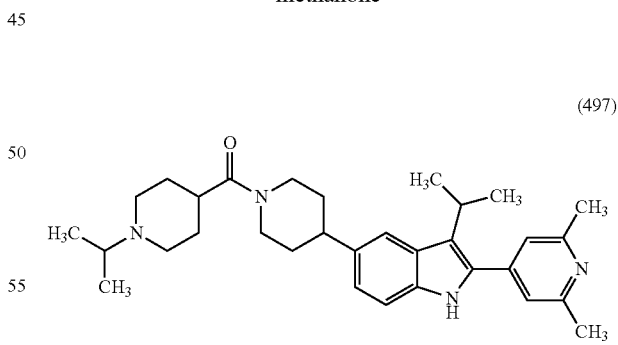

(497)

To a solution of (4-(2-(2,6-dimethylpyridin-4-yl)-3-isopropyl-1H-indol-5-yl) piperidin-1-yl)(piperidin-4-yl)methanone, 2 HCl (0.100 g, 0.188 mmol) and acetone (0.1 ml, 1.362 mmol) in methanol (3 mL) was added TEA (0.15 mL, 1.076 mmol) at 0° C. The resulting light yellow solution was stirred under nitrogen at 25° C. for 2 h. The reaction mixture was cooled to 0° C. and acetic acid (0.20 ml, 3.49 mmol) was added. The reaction mixture was stirred at 25° C. for 3 h. Again, the reaction mixture was cooled to 0° C. and sodium cyanoborohydride (0.059 g, 0.941 mmol) was added. The mixture was stirred at the same temperature for 12 h. The reaction mass was diluted with dichloromethane (10 mL). The reaction was quenched with water. The organic layer was dried over sodium sulfate and concentrated. The crude material was purified by Preparative LCMS, the fractions containing desired product was combined and dried using Genevac centrifugal evaporator to afford (4-(2-(2,6-dimethylpyridin-4-yl)-3-isopropyl-1H-indol-5-yl)piperidin-1-yl)(1-isopropylpiperidin-4-yl)methanone (0.0793 g, 0.155 mmol, 82% yield). LCMS retention time 1.64 min [E]. MS (E−) m/z: 501.3 (M+H).

Example 498

2-(4-(2-(2-fluoro-6-methylpyridin-4-yl)-3-isopropyl-1H-indol-5-yl)piperidin-1-yl)-N-methylacetamide (498)

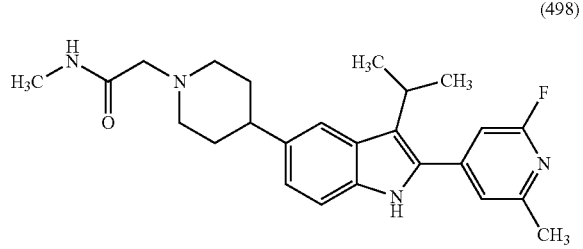

To a solution of 2-(2-fluoro-6-methylpyridin-4-yl)-3-isopropyl-5-(piperidin-4-yl)-1H-indole (0.025 g, 0.071 mmol) in THF (1 mL) and DMF (0.2 mL) solvent were added TEA (9.91 µl, 0.071 mmol) and 2-chloro-N-methylacetamide (7.65 mg, 0.071 mmol) at room temperature. The mixture was stirred at the same temperature for 3 h. The reaction mass was concentrated under vacuum to remove DCM solvent. The reaction mixture was purified by prep LCMS to afford 2-(4-(2-(2-fluoro-6-methylpyridin-4-yl)-3-isopropyl-1H-indol-5-yl)piperidin-1-yl)-N-methylacetamide (1.7 mg, 5.66% yield). LCMS retention time 2.06 min [E]. MS (E−) m/z: 423.3 (M+H).

The following examples were prepared according to the general process described in Example 498.

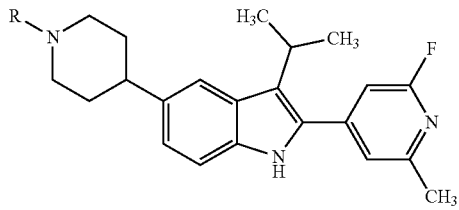

TABLE 18

| Ex. No. | R | LCMS [M + H]+ | Rt (min) | Method |
|---------|---|---------------|----------|--------|
| 499 | —C(O)CH3 | 394.2 | 2.07 | E |
| 500 | —CH2C(O)N(CH3)2 | 437.2 | 1.96 | E |

Example 501

2-(dimethylamino)-1-(4-(2-(2-fluoro-6-methylpyridin-4-yl)-3-isopropyl-1H-indol-5-yl) piperidin-1-yl) ethan-1-one (501)

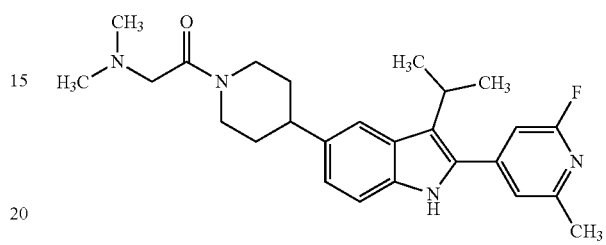

2-(dimethylamino)acetic acid (8.80 mg, 0.085 mmol and HATU (0.030 g, 0.078 mmol) were dissolved in DMF (2 mL). Next, 2-(2-fluoro-6-methylpyridin-4-yl)-3-isopropyl-5-(piperidin-4-yl)-1H-indole (0.025 g, 0.071 mmol) was added to the reaction mixture followed by the addition of TEA (0.020 mL, 0.142 mmol). The resulting reaction mixture was stirred for 3 h at room temperature. The solvent was removed from the reaction mixture to give a crude sample. The crude sample was purified by prep LCMS to afford 2-(dimethylamino)-1-(4-(2-(2-fluoro-6-methylpyridin-4-yl)-3-isopropyl-1H-indol-5-yl)piperidin-1-yl)ethanone (1.5 mg, 4.83% yield). LCMS retention time 1.88 min [E]. MS (E−) m/z: 437.3 (M+H).

The following example was prepared according to the general procedure described in Example 501.

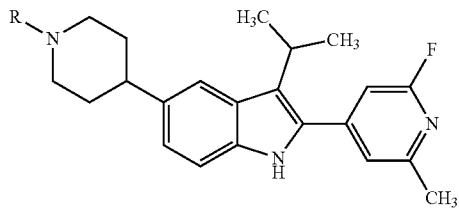

TABLE 19

| Ex. No. | R | LCMS [M + H]+ | Rt (min) | [Method] |
|---------|---|---------------|----------|----------|
| 502 | ![structure] | 477.3 | 1.95 | E |

Example 503

2-(4-(2-(2-cyclopropyl-6-methylpyridin-4-yl)-3-isopropyl-1H-indol-5-yl)piperidin-1-yl)-N-methylacetamide

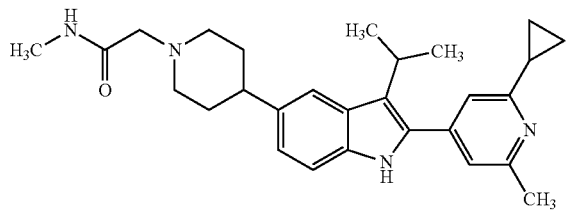

(503)

2-(4-(2-(2-cyclopropyl-6-methylpyridin-4-yl)-3-isopropyl-1H-indol-5-yl) piperidin-1-yl)-N-methylacetamide was prepared as described in Example 476, using 2-(2-cyclopropyl-6-methylpyridin-4-yl)-3-isopropyl-5-(piperidin-4-yl)-1H-indole as the starting intermediate (7.1 mg, 23.86% yield). LCMS retention time 2.29 min [E]. MS (E−) m/z: 445.3 (M+H).

The following examples were prepared according to the general procedure described in Example 503.

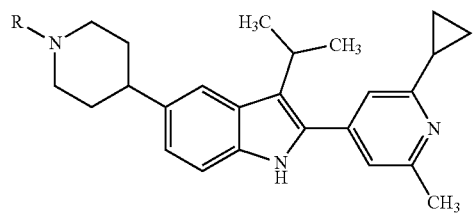

TABLE 20

| Ex. No. | R | LCMS [M + H]+ | Rt (min) | [Method] |
|---|---|---|---|---|
| 504 | —C(O)CH₃ | 416.3 | 2.28 | E |
| 505 | —CH₂C(O)N(CH₃)₂ | 459.3 | 2.10 | E |

Example 506

1-(4-(2-(2-cyclopropyl-6-methylpyridin-4-yl)-3-isopropyl-1H-indol-5-yl)piperidin-1-yl)-2-(dimethylamino)ethan-1-one

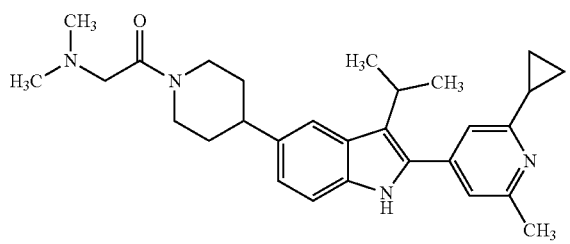

(506)

1-(4-(2-(2-cyclopropyl-6-methylpyridin-4-yl)-3-isopropyl-1H-indol-5-yl) piperidin-1-yl)-2-(dimethylamino)ethanone was prepared as described in Example 501, using 2-(2-cyclopropyl-6-methylpyridin-4-yl)-3-isopropyl-5-(piperidin-4-yl)-1H-indole as the starting intermediate (16 mg, 32.6% yield). LCMS retention time 2.00 min [E]. MS (E−) m/z: 459.3 (M+H).

The following example was prepared according to the general procedure described in Example 506.

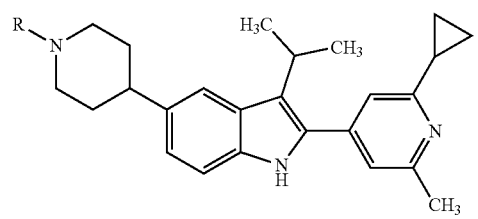

TABLE 21

| Ex. No. | R | LCMS [M + H]+ | Rt (min) | [Method] |
|---|---|---|---|---|
| 507 | ![structure] | 499.4 | 2.11 | E |

Example 508

1-(4-(2-(2-cyclopropyl-6-methylpyridin-4-yl)-3-isopropyl-1H-indol-5-yl)piperidin-1-yl)-2-(methylamino)ethan-1-one

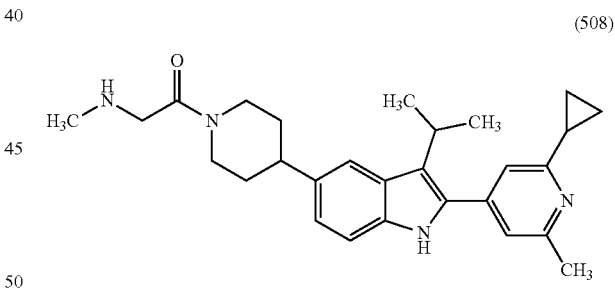

(508)

Intermediate 508A: Tert-Butyl (2-(4-(2-(2-cyclopropyl-6-methylpyridin-4-yl)-3-isopropyl-1H-indol-5-yl)piperidin-1-yl)-2-oxoethyl)carbamate

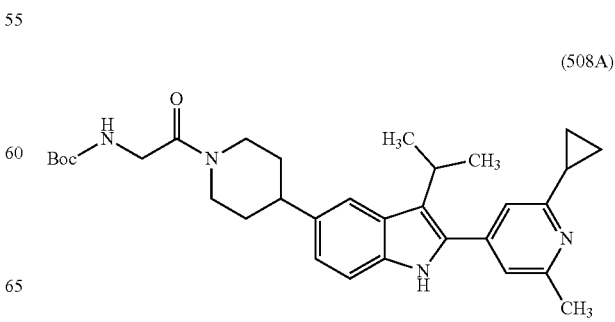

(508A)

Tert-butyl (2-(4-(2-(2-cyclopropyl-6-methylpyridin-4-yl)-3-isopropyl-1H-indol-5-yl)piperidin-1-yl)-2-oxoethyl)(methyl)carbamate was prepared as described in Example 501, using 2-(2-cyclopropyl-6-methylpyridin-4-yl)-3-isopropyl-5-(piperidin-4-yl)-1H-indole as the starting intermediate (35 mg, 80% yield). LCMS retention time 1.10 min [G]. MS (E−) m/z: 545.7 (M+H).

Example 508

To a solution of tert-butyl (2-(4-(2-(2-cyclopropyl-6-methylpyridin-4-yl)-3-isopropyl-1H-indol-5-yl)piperidin-1-yl)-2-oxoethyl)(methyl)carbamate (0.035 g, 0.064 mmol) in DCM (2 mL) was added 4 M HCl in dioxane (1.952 µl, 0.064 mmol) at room temperature. The mixture was stirred at same temperature for 1 h. The solution was concentrated to afford crude product. The crude sample was purified by prep LCMS to afford 1-(4-(2-(2-cyclopropyl-6-methylpyridin-4-yl)-3-isopropyl-1H-indol-5-yl) piperidin-1-yl)-2-(methylamino)ethanone (7.9 mg, 27.7% yield). LCMS retention time 1.89 min [E]. MS (E−) m/z: 445.3 (M+H).

Example 509

2-(dimethyl amino)-1-(4-(3-isopropyl-2-(2-methylpyridin-4-yl)-1H-indol-5-yl)piperidin-1-yl)ethan-1-one

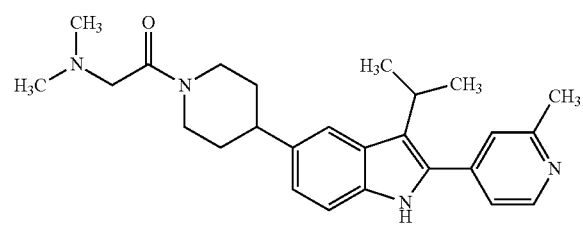

(509)

Intermediate 509A: Tert-Butyl 4-(3-isopropyl-2-(2-methylpyridin-4-yl)-1H-indol-5-yl) piperidine-1-carboxylate

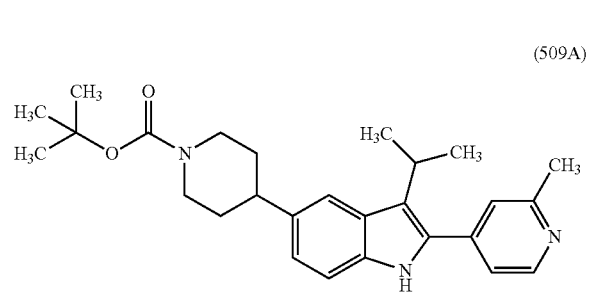 [SMILES: Cc1cc(-c2[nH]c3ccc(C4CCN(C(=O)OC(C)(C)C)CC4)cc3c2C(C)C)ccn1]

(509A)

To a mixture of tert-butyl 4-(3-isopropyl-2-(4,4,5,5-tetramethyl-1,3,2-dioxaborolan-2-yl)-1H-indol-5-yl)piperidine-1-carboxylate (0.2 g, 0.427 mmol) and 4-bromo-2-methylpyridine (0.081 g, 0.470 mmol) in a 25 ml round bottom flask were added dioxane (4 mL) and water (1 mL) followed by an aqueous solution of cesium carbonate (0.348 g, 1.067 mmol). The resulting reaction mixture was degassed for 10 minutes with nitrogen, then was added tetrakis (0.025 g, 0.021 mmol)). The reaction mixture was degassed again for 5 min. The resulting reaction mixture was heated at 100° C. for 3 h. The reaction mixture was diluted with ethyl acetate (100 mL), poured into a separation funnel and was washed with water (2×50 mL), brine (50 mL), dried over sodium sulfate, and concentrated to afford crude product. The crude material was purified using silica gel chromatography, eluting with 28% ethyl acetate in hexane, the fractions was collected and concentrated to afford tert-butyl 4-(3-isopropyl-2-(2-methylpyridin-4-yl)-1H-indol-5-yl)piperidine-1-carboxylate (0.09 g, 48.4% yield) as brown solid. LCMS retention time 1.38 min [B]. MS (E−) m/z: 434.5 (M+H).

Intermediate 509B: 3-isopropyl-2-(2-methylpyridin-4-yl)-5-(piperidin-4-yl)-1H-indole hydrochloride

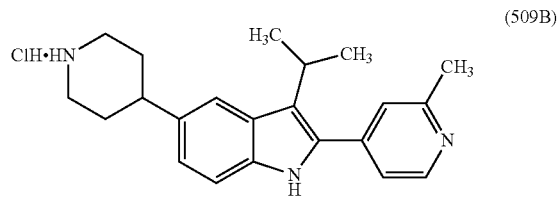

(509B)

To a solution of tert-butyl 4-(3-isopropyl-2-(2-methylpyridin-4-yl)-1H-indol-5-yl) piperidine-1-carboxylate (0.09 g, 0.208 mmol) in DCM (5 mL) was added 4 M HCl in dioxane (0.259 mL, 1.038 mmol) at room temperature. The reaction mixture was stirred at same temperature for 1 h. Solid slowly precipitated out from the reaction mass. The slurry was concentrated and the residue was triturated with diethyl ether (3×5 mL) to 3-isopropyl-2-(2-methylpyridin-4-yl)-5-(piperidin-4-yl)-1H-indole (0.065 g, 94% yield) as a pale yellow solid. LCMS retention time 0.77 min [B]. MS (E−) m/z: 334.5 (M+H).

Intermediate 509C: 2-chloro-1-(4-(3-isopropyl-2-(2-methylpyridin-4-yl)-1H-indol-5-yl) piperidin-1-yl) ethan-1-one

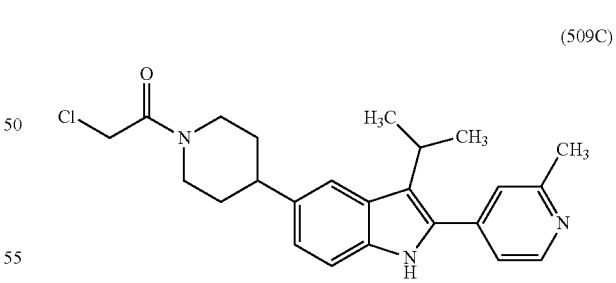

(509C)

To a solution of 3-isopropyl-2-(2-methylpyridin-4-yl)-5-(piperidin-4-yl)-1H-indole (0.065 g, 0.195 mmol) in THF (2 mL) were added DIPEA (0.071 mL, 0.406 mmol) and chloroacetyl chloride (0.018 g, 0.162 mmol) at 0° C. The color of the mixture changed slowly from pale yellow to brown. The reaction mixture was allowed to stir at room temperature for 1 h. The reaction mass was quenched with water (5 mL), extracted with DCM (2×25 mL), the organic layer was collected and dried over Na₂SO₄ and concentrated to afford 2-chloro-1-(4-(3-isopropyl-2-(2-methylpyridin-4- yl)-1H-indol-5-yl)piperidin-1-yl)ethanone (0.05 g, 75% yield) as a yellow solid. LCMS retention time 1.13 min [B]. MS (E−) m/z: 410.3 (M+H).

Example 509

2-Chloro-1-(4-(3-isopropyl-2-(2-methylpyridin-4-yl)-1H-indol-5-yl)piperidin-1-yl)ethanone (0.05 g, 0.122 mmol and DIPEA (0.032 mL, 0.183 mmol) were added to THF (1 mL). The solution was stirred. Dimethylamine (6.60 mg, 0.146 mmol) was added to the reaction solution. The resulting reaction mixture was stirred at 25° C. for 4 h. The reaction mixture was concentrated. The crude was dissolved in ethyl acetate and washed with water. The organic layer was dried over $Na_2SO_4$ and concentrated. The crude sample was purified by prep LCMS to afford 2-(dimethylamino)-1-(4-(3-isopropyl-2-(2-methylpyridin-4-yl)-1H-indol-5-yl)piperidin-1-yl)ethanone (23.6 m g, 46.3% yield). LCMS retention time 0.90 min [F]. MS (E−) m/z: 419.3 (M+H).

The following examples were prepared according to the general procedure described in Example 509.

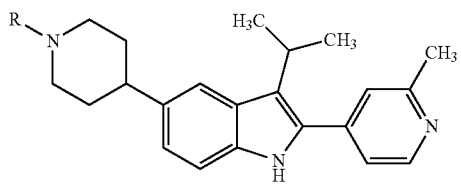

TABLE 22

| Ex. No. | R | LCMS [M + H]+ | Rt (min) | Method |
|---|---|---|---|---|
| 510 | —C(O)CH₂NHCH₃ | 405.3 | 1.307 | E |
| 511 | ![structure] Chiral | 465.20 | 1.84 | E |

Example 512

2-(4-(3-isopropyl-2-(2-methylpyridin-4-yl)-1H-indol-5-yl)piperidin-1-yl)-N,N-dimethylacetamide (512)

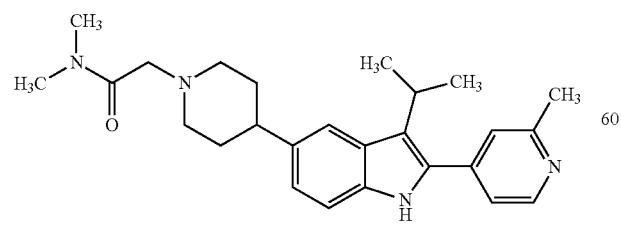

To a solution of 2-(2-cyclopropyl-6-methylpyridin-4-yl)-3-isopropyl-5-(piperidin-4-yl)-1H-indole (0.025 g, 0.067 mmol in DCM (1 mL) and DMF (0.2 mL) solvent were added TEA (9.33 μl, 0.067 mmol) and 2-chloro-N,N-dimethylacetamide (8.14 mg, 0.067 mmol) at room temperature. The reaction mixture was stirred at same temperature for 2 h. The reaction mixture was purified by prep LCMS to afford 2-(4-(2-(2-cyclopropyl-6-methylpyridin-4-yl)-3-isopropyl-1H-indol-5-yl)piperidin-1-yl)-N,N-dimethylacetamide (7.8 mg, 25.4% yield). LCMS retention time 1.43 min [E]. MS (E−) m/z: 419.3 (M+H).

The following Example was prepared according to the general procedure described in Example 512.

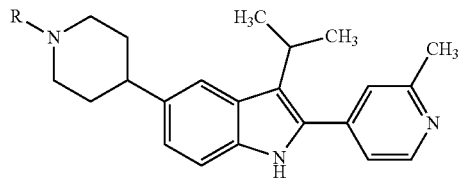

TABLE 23

| Ex. No. | R | LCMS [M + H]+ | Rt (min) | Method |
|---|---|---|---|---|
| 513 | —CH₂C(O)NH(CH₃) | 405.3 | 1.591 | E |

Example 514

2-(4-(2-(2-cyclopropyl-5-fluoropyridin-4-yl)-3-isopropyl-1H-indol-5-yl)piperidin-1-yl)-N-methylacetamide (514)

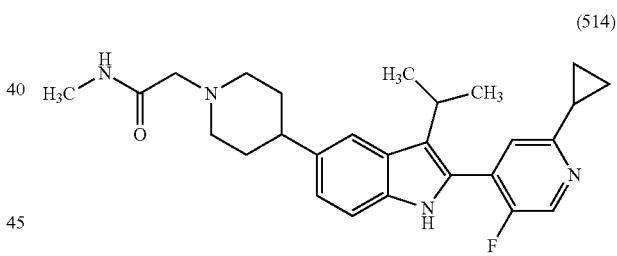

2-(4-(2-(2-cyclopropyl-5-fluoropyridin-4-yl)-3-isopropyl-1H-indol-5-yl)piperidin-1-yl)-N-methylacetamide was prepared in a manner similar to that described above using 2-(2-cyclopropyl-5-fluoropyridin-4-yl)-3-isopropyl-5-(piperidin-4-yl)-1H-indole as a starting intermediate. (9.9 mg, 33.4% yield). LCMS retention time 2.29 min [E]. MS (E−) m/z: 449.3 (M+H).

The following example was prepared according to the general procedure described in Example 514.

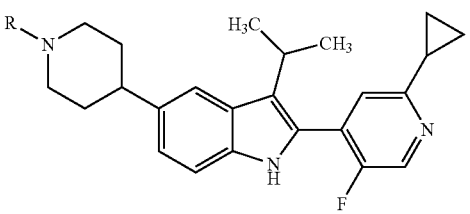

TABLE 24

| Ex. No. | R | LCMS [M + H]+ | Rt (min) | [Method] |
|---|---|---|---|---|
| 515 | —CH₂C(O)N(CH₃)₂ | 463.3 | 2.12 | E |

Example 516

1-(4-(2-(2-cyclopropyl-5-fluoropyridin-4-yl)-3-isopropyl-1H-indol-5-yl)piperidin-1-yl)-2-(dimethylamino)ethan-1-one

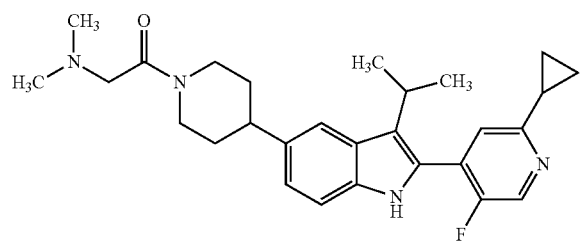
(516)

1-(4-(2-(2-cyclopropyl-5-fluoropyridin-4-yl)-3-isopropyl-1H-indol-5-yl)piperidin-1-yl)-2-(dimethylamino)ethanone was prepared as described for Example 501 using 2-(2-cyclopropyl-5-fluoropyridin-4-yl)-3-isopropyl-5-(piperidin-4-yl)-1H-indole (0.025 g, 0.066 mmol) as a starting intermediate (7.3 mg, 23.8% yield). LCMS retention time 2.04 min [E]. MS (E−) m/z: 463.3 (M+H).

The following Example was prepared according to the general procedure described in Example 516.

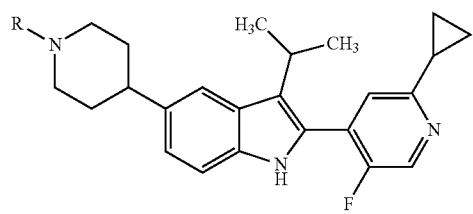

TABLE 25

| Ex. No. | R | LCMS [M + H]+ | Rt (min) | Method |
|---|---|---|---|---|
| 517 | ![structure] | 503.3 | 2.13 | E |

Example 518

1-(4-(2-(2-cyclopropyl-5-fluoropyridin-4-yl)-3-isopropyl-1H-indol-5-yl)piperidin-1-yl)-2-(methylamino)ethan-1-one

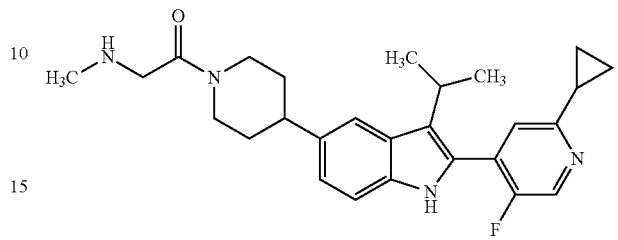
(518)

Intermediate 518A: Tert-Butyl (2-(4-(2-(2-cyclopropyl-5-fluoropyridin-4-yl)-3-isopropyl-1H-indol-5-yl)piperidin-1-yl)-2-oxoethyl)carbamate

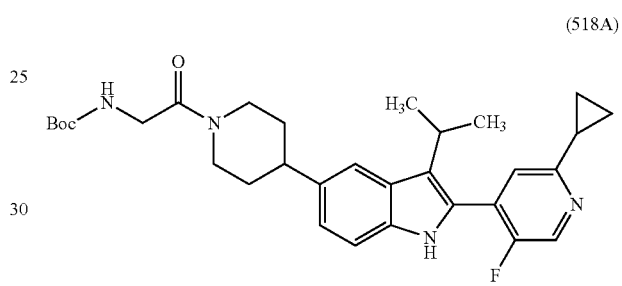
(518A)

Tert-butyl (2-(4-(2-(2-cyclopropyl-5-fluoropyridin-4-yl)-3-isopropyl-1H-indol-5-yl)piperidin-1-yl)-2-oxoethyl)(methyl)carbamate was prepared as described in Example 501 using 2-(2-cyclopropyl-5-fluoropyridin-4-yl)-3-isopropyl-5-(piperidin-4-yl)-1H-indole (0.025 g, 0.066 mmol) as a starting intermediate (0.035 g, 80.6% yield). LCMS retention time 1.50 min [D]. MS (E−) m/z: 549.3 (M+H).

Example 518

To a solution of tert-butyl (2-(4-(2-(2-cyclopropyl-5-fluoropyridin-4-yl)-3-isopropyl-1H-indol-5-yl)piperidin-1-yl)-2-oxoethyl)(methyl)carbamate (0.035 g, 0.064 mmol) in DCM (2 mL) was added 4 M HCl in dioxane (1.938 μl, 0.064 mmol) at room temperature. The mixture was stirred at same temperature for 1 h. The solution was concentrated to afford crude product. The crude sample was purified by prep LCMS to afford 1-(4-(2-(2-cyclopropyl-5-fluoropyridin-4-yl)-3-isopropyl-1H-indol-5-yl)piperidin-1-yl)-2-(methylamino)ethanone (3.5 mg, 12.5% yield). LCMS retention time 1.88 min [E]. MS (E−) m/z: 449.3 (M+H).

Example 519

2-(4-(3-isopropyl-2-(2-methoxypyridin-4-yl)-1H-indol-5-yl)piperidin-1-yl)-N-methylacetamide

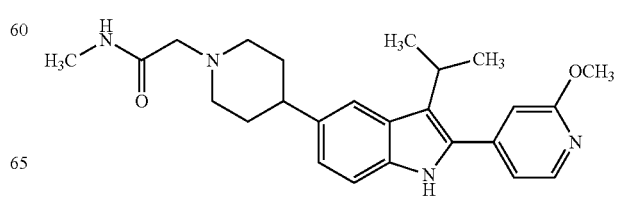
(519)

2-(4-(3-isopropyl-2-(2-methoxypyridin-4-yl)-1H-indol-5-yl)piperidin-1-yl)-N,N-dimethylacetamide was prepared as described in Example 498 using 3-isopropyl-2-(2-methoxypyridin-4-yl)-5-(piperidin-4-yl)-1H-indole as a starting intermediate. (22 mg, 44.2% yield). LCMS retention time 1.86 min [E]. MS (E−) m/z: 435.3 (M+H).

Example 520

3-isopropyl-2-(2-methoxypyridin-4-yl)-5-(1-((2-methyl-1H-imidazol-4-yl)methyl)piperidin-4-yl)-1H-indole

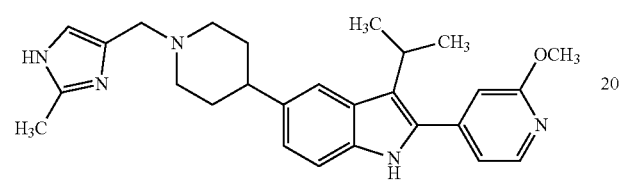

(520)

To a solution of 3-isopropyl-2-(2-methoxypyridin-4-yl)-5-(piperidin-4-yl)-1H-indole (0.05 g, 0.143 mmol) and 2-methyl-1H-imidazole-4-carbaldehyde (0.019 g, 0.172 mmol)) in methanol (4 mL) was added titanium(IV) isopropoxide (0.050 mL, 0.172 mmol) dropwise. The resulting light yellow solution was stirred under nitrogen at 25° C. for 4 h. Then sodium cyanoborohydride (10.79 mg, 0.172 mmol) was added and the mixture was stirred at the same temperature for 12 h. The reaction mass was diluted with dichloromethane (10 mL) and quenched with water. The organic layer was dried over sodium sulfate and concentrated. The crude was purified by prep LCMS to provide 3-isopropyl-2-(2-methoxypyridin-4-yl)-5-(1-((2-methyl-1H-imidazol-4-yl)methyl) piperidin-4-yl)-1H-indole (25 mg, 39.4%). LCMS retention time 1.58 min [E]. MS (E−) m/z: 444.3 (M+H).

Example 521

2-(dimethylamino)-1-(4-(3-isopropyl-2-(2-methoxypyridin-4-yl)-1H-indol-5-yl)piperidin-1-yl)ethan-1-one

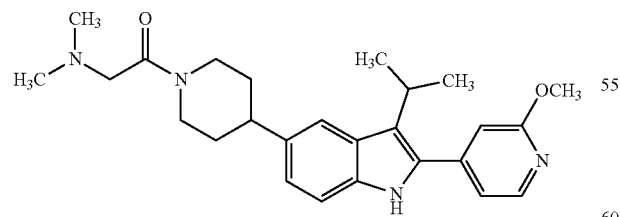

(521)

2-(Dimethylamino)-1-(4-(3-isopropyl-2-(2-methoxypyridin-4-yl)-1H-indol-5-yl)piperidin-1-yl)ethanone was prepared as described in Example 501 using 3-isopropyl-2-(2-methoxypyridin-4-yl)-5-(piperidin-4-yl)-1H-indole as a starting intermediate (11 mg, 22.9% yield). LCMS retention time 1.79 min [E]. MS (E−) m/z: 435.3 (M+H).

Example 522

2-(dimethylamino)-1-(4-(2-(2-fluoropyridin-4-yl)-3-isopropyl-1H-indol-5-yl)piperidin-1-yl)ethan-1-one

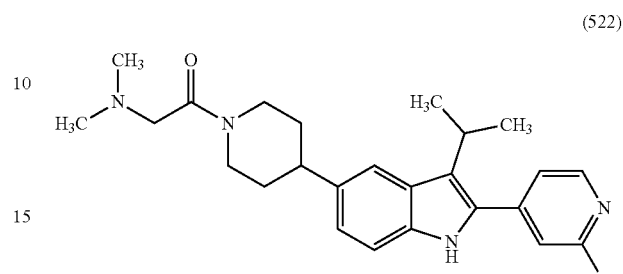

(522)

Intermediate 522A: Tert-Butyl 4-(2-(2-fluoropyridin-4-yl)-3-isopropyl-1H-indol-5-yl) piperidine-1-carboxylate

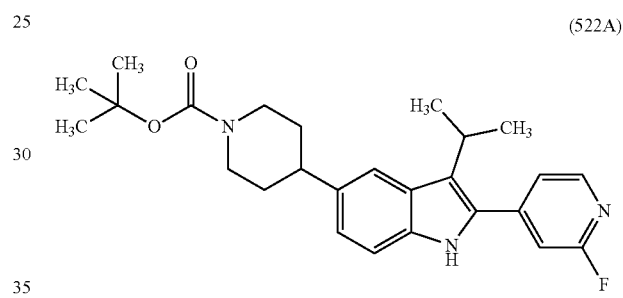

(522A)

To a mixture of tert-butyl 4-(2-bromo-3-isopropyl-1H-indol-5-yl)piperidine-1-carboxylate (0.15 g, 0.356 mmol), pyridin-4-ylboronic acid (0.048 g, 0.392 mmol) and cesium carbonate (0.290, 0.890 mmol) in a 25 ml round bottom flask were added dioxane (3 mL) and water (1 mL). The resulting reaction mixture was degasified for 10 min, Tetrakis (0.021 g, 0.018 mmol) was added, and the mixture was degasified again for 5 min. The resulting reaction mixture was heated at 95° C. for 12 h. The reaction mixture was diluted with EtOAc (50 mL), poured into a separatory funnel and washed with water (2×50 mL) and saturated aqueous NaCl solution (50 mL), dried (Na₂SO₄), and filtered. The filtrate was concentrated in vacuum to give crude product. The crude material was washed with diethyl ether (5×5 mL) to remove catalytic impurities. The material was concentrated to afford 4-(2-(2-fluoropyridin-4-yl)-3-isopropyl-1H-indol-5-yl) piperidine-1-carboxylate as an off white solid product (0.13 g, 83%). LCMS retention time 2.52 min [C]. MS (E−) m/z: 438.3 (M+H).

Intermediate 522B: 2-(2-fluoropyridin-4-yl)-3-isopropyl-5-(piperidin-4-yl)-1H-indole

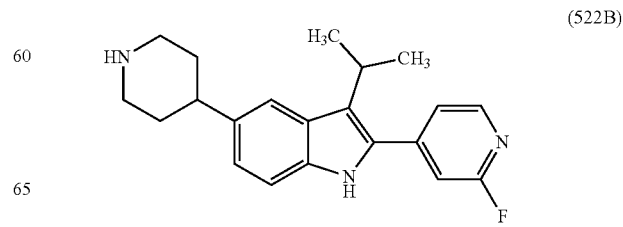

(522B)

Tert-butyl 4-(2-(2-fluoropyridin-4-yl)-3-isopropyl-1H-indol-5-yl)piperidine-1-carboxylate (0.13 g, 0.297 mmol) was dissolved in DCM (2 mL). Next, 4 M hydrochloric acid in dioxane (3.66 mL, 14.63 mmol) was added to the reaction solution. The reaction mixture was stirred at 25° C. for 60 minutes. The solvent was removed under vacuum and the resulting yellow colored solid product was washed with diethyl ether to remove nonpolar impurities to afford 2-(2-fluoropyridin-4-yl)-3-isopropyl-5-(piperidin-4-yl)-1H-indole as a yellow product (0.1 g, 100% yield). LCMS retention time 2.38 min [A]. MS (E−) m/z: 338.3 (M+H).

Intermediate 522C: 2-chloro-1-(4-(2-(2-fluoropyridin-4-yl)-3-isopropyl-1H-indol-5-yl) piperidin-1-yl) ethan-1-one

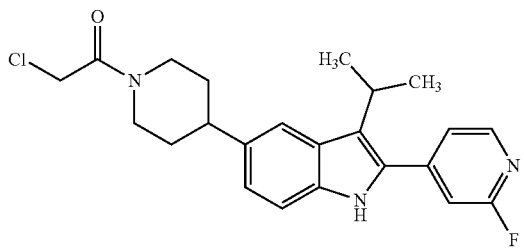

(522C)

To a solution of 2-(2-fluoropyridin-4-yl)-3-isopropyl-5-(piperidin-4-yl)-1H-indole (0.1 g, 0.296 mmol) and DIPEA (0.129 mL, 0.741 mmol) in THF (2 mL) solvent was added chloroacetyl chloride (0.037 g, 0.326 mmol) drop wise to the reaction mixture at 0° C. The color slowly changed from pale yellow to brown. The reaction mixture was allowed to stir at 25° C. for 2 hours. The reaction mass was quenched with water (10 mL) and extracted with DCM (2×25 mL). The combined organic layer was dried over $Na_2SO_4$ and concentrated to give 2-chloro-1-(4-(2-(2-fluoropyridin-4-yl)-3-isopropyl-1H-indol-5-yl)piperidin-1-yl)ethanone as a pale yellow solid (0.095 g, 77% yield). LCMS retention time 1.17 min [B]. MS (E−) m/z: 414.3 (M+H).

Example 522

To a stirred solution of 2-chloro-1-(4-(2-(2-fluoropyridin-4-yl)-3-isopropyl-1H-indol-5-yl)piperidin-1-yl)ethanone (0.03 g, 0.072 mmol) and DIPEA (0.019 mL, 0.109 mmol) in THF (1 mL) was added dimethylamine (3.92 mg, 0.087 mmol). The reaction mixture was stirred at 25° C. for 3 hours. The reaction mixture was diluted with EtOAc (20 mL) and washed with water (2×10 mL), dried over ($Na_2SO_4$), and filtered. The filtrate was concentrated under vacuum to give crude product. The product was washed with a mixture of DCM (2 ml) and diethyl ether (3×5 ml) to remove nonpolar impurities. The solid material was lyophilized to afford pale yellow solid product (17 mg, 55.5% yield). LCMS retention time 2.55 min [A]. MS (E−) m/z: 423.3 (M+H). HPLC Method: K Wavelength: 254 nm, Rt min: 7.17, Wavelength: 220 nm, Rt min: 7.17.

Example 523

2-(2-fluoropyridin-4-yl)-3-isopropyl-5-(1'-methyl-[1,4'-bipiperidin]-4-yl)-1H-indole

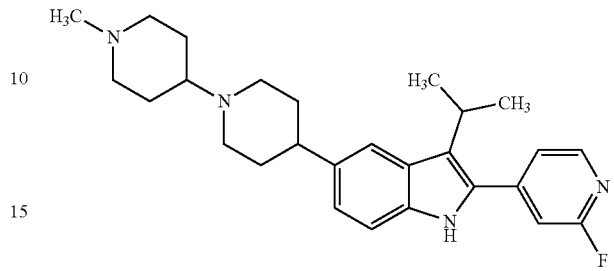

(523)

To a solution of 2-(2-fluoropyridin-4-yl)-3-isopropyl-5-(piperidin-4-yl)-1H-indole (0.04 g, 0.119 mmol) and 1-methylpiperidin-4-one (0.020 g, 0.178 mmol) in methanol (2 mL) was added titanium (IV) isopropoxide (0.084 g, 0.296 mmol). The resulting reaction mixture was stirred under nitrogen at 55° C. for 12 hrs. After reaching a temperature of 25° C., sodium cyanoborohydride (0.015 g, 0.237 mmol) was added and the resulting reaction mixture was heated to 50° C. for 12 hours. The reaction mass was concentrated. The crude material was dissolved in ethyl acetate (5 mL), washed with water (2×10 mL), dried over ($Na_2SO_4$), and filtered. The filtrate was concentrated under vacuum to give crude product. The crude material was purified by reverse phase prep method. Prep HPLC Rt: 9.37. Preparative purification Method: [I], LCMS retention time 1.90 min [A]. MS (E−) m/z: 435.3 (M+H). HPLC Method: K Wavelength: 254 nm. Rt min: 6.04. Wavelength: 220 nm. Rt min: 6.04. HPLC Method: J Wavelength: 254 nm, Rt min: 5.51. Wavelength: 220 nm, Rt min: 5.51.

Example 524

2-(dimethyl amino)-1-(4-(3-isopropyl-2-(pyridin-4-yl)-1H-indol-5-yl)piperidin-1-yl) ethan-1-one

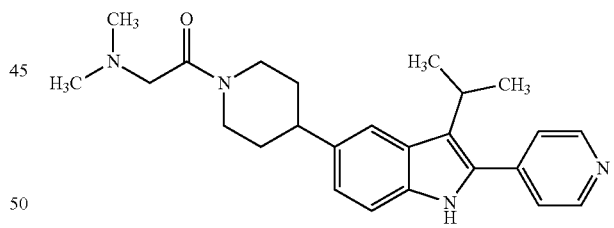

(524)

Intermediate 524A: Tert-Butyl 4-(3-isopropyl-2-(pyridin-4-yl)-1H-indol-5-yl)piperidine-1-carboxylate

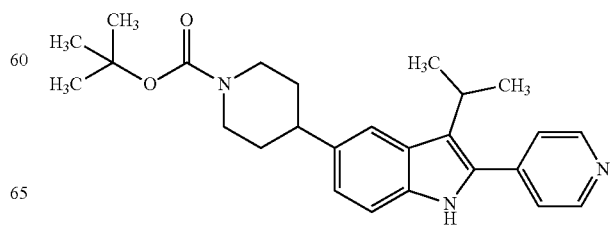

(524A)

Tert-butyl 4-(3-isopropyl-2-(pyridin-4-yl)-1H-indol-5-yl)piperidine-1-carboxylate (0.12 g, 80%) was prepared as described for Intermediate 2F, using tert-butyl 4-(2-bromo-3-isopropyl-1H-indol-5-yl)piperidine-1-carboxylate (0.15 g, 0.356 mmol) and pyridin-4-ylboronic acid (0.048 g, 0.392 mmol) to afford the title compound as an off-white solid. LCMS retention time 2.07 min [C]. MS (E−) m/z: 420.3 (M+H).

Intermediate 524B: 3-isopropyl-5-(piperidin-4-yl)-2-(pyridin-4-yl)-1H-indole

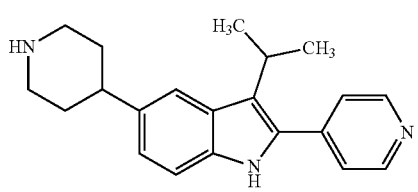

(524B)

3-isopropyl-5-(piperidin-4-yl)-2-(pyridin-4-yl)-1H-indole (0.09 g, 99%) was prepared as described for Example 2 using tert-butyl 4-(3-isopropyl-2-(pyridin-4-yl)-1H-indol-5-yl)piperidine-1-carboxylate (0.12 g, 0.286 mmol) and 4M hydrochloric acid in dioxane (3.66 mL, 14.63 mmol) to afford the title compound as a yellow solid. LCMS retention time 2.25 min [A]. MS (E−) m/z: 320.3 (M+H).

Intermediate 524C: 2-chloro-1-(4-(3-isopropyl-2-(pyridin-4-yl)-1H-indol-5-yl)piperidin-1-yl)ethan-1-one

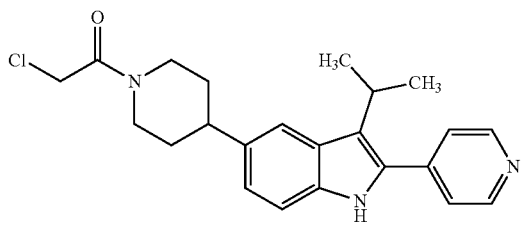

(525C)

2-chloro-1-(4-(3-isopropyl-2-(pyridin-4-yl)-1H-indol-5-yl)piperidin-1-yl) ethanone (0.08 g, 86% yield) was prepared as described for Intermediate 509C using 3-isopropyl-5-(piperidin-4-yl)-2-(pyridin-4-yl)-1H-indole (0.09 g, 0.282 mmol), DIPEA (0.129 mL, 0.741 mmol), chloroacetyl chloride (0.037 g, 0.326 mmol), and THF (2 mL), to afford the title compound as a pale yellow solid. LCMS retention time 1.07 min [B]. MS (E−) m/z: 396.3 (M+H).

Example 524

2-(dimethyl amino)-1-(4-(3-isopropyl-2-(pyridin-4-yl)-1H-indol-5-yl)piperidin-1-yl)ethanone (21 mg, 68.5% yield) was prepared as described in Example 509, using 2-chloro-1-(4-(3-isopropyl-2-(pyridin-4-yl)-1H-indol-5-yl)piperidin-1-yl)ethanone (0.03 g, 0.076 mmol) and dimethylamine (3.92 mg, 0.087 mmol) to afford the title compound as a pale yellow solid. HPLC Method: J Wavelength: 254 nm. Rt min: 9.51. Wavelength: 220 nm. Rt min: 9.51. LCMS retention time 2.31 min [H]. MS (E−) m/z: 405.3 (M+H).

Example 525

3-isopropyl-5-(1'-methyl-[1,4'-bipiperidin]-4-yl)-2-(pyridin-4-yl)-1H-indole

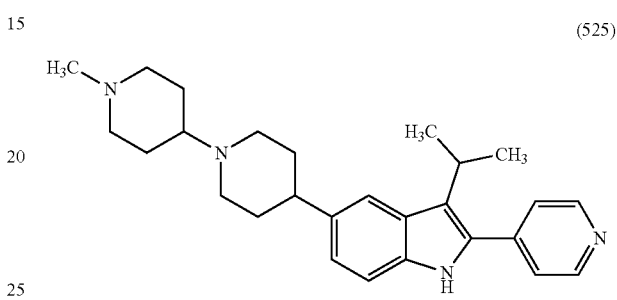

(525)

3-isopropyl-5-(1'-methyl-[1,4'-bipiperidin]-4-yl)-2-(pyridin-4-yl)-1H-indole (14 mg, 26.8%) was prepared as described in Example-23, using 3-isopropyl-5-(piperidin-4-yl)-2-(pyridin-4-yl)-1H-indole (0.04 g, 0.125 mmol) to afford title compound as yellow solid. LCMS retention time 1.74 min [H]. MS (E−) m/z: 417.3 (M+H). Prep HPLC Rt: min: 9.66, Purification Method: I. HPLC Method: K Wavelength: 254 nm. Rt min: 6.84. Wavelength: 220 nm. Rt min: 6.84. HPLC Method: J Wavelength: 254 nm. Rt min: 6.61 Wavelength: 220 nm, Rt min: 6.61.

Example 526

2-(4-(2-(2,6-dimethylpyridin-4-yl)-3-ethyl-1H-indol-5-yl)piperidin-1-yl)-N,N-dimethylacetamide

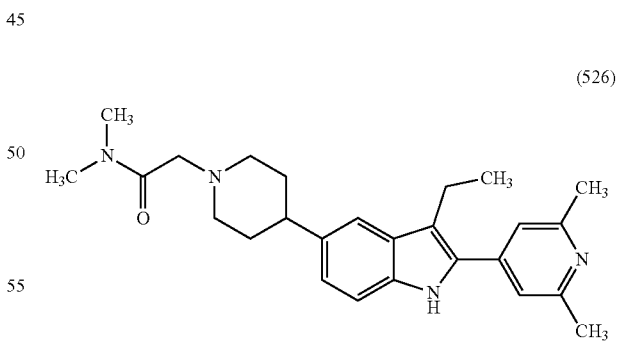

(526)

2-(4-(2-(2,6-dimethylpyridin-4-yl)-3-ethyl-1H-indol-5-yl)piperidin-1-yl)-N,N-dimethylacetamide was prepared as described in Intermediate 1F using 2-(2,6-dimethylpyridin-4-yl)-3-ethyl-5-(piperidin-4-yl)-1H-indole, 2 HCl as the starting intermediate (5 mg, 13.63% yield). LCMS retention time 1.65 min [E]. MS (E−) m/z: 419.3 (M+H).

The following example was prepared according to the general procedure described in Example 526.

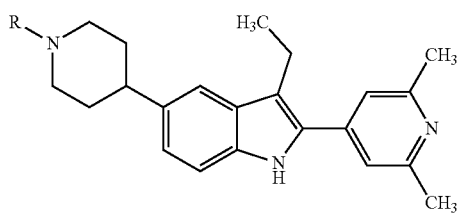

TABLE 26

| Ex. No. | R | LCMS [M + H]⁺ | Rt (min) | Method |
|---|---|---|---|---|
| 527 | —CH₂C(O)NHCH₃ | 405.2 | 1.810 | E |

Example 528

2-(dimethylamino)-1-(4-(2-(2,6-dimethylpyridin-4-yl)-3-ethyl-1H-indol-5-yl)piperidin-1-yl)ethan-1-one (528)

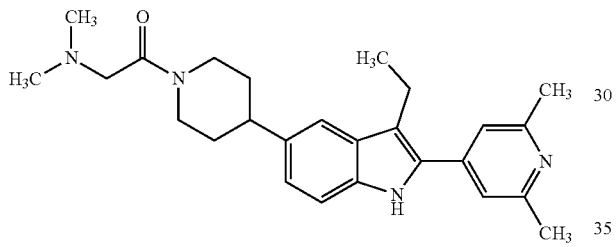

2-(dimethylamino)-1-(4-(2-(2,6-dimethylpyridin-4-yl)-3-ethyl-1H-indol-5-yl) piperidin-1-yl)ethanone was prepared as described in Example 2 using 2-(2,6-dimethylpyridin-4-yl)-3-ethyl-5-(piperidin-4-yl)-1H-indole, HCl as the starting intermediate (11 mg, 32.4% yield). LCMS retention time 1.58 min [E]. MS (E−) m/z: 419.3 (M+H).

The following examples were prepared according to the general procedure described in Example 528.

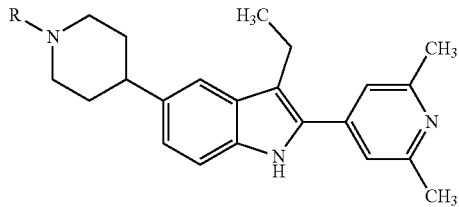

TABLE 27

| Ex. No. | R | LCMS [M + H]⁺ | Rt (min) | Method |
|---|---|---|---|---|
| 529 | —C(O)CH₂NH(CH₃) | 405.3 | 1.065 | E |
| 530 | ![structure] | 459.3 | 1.284 | F |

Example 531

2-(4-(3-(2,2-difluoroethyl)-2-(2,6-dimethylpyridin-4-yl)-1H-indol-5-yl)piperidin-1-yl)-N,N-dimethylacetamide (531)

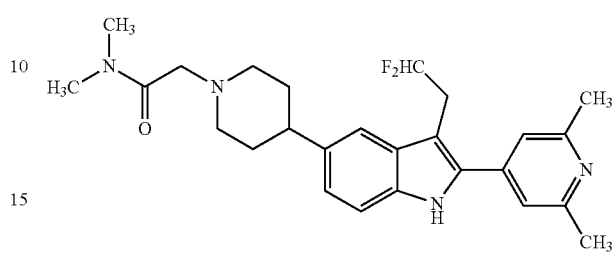

2-(4-(3-(2,2-difluoroethyl)-2-(2,6-dimethylpyridin-4-yl)-1H-indol-5-yl)piperidin-1-yl)-N,N-dimethylacetamide was prepared as described in Example 5 using 3-(2,2-difluoroethyl)-2-(2,6-dimethylpyridin-4-yl)-5-(piperidin-4-yl)-1H-indole hydrochloride as the starting intermediate (0.029 g, 64% yield). LCMS retention time 1.57 min [E]. MS (E−) m/z: 455.4 (M+H).

The following example was prepared according to the general procedure described in Example 531.

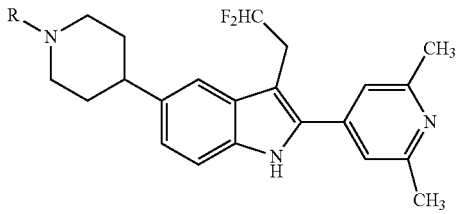

TABLE 28

| Ex. No. | R | LCMS [M + H]+ | Rt (min) | [Method] |
|---|---|---|---|---|
| 532 | —CH₂C(O)NH(CH₃) | 441.2 | 1.735 | E |

Example 533

1-(4-(3-(2,2-difluoroethyl)-2-(2,6-dimethylpyridin-4-yl)-1H-indol-5-yl)piperidin-1-yl)-2-(dimethylamino)ethan-1-one (533)

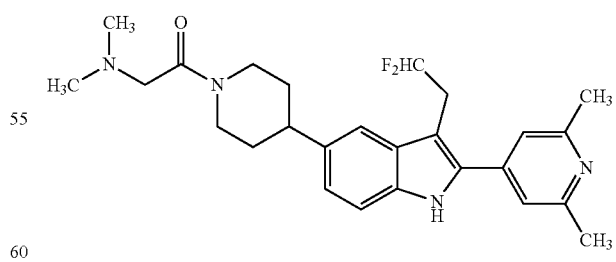

1-(4-(3-(2,2-difluoroethyl)-2-(2,6-dimethylpyridin-4-yl)-1H-indol-5-yl)piperidin-1-yl)-2-(dimethylamino)ethanone was prepared as described in Example 2 using 3-(2,2-difluoroethyl)-2-(2,6-dimethylpyridin-4-yl)-5-(piperidin-4-yl)-1H-indole hydrochloride as the starting intermediate (1.3 mg, 2.87% yield). LCMS retention time 1.52 min [E]. MS (E−) m/z: 455.3 (M+H).

The following example was prepared according to the general procedure described in Example 533.

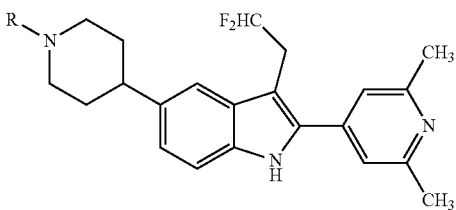

TABLE 29

| Ex. No. | R | LCMS [M + H]+ | Rt (min) | Method |
|---|---|---|---|---|
| 534 | 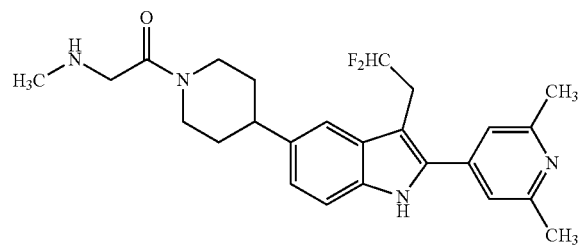 | 495.2 | 1.629 | E |

Example 535

1-(4-(3-(2,2-difluoroethyl)-2-(2,6-dimethylpyridin-4-yl)-1H-indol-5-yl)piperidin-1-yl)-2-(methylamino)ethan-1-one (535)

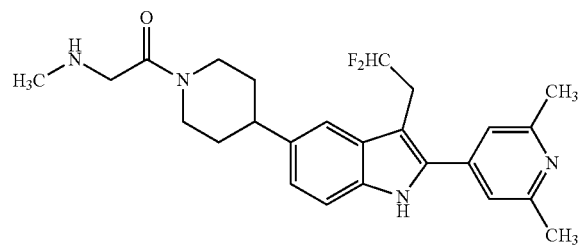

Intermediate 535A: Tert-Butyl (2-(4-(3-(2,2-difluoroethyl)-2-(2,6-dimethylpyridin-4-yl)-1H-indol-5-yl)piperidin-1-yl)-2-oxoethyl)(methyl)carbamate (535A)

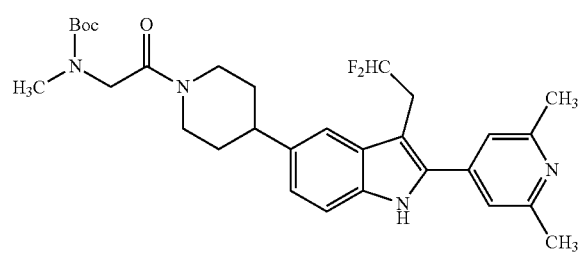

Tert-butyl (2-(4-(3-(2,2-difluoroethyl)-2-(2,6-dimethylpyridin-4-yl)-1H-indol-5-yl)piperidin-1-yl)-2-oxoethyl)(methyl)carbamate was prepared as described in Example 2 using 3-(2,2-difluoroethyl)-2-(2,6-dimethylpyridin-4-yl)-5-(piperidin-4-yl)-1H-indole hydrochloride as the starting intermediate (60 mg, 90% yield). LCMS retention time 1.17 min [B]. MS (E−) m/z: 541.2 (M+H).

Example 535

1-(4-(3-(2,2-difluoroethyl)-2-(2,6-dimethylpyridin-4-yl)-1H-indol-5-yl)piperidin-1-yl)-2-(methylamino)ethanone was prepared as described in Example 2 using tert-butyl (2-(4-(3-(2,2-difluoroethyl)-2-(2,6-dimethylpyridin-4-yl)-1H-indol-5-yl)piperidin-1-yl)-2-oxoethyl)(methyl)carbamate as the starting intermediate (18 mg, 36.5% yield). LCMS retention time 1.41 min [E]. MS (E−) m/z: 441.3 (M+H).

Example 536

3-(2,2-difluoroethyl)-2-(2,6-dimethylpyridin-4-yl)-5-(1-isopropylpiperidin-4-yl)-1H-indole (536)

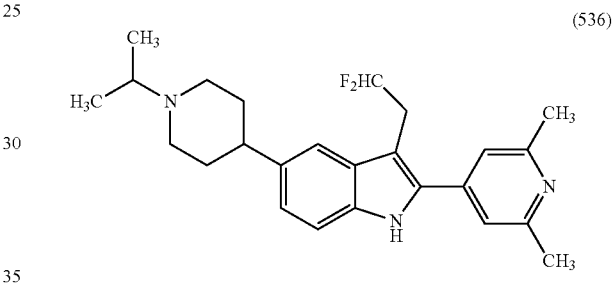

3-(2,2-difluoroethyl)-2-(2,6-dimethylpyridin-4-yl)-5-(1-isopropylpiperidin-4-yl)-1H-indole was prepared as described in Example 3 using 3-(2,2-difluoroethyl)-2-(2,6-dimethylpyridin-4-yl)-5-(piperidin-4-yl)-1H-indole hydrochloride as the starting intermediate (23 mg, 53.2% yield). LCMS retention time 1.44 min [E]. MS (E−) m/z: 412.3 (M+H).

The following examples were prepared according to the general procedure described in Example 536.

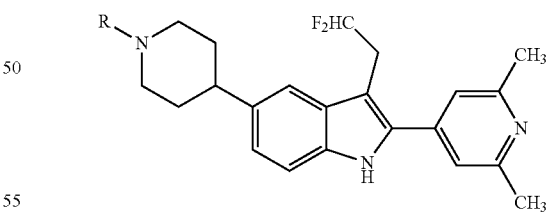

TABLE 30

| Ex. No. | Structure | LCMS [M + H] | Rt (min) | Method |
|---|---|---|---|---|
| 537 | 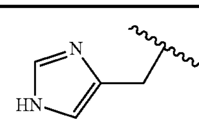 | 450.2 | 1.327 | E |

TABLE 30-continued

| Ex. No. | Structure | LCMS [M + H] | Rt (min) | Method |
|---|---|---|---|---|
| 538 | H₃C–(imidazole)–CH₂– | 464.2 | 1.359 | E |
| 539 | —CH₃ | 384.2 | 1.277 | E |
| 540 | (H₃C)₂CH–N(piperidine)– | 495.3 | 1.492 | E |

Example 541

2-(4-(3-(2,2-difluoroethyl)-2-(2,6-dimethylpyridin-4-yl)-1H-indol-5-yl)piperidin-1-yl)-N-methylethan-1-amine (541)

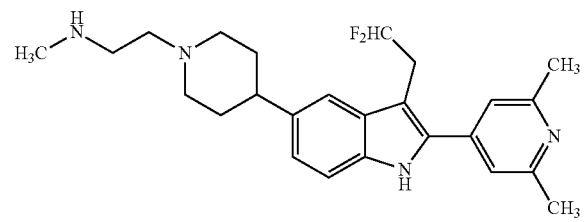

Intermediate 541A: Tert-Butyl (2-(4-(3-(2,2-difluoroethyl)-2-(2,6-dimethylpyridin-4-yl)-1H-indol-5-yl)piperidin-1-yl)ethyl)carbamate (541A)

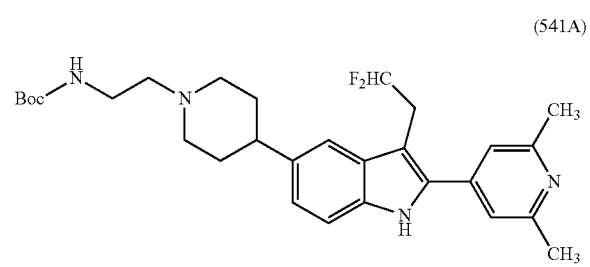 [SMILES: Cc1cc(-c2[nH]c3ccc(C4CCN(CCNC(=O)OC(C)(C)C)CC4)cc3c2CC(F)F)cc(C)n1]

Tert-butyl (2-(4-(3-(2,2-difluoroethyl)-2-(2,6-dimethylpyridin-4-yl)-1H-indol-5-yl)piperidin-1-yl)ethyl)(methyl)carbamate was prepared as described in Example 3 using 3-(2,2-difluoroethyl)-2-(2,6-dimethylpyridin-4-yl)-5-(piperidin-4-yl)-1H-indole hydrochloride as the starting intermediate (60 mg, 92% yield). LCMS retention time 1.21 min [B]. MS (E−) m/z: 527.3 (M+H).

Example 541

2-(4-(3-(2,2-difluoroethyl)-2-(2,6-dimethylpyridin-4-yl)-1H-indol-5-yl)piperidin-1-yl)-N-methylethanamine was prepared as described in Example 2 using tert-butyl (2-(4-(3-(2,2-difluoroethyl)-2-(2,6-dimethylpyridin-4-yl)-1H-indol-5-yl)piperidin-1-yl)ethyl) (methyl)carbamate as the starting intermediate (12 mg, 28.7% yield). LCMS retention time 1.49 min [E]. MS (E−) m/z: 427.3 (M+H).

Example 542

5-(1-((4-chlorophenyl)sulfonyl)piperidin-4-yl)-3-isopropyl-2-(2-methylpyridin-4-yl)-1H-indole (542)

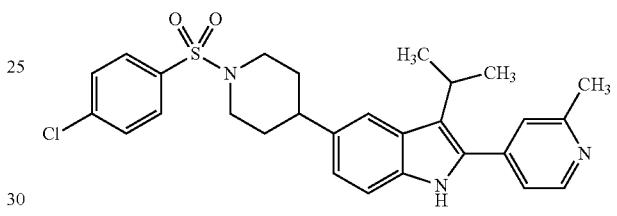

3-Isopropyl-2-(2-methylpyridin-4-yl)-5-(piperidin-4-yl)-1H-indole (0.015 g, 0.045 mmol) was dissolved in dichloromethane (0.500 mL) and added to a vial containing 4-chlorobenzenesulfonyl chloride (0.016 g, 0.090 mmol). N,N-diisopropylethylamine (0.039 mL, 0.225 mmol) was added to the reaction mixture. The reaction mixture was stirred at room temperature for 16 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-100% B over 15 minutes, then a 5-minute hold at 100% B; Flow: 20 mL/min. Fractions containing the desired product were combined and dried via centrifugal evaporation to afford 5-(1-((4-chlorophenyl)sulfonyl)piperidin-4-yl)-3-isopropyl-2-(2-methylpyridin-4-yl)-1H-indole (0.013 g, 57% yield). LCMS retention time 1.89 min [QC-TFA]. MS (E−) m/z: 508.1 (M+H).

The following examples were prepared according to the general procedure described in Example 542.

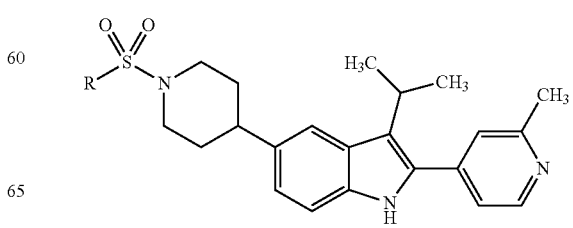

TABLE 31

| Ex. No. | R | LCMS [M + H] | Rt (min) | Method |
|---|---|---|---|---|
| 543 | (3-pyridyl) | 475.4 | 1.41 | QC-TFA |
| 544 | —CH(CH₃)₂ | 440.3 | 1.53 | QC-TFA |
| 545 | —CH₂CH₂CH₃ | 440.2 | 1.56 | QC-TFA |
| 546 | —CH₂CF₃ | 480.0 | 1.61 | QC-TFA |
| 547 | phenyl | 474.2 | 1.71 | QC-TFA |
| 548 | —CH₂CH(CH₃)₂ | 454.1 | 1.69 | QC-TFA |
| 549 | —CH₂CH₃ | 426.2 | 1.41 | QC-TFA |
| 550 | —CH₃ | 412.3 | 1.28 | QC-TFA |
| 551 | 4-fluorophenyl | 492.1 | 1.75 | QC-TFA |
| 552 | 4-acetamidophenyl | 531.3 | 1.40 | QC-TFA |
| 553 | 1,2-dimethylimidazol-4-yl | 492.3 | 1.15 | QC-TFA |
| 554 | 4-methylphenyl | 488.3 | 1.81 | QC-TFA |
| 555 | cyclopropyl | 438.3 | 1.45 | QC-TFA |
| 556 | benzyl | 488.3 | 1.69 | QC-TFA |

Example 557 p-Tolyl 4-(3-isopropyl-2-(2-methylpyridin-4-yl)-1H-indol-5-yl)piperidine-1-carboxylate

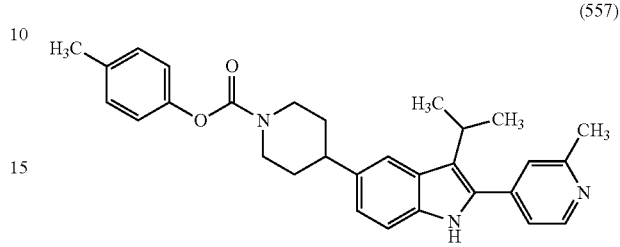

(557)

3-Isopropyl-2-(2-methylpyridin-4-yl)-5-(piperidin-4-yl)-1H-indole (0.015 g, 0.045 mmol) was dissolved in dichloromethane (0.500 mL) and added to a vial containing p-tolyl carbonochloridate (0.015 g, 0.090 mmol). N,N-diisopropylethylamine (0.039 mL, 0.225 mmol) was added to the reaction mixture. The reaction mixture was stirred at room temperature for 4 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-100% B over 15 minutes, then a 5-minute hold at 100% B; Flow: 20 mL/min. Fractions containing the desired product were combined and dried via centrifugal evaporation to afford p-tolyl 4-(3-isopropyl-2-(2-methylpyridin-4-yl)-1H-indol-5-yl)piperidine-1-carboxylate (0.002 g, 8% yield). LCMS retention time 1.92 min [QC-TFA]. MS (E−) m/z: 468.1 (M+H).

The following examples were prepared according to the general procedure described in Example 557.

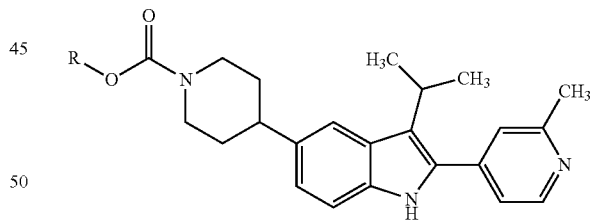

TABLE 32

| Ex. No. | R | LCMS [M + H] | Rt (min) | Method |
|---|---|---|---|---|
| 558 | —CH₂CH(CH₃)₂ | 434.3 | 1.87 | QC-TFA |
| 559 | —CH(CH₃)₂ | 420.3 | 1.73 | QC-TFA |
| 560 | —CH₂CH₃ | 406.3 | 1.60 | QC-TFA |
| 561 | —CH₂CH₂OCH₃ | 436.3 | 1.44 | QC-TFA |
| 562 | —CH₃ | 392.3 | 1.53 | QC-TFA |

The following examples were prepared in a similar manner to the above examples using the general method of Example 97.

TABLE 33

| Ex. No. | Structure | LCMS MH+ | Rt (min) | HPLC Method |
|---|---|---|---|---|
| 563 | 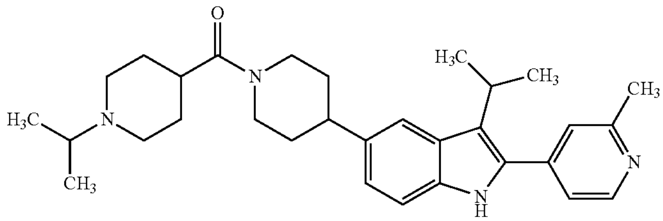 [SMILES: Cc1cc(-c2[nH]c3ccc(C4CCN(C(=O)C5CCN(C(C)C)CC5)CC4)cc3c2C(C)C)ccn1] | 487.2 | 0.95 | QC-TFA |
| 564 | 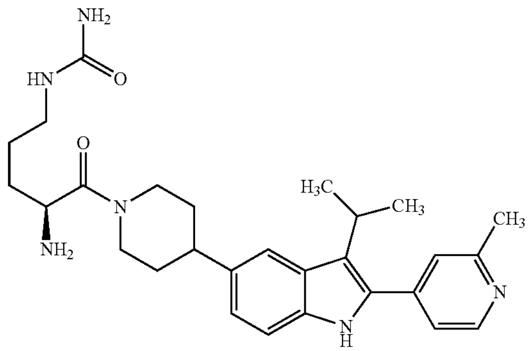 [SMILES: Cc1cc(-c2[nH]c3ccc(C4CCN(C(=O)[C@@H](N)CCCNC(N)=O)CC4)cc3c2C(C)C)ccn1] | 491.3 | 1.07 | QC-AA |
| 566 | 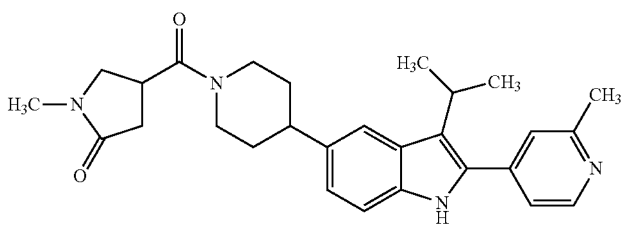 | 459.1 | 1.43 | QC-AA |
| 567 | 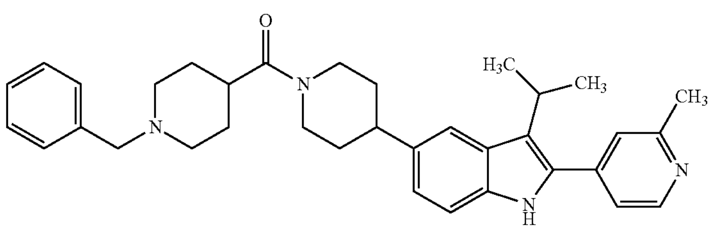 [SMILES: Cc1cc(-c2[nH]c3ccc(C4CCN(C(=O)C5CCN(Cc6ccccc6)CC5)CC4)cc3c2C(C)C)ccn1] | 535.1 | 1.62 | QC-AA |
| 568 | 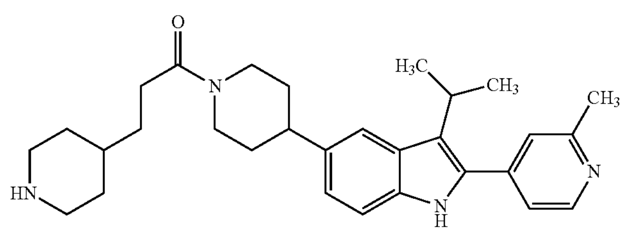 [SMILES: Cc1cc(-c2[nH]c3ccc(C4CCN(C(=O)CCC5CCNCC5)CC4)cc3c2C(C)C)ccn1] | 473.1 | 1.27 | QC-AA |
| 569 | 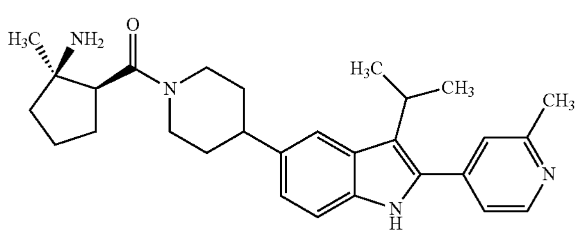 [SMILES: Cc1cc(-c2[nH]c3ccc(C4CCN(C(=O)[C@H]5CCC[C@@]5(C)N)CC4)cc3c2C(C)C)ccn1] | 459.3 | 1.0 | QC-TFA |

TABLE 33-continued

| Ex. No. | Structure | LCMS MH+ | Rt (min) | HPLC Method |
|---|---|---|---|---|
| 570 | 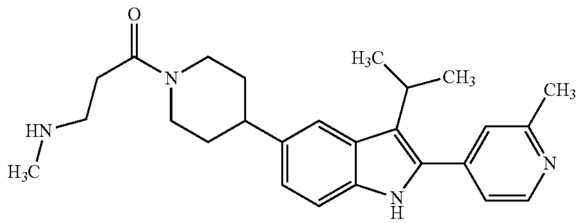 | 419.1 | 1.18 | QC-AA |
| 571 | 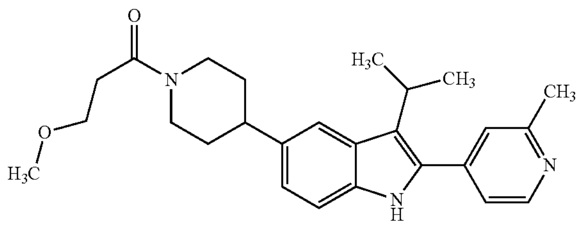 | 420.1 | 1.6 | QC-AA |
| 572 | 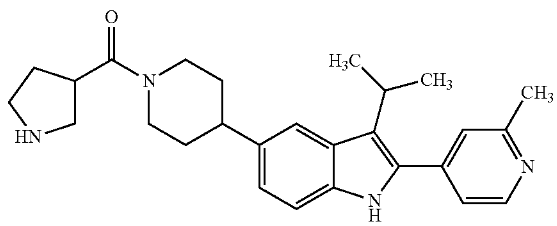 [SMILES: Cc1cc(-c2[nH]c3ccc(C4CCN(C(=O)C5CCNC5)CC4)cc3c2C(C)C)ccn1] | 431.3 | 0.85 | QC-TFA |
| 573 | 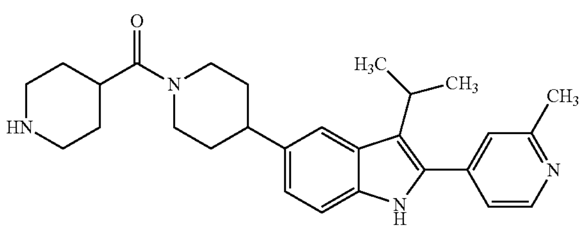 [SMILES: Cc1cc(-c2[nH]c3ccc(C4CCN(C(=O)C5CCNCC5)CC4)cc3c2C(C)C)ccn1] | 445.2 | 0.87 | QC-TFA |
| 574 | 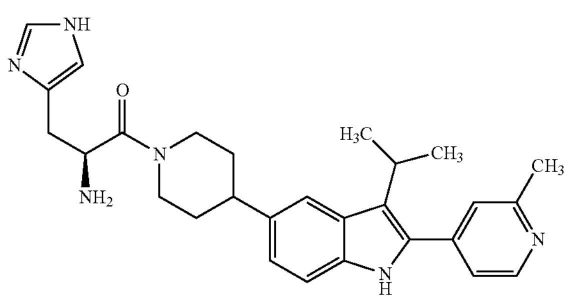 [SMILES: Cc1cc(-c2[nH]c3ccc(C4CCN(C(=O)[C@@H](N)Cc5c[nH]cn5)CC4)cc3c2C(C)C)ccn1] | 471.2 | 0.68 | QC-TFA |
| 575 | 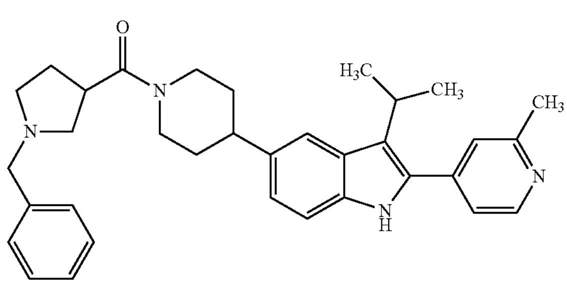 [SMILES: Cc1cc(-c2[nH]c3ccc(C4CCN(C(=O)C5CCN(Cc6ccccc6)C5)CC4)cc3c2C(C)C)ccn1] | 521.2 | 1.58 | QC-AA |

TABLE 33-continued

| Ex. No. | Structure | LCMS MH+ | Rt (min) | HPLC Method |
|---|---|---|---|---|
| 576 | 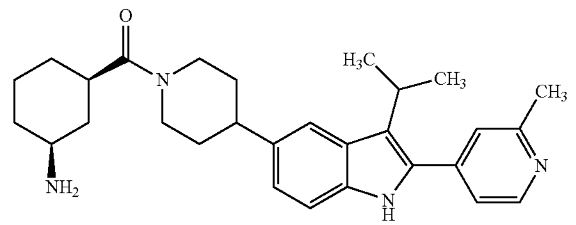 [SMILES: Cc1cc(-c2[nH]c3ccc(C4CCN(C(=O)[C@@H]5CCC[C@H](N)C5)CC4)cc3c2C(C)C)ccn1] | 459.1 | 1.29 | QC-AA |
| 577 | 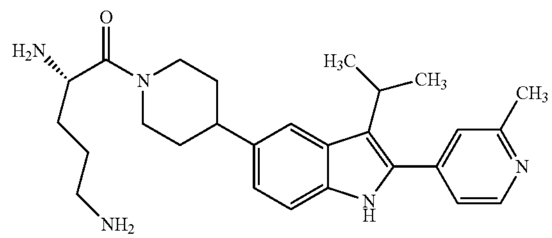 [SMILES: Cc1cc(-c2[nH]c3ccc(C4CCN(C(=O)[C@@H](N)CCCN)CC4)cc3c2C(C)C)ccn1] | 448.1 | 1.01 | QC-AA |
| 578 | 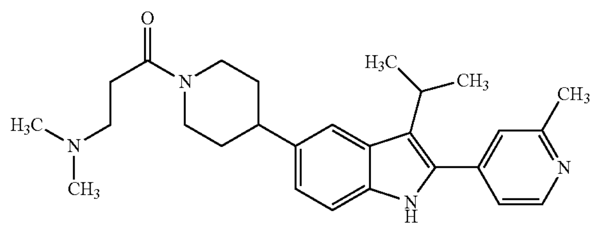 | 433.3 | 0.89 | QC-TFA |
| 579 | 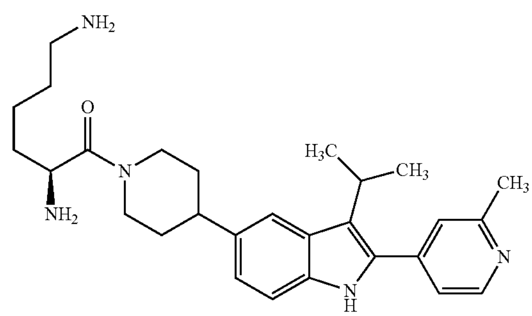 [SMILES: Cc1cc(-c2[nH]c3ccc(C4CCN(C(=O)[C@@H](N)CCCCN)CC4)cc3c2C(C)C)ccn1] | 462.3 | 0.69 | QC-TFA |
| 580 | 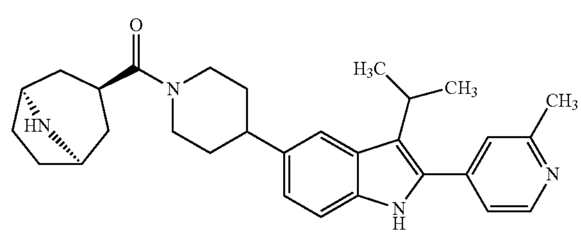 [SMILES: Cc1cc(-c2[nH]c3ccc(C4CCN(C(=O)[C@H]5C[C@H]6CC[C@@H](C5)N6)CC4)cc3c2C(C)C)ccn1] | 471.3 | 1 | QC-TFA |
| 581 | 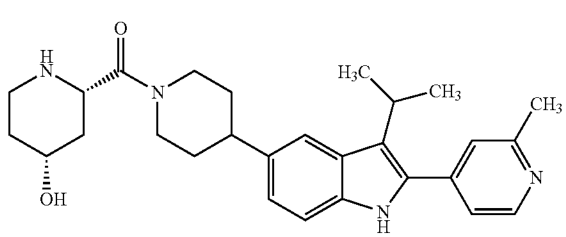 [SMILES: Cc1cc(-c2[nH]c3ccc(C4CCN(C(=O)[C@@H]5C[C@H](O)CCN5)CC4)cc3c2C(C)C)ccn1] | 461.1 | 0.8 | QC-TFA |

TABLE 33-continued

| Ex. No. | Structure | LCMS MH+ | Rt (min) | HPLC Method |
|---|---|---|---|---|
| 582 | 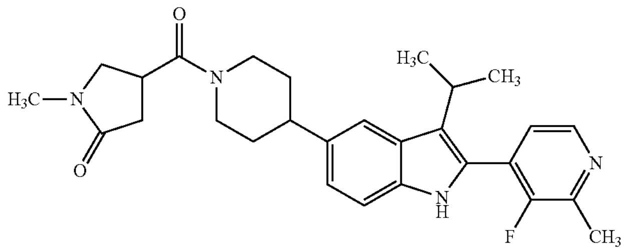 | 477.4 | 1.27 | QC-TFA |
| 583 | 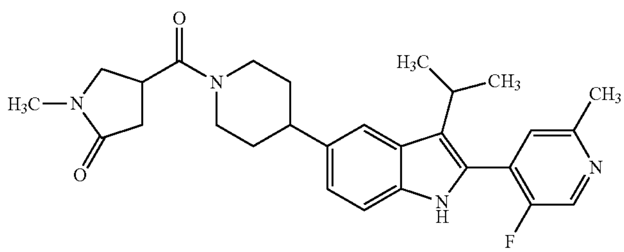 | 477.3 | 1.73 | QC-AA |
| 584 | 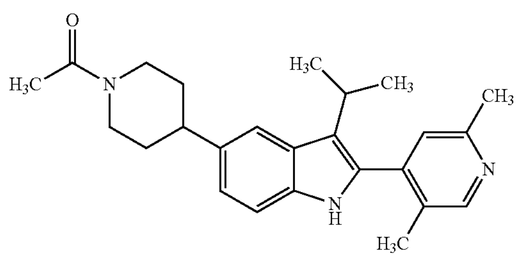 [SMILES: CC(=O)N1CCC(c2ccc3[nH]c(-c4cc(C)ncc4C)c(C(C)C)c3c2)CC1] | 390.1 | 1.74 | QC-AA |
| 585 | 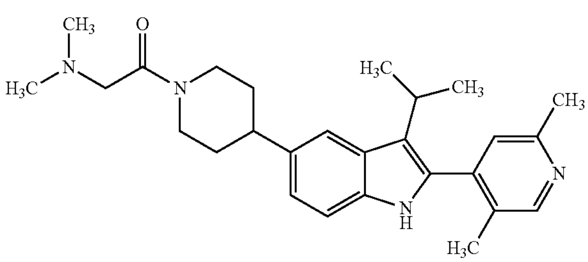 | 432.9 | 0.85 | QC-TFA |
| 586 | 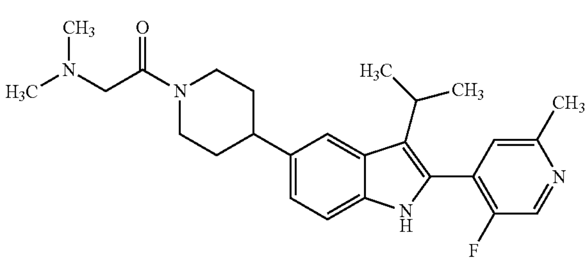 | 437.4 | 1.48 | QC-AA |

TABLE 33-continued

| Ex. No. | Structure | LCMS MH+ | Rt (min) | HPLC Method |
|---|---|---|---|---|
| 587 | 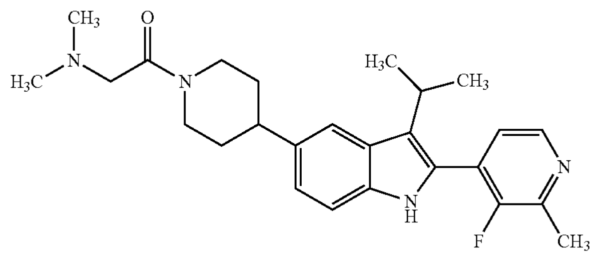 | 437.1 | 1.06 | QC-TFA |
| 588 | 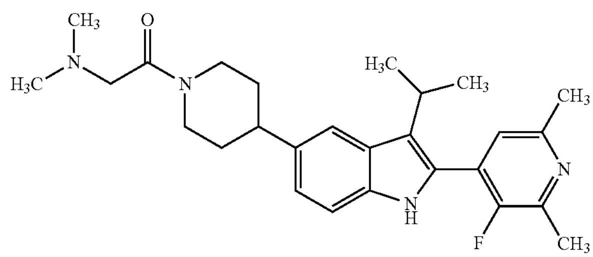 | 451.4 | 1.08 | QC-TFA |
| 589 | 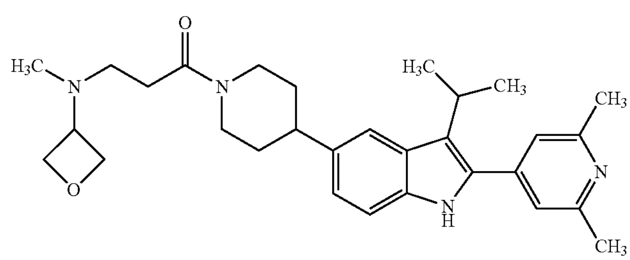 | 489.3 | 1.66 | QC-AA |
| 590 | 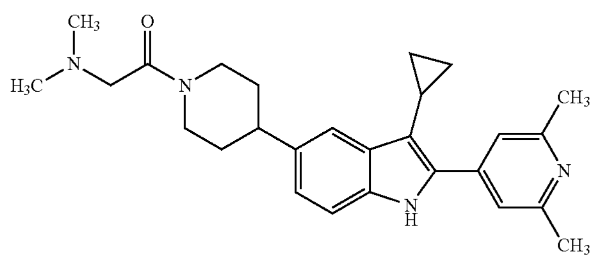 | 431.4 | 0.98 | QC-TFA |
| 591 | 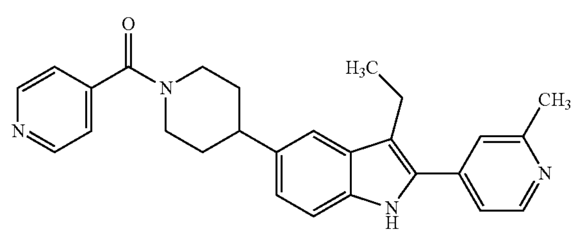 [SMILES: CCc1c(-c2ccnc(C)c2)[nH]c2ccc(C3CCN(C(=O)c4ccncc4)CC3)cc12] | 425.2 | 0.9 | QC-TFA |
| 592 | 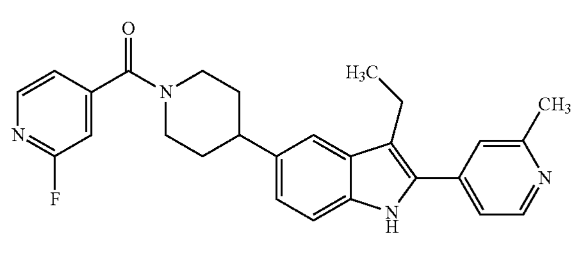 [SMILES: CCc1c(-c2ccnc(C)c2)[nH]c2ccc(C3CCN(C(=O)c4ccnc(F)c4)CC3)cc12] | 443.3 | 1.23 | QC-AA |

TABLE 33-continued

| Ex. No. | Structure | LCMS MH+ | Rt (min) | HPLC Method |
|---|---|---|---|---|
| 593 | 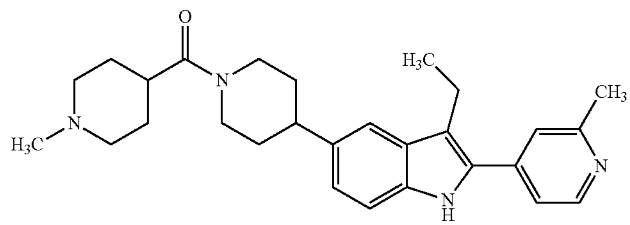 | 445.2 | 0.81 | QC-TFA |
| 594 | 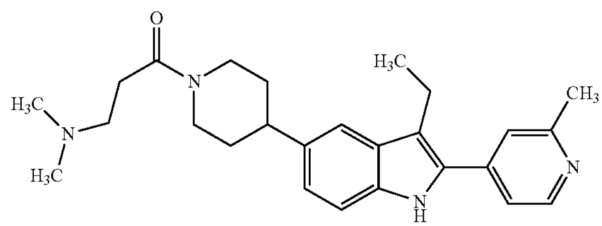 | 419.2 | 0.8 | QC-TFA |
| 595 | 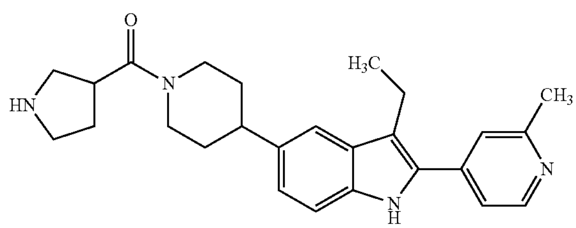 [SMILES: CCc1c(-c2ccnc(C)c2)[nH]c2ccc(C3CCN(C(=O)C4CCNC4)CC3)cc12] | 417.1 | 0.816 | QC-TFA |
| 596 | 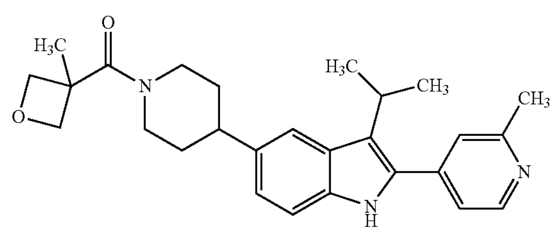 [SMILES: Cc1cc(-c2[nH]c3ccc(C4CCN(C(=O)C5(C)COC5)CC4)cc3c2C(C)C)ccn1] | 432.1 | 1.209 | QC-TFA |
| 597 | 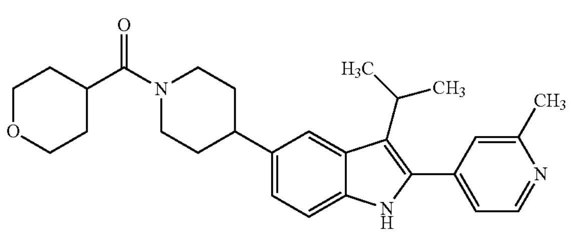 [SMILES: Cc1cc(-c2[nH]c3ccc(C4CCN(C(=O)C5CCOCC5)CC4)cc3c2C(C)C)ccn1] | 446.1 | 1.265 | QC-TFA |
| 598 | 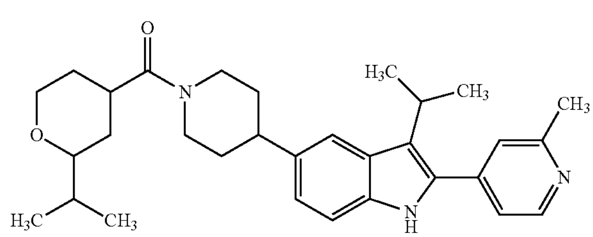 [SMILES: Cc1cc(-c2[nH]c3ccc(C4CCN(C(=O)C5CCOC(C(C)C)C5)CC4)cc3c2C(C)C)ccn1] | 488.1 | 1.652 | QC-TFA |

TABLE 33-continued
| Ex. No. | Structure | LCMS MH+ | Rt (min) | HPLC Method |
|---|---|---|---|---|
| 599 | 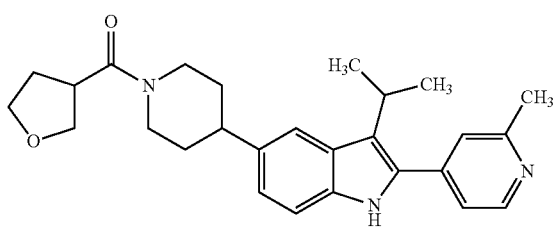 [SMILES: Cc1cc(-c2[nH]c3ccc(C4CCN(C(=O)C5CCOC5)CC4)cc3c2C(C)C)ccn1] | 432.1 | 1.236 | QC-TFA |
| 600 | 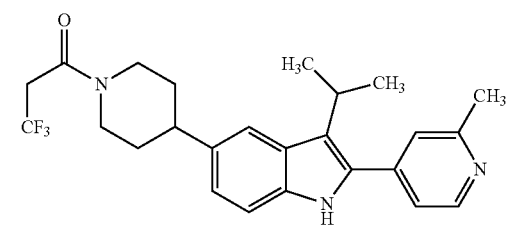 [SMILES: Cc1cc(-c2[nH]c3ccc(C4CCN(C(=O)CC(F)(F)F)CC4)cc3c2C(C)C)ccn1] | 444.1 | 1.433 | QC-TFA |
| 601 | 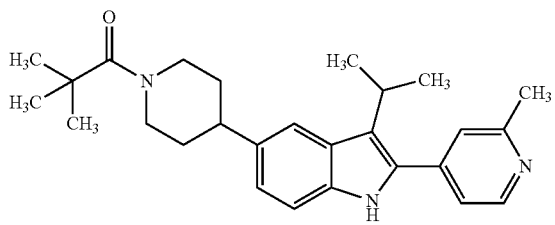 [SMILES: Cc1cc(-c2[nH]c3ccc(C4CCN(C(=O)C(C)(C)C)CC4)cc3c2C(C)C)ccn1] | 418.1 | 1.603 | QC-TFA |
| 602 | 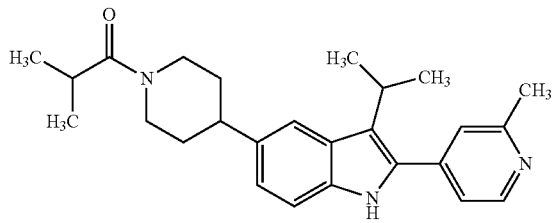 [SMILES: Cc1cc(-c2[nH]c3ccc(C4CCN(C(=O)C(C)C)CC4)cc3c2C(C)C)ccn1] | 404.1 | 1.442 | QC-TFA |
| 603 | 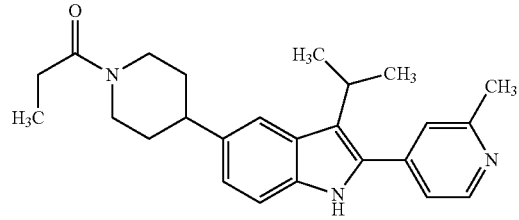 [SMILES: CCC(=O)N1CCC(c2ccc3[nH]c(-c4ccnc(C)c4)c(C(C)C)c3c2)CC1] | 390.2 | 1.323 | QC-TFA |
| 604 | 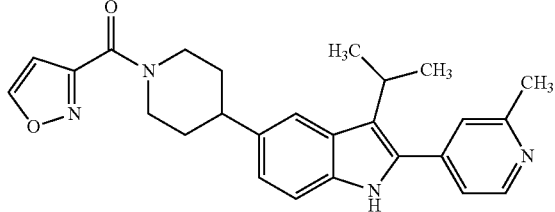 [SMILES: Cc1cc(-c2[nH]c3ccc(C4CCN(C(=O)c5ccon5)CC4)cc3c2C(C)C)ccn1] | 429 | 1.329 | QC-TFA |

TABLE 33-continued
| Ex. No. | Structure | LCMS MH+ | Rt (min) | HPLC Method |
|---|---|---|---|---|
| 605 | 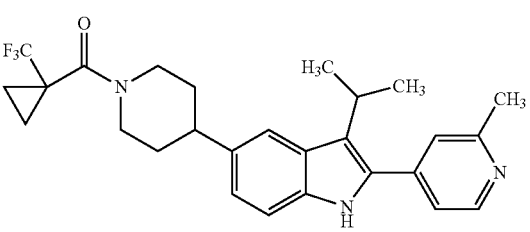 | 470 | 1.561 | QC-TFA |
| 606 | 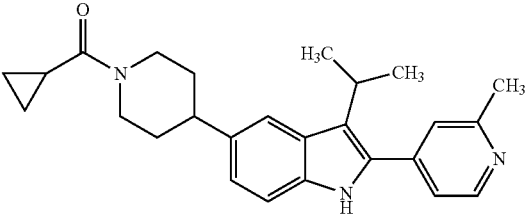 [SMILES: Cc1cc(-c2[nH]c3ccc(C4CCN(C(=O)C5CC5)CC4)cc3c2C(C)C)ccn1] | 402.2 | 1.386 | QC-TFA |
| 607 | 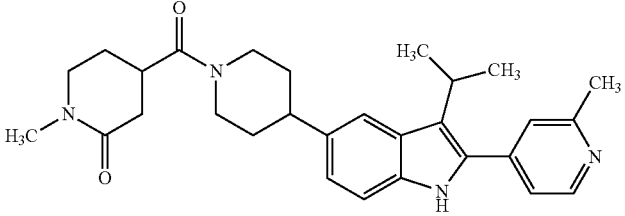 | 473.1 | 1.128 | QC-TFA |
| 608 | 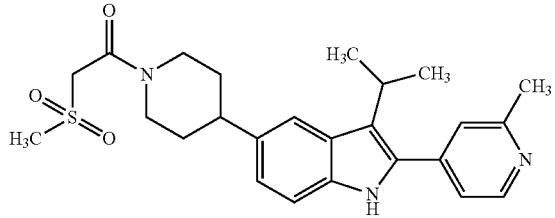 | 454.2 | 1.112 | QC-TFA |
| 609 | 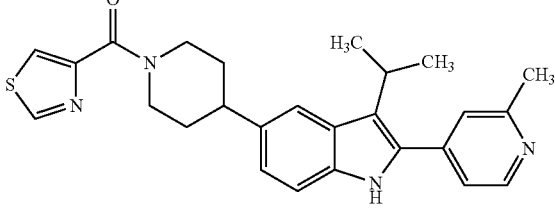 | 445.3 | 1.264 | QC-TFA |
| 610 | 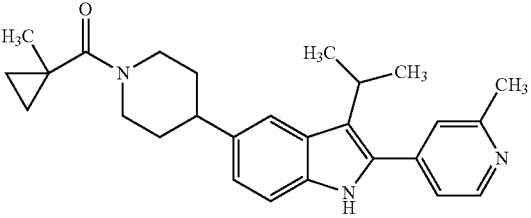 [SMILES: Cc1cc(-c2[nH]c3ccc(C4CCN(C(=O)C5(C)CC5)CC4)cc3c2C(C)C)ccn1] | 416.2 | 1.423 | QC-TFA |

TABLE 33-continued

| Ex. No. | Structure | LCMS MH+ | Rt (min) | HPLC Method |
|---|---|---|---|---|
| 611 | 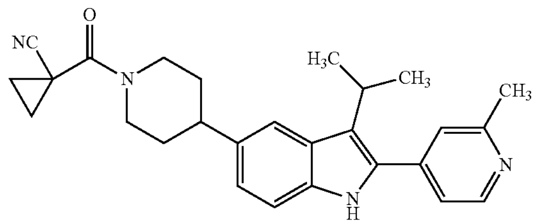 [SMILES: Cc1cc(-c2[nH]c3ccc(C4CCN(C(=O)C5(C#N)CC5)CC4)cc3c2C(C)C)ccn1] | 427.4 | 1.376 | QC-TFA |
| 612 | 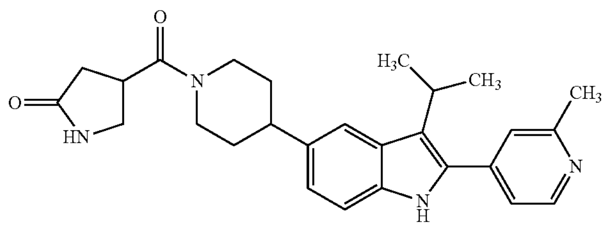 [SMILES: Cc1cc(-c2[nH]c3ccc(C4CCN(C(=O)C5CNC(=O)C5)CC4)cc3c2C(C)C)ccn1] | 445.1 | 1.033 | QC-TFA |
| 613 | 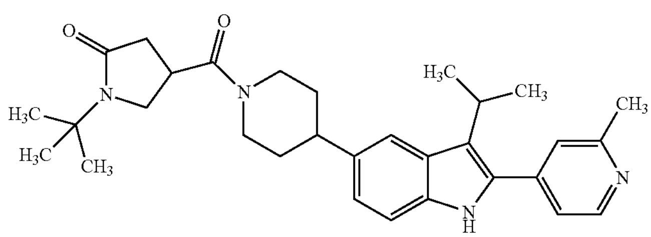 [SMILES: Cc1cc(-c2[nH]c3ccc(C4CCN(C(=O)C5CC(=O)N(C(C)(C)C)C5)CC4)cc3c2C(C)C)ccn1] | 501.3 | 1.401 | QC-TFA |
| 614 | 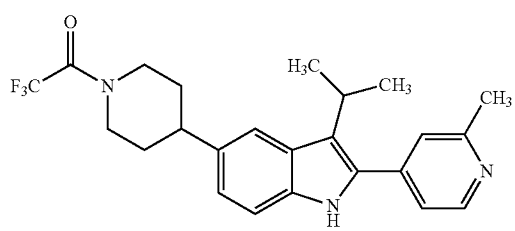 [SMILES: Cc1cc(-c2[nH]c3ccc(C4CCN(C(=O)C(F)(F)F)CC4)cc3c2C(C)C)ccn1] | 430 | 1.629 | QC-TFA |
| 615 | 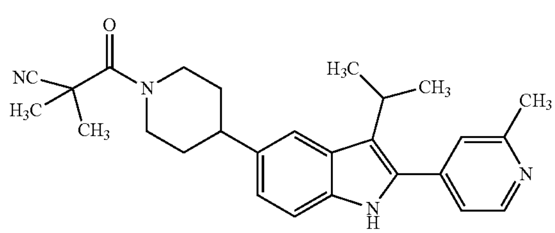 [SMILES: Cc1cc(-c2[nH]c3ccc(C4CCN(C(=O)C(C)(C)C#N)CC4)cc3c2C(C)C)ccn1] | 429.1 | 1.741 | QC-TFA |
| 616 | 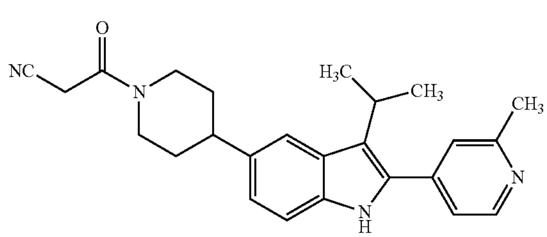 [SMILES: Cc1cc(-c2[nH]c3ccc(C4CCN(C(=O)CC#N)CC4)cc3c2C(C)C)ccn1] | 401.3 | 1.188 | QC-TFA |

TABLE 33-continued

| Ex. No. | Structure | LCMS MH+ | Rt (min) | HPLC Method |
|---|---|---|---|---|
| 617 | 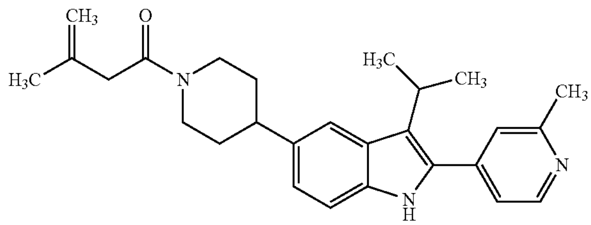 [SMILES: C=C(C)CC(=O)N1CCC(c2ccc3[nH]c(-c4ccnc(C)c4)c(C(C)C)c3c2)CC1] | 418.4 | 1.554 | QC-TFA |
| 618 | Isomer 1 | 459.2 | 0.66 | G |
| 619 | Isomer 2 | 459.2 | 0.66 | G |

TABLE 34

| Ex. No. | Structure | LCMS MH+ | Rt (min) | HPLC Method | General Method |
|---|---|---|---|---|---|
| 620 | 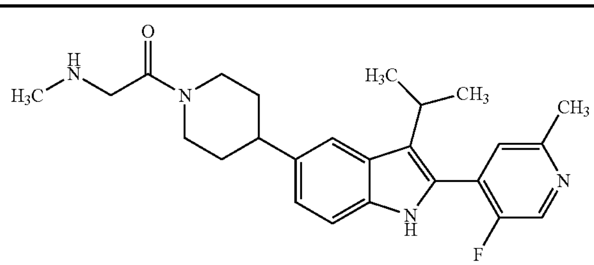 | 419.1 | 1.34 | QC-AA | 178 |
| 621 | 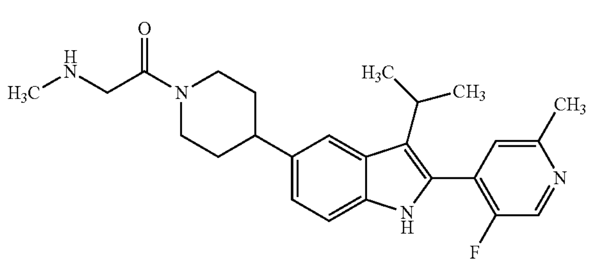 | 423.2 | 1.35 | QC-AA | 178 |

TABLE 34-continued
| Ex. No. | Structure | LCMS MH+ | Rt (min) | HPLC Method | General Method |
|---|---|---|---|---|---|
| 622 | 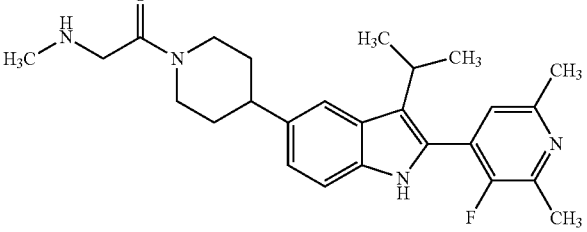 | 437.2 | 1.46 | QC-AA | 178 |
| 623 | 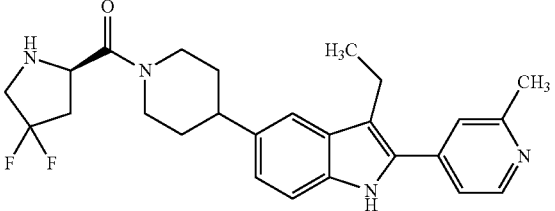 [SMILES: CCc1c(-c2ccnc(C)c2)[nH]c2ccc(C3CCN(C(=O)[C@H]4CC(F)(F)CN4)CC3)cc12] | 453.3 | 0.88 | QC-TFA | 178 |
| 624 | 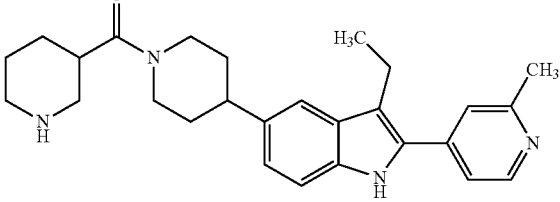 | 431.2 | 0.87 | QC-TFA | 178 |
| 625 | 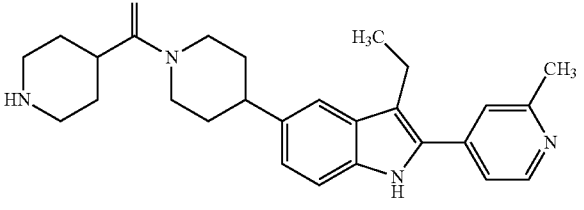 | 431.2 | 0.7 | QC-TFA | 178 |
| 626 | 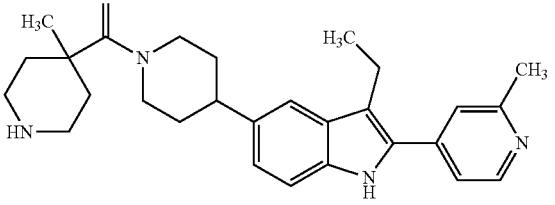 | 445.2 | 0.94 | QC-TFA | 178 |
| 627 | 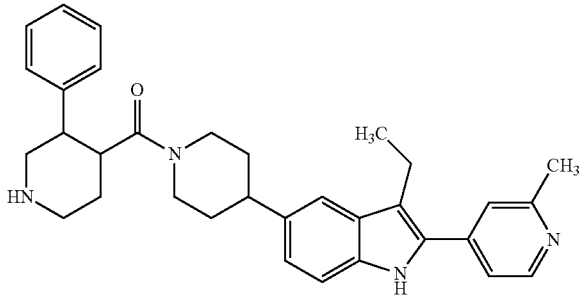 [SMILES: CCc1c(-c2ccnc(C)c2)[nH]c2ccc(C3CCN(C(=O)C4CCNCC4c4ccccc4)CC3)cc12] | 507.3 | 1.11 | QC-TFA | 178 |

TABLE 34-continued

| Ex. No. | Structure | LCMS MH+ | Rt (min) | HPLC Method | General Method |
|---|---|---|---|---|---|
| 628 | 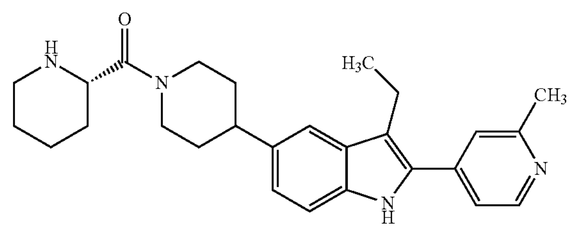 [SMILES: CCc1c(-c2ccnc(C)c2)[nH]c2ccc(C3CCN(C(=O)[C@@H]4CCCCN4)CC3)cc12] | 431.2 | 0.9 | QC-TFA | 178 |
| 629 | 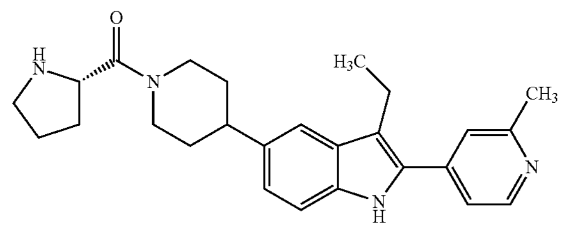 [SMILES: CCc1c(-c2ccnc(C)c2)[nH]c2ccc(C3CCN(C(=O)[C@@H]4CCCN4)CC3)cc12] | 417.3 | 0.74 | QC-TFA | 178 |
| 630 | 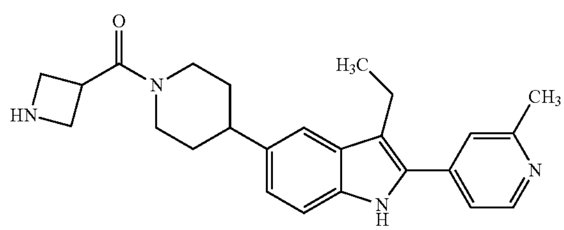 [SMILES: CCc1c(-c2ccnc(C)c2)[nH]c2ccc(C3CCN(C(=O)C4CNC4)CC3)cc12] | 403.2 | 0.7 | QC-TFA | 178 |
| 631 | 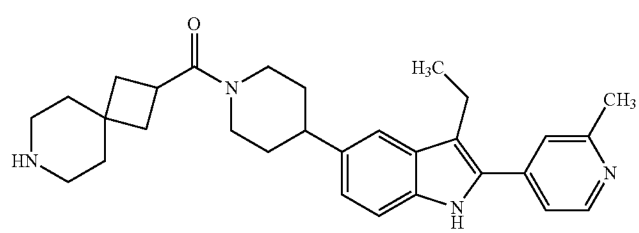 [SMILES: CCc1c(-c2ccnc(C)c2)[nH]c2ccc(C3CCN(C(=O)C4CC5(CCNCC5)C4)CC3)cc12] | 471.3 | 0.9 | QC-TFA | 178 |
| 632 | 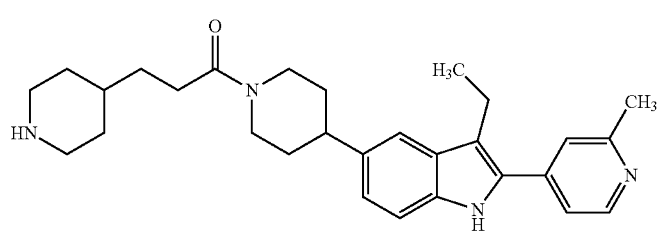 [SMILES: CCc1c(-c2ccnc(C)c2)[nH]c2ccc(C3CCN(C(=O)CCC4CCNCC4)CC3)cc12] | 459.3 | 0.88 | QC-TFA | 178 |
| 633 | 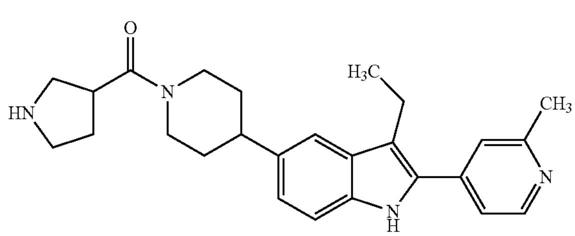 [SMILES: CCc1c(-c2ccnc(C)c2)[nH]c2ccc(C3CCN(C(=O)C4CCNC4)CC3)cc12] | 417.2 | 0.81 | QC-TFA | 178 |

TABLE 34-continued

| Ex. No. | Structure | LCMS MH+ | Rt (min) | HPLC Method | General Method |
|---|---|---|---|---|---|
| 634 | 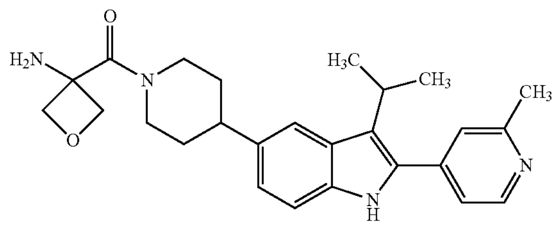 [SMILES: Cc1cc(-c2[nH]c3ccc(C4CCN(C(=O)C5(N)COC5)CC4)cc3c2C(C)C)ccn1] | 433.3 | 0.925 | QC-TFA | 178 |
| 635 | 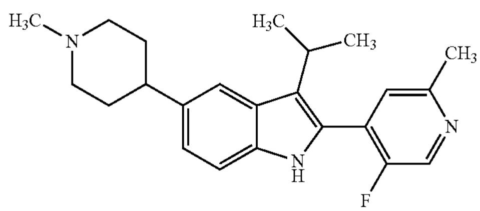 | 366.1 | 0.93 | QC-TFA | 308 |
| 636 | 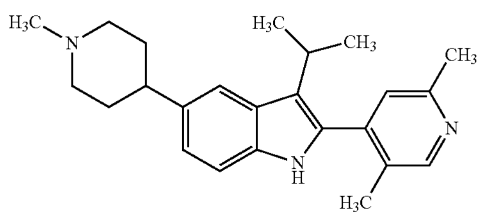 | 362.2 | 1.28 | QC-AA | 308 |
| 637 | 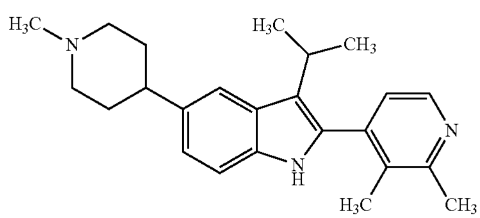 | 362.1 | 1.27 | QC-AA | 308 |
| 638 | 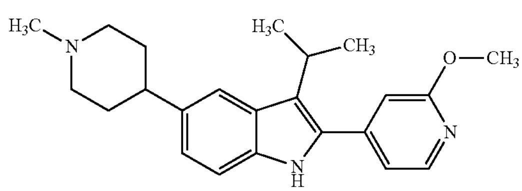 | 364 | 1.15 | QC-TFA | 308 |
| 639 | 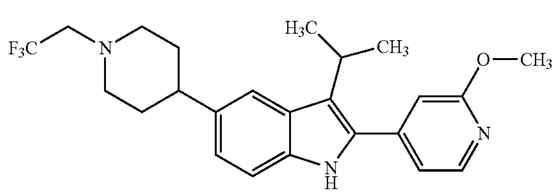 [SMILES: COc1cc(-c2[nH]c3ccc(C4CCN(CC(F)(F)F)CC4)cc3c2C(C)C)ccn1] | 432 | 2.56 | QC-AA | 308 |
| 640 | 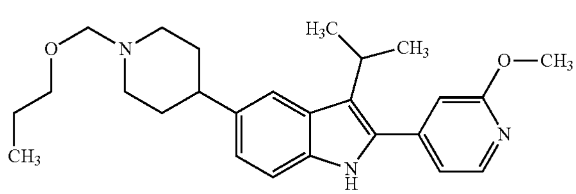 [SMILES: CCCOCN1CCC(c2ccc3[nH]c(-c4ccnc(OC)c4)c(C(C)C)c3c2)CC1] | 422.4 | 1.35 | QC-TFA | 308 |

TABLE 34-continued

| Ex. No. | Structure | LCMS MH+ | Rt (min) | HPLC Method | General Method |
|---|---|---|---|---|---|
| 641 | 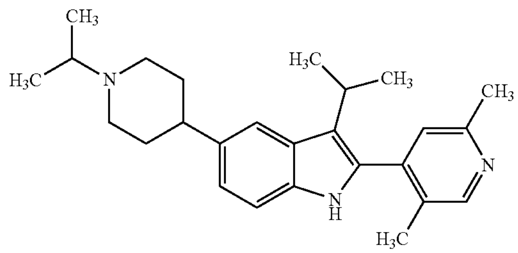 [SMILES: Cc1cc(-c2[nH]c3ccc(C4CCN(C(C)C)CC4)cc3c2C(C)C)c(C)cn1] | 390.1 | 0.93 | QC-TFA | 308 |
| 642 | 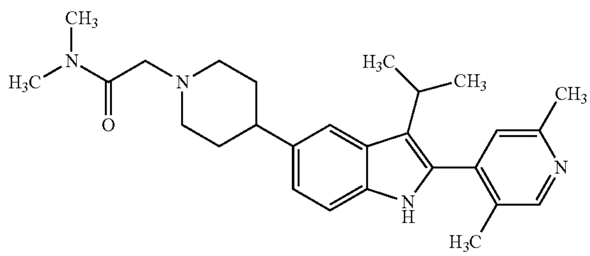 | 433.1 | 1.46 | QC-AA | 308 |
| 643 | 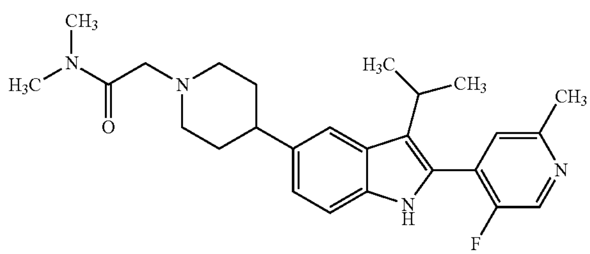 | 437.4 | 1.01 | QC-TFA | 308 |
| 644 | 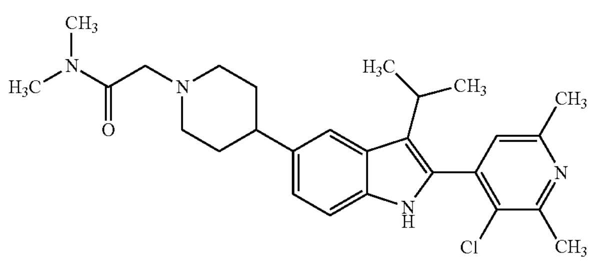 | 467 | 1.87 | QC-AA | 308 |
| 645 | 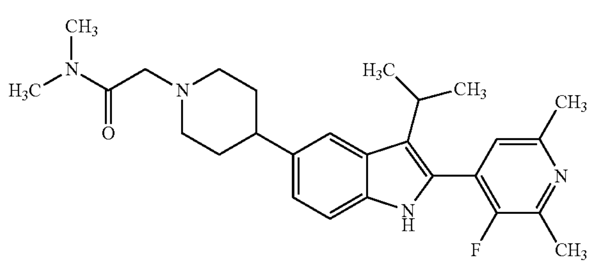 | 451.2 | 1.61 | QC-AA | 308 |
| 646 | 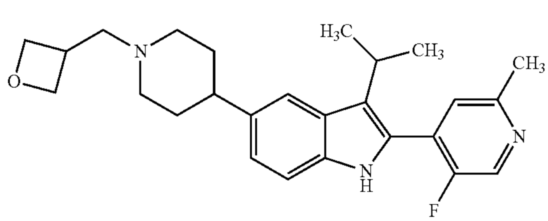 [SMILES: Cc1cc(-c2[nH]c3ccc(C4CCN(CC5COC5)CC4)cc3c2C(C)C)c(F)cn1] | 422.4 | 1.4 | QC-AA | 308 |

TABLE 34-continued

| Ex. No. | Structure | LCMS MH+ | Rt (min) | HPLC Method | General Method |
|---|---|---|---|---|---|
| 647 | 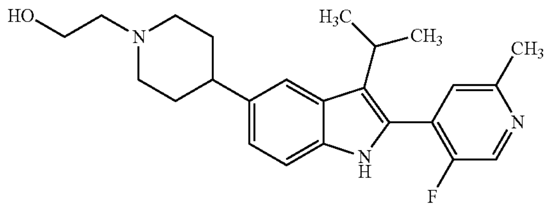 [SMILES: Cc1cc(-c2[nH]c3ccc(C4CCN(CCO)CC4)cc3c2C(C)C)c(F)cn1] | 396.3 | 0.95 | QC-TFA | 308 |
| 648 | 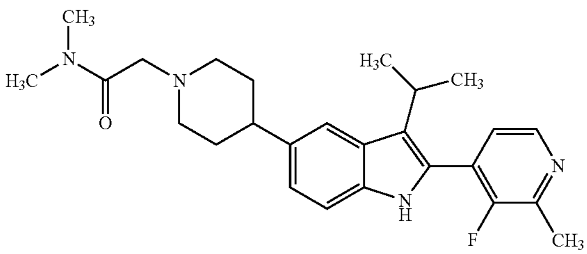 | 437.2 | 1.52 | QC-AA | 308 |
| 649 | 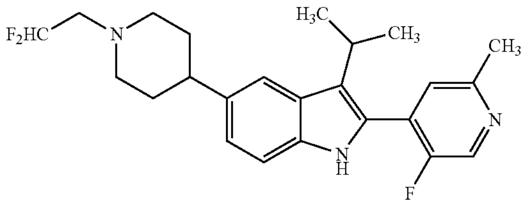 [SMILES: Cc1cc(-c2[nH]c3ccc(C4CCN(CC(F)F)CC4)cc3c2C(C)C)c(F)cn1] | 416.3 | 2.29 | QC-AA | 308 |
| 650 | 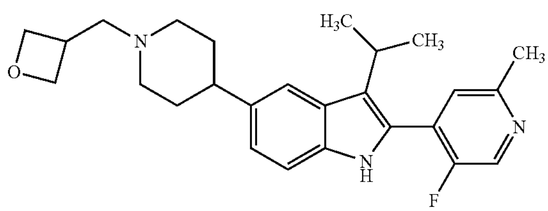 [SMILES: Cc1cc(-c2[nH]c3ccc(C4CCN(CC5COC5)CC4)cc3c2C(C)C)c(F)cn1] | 422.4 | 1.56 | QC-AA | 308 |
| 651 | 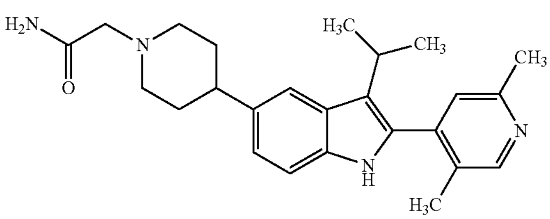 [SMILES: Cc1cc(-c2[nH]c3ccc(C4CCN(CC(N)=O)CC4)cc3c2C(C)C)c(C)cn1] | 405 | 0.75 | QC-TFA | 308 |
| 652 | 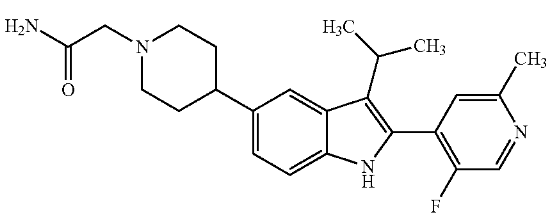 [SMILES: Cc1cc(-c2[nH]c3ccc(C4CCN(CC(N)=O)CC4)cc3c2C(C)C)c(F)cn1] | 409 | 1.57 | QC-AA | 308 |

TABLE 34-continued

| Ex. No. | Structure | LCMS MH+ | Rt (min) | HPLC Method | General Method |
|---|---|---|---|---|---|
| 653 | 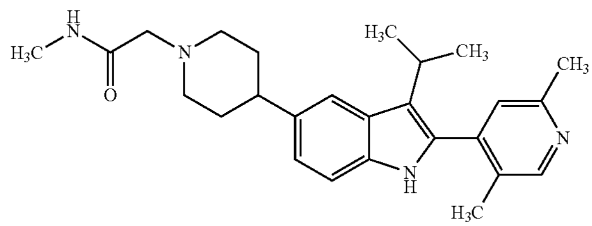 | 419 | 1.65 | QC-AA | 308 |
| 654 | 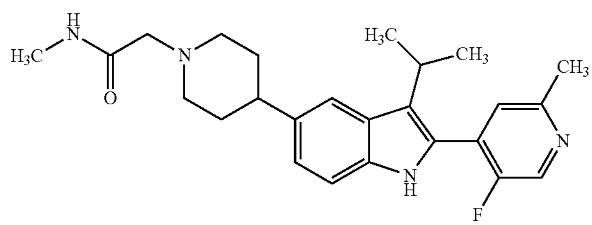 | 423.4 | 1.59 | QC-AA | 308 |
| 655 | 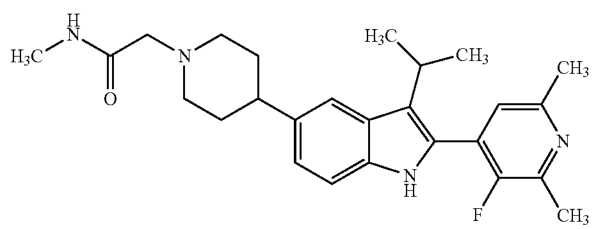 | 437 | 1.78 | QC-AA | 308 |
| 656 | 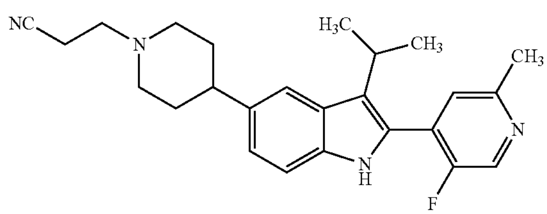 [SMILES: Cc1cc(-c2[nH]c3ccc(C4CCN(CCC#N)CC4)cc3c2C(C)C)c(F)cn1] | 405 | 1.99 | QC-AA | 308 |
| 657 | 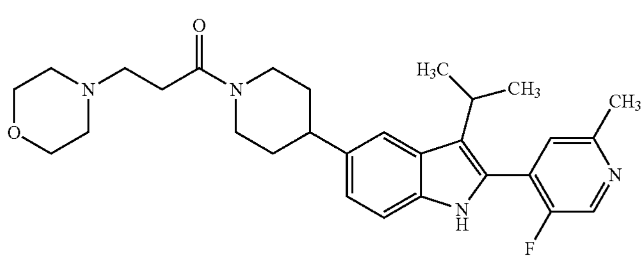 [SMILES: Cc1cc(-c2[nH]c3ccc(C4CCN(C(=O)CCN5CCOCC5)CC4)cc3c2C(C)C)c(F)cn1] | 493 | 1.7 | QC-AA | 308 |
| 658 | 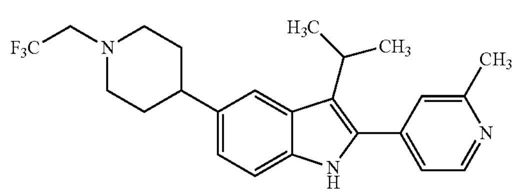 [SMILES: Cc1cc(-c2[nH]c3ccc(C4CCN(CC(F)(F)F)CC4)cc3c2C(C)C)ccn1] | 416.0 | 1.06 | QC-TFA | 308 |

TABLE 34-continued

| Ex. No. | Structure | LCMS MH+ | Rt (min) | HPLC Method | General Method |
|---|---|---|---|---|---|
| 659 | 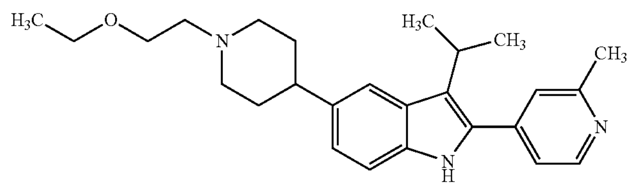 [SMILES: CCOCCN1CCC(c2ccc3[nH]c(-c4ccnc(C)c4)c(C(C)C)c3c2)CC1] | 405.9 | 0.98 | QC-TFA | 308 |
| 660 | 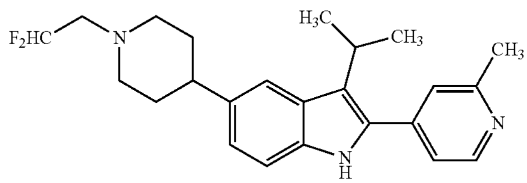 [SMILES: Cc1cc(-c2[nH]c3ccc(C4CCN(CC(F)F)CC4)cc3c2C(C)C)ccn1] | 398.1 | 0.86 | QC-TFA | 308 |
| 661 | 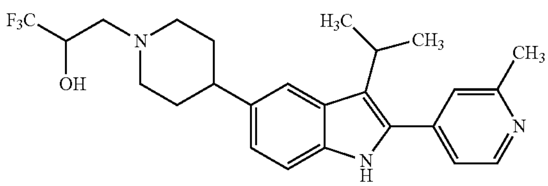 [SMILES: Cc1cc(-c2[nH]c3ccc(C4CCN(CC(O)C(F)(F)F)CC4)cc3c2C(C)C)ccn1] | 446.2 | 0.95 | QC-TFA | 308 |
| 662 | 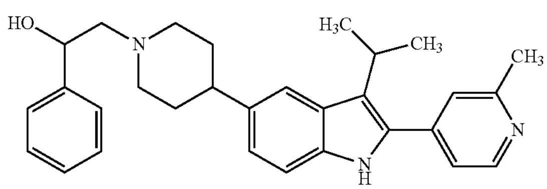 [SMILES: Cc1cc(-c2[nH]c3ccc(C4CCN(CC(O)c5ccccc5)CC4)cc3c2C(C)C)ccn1] | 454.1 | 1.04 | QC-TFA | 308 |
| 663 | 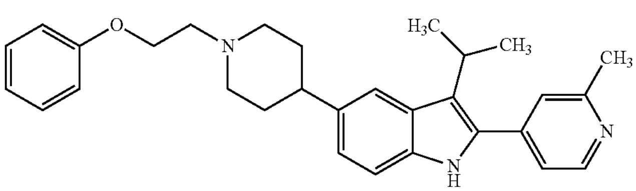 [SMILES: Cc1cc(-c2[nH]c3ccc(C4CCN(CCOc5ccccc5)CC4)cc3c2C(C)C)ccn1] | 454.1 | 1.21 | QC-TFA | 308 |
| 664 | 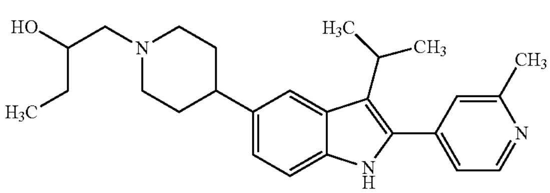 [SMILES: CCC(O)CN1CCC(c2ccc3[nH]c(-c4ccnc(C)c4)c(C(C)C)c3c2)CC1] | 406.4 | 0.93 | QC-TFA | 308 |
| 665 | 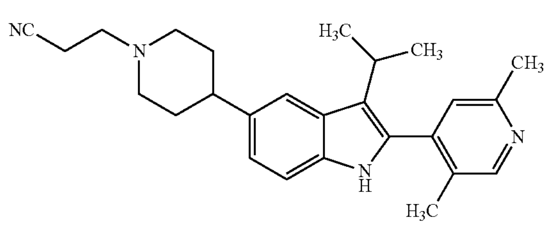 [SMILES: Cc1cc(-c2[nH]c3ccc(C4CCN(CCC#N)CC4)cc3c2C(C)C)c(C)cn1] | 401.0 | 0.88 | QC-TFA | 308 |

TABLE 34-continued

| Ex. No. | Structure | LCMS MH+ | Rt (min) | HPLC Method | General Method |
|---|---|---|---|---|---|
| 666 | 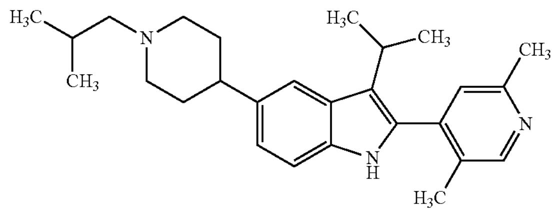 [SMILES: Cc1cc(-c2[nH]c3ccc(C4CCN(CC(C)C)CC4)cc3c2C(C)C)c(C)cn1] | 404.3 | 1.13 | QC-TFA | 308 |
| 667 | 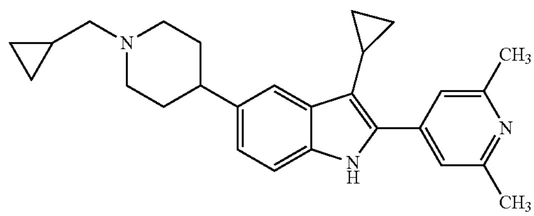 [SMILES: Cc1cc(-c2[nH]c3ccc(C4CCN(CC5CC5)CC4)cc3c2C2CC2)cc(C)n1] | 400.4 | 1.04 | QC-TFA | 308 |
| 668 | 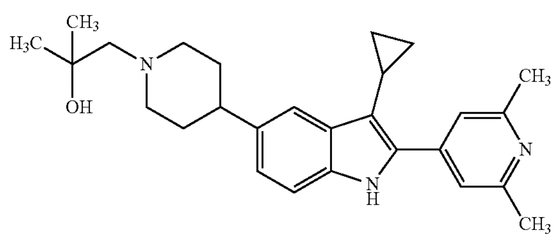 [SMILES: Cc1cc(-c2[nH]c3ccc(C4CCN(CC(C)(C)O)CC4)cc3c2C2CC2)cc(C)n1] | 418.2 | 1.41 | QC-AA | 308 |
| 669 | 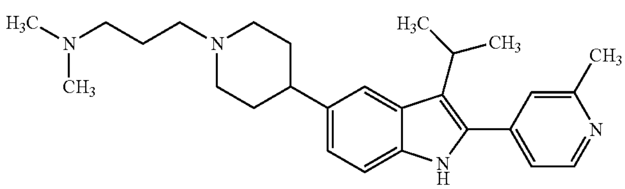 | 419.4 | 0.613 | QC-TFA | 308 |
| 670 | 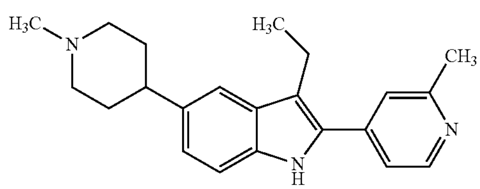 | 333.9 | 0.744 | QC-TFA | 308 |
| 671 | 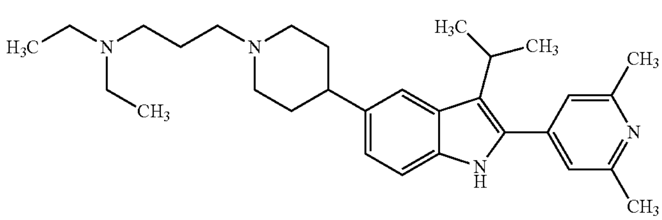 [SMILES: CCN(CC)CCCN1CCC(c2ccc3[nH]c(-c4cc(C)nc(C)c4)c(C(C)C)c3c2)CC1] | 461.5 | 0.794 | QC-TFA | 308 |
| 672 | 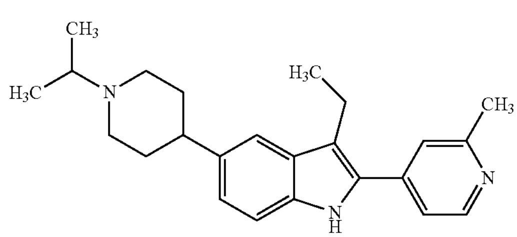 [SMILES: CCc1c(-c2ccnc(C)c2)[nH]c2ccc(C3CCN(C(C)C)CC3)cc12] | 362.3 | 0.862 | QC-TFA | 308 |

TABLE 34-continued
| Ex. No. | Structure | LCMS MH+ | Rt (min) | HPLC Method | General Method |
|---|---|---|---|---|---|
| 673 | 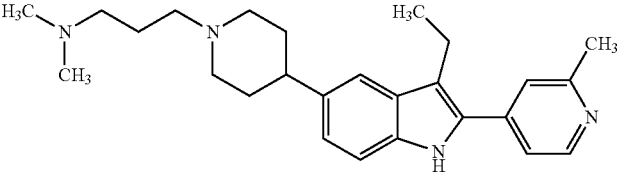 | 405.1 | 0.654 | QC-TFA | 308 |
| 674 | 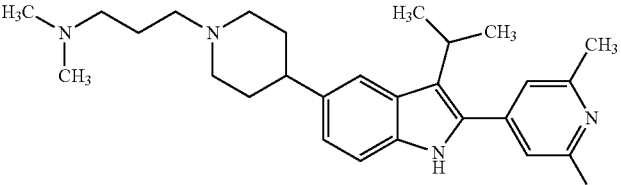 | 433.2 | 0.744 | QC-TFA | 308 |
| 675 | 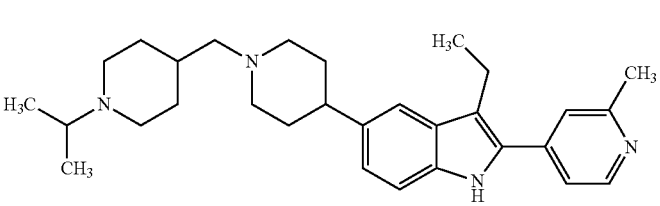 [SMILES: CCc1c(-c2ccnc(C)c2)[nH]c2ccc(C3CCN(CC4CCN(C(C)C)CC4)CC3)cc12] | 459.5 | 0.721 | QC-TFA | 308 |
| 676 | 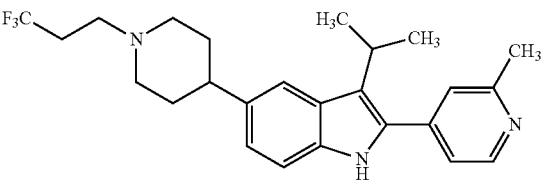 [SMILES: Cc1cc(-c2[nH]c3ccc(C4CCN(CCC(F)(F)F)CC4)cc3c2C(C)C)ccn1] | 430.3 | 1.04 | QC-TFA | 308 |
| 677 | 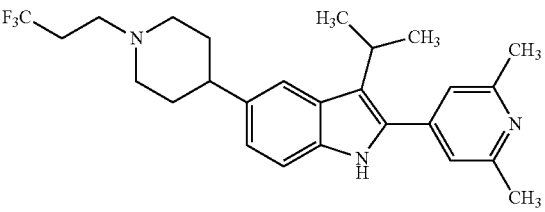 [SMILES: Cc1cc(-c2[nH]c3ccc(C4CCN(CCC(F)(F)F)CC4)cc3c2C(C)C)cc(C)n1] | 444.3 | 1.088 | QC-TFA | 308 |
| 678 | 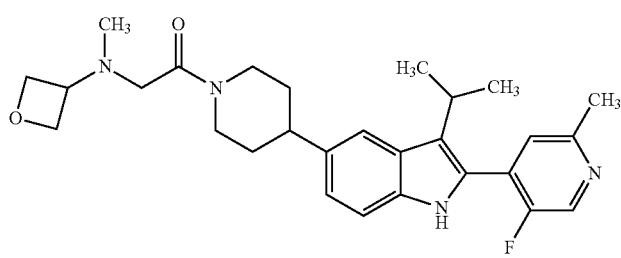 [SMILES: Cc1cc(-c2[nH]c3ccc(C4CCN(C(=O)CN(C)C5COC5)CC4)cc3c2C(C)C)c(F)cn1] | 479.4 | 1.09 | QC-TFA | 334 |
| 679 | 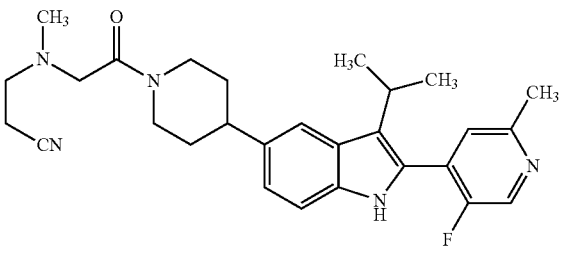 [SMILES: Cc1cc(-c2[nH]c3ccc(C4CCN(C(=O)CN(C)CCC#N)CC4)cc3c2C(C)C)c(F)cn1] | 476.4 | 1.84 | QC-AA | 334 |

TABLE 34-continued
| Ex. No. | Structure | LCMS MH+ | Rt (min) | HPLC Method | General Method |
|---|---|---|---|---|---|
| 680 | 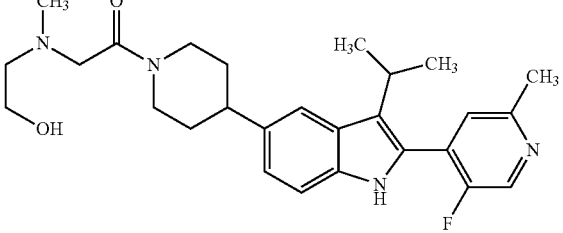 | 467 | 1.52 | QC-AA | 334 |
| 681 | 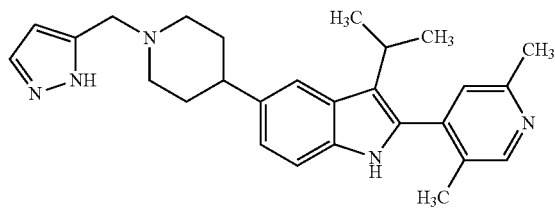 [SMILES: Cc1cc(-c2[nH]c3ccc(C4CCN(Cc5ccn[nH]5)CC4)cc3c2C(C)C)c(C)cn1] | 428.2 | 1.53 | QC-AA | 424 |
| 682 | 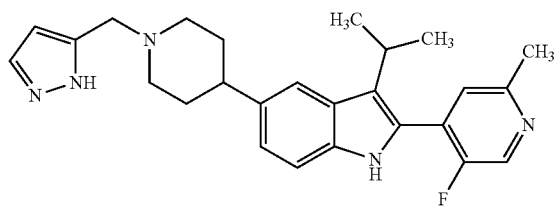 [SMILES: Cc1cc(-c2[nH]c3ccc(C4CCN(Cc5ccn[nH]5)CC4)cc3c2C(C)C)c(F)cn1] | 432.2 | 1.56 | QC-AA | 424 |
| 683 | 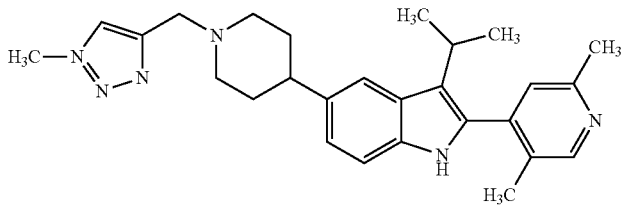 | 443.2 | 1.56 | QC-AA | 424 |
| 684 | 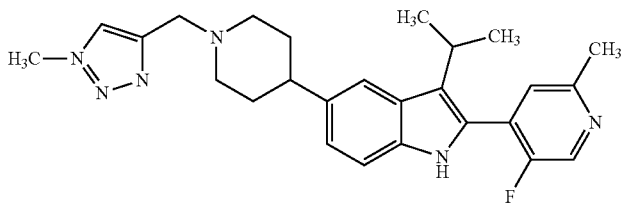 | 447.3 | 1.1 | QC-TFA | 424 |
| 685 | 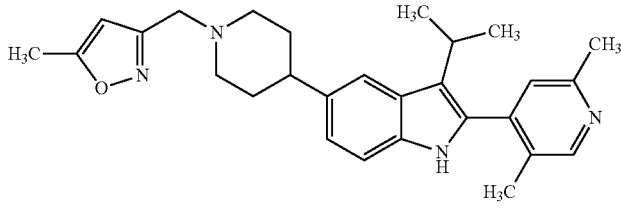 | 443.2 | 2.13 | QC-AA | 424 |

TABLE 34-continued

| Ex. No. | Structure | LCMS MH+ | Rt (min) | HPLC Method | General Method |
|---|---|---|---|---|---|
| 686 | 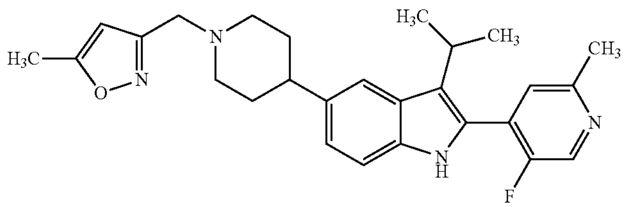 | 447.3 | 1.21 | QC-TFA | 424 |
| 687 | 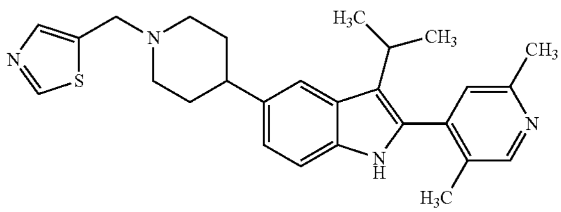 [SMILES: Cc1cc(-c2[nH]c3ccc(C4CCN(Cc5cncs5)CC4)cc3c2C(C)C)c(C)cn1] | 445.2 | 2.05 | QC-AA | 424 |
| 688 | 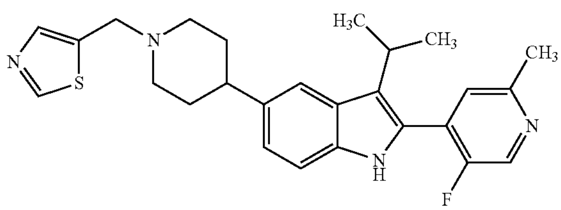 [SMILES: Cc1cc(-c2[nH]c3ccc(C4CCN(Cc5cncs5)CC4)cc3c2C(C)C)c(F)cn1] | 449.1 | 2.07 | QC-AA | 424 |
| 689 | 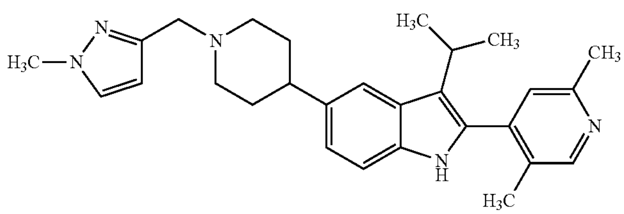 | 442.2 | 1.07 | QC-TFA | 424 |
| 690 | 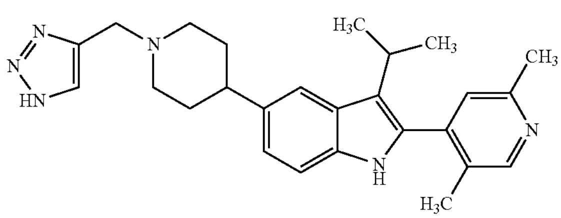 [SMILES: Cc1cc(-c2[nH]c3ccc(C4CCN(Cc5c[nH]nn5)CC4)cc3c2C(C)C)c(C)cn1] | 429.2 | 0.98 | QC-TFA | 424 |
| 691 | 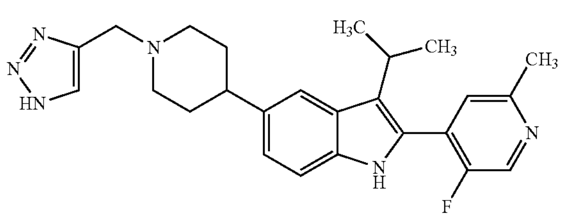 [SMILES: Cc1cc(-c2[nH]c3ccc(C4CCN(Cc5c[nH]nn5)CC4)cc3c2C(C)C)c(F)cn1] | 433.2 | 1.06 | QC-TFA | 424 |
| 692 | 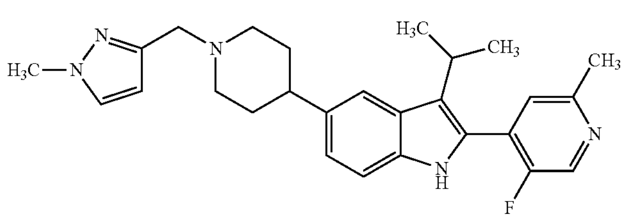 | 446.2 | 1.17 | QC-TFA | 424 |

TABLE 34-continued
| Ex. No. | Structure | LCMS MH+ | Rt (min) | HPLC Method | General Method |
|---|---|---|---|---|---|
| 693 | 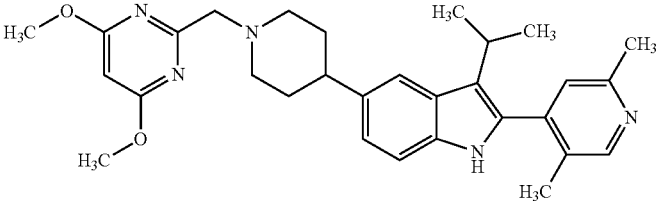 | 500.2 | 1.96 | QC-AA | 424 |
| 694 | 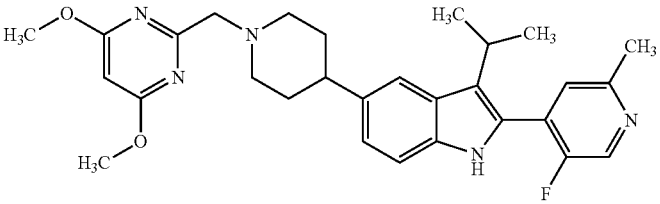 | 504.2 | 1.37 | QC-TFA | 424 |
| 695 | 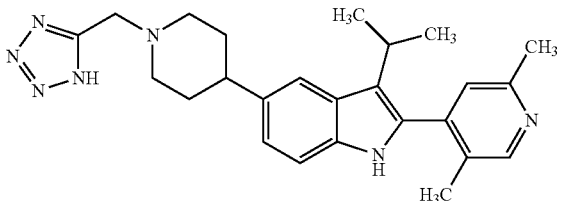 [SMILES: Cc1cc(-c2[nH]c3ccc(C4CCN(Cc5nnn[nH]5)CC4)cc3c2C(C)C)c(F)cn1] | 430.2 | 1.24 | QC-AA | 424 |
| 696 | 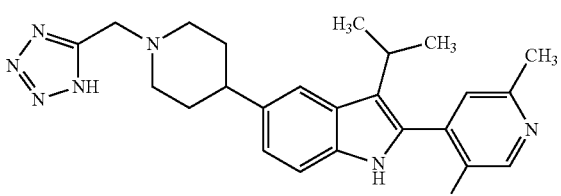 | 434.2 | 1.27 | QC-AA | 424 |
| 697 | 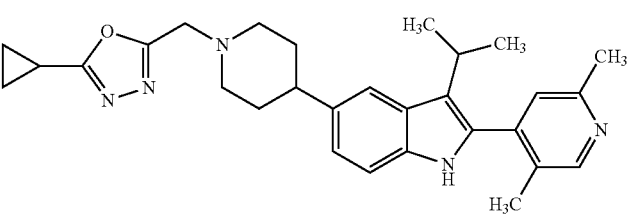 [SMILES: Cc1cc(-c2[nH]c3ccc(C4CCN(Cc5nnc(C6CC6)o5)CC4)cc3c2C(C)C)c(C)cn1] | 470.2 | 1.98 | QC-AA | 424 |
| 698 | 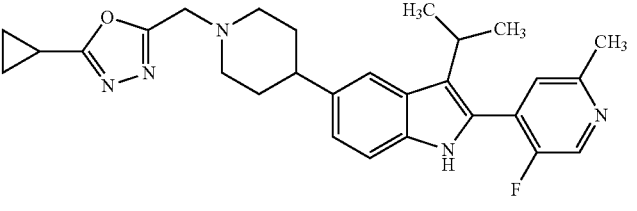 [SMILES: Cc1cc(-c2[nH]c3ccc(C4CCN(Cc5nnc(C6CC6)o5)CC4)cc3c2C(C)C)c(F)cn1] | 474.1 | 1.67 | QC-TFA | 424 |
| 699 | 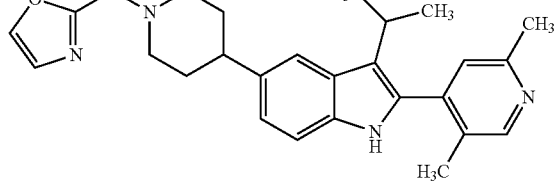 | 429.2 | 1.93 | QC-AA | 424 |

TABLE 34-continued

| Ex. No. | Structure | LCMS MH+ | Rt (min) | HPLC Method | General Method |
|---|---|---|---|---|---|
| 700 | 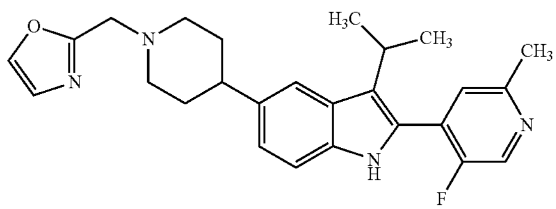 [SMILES: Cc1cc(-c2[nH]c3ccc(C4CCN(Cc5ncco5)CC4)cc3c2C(C)C)c(F)cn1] | 433.3 | 1.56 | QC-TFA | 424 |
| 701 | 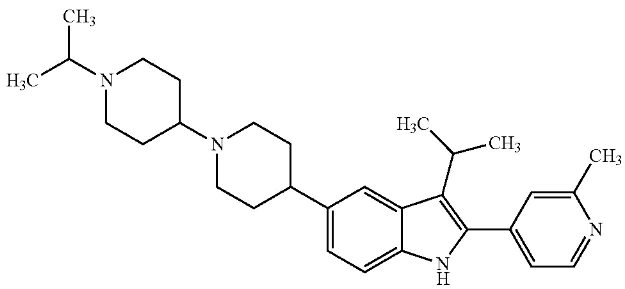 [SMILES: Cc1cc(-c2[nH]c3ccc(C4CCN(C5CCN(C(C)C)CC5)CC4)cc3c2C(C)C)ccn1] | 459.2 | 0.72 | QC-TFA | 424 |
| 702 | 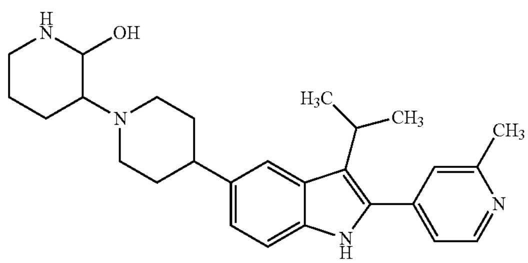 [SMILES: Cc1cc(-c2[nH]c3ccc(C4CCN(C5CCCNC5O)CC4)cc3c2C(C)C)ccn1] | 433.2 | 0.66 | QC-TFA | 424 |
| 703 | 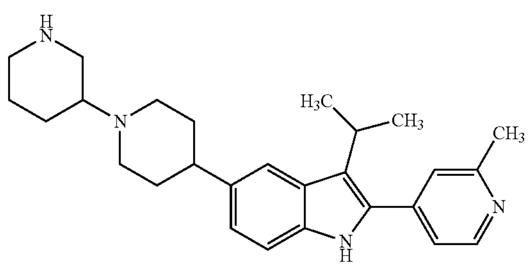 [SMILES: Cc1cc(-c2[nH]c3ccc(C4CCN(C5CCCNC5)CC4)cc3c2C(C)C)ccn1] | 417.4 | 1.82 | QC-AA | 424 |
| 704 | 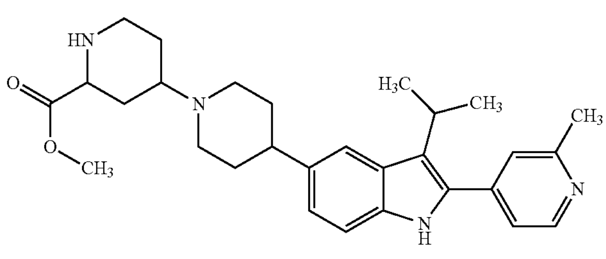 [SMILES: COC(=O)C1CC(N2CCC(c3ccc4[nH]c(-c5ccnc(C)c5)c(C(C)C)c4c3)CC2)CCN1] | 475.3 | 0.72 | QC-TFA | 424 |
| 705 | 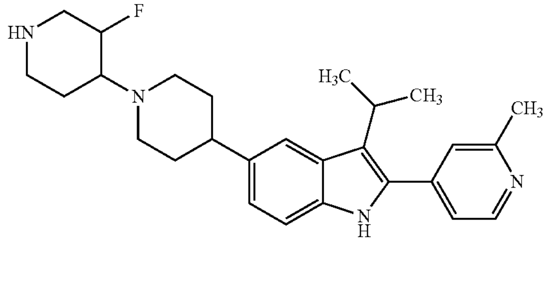 [SMILES: Cc1cc(-c2[nH]c3ccc(C4CCN(C5CCNCC5F)CC4)cc3c2C(C)C)ccn1] | 435.1 | 0.66 | QC-TFA | 424 |

TABLE 34-continued

| Ex. No. | Structure | LCMS MH+ | Rt (min) | HPLC Method | General Method |
|---|---|---|---|---|---|
| 706 | 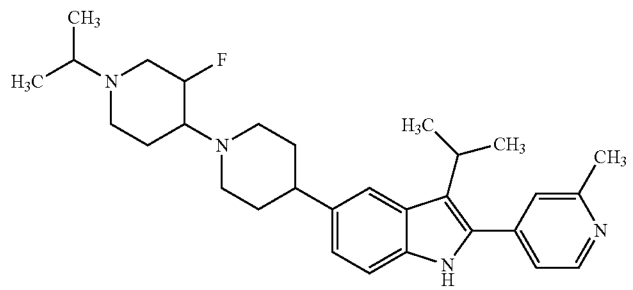 [SMILES: Cc1cc(-c2[nH]c3ccc(C4CCN(C5CCN(C(C)C)CC5F)CC4)cc3c2C(C)C)ccn1] | 477.4 | 1.87 | QC-AA | 424 |
| 707 | 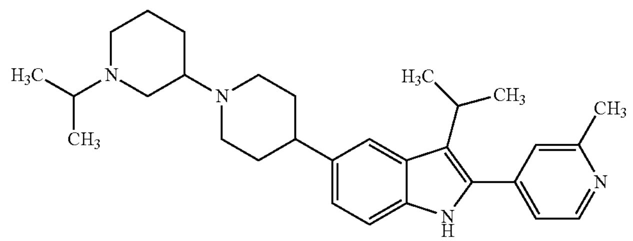 [SMILES: Cc1cc(-c2[nH]c3ccc(C4CCN(C5CCCN(C(C)C)C5)CC4)cc3c2C(C)C)ccn1] | 459.1 | 1.47 | QC-AA | 424 |
| 708 | 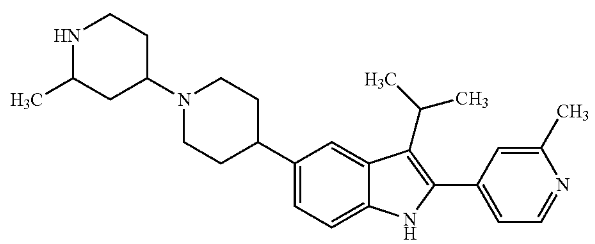 | 431.4 | 0.73 | QC-TFA | 424 |
| 709 | 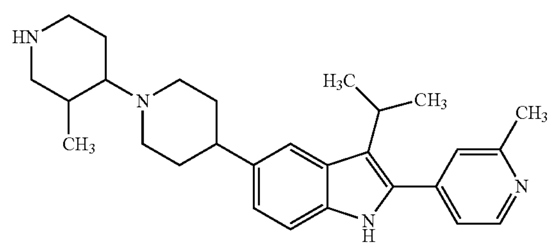 [SMILES: Cc1cc(-c2[nH]c3ccc(C4CCN(C5CCNCC5C)CC4)cc3c2C(C)C)ccn1] | 431.3 | 1.16 | QC-AA | 424 |
| 710 | 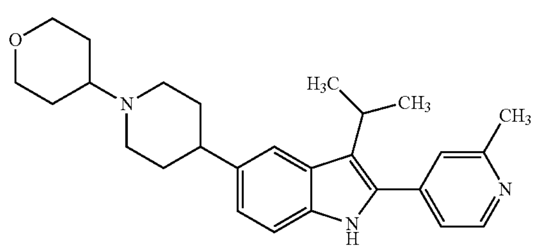 [SMILES: Cc1cc(-c2[nH]c3ccc(C4CCN(C5CCOCC5)CC4)cc3c2C(C)C)ccn1] | 418.1 | 0.89 | QC-TFA | 424 |
| 711 | 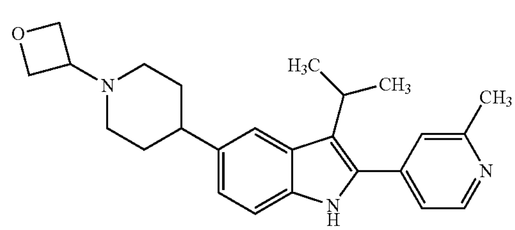 [SMILES: Cc1cc(-c2[nH]c3ccc(C4CCN(C5COC5)CC4)cc3c2C(C)C)ccn1] | 390.1 | 1.66 | QC-AA | 424 |

TABLE 34-continued

| Ex. No. | Structure | LCMS MH+ | Rt (min) | HPLC Method | General Method |
|---|---|---|---|---|---|
| 712 | 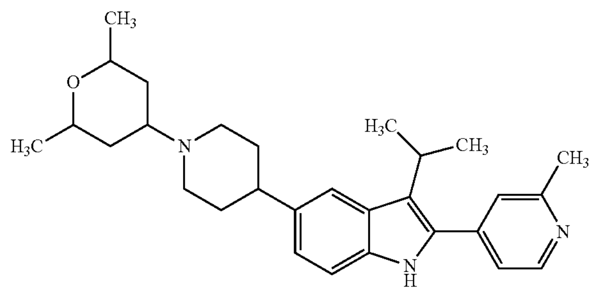 | 446.2 | 1.55 | QC-AA | 424 |
| 713 | 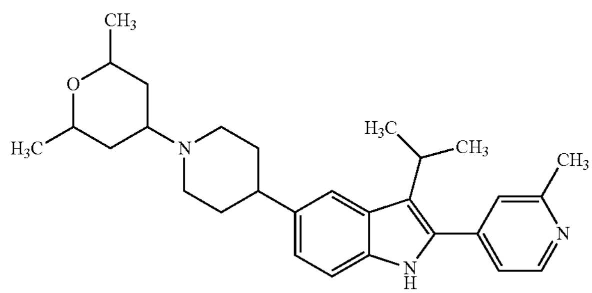 | 446.1 | 1.84 | QC-AA | 424 |
| 714 | 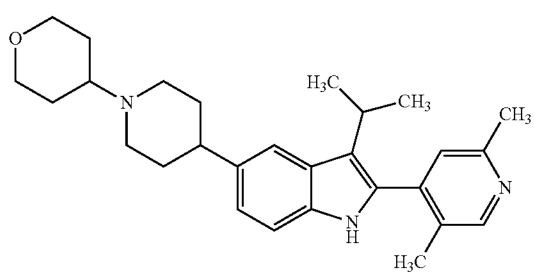 [SMILES: Cc1cc(-c2[nH]c3ccc(C4CCN(C5CCOCC5)CC4)cc3c2C(C)C)c(C)cn1] | 432.1 | 0.91 | QC-TFA | 424 |
| 715 | 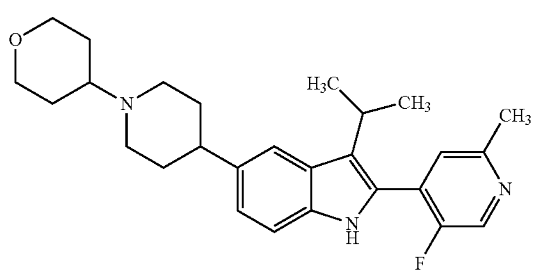 [SMILES: Cc1cc(-c2[nH]c3ccc(C4CCN(C5CCOCC5)CC4)cc3c2C(C)C)c(F)cn1] | 436.1 | 1.44 | QC-AA | 424 |
| 716 | 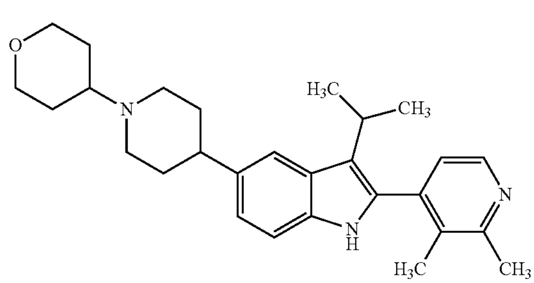 [SMILES: Cc1nccc(-c2[nH]c3ccc(C4CCN(C5CCOCC5)CC4)cc3c2C(C)C)c1C] | 432.1 | 1.4 | QC-AA | 424 |

TABLE 34-continued

| Ex. No. | Structure | LCMS MH+ | Rt (min) | HPLC Method | General Method |
|---|---|---|---|---|---|
| 717 | 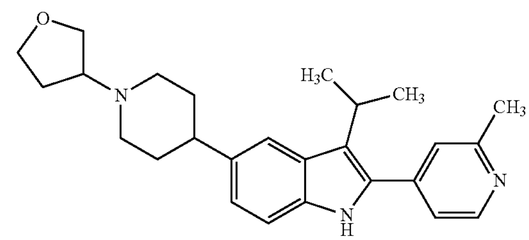 [SMILES: Cc1cc(-c2[nH]c3ccc(C4CCN(C5CCOC5)CC4)cc3c2C(C)C)ccn1] | 404.3 | 0.83 | QC-TFA | 424 |
| 718 | 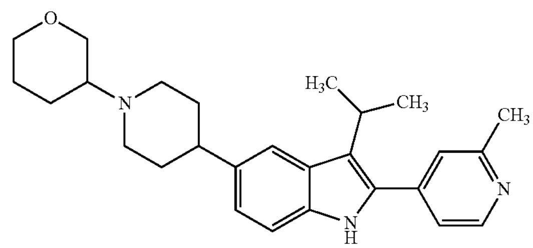 [SMILES: Cc1cc(-c2[nH]c3ccc(C4CCN(C5CCCOC5)CC4)cc3c2C(C)C)ccn1] | 418.1 | 1.57 | QC-AA | 424 |
| 719 | 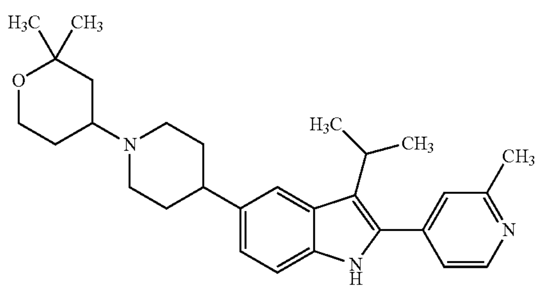 [SMILES: Cc1cc(-c2[nH]c3ccc(C4CCN(C5CCOC(C)(C)C5)CC4)cc3c2C(C)C)ccn1] | 446.3 | 1.01 | QC-TFA | 424 |
| 720 | 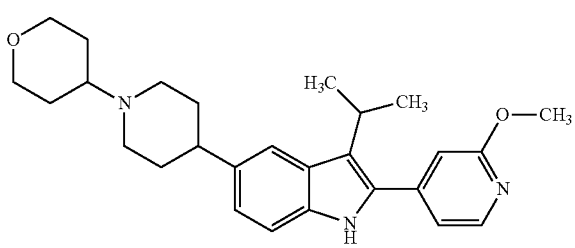 [SMILES: COc1cc(-c2[nH]c3ccc(C4CCN(C5CCOCC5)CC4)cc3c2C(C)C)ccn1] | 434.1 | 1.44 | QC-AA | 424 |
| 721 | 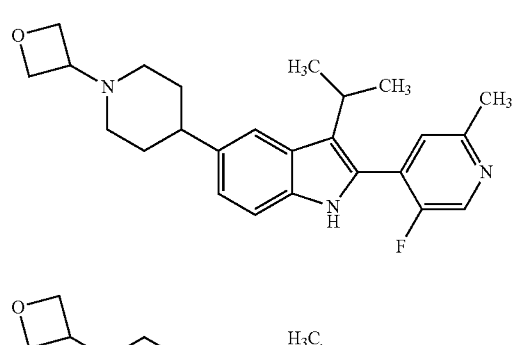 | 408.2 | 0.93 | QC-TFA | 424 |
| 722 | 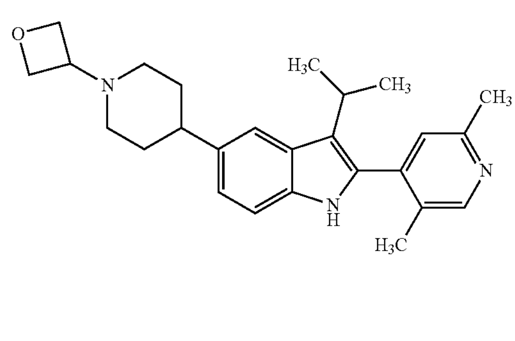 [SMILES: Cc1cc(-c2[nH]c3ccc(C4CCN(C5COC5)CC4)cc3c2C(C)C)c(C)cn1] | 404.4 | 1.86 | QC-AA | 424 |

TABLE 34-continued

| Ex. No. | Structure | LCMS MH+ | Rt (min) | HPLC Method | General Method |
|---|---|---|---|---|---|
| 723 | 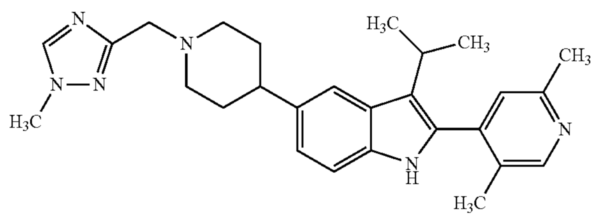 | 443.4 | 0.9 | QC-TFA | 424 |
| 724 | 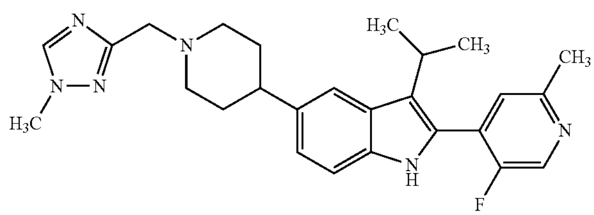 | 447.4 | 1.8 | QC-AA | 424 |
| 725 | 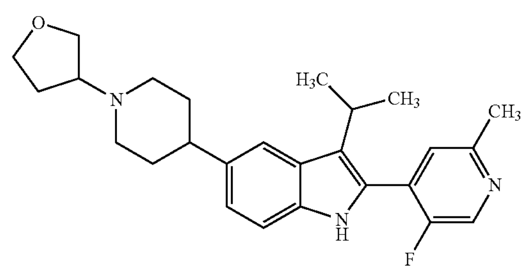 [SMILES: Cc1cc(-c2[nH]c3ccc(C4CCN(C5CCOC5)CC4)cc3c2C(C)C)c(F)cn1] | 422.4 | 1.73 | QC-AA | 424 |
| 726 | 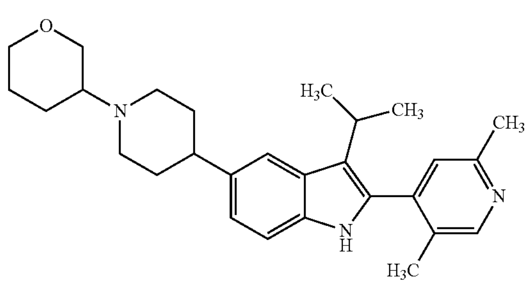 [SMILES: Cc1cc(-c2[nH]c3ccc(C4CCN(C5CCCOC5)CC4)cc3c2C(C)C)c(C)cn1] | 432.2 | 0.96 | QC-TFA | 424 |
| 727 | 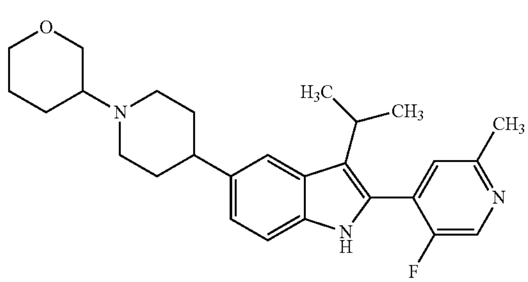 [SMILES: Cc1cc(-c2[nH]c3ccc(C4CCN(C5CCCOC5)CC4)cc3c2C(C)C)c(F)cn1] | 436 | 1.06 | QC-TFA | 424 |
| 728 | 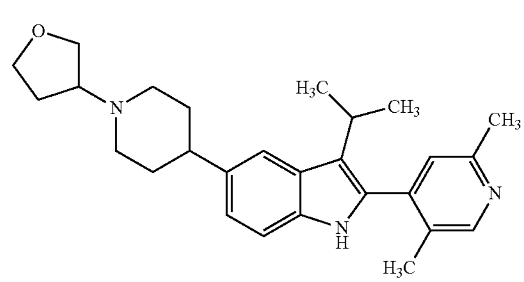 [SMILES: Cc1cc(-c2[nH]c3ccc(C4CCN(C5CCOC5)CC4)cc3c2C(C)C)c(C)cn1] | 418.2 | 1.62 | QC-AA | 424 |

TABLE 34-continued

| Ex. No. | Structure | LCMS MH+ | Rt (min) | HPLC Method | General Method |
|---|---|---|---|---|---|
| 729 | 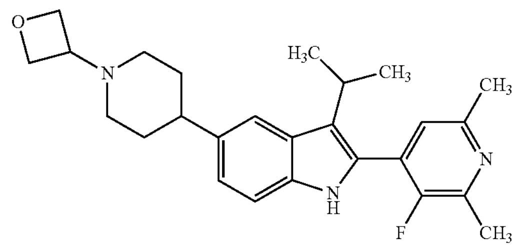 [SMILES: Cc1cc(-c2[nH]c3ccc(C4CCN(C5COC5)CC4)cc3c2C(C)C)c(F)c(C)n1] | 422.2 | 1.92 | QC-AA | 424 |
| 730 | 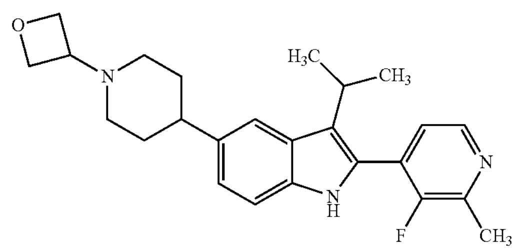 [SMILES: Cc1nccc(-c2[nH]c3ccc(C4CCN(C5COC5)CC4)cc3c2C(C)C)c1F] | 408.4 | 1.87 | QC-AA | 424 |
| 731 | 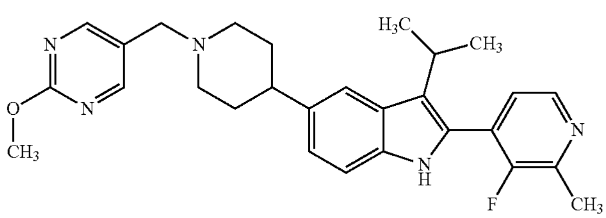 [SMILES: COc1ncc(CN2CCC(c3ccc4[nH]c(-c5ccnc(C)c5F)c(C(C)C)c4c3)CC2)cn1] | 474.4 | 1.95 | QC-AA | 424 |
| 732 | 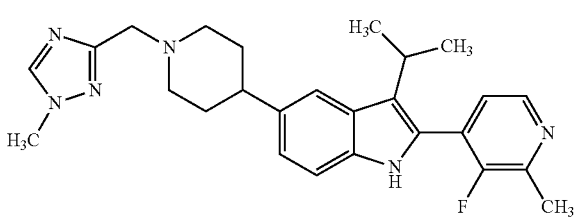 [SMILES: Cc1nccc(-c2[nH]c3ccc(C4CCN(Cc5ncn(C)n5)CC4)cc3c2C(C)C)c1F] | 447.2 | 1.79 | QC-AA | 424 |
| 733 | 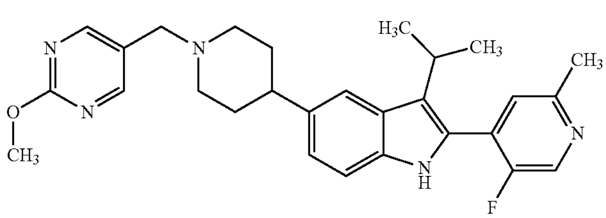 [SMILES: COc1ncc(CN2CCC(c3ccc4[nH]c(-c5cc(C)ncc5F)c(C(C)C)c4c3)CC2)cn1] | 474.2 | 1.99 | QC-AA | 424 |
| 734 | 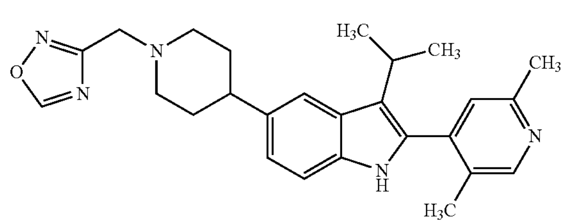 [SMILES: Cc1cc(-c2[nH]c3ccc(C4CCN(Cc5ncon5)CC4)cc3c2C(C)C)c(C)cn1] | 430 | 1.98 | QC-AA | 424 |

TABLE 34-continued

| Ex. No. | Structure | LCMS MH+ | Rt (min) | HPLC Method | General Method |
|---|---|---|---|---|---|
| 735 | 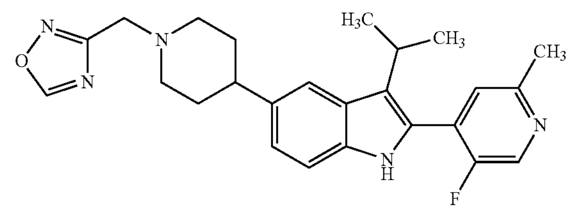 [SMILES: Cc1cc(-c2[nH]c3ccc(C4CCN(Cc5ncon5)CC4)cc3c2C(C)C)c(F)cn1] | 434 | 1.76 | QC-AA | 424 |
| 736 | 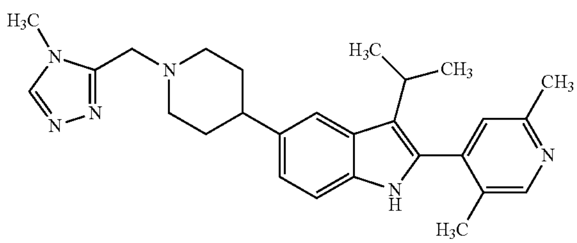 [SMILES: Cc1cc(-c2[nH]c3ccc(C4CCN(Cc5nncn5C)CC4)cc3c2C(C)C)c(C)cn1] | 443 | 1.63 | QC-AA | 424 |
| 737 | 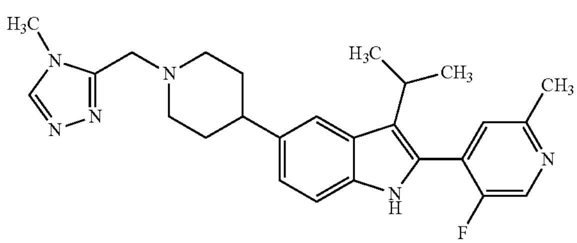 [SMILES: Cc1cc(-c2[nH]c3ccc(C4CCN(Cc5nncn5C)CC4)cc3c2C(C)C)c(F)cn1] | 447 | 1.66 | QC-AA | 424 |
| 738 | 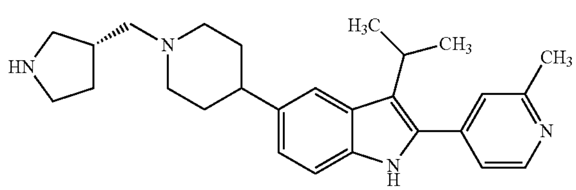 [SMILES: Cc1cc(-c2[nH]c3ccc(C4CCN(C[C@@H]5CCNC5)CC4)cc3c2C(C)C)ccn1] | 417.2 | 0.624 | QC-TFA | 424 |
| 739 | 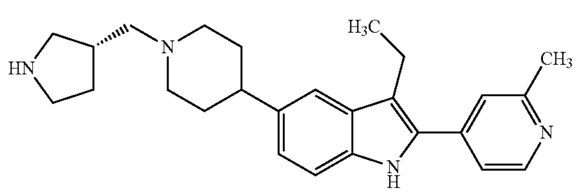 [SMILES: CCc1c(-c2ccnc(C)c2)[nH]c2ccc(C3CCN(C[C@@H]4CCNC4)CC3)cc12] | 403.1 | 0.573 | QC-TFA | 424 |
| 740 | 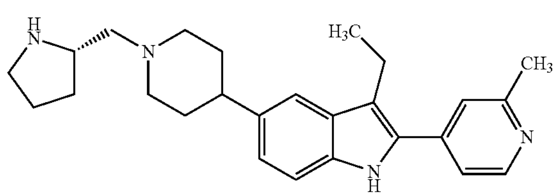 [SMILES: CCc1c(-c2ccnc(C)c2)[nH]c2ccc(C3CCN(C[C@@H]4CCCN4)CC3)cc12] | 403.3 | 0.644 | QC-TFA | 424 |
| 741 | 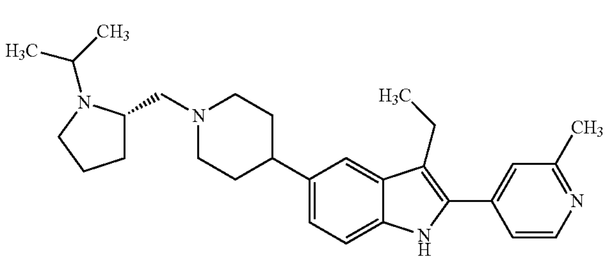 [SMILES: CCc1c(-c2ccnc(C)c2)[nH]c2ccc(C3CCN(C[C@@H]4CCCN4C(C)C)CC3)cc12] | 445.4 | 0.751 | QC-TFA | 424 |

TABLE 34-continued

| Ex. No. | Structure | LCMS MH+ | Rt (min) | HPLC Method | General Method |
|---|---|---|---|---|---|
| 742 | 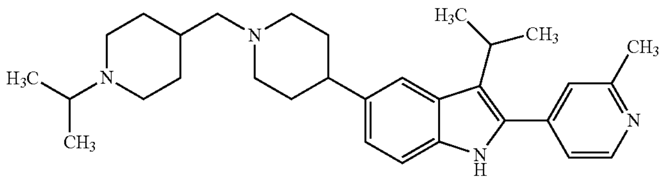 [SMILES: Cc1cc(-c2[nH]c3ccc(C4CCN(CC5CCN(C(C)C)CC5)CC4)cc3c2C(C)C)ccn1] | 473.4 | 0.808 | QC-TFA | 424 |
| 743 | 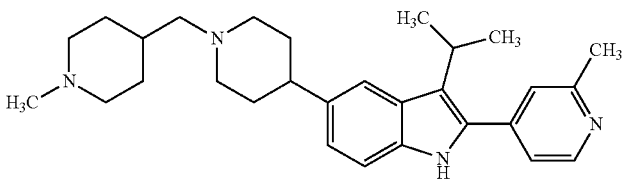 | 445.1 | 0.758 | QC-TFA | 424 |

TABLE 35

| Ex. No. | Structure | LCMS MH+ | Rt (min) | HPLC Method |
|---|---|---|---|---|
| 744 | 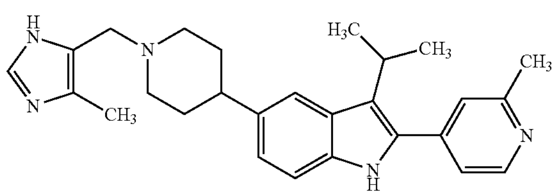 [SMILES: Cc1cc(-c2[nH]c3ccc(C4CCN(Cc5[nH]cnc5C)CC4)cc3c2C(C)C)ccn1] | 428.4 | 1.12 | QC-AA |
| 745 | 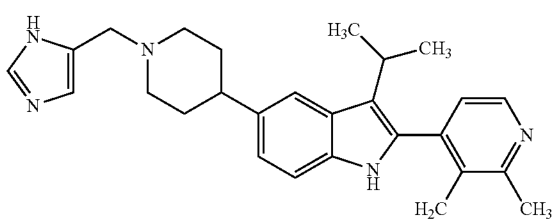 [SMILES: Cc1nccc(-c2[nH]c3ccc(C4CCN(Cc5cnc[nH]5)CC4)cc3c2C(C)C)c1C] | 429 | 0.91 | QC-TFA |
| 746 | 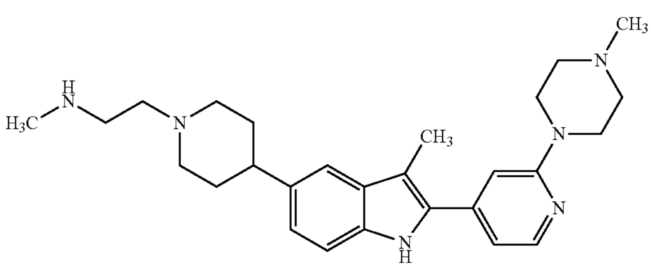 | 447.4 | 2.39 | QC-AA |
| 747 | 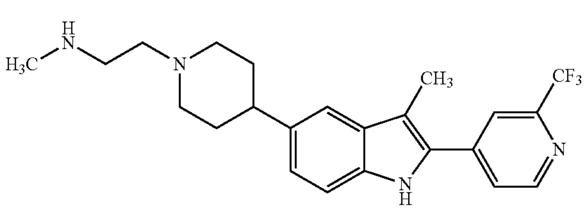 | 417.2 | 1.57 | QC-AA |

TABLE 35-continued

| Ex. No. | Structure | LCMS MH+ | Rt (min) | HPLC Method |
|---|---|---|---|---|
| 748 | 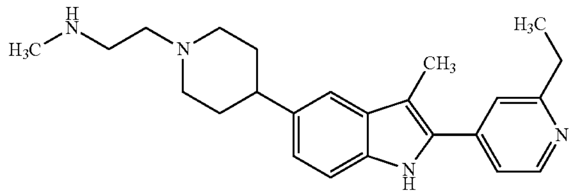 [SMILES: CCc1cc(-c2[nH]c3ccc(C4CCN(CCNC)CC4)cc3c2C)ccn1] | 377.2 | 0.87 | QC-TFA |
| 749 | 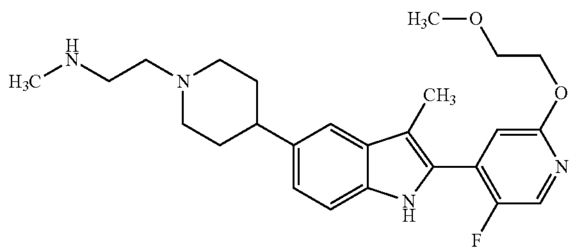 [SMILES: CNCCN1CCC(c2ccc3[nH]c(-c4cc(OCCOC)ncc4F)c(C)c3c2)CC1] | 441.2 | 1.51 | QC-AA |
| 750 | 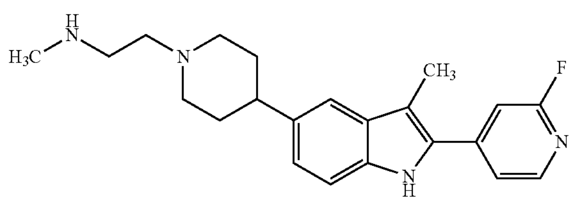 [SMILES: CNCCN1CCC(c2ccc3[nH]c(-c4ccnc(F)c4)c(C)c3c2)CC1] | 367.2 | 1.35 | QC-AA |
| 751 | 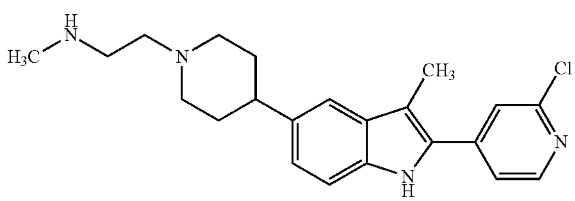 [SMILES: CNCCN1CCC(c2ccc3[nH]c(-c4ccnc(Cl)c4)c(C)c3c2)CC1] | 383.2 | 1.13 | QC-TFA |
| 752 | 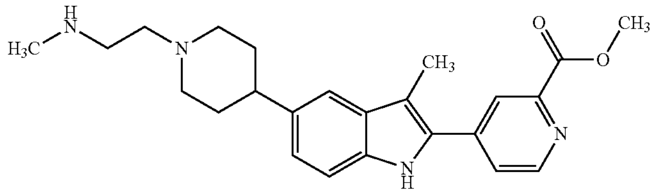 | 407.3 | 1.49 | QC-AA |
| 753 | 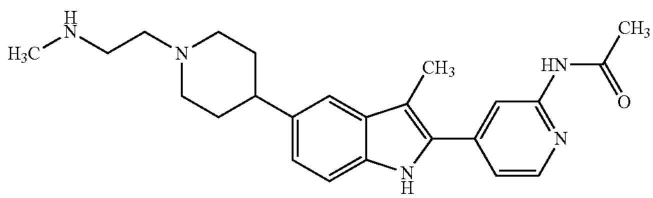 [SMILES: CNCCN1CCC(c2ccc3[nH]c(-c4ccnc(NC(C)=O)c4)c(C)c3c2)CC1] | 406.3 | 1.04 | QC-AA |
| 754 | 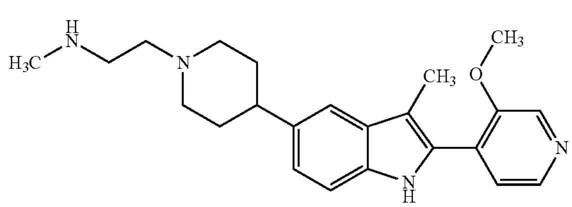 [SMILES: CNCCN1CCC(c2ccc3[nH]c(-c4ccncc4OC)c(C)c3c2)CC1] | 379.2 | 0.49 | QC-TFA |

TABLE 35-continued
| Ex. No. | Structure | LCMS MH+ | Rt (min) | HPLC Method |
|---|---|---|---|---|
| 755 | 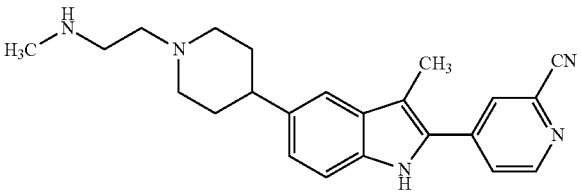 [SMILES: CNCCN1CCC(c2ccc3[nH]c(-c4ccnc(C#N)c4)c(C)c3c2)CC1] | 374.2 | 1.17 | QC-AA |
| 756 | 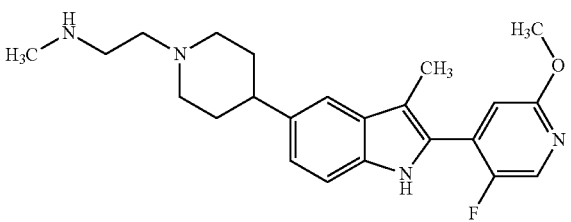 [SMILES: CNCCN1CCC(c2ccc3[nH]c(-c4cc(OC)ncc4F)c(C)c3c2)CC1] | 397.3 | 1.04 | QC-TFA |
| 757 | 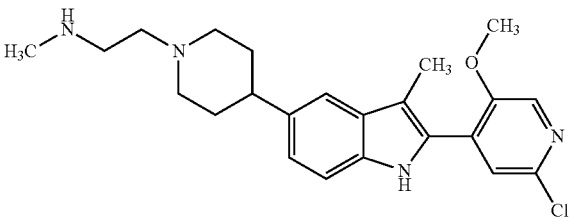 [SMILES: CNCCN1CCC(c2ccc3[nH]c(-c4cc(Cl)ncc4OC)c(C)c3c2)CC1] | 413.2 | 1.01 | QC-TFA |
| 758 | 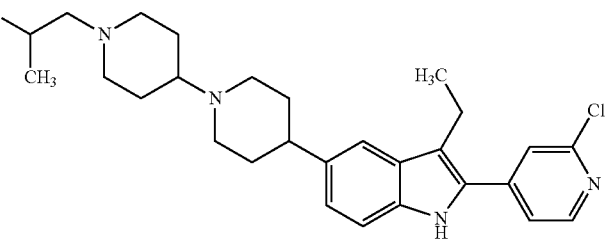 | 479.4 | 1.65 | QC-AA |
| 759 | 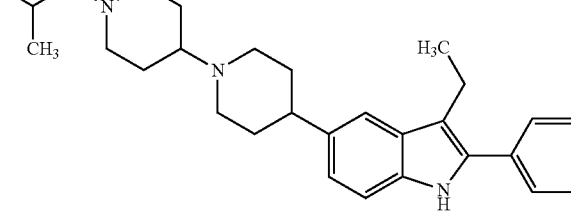 | 463.5 | 1.12 | QC-TFA |
| 760 | 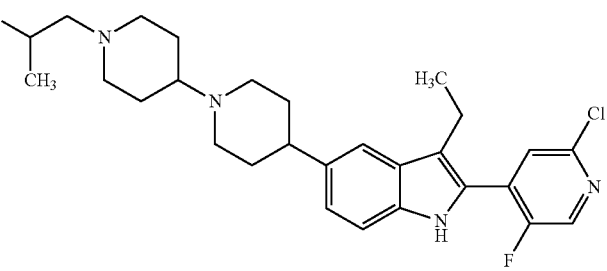 | 497.4 | 1.72 | QC-AA |

TABLE 35-continued

| Ex. No. | Structure | LCMS MH+ | Rt (min) | HPLC Method |
|---|---|---|---|---|
| 761 | 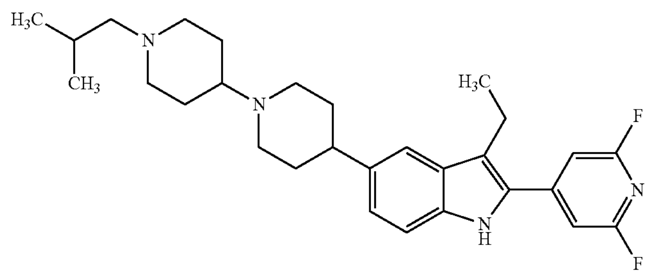 [SMILES: CCc1c(-c2cc(F)nc(F)c2)[nH]c2ccc(C3CCN(C4CCN(CC(C)C)CC4)CC3)cc12] | 481.4 | 1.31 | QC-TFA |
| 762 | 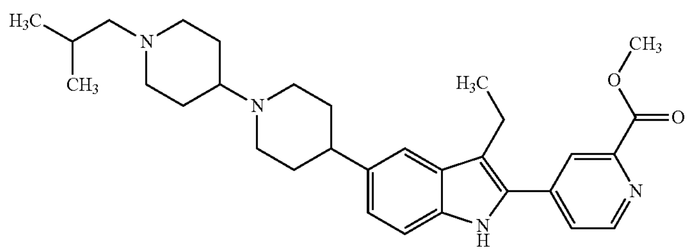 [SMILES: CCc1c(-c2ccnc(C(=O)OC)c2)[nH]c2ccc(C3CCN(C4CCN(CC(C)C)CC4)CC3)cc12] | 503.5 | 0.9 | QC-TFA |
| 763 | 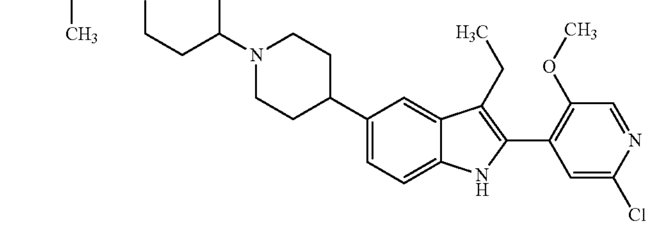 | 509.4 | 1.72 | QC-AA |
| 764 | 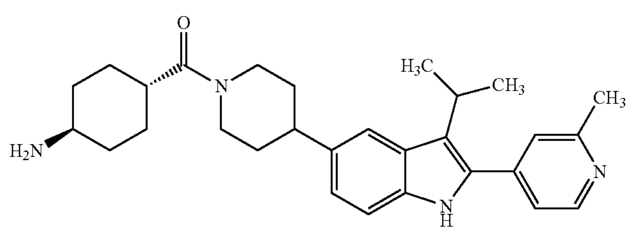 [SMILES: Cc1cc(-c2[nH]c3ccc(C4CCN(C(=O)[C@H]5CC[C@H](N)CC5)CC4)cc3c2C(C)C)ccn1] | 459.3 | 0.9 | QC-TFA |
| 765 | 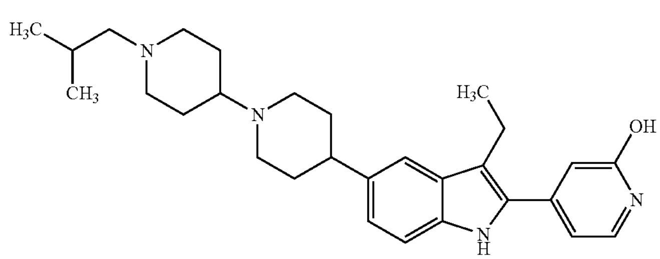 [SMILES: CCc1c(-c2ccnc(O)c2)[nH]c2ccc(C3CCN(C4CCN(CC(C)C)CC4)CC3)cc12] | 461.4 | 0.74 | QC-TFA |
| 766 | 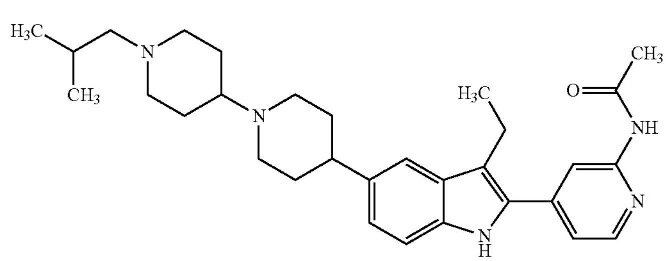 [SMILES: CCc1c(-c2ccnc(NC(C)=O)c2)[nH]c2ccc(C3CCN(C4CCN(CC(C)C)CC4)CC3)cc12] | 502.4 | 1.38 | QC-AA |

TABLE 35-continued

| Ex. No. | Structure | LCMS MH+ | Rt (min) | HPLC Method |
|---|---|---|---|---|
| 767 | 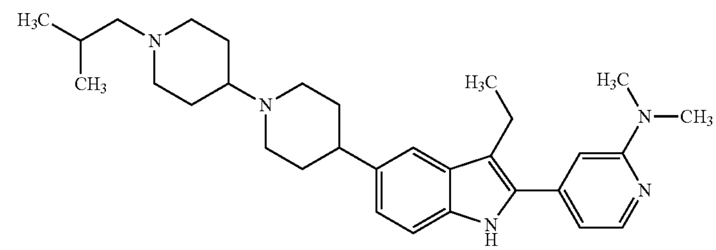 [SMILES: CCc1c(-c2ccnc(N(C)C)c2)[nH]c2ccc(C3CCN(C4CCN(CC(C)C)CC4)CC3)cc12] | 488.4 | 1.66 | QC-AA |
| 768 | 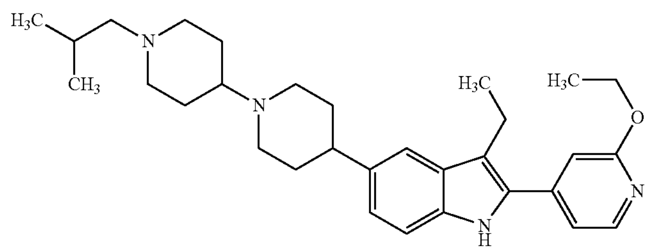 [SMILES: CCOc1cc(-c2[nH]c3ccc(C4CCN(C5CCN(CC(C)C)CC5)CC4)cc3c2CC)ccn1] | 489.4 | 1.78 | QC-AA |
| 769 | 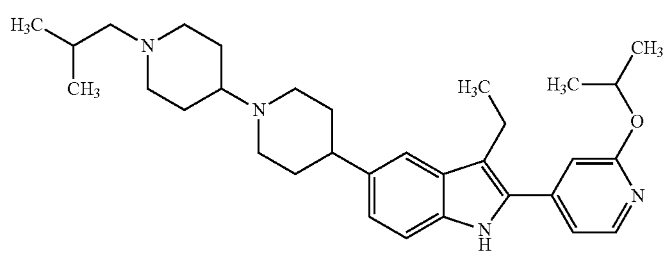 [SMILES: CCc1c(-c2ccnc(OC(C)C)c2)[nH]c2ccc(C3CCN(C4CCN(CC(C)C)CC4)CC3)cc12] | 503.5 | 1.91 | QC-AA |
| 770 | 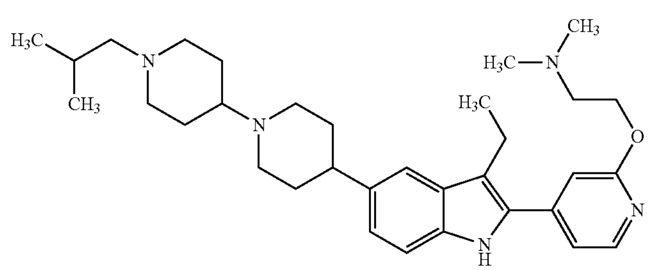 [SMILES: CCc1c(-c2ccnc(OCCN(C)C)c2)[nH]c2ccc(C3CCN(C4CCN(CC(C)C)CC4)CC3)cc12] | 532.4 | 0.76 | QC-TFA |
| 771 | 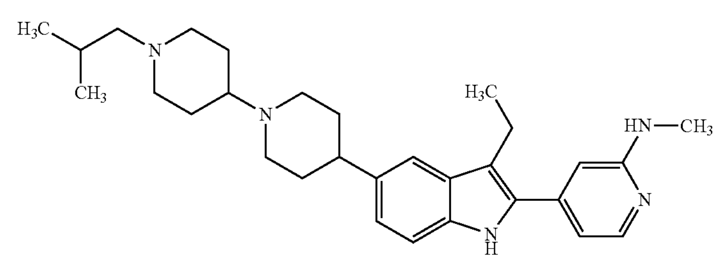 | 474 | 1.26 | QC-AA |
| 772 | 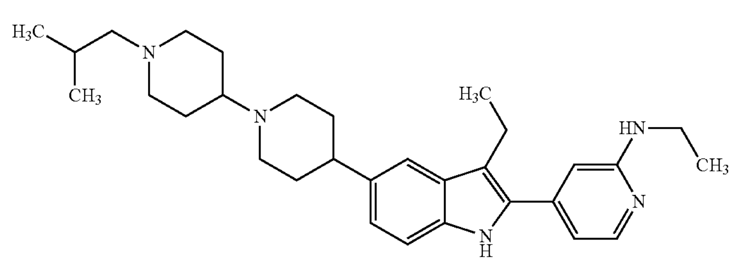 [SMILES: CCNc1cc(-c2[nH]c3ccc(C4CCN(C5CCN(CC(C)C)CC5)CC4)cc3c2CC)ccn1] | 488.4 | 0.78 | QC-TFA |

TABLE 35-continued

| Ex. No. | Structure | LCMS MH+ | Rt (min) | HPLC Method |
|---|---|---|---|---|
| 773 | 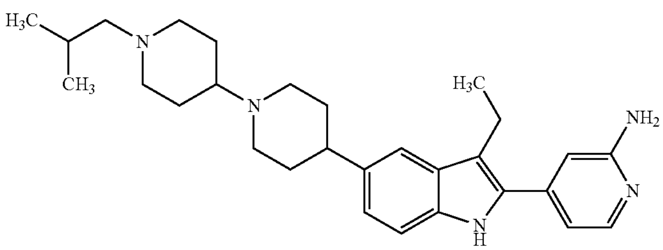 [SMILES: CCc1c(-c2ccnc(N)c2)[nH]c2ccc(C3CCN(C4CCN(CC(C)C)CC4)CC3)cc12] | 460.4 | 1.16 | QC-AA |
| 774 | 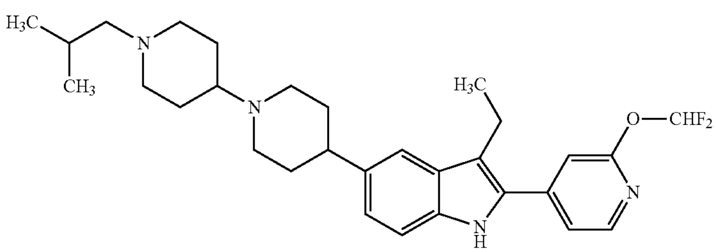 [SMILES: CCc1c(-c2ccnc(OC(F)F)c2)[nH]c2ccc(C3CCN(C4CCN(CC(C)C)CC4)CC3)cc12] | 511.4 | 1.81 | QC-AA |
| 775 | 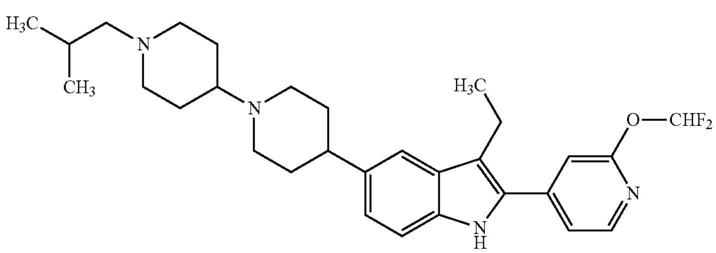 [SMILES: CCc1c(-c2ccnc(OC(F)F)c2)[nH]c2ccc(C3CCN(C4CCN(CC(C)C)CC4)CC3)cc12] | 511.3 | 1.03 | QC-TFA |
| 776 | 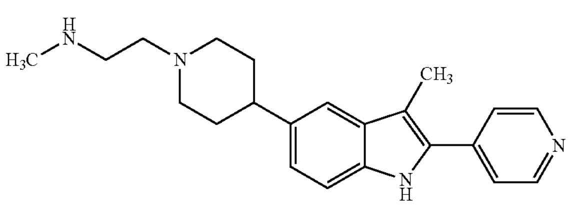 [SMILES: CNCCN1CCC(c2ccc3[nH]c(-c4ccncc4)c(C)c3c2)CC1] | 349.3 | 1.07 | QC-AA |
| 777 | 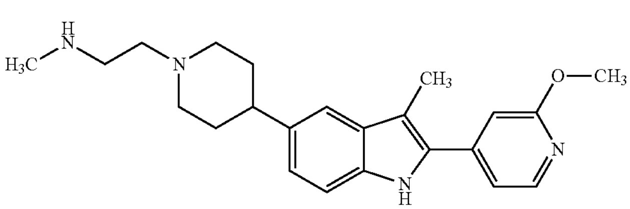 | 379.3 | 0.72 | QC-TFA |
| 778 | 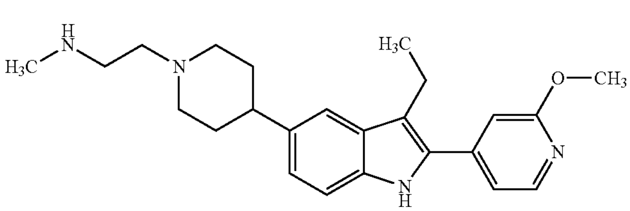 | 393.2 | 1 | QC-TFA |

TABLE 35-continued

| Ex. No. | Structure | LCMS MH+ | Rt (min) | HPLC Method |
|---|---|---|---|---|
| 779 | 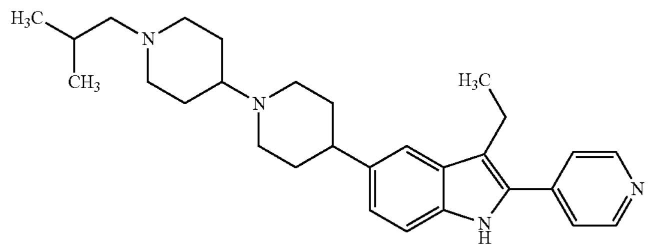 [SMILES: CCc1c(-c2ccncc2)[nH]c2ccc(C3CCN(C4CCN(CC(C)C)CC4)CC3)cc12] | 445.4 | 1.4 | QC-TFA |
| 780 | 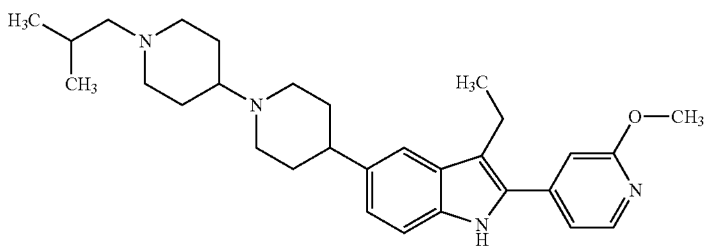 [SMILES: CCc1c(-c2ccnc(OC)c2)[nH]c2ccc(C3CCN(C4CCN(CC(C)C)CC4)CC3)cc12] | 475.5 | 0.93 | QC-TFA |
| 781 | 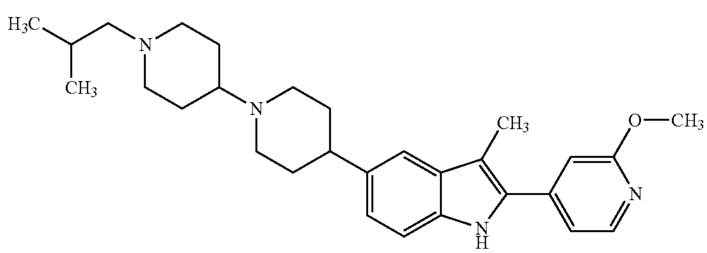 [SMILES: COc1cc(-c2[nH]c3ccc(C4CCN(C5CCN(CC(C)C)CC5)CC4)cc3c2C)ccn1] | 461.4 | 1.54 | QC-AA |
| 782 | 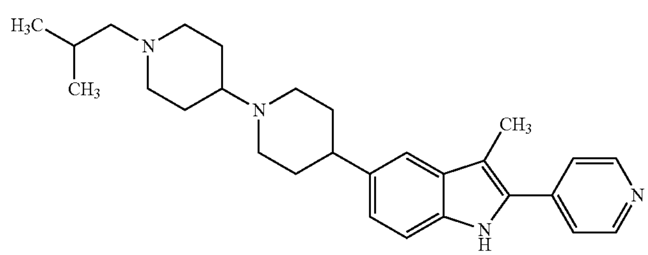 [SMILES: Cc1c(-c2ccncc2)[nH]c2ccc(C3CCN(C4CCN(CC(C)C)CC4)CC3)cc12] | 431.4 | 0.61 | QC-TFA |
| 783 | 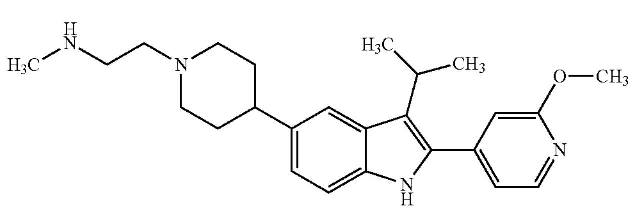 | 407.3 | 1.5 | QC-AA |
| 784 | 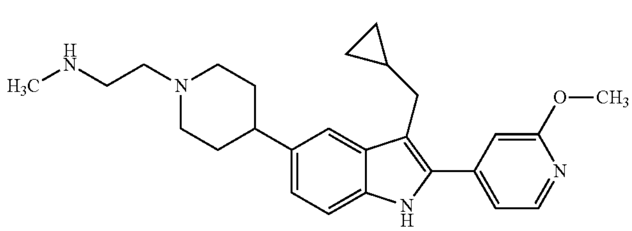 | 419.4 | 0.98 | QC-TFA |

TABLE 35-continued

| Ex. No. | Structure | LCMS MH+ | Rt (min) | HPLC Method |
|---|---|---|---|---|
| 785 | 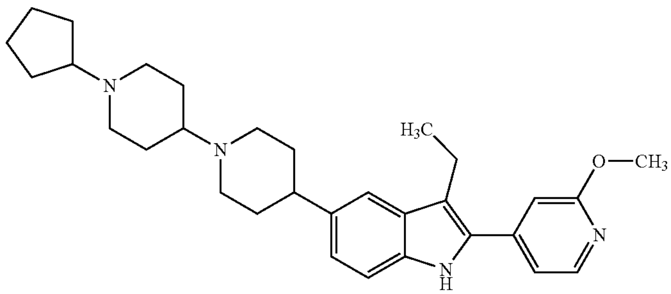 [SMILES: CCc1c(-c2ccnc(OC)c2)[nH]c2ccc(C3CCN(C4CCN(C5CCCC5)CC4)CC3)cc12] | 487.4 | 1.65 | QC-TFA |
| 786 | 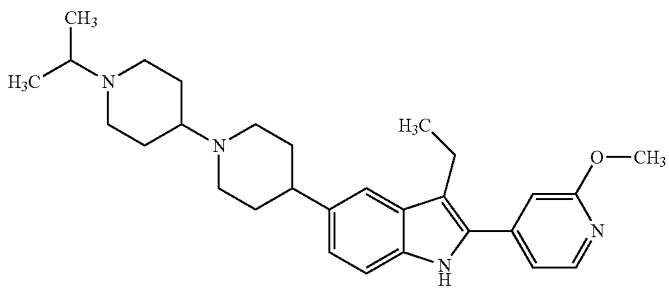 [SMILES: CCc1c(-c2ccnc(OC)c2)[nH]c2ccc(C3CCN(C4CCN(C(C)C)CC4)CC3)cc12] | 461.4 | 1.32 | QC-AA |
| 787 | 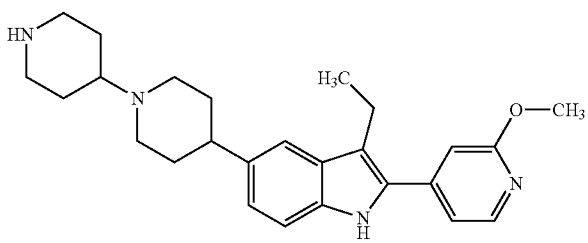 [SMILES: CCc1c(-c2ccnc(OC)c2)[nH]c2ccc(C3CCN(C4CCNCC4)CC3)cc12] | 419.3 | 0.82 | QC-TFA |
| 788 | 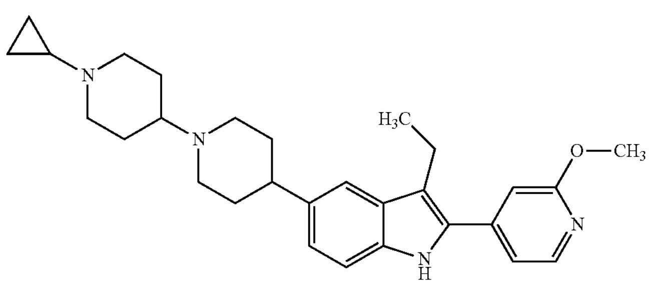 [SMILES: CCc1c(-c2ccnc(OC)c2)[nH]c2ccc(C3CCN(C4CCN(C5CC5)CC4)CC3)cc12] | 459.4 | 0.87 | QC-TFA |
| 789 | 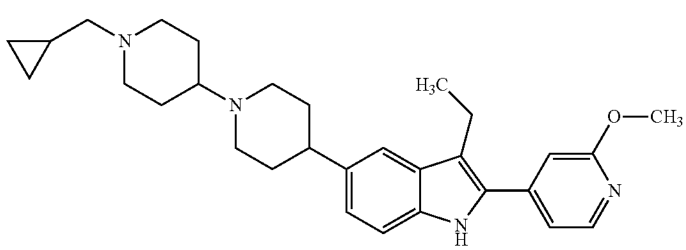 [SMILES: CCc1c(-c2ccnc(OC)c2)[nH]c2ccc(C3CCN(C4CCN(CC5CC5)CC4)CC3)cc12] | 473.4 | 1.46 | QC-AA |

TABLE 35-continued
| Ex. No. | Structure | LCMS MH+ | Rt (min) | HPLC Method |
|---|---|---|---|---|
| 790 | 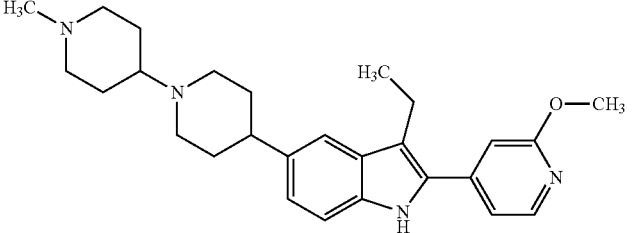 | 433.3 | 0.87 | QC-TFA |
| 791 | 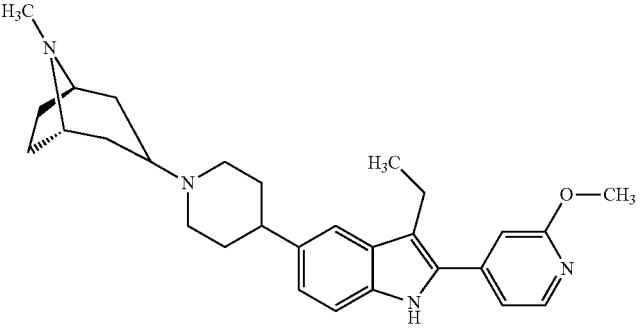 | 459.5 | 1.103 | QC-TFA |
| 792 | 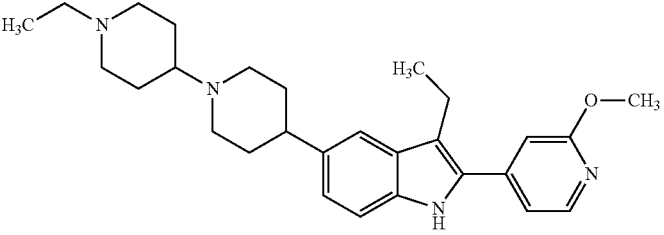 [SMILES: CCc1c(-c2ccnc(OC)c2)[nH]c2ccc(C3CCN(C4CCN(CC)CC4)CC3)cc12] | 447.4 | 0.86 | QC-TFA |
| 793 | 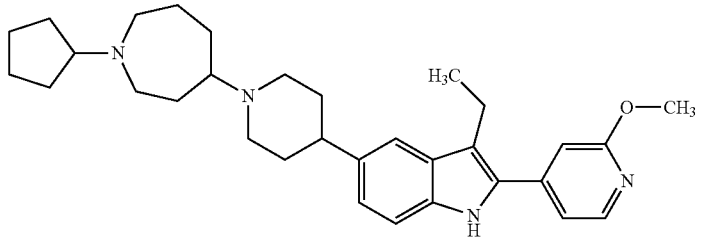 [SMILES: CCc1c(-c2ccnc(OC)c2)[nH]c2ccc(C3CCN(C4CCCN(C5CCCC5)CC4)CC3)cc12] | 501.4 | 0.95 | QC-TFA |
| 794 | 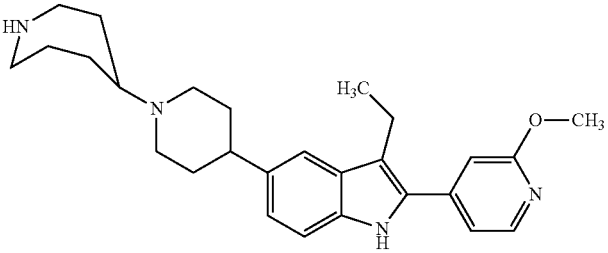 [SMILES: CCc1c(-c2ccnc(OC)c2)[nH]c2ccc(C3CCN(C4CCCNCC4)CC3)cc12] | 433.4 | 1.47 | QC-AA |

TABLE 35-continued

| Ex. No. | Structure | LCMS MH+ | Rt (min) | HPLC Method |
|---|---|---|---|---|
| 795 | 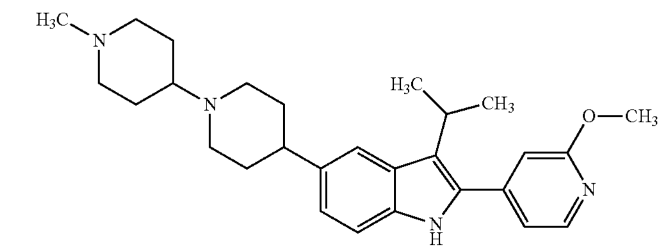 | 447.4 | 0.94 | QC-TFA |
| 796 | 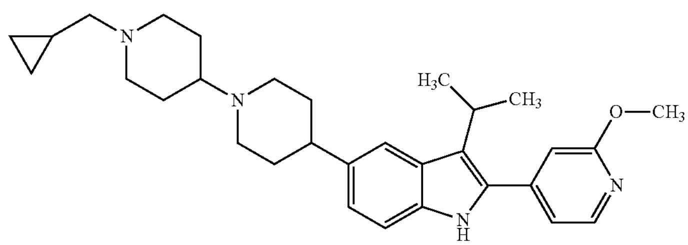 [SMILES: COc1cc(-c2[nH]c3ccc(C4CCN(C5CCN(CC6CC6)CC5)CC4)cc3c2C(C)C)ccn1] | 487.4 | 1.00 | QC-TFA |
| 797 | 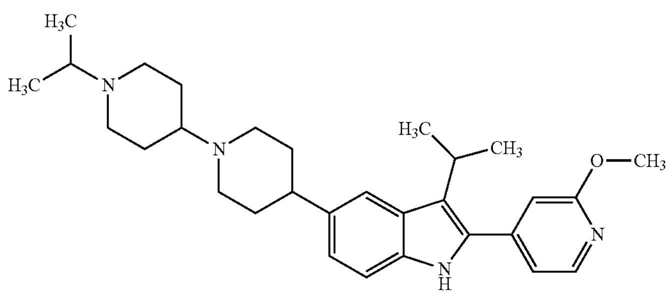 [SMILES: COc1cc(-c2[nH]c3ccc(C4CCN(C5CCN(C(C)C)CC5)CC4)cc3c2C(C)C)ccn1] | 475.4 | 0.99 | QC-TFA |
| 798 | 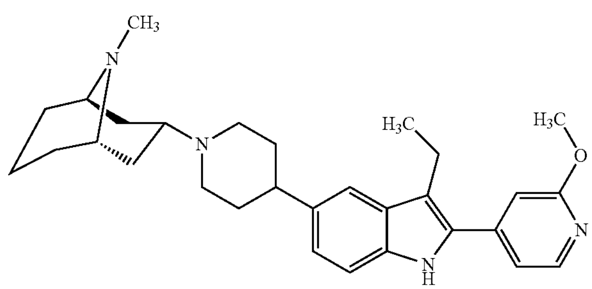 [SMILES: CCc1c(-c2ccnc(OC)c2)[nH]c2ccc(C3CCN(C4C[C@H]5CCC[C@@H](C4)N5C)CC3)cc12] | 473.3 | 0.89 | QC-TFA |
| 799 | 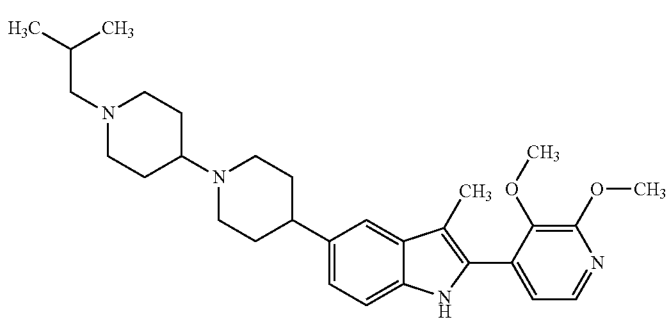 [SMILES: COc1nccc(-c2[nH]c3ccc(C4CCN(C5CCN(CC(C)C)CC5)CC4)cc3c2C)c1OC] | 491.4 | 1.56 | QC-AA |

TABLE 35-continued

| Ex. No. | Structure | LCMS MH+ | Rt (min) | HPLC Method |
|---|---|---|---|---|
| 800 | 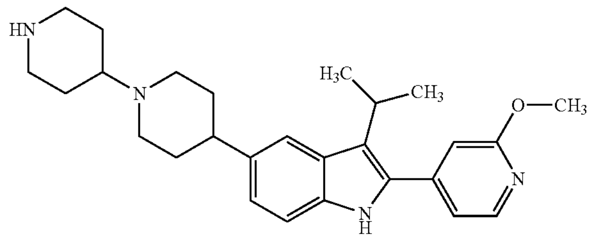 [SMILES: COc1cc(-c2[nH]c3ccc(C4CCN(C5CCNCC5)CC4)cc3c2C(C)C)ccn1] | 433.3 | 0.94 | QC-TFA |
| 801 | 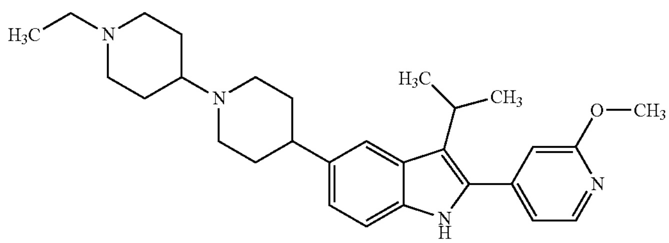 [SMILES: CCN1CCC(N2CCC(c3ccc4[nH]c(-c5ccnc(OC)c5)c(C(C)C)c4c3)CC2)CC1] | 461.5 | 0.96 | QC-TFA |
| 802 | 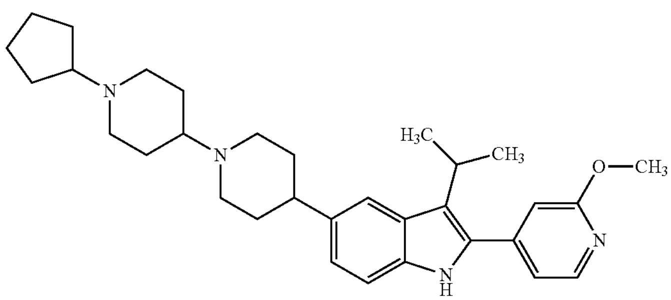 [SMILES: COc1cc(-c2[nH]c3ccc(C4CCN(C5CCN(C6CCCC6)CC5)CC4)cc3c2C(C)C)ccn1] | 501.4 | 1.03 | QC-TFA |
| 803 | 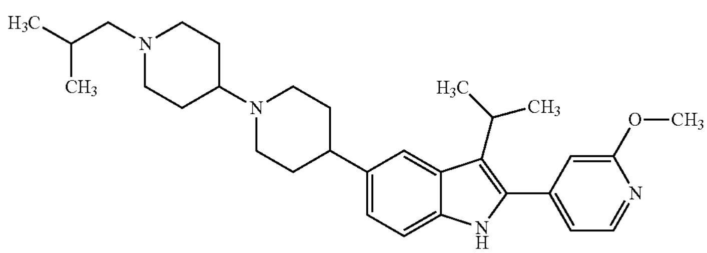 [SMILES: COc1cc(-c2[nH]c3ccc(C4CCN(C5CCN(CC(C)C)CC5)CC4)cc3c2C(C)C)ccn1] | 489.4 | 1.7 | QC-AA |
| 804 | 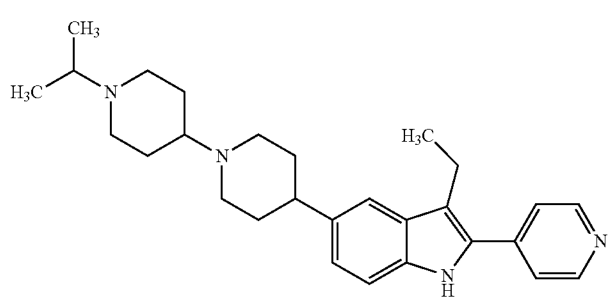 [SMILES: CCc1c(-c2ccncc2)[nH]c2ccc(C3CCN(C4CCN(C(C)C)CC4)CC3)cc12] | 431.4 | 1.2 | QC-AA |
| 805 | 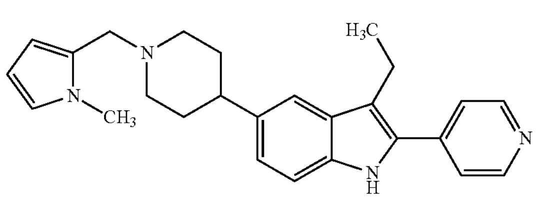 [SMILES: CCc1c(-c2ccncc2)[nH]c2ccc(C3CCN(Cc4cccn4C)CC3)cc12] | 399.2 | 0.89 | QC-TFA |

TABLE 35-continued

| Ex. No. | Structure | LCMS MH+ | Rt (min) | HPLC Method |
|---|---|---|---|---|
| 806 | 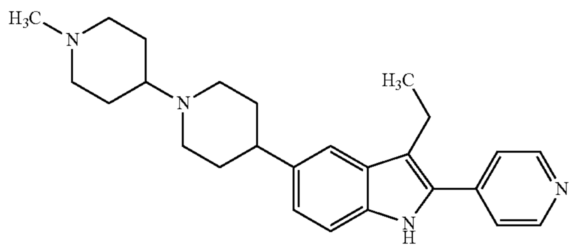 [SMILES: CCc1c(-c2ccncc2)[nH]c2ccc(C3CCN(C4CCN(C)CC4)CC3)cc12] | 403.3 | 1.12 | BCQC-AA |
| 807 | 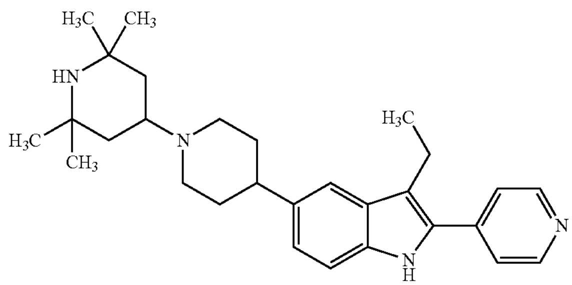 [SMILES: CCc1c(-c2ccncc2)[nH]c2ccc(C3CCN(C4CC(C)(C)NC(C)(C)C4)CC3)cc12] | 445.4 | 1.19 | QC-AA |
| 808 | 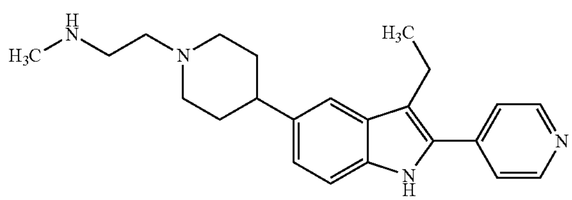 [SMILES: CCc1c(-c2ccncc2)[nH]c2ccc(C3CCN(CCNC)CC3)cc12] | 363.2 | 1.12 | QC-AA |
| 809 | 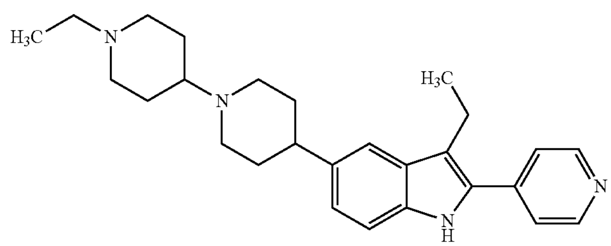 [SMILES: CCc1c(-c2ccncc2)[nH]c2ccc(C3CCN(C4CCN(CC)CC4)CC3)cc12] | 417.3 | 1.03 | QC-TFA |
| 810 | 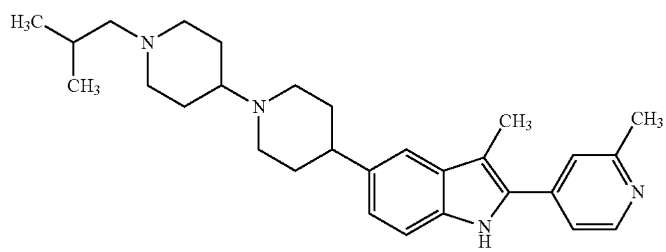 [SMILES: Cc1cc(-c2[nH]c3ccc(C4CCN(C5CCN(CC(C)C)CC5)CC4)cc3c2C)ccn1] | 445.3 | 1.23 | QC-AA |
| 811 | 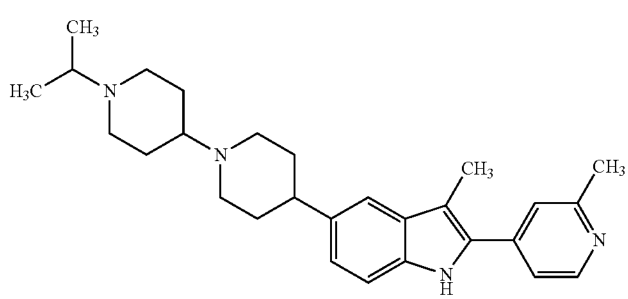 [SMILES: Cc1cc(-c2[nH]c3ccc(C4CCN(C5CCN(C(C)C)CC5)CC4)cc3c2C)ccn1] | 431.4 | 0.61 | QC-TFA |

TABLE 35-continued

| Ex. No. | Structure | LCMS MH+ | Rt (min) | HPLC Method |
|---|---|---|---|---|
| 812 | 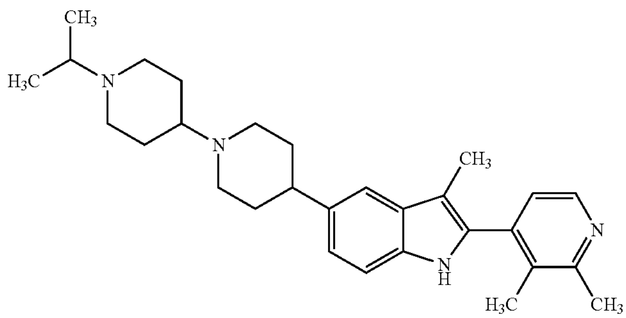 [SMILES: Cc1nccc(-c2[nH]c3ccc(C4CCN(C5CCN(C(C)C)CC5)CC4)cc3c2C)c1C] | 445.3 | 1.00 | QC-AA |
| 813 | 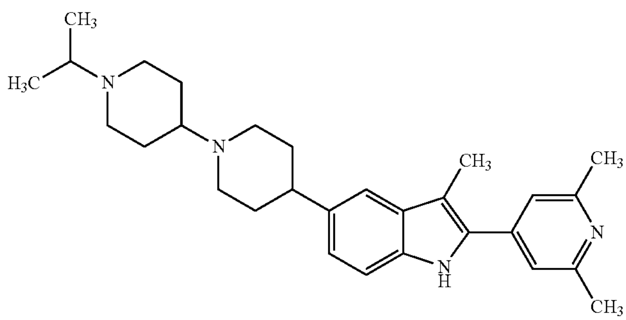 [SMILES: Cc1cc(-c2[nH]c3ccc(C4CCN(C5CCN(C(C)C)CC5)CC4)cc3c2C)cc(C)n1] | 445.3 | 0.99 | QC-AA |
| 814 | 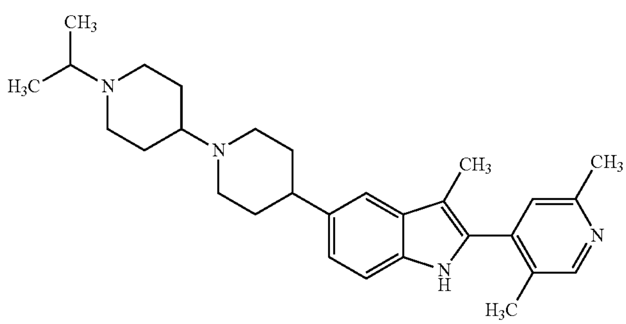 [SMILES: Cc1cc(-c2[nH]c3ccc(C4CCN(C5CCN(C(C)C)CC5)CC4)cc3c2C)c(C)cn1] | 445.3 | 0.58 | QC-TFA |
| 815 | 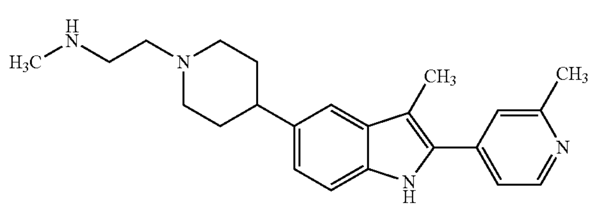 | 363.1 | 1.1 | QC-AA |
| 816 | 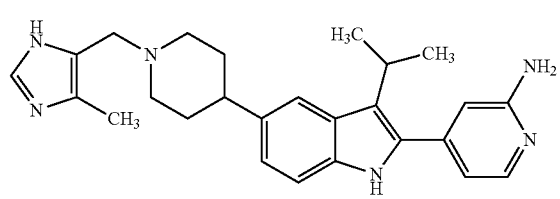 [SMILES: Cc1nc[nH]c1CN1CCC(c2ccc3[nH]c(-c4ccnc(N)c4)c(C(C)C)c3c2)CC1] | 429.1 | 0.91 | QC-TFA |

TABLE 35-continued

| Ex. No. | Structure | LCMS MH+ | Rt (min) | HPLC Method |
|---|---|---|---|---|
| 817 | 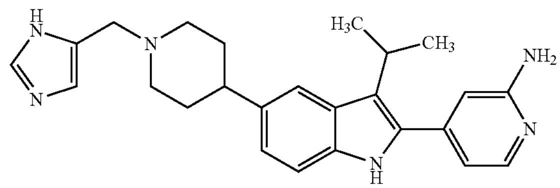 [SMILES: CC(C)c1c(-c2ccnc(N)c2)[nH]c2ccc(C3CCN(Cc4cnc[nH]4)CC3)cc12] | 415.4 | 0.6 | QC-TFA |
| 818 | 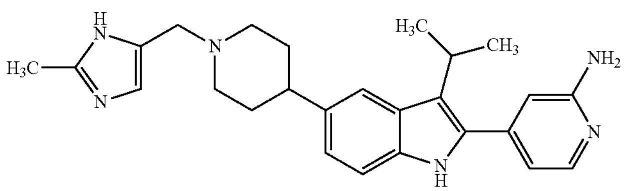 [SMILES: Cc1ncc(CN2CCC(c3ccc4[nH]c(-c5ccnc(N)c5)c(C(C)C)c4c3)CC2)[nH]1] | 429.3 | 0.947 | QC-TFA |
| 819 | 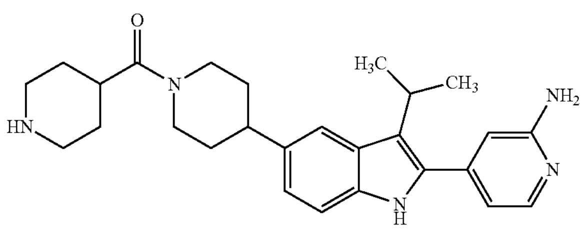 [SMILES: CC(C)c1c(-c2ccnc(N)c2)[nH]c2ccc(C3CCN(C(=O)C4CCNCC4)CC3)cc12] | 446.2 | 1.094 | QC-TFA |
| 820 | 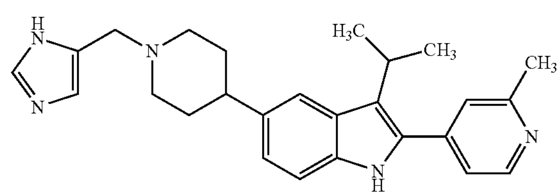 [SMILES: Cc1cc(-c2[nH]c3ccc(C4CCN(Cc5cnc[nH]5)CC4)cc3c2C(C)C)ccn1] | 414.1 | 1.06 | QC-AA |
| 821 | 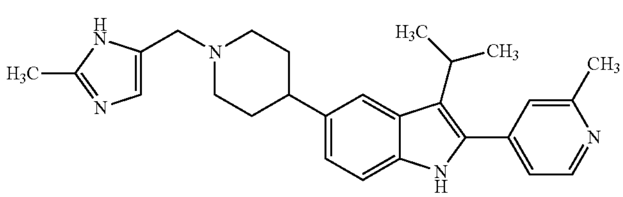 | 428.3 | 0.61 | QC-TFA |
| 822 | 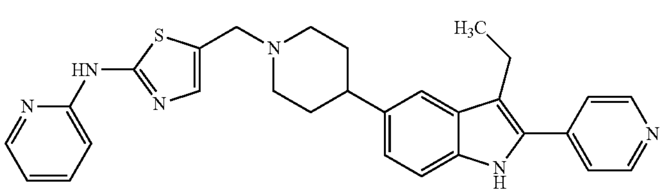 [SMILES: CCc1c(-c2ccncc2)[nH]c2ccc(C3CCN(Cc4cnc(Nc5ccccn5)s4)CC3)cc12] | 495.2 | 0.82 | QC-TFA |
| 823 | 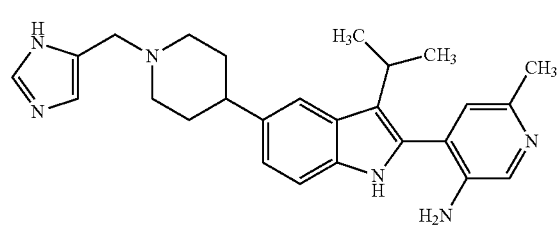 [SMILES: Cc1cc(-c2[nH]c3ccc(C4CCN(Cc5cnc[nH]5)CC4)cc3c2C(C)C)c(N)cn1] | 429.2 | 1.01 | QC-AA |

TABLE 35-continued

| Ex. No. | Structure | LCMS MH+ | Rt (min) | HPLC Method |
|---|---|---|---|---|
| 824 | 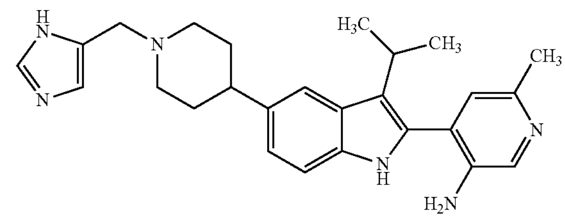 [SMILES: Cc1cc(-c2[nH]c3ccc(C4CCN(Cc5cnc[nH]5)CC4)cc3c2C(C)C)c(N)cn1] | 428.2 | 1.21 | QC-AA |
| 825 | 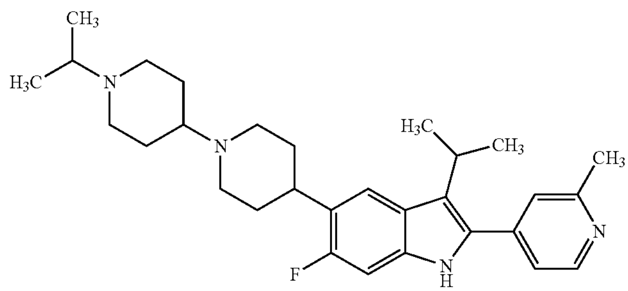 [SMILES: Cc1cc(-c2[nH]c3cc(F)c(C4CCN(C5CCN(C(C)C)CC5)CC4)cc3c2C(C)C)ccn1] | 477.4 | 0.74 | QC-TFA |
| 826 | 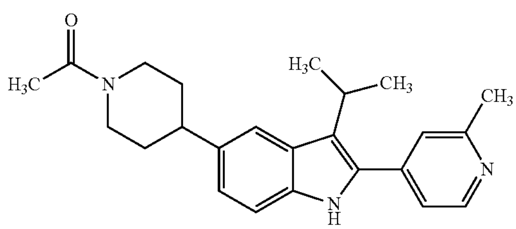 [SMILES: CC(=O)N1CCC(c2ccc3[nH]c(-c4ccnc(C)c4)c(C(C)C)c3c2)CC1] | 376.3 | 1.7 | QC-AA |
| 827 | 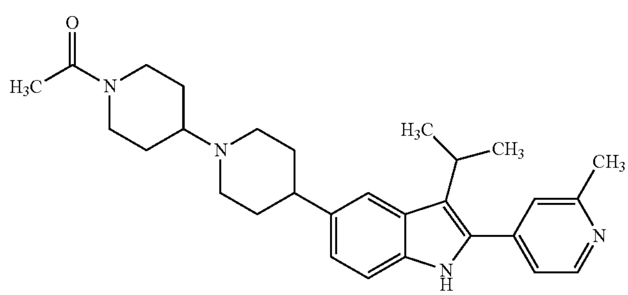 [SMILES: CC(=O)N1CCC(N2CCC(c3ccc4[nH]c(-c5ccnc(C)c5)c(C(C)C)c4c3)CC2)CC1] | 459.3 | 0.82 | QC-TFA |
| 828 | 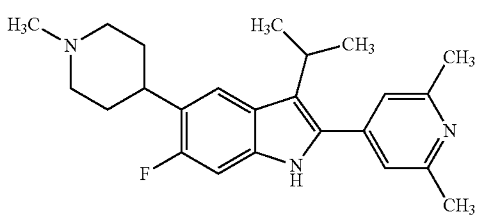 | 380 | 0.85 | QC-TFA |
| 829 | 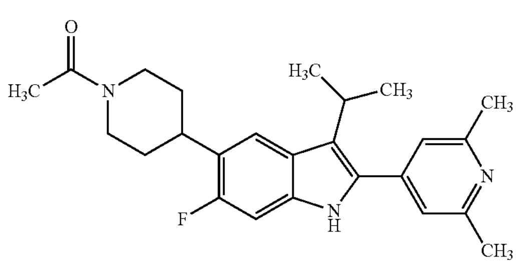 [SMILES: CC(=O)N1CCC(c2cc3c(C(C)C)c(-c4cc(C)nc(C)c4)[nH]c3cc2F)CC1] | 408.1 | 1.72 | QC-AA |

TABLE 35-continued

| Ex. No. | Structure | LCMS MH+ | Rt (min) | HPLC Method |
|---|---|---|---|---|
| 830 | 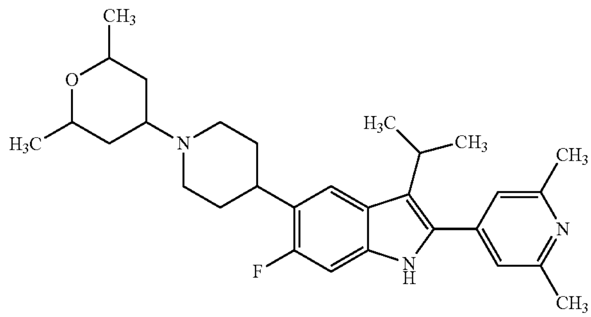 | 478.2 | 1.69 | QC-AA |
| 831 | 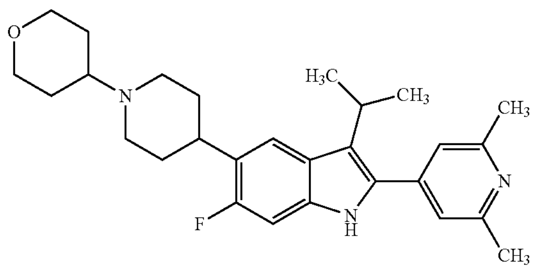 [SMILES: Cc1cc(-c2[nH]c3cc(F)c(C4CCN(C5CCOCC5)CC4)cc3c2C(C)C)cc(C)n1] | 450.1 | 1.46 | QC-AA |
| 832 | 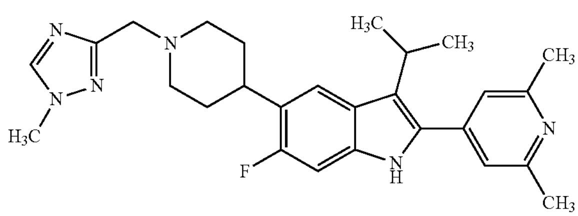 [SMILES: Cc1cc(-c2[nH]c3cc(F)c(C4CCN(Cc5ncn(C)n5)CC4)cc3c2C(C)C)cc(C)n1] | 461.2 | 1.77 | QC-AA |
| 833 | 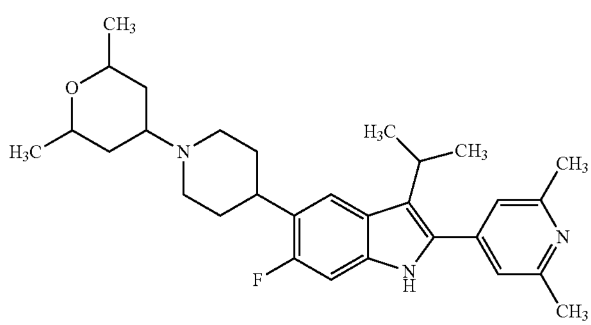 | 478.1 | 2.13 | QC-AA |
| 834 | 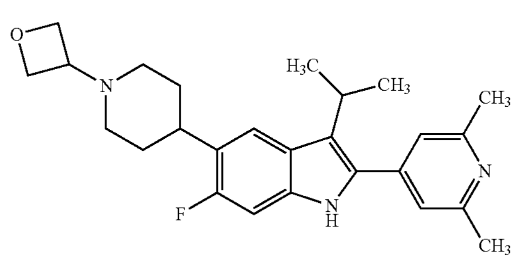 [SMILES: Cc1cc(-c2[nH]c3cc(F)c(C4CCN(C5COC5)CC4)cc3c2C(C)C)cc(C)n1] | 422.1 | 0.856 | QC-TFA |

TABLE 35-continued

| Ex. No. | Structure | LCMS MH+ | Rt (min) | HPLC Method |
|---|---|---|---|---|
| 835 | 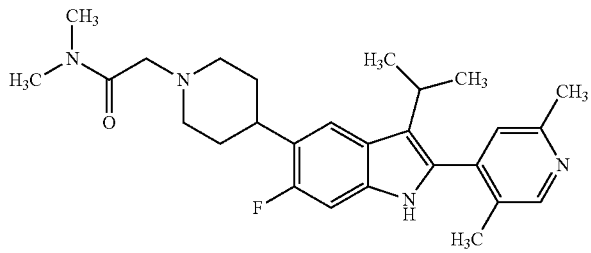 | 451.2 | 1.5 | QC-AA |
| 836 | 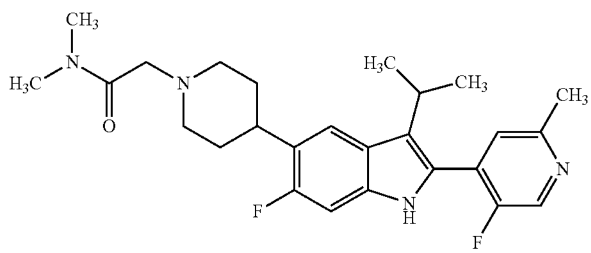 | 455.1 | 1.53 | QC-AA |
| 837 | 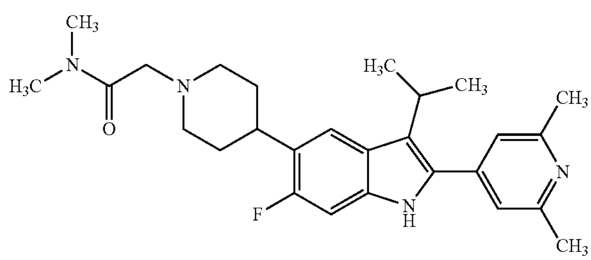 | 451.2 | 1.5 | QC-AA |
| 838 | 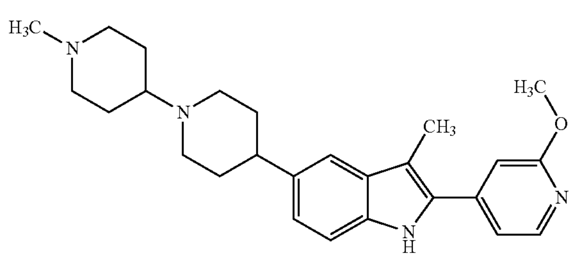 [SMILES: COc1cc(-c2[nH]c3ccc(C4CCN(C5CCN(C)CC5)CC4)cc3c2C)ccn1] | 419 | 1.27 | QC-AA |
| 839 | 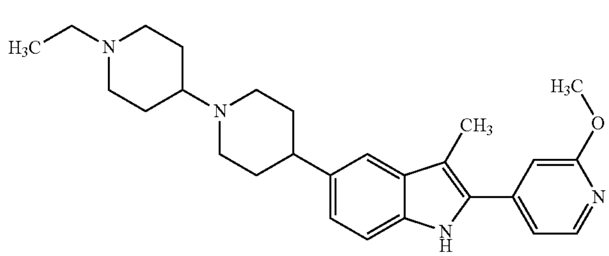 [SMILES: CCN1CCC(N2CCC(c3ccc4[nH]c(-c5ccnc(OC)c5)c(C)c4c3)CC2)CC1] | 433 | 1.19 | QC-AA |

TABLE 35-continued

| Ex. No. | Structure | LCMS MH+ | Rt (min) | HPLC Method |
|---|---|---|---|---|
| 840 | 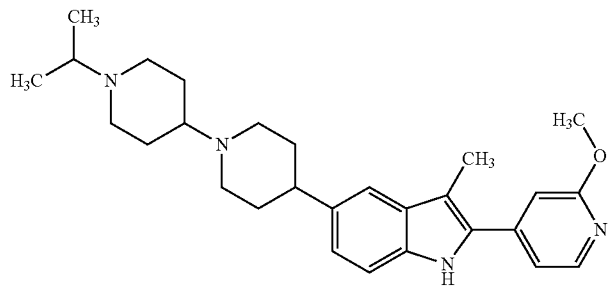 [SMILES: COc1cc(-c2[nH]c3ccc(C4CCN(C5CCN(C(C)C)CC5)CC4)cc3c2C)ccn1] | 447 | 1.25 | QC-AA |
| 841 | 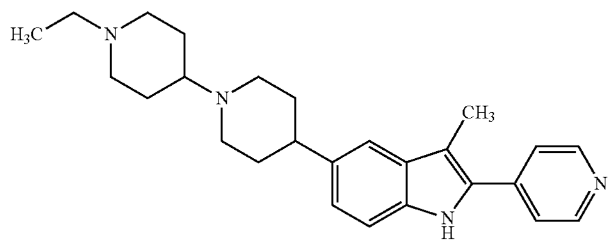 [SMILES: CCN1CCC(N2CCC(c3ccc4[nH]c(-c5ccncc5)c(C)c4c3)CC2)CC1] | 403 | 1.09 | QC-AA |
| 842 | 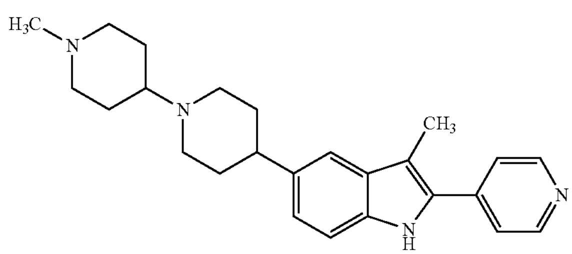 [SMILES: Cc1c(-c2ccncc2)[nH]c2ccc(C3CCN(C4CCN(C)CC4)CC3)cc12] | 389 | 0.92 | QC-AA |
| 843 | 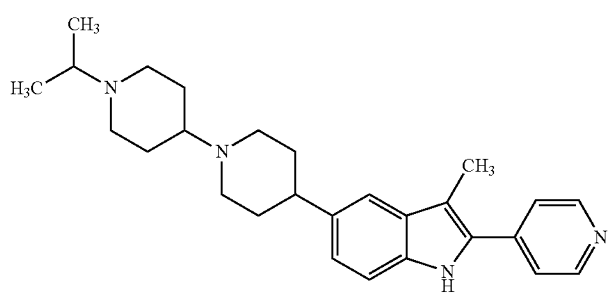 [SMILES: Cc1c(-c2ccncc2)[nH]c2ccc(C3CCN(C4CCN(C(C)C)CC4)CC3)cc12] | 417 | 1.04 | QC-AA |
| 844 | 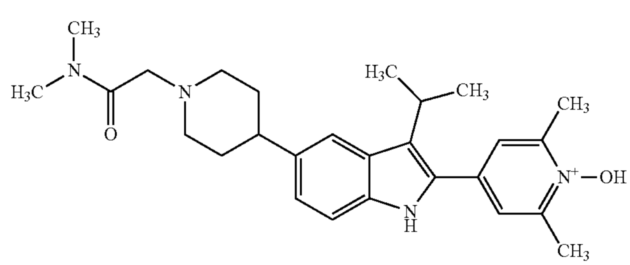 [SMILES: Cc1cc(-c2[nH]c3ccc(C4CCN(CC(=O)N(C)C)CC4)cc3c2C(C)C)cc(C)[n+]1O] | 449 | 1.03 | QC-TFA |

TABLE 35-continued

| Ex. No. | Structure | LCMS MH+ | Rt (min) | HPLC Method |
|---|---|---|---|---|
| 845 | 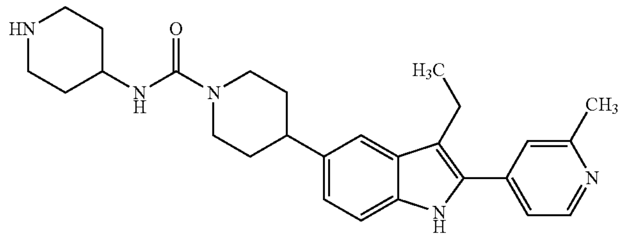 [SMILES: CCc1c(-c2ccnc(C)c2)[nH]c2ccc(C3CCN(C(=O)NC4CCNCC4)CC3)cc12] | 446.2 | 0.89 | QC-TFA |
| 846 | 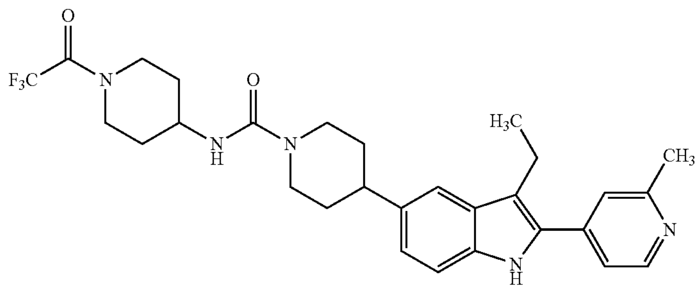 [SMILES: CCc1c(-c2ccnc(C)c2)[nH]c2ccc(C3CCN(C(=O)NC4CCN(C(=O)C(F)(F)F)CC4)CC3)cc12] | 542.2 | 1.43 | QC-TFA |
| 847 | 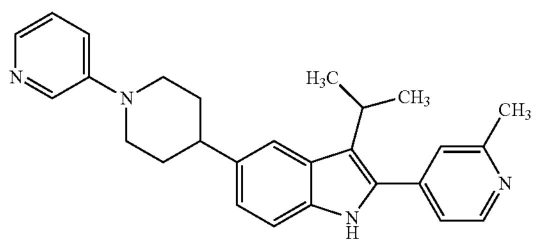 [SMILES: Cc1cc(-c2[nH]c3ccc(C4CCN(c5cccnc5)CC4)cc3c2C(C)C)ccn1] | 411.1 | 1.06 | QC-TFA |
| 848 | 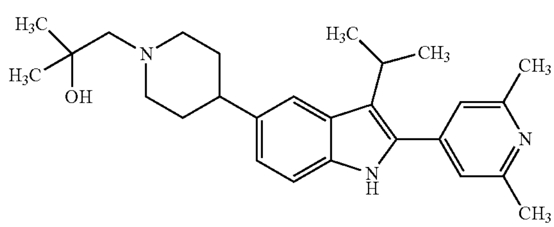 [SMILES: Cc1cc(-c2[nH]c3ccc(C4CCN(CC(C)(C)O)CC4)cc3c2C(C)C)cc(C)n1] | 420.4 | 0.95 | QC-TFA |
| 849 | 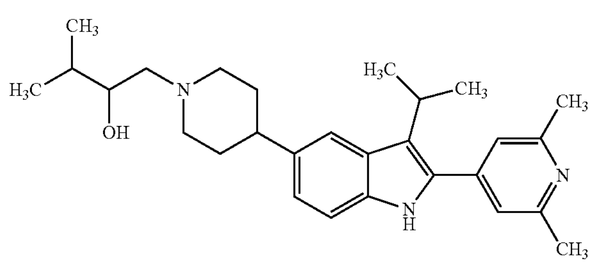 [SMILES: Cc1cc(-c2[nH]c3ccc(C4CCN(CC(O)C(C)C)CC4)cc3c2C(C)C)cc(C)n1] | 434.4 | 1.52 | QC-AA |
| 850 | 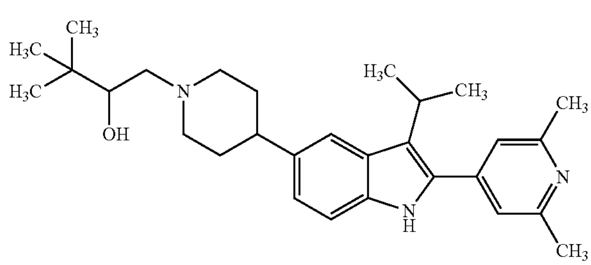 [SMILES: Cc1cc(-c2[nH]c3ccc(C4CCN(CC(O)C(C)(C)C)CC4)cc3c2C(C)C)cc(C)n1] | 448.4 | 1.17 | QC-TFA |

TABLE 35-continued

| Ex. No. | Structure | LCMS MH+ | Rt (min) | HPLC Method |
|---|---|---|---|---|
| 851 | 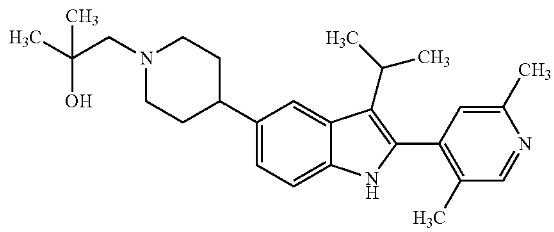 [SMILES: Cc1cc(-c2[nH]c3ccc(C4CCN(CC(C)(C)O)CC4)cc3c2C(C)C)c(C)cn1] | 420.1 | 0.93 | QC-TFA |
| 852 | 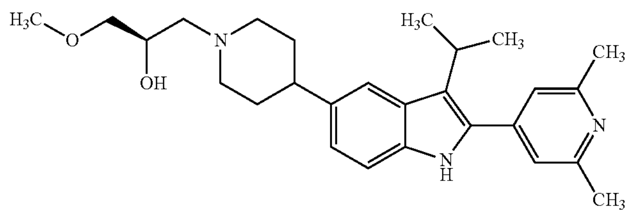 | 436.4 | 0.93 | QC-TFA |
| 853 | 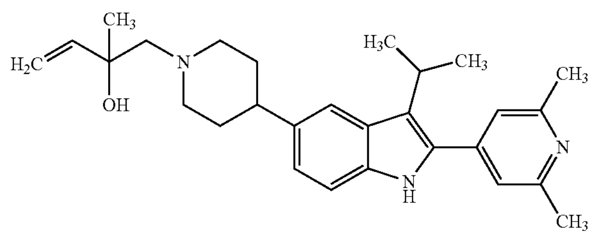 [SMILES: C=CC(C)(O)CN1CCC(c2ccc3[nH]c(-c4cc(C)nc(C)c4)c(C(C)C)c3c2)CC1] | 432.3 | 1.04 | QC-TFA |
| 854 | 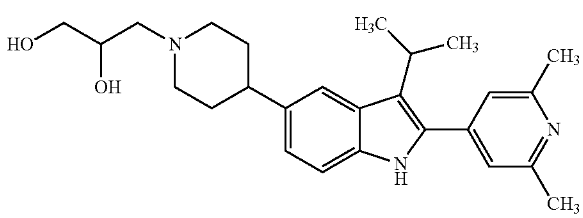 [SMILES: Cc1cc(-c2[nH]c3ccc(C4CCN(CC(O)CO)CC4)cc3c2C(C)C)cc(C)n1] | 422.2 | 0.81 | QC-TFA |
| 855 | 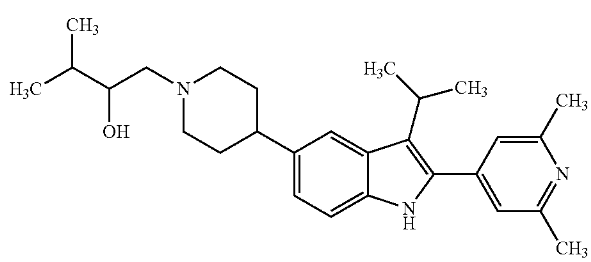 [SMILES: Cc1cc(-c2[nH]c3ccc(C4CCN(CC(O)C(C)C)CC4)cc3c2C(C)C)cc(C)n1] | 434.0 | 1.13 | QC-TFA |
| 856 | 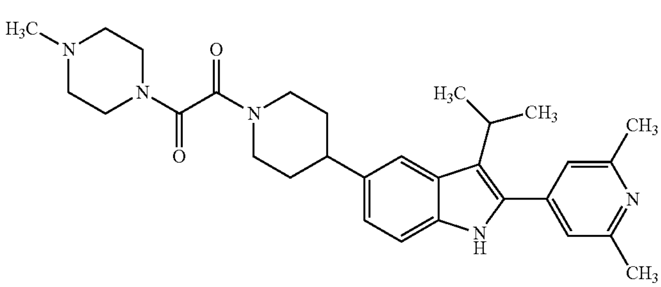 | 502.5 | 0.98 | QC-TFA |

TABLE 35-continued
| Ex. No. | Structure | LCMS MH+ | Rt (min) | HPLC Method |
|---|---|---|---|---|
| 857 | 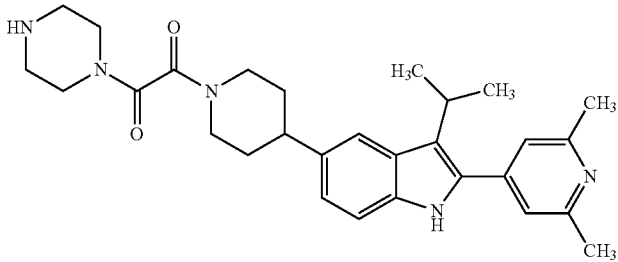 [SMILES: Cc1cc(-c2[nH]c3ccc(C4CCN(C(=O)C(=O)N5CCNCC5)CC4)cc3c2C(C)C)cc(C)n1] | 488.4 | 0.95 | QC-TFA |
| 858 | 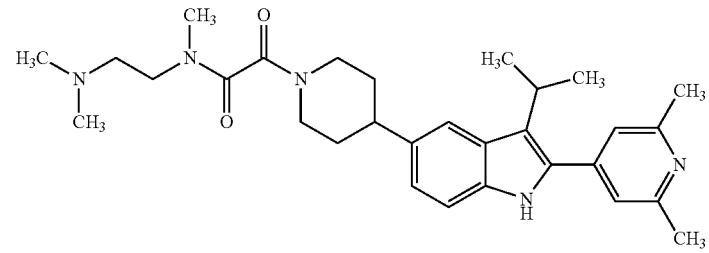 | 504.2 | 1.00 | QC-TFA |
| 859 | 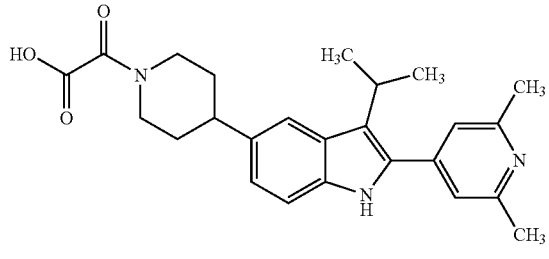 [SMILES: Cc1cc(-c2[nH]c3ccc(C4CCN(C(=O)C(=O)O)CC4)cc3c2C(C)C)cc(C)n1] | 420.2 | 1.11 | QC-TFA |
| 860 | 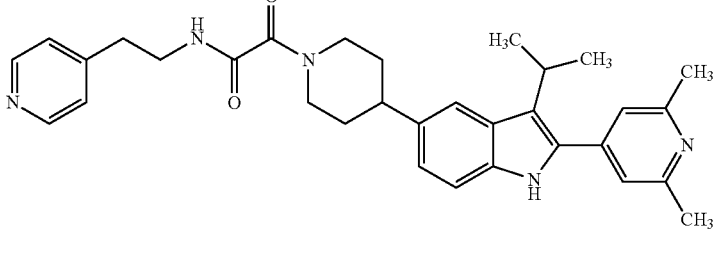 | 524.3 | 1.02 | QC-TFA |
| 861 | 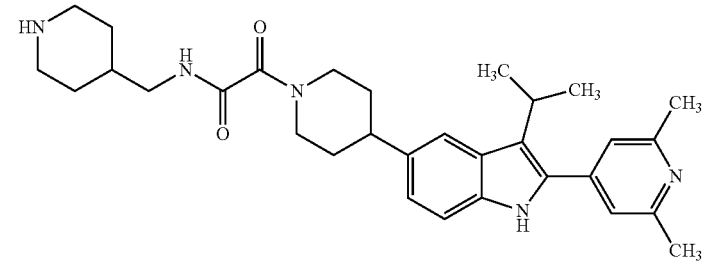 [SMILES: Cc1cc(-c2[nH]c3ccc(C4CCN(C(=O)C(=O)NCC5CCNCC5)CC4)cc3c2C(C)C)cc(C)n1] | 516.2 | 1.03 | QC-TFA |

TABLE 35-continued

| Ex. No. | Structure | LCMS MH+ | Rt (min) | HPLC Method |
|---|---|---|---|---|
| 862 | 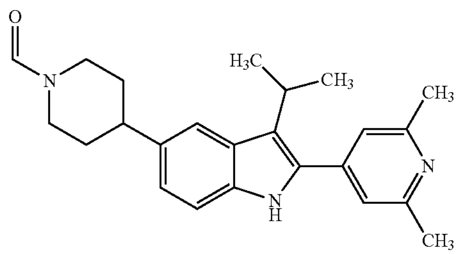 [SMILES: Cc1cc(-c2[nH]c3ccc(C4CCN(C=O)CC4)cc3c2C(C)C)cc(C)n1] | 376.0 | 1.18 | QC-TFA |
| 863 | 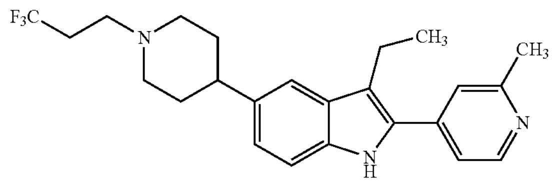 [SMILES: CCc1c(-c2ccnc(C)c2)[nH]c2ccc(C3CCN(CCC(F)(F)F)CC3)cc12] | 416.3 | 0.93 | QC-TFA |
| 864 | 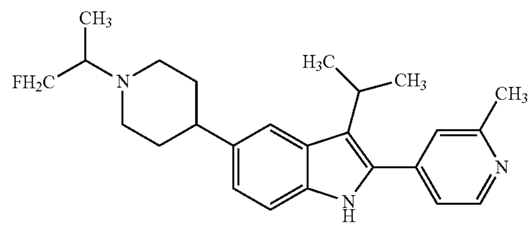 | 394.1 | 0.91 | QC-TFA |
| 865 | 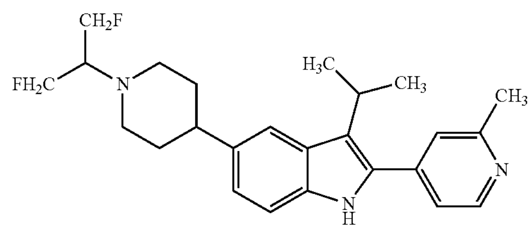 | 411.9 | 0.91 | QC-TFA |
| 866 | 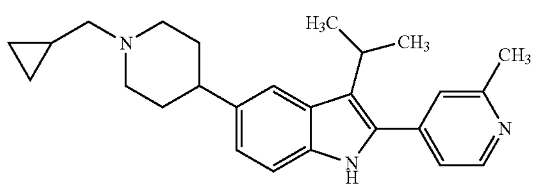 [SMILES: Cc1cc(-c2[nH]c3ccc(C4CCN(CC5CC5)CC4)cc3c2C(C)C)ccn1] | 387.9 | 0.98 | QC-TFA |
| 867 | 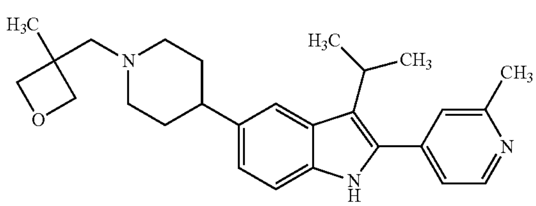 [SMILES: Cc1cc(-c2[nH]c3ccc(C4CCN(CC5(C)COC5)CC4)cc3c2C(C)C)ccn1] | 418.4 | 0.83 | QC-TFA |
| 868 | 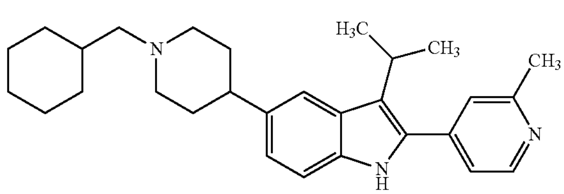 [SMILES: Cc1cc(-c2[nH]c3ccc(C4CCN(CC5CCCCC5)CC4)cc3c2C(C)C)ccn1] | 430.4 | 1.26 | QC-TFA |

TABLE 35-continued

| Ex. No. | Structure | LCMS MH+ | Rt (min) | HPLC Method |
|---|---|---|---|---|
| 869 | 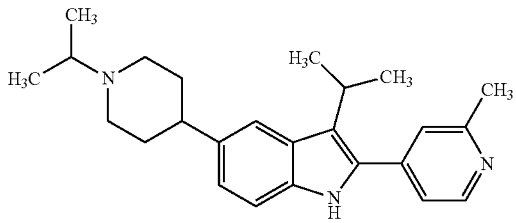 [SMILES: Cc1cc(-c2[nH]c3ccc(C4CCN(C(C)C)CC4)cc3c2C(C)C)ccn1] | 376.3 | 0.97 | QC-TFA |
| 870 | 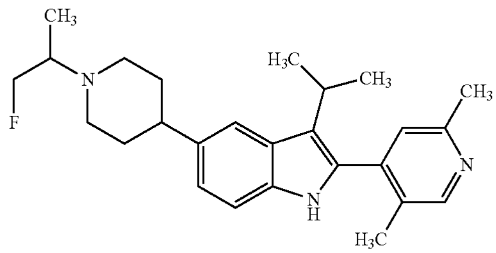 [SMILES: Cc1cc(-c2[nH]c3ccc(C4CCN(C(C)CF)CC4)cc3c2C(C)C)c(C)cn1] | 408.0 | 0.99 | QC-TFA |
| 871 | 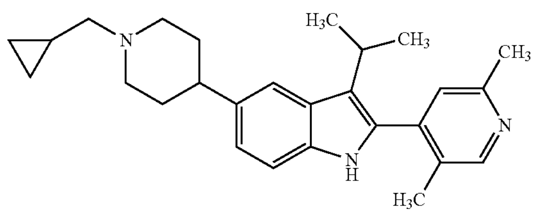 [SMILES: Cc1cc(-c2[nH]c3ccc(C4CCN(CC5CC5)CC4)cc3c2C(C)C)c(C)cn1] | 402.2 | 0.99 | QC-TFA |
| 872 | 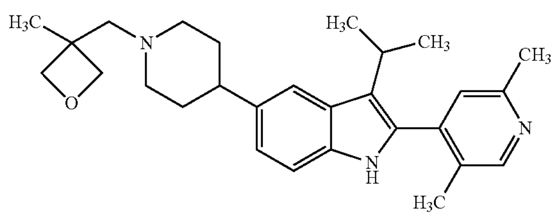 | 432.4 | 0.89 | QC-TFA |
| 873 | 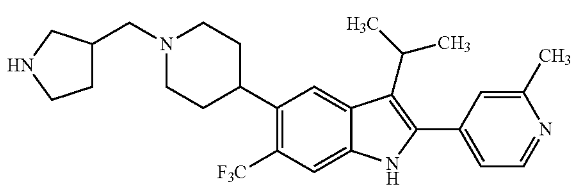 [SMILES: Cc1cc(-c2[nH]c3cc(C(F)(F)F)c(C4CCN(CC5CCNC5)CC4)cc3c2C(C)C)ccn1] | 485.4 | 0.807 | QC-TFA |
| 874 | 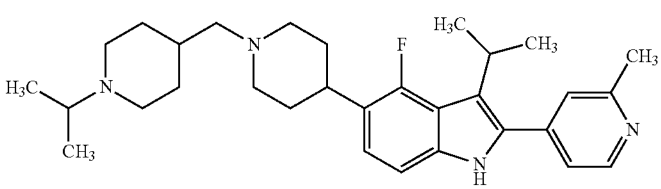 [SMILES: Cc1cc(-c2[nH]c3ccc(C4CCN(CC5CCN(C(C)C)CC5)CC4)c(F)c3c2C(C)C)ccn1] | 491.4 | 0.833 | QC-TFA |
| 875 | 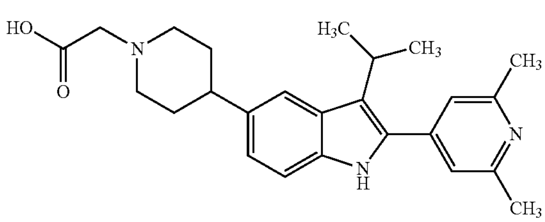 [SMILES: Cc1cc(-c2[nH]c3ccc(C4CCN(CC(=O)O)CC4)cc3c2C(C)C)cc(C)n1] | 406.3 | 0.814 | QC-TFA |

TABLE 35-continued

| Ex. No. | Structure | LCMS MH+ | Rt (min) | HPLC Method |
|---|---|---|---|---|
| 876 | 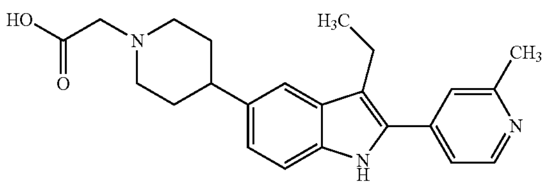 [SMILES: CCc1c(-c2ccnc(C)c2)[nH]c2ccc(C3CCN(CC(=O)O)CC3)cc12] | 378.3 | 0.723 | QC-TFA |
| 877 | 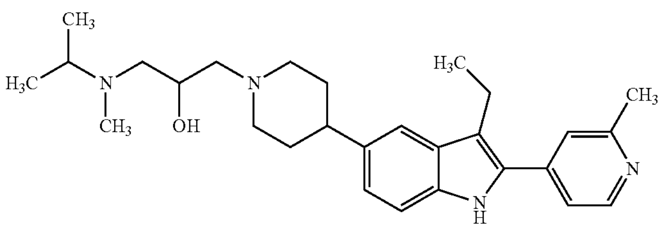 [SMILES: CCc1c(-c2ccnc(C)c2)[nH]c2ccc(C3CCN(CC(O)CN(C)C(C)C)CC3)cc12] | 449.1 | 0.698 | QC-TFA |
| 878 | 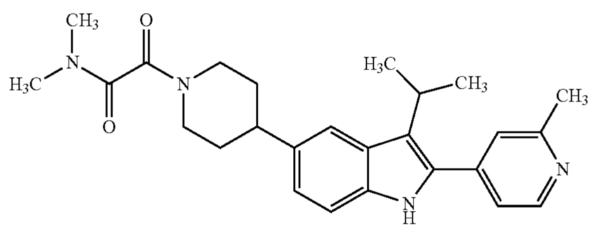 | 433.4 | 1.111 | QC-TFA |
| 879 | 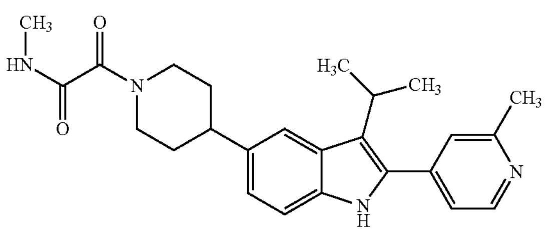 | 419.3 | 1.069 | QC-TFA |

Biological Assays

The pharmacological properties of the compounds of this invention may be confirmed by a number of biological assays. The exemplified biological assays, which follow, have been carried out with compounds of the invention.

TLR7/8/9 Inhibition Reporter Assays

HEK-Blue™-cells (Invivogen) overexpressing human TLR7, TLR8 or TLR9 receptors were used for screening inhibitors of these receptors using an inducible SEAP (secreted embryonic alkaline phosphatase) reporter gene under the control of the IFN-β minimal promoter fused to five NF-κB and AP-1-binding sites. Briefly, cells are seeded into Greiner 384 well plates (15000 cells per well for TLR7, 20,000 for TLR8 and 25,000 for TLR9) and then treated with test compounds in DMSO to yield a final dose response concentration range of 0.05 nM-50 µM. After a 30 minute compound pre-treatment at room temperature, the cells are then stimulated with a TLR7 ligand (gardiquimod at a final concentration of 7.5 µM), TLR8 ligand (R848 at a final concentration of 15.9 µM) or TLR9 ligand (ODN2006 at a final concentration of 5 nM) to activate NF-κB and AP-1 which induce the production of SEAP. After a 22 hour incubation at 37° C., 5% $CO_2$, SEAP levels are determined with the addition of HEK-Blue™ Detection reagent (Invivogen), a cell culture medium that allows for detection of SEAP, according to manufacturer's specifications. The percent inhibition is determined as the % reduction in the HEK-Blue signal present in wells treated with agonist plus DMSO alone compared to wells treated with a known inhibitor.

TABLE 35

TLR7/8/9 Inhibition Data

| Ex. No. | TLR7 $IC_{50}$ (nM) | TLR8 $IC_{50}$ (nM) | TLR9 $IC_{50}$ (nM) |
|---|---|---|---|
| 1 | 0.7 | 3.2 | 302 |
| 2 | 4.7 | 11.2 | 248 |
| 3 | 1.8 | 3.8 | 1889 |
| 5 | 6.1 | 3.9 | 946 |

TABLE 35-continued

TLR7/8/9 Inhibition Data

| Ex. No. | TLR7 IC$_{50}$ (nM) | TLR8 IC$_{50}$ (nM) | TLR9 IC$_{50}$ (nM) |
|---|---|---|---|
| 6 | 28.2 | 115.4 | 1475 |
| 7 | 590.4 | 195 | 3535 |
| 8 | 34.4 | 28.8 | 160 |
| 9 | 75.1 | 22.1 | 562 |
| 10 | 5.1 | 6.3 | 354 |
| 11 | 357.7 | 90.6 | 309 |
| 12 | 19.8 | 39.7 | 362 |
| 13 | 16.1 | 90 | 419 |
| 14 | 423 | 186.7 | 1197 |
| 15 | 1542 | 447.7 | 26502 |
| 16 | 1.5 | 1.4 | 2482 |
| 18 | 177.3 | 47 | 6269 |
| 19 | 123.6 | 10.9 | 1858 |
| 20 | 1661.2 | 127.6 | 7790 |
| 21 | 1.5 | 4 | 2980 |
| 22 | 80.6 | 75 | 1504 |
| 23 | 97 | 32.3 | 8794 |
| 24 | 1482.8 | 703.5 | 1692 |
| 26 | 199.4 | 481.1 | 6318 |
| 27 | 15.1 | 8.9 | 2972 |
| 28 | 7.2 | 33.9 | 3431 |
| 29 | 2.1 | 18.8 | 264 |
| 30 | 28.5 | 22.3 | 708 |
| 31 | 2.6 | 1 | 963 |
| 32 | 4072.1 | 3681.3 | 3988 |
| 33 | 2066.4 | 230.1 | 5650 |
| 34 | 1268.1 | 159.5 | 4614 |
| 35 | 26.7 | 28.8 | 4085 |
| 36 | 1268.7 | 453.9 | 4869 |
| 37 | 42650.5 | 634.9 | 6101 |
| 38 | 38.4 | 6.9 | 2153 |
| 39 | 7.2 | 22.3 | 955 |
| 40 | 16.5 | 4.1 | 1481 |
| 42 | 52.7 | 2.5 | 897 |
| 43 | 277.6 | 253.9 | 546 |
| 44 | 13.9 | 14.4 | 1641 |
| 46 | 1.5 | 12.5 | 2345 |
| 47 | 9 | 36.2 | 3502 |
| 50 | 3.2 | 1.9 | 12738 |
| 51 | 1 | 2.5 | 775 |
| 53 | 2.9 | 1.2 | 2303 |
| 56 | 4.6 | 23.9 | 804 |
| 57 | 489.2 | 280.7 | 1768 |
| 58 | 31.2 | 667.4 | 888 |
| 60 | 96.3 | 36.8 | 671 |
| 61 | 207.2 | 58.8 | 2370 |
| 62 | 22 | 19.4 | 2100 |
| 63 | 27.7 | 14.3 | 329 |
| 64 | 95.6 | 61.8 | 895 |
| 65 | 2183.5 | 549.6 | 1634 |
| 66 | 1227.3 | 158.8 | 554 |
| 67 | 1012.9 | 9 | 396 |
| 68 | 4189 | 1030.7 | 1028 |
| 69 | 277.4 | 180.7 | 114 |
| 70 | 119.7 | 47.2 | 1113 |
| 71 | 7201.4 | 5637.7 | 2833 |
| 73 | 4.4 | 3.1 | 4720 |
| 74 | 13.1 | 437.3 | 1164 |
| 75 | 5 | 97.1 | 180 |
| 76 | 1.4 | 2.7 | 440 |
| 77 | 0.5 | 4.1 | 344 |
| 78 | 0.8 | 2.7 | 145 |
| 79 | 1.5 | 2 | 1351 |
| 80 | 2.7 | 1.3 | 583 |
| 81 | 613.9 | 906.6 | 696 |
| 82 | 7.3 | 29.2 | N.D. |
| 83 | 11 | 3.6 | N.D. |
| 84 | 75.9 | 39.4 | 464 |
| 86 | 23618.6 | >50,000 | 2548 |
| 88 | 11.9 | 7 | 71 |
| 89 | 13.6 | 10.7 | 548 |
| 91 | 3.2 | 15.3 | 92 |
| 92 | 0.6 | 5.2 | 446 |
| 93 | 3.3 | 9.2 | 122 |
| 94 | 535.5 | 3143.4 | 122 |
| 96 | 9.1 | 23.3 | 1323 |
| 97 | 1.3 | 5.9 | 399 |
| 98 | 1.6 | 8 | 579 |
| 99 | 3.1 | 13 | 497 |
| 100 | 8 | 63.8 | 22410 |
| 101 | 9.3 | 52.4 | 36899 |
| 102 | 7.5 | 72.6 | 36195 |
| 103 | 8.6 | 80.8 | 27744 |
| 104 | 14.9 | 248.7 | 12038 |
| 105 | 3.3 | 21.8 | 12028 |
| 106 | 8.2 | 67.4 | 30599 |
| 107 | 14.6 | 28.4 | 13419 |
| 108 | 7.4 | 102.8 | 33112 |
| 109 | 10.7 | 149.5 | 41365 |
| 110 | 3.9 | 8.1 | 385 |
| 111 | 75.9 | 255.3 | 12852 |
| 112 | 6.2 | 99.9 | 15787 |
| 113 | 5.9 | 78.6 | 15664 |
| 114 | 3.1 | 82.5 | 47202 |
| 115 | 5.4 | 131.1 | 44647 |
| 116 | 3.4 | 127.3 | 32248 |
| 117 | 6.6 | 116.5 | >50,000 |
| 118 | N.D. | 79.8 | >50,000 |
| 119 | 6.9 | 96.1 | 5437 |
| 120 | 12.5 | 158.3 | 16164 |
| 121 | 30 | 98 | 10739 |
| 122 | 6.7 | 44.4 | N.D. |
| 123 | 20.5 | 114.4 | 36637 |
| 124 | 1.9 | 10.1 | 394 |
| 125 | 47.4 | 224.2 | 45550 |
| 126 | 6.5 | 87.5 | 13097 |
| 127 | 60.1 | 209.6 | 31667 |
| 128 | 3.9 | 15.5 | 730 |
| 129 | 18.1 | 69.8 | 32337 |
| 130 | 29.7 | 73.5 | 11775 |
| 131 | 12 | 77.1 | 17512 |
| 132 | 4.2 | 90.8 | 46920 |
| 133 | 12.4 | 61.7 | >50,000 |
| 134 | 11.4 | 90.3 | 34560 |
| 135 | 33.1 | 99.9 | 13258 |
| 136 | 23.3 | 134.2 | 30025 |
| 137 | 8.2 | 39.1 | 1785 |
| 138 | 7.6 | 107.5 | N.D. |
| 139 | 5.7 | 47.7 | 8859 |
| 140 | 16.4 | 124.2 | 28825 |
| 141 | 4.8 | 60.5 | 39967 |
| 142 | 18.2 | 96.3 | >50,000 |
| 143 | 5.3 | 171.8 | 25011 |
| 144 | 20 | 169.6 | >50,000 |
| 145 | 28.7 | 346.6 | >50,000 |
| 146 | 7.4 | 85.9 | 46804 |
| 147 | 6.7 | 42.3 | 3838 |
| 148 | 2.2 | 9.8 | 900 |
| 149 | 21.6 | 143.2 | 16103 |
| 150 | 7.3 | 71.6 | 53103 |
| 151 | 15 | 83.8 | 46746 |
| 152 | 5 | 49.8 | 30450 |
| 153 | 9.9 | 26 | 675 |
| 154 | 5.9 | 29.5 | >50,000 |
| 155 | 2.7 | 31.7 | 26006 |
| 156 | 29.9 | 186.8 | 18650 |
| 157 | 16.5 | 65.7 | 2500 |
| 158 | 6 | 85.4 | 5718 |
| 159 | 4.8 | 47.2 | 24429 |
| 160 | 7.1 | 35.8 | >50,000 |
| 161 | 7.9 | 49.4 | >50,000 |
| 162 | 18.5 | 129.2 | 16243 |
| 163 | 0.9 | 8.4 | 778 |
| 164 | 4.6 | 39.7 | 14202 |
| 165 | 13.3 | 66.1 | 17248 |
| 166 | 0.5 | 79.8 | >50,000 |
| 167 | 5.9 | 50.9 | 250 |
| 168 | 2.2 | 9.4 | 1239 |

TABLE 35-continued

TLR7/8/9 Inhibition Data

| Ex. No. | TLR7 IC$_{50}$ (nM) | TLR8 IC$_{50}$ (nM) | TLR9 IC$_{50}$ (nM) |
|---|---|---|---|
| 169 | 11.7 | 73.7 | >50,000 |
| 170 | 12.1 | 206.3 | >50,000 |
| 171 | 2.6 | 18.3 | 542 |
| 172 | 7.9 | 100.8 | 5102 |
| 173 | 6.2 | 88.3 | 43338 |
| 174 | 5.5 | 81.1 | 35106 |
| 175 | 1.5 | 7.1 | 213 |
| 176 | 11.1 | 21.7 | 663 |
| 177 | 13.1 | 67.2 | 937 |
| 178 | 5.4 | 27.3 | 549 |
| 179 | 1.6 | 5.7 | 204 |
| 180 | 1.9 | 18.6 | 453 |
| 181 | 2.6 | 21.5 | 537 |
| 182 | 1.3 | 12 | 151 |
| 183 | 0.9 | 19.7 | 323 |
| 184 | 7.2 | 88.7 | 2299 |
| 185 | 3.2 | 9.7 | 286 |
| 186 | 3.2 | 22.2 | 516 |
| 187 | 1.7 | 10.5 | 971 |
| 188 | 2.1 | 12.8 | 972 |
| 189 | 7 | 74.3 | 15059 |
| 190 | 1.6 | 9.6 | 281 |
| 191 | 3.5 | 14.4 | 317 |
| 192 | N.D. | 7.2 | 154 |
| 193 | N.D. | 14.8 | 228 |
| 194 | 0.6 | 9.3 | 213 |
| 195 | 6 | 54 | 5268 |
| 196 | 1.2 | 16.2 | 195 |
| 197 | 2.8 | 23.9 | 322 |
| 198 | 8.9 | 104 | 30810 |
| 199 | 3.6 | 86.1 | 46558 |
| 200 | 44.4 | 409.2 | 11173 |
| 201 | 5 | 84.1 | 5501 |
| 202 | N.D. | 327.2 | 39945 |
| 203 | 2 | 112.7 | 3178 |
| 204 | 5.7 | 62.9 | 17227 |
| 205 | 4.4 | 76.3 | 19197 |
| 206 | 5.4 | 100.4 | 41919 |
| 207 | N.D. | 90.4 | 47447 |
| 208 | 8.6 | 15.5 | 824 |
| 209 | 3.5 | 13 | 604 |
| 210 | 2 | 6.2 | 225 |
| 211 | 1.1 | 4.2 | 245 |
| 212 | 3.1 | 6.5 | 648 |
| 213 | 7.1 | 13.8 | 331 |
| 214 | 6.2 | 12.8 | 1220 |
| 215 | 4.9 | 6 | 680 |
| 216 | 2.8 | 7 | 315 |
| 217 | 6.2 | 25.8 | 1018 |
| 218 | 4.9 | 10.5 | 949 |
| 219 | 22.5 | 47.7 | 2248 |
| 220 | 13.9 | 36 | 1299 |
| 221 | 6.8 | 17.2 | 2014 |
| 222 | 2.7 | 15.9 | 2245 |
| 223 | 3.7 | 10.7 | 1155 |
| 224 | 286.2 | 820.4 | 4134 |
| 225 | 11.6 | 26.8 | 651 |
| 226 | 5.4 | 12.4 | 759 |
| 227 | 3.8 | 9.1 | 1498 |
| 228 | 11.5 | 28.2 | 1112 |
| 229 | 6.4 | 7.1 | 165 |
| 230 | 4 | 17 | 74 |
| 231 | 8.6 | 10.1 | 1134 |
| 232 | 3.6 | 7.7 | 627 |
| 233 | 6.3 | 6.4 | 970 |
| 234 | 11.4 | 24.9 | 1717 |
| 235 | 5.2 | 14.1 | 965 |
| 236 | 46.5 | 67.2 | 2090 |
| 237 | 24.9 | 51.1 | 1893 |
| 238 | 5.2 | 10.2 | 942 |
| 239 | 6.7 | 8.9 | 1588 |
| 240 | 8.3 | 7.9 | 1093 |
| 241 | 6.4 | 10.7 | 444 |
| 242 | 5.2 | 24.7 | 1021 |
| 243 | 10 | 20 | 817 |
| 244 | 8.2 | 20.3 | 990 |
| 245 | 9.6 | 32.4 | 954 |
| 246 | 2.6 | 5.3 | 663 |
| 247 | 3 | 4 | 462 |
| 248 | 2.3 | 10.2 | 343 |
| 249 | 15.4 | 36.3 | 973 |
| 250 | 11.7 | 36.4 | 1200 |
| 251 | 4.3 | 9 | 817 |
| 252 | 8.3 | 24.4 | 1813 |
| 253 | 19.7 | 37.1 | 1345 |
| 254 | 9 | 17.6 | N.D. |
| 255 | 6.9 | 20.4 | 654 |
| 256 | 4.4 | 9.2 | 403 |
| 257 | 9.8 | 13.8 | 607 |
| 258 | 7.6 | 15.6 | 903 |
| 259 | 4.5 | 12.2 | 483 |
| 260 | 1.5 | 5.1 | 379 |
| 261 | 5.7 | 22.3 | 451 |
| 262 | 2 | 6 | 715 |
| 263 | 3.7 | 13.6 | 279 |
| 264 | N.D. | N.D. | N.D. |
| 265 | 1.5 | 2.8 | 73 |
| 266 | 3.2 | 10.8 | 522 |
| 267 | 2.6 | 11.1 | 348 |
| 268 | 3 | 7.2 | 416 |
| 269 | 3.7 | 19.8 | 227 |
| 270 | 6.4 | 15.5 | 192 |
| 271 | N.D. | N.D. | N.D. |
| 272 | 1.2 | 3.1 | 46 |
| 273 | 1.5 | 5.4 | 66 |
| 274 | 1.9 | 9.1 | 261 |
| 275 | 1.6 | 6.8 | 67 |
| 276 | 6.3 | 18.6 | 853 |
| 277 | 2 | 6.6 | 201 |
| 278 | 6.1 | 28.5 | 288 |
| 279 | 2.3 | 11 | 512 |
| 280 | 3 | 6.1 | 350 |
| 281 | 1.2 | 2 | 129 |
| 282 | 3.7 | 9 | 2700 |
| 283 | 2.6 | 8.9 | 248 |
| 284 | N.D. | N.D. | N.D. |
| 285 | 4 | 13.9 | 423 |
| 286 | 6.2 | 14 | 261 |
| 287 | 5.2 | 22 | 328 |
| 288 | 10 | 34.6 | 1473 |
| 289 | 6 | 16.9 | 697 |
| 290 | 12 | 66.8 | 870 |
| 291 | 18.1 | 124 | 3198 |
| 292 | 3.1 | 12.3 | 365 |
| 293 | 22.8 | 72.2 | 711 |
| 294 | 14.1 | 58.3 | 1883 |
| 295 | 30 | 142.3 | 3173 |
| 296 | 10.5 | 46.2 | 553 |
| 297 | 13.4 | 43.6 | 710 |
| 298 | 25.6 | 100.1 | 2671 |
| 299 | 24 | 112.3 | 2627 |
| 300 | 28.8 | 70.7 | 1663 |
| 301 | 19.6 | 117.8 | 1579 |
| 302 | 8.2 | 63.1 | 1264 |
| 303 | 7.8 | 35.4 | 402 |
| 304 | 10.3 | 42.6 | 441 |
| 305 | 4.9 | 11.1 | 271 |
| 306 | N.D. | N.D. | N.D. |
| 307 | 17.7 | 87.2 | 3681 |
| 308 | 1.5 | 4.3 | 359 |
| 309 | 2 | 5.5 | 789 |
| 310 | 230 | 895.4 | 29938 |
| 311 | 1.8 | 2.5 | 270 |
| 312 | 5.4 | 14 | 1387 |
| 313 | 39.9 | 6.3 | 8065 |
| 314 | 1.4 | 3.2 | 147 |
| 315 | 6.6 | 9 | 1055 |
| 316 | 11.9 | 2.3 | 780 |

TABLE 35-continued

TLR7/8/9 Inhibition Data

| Ex. No. | TLR7 IC$_{50}$ (nM) | TLR8 IC$_{50}$ (nM) | TLR9 IC$_{50}$ (nM) |
|---|---|---|---|
| 317 | 13.7 | 13.2 | 1125 |
| 318 | 25.4 | 12.6 | 779 |
| 319 | 2.7 | 4 | 355 |
| 320 | 18.2 | 21.8 | 192 |
| 321 | 17.1 | 68.5 | >50,000 |
| 322 | 2.1 | 3.7 | 401 |
| 323 | 1.4 | 3.9 | 359 |
| 324 | 7.4 | 4.4 | 413 |
| 325 | 3.1 | 3.8 | 343 |
| 326 | 16.1 | 29.2 | 1124 |
| 327 | 15.6 | 52.9 | 3716 |
| 328 | 49.8 | 77.1 | 7221 |
| 329 | 2.1 | 2.8 | 437 |
| 330 | 3.7 | 4.2 | 999 |
| 331 | 2.4 | 3.5 | 566 |
| 332 | 5.2 | 4.5 | 396 |
| 333 | 0.8 | 1.4 | 364 |
| 334 | 2.3 | 7.6 | 474 |
| 335 | 3.5 | 14.2 | 1344 |
| 336 | 1.5 | 9.7 | 272 |
| 337 | 6.7 | 18.3 | 467 |
| 338 | 5.8 | 23.5 | 553 |
| 339 | 2.8 | 13.3 | 869 |
| 340 | 14.7 | 103.8 | 36006 |
| 341 | 22.7 | 211.4 | 25398 |
| 342 | 26.2 | 67.1 | 656 |
| 343 | 9.8 | 20.3 | 685 |
| 344 | 2.5 | 8.4 | 485 |
| 345 | 12.3 | 34 | 544 |
| 346 | 4.3 | 16.7 | 1111 |
| 347 | 17.4 | 47.9 | 752 |
| 348 | 3.6 | 11.3 | 425 |
| 349 | 5.2 | 21.9 | 1359 |
| 350 | 5.3 | 29 | 3907 |
| 351 | 3.1 | 7.3 | 559 |
| 352 | 3.3 | 10.4 | 365 |
| 353 | 4 | 9.5 | 429 |
| 354 | 3.5 | 11.2 | 447 |
| 355 | 8.8 | 34 | 1069 |
| 356 | 3.3 | 13.9 | 657 |
| 357 | 13.9 | 104.4 | 2347 |
| 358 | 12.9 | 23.7 | 943 |
| 359 | 7.1 | 11.7 | 826 |
| 360 | 4 | 15.8 | 795 |
| 361 | 7.8 | 31.8 | 3002 |
| 362 | 33.6 | 55.1 | 16132 |
| 363 | 8.3 | 34.2 | 1801 |
| 364 | 4.4 | 13.4 | 584 |
| 365 | 6.5 | 22.9 | 854 |
| 366 | 3.2 | 10.9 | 370 |
| 367 | 6.5 | 54.1 | 1895 |
| 368 | 4.5 | 21 | 742 |
| 369 | 10.3 | 93.8 | 1057 |
| 370 | 4.7 | 28.8 | 889 |
| 371 | 3.7 | 20.4 | 241 |
| 372 | 1.9 | 14.1 | 602 |
| 373 | 2.5 | 17.5 | 429 |
| 374 | 5.6 | 21.4 | 548 |
| 375 | 13.1 | 80.6 | 1777 |
| 376 | 5.3 | 20.9 | 628 |
| 377 | 4.4 | 17.5 | 514 |
| 378 | 1.7 | 11.8 | 389 |
| 379 | 7.7 | 55.2 | 3920 |
| 380 | 2 | 10.5 | 354 |
| 381 | 2.2 | 9.8 | 348 |
| 382 | 7.6 | 44.1 | 769 |
| 383 | 1.7 | 11.1 | 572 |
| 384 | 14.4 | 57 | 630 |
| 385 | 3.2 | 22 | 539 |
| 386 | 3.6 | 17.7 | 280 |
| 387 | 0.6 | 13.3 | 909 |
| 388 | 4.3 | 20.9 | 831 |
| 389 | 10.3 | 31.3 | 880 |
| 390 | 17.9 | 191.3 | 25850 |
| 391 | 1.3 | 6.4 | 691 |
| 392 | 3.2 | 10.4 | 253 |
| 393 | 7.9 | 37.8 | 800 |
| 394 | 14.6 | 151.9 | 833 |
| 395 | 9.7 | 41.1 | 995 |
| 396 | 4.4 | 55.2 | 1603 |
| 397 | 2.2 | 18.6 | 705 |
| 398 | 3.5 | 26 | 771 |
| 399 | 6.1 | 66.9 | 688 |
| 400 | 3.4 | 16.8 | 451 |
| 401 | 9 | 53 | 1060 |
| 402 | 11.1 | 61.1 | 1816 |
| 403 | 14.6 | 209.1 | 17563 |
| 404 | 64.5 | 437.3 | 11300 |
| 405 | 2.1 | 12.9 | 527 |
| 406 | 7.8 | 73.8 | 1071 |
| 407 | 7 | 71 | 495 |
| 408 | 7.6 | 72.5 | 846 |
| 409 | 4.1 | 67.9 | 2533 |
| 410 | 4.5 | 27 | 481 |
| 411 | 2.9 | 24 | 1226 |
| 412 | 4.7 | 34 | 568 |
| 413 | 9.6 | 91.8 | 2496 |
| 414 | 2.4 | 16.8 | 924 |
| 415 | 7.9 | 39.7 | 1859 |
| 416 | 4.5 | 49.7 | 4761 |
| 417 | 10.3 | 72.3 | 9381 |
| 418 | 3 | 30.6 | 2051 |
| 419 | 10.7 | 116.8 | 45483 |
| 420 | 1.5 | 9.9 | 632 |
| 421 | 5.4 | 25.9 | 656 |
| 422 | 5.5 | 73.4 | 41272 |
| 423 | 2.8 | 20.8 | 1327 |
| 424 | 8.3 | 7.2 | 255 |
| 425 | 3.7 | 2.5 | 143 |
| 426 | 6.1 | 2.6 | 90 |
| 427 | 8.3 | 8.1 | 173 |
| 428 | 1.9 | 1.9 | 120 |
| 429 | 2.2 | 5.5 | 484 |
| 430 | 10.1 | 5.9 | 369 |
| 431 | 8.4 | 6.7 | 457 |
| 432 | 5.6 | 8.7 | 646 |
| 433 | 4.6 | 2.4 | 234 |
| 434 | 35.3 | 10.5 | 755 |
| 435 | 9.1 | 4.2 | 609 |
| 436 | 4.5 | 4.7 | 94 |
| 437 | 8.6 | 6.7 | 267 |
| 438 | 1.2 | 3.1 | 69 |
| 439 | 7.7 | 6.3 | 202 |
| 440 | 5.3 | 2.3 | 210 |
| 441 | 1.6 | 1.7 | 303 |
| 442 | 5.3 | 6.7 | 1194 |
| 443 | 22.9 | 10.9 | 1681 |
| 444 | 3.3 | 1.6 | 617 |
| 445 | 3.6 | 0.7 | 314 |
| 446 | 1.3 | 2.6 | 292 |
| 447 | 5.4 | 7 | 446 |
| 448 | 51.2 | 55.6 | 47435 |
| 449 | 13.5 | 14.3 | 2928 |
| 450 | 7.8 | 7.9 | 572 |
| 451 | 5.9 | 12.2 | 1561 |
| 452 | 4.9 | 16.7 | 1394 |
| 453 | 8.5 | 6.5 | 255 |
| 454 | 11 | 10.2 | 358 |
| 455 | 10.9 | 7.6 | 390 |
| 456 | 4.2 | 5.8 | 340 |
| 457 | 2.7 | 8.7 | 274 |
| 458 | 16.6 | 21.3 | 534 |
| 459 | 3.7 | 3.6 | 1215 |
| 460 | 6.2 | 5.8 | 396 |
| 461 | 9.3 | 7.5 | 621 |
| 462 | 70.4 | 209.7 | 5261 |
| 463 | 8.3 | 17.7 | 3357 |
| 464 | 6.3 | 6.3 | 2556 |

TABLE 35-continued

TLR7/8/9 Inhibition Data

| Ex. No. | TLR7 IC$_{50}$ (nM) | TLR8 IC$_{50}$ (nM) | TLR9 IC$_{50}$ (nM) |
|---|---|---|---|
| 465 | 7 | 4.7 | 147 |
| 466 | 6.5 | 3.7 | 273 |
| 467 | 2.5 | 5.8 | 155 |
| 468 | 17.8 | 35.5 | 1344 |
| 469 | 2.1 | 2.9 | 280 |
| 470 | 5.9 | 23.8 | 532 |
| 471 | 2.4 | 8 | 610 |
| 472 | 7.5 | 13.2 | 601 |
| 473 | 10.1 | 21.1 | 835 |
| 474 | 2.5 | 3.2 | 506 |
| 475 | 4.1 | 2.2 | 335 |
| 476 | 6072.8 | 1036.5 | 3263 |
| 477 | 3080.1 | 1107.9 | 2192 |
| 478 | 10.2 | 46.4 | 1333 |
| 479 | 98.4 | 132.7 | 3400 |
| 480 | 2875.9 | 7056 | 707 |
| 481 | 16 | 95.4 | 677 |
| 482 | 10.6 | 19.2 | 3692 |
| 483 | 46.2 | 76.6 | 1440 |
| 484 | 77.6 | 96.3 | 279 |
| 485 | 11.8 | 34.8 | 3036 |
| 486 | 49 | 213.2 | 2762 |
| 487 | 33.4 | 79.1 | 2141 |
| 488-A | 2.7 | 21 | 240 |
| 488-B | 2.4 | 33.1 | 308 |
| 489-A | 1.1 | 13.9 | 849 |
| 489-B | 1.3 | 20 | 1011 |
| 490 | 186.2 | 67.4 | >50,000 |
| 491-A | 155.6 | 109.5 | 354 |
| 491-B | 526 | 34.9 | 324 |
| 492 | 15.8 | 54.1 | 539 |
| 493 | 84.5 | 497.9 | 1639 |
| 494 | 36.5 | 66.4 | 2040 |
| 495 | N.D. | 12500 | 144 |
| 496 | 7193.3 | 9587.8 | >50,000 |
| 497 | 2.7 | 13.1 | 266 |
| 498 | 834.3 | 1239.8 | 6936 |
| 499 | 3692.6 | 10691.5 | >50,000 |
| 500 | 6.3 | 14.2 | 3323 |
| 501 | 5.5 | 30.3 | 992 |
| 502 | 28.4 | 155.6 | 24718 |
| 503 | 10.8 | 24.1 | 1231 |
| 504 | 64.2 | 638.5 | 33943 |
| 505 | 5.9 | 27.1 | 710 |
| 506 | 11.1 | 42.7 | 1098 |
| 507 | 52 | 345.6 | 19047 |
| 508 | 8.8 | 57.9 | 592 |
| 509 | 20 | 21.9 | 3710 |
| 510 | 8.8 | 8.6 | 695 |
| 511 | 32.6 | 31.3 | 1459 |
| 512 | 13 | 11.7 | 1064 |
| 513 | 13.5 | 9.8 | 2259 |
| 514 | 60.3 | 269.2 | 10915 |
| 515 | 19.8 | 135.8 | 2223 |
| 516 | 12.1 | 190.1 | 1461 |
| 517 | 143.9 | 1148 | >50,000 |
| 518 | 15.1 | 256.6 | 1608 |
| 519 | 23.1 | 59.5 | 3212 |
| 520 | 42.7 | 27.1 | 437 |
| 521 | 41.6 | 115.4 | 3714 |
| 522 | 23.6 | 47.9 | 2013 |
| 523 | 25.8 | 25.5 | 503 |
| 524 | 33.6 | 29.2 | 2805 |
| 525 | 44.3 | 6 | 190 |
| 526 | 10.5 | 24.7 | 102 |
| 527 | 54.1 | 63.6 | 608 |
| 528 | 16 | 50.9 | 150 |
| 529 | 6.6 | 28.2 | 119 |
| 530 | 52.2 | 397.6 | 5268 |
| 531 | 15.7 | 63.9 | 221 |
| 532 | 17.4 | 81.8 | 813 |
| 533 | 77.8 | 284.6 | 1485 |
| 534 | 63.8 | 659.9 | 45350 |
| 535 | 10 | 86.5 | 258 |
| 536 | 12.1 | 20.3 | 123 |
| 537 | 36.2 | 53.3 | 32 |
| 538 | 39.6 | 34.6 | 69 |
| 539 | 23.3 | 81.2 | 4819 |
| 540 | 11.8 | 25.6 | 131 |
| 541 | 11.5 | 22.2 | 110 |
| 542 | 1164.5 | 1475.9 | >50,000 |
| 543 | 119.1 | 205.5 | 9751 |
| 544 | 119.3 | 244.8 | 12154 |
| 545 | 101.5 | 265.5 | >50,000 |
| 546 | 163.9 | 820.1 | >50,000 |
| 547 | 332.9 | 1037.9 | >50,000 |
| 548 | 335.6 | 699.5 | >50,000 |
| 549 | 55.6 | 163.9 | >50,000 |
| 550 | 39 | 162.5 | >50,000 |
| 551 | 486.1 | 1029 | >50,000 |
| 552 | 129.8 | 111.2 | >50,000 |
| 553 | 74.2 | 84.3 | 31625 |
| 554 | 441.1 | 1074.3 | >50,000 |
| 555 | 34.9 | 92.1 | >50,000 |
| 556 | 219.9 | 731.1 | >50,000 |
| 557 | 1525.9 | 3246.6 | 6045 |
| 558 | 3396.6 | 1843.2 | 15018 |
| 559 | 500.3 | 878.4 | 13477 |
| 560 | 247 | 607.1 | 10413 |
| 561 | 201.6 | 362.6 | 43897 |
| 562 | 287.2 | 1403.2 | >50,000 |
| 563 | 16.5 | 18.9 | 1154 |
| 564 | 202.3 | 80.1 | 6556 |
| 566 | 78.8 | 117.9 | >50,000 |
| 567 | 26.7 | 22.9 | 876 |
| 568 | 11.9 | 13.6 | 572 |
| 569 | 14.4 | 15 | 912 |
| 570 | 13.1 | 12 | 971 |
| 571 | 79.3 | 101.8 | N.D. |
| 572 | 5.1 | 18.6 | 692 |
| 573 | 12.9 | 33.9 | 379 |
| 574 | 82.9 | 15.6 | 851 |
| 575 | 34 | 18.5 | 1062 |
| 576 | 15.1 | 24.1 | 731 |
| 577 | 120.6 | 58.4 | 8128 |
| 578 | 7.1 | 5.7 | 722 |
| 579 | 201.2 | 98 | 4357 |
| 580 | 67.2 | 53.7 | 508 |
| 581 | 10.6 | 6.9 | 967 |
| 582 | 30.1 | 48 | >50,000 |
| 583 | 15.6 | 36.8 | >50,000 |
| 584 | 43 | 45.9 | >50,000 |
| 585 | 10.8 | 5.2 | 1672 |
| 586 | 2.6 | 6.2 | 3044 |
| 587 | 2.7 | 5.2 | 2912 |
| 588 | 0.5 | 1.3 | 845 |
| 589 | 4.7 | 27.6 | 2109 |
| 590 | 4.2 | 18.4 | 142 |
| 591 | 251.4 | 240.9 | 15436 |
| 592 | 275.8 | 235.1 | 17144 |
| 593 | 43 | 17.4 | 513 |
| 594 | 30.2 | 39.4 | 610 |
| 595 | 84.7 | 32.7 | 348 |
| 596 | 33.3 | 102.1 | 44477 |
| 597 | 45.6 | 117.3 | 26890 |
| 598 | 99.6 | 373.6 | 9940 |
| 599 | 18.5 | 177.5 | 43812 |
| 600 | 119.9 | 269.3 | >50,000 |
| 601 | 99.2 | 384.9 | 34094 |
| 602 | 24.7 | 158.1 | 32036 |
| 603 | 49 | 228.1 | 37306 |
| 604 | 24.9 | 189.6 | 22991 |
| 605 | 77.7 | 124.4 | 14263 |
| 606 | 56.5 | 185.6 | 40874 |
| 607 | 94 | 185.6 | >50,000 |
| 608 | 51.4 | 184.3 | 1852 |
| 609 | 38.2 | 214 | 21533 |
| 610 | 48.6 | 163 | 47322 |

TABLE 35-continued

TLR7/8/9 Inhibition Data

| Ex. No. | TLR7 IC$_{50}$ (nM) | TLR8 IC$_{50}$ (nM) | TLR9 IC$_{50}$ (nM) |
|---|---|---|---|
| 611 | 19.7 | 107.5 | 9446 |
| 612 | 73 | 162.3 | 16667 |
| 613 | 55.1 | 206.3 | 7627 |
| 614 | 119 | 469.1 | 17546 |
| 615 | 80.9 | 243 | 12165 |
| 616 | 33.7 | 120.6 | 32904 |
| 617 | 251.4 | 531.1 | 47697 |
| 618 | N.D. | 106.8 | >50,000 |
| 619 | 51.1 | 67.9 | >50,000 |
| 620 | 8.1 | 3.5 | 3566 |
| 621 | 2.4 | 5 | 1590 |
| 622 | 1.2 | 6.1 | 4009 |
| 623 | 200.6 | 226 | 14503 |
| 624 | 128.4 | 44.1 | 311 |
| 625 | 84.5 | 83.5 | 177 |
| 626 | 62.6 | 53.5 | 169 |
| 627 | 530.9 | 324.6 | 546 |
| 628 | 39.2 | 18.3 | 363 |
| 629 | 60.4 | 18.7 | 482 |
| 630 | 70.4 | 40.2 | 333 |
| 631 | 75.6 | 36.8 | 434 |
| 632 | 91.8 | 35.8 | 795 |
| 633 | 39 | 83.3 | 311 |
| 634 | 73.5 | 223.2 | >50,000 |
| 635 | 5.6 | 5.1 | 3689 |
| 636 | 9.8 | 1 | 1374 |
| 637 | 36.4 | 42.1 | 1543 |
| 638 | 15.6 | 55.1 | 3305 |
| 639 | 3112.8 | 13444.3 | 19412 |
| 640 | 4198.6 | 3303.5 | 3190 |
| 641 | 33 | 9.7 | 2674 |
| 642 | 16.1 | 5.6 | 4098 |
| 643 | 4.5 | 4.7 | 4397 |
| 644 | 7.7 | 6 | 2301 |
| 645 | 1.7 | 5.8 | 7430 |
| 646 | 12 | 4.8 | 5847 |
| 647 | 3.9 | 2.3 | 2662 |
| 648 | 3 | 3.7 | 2235 |
| 649 | 45.7 | 16.2 | >50,000 |
| 650 | 4.7 | 1.8 | 3404 |
| 651 | 5.3 | 2.1 | 3739 |
| 652 | 1.5 | 3 | 1291 |
| 653 | 13.9 | 4.4 | 4157 |
| 654 | 2.8 | 3.2 | 3144 |
| 655 | 1.3 | 4.2 | 1753 |
| 656 | 9.3 | 1.9 | >50,000 |
| 657 | 5.9 | 5.3 | 5685 |
| 658 | 434.5 | 645 | 7286 |
| 659 | 31.7 | 16.7 | 1448 |
| 660 | 103.7 | 78.9 | >50,000 |
| 661 | 30.9 | 3.1 | 1937 |
| 662 | 60.6 | 29.6 | 1148 |
| 663 | 111.8 | 31.2 | 1100 |
| 664 | 10.2 | 4.5 | 1568 |
| 665 | 13.6 | 2.2 | 6211 |
| 666 | 5.8 | 2.6 | 948 |
| 667 | 19 | 32.1 | 86 |
| 668 | 14.3 | 7.6 | 149 |
| 669 | 2.6 | 1.9 | 221 |
| 670 | 68.1 | 64.8 | 663 |
| 671 | 0.6 | 2.6 | 76 |
| 672 | 252.1 | 116.4 | 894 |
| 673 | 70.5 | 23.1 | 287 |
| 674 | 0.8 | 2.8 | 156 |
| 675 | 44.7 | 11.9 | 42 |
| 676 | 19 | 12.3 | 1930 |
| 677 | 3.4 | 6.7 | 1691 |
| 678 | 12.3 | 30.6 | >50,000 |
| 679 | 12.7 | 19.8 | 4380 |
| 680 | 2 | 4 | 2970 |
| 681 | 15.5 | 0.6 | 1531 |
| 682 | 7.5 | 1.7 | 2722 |
| 683 | 10.1 | 0.6 | 1800 |
| 684 | 19.5 | 3.8 | 3158 |
| 685 | 62.5 | 3.4 | 7510 |
| 686 | 35.2 | 4.1 | 9448 |
| 687 | 25.6 | 1.8 | 4918 |
| 688 | 12.1 | 2 | 6188 |
| 689 | 23.2 | 0.8 | 1444 |
| 690 | 11 | 1.9 | 3509 |
| 691 | 7 | 2.6 | 2566 |
| 692 | 10.3 | 0.9 | 1485 |
| 693 | 33.1 | 5.2 | 1680 |
| 694 | 20.7 | 7.8 | 3688 |
| 695 | 1308.8 | 111.4 | >50,000 |
| 696 | 408.3 | 104.5 | >50,000 |
| 697 | 223.3 | 20.7 | >50,000 |
| 698 | 54.2 | 37.6 | 12400 |
| 699 | 38.7 | 4.2 | 40311 |
| 700 | 55.8 | 16 | >50,000 |
| 701 | 6.5 | 5.8 | 163 |
| 702 | 14.4 | 2.9 | 432 |
| 703 | 8.8 | 1.8 | 526 |
| 704 | 20.9 | 4.1 | 551 |
| 705 | 21.9 | 6.2 | 708 |
| 706 | 23 | 5 | 340 |
| 707 | 7.6 | 2.8 | 217 |
| 708 | 8.1 | 6.3 | 492 |
| 709 | 32.4 | 12.6 | 393 |
| 710 | 8 | 3 | 554 |
| 711 | 11 | 11.2 | 2155 |
| 712 | 36.8 | 16.4 | 1190 |
| 713 | 3.5 | 14.8 | 550 |
| 714 | 31.4 | 2.7 | 2214 |
| 715 | 20.7 | 3.8 | 2987 |
| 716 | 144.2 | 73.3 | 1905 |
| 717 | 15.8 | 5.9 | 1594 |
| 718 | 22.8 | 6.1 | 855 |
| 719 | 23.9 | 5.2 | 638 |
| 720 | 51 | 82.5 | 2895 |
| 721 | 13.8 | 7.4 | 19754 |
| 722 | 24.4 | 6.3 | 5887 |
| 723 | 78.4 | 8.4 | 14504 |
| 724 | 13.8 | 9.6 | N.D. |
| 725 | 3 | 4.5 | 2988 |
| 726 | 14.2 | 1.1 | 1451 |
| 727 | 7.3 | 3.5 | 2923 |
| 728 | 6.7 | 1.1 | 1336 |
| 729 | 10.1 | 33.6 | 3619 |
| 730 | 9.2 | 8.2 | 9406 |
| 731 | 8.9 | 2.7 | 1314 |
| 732 | 22.5 | 10.3 | 10060 |
| 733 | 11.1 | 4.2 | 1813 |
| 734 | 13.8 | 6.8 | 8988 |
| 735 | 22.3 | 50 | >50,000 |
| 736 | 42.3 | 6.5 | 20128 |
| 737 | 14.5 | 5.1 | >50,000 |
| 738 | 11.2 | 2.5 | 282 |
| 739 | 120.3 | 8.2 | 96 |
| 740 | 67.9 | 6 | 111 |
| 741 | 171.5 | 32.7 | 213 |
| 742 | 9.2 | 5.5 | 101 |
| 743 | 6.5 | 5.1 | 282 |
| 744 | 28.1 | 13.5 | 281 |
| 745 | 99.9 | 129.6 | N.D. |
| 746 | 4028.7 | >50,000 | 69 |
| 747 | 409.9 | N.D. | 525 |
| 748 | 495.4 | N.D. | 95 |
| 749 | 4833.8 | N.D. | 640 |
| 750 | 331.5 | N.D. | 270 |
| 751 | 471.8 | 55.6 | 324 |
| 752 | 230.7 | 114.4 | 199 |
| 753 | N.D. | N.D. | N.D. |
| 754 | 5859.6 | 27.5 | 325 |
| 755 | 2650.2 | 86.6 | 599 |
| 756 | 3121.8 | 184.8 | 3303 |
| 757 | 6672 | 93.2 | 1295 |
| 758 | 967.4 | 135.5 | 751 |

TABLE 35-continued

TLR7/8/9 Inhibition Data

| Ex. No. | TLR7 IC$_{50}$ (nM) | TLR8 IC$_{50}$ (nM) | TLR9 IC$_{50}$ (nM) |
|---|---|---|---|
| 759 | 1522.7 | 257.2 | 655 |
| 760 | 537.2 | 106.6 | 2388 |
| 761 | 4257.1 | 374.8 | 800 |
| 762 | 707.8 | 14.3 | 223 |
| 763 | 4948.2 | 514.3 | 1900 |
| 764 | 173.9 | 262.1 | 603 |
| 765 | 10977.5 | 340.7 | 181 |
| 766 | 3976.3 | 245.4 | 83 |
| 767 | 3747.2 | 1231 | 98 |
| 768 | 7224.4 | 1188.5 | 1281 |
| 769 | 5375.7 | 1049.7 | 1500 |
| 770 | 6730.2 | >50,000 | 310 |
| 771 | 3373 | N.D. | 169 |
| 772 | 9850.3 | N.D. | 205 |
| 773 | 613.3 | 113.8 | 45 |
| 774 | 3702 | N.D. | 663 |
| 775 | 5659 | N.D. | 379 |
| 776 | 545.4 | 41.7 | 63 |
| 777 | 515 | 318.3 | 372 |
| 778 | 330.4 | 100.4 | 1940 |
| 779 | 2110.9 | 86.6 | 159 |
| 780 | 501.8 | 81.1 | 412 |
| 781 | 577.4 | 316 | 206 |
| 782 | 1314 | 382.6 | 124 |
| 783 | 55.1 | N.D. | 1011 |
| 784 | 94 | N.D. | 685 |
| 785 | 790.4 | 116.7 | 282 |
| 786 | 308.9 | 50.4 | 206 |
| 787 | 458.6 | N.D. | 480 |
| 788 | 355.8 | N.D. | 611 |
| 789 | 599.3 | 268.9 | 408 |
| 790 | 1697.3 | 1409.8 | 1777 |
| 791 | 666 | 158.3 | 1600 |
| 792 | 304.1 | 84.9 | 686 |
| 793 | 371.1 | 29.6 | 252 |
| 794 | 673.7 | 40.9 | 1100 |
| 795 | 128.8 | 12.5 | 851 |
| 796 | 154.5 | 13.9 | 563 |
| 797 | 140.8 | 23.1 | 596 |
| 798 | 624.2 | 165.3 | 67 |
| 799 | 1667.7 | 360.4 | 180 |
| 800 | 167.3 | 185.1 | 729 |
| 801 | 560.7 | 218.2 | 740 |
| 802 | 388.6 | 99.3 | 487 |
| 803 | 79.7 | 332.7 | 986 |
| 804 | 211.6 | 11.2 | 82 |
| 805 | 609.9 | N.D. | 1208 |
| 806 | 1213.1 | N.D. | 365 |
| 807 | 225.5 | 8.6 | 117 |
| 808 | 679.1 | N.D. | 610 |
| 809 | 883.9 | N.D. | 306 |
| 810 | 145 | 16.2 | 19 |
| 811 | 117.1 | 47.2 | 23 |
| 812 | 404.5 | 44.5 | 35 |
| 813 | 532.6 | 114.4 | 42 |
| 814 | 50.7 | 2.4 | 101 |
| 815 | 123.6 | 73.4 | 313 |
| 816 | 215.2 | 47.3 | 86 |
| 817 | 224.1 | 56 | 177 |
| 818 | 283 | 53.3 | 230 |
| 819 | 415 | 587.5 | 712 |
| 820 | 71.5 | 5.8 | 209 |
| 821 | 36.3 | 4.8 | 192 |
| 822 | 840.6 | 12940.4 | 1088 |
| 823 | 36.2 | 7.6 | 400 |
| 824 | 13.8 | 1.2 | 729 |
| 825 | 6.5 | 8.1 | 380 |
| 826 | 42.6 | 185.5 | 43369 |
| 827 | 12.7 | 5.2 | 753 |
| 828 | 1.2 | 4.8 | 267 |
| 829 | 17.5 | 63.4 | 3072 |
| 830 | 4.8 | 17.3 | 229 |
| 831 | 6.2 | 11.6 | 567 |
| 832 | 6.2 | 25.4 | 3076 |
| 833 | 9.4 | 29.6 | 556 |
| 834 | 4.4 | 23.8 | N.D. |
| 835 | 2.9 | 3.4 | 1951 |
| 836 | 3.9 | 11.8 | 4732 |
| 837 | 1.9 | 11.4 | 194 |
| 838 | 581.3 | N.D. | 613 |
| 839 | 688.8 | N.D. | 4444 |
| 840 | 465.5 | N.D. | 379 |
| 841 | 491.7 | N.D. | 87 |
| 842 | 387.7 | N.D. | 93 |
| 843 | 291.7 | 28.4 | 38 |
| 844 | 14.2 | 31.7 | 9544 |
| 845 | 148.3 | 92.9 | 1169 |
| 846 | 1594.1 | 1543.6 | >50,000 |
| 847 | 61.9 | 206.2 | N.D. |
| 848 | 2.3 | 1.7 | 398 |
| 849 | 1.4 | 2.3 | 291 |
| 850 | 3.8 | 4.7 | 312 |
| 851 | 10.4 | 0.7 | 1687 |
| 852 | 4.1 | 3.8 | 631 |
| 853 | 2.3 | 1 | 293 |
| 854 | 1 | 1.8 | 159 |
| 855 | 21.1 | 1.5 | 3305 |
| 856 | 2.9 | 30.6 | 832 |
| 857 | 1.3 | 13.6 | 441 |
| 858 | 1.9 | 5.7 | 519 |
| 859 | 44.1 | 538.8 | >50,000 |
| 860 | 9.7 | 89.2 | 15666 |
| 861 | 13.5 | 59 | 3418 |
| 862 | 5.1 | 120.5 | >50,000 |
| 863 | 469.3 | 53 | 2449 |
| 864 | 16.7 | 10.7 | 917 |
| 865 | 36.7 | 28.3 | 1029 |
| 866 | 38.1 | 12.2 | 1687 |
| 867 | 16.3 | 3.7 | 794 |
| 868 | 53.5 | 33.8 | 925 |
| 869 | 13.2 | 12.3 | 803 |
| 870 | 19.7 | 4.1 | 1439 |
| 871 | 10 | 3.2 | 1838 |
| 872 | 20.6 | 2.8 | 2317 |
| 873 | 13.5 | 466.8 | 96 |
| 874 | 15.4 | 33.6 | 445 |
| 875 | 31 | 248.5 | 10079 |
| 876 | 957.5 | 1935.7 | 46709 |
| 877 | 30.6 | 2.9 | 16 |
| 878 | 55.1 | 175.1 | 27992 |
| 879 | 37 | 167.9 | >50,000 |

In Vivo Mouse TLR7 and TLR9 PD Model:

Adult male C57BL/6 mice were used for the experiments. Mice (7 to 10 per group) were randomized into different treatment groups based on body weight. Mice from the respective treatment groups were administered orally with vehicle or test compound. Thirty min after the oral administration of vehicle or test compound, mice were challenged with intraperitoneal injection of gardiquimod for TLR7 PD model and CpG-ODN for TLR9 PD model. Ninety minutes after gardiquimod injection and 120 minutes after CpG-ODN injection, mice were bled under isoflurane anaesthesia and plasma IL-6 level was estimated by using commercially available ELISA kit (BD Biosciences). At the end of experiment, mean cytokine data was plotted and one way ANOVA with Dunnett's test was performed to calculate the significance of test compound treated group vs. vehicle control group. Percent inhibition of cytokine induction was calculated for test compound treated group vs vehicle control group. Data from multiple studies with different test compounds is shown in Table 36.

TABLE 36

Percent inhibition of IL-6 in mouse TLR7 and TLR9 PD model

| Ex. No. | Dose (mg/kg) | % inhibition of IL6 |
|---|---|---|
| TLR7 PD model | | |
| 1 | 0.015 | 16 |
|  | 0.03 | 28 |
|  | 0.05 | 66 |
|  | 0.15 | 83 |
|  | 0.5 | 98 |
| 308 | 0.002 | 30 |
|  | 0.008 | 47 |
|  | 0.032 | 81 |
|  | 0.160 | 98 |
| 309 | 0.0005 | 12 |
|  | 0.005 | 65 |
|  | 0.05 | 89 |
|  | 0.25 | 91 |
| TLR9 PD model | | |
| 1 | 1 | 16 |
|  | 3 | 29 |
|  | 10 | 33 |
|  | 30 | 38 |

MRL/lpr Model of Systemic Lupus Erythematosus (SLE)

Male MRL/lpr mice of 12-14 weeks age were screened and randomized based on the titers of anti-dsDNA antibodies and urinary NGAL (Neutrophil Gelatinase Associated Lipocalin). Mice were treated orally, once daily for 8 weeks with vehicle or test compound. The effect of test compound on disease severity was assessed by measuring end points including proteinuria, urinary-NGAL, anti-dsDNA Ab titer, and lymphadenopathy. These end points were assessed before the start of treatment and after 4 and 8 weeks of treatment. At the end of experiment, all mice were euthanized by $CO_2$ asphyxiation and kidney samples were subjected for histology. At the end of experiment, one way ANOVA with Dunnett's test was performed to calculate the significance of test compound treated group vs. vehicle control group. Percent reduction in disease severity was calculated for each parameter, for test compound treated group vs vehicle control group.

| Example No. | Dose (mg/kg) | % inhibition | | | | | |
|---|---|---|---|---|---|---|---|
| | | Anti-dsDNA antibody titer | Urinary NGAL | Proteinuria | IL-12p40 | IL-10 | Lymphadenopathy |
| 1 | 0.1 | 1 | 52 | 69 | 12 | 24 | 3 |
|  | 1 | 14 | 69 | 92 | 26 | 32 | 31 |
|  | 5 | 20 | 72 | 92 | 30 | 39 | 33 |
|  | 20 | 53 | 81 | 93 | 35 | 53 | 53 |

What is claimed is:

1. A compound of Formula (I)

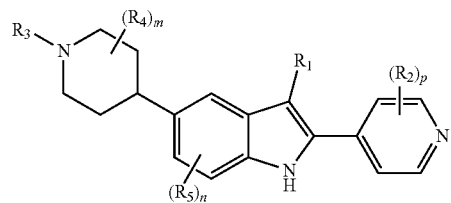

N-oxide, or salt thereof, wherein:

$R_1$ is H, Cl, —CN, $C_{1-4}$ alkyl, $C_{1-3}$ fluoroalkyl, $C_{1-3}$ hydroxy-fluoroalkyl, —$CR_z$=$CH_2$, $C_{3-6}$ cycloalkyl, —$CH_2(C_{3-6}$ cycloalkyl), —C(O)O($C_{1-3}$ alkyl), or tetrahydropyranyl;

each $R_2$ is independently halo, —CN, —OH, —$NO_2^+$, $C_{1-3}$ alkyl, $C_{1-2}$ fluoroalkyl, $C_{1-3}$ hydroxyalkyl, $C_{1-3}$ aminoalkyl, —$(CH_2)_{0-4}$O($C_{1-3}$ alkyl), $C_{1-3}$ fluoroalkoxy, $C_{2-4}$ alkoxyalkoxy, —O$(CH_2)_{1-2}$$NR_xR_x$, —C(O)O($C_{1-3}$ alkyl), —C(O)$NR_yR_y$, —$NR_yR_y$, —$NR_xC(O)(C_{1-3}$ alkyl), —$NR_x(CH_2$-cyclopropyl), $C_{3-6}$ cycloalkyl, methylpiperidinyl, methylpiperazinyl, amino-oxadiazolyl, imidazolyl, triazolyl, or —C(O)(thiazolyl);

$R_3$ is:

(a) -$L_1$-A; or (b) H, $C_{1-6}$ alkyl, $C_{1-3}$ fluoroalkyl, $C_{1-3}$ cyanoalkyl, $C_{1-6}$ hydroxyalkyl, $C_{1-3}$ hydroxy-fluoroalkyl, —$CR_xR_x$-$CR_x(OH)CR_x$=$CR_xR_x$, —$(CR_xR_x)_{1-4}$O($C_{1-3}$ alkyl), —$(CR_xR_x)_{1-4}$O($CR_xR_x)_{1-3}$O($C_{1-3}$ alkyl), —$CR_xR_x$-$CR_x(OH)CH_2$O($C_{1-3}$ alkyl), —$(CR_xR_x)_{1-3}$S($C_{1-3}$ alkyl), —$(CH_2)_{1-3}$C(O)OC($CH_3$)$_3$, —$(CR_xR_x)_{0-3}$$NR_xR_y$, —$(CR_xR_x)_{0-3}$$NR_x(C_{1-4}$ hydroxyalkyl), —$CR_xR_xCR_x(OH)CH_2NR_xR_y$, —C(O)H, —C(O)($C_{1-6}$ alkyl), —C(O)($C_{1-3}$ hydroxyalkyl), —C(O)($C_{1-3}$ fluoroalkyl), —C(O)($C_{1-3}$ chloroalkyl), —C(O)($C_{1-3}$ cyanoalkyl), —$(CR_xR_x)_{0-3}$C(O)OH, —C(O)$(CH_2)_{0-2}$O($C_{1-4}$ alkyl), —C(O)$(CR_xR_x)_{0-2}$O($CR_xR_x)_{1-2}$O($C_{1-3}$ alkyl), —C(O)$CR_xR_x$S(O)$_2$($C_{1-3}$ alkyl), —C(O)$CR_xR_xNR_x$S(O)$_2$($C_{1-3}$ alkyl), —C(O)$CR_xR_x$OC(O)($C_{1-3}$ alkyl), —C(O)$(CR_xR_x)_{0-3}NR_xR_y$, —C(O)$(CR_xR_x)_{0-1}NR_x(C_{1-3}$ cyanoalkyl), —C(O)$(CR_xR_x)_{0-2}NR_y(C_{1-6}$ hydroxyalkyl), —C(O)$(CR_xR_x)_{0-1}NR_x(C_{1-3}$ fluoroalkyl), —C(O)$(CR_xR_x)_{0-1}NR_x(C_{1-5}$ hydroxy-fluoroalkyl), —C(O)$(CR_xR_x)_{0-1}NR_x(CH_2)_{1-2}$O($C_{1-3}$ hydroxyalkyl), —C(O)$(CR_xR_x)_{0-1}NR_x(CH_2)_{1-2}NR_xC(O)(C_{1-2}$ alkyl), —C(O)$(CR_xR_x)_{0-1}NR_x((CR_xR_x)_{1-2}O(C_{1-2}$ alkyl)), —C(O)$CR_x(NH_2)(CR_xR_x)_{1-4}NR_xR_x$, —C(O)$CR_x(NH_2)(CR_xR_x)_{1-4}NR_xC(O)NR_xR_x$, —C(O)$(CR_xR_x)_{0-3}NR_x(CH_2)_{0-1}C(O)(C_{1-3}$ alkyl), —C(O)$(CR_xR_x)_{0-1}NR_x(CH_2)_{0-1}C(O)(C_{1-3}$ cyanoalkyl), —C(O)$(CR_xR_x)_{0-1}NR_x(CH_2)_{1-2}C(O)NR_yR_y$, —C(O)$(CR_xR_x)_{1-3}C(O)NR_yR_y$, —C(O)$(CR_xR_x)_{0-1}NR_x(CHR_y(CH_2OH))$, —$(CR_xR_x)_{1-2}C(O)NR_yR_y$, —$(CR_xR_x)_{1-2}C(O)NR_y(C_{1-3}$ fluoroalkyl), —$(CR_xR_x)_{1-2}C(O)NR_y(C_{1-4}$ hydroxyalkyl), —$(CR_xR_x)_{1-2}C(O)NR_y(C_{1-3}$ cyanoalkyl), —$(CR_xR_x)_{1-2}C(O)NR_x(CH_2)_{1-2}O(C_{1-3}$ alkyl), —$(CR_xR_x)_{1-2}C(O)NR_xCH(C_{1-4}$ alkyl)($C_{1-3}$ hydroxyalkyl), —$(CH_2)_{1-2}C(O)NR_x(CH_2)_{1-2}C(O)NR_xR_x$, —$(CH_2)_{1-2}C(O)NR_x(CH_2)_{1-2}$S(O)$_2$OH, —$(CH_2)_{1-2}C(O)NR_x(CH_2)_{1-2}NR_xC(O)(C_{1-3}$ alkyl), —$(CH_2)_{1-2}C(O)NR_x(CH_2)_{1-3}NR_xR_x$, —$(CH_2)_{1-2}C(O)N(CH_2CH_3)(CH_2)_{1-3}NR_xR_x$, —$(CH_2)_{0-2}$S(O)$_2$ ($C_{1-4}$ alkyl), —$(CH_2)_{0-2}S(O)_2(C_{1-3}$ fluoroalkyl), —$(CH_2)_{0-2}S(O)_2NR_yR_x$, —$C(O)C(O)OH$, —$C(O)C(O)NR_yR_y$, or —$C(O)C(O)NR_y(CR_xR_x)_{1-2}NR_yR_y$;

$L_1$ is a bond, —$(CR_xR_x)_{1-2}$—, —$(CR_xR_x)_{1-2}CR_x(OH)$—, —$(CR_xR_x)_{1-2}O$—, —$CR_xR_xC(O)$—, —$(CR_xR_x)_2NR_x(CR_xR_x)_{0-1}$—, —$CR_xR_xC(O)NR_x(CR_xR_x)_{0-4}$—, —$C(O)(CR_xR_x)_{0-3}$—, —$C(O)(CR_xR_x)_{0-2}NR_x(CR_xR_x)_{0-2}$—, —$C(O)(CR_xR_x)_{0-2}N(C_{1-2}$ hydroxyalkyl)$(CR_xR_x)_{0-2}$—, —$C(O)(CR_xR_x)_{0-2}NR_x(CR_xR_x)_{1-2}CR_x(OH)$—, —$C(O)(CR_xR_x)_{1-2}C(O)NR_x$—, —$(CR_xR_x)_{0-2}C(O)NR_x(CR_xR_x)_{1-2}CR_x(OH)$—, —$(CR_xR_x)_{0-2}C(O)N(C_{1-2}$ hydroxyalkyl)$(CR_xR_x)_{1-2}$—, —$C(O)(CR_xR_x)_{0-1}O$—, —$C(O)(CR_xR_x)_{1-2}NHS(O)_2$—, —$C(O)CR_x(NH_2)CR_xR_x$—, —$C(O)C(O)(CR_xR_x)_{0-2}$—, —$C(O)C(O)NR_x(CR_xR_x)_{0-2}$—, —$C(O)NR_x(CR_xR_x)_{1-2}$—, or —$S(O)_2$—;

A is 2-oxa-6-azaspiro[3,3]heptanyl, 4-oxaspiro[2.5]octanyl, 7-azaspiro[3.5]nonanyl, 8-azabicyclo[3.2.1]octanyl, 8-oxa-3-azabicyclo[3.2.1]octanyl, 9-azabicyclo[3.3.1]nonanyl, adamantanyl, azepanyl, azetidinyl, $C_{3-6}$ cycloalkyl, diazepanyl, dihydroinonyl, dihydropyrimidinonyl, dioxidoisothiazolidinyl, dioxidothiazinanyl, dioxotetrahydrothiophenyl, dioxotetrahydrothiopyranyl, dioxothiomorpholinyl, furanyl, imidazolyl, imidazolidinonyl, indolyl, isoquinolinyl, isoxazolyl, morpholinyl, morpholinonyl, naphthalenyl, octahydrocyclopenta[b]pyranyl, oxazolidinonyl, oxadiazolyl, oxetanyl, oxazolyl, phenyl, piperidinyl, piperidinonyl, piperazinyl, piperazinonyl, pyrazinyl, pyrazolyl, pyridazinonyl, pyridinonyl, pyridinyl, pyrimidinyl, pyrrolidinonyl, pyrrolidinyl, pyrrolyl, quinolinyl, quinolizinonyl, tetrahydrofuranyl, tetrahydropyranyl, tetrazolyl, thiadiazolyl, thiazolyl, or triazolyl, each substituted with -$L_2$-$R_a$ and zero to 4 $R_b$;

$L_2$ is a bond or —$CR_xR_x$—;

$R_a$ is:
(a) H, F, $C_1$, —CN, —OH, $C_{1-6}$ alkyl, $C_{1-3}$ fluoroalkyl, $C_{1-5}$ hydroxyalkyl, —$(CH_2)_{0-4}O(C_{1-3}$ alkyl), —$(CR_xR_x)_{1-3}S(C_{1-3}$ alkyl), —$(CR_xR_x)_{1-3}NHC(O)O(C_{1-4}$ alkyl), —$(CR_xR_x)_{1-3}NR_yR_y$, —$(CR_xR_x)_{1-3}C(O)NR_yR_y$, —$O(C_{1-3}$ fluoroalkyl), —$S(O)_2NR_xR_x$, —$O(CR_xR_x)_{1-3}NR_xR_x$, —$NHS(O)_2(C_{1-3}$ alkyl), —$NR_xR_x$, —$NR_x(C_{1-4}$ alkyl), —$NR_xC(O)(C_{1-4}$ alkyl), —$(CR_xR_x)_{0-3}C(O)OH$, —$C(O)(C_{1-5}$ alkyl), —$C(O)(C_{1-3}$ fluoroalkyl), —$C(O)O(C_{1-4}$ alkyl), —$C(O)NH(C_{1-3}$ cyanoalkyl), —$C(O)NR_yR_y$, —$C(O)NR_xCH_2C(O)NR_xR_x$, or —$C(O)NR_xCH_2CH_2NHC(O)(C_{1-3}$ alkyl);

(b) $C_{3-6}$ cycloalkyl or —$C(O)NH(C_{3-6}$ cycloalkyl), wherein each cycloalkyl is substituted with zero to 2 substituents independently selected from —OH, $C_{1-3}$ alkyl, $C_{1-3}$ hydroxyalkyl, $C_{1-3}$ fluoroalkyl, and —$C(O)O(C_{1-3}$ alkyl); or (c) $A_1$, —$CH_2A_1$, —$C(O)A_1$, —$NR_xA_1$, or —$C(O)NR_xA_1$, wherein $A_1$ is furanyl, imidazolyl, indolyl, isoxazolyl, morpholinyl, octahydropyrrolo[3,4-c]pyrrolyl, oxazolyl, oxetanyl, phenyl, piperazinyl, piperidinyl, pyrazolyl, pyridinyl, pyrimidinyl, pyrrolidinyl, pyrrolyl, tetrahydrofuranyl, tetrahydropyranyl, thiadiazolyl, thiazolyl, thiophenyl, or triazolyl, each substituted with zero to three substituents independently selected from —OH, $C_{1-3}$ alkyl, $C_{1-3}$ hydroxyalkyl, —$C(O)(C_{1-2}$ alkyl), —$C(O)O(C_{1-3}$ alkyl), —$NR_xR_x$, phenyl, trifluoromethyl-phenyl, —$CH_2$(bromophenyl), and —$CH_2CH_2$(pyrrolidinyl);

each $R_4$ is independently F, —OH, $C_{1-2}$ alkyl, or —$OCH_3$; or two $R_4$ attached to the same carbon atom form =O;

each $R_5$ is independently F, $C_1$, —CN, $C_{1-2}$ alkyl, $C_{1-2}$ fluoroalkyl, or —$OCH_3$;

each $R_b$ is independently F, —$CH_3$, —$CF_3$, or —$OCH_3$;

each $R_x$ is independently H or —$CH_3$;

each $R_y$ is independently H or $C_{1-6}$ alkyl;

$R_z$ is H, $C_{1-2}$ alkyl, or $C_{1-2}$ fluoroalkyl;

m is zero, 1, 2, 3, or 4;

n is zero, 1, or 2; and p is zero, 1, 2, 3, or 4.

2. The compound according to claim 1, N-oxide, or salt thereof, wherein:

$R_1$ is H, Cl, —CN, $C_{1-4}$ alkyl, $C_{1-3}$ fluoroalkyl, $C_{1-3}$ hydroxy-fluoroalkyl, —$CR_z$=$CH_2$, $C_{3-6}$ cycloalkyl, —$CH_2(C_{3-6}$ cycloalkyl), —$C(O)O(C_{1-3}$ alkyl), or tetrahydropyranyl;

each $R_2$ is independently halo, —CN, —OH, —$NO_2$, $C_{1-3}$ alkyl, $C_{1-2}$ fluoroalkyl, $C_{1-3}$ hydroxyalkyl, $C_{1-3}$ aminoalkyl, —$(CH_2)_{0-4}O(C_{1-3}$ alkyl), $C_{1-3}$ fluoroalkoxy, $C_{2-4}$ alkoxyalkoxy, —$O(CH_2)_{1-2}NR_xR_x$, —$C(O)O(C_{1-3}$ alkyl), —$C(O)NR_yR_y$, —$NR_yR_y$, —$NR_xC(O)(C_{1-3}$ alkyl), —$NR_x(CH_2$-cyclopropyl), $C_{3-6}$ cycloalkyl, methylpiperidinyl, methylpiperazinyl, amino-oxadiazolyl, imidazolyl, triazolyl, or —$C(O)$(thiazolyl);

$R_3$ is:

(a) -$L_1$-A; or (b) H, $C_{1-6}$ alkyl, $C_{1-3}$ fluoroalkyl, $C_{1-3}$ cyanoalkyl, $C_{1-6}$ hydroxyalkyl, $C_{1-3}$ hydroxy-fluoroalkyl, —$CR_xR_x$-$CR_x(OH)CR_x$=$CR_xR_x$, —$(CR_xR_x)_{1-4}O(C_{1-3}$ alkyl), —$(CR_xR_x)_{1-4}O(CR_xR_x)_{1-3}O(C_{1-3}$ alkyl), —$CH_2CH(OH)CH_2O(C_{1-3}$ alkyl), —$(CR_xR_x)_{1-3}S(C_{1-3}$ alkyl), —$(CH_2)_{1-3}C(O)OC(CH_3)_3$, —$(CR_xR_x)_{0-3}NR_yR_y$, —$(CR_xR_x)_{0-3}NR_x(C_{1-4}$ hydroxyalkyl), —$CH_2CH(OH)CH_2NR_xR_y$, —$C(O)H$, —$C(O)(C_{1-6}$ alkyl), —$C(O)(C_{1-3}$ hydroxyalkyl), —$C(O)(C_{1-3}$ fluoroalkyl), —$C(O)(C_{1-3}$ chloroalkyl), —$C(O)(C_{1-3}$ cyanoalkyl), —$(CR_xR_x)_{0-3}C(O)OH$, —$C(O)(CH_2)_{0-2}O(C_{1-4}$ alkyl), —$C(O)(CR_xR_x)_{0-2}O(CR_xR_x)_{1-2}O(C_{1-3}$ alkyl), —$C(O)CR_xR_xS(O)_2(C_{1-3}$ alkyl), —$C(O)CR_xR_xNR_xS(O)_2(C_{1-3}$ alkyl), —$C(O)CR_xR_xOC(O)(C_{1-3}$ alkyl), —$C(O)(CR_xR_x)_{0-3}NR_yR_y$, —$C(O)(CR_xR_x)_{0-1}NR_x(C_{1-3}$ cyanoalkyl), —$C(O)(CR_xR_x)_{0-2}NR_y(C_{1-6}$ hydroxyalkyl), —$C(O)(CR_xR_x)_{0-1}NR_x(C_{1-3}$ fluoroalkyl), —$C(O)(CR_xR_x)_{0-1}NR_x(C_{1-5}$ hydroxy-fluoroalkyl), —$C(O)(CR_xR_x)_{0-1}NR_x(CH_2)_{1-2}O(C_{1-3}$ hydroxyalkyl), —$C(O)(CR_xR_x)_{0-1}NR_x(CH_2)_{1-2}NR_xC(O)(C_{1-2}$ alkyl), —$C(O)(CR_xR_x)_{0-1}NR_x(CR_xR_x)_{1-2}O(C_{1-2}$ alkyl), —$C(O)CR_x(NH_2)(CR_xR_x)_{1-4}NR_xR_x$, —$C(O)CR_x(NH_2)(CR_xR_x)_{1-4}NR_xC(O)NR_xR_x$, —$C(O)(CR_xR_x)_{0-3}NR_x(CH_2)_{0-1}C(O)(C_{1-3}$ alkyl), —$C(O)(CR_xR_x)_{0-1}NR_x(CH_2)_{0-1}C(O)(C_{1-3}$ cyanoalkyl), —$C(O)(CR_xR_x)_{0-1}NR_xCH_2C(O)NR_xR_y$, —$C(O)(CR_xR_x)_{0-1}NR_x(CH_2)_{1-2}C(O)NR_yR_y$, —$C(O)(CR_xR_x)_{0-1}NR_x(CHR_y(CH_2OH))$, —$(CR_xR_x)_{1-2}C(O)NR_yR_y$, —$(CR_xR_x)_{1-2}C(O)NR_y(C_{1-3}$ fluoroalkyl), —$(CR_xR_x)_{1-2}C(O)NR_y(C_{1-4}$ hydroxyalkyl), —$(CR_xR_x)_{1-2}C(O)NR_y(C_{1-3}$ cyanoalkyl), —$(CR_xR_x)_{1-2}C(O)NR_x(CH_2)_{1-2}O(C_{1-3}$ alkyl), —$(CR_xR_x)_{1-2}C(O)NR_xCH(C_{1-4}$ alkyl)$C_{1-3}$ hydroxyalkyl), —$(CH_2)_{1-2}C(O)NR_x(CH_2)_{1-2}C(O)NR_xR_x$, —$(CH_2)_{1-2}C(O)NR_x(CH_2)_{1-2}S(O)_2OH$, —$(CH_2)_{1-2}C(O)NR_x(CH_2)_{1-2}NR_xC(O)(C_{1-3}$ alkyl), —$(CH_2)_{1-2}C(O)NR_x(CH_2)_{1-3}NR_xR_x$, —$(CH_2)_{1-2}C(O)N(CH_2CH_3)(CH_2)_{1-3}NR_xR_x$, —$(CH_2)_{0-2}S(O)_2(C_{1-4}$ alkyl), —$(CH_2)_{0-2}S(O)_2(C_{1-3}$ fluoroalkyl), —(CH$_2$)$_{0-2}$S(O)$_2$NR$_y$R$_x$, —C(O)C(O)OH, —C(O)C(O)NR$_y$R$_y$, or —C(O)C(O)NR$_y$(CR$_x$R$_x$) 1-2NR$_y$R$_y$;

L$_1$ is a bond, —(CR$_x$R$_x$)$_{1-2}$—, —(CR$_x$R$_x$)$_{1-2}$CR$_x$(OH)—, —(CR$_x$R$_x$)$_{1-2}$O—, —CR$_x$R$_x$C(O)—, —(CR$_x$R$_x$)$_2$NR$_x$(CR$_x$R$_x$)$_{0-1}$—, —CR$_x$R$_x$C(O)NR$_x$(CR$_x$R$_x$)$_{0-4}$—, —C(O)(CR$_x$R$_x$)$_{0-3}$—, —C(O)(CR$_x$R$_x$)$_{0-2}$NR$_x$(CR$_x$R$_x$)$_{0-2}$—, —C(O)(CR$_x$R$_x$)$_{0-2}$N(C$_{1-2}$ hydroxyalkyl)(CR$_x$R$_x$)$_{0-2}$—, —C(O)(CR$_x$R$_x$)$_{0-2}$NR$_x$(CR$_x$R$_x$)$_{1-2}$CR$_x$(OH)—, —C(O)(CR$_x$R$_x$)$_{1-2}$C(O)NR$_x$—, —(CR$_x$R$_x$)$_{0-2}$C(O)NR$_x$(CR$_x$R$_x$)$_{1-2}$CR$_x$(OH)—, —(CR$_x$R$_x$)$_{0-2}$C(O)N(C$_{1-2}$ hydroxyalkyl)(CR$_x$R$_x$)$_{1-2}$—, —C(O)(CR$_x$R$_x$)$_{0-1}$O—, —C(O)(CR$_x$R$_x$)$_{1-2}$NHS(O)$_2$—, —C(O)CR$_x$(NH$_2$)CR$_x$R$_x$—, —C(O)C(O)(CR$_x$R$_x$)$_{0-2}$—, —C(O)C(O)NH(CH$_2$)$_{1-2}$—, —C(O)NR$_x$(CR$_x$R$_x$)$_{1-2}$—, or —S(O)$_2$—;

A is 2-oxa-6-azaspiro[3,3]heptanyl, 4-oxaspiro[2.5]octanyl, 7-azaspiro[3.5]nonanyl, 8-azabicyclo[3.2.1]octanyl, 8-oxa-3-azabicyclo[3.2.1]octanyl, 9-azabicyclo[3.3.1]nonanyl, adamantanyl, azepanyl, azetidinyl, C$_{3-6}$ cycloalkyl, dihydroinonyl, dihydropyrimidinonyl, dioxidoisothiazolidinyl, dioxidothiazinanyl, dioxotetrahydrothiophenyl, dioxotetrahydrothiopyranyl, dioxothiomorpholinyl, imidazolyl, imidazolidinonyl, isoxazolyl, morpholinyl, morpholinonyl, octahydrocyclopenta[b]pyranyl, oxazolidinonyl, oxadiazolyl, oxetanyl, oxazolyl, phenyl, piperidinyl, piperidinonyl, piperazinyl, piperazinonyl, pyrazolyl, pyridazinonyl, pyridinonyl, pyridinyl, pyrimidinyl, pyrrolidinonyl, pyrrolidinyl, pyrrolyl, quinolizinonyl, tetrahydrofuranyl, tetrahydropyranyl, tetrazolyl, thiazolyl, or triazolyl, each substituted with -L$_2$-R$_a$ and zero to 4 R$_b$;

L$_2$ is a bond or —CR$_x$R$_x$—;

R$_a$ is:
(a) H, F, C$_1$, —CN, —OH, C$_{1-6}$ alkyl, C$_{1-3}$ fluoroalkyl, C$_{1-5}$ hydroxyalkyl, —(CH$_2$)$_{0-4}$O(C$_{1-3}$ alkyl), —(CR$_x$R$_x$)$_{1-3}$S(C$_{1-3}$ alkyl), —(CR$_x$R$_x$)$_{1-3}$NHC(O)O(C$_{1-4}$ alkyl), —(CR$_x$R$_x$)$_{1-3}$NR$_y$R$_y$, —(CR$_x$R$_x$)$_{1-3}$C(O)NR$_y$R$_y$, —O(C$_{1-3}$ fluoroalkyl), —S(O)$_2$NR$_x$R$_x$, —O(CR$_x$R$_x$)$_{1-3}$NR$_x$R$_x$, —NHS(O)$_2$(C$_{1-3}$ alkyl), —NR$_x$R$_x$, —NR$_x$(C$_{1-4}$ alkyl), —NR$_x$C(O)(C$_{1-4}$ alkyl), —(CR$_x$R$_x$)$_{0-3}$C(O)OH, —C(O)(C$_{1-5}$ alkyl), —C(O)(C$_{1-3}$ fluoroalkyl), —C(O)O(C$_{1-4}$ alkyl), —C(O)NH(C$_{1-3}$ cyanoalkyl), —C(O)NR$_y$R$_y$, —C(O)NR$_x$CH$_2$C(O)NR$_x$R$_x$, or —C(O)NR$_x$CH$_2$CH$_2$NHC(O)(C$_{1-3}$ alkyl);
(b) C$_{3-6}$ cycloalkyl or —C(O)NH(C$_{3-6}$ cycloalkyl), wherein each cycloalkyl is substituted with zero to 2 substituents independently selected from —OH, C$_{1-3}$ alkyl, C$_{1-3}$ hydroxyalkyl, C$_{1-3}$ fluoroalkyl, and —C(O)O(C$_{1-3}$ alkyl); or
(c) A$_1$, —CH$_2$A$_1$, —C(O)A$_1$, —NR$_x$A$_1$, or —C(O)NR$_x$A$_1$, wherein A$_1$ is furanyl, imidazolyl, indolyl, isoxazolyl, morpholinyl, octahydropyrrolo[3,4-c]pyrrolyl, oxazolyl, oxetanyl, phenyl, piperazinyl, piperidinyl, pyrazolyl, pyridinyl, pyrimidinyl, pyrrolidinyl, pyrrolyl, tetrahydrofuranyl, tetrahydropyranyl, thiadiazolyl, thiazolyl, thiophenyl, or triazolyl, each substituted with zero to three substituents independently selected from —OH, C$_{1-3}$ alkyl, C$_{1-3}$ hydroxyalkyl, —C(O)(C$_{1-2}$ alkyl), —C(O)O(C$_{1-3}$ alkyl), —NR$_x$R$_x$, phenyl, trifluoromethyl-phenyl, —CH$_2$(bromophenyl), and —CH$_2$CH$_2$(pyrrolidinyl); and R$_z$ is H, C$_{1-2}$ alkyl, or —CF$_3$.

3. The compound according to claim 1, N-oxide, or salt thereof, wherein:

R$_1$ is H, —CH$_3$, —CH$_2$CH$_3$, —CH(CH$_3$)$_2$, —C(CH$_3$)$_3$, —CHF$_2$, —CH$_2$CHF$_2$, —CH(CH$_3$)CF$_3$, —C(CF$_3$)=CH$_2$, —C(O)OCH$_3$, cyclopropyl, or —CH$_2$(cyclopropyl);

each R$_2$ is independently F, C$_1$, Br, —CN, —OH, —CH$_3$, —CH$_2$CH$_3$, —CF$_3$, —CH$_2$OH, —C(CH$_3$)$_2$OH, —CH$_2$NH$_2$, —OCH$_3$, —OCH$_2$CH$_3$, —OCH(CH$_3$)$_2$, —OCH$_2$CH$_2$OCH$_3$, —OCH$_2$CH$_2$N(CH$_3$)$_2$, —OCHF$_2$, —C(O)OCH$_3$, —C(O)NH$_2$, —C(O)NH(CH$_2$CH$_3$), —C(O)(thiazolyl), —NH$_2$, —NH(CH$_3$), —NH(CH$_2$CH$_3$), —N(CH$_3$)$_2$, —NHC(O)CH$_3$, —NHC(O)C(CH$_3$)$_3$, —NH(CH$_2$-cyclopropyl), —NO$_2^+$, cyclopropyl, methylpiperidinyl, methylpiperazinyl, aminooxadiazolyl, imidazolyl, or triazolyl;

R$_3$ is:
(a) -L$_1$-A; or
(b) H, —CH$_3$, —CH$_2$CH$_3$, —CH$_2$CH$_2$CH$_3$, —CH(CH$_3$)$_2$, —CH$_2$CH(CH$_3$)$_2$, —CH$_2$C(CH$_3$)$_3$, —CH(CH$_2$CH$_3$)$_2$, —CH$_2$CHF$_2$, —CH$_2$CF$_3$, —CH$_2$CH$_2$CF$_3$, —CH(CH$_3$)CH$_2$F, —CH(CH$_2$F)$_2$, —CH$_2$CH$_2$OH, —CH$_2$CH$_2$CH$_2$OH, —CH$_2$CH(CH$_3$)OH, —CH$_2$CH(OH)CH$_2$CH$_3$, —CH$_2$C(CH$_3$)$_2$OH, —CH$_2$CH(OH)CH(CH$_3$)$_2$, —CH$_2$CH(OH)C(CH$_3$)$_3$, —CH$_2$CH(OH)CH$_2$OH, —CH$_2$CH(OH)CF$_3$, —CH$_2$C(CH$_3$)(OH)CH=CH$_2$, —CH$_2$CN, —CH$_2$CH$_2$CN, —C(O)H, —C(O)OH, —CH$_2$C(O)OH, —CH$_2$C(CH$_3$)$_2$C(O)OH, —CH$_2$CH$_2$OCH$_3$, —CH$_2$CH$_2$OCH$_2$CH$_3$, —CH$_2$CH(CH$_3$)OCH$_3$, —CH$_2$CH$_2$OCH$_2$CH$_2$OCH$_3$, —CH$_2$CH$_2$CH$_2$OCH$_3$, —CH$_2$CH(OH)CH$_2$OCH$_3$, —NH(CH$_3$), —NH(CH$_2$C(CH$_3$)$_2$OH), —CH$_2$CH$_2$NHCH$_3$, —CH$_2$CH$_2$NH(CH$_3$), —CH$_2$CH$_2$CH$_2$N(CH$_3$)$_2$, —CH$_2$CH(OH)CH$_2$N(CH$_3$)CH(CH$_3$)$_2$, —S(O)$_2$CH$_3$, —S(O)$_2$CH$_2$CH$_3$, —S(O)$_2$CH$_2$CH$_2$CH$_3$, —S(O)$_2$CH(CH$_3$)$_2$, —S(O)$_2$CH$_2$CH(CH$_3$)$_2$, —S(O)$_2$CH$_2$CF$_3$, —C(O)CH$_3$, —C(O)CH$_2$CH$_3$, —C(O)CH(CH$_3$)$_2$, —C(O)CH$_2$CH(CH$_3$)$_2$, —C(O)C(CH$_3$)$_3$, —C(O)CH(CH$_2$CH$_3$)$_2$, —C(O)CHF$_2$, —C(O)CF$_3$, —C(O)CH$_2$CF$_3$, —C(O)CH$_2$OH, —C(O)CH$_2$CH$_2$OH, —C(O)C(CH$_3$)$_2$OH, —C(O)CH$_2$CH(CH$_3$)OH, —C(O)CH$_2$(CH$_2$CH$_2$OH)(CH$_2$CH$_2$CH$_3$), —C(O)CH$_2$CN, —C(O)C(CH$_3$)$_2$CN, —C(O)CH$_2$OCH$_3$, —C(O)CH$_2$CH$_2$OCH$_3$, —C(O)CH$_2$NH$_2$, —C(O)CH$_2$NHCH$_3$, —C(O)CH(CH$_3$)NHCH$_3$, —C(O)C(CH$_3$)$_2$NH$_2$, —C(O)C(CH$_3$)$_2$NHCH$_3$, —C(O)CH$_2$CH$_2$N(CH$_3$)$_2$, —C(O)CH$_2$NHCH$_2$CH$_2$CH$_3$, —C(O)CH$_2$NHCH(CH$_3$)$_2$, —C(O)CH$_2$NHC(CH$_3$)$_3$, —C(O)CH$_2$NHCH$_2$CH(CH$_3$)$_2$, —C(O)CH$_2$NHCH(CH$_3$)CH$_2$CH$_3$, —C(O)CH$_2$NHCH$_2$CH$_2$CH(CH$_3$)$_2$, —C(O)CH$_2$NHCH$_2$C(CH$_3$)$_3$, —C(O)CH$_2$NHCH(CH$_2$CH$_3$)$_2$, —C(O)CH$_2$NHCH$_2$C(CH$_3$)$_3$, —C(O)CH$_2$NHCH$_2$CH$_2$OH, —C(O)CH$_2$NH(CH$_2$CH(OH)CH$_3$), —C(O)CH$_2$NH(CH$_2$CH$_2$CH(OH)CH$_3$), —C(O)CH$_2$NH(CH$_2$C(CH$_3$)$_2$OH), —C(O)CH$_2$NHCH(CH$_2$OH)CH$_2$CH(CH$_3$)$_2$, —C(O)CH$_2$NHCH$_2$CH(OH)CH$_2$OH, —C(O)CH$_2$NHCH$_2$CH$_2$OCH$_3$, —C(O)CH$_2$NHCH$_2$CH$_2$OCH$_2$CH$_3$, —C(O)CH$_2$OCH$_2$CH$_2$OCH$_3$, —C(O)CH$_2$S(O)$_2$CH$_3$, —C(O)CH$_2$NHS(O)$_2$CH$_3$, —C(O)CH$_2$NHC(O)CH$_3$, —C(O)CH$_2$N(CH$_3$)$_2$, —C(O)CH$_2$N(CH$_3$)CH$_2$CH$_3$, —C(O)CH$_2$N(CH$_3$)CH(CH$_3$)$_2$, —C(O)CH$_2$N(CH$_3$)C(CH$_3$)$_3$, —C(O)CH$_2$N(CH$_3$)CH$_2$CH (CH₃)₂, —C(O)CH₂N(CH₃)CH₂CH₂OH, —C(O)CH₂N(CH₃)CH₂CH₂OH), —C(O)CH₂N(CH₃)(CH₂C(CH₃)₂OH), —C(O)CH₂N(CH₃)(CH₂CH₂F), —C(O)CH₂N(CH₃)(CH₂CHF₂), —C(O)CH₂N(CH₃)(CH₂CN), —C(O)CH₂N(CH₃)CH₂CH₂CN, —C(O)CH₂N(CH₃)CH₂CH₂OCH₃, —C(O)CH₂N(CH(CH₃)₂)₂, —C(O)CH₂N(CH₂CH₂OH)(CH₃), —C(O)CH₂N(CH₂CH₂OH)(CH₂CH₃), —C(O)CH₂N(CH₂CH₂OH)(CH(CH₃)₂), —C(O)CH₂N(CH₂CH₂OH)(CH₂CH(CH₃)CH₂CH₃), —C(O)CH₂CH₂NH(CH₃), —C(O)CH₂CH₂N(CH₃)₂, —C(O)CH₂CH₂N(CH₃)CH₂CH₂OH, —C(O)CH₂CH₂N(CH₃)C(O)CH₃, —C(O)CH₂N(CH₂CH₃)₂, —C(O)CH(NH₂)CH₂CH₂CH₂NH₂, —C(O)CH(NH₂)CH₂CH₂CH₂CH₂NH₂, —C(O)CH(NH₂)CH₂CH₂CH₂NHC(O)NH₂, —C(O)OCH₃, —C(O)OCH₂CH₃, —C(O)OCH(CH₃)₂, —C(O)OCH₂CH(CH₃)₂, —C(O)OCH₂CH₂OCH₃, —C(O)C(O)OH, —C(O)C(O)NH(CH₃), —C(O)C(O)N(CH₃)₂, —C(O)C(O)N(CH₃)CH₂CH₂N(CH₃)₂, —CH₂C(O)NH₂, —CH₂C(O)NH(CH₃), —CH₂C(O)NH(CH₂CH₃), —CH₂C(O)NH(CH₂CH₂CH₃), —CH₂C(O)NHCH(CH₃)₂, —CH₂C(O)NH(CH(CH₃)CH₂CH₃), —CH₂C(O)NHCH₂CH(CH₃)₂, —CH₂C(O)NHC(CH₃)₃, —CH₂C(O)NH(CH₂CH₂CH(CH₃)₂), —CH₂C(O)NHCH(CH₂CH₃)₂, —CH₂C(O)NH(CH₂CH₂C(CH₃)₃), —CH₂C(O)NH(CH₂CF₃), —CH₂C(O)NH(CH(CH₃)CF₃), —CH₂C(O)NHCH₂CH₂OH, —CH₂C(O)NH(CH₂CH₂CH(CH₃)OH), —CH₂C(O)NH(CH₂CH(CH₃)OH), —CH₂C(O)NH(CH₂CH₂OCH₃), —CH₂C(O)NH(CH₂CH₂OCH₂CH₃), —CH₂C(O)NH(CH₂CN), —CH₂C(O)NHCH(CH₂OH)(CH₂CH(CH₃)₂), —CH₂CH₂C(O)NH₂, —CH₂C(O)N(CH₃)₂, —CH₂C(O)N(CH₃)CH₂CH₃, —CH₂C(O)N(CH₃)CH(CH₃)₂, —CH₂C(O)N(CH₃)CH₂CH(CH₃)₂, —CH₂C(O)N(CH₃)C(CH₃)₃, —CH₂C(O)N(CH₃)CH₂CH₂CH₂OH, —CH₂C(O)N(CH₃)CH₂C(CH₃)₂OH, —CH₂C(O)N(CH₃)CH₂CH₂OCH₃, —CH₂C(O)N(CH₃)CH₂CN, —CH₂C(O)N(CH₂CH₃)₂, —CH₂C(O)N(CH(CH₃)₂)₂, —CH(CH₃)C(O)N(CH₃)₂, —CH₂C(O)N(CH₂CH₂OH)(CH₂CH₃), —CH₂C(O)N(CH₂CH₂OH)(CH₂CH₂CH₃), —CH₂C(O)N(CH₂CH₂OH)(CH₂CH₂CH₂CH₃), —CH₂C(O)N(CH₂CH₂OH)(CH(CH₃)₂), or —CH₂C(O)N(CH₂CH₂OH)(CH₂CH(CH₃)CH₂CH₃);

$L_1$ is a bond, —(CH₂)₁₋₂—, —CH₂CH(OH)—, —CH₂CH₂O—, —CH₂C(O)—, —CH₂C(O)NH—, —CH₂C(O)N(CH₃)—, —CH₂C(O)NHCH₂—, —CH₂C(O)NR$_x$CH₂CH₂—, —CH₂C(O)NHCH₂—, —CH₂C(O)N(CH₃)CH₂CH₂—, —CH₂C(O)N(CH₃)CH₂CH(OH)—, —CH₂C(O)NHCH₂C(CH₃)₂—, —CH₂C(O)N(CH₂CH₂OH)CH₂—, —C(O)(CH₂)₀₋₂—, —C(O)CH₂C(O)NR$_x$—, —C(O)CH₂CH₂NR$_x$—, —C(O)NH—, —C(O)CH₂NR$_x$(CH₂)₀₋₂—, —C(O)CH₂NHCH₂C(CH₃)₂—, —C(O)CH₂N(CH₃)CH₂CH(OH)—, —C(O)CH₂N(CH₂CH₂OH)CH₂—, —C(O)CH₂CH₂NHS(O)₂—, —C(O)CH(NH₂)CH₂—, —C(O)O—, —C(O)C(O)—, —C(O)C(O)NH(CH₂)₁₋₂—, or —S(O)₂—;

A is 2-oxa-6-azaspiro[3.3]heptanyl, 4-oxaspiro[2.5]octanyl, 7-azaspiro[3.5]nonanyl, 8-azabicyclo[3.2.1]octanyl, 8-oxa-3-azabicyclo[3.2.1]octanyl, 9-azabicyclo[3.3.1]nonanyl, adamantanyl, azepanyl, azetidinyl, $C_{3-6}$ cycloalkyl, dihydroinonyl, dihydropyrimidinonyl, dioxidoisothiazolidinyl, dioxidothiazinanyl, dioxotetrahydrothiophenyl, dioxotetrahydrothiopyranyl, dioxothiomorpholinyl, imidazolyl, imidazolidinonyl, isoxazolyl, morpholinyl, morpholinonyl, octahydrocyclopenta[b]pyranyl, oxadiazolyl, oxetanyl, oxazolidinonyl, oxazolyl, phenyl, piperidinyl, piperidinonyl, piperazinyl, piperazinonyl, pyrazolyl, pyridazinonyl, pyridinonyl, pyridinyl, pyrimidinyl, pyrrolidinonyl, pyrrolidinyl, pyrrolyl, quinolizinonyl, tetrahydrofuranyl, tetrahydropyranyl, tetrazolyl, thiazolyl, or triazolyl, each substituted with -L₂-R$_a$ and zero to 4 R$_b$;

L₂ is bond or —CH₂—;

R$_a$ is H, F, C₁, —CN, —OH, —CH₃, —CH₂CH₃, —CH(CH₃)₂, —C(CH₃)₃, —CH₂CH(CH₃)₂, —CH₂OH, —CH₂CH₂OH, —CF₃, —CH₂OCH₃, —CH₂CH₂OCH₃, —OCH₃, —C(O)CH₃, —C(O)CH₂C(CH₃)₃, —C(O)CF₃, —C(O)OCH₃, —CH₂C(O)N(CH₃)₂, —CH₂CH₂NH(CH₃), cyclopropyl, cyclopentyl, —NH₂, —N(CH₃)₂, —NH(pyridinyl), —C(O)NH₂, —NHC(O)CH₃, phenyl, or morpholinyl;

each R$_b$ is independently F, —CH₃, —CF₃, or —OCH₃;
each R₄ is independently F, —OH, or —CH₃; or two R₄ attached to the same carbon atom form =O;
each R₅ is independently F, —CH₃, or —CF₃;
m is zero, 1, 2, 3, or 4;
n is zero, 1, or 2.

4. The compound according to claim 1, N-oxide, or salt thereof, wherein:
R₃ is -L₁-A.

5. The compound according to claim 1, N-oxide, or salt thereof, wherein R₃ is H.

6. The compound according to claim 1, N-oxide, or salt thereof, wherein R₃ is:
—CH₃, —CH₂CH₃, —CH₂CH₂CH₃, —CH(CH₃)₂, —CH₂CH(CH₃)₂, —CH₂C(CH₃)₃, —CH(CH₂CH₃)₂, —CH₂CHF₂, —CH₂CF₃, —CH₂CH₂CF₃, —CH(CH₃)CH₂F, —CH(CH₂F)₂, —CH₂CH₂OH, —CH₂CH₂CH₂OH, —CH₂CH(CH₃)OH, —CH₂CH(OH)CH₂CH₃, —CH₂C(CH₃)₂OH, —CH₂CH(OH)CH(CH₃)₂, —CH₂CH(OH)C(CH₃)₃, —CH₂CH(OH)CH₂OH, —CH₂CH(OH)CF₃, —CH₂C(CH₃)(OH)CH=CH₂, —CH₂CN, —CH₂CH₂CN, —C(O)H, —C(O)OH, —CH₂C(O)OH, —CH₂C(CH₃)₂C(O)OH, —CH₂CH₂OCH₃, —CH₂CH₂OCH₂CH₃, —CH₂CH(CH₃)OCH₃, —CH₂CH₂OCH₂CH₂OCH₃, —CH₂CH₂CH₂OCH₃, —CH₂CH(OH)CH₂OCH₃, —NH(CH₃), —NH(CH₂C(CH₃)₂OH), —CH₂CH₂NHCH₃, —CH₂CH₂NH(CH₃), —CH₂CH₂CH₂N(CH₃)₂, —CH₂CH(OH)CH₂N(CH₃)CH(CH₃)₂, —S(O)₂CH₃, —S(O)₂CH₂CH₃, —S(O)₂CH₂CH₂CH₃, —S(O)₂CH(CH₃)₂, —S(O)₂CH₂CH(CH₃)₂, —S(O)₂CH₂CF₃, —C(O)CH₃, —C(O)CH₂CH₃, —C(O)CH(CH₃)₂, —C(O)CH₂CH(CH₃)₂, —C(O)C(CH₃)₃, —C(O)CH(CH₂CH₃)₂, —C(O)CHF₂, —C(O)CF₃, —C(O)CH₂CF₃, —C(O)CH₂OH, —C(O)CH₂CH₂OH, —C(O)C(CH₃)₂OH, —C(O)CH₂CH(CH₃)OH, —C(O)CH₂(CH₂CH₂OH)(CH₂CH₂CH₂CH₃), —C(O)CH₂CN, —C(O)C(CH₃)₂CN, —C(O)CH₂OCH₃, —C(O)CH₂CH₂OCH₃, —C(O)CH₂NH₂, —C(O)CH₂NHCH₃, —C(O)CH(CH₃)NHCH₃, —C(O)C(CH₃)₂NH₂, —C(O)C(CH₃)₂NHCH₃, —C(O)CH₂CH₂CH₂N(CH₃)₂, —C(O)CH₂NHCH₂CH₂CH₃, —C(O)CH₂NHCH(CH₃)₂, —C(O)CH₂NHC(CH₃)₃, —C(O)CH₂NHCH₂CH(CH₃)₂, —C(O)CH₂NHCH(CH₃)CH₂CH₃, —C(O)CH₂NHCH₂CH₂CH(CH₃)₂, —C(O)CH₂NHCH₂C —C(O)CH$_2$NHCH(CH$_2$CH$_3$)$_2$, —C(O)CH$_2$NHCH$_2$C(CH$_3$)$_3$, —C(O)CH$_2$NHCH$_2$CH$_2$OH, —C(O)CH$_2$NHCH(CH$_2$CH(OH)CH$_3$), —C(O)CH$_2$NHCH$_2$CH$_2$CH(OH)CH$_3$, —C(O)CH$_2$NH(CH$_2$C(CH$_3$)$_2$OH), —C(O)CH$_2$NHCH(CH$_2$OH)CH$_2$CH(CH$_3$)$_2$, —C(O)CH$_2$NHCH$_2$CH(OH)CH$_2$OH, —C(O)CH$_2$NHCH$_2$CH$_2$OCH$_3$, —C(O)CH$_2$NHCH$_2$CH$_2$OCH$_2$CH$_3$, —C(O)CH$_2$OCH$_2$CH$_2$OCH$_3$, —C(O)CH$_2$S(O)$_2$CH$_3$, —C(O)CH$_2$NHS(O)$_2$CH$_3$, —C(O)CH$_2$NHC(O)CH$_3$, —C(O)CH$_2$N(CH$_3$)$_2$, —C(O)CH$_2$N(CH$_3$)CH$_2$CH$_3$, —C(O)CH$_2$N(CH$_3$)CH(CH$_3$)$_2$, —C(O)CH$_2$N(CH$_3$)C(CH$_3$)$_3$, —C(O)CH$_2$N(CH$_3$)CH$_2$CH(CH$_3$)$_2$, —C(O)CH$_2$N(CH$_3$)CH$_2$CH$_2$OH, —C(O)CH$_2$N(CH$_3$)CH$_2$CH$_2$CH$_2$OH), —C(O)CH$_2$N(CH$_3$)(CH$_2$C(CH$_3$)$_2$OH), —C(O)CH$_2$N(CH$_3$)(CH$_2$CH$_2$F), —C(O)CH$_2$N(CH$_3$)(CH$_2$CHF$_2$), —C(O)CH$_2$N(CH$_3$)(CH$_2$CN), —C(O)CH$_2$N(CH$_3$)CH$_2$CH$_2$CN, —C(O)CH$_2$N(CH$_3$)CH$_2$CH$_2$OCH$_3$, —C(O)CH$_2$N(CH(CH$_3$)$_2$)$_2$, —C(O)CH$_2$N(CH$_2$CH$_2$OH)(CH$_3$), —C(O)CH$_2$N(CH$_2$CH$_2$OH)(CH$_2$CH$_3$), —C(O)CH$_2$N(CH$_2$CH$_2$OH)(CH(CH$_3$)$_2$), —C(O)CH$_2$CH$_2$N(CH$_3$)C(O)CH$_3$, —C(O)CH$_2$CH$_2$NH(CH$_3$), —C(O)CH$_2$N(CH$_2$CH$_2$OH)(CH$_2$CH(CH$_3$)CH$_2$CH$_3$), —C(O)CH$_2$CH$_2$N(CH$_3$)$_2$, —C(O)CH$_2$CH$_2$N(CH$_3$)CH$_2$CH$_2$OH, —C(O)CH(NH$_{12}$)CH$_2$CH$_2$CH$_2$NH$_2$, —C(O)CH(NH$_{12}$)CH$_2$CH$_2$CH$_2$CH$_2$NH$_2$, —C(O)CH(NH$_{12}$)CH$_2$CH$_2$CH$_2$NHC(O)NH$_{12}$, —C(O)OCH$_3$, —C(O)OCH$_2$CH$_3$, —C(O)OCH(CH$_3$)$_2$, —C(O)OCH$_2$CH(CH$_3$)$_2$, —C(O)OCH$_2$CH$_2$OCH$_3$, —C(O)C(O)OH, —C(O)C(O)NH(CH$_3$), —C(O)C(O)N(CH$_3$)$_2$, —C(O)C(O)N(CH$_3$)CH$_2$CH$_2$N(CH$_3$)$_2$, —CH$_2$C(O)NH$_2$, —CH$_2$C(O)NH(CH$_3$), —CH$_2$C(O)NH(CH$_2$CH$_3$), —CH$_2$C(O)NH(CH$_2$CH$_2$CH$_3$), —CH$_2$C(O)NHCH(CH$_3$)$_2$, —CH$_2$C(O)NHCH$_2$CH(CH$_3$)$_2$, —CH$_2$C(O)NH(CH(CH$_3$)CH$_2$CH$_3$), —CH$_2$C(O)NHC(CH$_3$)$_3$, —CH$_2$C(O)NHCH$_2$C(CH$_3$)$_3$, —CH$_2$C(O)NH(CH$_2$CH$_2$CH(CH$_3$)$_2$), —CH$_2$C(O)NHCH(CH$_2$CH$_3$)$_2$, —CH$_2$C(O)NH(CH$_2$CH$_2$C(CH$_3$)$_3$), —CH$_2$C(O)NH(CH$_2$CF$_3$), —CH$_2$C(O)NH(CH(CH$_3$)CF$_3$), —CH$_2$C(O)NHCH$_2$CH$_2$OH, —CH$_2$C(O)NH(CH$_2$CH$_2$CH(CH$_3$)OH), —CH$_2$C(O)NH(CH$_2$CH(CH$_3$)OH), —CH$_2$C(O)NH(CH$_2$CH$_2$OCH$_3$), —CH$_2$C(O)NH(CH$_2$CH$_2$OCH$_3$), —CH$_2$C(O)NH(CH$_2$CN), —CH$_2$C(O)NHCH(CH$_2$OH)(CH$_2$CH(CH$_3$)$_2$), —CH$_2$CH$_2$C(O)NH$_2$, —CH$_2$C(O)N(CH$_3$)$_2$, —CH$_2$C(O)N(CH$_3$)CH$_2$CH$_3$, —CH$_2$C(O)N(CH$_3$)CH(CH$_3$)$_2$, —CH$_2$C(O)N(CH$_3$)CH$_2$CH(CH$_3$)$_2$, —CH$_2$C(O)N(CH$_3$)C(CH$_3$)$_3$, —CH$_2$C(O)N(CH$_3$)CH$_2$CH$_2$CH$_2$OH, —CH$_2$C(O)N(CH$_3$)CH$_2$C(CH$_3$)$_2$OH, —CH$_2$C(O)N(CH$_3$)CH$_2$CH$_2$OCH$_3$, —CH$_2$C(O)N(CH$_3$)CH$_2$CN, —CH$_2$C(O)N(CH$_2$CH$_3$)$_2$, —CH$_2$C(O)N(CH(CH$_3$)$_2$)$_2$, —CH(CH$_3$)C(O)N(CH$_3$)$_2$, —CH$_2$C(O)N(CH$_2$CH$_2$OH)(CH$_2$CH$_3$), —CH$_2$C(O)N(CH$_2$CH$_2$OH)(CH$_2$CH$_2$CH$_3$), —CH$_2$C(O)N(CH$_2$CH$_2$OH)(CH$_2$CH$_2$CH$_2$CH$_3$), —CH$_2$C(O)N(CH$_2$CH$_2$OH)(CH(CH$_3$)$_2$), or —CH$_2$C(O)N(CH$_2$CH$_2$OH)(CH$_2$CH(CH$_3$)CH$_2$CH$_3$).

7. The compound according to claim 1, N-oxide, or salt thereof, wherein said compound is selected from: 2-(2,6-dimethylpyridin-4-yl)-3-isopropyl-5-(piperidin-4-yl)-1H-indole hydrochloride (1); 2-(2,6-dimethylpyridin-4-yl)-3-ethyl-5-(piperidin-4-yl)-1H-indole (2); 2-(2-fluoro-6-methylpyridin-4-yl)-3-isopropyl-5-(piperidin-4-yl)-1H-indole (3); 3-isopropyl-2-(2-methylpyridin-4-yl)-5-(piperidin-4-yl)-1H-indole (5); 3-isopropyl-5-(piperidin-4-yl)-2-(2-(trifluoromethyl)pyridin-4-yl)-1H-indole (6); 2-(3-fluoropyridin-4-yl)-3-isopropyl-5-(piperidin-4-yl)-1H-indole (7); 4-(3-isopropyl-5-(piperidin-4-yl)-1H-indol-2-yl)pyridin-2-amine (8); 4-(3-isopropyl-5-(piperidin-4-yl)-1H-indol-2-yl)-5-methylpyridin-2-amine (9); 4-(3-isopropyl-5-(piperidin-4-yl)-1H-indol-2-yl)-6-methylpyridin-3-amine (10); 4-(3-isopropyl-5-(piperidin-4-yl)-1H-indol-2-yl)-3-methylpyridin-2-amine (11); 4-(3-isopropyl-5-(piperidin-4-yl)-1H-indol-2-yl)-6-methylpyridin-2-amine (12); 4-(3-isopropyl-5-(piperidin-4-yl)-1H-indol-2-yl)-2-methylpyridin-3-amine (13); (4-(3-isopropyl-5-(piperidin-4-yl)-1H-indol-2-yl)pyridin-2-yl)methanamine (14); 4-(3-isopropyl-5-(piperidin-4-yl)-1H-indol-2-yl)-6-methylnicotinamide (15); 2-(5-fluoro-2-methylpyridin-4-yl)-3-isopropyl-5-(piperidin-4-yl)-1H-indole (16); 2-(5-chloro-2-fluoropyridin-4-yl)-3-isopropyl-5-(piperidin-4-yl)-1H-indole (18); (4-(3-isopropyl-5-(piperidin-4-yl)-1H-indol-2-yl)pyridin-3-yl)methanol (19); 2-(3,5-dichloropyridin-4-yl)-3-isopropyl-5-(piperidin-4-yl)-1H-indole (20); 2-(2-chloro-3-fluoropyridin-4-yl)-3-isopropyl-5-(piperidin-4-yl)-1H-indole (21); (4-(3-isopropyl-5-(piperidin-4-yl)-1H-indol-2-yl)pyridin-2-yl)methanol (22); 3-isopropyl-2-(3-methylpyridin-4-yl)-5-(piperidin-4-yl)-1H-indole (23); 4-(3-isopropyl-5-(piperidin-4-yl)-1H-indol-2-yl)-N,N-dimethylpyridin-2-amine (24); 6-chloro-4-(3-isopropyl-5-(piperidin-4-yl)-1H-indol-2-yl)nicotinonitrile (26); 2-(2,6-dimethyl-3-nitropyridin-4-yl)-3-isopropyl-5-(piperidin-4-yl)-1H-indole (27); 2-(2-fluoro-5-methylpyridin-4-yl)-3-isopropyl-5-(piperidin-4-yl)-1H-indole (28); 4-(3-isopropyl-5-(piperidin-4-yl)-1H-indol-2-yl)-2,6-dimethylpyridin-3-amine (29); 2-(2,3-dimethylpyridin-4-yl)-3-isopropyl-5-(piperidin-4-yl)-1H-indole (30); 2-(2,5-dimethylpyridin-4-yl)-3-isopropyl-5-(piperidin-4-yl)-1H-indole (31); 2-((cyclopropylmethyl)amino)-4-(3-isopropyl-5-(piperidin-4-yl)-1H-indol-2-yl)-6-methylnicotinonitrile (32); 4-(3-isopropyl-5-(piperidin-4-yl)-1H-indol-2-yl)-3-(trifluoromethyl)picolinonitrile (33); N-(4-(3-isopropyl-5-(piperidin-4-yl)-1H-indol-2-yl)-6-methylpyridin-3-yl)acetamide (34); 2-(2-chloro-3-methylpyridin-4-yl)-3-isopropyl-5-(piperidin-4-yl)-1H-indole (35); 2-chloro-4-(3-isopropyl-5-(piperidin-4-yl)-1H-indol-2-yl)nicotinonitrile (36); N-(4-(3-isopropyl-5-(piperidin-4-yl)-1H-indol-2-yl)pyridin-3-yl) pivalamide (37); 3-isopropyl-5-(piperidin-4-yl)-2-(pyridin-4-yl)-1H-indole (38); 3-isopropyl-5-(piperidin-4-yl)-2-(2,3,6-trimethylpyridin-4-yl)-1H-indole (39); 2-(3-bromo-2,6-dimethylpyridin-4-yl)-3-isopropyl-5-(piperidin-4-yl)-1H-indole (40); (4-(3-isopropyl-5-(piperidin-4-yl)-1H-indol-2-yl)-6-methylpyridin-3-yl)methanol (42); 3-isopropyl-5-(piperidin-4-yl)-2-(2,3,5,6-tetramethylpyridin-4-yl)-1H-indole (43); 2-(3-chloro-2-methylpyridin-4-yl)-3-isopropyl-5-(piperidin-4-yl)-1H-indole (44); 3-isopropyl-2-(2-methoxy-6-methylpyridin-4-yl)-5-(piperidin-4-yl)-1H-indole (46); 2-(5-fluoro-2-methoxypyridin-4-yl)-3-isopropyl-5-(piperidin-4-yl)-1H-indole (47); 2-(3-chloro-2,6-dimethylpyridin-4-yl)-3-isopropyl-5-(piperidin-4-yl)-1H-indole (50); 2-(3-fluoro-2,6-dimethylpyridin-4-yl)-3-isopropyl-5-(piperidin-4-yl)-1H-indole (51); 2-(3-fluoro-2-methylpyridin-4-yl)-3-isopropyl-5-(piperidin-4-yl)-1H-indole (53); 2-(2-cyclopropyl-5-fluoropyridin-4-yl)-3-isopropyl-5-(piperidin-4-yl)-1H-indole (54); 2-(2-ethyl-5-fluoropyridin-4-yl)-3-isopropyl-5-(piperidin-4-yl)-1H-indole (55); 2-(2,6-dimethyl-1-(l1-oxidanyl)-1λ4-pyridin-4-yl)-3-isopropyl-5-(piperidin-4-yl)-1H-indole (56); 2-(2,6-dimethyl-1-(l1-oxidanyl)-1λ4-pyridin-4-yl)-3-isopropyl-5-(piperidin-4-yl)-1H-indole (57); 2-(4-(3-isopropyl-5-(piperidin-4-yl)-1H-indol-2-yl)pyridin-2-yl)propan-2-ol (58); 3-ethyl-5-(piperidin-4-yl)-2-(pyridin-4-yl)-1H-indole (60); 3-ethyl-2-(2-methoxypyridin-4-yl)-5-(piperidin-4-yl)-1H-indole (61); 2-(2- chloropyridin-4-yl)-3-ethyl-5-(piperidin-4-yl)-1H-indole (62); 3-ethyl-2-(2-methylpyridin-4-yl)-5-(piperidin-4-yl)-1H-indole (63); 4-(3-ethyl-5-(piperidin-4-yl)-1H-indol-2-yl) picolinonitrile (64); 3-(4-(3-ethyl-5-(piperidin-4-yl)-1H-indol-2-yl)pyridin-2-yl)-1,2,4-oxadiazol-5-amine (65); 2-(2-(4H-1,2,4-triazol-3-yl)pyridin-4-yl)-3-ethyl-5-(piperidin-4-yl)-1H-indole (66); 2-(2-(1H-imidazol-1-yl) pyridin-4-yl)-3-ethyl-5-(piperidin-4-yl)-1H-indole (67); N-(4-(3-ethyl-5-(piperidin-4-yl)-1H-indol-2-yl)pyridin-2-yl)acetamide (68); 4-(3-ethyl-5-(piperidin-4-yl)-1H-indol-2-yl) pyridin-2-amine (69); 2-(2,3-dimethylpyridin-4-yl)-3-ethyl-5-(piperidin-4-yl)-1H-indole (70); 2-amino-4-(3-ethyl-5-(piperidin-4-yl)-1H-indol-2-yl)pyridin-3-ol (71); 6-fluoro-3-isopropyl-2-(2-methylpyridin-4-yl)-5-(piperidin-4-yl)-1H-indole (73); 3-isopropyl-2-(2-methylpyridin-4-yl)-5-(piperidin-4-yl)-6-(trifluoromethyl)-1H-indole (74); 3-isopropyl-6-methyl-2-(2-methylpyridin-4-yl)-5-(piperidin-4-yl)-1H-indole (75); 4-fluoro-3-isopropyl-2-(2-methylpyridin-4-yl)-5-(piperidin-4-yl)-1H-indole (76); 2-(2,6-dimethylpyridin-4-yl)-4-fluoro-3-isopropyl-5-(piperidin-4-yl)-1H-indole (77); 2-(2,6-dimethylpyridin-4-yl)-6-fluoro-3-isopropyl-5-(piperidin-4-yl)-1H-indole (78); 6-fluoro-2-(5-fluoro-2-methylpyridin-4-yl)-3-isopropyl-5-(piperidin-4-yl)-1H-indole (79); 2-(2,5-dimethylpyridin-4-yl)-6-fluoro-3-isopropyl-5-(piperidin-4-yl)-1H-indole (80); 3-ethyl-7-fluoro-2-(2-methylpyridin-4-yl)-5-(piperidin-4-yl)-1H-indole (81); 3-ethyl-4-methyl-2-(2-methylpyridin-4-yl)-5-(piperidin-4-yl)-1H-indole (82); 3-ethyl-4,6-difluoro-2-(2-methylpyridin-4-yl)-5-(piperidin-4-yl)-1H-indole (83); 3-(2,2-difluoroethyl)-2-(2-methylpyridin-4-yl)-5-(piperidin-4-yl)-1H-indole (84); 3-(tert-butyl)-2-(2-methylpyridin-4-yl)-5-(piperidin-4-yl)-1H-indole (86); 3-cyclopropyl-2-(2-methylpyridin-4-yl)-5-(piperidin-4-yl)-1H-indole (88); 3-(cyclopropylmethyl)-2-(2-methylpyridin-4-yl)-5-(piperidin-4-yl)-1H-indole (89); 2-(2,6-dimethylpyridin-4-yl)-5-(piperidin-4-yl)-3-(3,3,3-trifluoroprop-1-en-2-yl)-1H-indole (91); 2-(2,6-dimethylpyridin-4-yl)-5-(piperidin-4-yl)-3-(1,1,1-trifluoropropan-2-yl)-1H-indole (92); 3-cyclopropyl-2-(2,6-dimethylpyridin-4-yl)-5-(piperidin-4-yl)-1H-indole (93); 2-(2,6-dimethylpyridin-4-yl)-5-(piperidin-4-yl)-1H-indole (94); 3-(tert-butyl)-2-(2,6-dimethylpyridin-4-yl)-5-(piperidin-4-yl)-1H-indole (96); 3-(dimethylamino)-1-(4-(2-(2,6-dimethylpyridin-4-yl)-3-isopropyl-1H-indol-5-yl) piperidin-1-yl)propan-1-one (97); 2-(dimethylamino)-1-(4-(2-(2,6-dimethylpyridin-4-yl)-3-isopropyl-1H-indol-5-yl)piperidin-1-yl)ethan-1-one (98); 2-(diethylamino)-1-(4-(2-(2,6-dimethylpyridin-4-yl)-3-isopropyl-1H-indol-5-yl)piperidin-1-yl)ethan-1-one (99); 4-(4-(2-(2,6-dimethylpyridin-4-yl)-3-isopropyl-1H-indol-5-yl) piperidine-1-carbonyl)-1-methylpyrrolidin-2-one (100); 4-(4-(2-(2,6-dimethylpyridin-4-yl)-3-isopropyl-1H-indol-5-yl)piperidine-1-carbonyl)-1-methylpyrrolidin-2-one (101 and 102); (4-(2-(2,6-dimethylpyridin-4-yl)-3-isopropyl-1H-indol-5-yl)piperidin-1-yl)(tetrahydrofuran-2-yl) methanone (103); 1-(4-(2-(2,6-dimethylpyridin-4-yl)-3-isopropyl-1H-indol-5-yl) piperidin-1-yl)-2-ethylbutan-1-one (104); 1-(4-(2-(2,6-dimethylpyridin-4-yl)-3-isopropyl-1H-indol-5-yl) piperidin-1-yl)-2,2-difluoroethan-1-one (105); 1-(4-(2-(2,6-dimethylpyridin-4-yl)-3-isopropyl-1H-indol-5-yl)piperidin-1-yl)-2-(tetrahydro-2H-pyran-4-yl)ethan-1-one (106); (4-(2-(2,6-dimethylpyridin-4-yl)-3-isopropyl-1H-indol-5-yl) piperidin-1-yl)(1-hydroxycyclopropyl)methanone (107); (2,2-difluorocyclopropyl)(4-(2-(2,6-dimethylpyridin-4-yl)-3-isopropyl-1H-indol-5-yl)piperidin-1-yl)methanone (108); (S)-1-(4-(2-(2,6-dimethylpyridin-4-yl)-3-isopropyl-1H-indol-5-yl)piperidin-1-yl)-3-hydroxybutan-1-one (109); (4-(2-(2,6-dimethylpyridin-4-yl)-3-isopropyl-1H-indol-5-yl) piperidin-1-yl)(1-methylpiperidin-4-yl)methanone (110); 4-(dimethylamino)-1-(4-(2-(2,6-dimethylpyridin-4-yl)-3-isopropyl-1H-indol-5-yl)piperidin-1-yl)butan-1-one (111); (4-(2-(2,6-dimethylpyridin-4-yl)-3-isopropyl-1H-indol-5-yl)piperidin-1-yl)(pyridin-3-yl) methanone (112); (4-(2-(2, 6-dimethylpyridin-4-yl)-3-isopropyl-1H-indol-5-yl)piperidin-1-yl)(pyridin-4-yl)methanone (113); 1-(4-(2-(2,6-dimethylpyridin-4-yl)-3-isopropyl-1H-indol-5-yl)piperidin-1-yl)-2-(2-methoxyethoxy)ethan-1-one (114); 1-(4-(2-(2,6-dimethylpyridin-4-yl)-3-isopropyl-1H-indol-5-yl)piperidin-1-yl)-2-methoxyethan-1-one (115); 1-(4-(2-(2,6-dimethylpyridin-4-yl)-3-isopropyl-1H-indol-5-yl)piperidin-1-yl)-2-hydroxyethan-1-one (116); 1-(4-(2-(2,6-dimethylpyridin-4-yl)-3-isopropyl-1H-indol-5-yl)piperidin-1-yl)-3-hydroxypropan-1-one (117); 1-(4-(2-(2,6-dimethylpyridin-4-yl)-3-isopropyl-1H-indol-5-yl)piperidin-1-yl)-3-methoxypropan-1-one (118); (3,5-dimethylisoxazol-4-yl)(4-(2-(2,6-dimethylpyridin-4-yl)-3-isopropyl-1H-indol-5-yl) piperidin-1-yl)methanone (119); N-(3-(4-(2-(2, 6-dimethylpyridin-4-yl)-3-isopropyl-1H-indol-5-yl) piperidin-1-yl)-3-oxopropyl)benzenesulfonamide (120); (3,5-dimethyl-1H-pyrazol-4-yl)(4-(2-(2,6-dimethylpyridin-4-yl)-3-isopropyl-1H-indol-5-yl)piperidin-1-yl) methanone (121); 5-(2-(4-(2-(2,6-dimethylpyridin-4-yl)-3-isopropyl-1H-indol-5-yl) piperidin-1-yl)-2-oxoethyl)-1,3-dimethylimidazolidine-2,4-dione (122); 1-cyclopropyl-3-(4-(2-(2,6-dimethylpyridin-4-yl)-3-isopropyl-1H-indol-5-yl) piperidine-1-carbonyl) pyridin-2(1H)-one (123); 1-(4-(2-(2, 6-dimethylpyridin-4-yl)-3-isopropyl-1H-indol-5-yl) piperidin-1-yl)-3-(2-methyl-1H-imidazol-1-yl)propan-1-one (124); 3-(3,5-dimethyl-1H-pyrazol-1-yl)-1-(4-(2-(2,6-dimethylpyridin-4-yl)-3-isopropyl-1H-indol-5-yl) piperidin-1-yl)propan-1-one (125); (4-(2-(2,6-dimethylpyridin-4-yl)-3-isopropyl-1H-indol-5-yl) piperidin-1-yl)(3-methylisoxazol-4-yl)methanone (126); 1-(3-(2-(4-(2-(2,6-dimethylpyridin-4-yl)-3-isopropyl-1H-indol-5-yl)piperidin-1-yl)-2-oxoethyl) morpholino)-3,3-dimethylbutan-1-one (127); 1-(4-(2-(2,6-dimethylpyridin-4-yl)-3-isopropyl-1H-indol-5-yl)piperidin-1-yl)-3-morpholinopropan-1-one (128); 6-(2-(4-(2-(2,6-dimethylpyridin-4-yl)-3-isopropyl-1H-indol-5-yl)piperidin-1-yl)-2-oxoethyl) dihydropyrimidine-2,4(1H,3H)-dione (129); 5-(2-(4-(2-(2,6-dimethylpyridin-4-yl)-3-isopropyl-1H-indol-5-yl)piperidin-1-yl)-2-oxoethyl)-1-methylimidazolidine-2,4-dione (130); (4-(2-(2, 6-dimethylpyridin-4-yl)-3-isopropyl-1H-indol-5-yl) piperidin-1-yl)(1,3,5-trimethyl-1H-pyrazol-4-yl)methanone (131); (4-(2-(2,6-dimethylpyridin-4-yl)-3-isopropyl-1H-indol-5-yl)piperidin-1-yl)(1-methyl-1H-pyrazol-4-yl)methanone (132); 1-(4-(2-(2,6-dimethylpyridin-4-yl)-3-isopropyl-1H-indol-5-yl)piperidine-1-carbonyl) cyclopropane-1-carboxamide (133); N-(3-(4-(2-(2,6-dimethylpyridin-4-yl)-3-isopropyl-1H-indol-5-yl)piperidin-1-yl)-3-oxopropyl)-N-methylacetamide (134); 4-(4-(2-(2,6-dimethylpyridin-4-yl)-3-isopropyl-1H-indol-5-yl)piperidine-1-carbonyl)-6-methylpyridazin-3(2H)-one (135); 2-(1,3-dimethyl-1H-pyrazol-5-yl)-1-(4-(2-(2,6-dimethylpyridin-4-yl)-3-isopropyl-1H-indol-5-yl)piperidin-1-yl)ethan-1-one (136); 1-(4-(2-(2,6-dimethylpyridin-4-yl)-3-isopropyl-1H-indol-5-yl)piperidin-1-yl)-2-(1-methyl-1H-imidazol-4-yl)ethan-1-one (137); 3-(4-(2-(2,6-dimethylpyridin-4-yl)-3-isopropyl-1H-indol-5-yl)piperidine-1-carbonyl)-1,6-dimethylpyridin-2(1H)-one (138); 2-(3-amino-1H-pyrazol-5-yl)-1-(4-(2-(2, 6-dimethylpyridin-4-yl)-3-isopropyl-1H-indol-5-yl) piperidin-1-yl)ethan-1-one (139); 2-(2-aminothiazol-4-yl)-1-(4-(2-(2,6-dimethylpyridin-4-yl)-3-isopropyl-1H-indol-5-yl)piperidin-1-yl)ethan-1-one (140); (1,3-dimethyl-1H-pyrazol-4-yl)(4-(2-(2,6-dimethylpyridin-4-yl)-3-isopropyl-1H-indol-5-yl)piperidin-1-yl)methanone (141); 3-(4-(2-(2, 6-dimethylpyridin-4-yl)-3-isopropyl-1H-indol-5-yl) piperidin-1-yl)-3-oxo-N-(thiazol-2-yl)propanamide (142); 1-(4-(2-(2,6-dimethylpyridin-4-yl)-3-isopropyl-1H-indol-5-yl)piperidin-1-yl)-3-(3-methyl-1H-pyrazol-1-yl)propan-1-one (143); 6-(4-(2-(2,6-dimethylpyridin-4-yl)-3-isopropyl-1H-indol-5-yl)piperidine-1-carbonyl)-2,3-dihydroindolizin-5(1H)-one (144); 3-(4-(2-(2,6-dimethylpyridin-4-yl)-3-isopropyl-1H-indol-5-yl)piperidine-1-carbonyl)-4H-quinolizin-4-one (145); 1-(4-(2-(2,6-dimethylpyridin-4-yl)-3-isopropyl-1H-indol-5-yl)piperidin-1-yl)-3-(pyrimidin-2-ylamino) propan-1-one (146); 1-(4-(2-(2,6-dimethylpyridin-4-yl)-3-isopropyl-1H-indol-5-yl) piperidin-1-yl)-2-((1,1-dioxidotetrahydrothiophen-3-yl)(methyl)amino)ethan-1-one (147); 1-(4-(2-(2,6-dimethylpyridin-4-yl)-3-isopropyl-1H-indol-5-yl)piperidin-1-yl)-2-((2-methoxyethyl)(methyl)amino)ethan-1-one (148); 1-(4-(2-(2,6-dimethylpyridin-4-yl)-3-isopropyl-1H-indol-5-yl)piperidin-1-yl)-2-(5-morpholino-2H-tetrazol-2-yl)ethan-1-one (149); N-(2-(4-(2-(2,6-dimethylpyridin-4-yl)-3-isopropyl-1H-indol-5-yl)piperidin-1-yl)-2-oxoethyl)methanesulfonamide (150); 1-(2-(4-(2-(2,6-dimethylpyridin-4-yl)-3-isopropyl-1H-indol-5-yl)piperidin-1-yl)-2-oxoethyl)imidazolidine-2,4-dione (151); 1-(4-(2-(2,6-dimethylpyridin-4-yl)-3-isopropyl-1H-indol-5-yl)piperidin-1-yl)-2-(1,1-dioxidoisothiazolidin-2-yl)ethan-1-one (152); 2-(diisopropylamino)-1-(4-(2-(2,6-dimethylpyridin-4-yl)-3-isopropyl-1H-indol-5-yl)piperidin-1-yl)ethan-1-one (153); 1-(2-(4-(2-(2,6-dimethylpyridin-4-yl)-3-isopropyl-1H-indol-5-yl)piperidin-1-yl)-2-oxoethyl) pyrrolidin-2-one (154); 1-(4-(2-(2,6-dimethylpyridin-4-yl)-3-isopropyl-1H-indol-5-yl) piperidin-1-yl)-2-(2H-tetrazol-2-yl)ethan-1-one (155); 1-(4-(2-(2,6-dimethylpyridin-4-yl)-3-isopropyl-1H-indol-5-yl)piperidin-1-yl)-2-(3-(trifluoromethyl)-1H-pyrazol-1-yl) ethan-1-one (156); 1-(2-(4-(2-(2,6-dimethylpyridin-4-yl)-3-isopropyl-1H-indol-5-yl) piperidin-1-yl)-2-oxoethyl)pyridin-2(1H)-one (157); 1-(4-(2-(2,6-dimethylpyridin-4-yl)-3-isopropyl-1H-indol-5-yl)piperidin-1-yl)-2-(1H-1,2,3-triazol-1-yl)ethan-1-one (158); 1-(4-(2-(2,6-dimethylpyridin-4-yl)-3-isopropyl-1H-indol-5-yl)piperidin-1-yl)-2-(5-methyl-1H-tetrazol-1-yl) ethan-1-one (159); 3-(2-(4-(2-(2,6-dimethylpyridin-4-yl)-3-isopropyl-1H-indol-5-yl)piperidin-1-yl)-2-oxoethyl)-1-methylimidazolidine-2,4-dione (160); 4-(2-(4-(2-(2,6-dimethylpyridin-4-yl)-3-isopropyl-1H-indol-5-yl)piperidin-1-yl)-2-oxoethyl) morpholin-3-one (161); 2-(3-cyclopropyl-1H-pyrazol-1-yl)-1-(4-(2-(2,6-dimethylpyridin-4-yl)-3-isopropyl-1H-indol-5-yl)piperidin-1-yl)ethan-1-one (162); 1-(4-(2-(2,6-dimethylpyridin-4-yl)-3-isopropyl-1H-indol-5-yl)piperidin-1-yl)-2-(4-methylpiperazin-1-yl)ethan-1-one (163); 3-(2-(4-(2-(2,6-dimethylpyridin-4-yl)-3-isopropyl-1H-indol-5-yl) piperidin-1-yl)-2-oxoethyl)oxazolidin-2-one (164); 1-(4-(2-(2,6-dimethylpyridin-4-yl)-3-isopropyl-1H-indol-5-yl)piperidin-1-yl)-2-(1H-tetrazol-1-yl)ethan-1-one (165); N-(2-(4-(2-(2,6-dimethylpyridin-4-yl)-3-isopropyl-1H-indol-5-yl)piperidin-1-yl)-2-oxoethyl) acetamide (166); 1-(4-(2-(2,6-dimethylpyridin-4-yl)-3-isopropyl-1H-indol-5-yl)piperidin-1-yl)-2-(1,1-dioxido-1,2-thiazinan-2-yl)ethan-1-one (167); (R)-3-amino-1-(2-(4-(2-(2,6-dimethylpyridin-4-yl)-3-isopropyl-1H-indol-5-yl)piperidin-1-yl)-2-oxoethyl) pyrrolidin-2-one (168); (S)-1-(2-(4-(2-(2,6-dimethylpyridin-4-yl)-3-isopropyl-1H-indol-5-yl) piperidin-1-yl)-2-oxoethyl)-4-hydroxypyrrolidin-2-one (169); 1-(4-(2-(2,6-dimethylpyridin-4-yl)-3-isopropyl-1H-indol-5-yl)piperidin-1-yl)-2-(1H-1,2,4-triazol-1-yl) ethan-1-one (170); 1-(4-(2-(2,6-dimethylpyridin-4-yl)-3-isopropyl-1H-indol-5-yl) piperidin-1-yl)-2-(4-(2-hydroxyethyl) piperazin-1-yl)ethan-1-one (171); (1-(dimethylamino) cyclopropyl)(4-(2-(2,6-dimethylpyridin-4-yl)-3-isopropyl-1H-indol-5-yl)piperidin-1-yl)methanone (172); 1-(4-(2-(2,6-dimethylpyridin-4-yl)-3-isopropyl-1H-indol-5-yl)piperidin-1-yl)-2-hydroxy-2-methylpropan-1-one (173); 1-(4-(2-(2,6-dimethylpyridin-4-yl)-3-isopropyl-1H-indol-5-yl)piperidin-1-yl)ethan-1-one (174); 1-(4-(2-(2,6-dimethylpyridin-4-yl)-3-isopropyl-1H-indol-5-yl)piperidin-1-yl)-3-((2-hydroxyethyl)(methyl)amino)propan-1-one (175); (1,4-dimethylpiperidin-4-yl)(4-(2-(2,6-dimethylpyridin-4-yl)-3-isopropyl-1H-indol-5-yl)piperidin-1-yl)methanone (176); (4-(2-(2,6-dimethylpyridin-4-yl)-3-isopropyl-1H-indol-5-yl)piperidin-1-yl)(1-isopropyl-4-methylpiperidin-4-yl) methanone (177); (4-(2-(2,6-dimethylpyridin-4-yl)-3-isopropyl-1H-indol-5-yl)piperidin-1-yl)(piperidin-4-yl) methanone (178); 4-(2-(2,6-dimethylpyridin-4-yl)-3-isopropyl-1H-indol-5-yl)-N-methylpiperidine-1-carboxamide (179) (Check structure); (S)-azetidin-2-yl(4-(2-(2,6-dimethylpyridin-4-yl)-3-isopropyl-1H-indol-5-yl) piperidin-1-yl)methanone (180); (4-(2-(2,6-dimethylpyridin-4-yl)-3-isopropyl-1H-indol-5-yl)piperidin-1-yl)(pyrrolidin-3-yl)methanone (Homochiral) (181 and 182); 1-(4-(2-(2,6-dimethylpyridin-4-yl)-3-isopropyl-1H-indol-5-yl)piperidin-1-yl)-3-(methylamino)propan-1-one (183); 2-amino-1-(4-(2-(2,6-dimethylpyridin-4-yl)-3-isopropyl-1H-indol-5-yl)piperidin-1-yl)ethan-1-one (184); (4-(2-(2,6-dimethylpyridin-4-yl)-3-isopropyl-1H-indol-5-yl) piperidin-1-yl)((2S,3R)-3-hydroxypyrrolidin-2-yl) methanone (185); (4-(2-(2,6-dimethylpyridin-4-yl)-3-isopropyl-1H-indol-5-yl)piperidin-1-yl)(pyrrolidin-3-yl) methanone (186); 1-(4-(2-(2,6-dimethylpyridin-4-yl)-3-isopropyl-1H-indol-5-yl)piperidin-1-yl)-2-methyl-2-(methylamino)propan-1-one (187); (S)-3-amino-1-(2-(4-(2-(2,6-dimethylpyridin-4-yl)-3-isopropyl-1H-indol-5-yl)piperidin-1-yl)-2-oxoethyl)pyrrolidin-2-one (188); (S)-(4,4-difluoropyrrolidin-2-yl)(4-(2-(2,6-dimethylpyridin-4-yl)-3-isopropyl-1H-indol-5-yl)piperidin-1-yl)methanone (189); (4-(2-(2,6-dimethylpyridin-4-yl)-3-isopropyl-1H-indol-5-yl)piperidin-1-yl)((2 S,4R)-4-fluoropyrrolidin-2-yl)methanone (190); (S)-1-(4-(2-(2,6-dimethylpyridin-4-yl)-3-isopropyl-1H-indol-5-yl)piperidin-1-yl)-2-(methylamino) propan-1-one (191); (R)-(4-(2-(2,6-dimethylpyridin-4-yl)-3-isopropyl-1H-indol-5-yl)piperidin-1-yl)(2-methylpyrrolidin-2-yl)methanone (192); (R)-1-(4-(2-(2,6-dimethylpyridin-4-yl)-3-isopropyl-1H-indol-5-yl) piperidin-1-yl)-2-(pyrrolidin-2-yl)ethan-1-one (193); 2-amino-1-(4-(2-(2,6-dimethylpyridin-4-yl)-3-isopropyl-1H-indol-5-yl)piperidin-1-yl)-2-methylpropan-1-one (194); (1-aminocyclopropyl)(4-(2-(2,6-dimethylpyridin-4-yl)-3-isopropyl-1H-indol-5-yl) piperidin-1-yl)methanone (195); (4-(2-(2,6-dimethylpyridin-4-yl)-3-isopropyl-1H-indol-5-yl)piperidin-1-yl)((2S,4S)-4-fluoropyrrolidin-2-yl)methanone (196); (4-(2-(2,6-dimethylpyridin-4-yl)-3-isopropyl-1H-indol-5-yl)piperidin-1-yl)(4-methylpiperidin-4-yl) methanone (197); (4-(2-(2,6-dimethylpyridin-4-yl)-3-isopropyl-1H-indol-5-yl)piperidin-1-yl)(tetrahydro-2H-pyran-4-yl)methanone (198); (4-(2-(2,6-dimethylpyridin-4-yl)-3-isopropyl-1H-indol-5-yl)piperidin-1-yl)(tetrahydrofuran-3-yl)methanone (199); (4-(2-(2,6-dimethylpyridin-4-yl)-3-isopropyl-1H-indol-5-yl)piperidin-1-yl)(2-isopropyltetrahydro-2H-pyran-4-yl)methanone (200); (4-(2-(2,6-dimethylpyridin-4-yl)-3-isopropyl-1H-indol-5-yl) piperidin-1-yl)(thiazol-4-yl)methanone (201); 1-(4-(2-(2,6-dimethylpyridin-4-yl)-3-isopropyl-1H-indol-5-yl)piperidin-1-yl)-2-methylpropan-1-one (202); (4-(2-(2,6-dimethylpyridin-4-yl)-3-isopropyl-1H-indol-5-yl)piperidin-1-yl) (isoxazol-3-yl)methanone (203); 2-(4-(2-(2,6-dimethylpyridin-4-yl)-3-isopropyl-1H-indol-5-yl)piperidin-1-yl)-N-methyl-2-oxoacetamide (204); 2-(4-(2-(2,6- dimethylpyridin-4-yl)-3-isopropyl-1H-indol-5-yl)piperidin-1-yl)-N-methyl-2-oxoacetamide (205); 1-(4-(2-(2,6-dimethylpyridin-4-yl)-3-isopropyl-1H-indol-5-yl)piperidin-1-yl)propan-1-one (206); (4-(2-(2,6-dimethylpyridin-4-yl)-3-isopropyl-1H-indol-5-yl)piperidin-1-yl)(3-methyloxetan-3-yl)methanone (207); 2-(4-(2-(2,6-dimethylpyridin-4-yl)-3-isopropyl-1H-indol-5-yl)piperidin-1-yl)-1-(piperidin-1-yl)ethan-1-one (208); (R)-2-(4-(2-(2,6-dimethylpyridin-4-yl)-3-isopropyl-1H-indol-5-yl)piperidin-1-yl)-1-(3-hydroxypiperidin-1-yl)ethan-1-one (209); (S)-2-(4-(2-(2,6-dimethylpyridin-4-yl)-3-isopropyl-1H-indol-5-yl)piperidin-1-yl)-1-(3-hydroxypiperidin-1-yl)ethan-1-one (210); 2-(4-(2-(2,6-dimethylpyridin-4-yl)-3-isopropyl-1H-indol-5-yl)piperidin-1-yl)-N-((1r,4r)-4-hydroxycyclohexyl)acetamide (211); N-cyclopropyl-2-(4-(2-(2,6-dimethylpyridin-4-yl)-3-isopropyl-1H-indol-5-yl)piperidin-1-yl)acetamide (212); N-cyclobutyl-2-(4-(2-(2,6-dimethylpyridin-4-yl)-3-isopropyl-1H-indol-5-yl)piperidin-1-yl)acetamide (213); 2-(4-(2-(2,6-dimethylpyridin-4-yl)-3-isopropyl-1H-indol-5-yl)piperidin-1-yl)-N-(2,2,2-trifluoroethyl)acetamide (214); 1-(3,3-difluoroazetidin-1-yl)-2-(4-(2-(2,6-dimethylpyridin-4-yl)-3-isopropyl-1H-indol-5-yl)piperidin-1-yl)ethan-1-one (215); 1-(3,3-difluoropyrrolidin-1-yl)-2-(4-(2-(2,6-dimethylpyridin-4-yl)-3-isopropyl-1H-indol-5-yl)piperidin-1-yl)ethan-1-one (216); N-(tert-butyl)-2-(4-(2-(2,6-dimethylpyridin-4-yl)-3-isopropyl-1H-indol-5-yl)piperidin-1-yl)acetamide (217); 2-(4-(2-(2,6-dimethylpyridin-4-yl)-3-isopropyl-1H-indol-5-yl)piperidin-1-yl)-N-isopropylacetamide (218); 2-(4-(2-(2,6-dimethylpyridin-4-yl)-3-isopropyl-1H-indol-5-yl)piperidin-1-yl)-N-neopentylacetamide (219); 2-(4-(2-(2,6-dimethylpyridin-4-yl)-3-isopropyl-1H-indol-5-yl)piperidin-1-yl)-N-(pentan-3-yl)acetamide (220); 2-(4-(2-(2,6-dimethylpyridin-4-yl)-3-isopropyl-1H-indol-5-yl)piperidin-1-yl)-N-isobutylacetamide (221); 2-(4-(2-(2,6-dimethylpyridin-4-yl)-3-isopropyl-1H-indol-5-yl)piperidin-1-yl)-N-(2-hydroxyethyl)acetamide (222); N-(cyclopropylmethyl)-2-(4-(2-(2,6-dimethylpyridin-4-yl)-3-isopropyl-1H-indol-5-yl) piperidin-1-yl)acetamide (223); N-(adamantan-1-yl)-2-(4-(2-(2,6-dimethylpyridin-4-yl)-3-isopropyl-1H-indol-5-yl)piperidin-1-yl)acetamide (224); 2-(4-(2-(2,6-dimethylpyridin-4-yl)-3-isopropyl-1H-indol-5-yl)piperidin-1-yl)-N-((1r,3 s,5R,7S)-3-hydroxyadamantan-1-yl)acetamide (225); 2-(4-(2-(2,6-dimethylpyridin-4-yl)-3-isopropyl-1H-indol-5-yl) piperidin-1-yl)-1-(3-methoxyazetidin-1-yl)ethan-1-one (226); 1-(azetidin-1-yl)-2-(4-(2-(2,6-dimethylpyridin-4-yl)-3-isopropyl-1H-indol-5-yl)piperidin-1-yl)ethan-1-one (227); 2-(4-(2-(2,6-dimethylpyridin-4-yl)-3-isopropyl-1H-indol-5-yl)piperidin-1-yl)-N,N-diethylacetamide (228); 2-(4-(2-(2,6-dimethylpyridin-4-yl)-3-isopropyl-1H-indol-5-yl) piperidin-1-yl)-1-(3-hydroxyazetidin-1-yl)ethan-1-one (229); 2-(4-(2-(2,6-dimethylpyridin-4-yl)-3-isopropyl-1H-indol-5-yl)piperidin-1-yl)-1-(4-hydroxypiperidin-1-yl)ethan-1-one (230); 2-(4-(2-(2,6-dimethylpyridin-4-yl)-3-isopropyl-1H-indol-5-yl) piperidin-1-yl)-N-(2-methoxyethyl)acetamide (231); 2-(4-(2-(2,6-dimethylpyridin-4-yl)-3-isopropyl-1H-indol-5-yl)piperidin-1-yl)-1-morpholinoethan-1-one (232); 2-(4-(2-(2,6-dimethylpyridin-4-yl)-3-isopropyl-1H-indol-5-yl)piperidin-1-yl)-N-(3-methyloxetan-3-yl)acetamide (233); N-(sec-butyl)-2-(4-(2-(2,6-dimethylpyridin-4-yl)-3-isopropyl-1H-indol-5-yl)piperidin-1-yl)acetamide (234); 2-(4-(2-(2,6-dimethylpyridin-4-yl)-3-isopropyl-1H-indol-5-yl)piperidin-1-yl)-N-ethylacetamide (235); N-(3,3-dimethylbutyl)-2-(4-(2-(2,6-dimethylpyridin-4-yl)-3-isopropyl-1H-indol-5-yl) piperidin-1-yl)acetamide (236); 2-(4-(2-(2,6-dimethylpyridin-4-yl)-3-isopropyl-1H-indol-5-yl)piperidin-1-yl)-N-isopentylacetamide (237); 2-(4-(2-(2,6-dimethylpyridin-4-yl)-3-isopropyl-1H-indol-5-yl)piperidin-1-yl)-N-propylacetamide (238); N-(cyanomethyl)-2-(4-(2-(2,6-dimethylpyridin-4-yl)-3-isopropyl-1H-indol-5-yl)piperidin-1-yl)acetamide (239); 2-(4-(2-(2,6-dimethylpyridin-4-yl)-3-isopropyl-1H-indol-5-yl)piperidin-1-yl)-N-(2-ethoxyethyl)acetamide (240); 2-(4-(2-(2,6-dimethylpyridin-4-yl)-3-isopropyl-1H-indol-5-yl)piperidin-1-yl)-1-(piperidin-1-yl)ethan-1-one (241); 2-(4-(2-(2,6-dimethylpyridin-4-yl)-3-isopropyl-1H-indol-5-yl)piperidin-1-yl)-1-(pyrrolidin-1-yl)ethan-1-one (242); 2-(4-(2-(2,6-dimethylpyridin-4-yl)-3-isopropyl-1H-indol-5-yl)piperidin-1-yl)-N-(1-methylcyclobutyl)acetamide (243); 2-(4-(2-(2,6-dimethylpyridin-4-yl)-3-isopropyl-1H-indol-5-yl)piperidin-1-yl)-N-isopropyl-N-methylacetamide (244); 2-(4-(2-(2,6-dimethylpyridin-4-yl)-3-isopropyl-1H-indol-5-yl)piperidin-1-yl)-N-isobutyl-N-methylacetamide (245); 2-(4-(2-(2,6-dimethylpyridin-4-yl)-3-isopropyl-1H-indol-5-yl)piperidin-1-yl)-N-ethyl-N-methylacetamide (246); N-(cyanomethyl)-2-(4-(2-(2,6-dimethylpyridin-4-yl)-3-isopropyl-1H-indol-5-yl)piperidin-1-yl)-N-methylacetamide (247); N-cyclopropyl-2-(4-(2-(2,6-dimethylpyridin-4-yl)-3-isopropyl-1H-indol-5-yl) piperidin-1-yl)-N-methylacetamide (248); 1-(3,3-dimethylpiperidin-1-yl)-2-(4-(2-(2,6-dimethylpyridin-4-yl)-3-isopropyl-1H-indol-5-yl)piperidin-1-yl)ethan-1-one (249); N-(tert-butyl)-2-(4-(2-(2,6-dimethylpyridin-4-yl)-3-isopropyl-1H-indol-5-yl)piperidin-1-yl)-N-methylacetamide (250); 2-(4-(2-(2,6-dimethylpyridin-4-yl)-3-isopropyl-1H-indol-5-yl) piperidin-1-yl)-N-(1-methylcyclopropyl)acetamide (251); (R)-2-(4-(2-(2,6-dimethylpyridin-4-yl)-3-isopropyl-1H-indol-5-yl)piperidin-1-yl)-N-(1,1,1-trifluoropropan-2-yl)acetamide (252); 2-(4-(2-(2,6-dimethylpyridin-4-yl)-3-isopropyl-1H-indol-5-yl) piperidin-1-yl)-N,N-diisopropylacetamide (253); 2-(4-(2-(2,6-dimethylpyridin-4-yl)-3-isopropyl-1H-indol-5-yl) piperidin-1-yl)-N-(2-methoxyethyl)-N-methylacetamide (254); 2-(4-(2-(2,6-dimethylpyridin-4-yl)-3-isopropyl-1H-indol-5-yl) piperidin-1-yl)-N-((1-methylcyclopropyl)methyl)acetamide (255); 2-(4-(2-(2,6-dimethylpyridin-4-yl)-3-isopropyl-1H-indol-5-yl)piperidin-1-yl)-1-(2-oxa-6-azaspiro[3.3] heptan-6-yl)ethan-1-one (256); 1-(4,4-difluoropiperidin-1-yl)-2-(4-(2-(2,6-dimethylpyridin-4-yl)-3-isopropyl-1H-indol-5-yl)piperidin-1-yl)ethan-1-one (257); 2-(4-(2-(2,6-dimethylpyridin-4-yl)-3-isopropyl-1H-indol-5-yl)piperidin-1-yl)-1-(3-fluoropiperidin-1-yl)ethan-1-one (258); 2-(4-(2-(2,6-dimethylpyridin-4-yl)-3-isopropyl-1H-indol-5-yl)piperidin-1-yl)-1-(2-methylpyrrolidin-1-yl)ethan-1-one (259); 2-(4-(2-(2,6-dimethylpyridin-4-yl)-3-isopropyl-1H-indol-5-yl)piperidin-1-yl)-N-(2-hydroxypropyl) acetamide (260); 2-(4-(2-(2,6-dimethylpyridin-4-yl)-3-isopropyl-1H-indol-5-yl)piperidin-1-yl)-1-(2,5-dimethylpyrrolidin-1-yl)ethan-1-one (261); 2-(4-(2-(2,6-dimethylpyridin-4-yl)-3-isopropyl-1H-indol-5-yl)piperidin-1-yl)-N-(3-hydroxybutyl)acetamide (262); (S)-2-(4-(2-(2,6-dimethylpyridin-4-yl)-3-isopropyl-1H-indol-5-yl)piperidin-1-yl)-1-(2-(methoxymethyl)pyrrolidin-1-yl)ethan-1-one (263); 2-(4-(2-(2,6-dimethylpyridin-4-yl)-3-isopropyl-1H-indol-5-yl)piperidin-1-yl)-N-(2-methyl-2-morpholinopropyl)acetamide (264); 2-(4-(2-(2,6-dimethylpyridin-4-yl)-3-isopropyl-1H-indol-5-yl)piperidin-1-yl)-1-(4-(2-methoxyethyl)piperazin-1-yl)ethan-1-one (265); 2-(4-(2-(2,6-dimethylpyridin-4-yl)-3-isopropyl-1H-indol-5-yl)piperidin-1-yl)-N-((tetrahydrofuran-2-yl)methyl) acetamide (266); 2-(4-(2-(2,6-dimethylpyridin-4-yl)-3-isopropyl-1H-indol-5-yl)piperidin-1-yl)-N-(4-methyltetrahydro-2H-pyran-4-yl)acetamide (267); 2-(4-(2-(2,6-dimethylpyridin-4-yl)-3-isopropyl-1H-indol-5-yl)

piperidin-1-yl)-N-(2-hydroxy-2-methylpropyl)acetamide (268); 2-(4-(2-(2,6-dimethylpyridin-4-yl)-3-isopropyl-1H-indol-5-yl)piperidin-1-yl)-1-(4-methylpiperidin-1-yl)ethan-1-one (269); 2-(4-(2-(2,6-dimethylpyridin-4-yl)-3-isopropyl-1H-indol-5-yl)piperidin-1-yl)-1-(2-methylpiperidin-1-yl)ethan-1-one (270); 2-(4-(2-(2,6-dimethylpyridin-4-yl)-3-isopropyl-1H-indol-5-yl)piperidin-1-yl)-1-(3-methylpiperidin-1-yl)ethan-1-one (271); 4-(2-(4-(2-(2,6-dimethylpyridin-4-yl)-3-isopropyl-1H-indol-5-yl)piperidin-1-yl)acetyl)piperazin-2-one (272); (S)-2-(4-(2-(2,6-dimethylpyridin-4-yl)-3-isopropyl-1H-indol-5-yl)piperidin-1-yl)-1-(3-hydroxypyrrolidin-1-yl)ethan-1-one (273); (S)-2-(4-(2-(2,6-dimethylpyridin-4-yl)-3-isopropyl-1H-indol-5-yl)piperidin-1-yl)-1-(2-(hydroxymethyl)pyrrolidin-1-yl)ethan-1-one (274); (R)-2-(4-(2-(2,6-dimethylpyridin-4-yl)-3-isopropyl-1H-indol-5-yl)piperidin-1-yl)-1-(3-hydroxypyrrolidin-1-yl)ethan-1-one (275); (S)-2-(4-(2-(2,6-dimethylpyridin-4-yl)-3-isopropyl-1H-indol-5-yl)piperidin-1-yl)-N-(1-hydroxy-4-methylpentan-2-yl)acetamide (276); 2-(4-(2-(2,6-dimethylpyridin-4-yl)-3-isopropyl-1H-indol-5-yl)piperidin-1-yl)-1-(3-hydroxypiperidin-1-yl)ethan-1-one (277); N-cyclohexyl-2-(4-(2-(2,6-dimethylpyridin-4-yl)-3-isopropyl-1H-indol-5-yl)piperidin-1-yl)-N-methylacetamide (278); 2-(4-(2-(2,6-dimethylpyridin-4-yl)-3-isopropyl-1H-indol-5-yl)piperidin-1-yl)-N-(tetrahydro-2H-pyran-3-yl)acetamide (279); 2-(4-(2-(2,6-dimethylpyridin-4-yl)-3-isopropyl-1H-indol-5-yl)piperidin-1-yl)-N-(tetrahydro-2H-pyran-4-yl)acetamide (280); 2-(4-(2-(2,6-dimethylpyridin-4-yl)-3-isopropyl-1H-indol-5-yl)piperidin-1-yl)-1-(1,1-dioxidothiomorpholino)ethan-1-one (281); 2-(4-(2-(2,6-dimethylpyridin-4-yl)-3-isopropyl-1H-indol-5-yl)piperidin-1-yl)-N-(tetrahydrofuran-3-yl)acetamide (282); 2-(4-(2-(2,6-dimethylpyridin-4-yl)-3-isopropyl-1H-indol-5-yl)piperidin-1-yl)-1-(4-fluoropiperidin-1-yl)ethan-1-one (283); 1-(3-oxa-8-azabicyclo[3.2.1] octan-8-yl)-2-(4-(2-(2,6-dimethylpyridin-4-yl)-3-isopropyl-1H-indol-5-yl)piperidin-1-yl) ethan-1-one (284); 1-(3,3-difluoropiperidin-1-yl)-2-(4-(2-(2,6-dimethylpyridin-4-yl)-3-isopropyl-1H-indol-5-yl)piperidin-1-yl)ethan-1-one (285); 2-(4-(2-(2,6-dimethylpyridin-4-yl)-3-isopropyl-1H-indol-5-yl)piperidin-1-yl)-1-(2-oxa-7-azaspiro[3.5]nonan-7-yl) ethan-1-one (286); 2-(4-(2-(2,6-dimethylpyridin-4-yl)-3-isopropyl-1H-indol-5-yl) piperidin-1-yl)-N-methyl-N-(tetrahydro-2H-pyran-4-yl)acetamide (287); 2-(4-(2-(2,6-dimethylpyridin-4-yl)-3-isopropyl-1H-indol-5-yl)piperidin-1-yl)-N-(3-hydroxypropyl)-N-methylacetamide (288); 2-(4-(2-(2,6-dimethylpyridin-4-yl)-3-isopropyl-1H-indol-5-yl) piperidin-1-yl)-N-methyl-N-(tetrahydrofuran-3-yl)acetamide (289); 2-(4-(2-(2,6-dimethylpyridin-4-yl)-3-isopropyl-1H-indol-5-yl)piperidin-1-yl)-1-((2R,4R)-2-(hydroxymethyl)-4-methylpyrrolidin-1-yl)ethan-1-one (290); 2-(4-(2-(2,6-dimethylpyridin-4-yl)-3-isopropyl-1H-indol-5-yl)piperidin-1-yl)-1-((2S,4S)-2-(hydroxymethyl)-4-(trifluoromethyl)pyrrolidin-1-yl)ethan-1-one (291); 2-(4-(2-(2,6-dimethylpyridin-4-yl)-3-isopropyl-1H-indol-5-yl)piperidin-1-yl)-1-((2R,4R)-2-(hydroxymethyl)-4-methoxypyrrolidin-1-yl)ethan-1-one (292); N-benzyl-2-(4-(2-(2,6-dimethylpyridin-4-yl)-3-isopropyl-1H-indol-5-yl)piperidin-1-yl)-N-(2-hydroxyethyl) acetamide (293); 2-(4-(2-(2,6-dimethylpyridin-4-yl)-3-isopropyl-1H-indol-5-yl)piperidin-1-yl)-N-ethyl-N-(2-hydroxyethyl)acetamide (294); 2-(4-(2-(2,6-dimethylpyridin-4-yl)-3-isopropyl-1H-indol-5-yl)piperidin-1-yl)-N-(2-hydroxyethyl)-N-propylacetamide (295); 2-(4-(2-(2,6-dimethylpyridin-4-yl)-3-isopropyl-1H-indol-5-yl)piperidin-1-yl)-N-(2-hydroxy-2-phenylethyl)-N-methylacetamide (296); 2-(4-(2-(2,6-dimethylpyridin-4-yl)-3-isopropyl-1H-indol-5-yl)piperidin-1-yl)-N-(2-hydroxyethyl)-N-(2-methylbutyl)acetamide (297); N-butyl-2-(4-(2-(2,6-dimethylpyridin-4-yl)-3-isopropyl-1H-indol-5-yl)piperidin-1-yl)-N-(2-hydroxyethyl)acetamide (298); 2-(4-(2-(2,6-dimethylpyridin-4-yl)-3-isopropyl-1H-indol-5-yl)piperidin-1-yl)-N-(2-hydroxyethyl)-N-isopropylacetamide (299); 2-(4-(2-(2,6-dimethylpyridin-4-yl)-3-isopropyl-1H-indol-5-yl)piperidin-1-yl)-N-(4-fluorobenzyl)-N-(2-hydroxyethyl)acetamide (300); 2-(4-(2-(2,6-dimethylpyridin-4-yl)-3-isopropyl-1H-indol-5-yl)piperidin-1-yl)-1-((2R,4R)-2-(hydroxymethyl)-4-(trifluoromethyl)pyrrolidin-1-yl)ethan-1-one (301); (R)-2-(4-(2-(2,6-dimethylpyridin-4-yl)-3-isopropyl-1H-indol-5-yl)piperidin-1-yl)-1-(2-(hydroxymethyl)pyrrolidin-1-yl) ethan-1-one (302); 2-(4-(2-(2,6-dimethylpyridin-4-yl)-3-isopropyl-1H-indol-5-yl) piperidin-1-yl)-N-(2-(1-hydroxycyclopentyl)ethyl)-N-methylacetamide (303); (R)-2-(4-(2-(2,6-dimethylpyridin-4-yl)-3-isopropyl-1H-indol-5-yl)piperidin-1-yl)-1-(3-(hydroxymethyl)morpholino)ethan-1-one (304); 2-(4-(2-(2,6-dimethylpyridin-4-yl)-3-isopropyl-1H-indol-5-yl) piperidin-1-yl)-N-(2-hydroxy-2-methylpropyl)-N-methylacetamide (305); (S)-1-(4,4-difluoro-2-(hydroxymethyl)pyrrolidin-1-yl)-2-(4-(2-(2,6-dimethylpyridin-4-yl)-3-isopropyl-1H-indol-5-yl)piperidin-1-yl)ethan-1-one (306); (S)-2-(4-(2-(2,6-dimethylpyridin-4-yl)-3-isopropyl-1H-indol-5-yl)piperidin-1-yl)-N-methyl-N-(tetrahydrofuran-3-yl)acetamide (307); 2-(4-(2-(2,6-dimethylpyridin-4-yl)-3-isopropyl-1H-indol-5-yl)piperidin-1-yl)-N,N-dimethylacetamide (308); 2-(4-(2-(2,6-dimethylpyridin-4-yl)-3-isopropyl-1H-indol-5-yl)piperidin-1-yl)-N-methylacetamide (309); 2-(2,6-dimethylpyridin-4-yl)-3-isopropyl-5-(1-(2,2,2-trifluoroethyl)piperidin-4-yl)-1H-indole (310); 3-(4-(2-(2,6-dimethylpyridin-4-yl)-3-isopropyl-1H-indol-5-yl)piperidin-1-yl)propan-1-ol (311); 2-(4-(2-(2,6-dimethylpyridin-4-yl)-3-isopropyl-1H-indol-5-yl) piperidin-1-yl)acetonitrile (312); 3-(4-(2-(2,6-dimethylpyridin-4-yl)-3-isopropyl-1H-indol-5-yl)piperidin-1-yl)-1,1,1-trifluoropropan-2-ol (313); 3-(4-(2-(2,6-dimethylpyridin-4-yl)-3-isopropyl-1H-indol-5-yl)piperidin-1-yl)propanamide (314); 3-(4-(2-(2,6-dimethylpyridin-4-yl)-3-isopropyl-1H-indol-5-yl)piperidin-1-yl)propanenitrile (315); 3-(4-(2-(2,6-dimethylpyridin-4-yl)-3-isopropyl-1H-indol-5-yl)piperidin-1-yl)-1,1,1-trifluoropropan-2-ol (316); 3-(4-(2-(2,6-dimethylpyridin-4-yl)-3-isopropyl-1H-indol-5-yl)piperidin-1-yl)-1,1,1-trifluoropropan-2-ol (317); 5-(1-benzylpiperidin-4-yl)-2-(2,6-dimethylpyridin-4-yl)-3-isopropyl-1H-indole (318); (3-((4-(2-(2,6-dimethylpyridin-4-yl)-3-isopropyl-1H-indol-5-yl)piperidin-1-yl)methyl)oxetan-3-yl)methanol (319); 4-benzyl-2-((4-(2-(2,6-dimethylpyridin-4-yl)-3-isopropyl-1H-indol-5-yl)piperidin-1-yl)methyl) morpholine (320); 3-(4-(2-(2,6-dimethylpyridin-4-yl)-3-isopropyl-1H-indol-5-yl) piperidin-1-yl)-2,2-dimethylpropanoic acid (321); 2-(2,6-dimethylpyridin-4-yl)-5-(1-ethylpiperidin-4-yl)-3-isopropyl-1H-indole (322); 2-(2,6-dimethylpyridin-4-yl)-3-isopropyl-5-(1-propylpiperidin-4-yl)-1H-indole (323); 2-(2,6-dimethylpyridin-4-yl)-3-isopropyl-5-(1-(2-(2-methoxyethoxy)ethyl)piperidin-4-yl)-1H-indole (324); 2-(2,6-dimethylpyridin-4-yl)-3-isopropyl-5-(1-(2-methoxyethyl)piperidin-4-yl)-1H-indole (325); 5-(1-cyclopentylpiperidin-4-yl)-2-(2,6-dimethylpyridin-4-yl)-3-isopropyl-1H-indole (326); 5-(1-(2,2-difluoroethyl)piperidin-4-yl)-2-(2,6-dimethylpyridin-4-yl)-3-isopropyl-1H-indole (327); 5-(1-(cyclohexylmethyl)piperidin-4-yl)-2-(2,6-dimethylpyridin-4-yl)-3-isopropyl-1H-indole (328); 2-(4-(2-(2,6-dimethylpyridin-4-yl)-3-isopropyl-1H-indol-5-yl)piperidin-1-yl)ethan-1-ol (329); 2-(2,6-dimethylpyridin-4-yl)-3-isopropyl-5-(1-(3-methoxypropyl)piperidin-4-yl)-1H-indole (330); 1-(4-(2-(2,6-dimethylpyridin-4-yl)-3-isopropyl-1H-indol-5-yl)piperidin-1-yl)propan-2-ol (331); 2-(2,6-dimethylpyridin-4-yl)-3-isopropyl-5-(1-(2-methoxypropyl)piperidin-4-yl)-1H-indole (332); 2-(2,6-dimethylpyridin-4-yl)-3-isopropyl-5-(1-(oxetan-3-ylmethyl)piperidin-4-yl)-1H-indole (333); 2-(cyclobutylamino)-1-(4-(2-(2,6-dimethylpyridin-4-yl)-3-isopropyl-1H-indol-5-yl)piperidin-1-yl)ethan-1-one (334); 1-(4-(2-(2,6-dimethylpyridin-4-yl)-3-isopropyl-1H-indol-5-yl)piperidin-1-yl)-2-(isopropylamino)ethan-1-one (335); 1-(4-(2-(2,6-dimethylpyridin-4-yl)-3-isopropyl-1H-indol-5-yl)piperidin-1-yl)-2-((2-hydroxyethyl) amino)ethan-1-one (336); 1-(4-(2-(2,6-dimethylpyridin-4-yl)-3-isopropyl-1H-indol-5-yl)piperidin-1-yl)-2-(neopentylamino)ethan-1-one (337); 1-(4-(2-(2,6-dimethylpyridin-4-yl)-3-isopropyl-1H-indol-5-yl)piperidin-1-yl)-2-(isobutylamino)ethan-1-one (338); 2-((cyclopropylmethyl)amino)-1-(4-(2-(2,6-dimethylpyridin-4-yl)-3-isopropyl-1H-indol-5-yl)piperidin-1-yl)ethan-1-one (339); 2-(3,3-difluoroazetidin-1-yl)-1-(4-(2-(2,6-dimethylpyridin-4-yl)-3-isopropyl-1H-indol-5-yl)piperidin-1-yl)ethan-1-one (340); 2-(3,3-difluoropyrrolidin-1-yl)-1-(4-(2-(2,6-dimethylpyridin-4-yl)-3-isopropyl-1H-indol-5-yl)piperidin-1-yl)ethan-1-one (341); 2-(adamantan-1-ylamino)-1-(4-(2-(2,6-dimethylpyridin-4-yl)-3-isopropyl-1H-indol-5-yl)piperidin-1-yl)ethan-1-one (342); 1-(4-(2-(2,6-dimethylpyridin-4-yl)-3-isopropyl-1H-indol-5-yl)piperidin-1-yl)-2-((3-hydroxyadamantan-1-yl)amino)ethan-1-one (343); 1-(4-(2-(2,6-dimethylpyridin-4-yl)-3-isopropyl-1H-indol-5-yl)piperidin-1-yl)-2-(isopropylamino)ethan-1-one (344); 1-(4-(2-(2,6-dimethylpyridin-4-yl)-3-isopropyl-1H-indol-5-yl)piperidin-1-yl)-2-(pentan-3-ylamino)ethan-1-one (345); 1-(4-(2-(2,6-dimethylpyridin-4-yl)-3-isopropyl-1H-indol-5-yl)piperidin-1-yl)-2-((2-methoxyethyl)amino)ethan-1-one (346); 2-((3,3-dimethylbutyl) amino)-1-(4-(2-(2,6-dimethylpyridin-4-yl)-3-isopropyl-1H-indol-5-yl)piperidin-1-yl) ethan-1-one (347); 1-(4-(2-(2,6-dimethylpyridin-4-yl)-3-isopropyl-1H-indol-5-yl) piperidin-1-yl)-2-(propylamino)ethan-1-one (348); 1-(4-(2-(2,6-dimethylpyridin-4-yl)-3-isopropyl-1H-indol-5-yl)piperidin-1-yl)-2-((2-ethoxyethyl)amino)ethan-1-one (349); 1-(4-(2-(2,6-dimethylpyridin-4-yl)-3-isopropyl-1H-indol-5-yl)piperidin-1-yl)-2-morpholinoethan-1-one (350); 1-(4-(2-(2,6-dimethylpyridin-4-yl)-3-isopropyl-1H-indol-5-yl)piperidin-1-yl)-2-(piperidin-1-yl)ethan-1-one (351); 1-(4-(2-(2,6-dimethylpyridin-4-yl)-3-isopropyl-1H-indol-5-yl)piperidin-1-yl)-2-(pyrrolidin-1-yl)ethan-1-one (352); 1-(4-(2-(2,6-dimethylpyridin-4-yl)-3-isopropyl-1H-indol-5-yl)piperidin-1-yl)-2-((1-methylcyclobutyl)amino)ethan-1-one (353); 1-(4-(2-(2,6-dimethylpyridin-4-yl)-3-isopropyl-1H-indol-5-yl)piperidin-1-yl)-2-(isopropyl(methyl)amino)ethan-1-one (354); 1-(4-(2-(2,6-dimethylpyridin-4-yl)-3-isopropyl-1H-indol-5-yl)piperidin-1-yl)-2-(isobutyl (methyl)amino)ethan-1-one (355); 1-(4-(2-(2,6-dimethylpyridin-4-yl)-3-isopropyl-1H-indol-5-yl)piperidin-1-yl)-2-(ethyl(methyl)amino)ethan-1-one (356); 2-(cyclopropyl (methyl)amino)-1-(4-(2-(2,6-dimethylpyridin-4-yl)-3-isopropyl-1H-indol-5-yl)piperidin-1-yl)ethan-1-one (357); 2-(3,3-dimethylpiperidin-1-yl)-1-(4-(2-(2,6-dimethylpyridin-4-yl)-3-isopropyl-1H-indol-5-yl)piperidin-1-yl)ethan-1-one (358); 2-(tert-butyl(methyl) amino)-1-(4-(2-(2,6-dimethylpyridin-4-yl)-3-isopropyl-1H-indol-5-yl)piperidin-1-yl) ethan-1-one (359); 1-(4-(2-(2,6-dimethylpyridin-4-yl)-3-isopropyl-1H-indol-5-yl)piperidin-1-yl)-2-((1-methylcyclopropyl)amino)ethan-1-one (360); 1-(4-(2-(2,6-dimethylpyridin-4-yl)-3-isopropyl-1H-indol-5-yl)piperidin-1-yl)-2-((1-methylcyclobutyl)amino)ethan-1-one (361); 2-(4,4-difluoropiperidin-1-yl)-1-(4-(2-(2,6-dimethylpyridin-4-yl)-3-isopropyl-1H-indol-5-yl)piperidin-1-yl)ethan-1-one (362); 1-(4-(2-(2,6-dimethylpyridin-4-yl)-3-isopropyl-1H-indol-5-yl)piperidin-1-yl)-2-(3-fluoropiperidin-1-yl)ethan-1-one (363); 1-(4-(2-(2,6-dimethylpyridin-4-yl)-3-isopropyl-1H-indol-5-yl)piperidin-1-yl)-2-(2-oxa-6-azaspiro[3.3]heptan-6-yl)ethan-1-one (364); 1-(4-(2-(2,6-dimethylpyridin-4-yl)-3-isopropyl-1H-indol-5-yl)piperidin-1-yl)-2-(((1-methylcyclopropyl)methyl)amino)ethan-1-one (365); 1-(4-(2-(2,6-dimethylpyridin-4-yl)-3-isopropyl-1H-indol-5-yl)piperidin-1-yl)-2-(2-methylpyrrolidin-1-yl)ethan-1-one (366); 1-(4-(2-(2,6-dimethylpyridin-4-yl)-3-isopropyl-1H-indol-5-yl)piperidin-1-yl)-2-((2-hydroxypropyl)amino)ethan-1-one (367); 1-(4-(2-(2,6-dimethylpyridin-4-yl)-3-isopropyl-1H-indol-5-yl)piperidin-1-yl)-2-(2,5-dimethylpyrrolidin-1-yl)ethan-1-one (368); 1-(4-(2-(2,6-dimethylpyridin-4-yl)-3-isopropyl-1H-indol-5-yl)piperidin-1-yl)-2-((3-hydroxybutyl)amino)ethan-1-one (369); (S)-1-(4-(2-(2,6-dimethylpyridin-4-yl)-3-isopropyl-1H-indol-5-yl)piperidin-1-yl)-2-(2-(methoxymethyl)pyrrolidin-1-yl)ethan-1-one (370); 1-(4-(2-(2,6-dimethylpyridin-4-yl)-3-isopropyl-1H-indol-5-yl)piperidin-1-yl)-2-((2-methyl-2-morpholinopropyl)amino)ethan-1-one (371); 1-(4-(2-(2,6-dimethylpyridin-4-yl)-3-isopropyl-1H-indol-5-yl)piperidin-1-yl)-2-(4-(2-methoxyethyl) piperazin-1-yl)ethan-1-one (372); 1-(4-(2-(2,6-dimethylpyridin-4-yl)-3-isopropyl-1H-indol-5-yl)piperidin-1-yl)-2-(((tetrahydrofuran-2-yl)methyl)amino)ethan-1-one (373); 1-(4-(2-(2,6-dimethylpyridin-4-yl)-3-isopropyl-1H-indol-5-yl)piperidin-1-yl)-2-((4-methyltetrahydro-2H-pyran-4-yl)amino)ethan-1-one (374); 1-(4-(2-(2,6-dimethylpyridin-4-yl)-3-isopropyl-1H-indol-5-yl)piperidin-1-yl)-2-((2-hydroxy-2-methylpropyl)amino)ethan-1-one (375); 1-(4-(2-(2,6-dimethylpyridin-4-yl)-3-isopropyl-1H-indol-5-yl) piperidin-1-yl)-2-(4-methylpiperidin-1-yl)ethan-1-one (376); 1-(4-(2-(2,6-dimethylpyridin-4-yl)-3-isopropyl-1H-indol-5-yl)piperidin-1-yl)-2-(2-methylpiperidin-1-yl)ethan-1-one (377); 1-(4-(2-(2,6-dimethylpyridin-4-yl)-3-isopropyl-1H-indol-5-yl)piperidin-1-yl)-2-(3-methylpiperidin-1-yl)ethan-1-one (378); 4-(2-(4-(2-(2,6-dimethylpyridin-4-yl)-3-isopropyl-1H-indol-5-yl)piperidin-1-yl)-2-oxoethyl)piperazin-2-one (379); (S)-1-(4-(2-(2,6-dimethylpyridin-4-yl)-3-isopropyl-1H-indol-5-yl)piperidin-1-yl)-2-(3-hydroxypyrrolidin-1-yl) ethan-1-one (380); (S)-1-(4-(2-(2,6-dimethylpyridin-4-yl)-3-isopropyl-1H-indol-5-yl)piperidin-1-yl)-2-(2-(hydroxymethyl)pyrrolidin-1-yl) ethan-1-one (381); 1-(4-(2-(2,6-dimethylpyridin-4-yl)-3-isopropyl-1H-indol-5-yl)piperidin-1-yl)-2-((1-hydroxy-4-methylpentan-2-yl)amino)ethan-1-one (382); 1-(4-(2-(2,6-dimethylpyridin-4-yl)-3-isopropyl-1H-indol-5-yl)piperidin-1-yl)-2-(3-hydroxypiperidin-1-yl)ethan-1-one (383); 2-(cyclohexyl(methyl)amino)-1-(4-(2-(2,6-dimethylpyridin-4-yl)-3-isopropyl-1H-indol-5-yl)piperidin-1-yl)ethan-1-one (384); 1-(4-(2-(2,6-dimethylpyridin-4-yl)-3-isopropyl-1H-indol-5-yl)piperidin-1-yl)-2-((tetrahydro-2H-pyran-3-yl)amino)ethan-1-one (385); 1-(4-(2-(2,6-dimethylpyridin-4-yl)-3-isopropyl-1H-indol-5-yl)piperidin-1-yl)-2-((tetrahydro-2H-pyran-4-yl)amino)ethan-1-one (386); 1-(4-(2-(2,6-dimethylpyridin-4-yl)-3-isopropyl-1H-indol-5-yl)piperidin-1-yl)-2-((tetrahydrofuran-3-yl)amino)ethan-1-one (387); 1-(4-(2-(2,6-dimethylpyridin-4-yl)-3-isopropyl-1H-indol-5-yl)piperidin-1-yl)-2-(4-fluoropiperidin-1-yl)ethan-1-one (388); 2-(8-oxa-3-azabicyclo[3.2.1]octan-3-yl)-1-(4-(2-(2,6-dimethylpyridin-4-yl)-3-isopropyl-1H-indol-5-yl)piperidin-1-yl)ethan-1-one (389); 2-(3,3-difluoropiperidin-1-yl)-1-(4-(2-(2,6-dimethylpyridin-4-yl)-3-isopropyl-1H-indol-5-yl)piperidin-1-yl)ethan-1-one (390); (R)-1-(4-(2-(2,6- dimethylpyridin-4-yl)-3-isopropyl-1H-indol-5-yl)piperidin-1-yl)-2-(3-hydroxypyrrolidin-1-yl)ethan-1-one (391); 2-(sec-butylamino)-1-(4-(2-(2,6-dimethylpyridin-4-yl)-3-isopropyl-1H-indol-5-yl)piperidin-1-yl)ethan-1-one (392); 1-(4-(2-(2,6-dimethylpyridin-4-yl)-3-isopropyl-1H-indol-5-yl)piperidin-1-yl)-2-(isopentylamino)ethan-1-one (393); 1-(4-(2-(2,6-dimethylpyridin-4-yl)-3-isopropyl-1H-indol-5-yl)piperidin-1-yl)-2-((2S,4S)-2-(hydroxymethyl)-4-(trifluoromethyl)pyrrolidin-1-yl)ethan-1-one (394); 1-(4-(2-(2,6-dimethylpyridin-4-yl)-3-isopropyl-1H-indol-5-yl) piperidin-1-yl)-2-((2R,4R)-2-(hydroxymethyl)-4-methoxypyrrolidin-1-yl)ethan-1-one (395); 2-(benzyl(2-hydroxyethyl)amino)-1-(4-(2-(2,6-dimethylpyridin-4-yl)-3-isopropyl-1H-indol-5-yl)piperidin-1-yl)ethan-1-one (396); 1-(4-(2-(2,6-dimethylpyridin-4-yl)-3-isopropyl-1H-indol-5-yl)piperidin-1-yl)-2-(ethyl(2-hydroxyethyl)amino)ethan-1-one (397); 1-(4-(2-(2,6-dimethylpyridin-4-yl)-3-isopropyl-1H-indol-5-yl)piperidin-1-yl)-2-((2-hydroxyethyl)(propyl)amino)ethan-1-one (398); 1-(4-(2-(2,6-dimethylpyridin-4-yl)-3-isopropyl-1H-indol-5-yl)piperidin-1-yl)-2-((2-hydroxy-2-phenylethyl)(methyl)amino) ethan-1-one (399); (R)-1-(4-(2-(2,6-dimethylpyridin-4-yl)-3-isopropyl-1H-indol-5-yl) piperidin-1-yl)-2-(3-(hydroxymethyl)morpholino)ethan-1-one (400); 1-(4-(2-(2,6-dimethylpyridin-4-yl)-3-isopropyl-1H-indol-5-yl)piperidin-1-yl)-2-((2-hydroxy-2-methylpropyl)(methyl)amino)ethan-1-one (401); (R)-1-(4-(2-(2,6-dimethylpyridin-4-yl)-3-isopropyl-1H-indol-5-yl)piperidin-1-yl)-2-(methyl(tetrahydrofuran-3-yl)amino)ethan-1-one (402); (S)-2-(4,4-difluoro-2-(hydroxymethyl)pyrrolidin-1-yl)-1-(4-(2-(2,6-dimethylpyridin-4-yl)-3-isopropyl-1H-indol-5-yl)piperidin-1-yl)ethan-1-one (403); 1-(4-(2-(2,6-dimethylpyridin-4-yl)-3-isopropyl-1H-indol-5-yl)piperidin-1-yl)-2-((2R)-2-(hydroxymethyl)-4-(trifluoromethyl)pyrrolidin-1-yl)ethan-1-one (404); (S)-1-(4-(2-(2,6-dimethylpyridin-4-yl)-3-isopropyl-1H-indol-5-yl)piperidin-1-yl)-2-(3-(hydroxymethyl) morpholino)ethan-1-one (405); 1-(4-(2-(2,6-dimethylpyridin-4-yl)-3-isopropyl-1H-indol-5-yl)piperidin-1-yl)-2-((2-hydroxyethyl)(2-methylbutyl)amino)ethan-1-one (406); 1-(4-(2-(2,6-dimethylpyridin-4-yl)-3-isopropyl-1H-indol-5-yl)piperidin-1-yl)-2-((4-fluorobenzyl)(2-hydroxyethyl)amino)ethan-1-one (407); 1-(4-(2-(2,6-dimethylpyridin-4-yl)-3-isopropyl-1H-indol-5-yl)piperidin-1-yl)-2-((2-(1-hydroxycyclopentyl)ethyl) (methyl)amino)ethan-1-one (408); 1-(4-(2-(2,6-dimethylpyridin-4-yl)-3-isopropyl-1H-indol-5-yl)piperidin-1-yl)-2-((2S,4S)-4-fluoro-2-(hydroxymethyl)pyrrolidin-1-yl)ethan-1-one (409); 1-(4-(2-(2,6-dimethylpyridin-4-yl)-3-isopropyl-1H-indol-5-yl)piperidin-1-yl)-2-((2R,4R)-2-(hydroxymethyl)-4-methylpyrrolidin-1-yl)ethan-1-one (410); 1-(4-(2-(2,6-dimethylpyridin-4-yl)-3-isopropyl-1H-indol-5-yl)piperidin-1-yl)-2-((3-hydroxypropyl) (methyl)amino)ethan-1-one (411); (R)-1-(4-(2-(2,6-dimethylpyridin-4-yl)-3-isopropyl-1H-indol-5-yl)piperidin-1-yl)-2-(2-(hydroxymethyl)pyrrolidin-1-yl)ethan-1-one (412); 1-(4-(2-(2,6-dimethylpyridin-4-yl)-3-isopropyl-1H-indol-5-yl)piperidin-1-yl)-2-(methyl (tetrahydrofuran-3-yl)amino)ethan-1-one (413); 2-(butyl(2-hydroxyethyl)amino)-1-(4-(2-(2,6-dimethylpyridin-4-yl)-3-isopropyl-1H-indol-5-yl)piperidin-1-yl)ethan-1-one (414); 1-(4-(2-(2,6-dimethylpyridin-4-yl)-3-isopropyl-1H-indol-5-yl)piperidin-1-yl)-2-((2-hydroxyethyl)(isopropyl)amino)ethan-1-one (415); 1-(4-(2-(2,6-dimethylpyridin-4-yl)-3-isopropyl-1H-indol-5-yl)piperidin-1-yl)-2-(methyl(oxetan-3-yl)amino)ethan-1-one (416); 1-(4-(2-(2,6-dimethylpyridin-4-yl)-3-isopropyl-1H-indol-5-yl)piperidin-1-yl)-2-(methyl ((5-methylisoxazol-3-yl)methyl)amino)ethan-1-one (417); 1-(4-(2-(2,6-dimethylpyridin-4-yl)-3-isopropyl-1H-indol-5-yl)piperidin-1-yl)-2-(((2-methoxypyrimidin-5-yl)methyl)(methyl)amino)ethan-1-one (418); 1-(4-(2-(2,6-dimethylpyridin-4-yl)-3-isopropyl-1H-indol-5-yl)piperidin-1-yl)-2-(methyl((1-methyl-1H-1,2,4-triazol-3-yl)methyl)amino) ethan-1-one (419); 1-(4-(2-(2,6-dimethylpyridin-4-yl)-3-isopropyl-1H-indol-5-yl) piperidin-1-yl)-2-((2-hydroxyethyl)(methyl)amino)ethan-1-one (420); 1-(4-(2-(2,6-dimethylpyridin-4-yl)-3-isopropyl-1H-indol-5-yl)piperidin-1-yl)-2-((2-fluoroethyl) (methyl)amino)ethan-1-one (421); 2-((2,2-difluoroethyl)(methyl)amino)-1-(4-(2-(2,6-dimethylpyridin-4-yl)-3-isopropyl-1H-indol-5-yl)piperidin-1-yl) ethan-1-one (422); 2-((2-(4-(2-(2,6-dimethylpyridin-4-yl)-3-isopropyl-1H-indol-5-yl)piperidin-1-yl)-2-oxoethyl)(methyl)amino)acetonitrile (423); 2-(2,6-dimethylpyridin-4-yl)-3-isopropyl-5-(1-(((6-methoxypyridin-3-yl)methyl)piperidin-4-yl)-1H-indole (424); 5-(1-((1H-imidazol-4-yl)methyl)piperidin-4-yl)-2-(2,6-dimethylpyridin-4-yl)-3-isopropyl-1H-indole (425); 2-(2,6-dimethylpyridin-4-yl)-3-isopropyl-5-(1-((2-methyl-1H-imidazol-4-yl)methyl)piperidin-4-yl)-1H-indole (426); 2-(2,6-dimethylpyridin-4-yl)-3-isopropyl-5-(1'-isopropyl-[1,4'-bipiperidin]-4-yl)-1H-indole (427); 2-(4-(2-(2,6-dimethylpyridin-4-yl)-3-isopropyl-1H-indol-5-yl)piperidin-1-yl)-N-methylethan-1-amine (428); 2-(2,6-dimethylpyridin-4-yl)-3-isopropyl-5-(1-methylpiperidin-4-yl)-1H-indole (429); 2-(2,6-dimethylpyridin-4-yl)-3-isopropyl-5-(1-((2-methoxypyrimidin-5-yl)methyl)piperidin-4-yl)-1H-indole (430); 2-(2,6-dimethylpyridin-4-yl)-3-isopropyl-5-(1-(pyridin-2-ylmethyl)piperidin-4-yl)-1H-indole (431); 3-((4-(2-(2,6-dimethylpyridin-4-yl)-3-isopropyl-1H-indol-5-yl)piperidin-1-yl)methyl)isoxazole (432); 2-(2,6-dimethylpyridin-4-yl)-3-isopropyl-5-(1-(pyridin-3-ylmethyl)piperidin-4-yl)-1H-indole (433); 2-(2,6-dimethylpyridin-4-yl)-3-isopropyl-5-(1-(pyrimidin-5-ylmethyl)piperidin-4-yl)-1H-indole (434); 2-(2,6-dimethylpyridin-4-yl)-3-isopropyl-5-(1-(pyridin-4-ylmethyl)piperidin-4-yl)-1H-indole (435); 2-(2,6-dimethylpyridin-4-yl)-3-isopropyl-5-(1-(pentan-3-yl)piperidin-4-yl)-1H-indole (436); 2-(2,6-dimethylpyridin-4-yl)-3-isopropyl-5-(1-((6-methylpyridin-3-yl)methyl)piperidin-4-yl)-1H-indole (437); 5-(1-((1H-pyrazol-4-yl)methyl)piperidin-4-yl)-2-(2,6-dimethylpyridin-4-yl)-3-isopropyl-1H-indole (438); 2-(2,6-dimethylpyridin-4-yl)-3-isopropyl-5-(1-((3-methyl-1H-pyrazol-4-yl)methyl)piperidin-4-yl)-1H-indole (439); 2-(2,6-dimethylpyridin-4-yl)-3-isopropyl-5-(1-((1-methyl-1H-pyrazol-4-yl)methyl)piperidin-4-yl)-1H-indole (440); 5-(1-((1H-pyrazol-5-yl)methyl)piperidin-4-yl)-2-(2,6-dimethylpyridin-4-yl)-3-isopropyl-1H-indole (441); 2-(2,6-dimethylpyridin-4-yl)-3-isopropyl-5-(1-((1-methyl-1H-1,2,3-triazol-4-yl)methyl) piperidin-4-yl)-1H-indole (442); 3-((4-(2-(2,6-dimethylpyridin-4-yl)-3-isopropyl-1H-indol-5-yl)piperidin-1-yl)methyl)-5-methylisoxazole (443); 5-((4-(2-(2,6-dimethylpyridin-4-yl)-3-isopropyl-1H-indol-5-yl) piperidin-1-yl)methyl)thiazole (444); 2-(2,6-dimethylpyridin-4-yl)-3-isopropyl-5-(1-((1-methyl-1H-pyrazol-3-yl)methyl)piperidin-4-yl)-1H-indole (445); 5-(1-((1H-1,2,3-triazol-4-yl)methyl)piperidin-4-yl)-2-(2,6-dimethylpyridin-4-yl)-3-isopropyl-1H-indole (446); 5-(1-((4,6-dimethoxypyrimidin-2-yl)methyl)piperidin-4-yl)-2-(2,6-dimethylpyridin-4-yl)-3-isopropyl-1H-indole (447); 2-cyclopropyl-5-((4-(2-(2,6-dimethylpyridin-4-yl)-3-isopropyl-1H-indol-5-yl)piperidin-1-yl)methyl)-1,3,4-oxadiazole (448); 2-((4-(2-(2,6-dimethylpyridin-4-yl)-3-isopropyl-1H-indol-5-yl)piperidin-1-yl)methyl)oxazole (449); 2-(2,6-dimethylpyridin-4-yl)-3-isopropyl-5-(1-(tetrahydro-2H-pyran-4-yl)piperidin-4-yl)-1H-indole (450); 2-(2,6-dimethylpyridin-4-yl)-3-isopropyl-5-(1-((1-methyl-1H-1,2, 4-triazol-3-yl)methyl)piperidin-4-yl)-1H-indole (451); 2-(2,6-dimethylpyridin-4-yl)-3-isopropyl-5-(1-(oxetan-3-yl)piperidin-4-yl)-1H-indole (452); 2-(2,6-dimethylpyridin-4-yl)-5-(1-(2,2-dimethyltetrahydro-2H-pyran-4-yl)piperidin-4-yl)-3-isopropyl-1H-indole (453); 2-(2,6-dimethylpyridin-4-yl)-5-(1-(2,6-dimethyltetrahydro-2H-pyran-4-yl)piperidin-4-yl)-3-isopropyl-1H-indole (454); 2-(2,6-dimethylpyridin-4-yl)-5-(1-(2,6-dimethyltetrahydro-2H-pyran-4-yl)piperidin-4-yl)-3-isopropyl-1H-indole (455); 2-(2,6-dimethylpyridin-4-yl)-3-isopropyl-5-(1-(5-methyl-4-oxaspiro[2.5]octan-7-yl)piperidin-4-yl)-1H-indole (456); 2-(2,6-dimethylpyridin-4-yl)-3-isopropyl-5-(1-(tetrahydro-2H-pyran-3-yl)piperidin-4-yl)-1H-indole (457); 2-(2,6-dimethylpyridin-4-yl)-3-isopropyl-5-(1-(octahydrocyclopenta[b]pyran-4-yl)piperidin-4-yl)-1H-indole (458); 4-(4-(2-(2,6-dimethylpyridin-4-yl)-3-isopropyl-1H-indol-5-yl)piperidin-1-yl)tetrahydro-2H-thiopyran 1,1-dioxide (459); 2-(2,6-dimethylpyridin-4-yl)-3-isopropyl-5-(1-(pyrimidin-2-ylmethyl) piperidin-4-yl)-1H-indole (460); 2-(2,6-dimethylpyridin-4-yl)-3-isopropyl-5-(1-((1-methyl-1H-pyrazol-5-yl)methyl)piperidin-4-yl)-1H-indole (461); 5-(1-((2H-tetrazol-5-yl) methyl)piperidin-4-yl)-2-(2,6-dimethylpyridin-4-yl)-3-isopropyl-1H-indole (462); 3-((4-(2-(2,6-dimethylpyridin-4-yl)-3-isopropyl-1H-indol-5-yl)piperidin-1-yl)methyl)-1,2,4-oxadiazole (463); 2-(2,6-dimethylpyridin-4-yl)-3-isopropyl-5-(1-((4-methyl-4H-1,2,4-triazol-3-yl)methyl)piperidin-4-yl)-1H-indole (464); 2-(2,6-dimethylpyridin-4-yl)-3-isopropyl-5-(1-((1-isopropylpyrrolidin-3-yl)methyl)piperidin-4-yl)-1H-indole (465); 2-(2,6-dimethylpyridin-4-yl)-3-isopropyl-5-(1-(pyrrolidin-3-ylmethyl)piperidin-4-yl)-1H-indole (466); 5-(1-(cyclobutylmethyl)piperidin-4-yl)-2-(2,6-dimethylpyridin-4-yl)-3-isopropyl-1H-indole (467); 5-(1-(cyclopentylmethyl)piperidin-4-yl)-2-(2,6-dimethylpyridin-4-yl)-3-isopropyl-1H-indole (468); 2-(2,6-dimethylpyridin-4-yl)-3-isopropyl-5-(1-((tetrahydrofuran-3-yl)methyl)piperidin-4-yl)-1H-indole (469); 2-(2,6-dimethylpyridin-4-yl)-3-isopropyl-5-(1-neopentylpiperidin-4-yl)-1H-indole (470); 2-(2,6-dimethylpyridin-4-yl)-5-(1-isobutylpiperidin-4-yl)-3-isopropyl-1H-indole (471); 2-(2,6-dimethylpyridin-4-yl)-5-(1-(1-fluoropropan-2-yl)piperidin-4-yl)-3-isopropyl-1H-indole (472); 5-(1-(1,3-difluoropropan-2-yl)piperidin-4-yl)-2-(2,6-dimethylpyridin-4-yl)-3-isopropyl-1H-indole (473); 5-(1-(cyclopropylmethyl)piperidin-4-yl)-2-(2,6-dimethylpyridin-4-yl)-3-isopropyl-1H-indole (474); 2-(2,6-dimethylpyridin-4-yl)-3-isopropyl-5-(1-((3-methyloxetan-3-yl)methyl)piperidin-4-yl)-1H-indole (475); 4-(3-isopropyl-5-(piperidin-4-yl)-1H-indol-2-yl)-N-(2,2,2-trifluoroethyl) picolinamide (476); 4-(3-isopropyl-5-(piperidin-4-yl)-1H-indol-2-yl)-N-(thiazol-2-yl)picolinamide (477); 2-(2-cyclopropyl-6-methylpyridin-4-yl)-3-isopropyl-5-(piperidin-4-yl)-1H-indole (478); 2-(2-ethyl-6-methylpyridin-4-yl)-3-isopropyl-5-(piperidin-4-yl)-1H-indole (479); 3-isopropyl-2-(2-methyl-6-(4-methylpiperazin-1-yl)pyridin-4-yl)-5-(piperidin-4-yl)-1H-indole (480); 2-(2-cyclopropyl-5-fluoropyridin-4-yl)-3-isopropyl-5-(piperidin-4-yl)-1H-indole (481); 2-(2-ethyl-5-fluoropyridin-4-yl)-3-isopropyl-5-(piperidin-4-yl)-1H-indole (482); 2-(2-cyclopropylpyridin-4-yl)-3-isopropyl-5-(piperidin-4-yl)-1H-indole (483); 2-(2-cyclopropylpyridin-4-yl)-3-isopropyl-5-(1-((2-methyl-1H-imidazol-4-yl)methyl)piperidin-4-yl)-1H-indole (484); 3-isopropyl-2-(2-methoxypyridin-4-yl)-5-(piperidin-4-yl)-1H-indole (485); 2-(2-cyclopropyl-6-methoxypyridin-4-yl)-3-isopropyl-5-(piperidin-4-yl)-1H-indole (486); 2-(2-ethyl-6-methoxypyridin-4-yl)-3-isopropyl-5-(piperidin-4-yl)-1H-indole (487); 4-(2-(2,6-dimethylpyridin-4-yl)-3-isopropyl-1H-indol-5-yl)piperidin-3-ol (488); 5-(3,3-difluoropiperidin-4-yl)-2-(2,6-dimethylpyridin-4-yl)-3-isopropyl-1H-indole (489); 4-(3-isopropyl-2-(2-methylpyridin-4-yl)-1H-indol-5-yl)piperidin-2-one (490); 4-(3-ethyl-5-(3-fluoropiperidin-4-yl)-1H-indol-2-yl)pyridin-2-amine (491); 3-(2,2-difluoroethyl)-2-(2,6-dimethylpyridin-4-yl)-5-(piperidin-4-yl)-1H-indole (492); 2-(4-(3-(2,2-difluoroethyl)-2-(2,6-dimethylpyridin-4-yl)-1H-indol-5-yl)piperidin-1-yl)-N,N-dimethylpropanamide (493); 2-(2-chloropyridin-4-yl)-3-(2,2-difluoroethyl)-5-(piperidin-4-yl)-1H-indole (494); methyl 2-(2,6-dimethylpyridin-4-yl)-5-(piperidin-4-yl)-1H-indole-3-carboxylate (495); 2-(2,6-dimethylpyridin-4-yl)-3-isopropyl-5-(1,2,2,6,6-pentamethylpiperidin-4-yl)-1H-indole (496); (4-(2-(2,6-dimethylpyridin-4-yl)-3-isopropyl-1H-indol-5-yl)piperidin-1-yl)(1-isopropylpiperidin-4-yl)methanone (497); 2-(4-(2-(2-fluoro-6-methylpyridin-4-yl)-3-isopropyl-1H-indol-5-yl)piperidin-1-yl)-N-methylacetamide (498); 1-(4-(2-(2-fluoro-6-methylpyridin-4-yl)-3-isopropyl-1H-indol-5-yl)piperidin-1-yl)ethan-1-one (499); 2-(4-(2-(2-fluoro-6-methylpyridin-4-yl)-3-isopropyl-1H-indol-5-yl)piperidin-1-yl)-N,N-dimethylacetamide (500); 2-(dimethylamino)-1-(4-(2-(2-fluoro-6-methylpyridin-4-yl)-3-isopropyl-1H-indol-5-yl) piperidin-1-yl)ethan-1-one (501); 4-(2-(2-fluoro-6-methylpyridin-4-yl)-3-isopropyl-1H-indol-5-yl)piperidine-1-carbonyl)-1-methylpyrrolidin-2-one (502); 2-(4-(2-(2-cyclopropyl-6-methylpyridin-4-yl)-3-isopropyl-1H-indol-5-yl)piperidin-1-yl)-N-methylacetamide (503); 1-(4-(2-(2-cyclopropyl-6-methylpyridin-4-yl)-3-isopropyl-1H-indol-5-yl)piperidin-1-yl)ethan-1-one (504); 2-(4-(2-(2-cyclopropyl-6-methylpyridin-4-yl)-3-isopropyl-1H-indol-5-yl) piperidin-1-yl)-N,N-dimethylacetamide (505); 1-(4-(2-(2-cyclopropyl-6-methylpyridin-4-yl)-3-isopropyl-1H-indol-5-yl)piperidin-1-yl)-2-(dimethylamino)ethan-1-one (506); 4-(4-(2-(2-cyclopropyl-6-methylpyridin-4-yl)-3-isopropyl-1H-indol-5-yl)piperidine-1-carbonyl)-1-methylpyrrolidin-2-one (507); 1-(4-(2-(2-cyclopropyl-6-methylpyridin-4-yl)-3-isopropyl-1H-indol-5-yl)piperidin-1-yl)-2-(methylamino)ethan-1-one (508); 2-(dimethylamino)-1-(4-(3-isopropyl-2-(2-methylpyridin-4-yl)-1H-indol-5-yl)piperidin-1-yl)ethan-1-one (509); 1-(4-(3-isopropyl-2-(2-methylpyridin-4-yl)-1H-indol-5-yl) piperidin-1-yl)-2-(methylamino)ethan-1-one (510); (R)-2-((2,3-dihydroxypropyl)amino)-1-(4-(3-isopropyl-2-(2-methylpyridin-4-yl)-1H-indol-5-yl)piperidin-1-yl) ethan-1-one (511); 2-(4-(3-isopropyl-2-(2-methylpyridin-4-yl)-1H-indol-5-yl)piperidin-1-yl)-N,N-dimethylacetamide (512); 1-(4-(3-isopropyl-2-(2-methylpyridin-4-yl)-1H-indol-5-yl) piperidin-1-yl)-3-(methylamino)propan-2-one (513); 2-(4-(2-(2-cyclopropyl-5-fluoropyridin-4-yl)-3-isopropyl-1H-indol-5-yl)piperidin-1-yl)-N-methylacetamide (514); 2-(4-(2-(2-cyclopropyl-5-fluoropyridin-4-yl)-3-isopropyl-1H-indol-5-yl)piperidin-1-yl)-N,N-dimethylacetamide (515); 1-(4-(2-(2-cyclopropyl-5-fluoropyridin-4-yl)-3-isopropyl-1H-indol-5-yl)piperidin-1-yl)-2-(dimethylamino)ethan-1-one (516); 4-(4-(2-(2-cyclopropyl-5-fluoropyridin-4-yl)-3-isopropyl-1H-indol-5-yl)piperidine-1-carbonyl)-1-methylpyrrolidin-2-one (517); 1-(4-(2-(2-cyclopropyl-5-fluoropyridin-4-yl)-3-isopropyl-1H-indol-5-yl)piperidin-1-yl)-2-(methylamino)ethan-1-one (518); 2-(4-(3-isopropyl-2-(2-methoxypyridin-4-yl)-1H-indol-5-yl) piperidin-1-yl)-N-methylacetamide (519); 3-isopropyl-2-(2-methoxypyridin-4-yl)-5-(1-((2-methyl-1H-imidazol-4-yl)methyl) piperidin-4-yl)-1H-indole (520); 2-(dimethylamino)-1-(4-(3-isopropyl-2-(2-methoxypyridin-4-yl)-1H-indol-5-yl)piperidin-1-yl)ethan-1-one (521); 2-(dimethylamino)-1-(4-(2-(2-fluoropyridin-4-yl)-3-isopropyl-1H-indol-5-yl)piperidin-1-yl)ethan-1-one (522); 2-(2- fluoropyridin-4-yl)-3-isopropyl-5-(1'-methyl-[1,4'-bipiperidin]-4-yl)-1H-indole (523); 2-(dimethylamino)-1-(4-(3-isopropyl-2-(pyridin-4-yl)-1H-indol-5-yl)piperidin-1-yl) ethan-1-one (524); 3-isopropyl-5-(1'-methyl-[1,4'-bipiperidin]-4-yl)-2-(pyridin-4-yl)-1H-indole (525); 2-(4-(2-(2,6-dimethylpyridin-4-yl)-3-ethyl-1H-indol-5-yl) piperidin-1-yl)-N,N-dimethylacetamide (526); 2-(4-(2-(2,6-dimethylpyridin-4-yl)-3-ethyl-1H-indol-5-yl)piperidin-1-yl)-N-methylacetamide (527); 2-(dimethylamino)-1-(4-(2-(2,6-dimethylpyridin-4-yl)-3-ethyl-1H-indol-5-yl)piperidin-1-yl)ethan-1-one (528); 1-(4-(2-(2,6-dimethylpyridin-4-yl)-3-ethyl-1H-indol-5-yl)piperidin-1-yl)-2-(methylamino) ethan-1-one (529); 4-(4-(2-(2,6-dimethylpyridin-4-yl)-3-ethyl-1H-indol-5-yl)piperidine-1-carbonyl)-1-methylpyrrolidin-2-one (530); 2-(4-(3-(2,2-difluoroethyl)-2-(2,6-dimethylpyridin-4-yl)-1H-indol-5-yl)piperidin-1-yl)-N,N-dimethylacetamide (531); 2-(4-(3-(2,2-difluoroethyl)-2-(2,6-dimethylpyridin-4-yl)-1H-indol-5-yl)piperidin-1-yl)-N-methylacetamide (532); 1-(4-(3-(2,2-difluoroethyl)-2-(2,6-dimethylpyridin-4-yl)-1H-indol-5-yl)piperidin-1-yl)-2-(dimethylamino)ethan-1-one (533); 4-(4-(3-(2,2-difluoroethyl)-2-(2,6-dimethylpyridin-4-yl)-1H-indol-5-yl) piperidine-1-carbonyl)-1-methylpyrrolidin-2-one (534); 1-(4-(3-(2,2-difluoroethyl)-2-(2,6-dimethylpyridin-4-yl)-1H-indol-5-yl)piperidin-1-yl)-2-(methylamino)ethan-1-one (535); 3-(2,2-difluoroethyl)-2-(2,6-dimethylpyridin-4-yl)-5-(1-isopropylpiperidin-4-yl)-1H-indole (536); 5-(1-((1H-imidazol-4-yl)methyl)piperidin-4-yl)-3-(2,2-difluoroethyl)-2-(2,6-dimethylpyridin-4-yl)-1H-indole (537); 3-(2,2-difluoroethyl)-2-(2,6-dimethylpyridin-4-yl)-5-(1-((2-methyl-1H-imidazol-4-yl)methyl)piperidin-4-yl)-1H-indole (538); 3-(2,2-difluoroethyl)-2-(2,6-dimethylpyridin-4-yl)-5-(1-methylpiperidin-4-yl)-1H-indole (539); 3-(2,2-difluoroethyl)-2-(2,6-dimethylpyridin-4-yl)-5-(1'-isopropyl-[1,4'-bipiperidin]-4-yl)-1H-indole (540); 2-(4-(3-(2,2-difluoroethyl)-2-(2,6-dimethylpyridin-4-yl)-1H-indol-5-yl)piperidin-1-yl)-N-methylethan-1-amine (541); 5-(1-((4-chlorophenyl)sulfonyl)piperidin-4-yl)-3-isopropyl-2-(2-methylpyridin-4-yl)-1H-indole (542); 3-isopropyl-2-(2-methylpyridin-4-yl)-5-(1-(pyridin-3-ylsulfonyl)piperidin-4-yl)-1H-indole (543); 3-isopropyl-5-(1-(isopropylsulfonyl)piperidin-4-yl)-2-(2-methylpyridin-4-yl)-1H-indole (544); 3-isopropyl-2-(2-methylpyridin-4-yl)-5-(1-(propylsulfonyl)piperidin-4-yl)-1H-indole (545); 3-isopropyl-2-(2-methylpyridin-4-yl)-5-(1-((2,2,2-trifluoroethyl)sulfonyl)piperidin-4-yl)-1H-indole (546); 3-isopropyl-2-(2-methylpyridin-4-yl)-5-(1-(phenylsulfonyl)piperidin-4-yl)-1H-indole (547); 5-(1-(isobutylsulfonyl)piperidin-4-yl)-3-isopropyl-2-(2-methylpyridin-4-yl)-1H-indole (548); 5-(1-(ethylsulfonyl)piperidin-4-yl)-3-isopropyl-2-(2-methylpyridin-4-yl)-1H-indole (549); 3-isopropyl-2-(2-methylpyridin-4-yl)-5-(1-(methylsulfonyl)piperidin-4-yl)-1H-indole (550); 5-(1-((4-fluorophenyl)sulfonyl)piperidin-4-yl)-3-isopropyl-2-(2-methylpyridin-4-yl)-1H-indole (551); N-(4-((4-(3-isopropyl-2-(2-methylpyridin-4-yl)-1H-indol-5-yl) piperidin-1-yl)sulfonyl)phenyl)acetamide (552); 5-(1-((1,2-dimethyl-1H-imidazol-4-yl)sulfonyl)piperidin-4-yl)-3-isopropyl-2-(2-methylpyridin-4-yl)-1H-indole (553); 5-(1-((4-fluorophenyl)sulfonyl)piperidin-4-yl)-3-isopropyl-2-(2-methylpyridin-4-yl)-1H-indole (554); 5-(1-(cyclopropylsulfonyl)piperidin-4-yl)-3-isopropyl-2-(2-methylpyridin-4-yl)-1H-indole (555); 5-(1-(benzylsulfonyl)piperidin-4-yl)-3-isopropyl-2-(2-methylpyridin-4-yl)-1H-indole (556); p-tolyl 4-(3-isopropyl-2-(2-methylpyridin-4-yl)-1H-indol-5-yl)piperidine-1-carboxylate (557); isobutyl 4-(3-isopropyl-2-(2-methylpyridin-4-yl)-1H-indol-5-yl)piperidine-1-carboxylate (558); isopropyl 4-(3-isopropyl-2-(2-methylpyridin-4-yl)-1H-indol-5-yl)piperidine-1-carboxylate (559); ethyl 4-(3-isopropyl-2-(2-methylpyridin-4-yl)-1H-indol-5-yl)piperidine-1-carboxylate (560); 2-methoxyethyl 4-(3-isopropyl-2-(2-methylpyridin-4-yl)-1H-indol-5-yl)piperidine-1-carboxylate (561); methyl 4-(3-isopropyl-2-(2-methylpyridin-4-yl)-1H-indol-5-yl) piperidine-1-carboxylate (562); (4-(3-isopropyl-2-(2-methylpyridin-4-yl)-1H-indol-5-yl) piperidin-1-yl)(1-isopropylpiperidin-4-yl)methanone (563); (S)-1-(4-amino-5-(4-(3-isopropyl-2-(2-methylpyridin-4-yl)-1H-indol-5-yl) piperidin-1-yl)-5-oxopentyl)urea (564); 4-(4-(3-isopropyl-2-(2-methylpyridin-4-yl)-1H-indol-5-yl)piperidine-1-carbonyl)-1-methylpyrrolidin-2-one (566); (1-benzylpiperidin-4-yl)(4-(3-isopropyl-2-(2-methylpyridin-4-yl)-1H-indol-5-yl)piperidin-1-yl)methanone (567); 1-(4-(3-isopropyl-2-(2-methylpyridin-4-yl)-1H-indol-5-yl) piperidin-1-yl)-3-(piperidin-4-yl)propan-1-one (568); ((1S, 2R)-2-amino-2-methylcyclopentyl)(4-(3-isopropyl-2-(2-methylpyridin-4-yl)-1H-indol-5-yl)piperidin-1-yl) methanone (569); 1-(4-(3-isopropyl-2-(2-methylpyridin-4-yl)-1H-indol-5-yl)piperidin-1-yl)-3-(methylamino)propan-1-one (570); 1-(4-(3-isopropyl-2-(2-methylpyridin-4-yl)-1H-indol-5-yl)piperidin-1-yl)-3-methoxypropan-1-one (571); (4-(3-isopropyl-2-(2-methylpyridin-4-yl)-1H-indol-5-yl)piperidin-1-yl)(pyrrolidin-3-yl) methanone (572); (4-(3-isopropyl-2-(2-methylpyridin-4-yl)-1H-indol-5-yl)piperidin-1-yl) (piperidin-4-yl)methanone (573); (S)-2-amino-3-(1H-imidazol-4-yl)-1-(4-(3-isopropyl-2-(2-methylpyridin-4-yl)-1H-indol-5-yl)piperidin-1-yl)propan-1-one (574); (1-benzylpyrrolidin-3-yl)(4-(3-isopropyl-2-(2-methylpyridin-4-yl)-1H-indol-5-yl)piperidin-1-yl) methanone (575); ((1R,3S)-3-aminocyclohexyl)(4-(3-isopropyl-2-(2-methylpyridin-4-yl)-1H-indol-5-yl)piperidin-1-yl)methanone (576); (S)-2,5-diamino-1-(4-(3-isopropyl-2-(2-methylpyridin-4-yl)-1H-indol-5-yl)piperidin-1-yl)pentan-1-one (577); 3-(dimethylamino)-1-(4-(3-isopropyl-2-(2-methylpyridin-4-yl)-1H-indol-5-yl)piperidin-1-yl)propan-1-one (578); (S)-2,6-diamino-1-(4-(3-isopropyl-2-(2-methylpyridin-4-yl)-1H-indol-5-yl)piperidin-1-yl)hexan-1-one (579); ((1R,3r,5S)-8-azabicyclo[3.2.1]octan-3-yl) (4-(3-isopropyl-2-(2-methylpyridin-4-yl)-1H-indol-5-yl)piperidin-1-yl)methanone (580); ((2S, 4R)-4-hydroxypiperidin-2-yl)(4-(3-isopropyl-2-(2-methylpyridin-4-yl)-1H-indol-5-yl)piperidin-1-yl) methanone (581); 4-(4-(3-fluoro-2-methylpyridin-4-yl)-3-isopropyl-1H-indol-5-yl)piperidine-1-carbonyl)-1-methylpyrrolidin-2-one (582); 4-(4-(2-(5-fluoro-2-methylpyridin-4-yl)-3-isopropyl-1H-indol-5-yl)piperidine-1-carbonyl)-1-methylpyrrolidin-2-one (583); 1-(4-(2-(2,5-dimethylpyridin-4-yl)-3-isopropyl-1H-indol-5-yl)piperidin-1-yl)ethan-1-one (584); 2-(dimethylamino)-1-(4-(2-(2,5-dimethylpyridin-4-yl)-3-isopropyl-1H-indol-5-yl)piperidin-1-yl)ethan-1-one (585); 2-(dimethylamino)-1-(4-(2-(5-fluoro-2-methylpyridin-4-yl)-3-isopropyl-1H-indol-5-yl) piperidin-1-yl)ethan-1-one (586); 2-(dimethylamino)-1-(4-(2-(3-fluoro-2-methylpyridin-4-yl)-3-isopropyl-1H-indol-5-yl)piperidin-1-yl)ethan-1-one (587); 2-(dimethylamino)-1-(4-(2-(3-fluoro-2,6-dimethylpyridin-4-yl)-3-isopropyl-1H-indol-5-yl)piperidin-1-yl)ethan-1-one (588); 1-(4-(2-(2,6-dimethylpyridin-4-yl)-3-isopropyl-1H-indol-5-yl)piperidin-1-yl)-3-(methyl (oxetan-3-yl)amino)propan-1-one (589); 1-(4-(3-cyclopropyl-2-(2,6-dimethylpyridin-4-yl)-1H-indol-5-yl)piperidin-1-yl)-2-(dimethylamino)ethan-1-one (590); (4-(3-ethyl-2-(2-methylpyridin-4-yl)-1H-indol-5-yl) piperidin-1-yl)(pyridin-4-yl)methanone (591); (4-(3-ethyl-2-(2-methylpyridin-4-yl)-1H-indol-5-yl)piperidin-1-yl)(2-fluoropyridin-4-yl) methanone (592); (4-(3-ethyl-2-(2- methylpyridin-4-yl)-1H-indol-5-yl)piperidin-1-yl)(1-methylpiperidin-4-yl)methanone (593); 3-(dimethylamino)-1-(4-(3-ethyl-2-(2-methylpyridin-4-yl)-1H-indol-5-yl)piperidin-1-yl)propan-1-one (594); (4-(3-ethyl-2-(2-methylpyridin-4-yl)-1H-indol-5-yl)piperidin-1-yl)(pyrrolidin-3-yl)methanone (595); (4-(3-isopropyl-2-(2-methylpyridin-4-yl)-1H-indol-5-yl)piperidin-1-yl)(3-methyloxetan-3-yl)methanone (596); (4-(3-isopropyl-2-(2-methylpyridin-4-yl)-1H-indol-5-yl)piperidin-1-yl)(tetrahydro-2H-pyran-4-yl)methanone (597); (4-(3-isopropyl-2-(2-methylpyridin-4-yl)-1H-indol-5-yl)piperidin-1-yl)(2-isopropyltetrahydro-2H-pyran-4-yl)methanone (598); (4-(3-isopropyl-2-(2-methylpyridin-4-yl)-1H-indol-5-yl)piperidin-1-yl)(tetrahydrofuran-3-yl)methanone (599); 3,3,3-trifluoro-1-(4-(3-isopropyl-2-(2-methylpyridin-4-yl)-1H-indol-5-yl)piperidin-1-yl)propan-1-one (600); 1-(4-(3-isopropyl-2-(2-methylpyridin-4-yl)-1H-indol-5-yl)piperidin-1-yl)-2,2-dimethylpropan-1-one (601); 1-(4-(3-isopropyl-2-(2-methylpyridin-4-yl)-1H-indol-5-yl)piperidin-1-yl)-2-methylpropan-1-one (602); 1-(4-(3-isopropyl-2-(2-methylpyridin-4-yl)-1H-indol-5-yl)piperidin-1-yl)propan-1-one (603); (4-(3-isopropyl-2-(2-methylpyridin-4-yl)-1H-indol-5-yl)piperidin-1-yl)(isoxazol-3-yl)methanone (604); (4-(3-isopropyl-2-(2-methylpyridin-4-yl)-1H-indol-5-yl)piperidin-1-yl)(1-(trifluoromethyl)cyclopropyl)methanone (605); cyclopropyl(4-(3-isopropyl-2-(2-methylpyridin-4-yl)-1H-indol-5-yl)piperidin-1-yl)methanone (606); 4-(4-(3-isopropyl-2-(2-methylpyridin-4-yl)-1H-indol-5-yl)piperidine-1-carbonyl)-1-methylpiperidin-2-one (607); 1-(4-(3-isopropyl-2-(2-methylpyridin-4-yl)-1H-indol-5-yl)piperidin-1-yl)-2-(methylsulfonyl)ethan-1-one (608); (4-(3-isopropyl-2-(2-methylpyridin-4-yl)-1H-indol-5-yl)piperidin-1-yl)(thiazol-4-yl)methanone (609); (4-(3-isopropyl-2-(2-methylpyridin-4-yl)-1H-indol-5-yl)piperidin-1-yl)(1-methylcyclopropyl)methanone (610); 1-(4-(3-isopropyl-2-(2-methylpyridin-4-yl)-1H-indol-5-yl)piperidine-1-carbonyl)cyclopropane-1-carbonitrile (611); 4-(4-(3-isopropyl-2-(2-methylpyridin-4-yl)-1H-indol-5-yl)piperidine-1-carbonyl)pyrrolidin-2-one (612); 1-(tert-butyl)-4-(4-(3-isopropyl-2-(2-methylpyridin-4-yl)-1H-indol-5-yl)piperidine-1-carbonyl)pyrrolidin-2-one (613); 2,2,2-trifluoro-1-(4-(3-isopropyl-2-(2-methylpyridin-4-yl)-1H-indol-5-yl)piperidin-1-yl)ethan-1-one (614); 3-(4-(3-isopropyl-2-(2-methylpyridin-4-yl)-1H-indol-5-yl)piperidin-1-yl)-2,2-dimethyl-3-oxopropanenitrile (615); 3-(4-(3-isopropyl-2-(2-methylpyridin-4-yl)-1H-indol-5-yl)piperidin-1-yl)-3-oxopropanenitrile (616); 3-(4-(3-isopropyl-2-(2-methylpyridin-4-yl)-1H-indol-5-yl)piperidin-1-yl)-3-oxopropanenitrile (617); 1-(4-(3-isopropyl-2-(2-methylpyridin-4-yl)-1H-indol-5-yl)piperidin-1-yl)-3-methylbutan-1-one (617); 4-(4-(3-isopropyl-2-(2-methylpyridin-4-yl)-1H-indol-5-yl)piperidine-1-carbonyl)-1-methylpyrrolidin-2-one (618); 4-(4-(3-isopropyl-2-(2-methylpyridin-4-yl)-1H-indol-5-yl) piperidine-1-carbonyl)-1-methylpyrrolidin-2-one (619); 1-(4-(2-(2,5-dimethylpyridin-4-yl)-3-isopropyl-1H-indol-5-yl)piperidin-1-yl)-2-(methylamino)ethan-1-one (620); 1-(4-(2-(5-fluoro-2-methylpyridin-4-yl)-3-isopropyl-1H-indol-5-yl)piperidin-1-yl)-2-(methylamino)ethan-1-one (621); 1-(4-(2-(3-fluoro-2,6-dimethylpyridin-4-yl)-3-isopropyl-1H-indol-5-yl)piperidin-1-yl)-2-(methylamino)ethan-1-one (622); (R)-(4,4-difluoropyrrolidin-2-yl)(4-(3-ethyl-2-(2-methylpyridin-4-yl)-1H-indol-5-yl)piperidin-1-yl)methanone (623); (4-(3-ethyl-2-(2-methylpyridin-4-yl)-1H-indol-5-yl)piperidin-1-yl) (piperidin-3-yl)methanone (624); (4-(3-ethyl-2-(2-methylpyridin-4-yl)-1H-indol-5-yl) piperidin-1-yl) (piperidin-4-yl)methanone (625); (4-(3-ethyl-2-(2-methylpyridin-4-yl)-1H-indol-5-yl)piperidin-1-yl)(4-methylpiperidin-4-yl)methanone (626); (4-(3-ethyl-2-(2-methylpyridin-4-yl)-1H-indol-5-yl)piperidin-1-yl)(3-phenylpiperidin-4-yl)methanone (627); (S)-(4-(3-ethyl-2-(2-methylpyridin-4-yl)-1H-indol-5-yl)piperidin-1-yl)(piperidin-2-yl)methanone (628); (S)-3-ethyl-2-(2-methylpyridin-4-yl)-5-(1-propylpiperidin-4-yl)-1H-indole (629); azetidin-3-yl(4-(3-ethyl-2-(2-methylpyridin-4-yl)-1H-indol-5-yl) piperidin-1-yl)methanone (630); (4-(3-ethyl-2-(2-methylpyridin-4-yl)-1H-indol-5-yl) piperidin-1-yl)(7-azaspiro[3.5]nonan-2-yl)methanone (631); 1-(4-(3-ethyl-2-(2-methylpyridin-4-yl)-1H-indol-5-yl)piperidin-1-yl)-3-(piperidin-4-yl)propan-1-one (632); (4-(3-ethyl-2-(2-methylpyridin-4-yl)-1H-indol-5-yl)piperidin-1-yl)(pyrrolidin-3-yl) methanone (633); (3-aminooxetan-3-yl)(4-(3-isopropyl-2-(2-methylpyridin-4-yl)-1H-indol-5-yl)piperidin-1-yl)methanone (634); 2-(5-fluoro-2-methylpyridin-4-yl)-3-isopropyl-5-(1-methylpiperidin-4-yl)-1H-indole (635); 2-(2,5-dimethylpyridin-4-yl)-3-isopropyl-5-(1-methylpiperidin-4-yl)-1H-indole (636); 2-(2,3-dimethylpyridin-4-yl)-3-isopropyl-5-(1-methylpiperidin-4-yl)-1H-indole (637); 3-isopropyl-2-(2-methoxypyridin-4-yl)-5-(1-methylpiperidin-4-yl)-1H-indole (638); 3-isopropyl-2-(2-methoxypyridin-4-yl)-5-(1-(2,2,2-trifluoroethyl)piperidin-4-yl)-1H-indole (639); 5-(1-(2-ethoxyethyl) piperidin-4-yl)-3-isopropyl-2-(2-methoxypyridin-4-yl)-1H-indole (640); 2-(2,5-dimethylpyridin-4-yl)-3-isopropyl-5-(1-isopropylpiperidin-4-yl)-1H-indole (641); 2-(4-(2-(2,5-dimethylpyridin-4-yl)-3-isopropyl-1H-indol-5-yl)piperidin-1-yl)-N,N-dimethylacetamide (642); 2-(4-(2-(5-fluoro-2-methylpyridin-4-yl)-3-isopropyl-1H-indol-5-yl)piperidin-1-yl)-N,N-dimethylacetamide (643); 2-(4-(2-(3-chloro-2,6-dimethylpyridin-4-yl)-3-isopropyl-1H-indol-5-yl)piperidin-1-yl)-N,N-dimethylacetamide (644); 2-(4-(2-(3-fluoro-2,6-dimethylpyridin-4-yl)-3-isopropyl-1H-indol-5-yl)piperidin-1-yl)-N,N-dimethylacetamide (645); 2-(5-fluoro-2-methylpyridin-4-yl)-3-isopropyl-5-(1-(oxetan-3-ylmethyl)piperidin-4-yl)-1H-indole (646); 2-(4-(2-(5-fluoro-2-methylpyridin-4-yl)-3-isopropyl-1H-indol-5-yl)piperidin-1-yl)ethan-1-ol (647); 2-(4-(2-(3-fluoro-2-methylpyridin-4-yl)-3-isopropyl-1H-indol-5-yl)piperidin-1-yl)-N,N-dimethylacetamide (648); 5-(1-(2,2-difluoroethyl)piperidin-4-yl)-2-(5-fluoro-2-methylpyridin-4-yl)-3-isopropyl-1H-indole (649); 2-(5-fluoro-2-methylpyridin-4-yl)-3-isopropyl-5-(1-(oxetan-3-ylmethyl)piperidin-4-yl)-1H-indole (650); 2-(4-(2-(2,5-dimethylpyridin-4-yl)-3-isopropyl-1H-indol-5-yl)piperidin-1-yl)acetamide (651); 2-(4-(2-(5-fluoro-2-methylpyridin-4-yl)-3-isopropyl-1H-indol-5-yl)piperidin-1-yl)acetamide (652); 2-(4-(2-(2,5-dimethylpyridin-4-yl)-3-isopropyl-1H-indol-5-yl)piperidin-1-yl)-N-methylacetamide (653); 2-(4-(2-(5-fluoro-2-methylpyridin-4-yl)-3-isopropyl-1H-indol-5-yl)piperidin-1-yl)-N-methylacetamide (654); 2-(4-(2-(3-fluoro-2,6-dimethylpyridin-4-yl)-3-isopropyl-1H-indol-5-yl)piperidin-1-yl)-N-methylacetamide (655); 3-(4-(2-(5-fluoro-2-methylpyridin-4-yl)-3-isopropyl-1H-indol-5-yl)piperidin-1-yl)propanenitrile (656); 1-(4-(2-(5-fluoro-2-methylpyridin-4-yl)-3-isopropyl-1H-indol-5-yl)piperidin-1-yl)-3-morpholinopropan-1-one (657); 3-isopropyl-2-(2-methylpyridin-4-yl)-5-(1-(2,2,2-trifluoroethyl)piperidin-4-yl)-1H-indole (658); 5-(1-(2-ethoxyethyl)piperidin-4-yl)-3-isopropyl-2-(2-methylpyridin-4-yl)-1H-indole (659); 5-(1-(2,2-difluoroethyl)piperidin-4-yl)-3-isopropyl-2-(2-methylpyridin-4-yl)-1H-indole (660); 1,1,1-trifluoro-3-(4-(3-isopropyl-2-(2-methylpyridin-4-yl)-1H-indol-5-yl)piperidin-1-yl)propan-2-ol (661); 2-(4-(3-isopropyl-2-(2-methylpyridin-4-yl)-1H-indol-5-yl)piperidin-1-yl)-1- phenylethan-1-ol (662); 3-isopropyl-2-(2-methylpyridin-4-yl)-5-(1-(2-phenoxyethyl)piperidin-4-yl)-1H-indole (663); 1-(4-(3-isopropyl-2-(2-methylpyridin-4-yl)-1H-indol-5-yl)piperidin-1-yl)butan-2-ol (664); 3-(4-(2-(2,5-dimethylpyridin-4-yl)-3-isopropyl-1H-indol-5-yl)piperidin-1-yl) propanenitrile (665); 2-(2,5-dimethylpyridin-4-yl)-5-(1-isobutylpiperidin-4-yl)-3-isopropyl-1H-indole (666); 3-cyclopropyl-5-(1-(cyclopropylmethyl)piperidin-4-yl)-2-(2,6-dimethylpyridin-4-yl)-1H-indole (667); 1-(4-(3-cyclopropyl-2-(2,6-dimethylpyridin-4-yl)-1H-indol-5-yl)piperidin-1-yl)-2-methylpropan-2-ol (668); 3-(4-(3-isopropyl-2-(2-methylpyridin-4-yl)-1H-indol-5-yl)piperidin-1-yl)-N,N-dimethylpropan-1-amine (669); 3-ethyl-5-(1-methylpiperidin-4-yl)-2-(2-methylpyridin-4-yl)-1H-indole (670); 3-(4-(2-(2,6-dimethylpyridin-4-yl)-3-isopropyl-1H-indol-5-yl)piperidin-1-yl)-N,N-diethylpropan-1-amine (671); 3-ethyl-5-(1-isopropylpiperidin-4-yl)-2-(2-methylpyridin-4-yl)-1H-indole (672); 3-(4-(3-ethyl-2-(2-methylpyridin-4-yl)-1H-indol-5-yl)piperidin-1-yl)-N,N-dimethylpropan-1-amine (673); 3-(4-(2-(2,6-dimethylpyridin-4-yl)-3-isopropyl-1H-indol-5-yl)piperidin-1-yl)-N,N-dimethylpropan-1-amine (674); 3-ethyl-5-(1-((1-isopropylpiperidin-4-yl)methyl)piperidin-4-yl)-2-(2-methylpyridin-4-yl)-1H-indole (675); 3-isopropyl-2-(2-methylpyridin-4-yl)-5-(1-(3,3,3-trifluoropropyl)piperidin-4-yl)-1H-indole (676); 2-(2,6-dimethylpyridin-4-yl)-3-isopropyl-5-(1-(3,3,3-trifluoropropyl) piperidin-4-yl)-1H-indole (677); 1-(4-(2-(5-fluoro-2-methylpyridin-4-yl)-3-isopropyl-1H-indol-5-yl)piperidin-1-yl)-2-(methyl(oxetan-3-yl)amino)ethan-1-one (678); 3-((2-(4-(2-(5-fluoro-2-methylpyridin-4-yl)-3-isopropyl-1H-indol-5-yl)piperidin-1-yl)-2-oxoethyl) (methyl)amino)propanenitrile (679); 1-(4-(2-(5-fluoro-2-methylpyridin-4-yl)-3-isopropyl-1H-indol-5-yl)piperidin-1-yl)-2-((2-hydroxyethyl)(methyl)amino)ethan-1-one (680); 5-(1-((1H-pyrazol-5-yl)methyl)piperidin-4-yl)-2-(2,5-dimethylpyridin-4-yl)-3-isopropyl-1H-indole (681); 5-(1-((1H-pyrazol-5-yl)methyl)piperidin-4-yl)-2-(5-fluoro-2-methylpyridin-4-yl)-3-isopropyl-1H-indole (682); 2-(2,5-dimethylpyridin-4-yl)-3-isopropyl-5-(1-((1-methyl-1H-1,2,3-triazol-4-yl)methyl)piperidin-4-yl)-1H-indole (683); 2-(5-fluoro-2-methylpyridin-4-yl)-3-isopropyl-5-(1-((1-methyl-1H-1,2,3-triazol-4-yl) methyl)piperidin-4-yl)-1H-indole (684); 3-((4-(2-(2,5-dimethylpyridin-4-yl)-3-isopropyl-1H-indol-5-yl)piperidin-1-yl)methyl)-5-methylisoxazole (685); 3-((4-(2-(5-fluoro-2-methylpyridin-4-yl)-3-isopropyl-1H-indol-5-yl)piperidin-1-yl)methyl)-5-methylisoxazole (686); 5-((4-(2-(2,5-dimethylpyridin-4-yl)-3-isopropyl-1H-indol-5-yl)piperidin-1-yl) methyl)thiazole (687); 5-((4-(2-(5-fluoro-2-methylpyridin-4-yl)-3-isopropyl-1H-indol-5-yl)piperidin-1-yl)methyl)thiazole (688); 2-(2,5-dimethylpyridin-4-yl)-3-isopropyl-5-(1-((1-methyl-1H-pyrazol-3-yl)methyl) piperidin-4-yl)-1H-indole (689); 5-(1-((1H-1,2,3-triazol-4-yl)methyl)piperidin-4-yl)-2-(2,5-dimethylpyridin-4-yl)-3-isopropyl-1H-indole (690); 5-(1-((1H-1,2,3-triazol-4-yl) methyl)piperidin-4-yl)-2-(2,5-dimethylpyridin-4-yl)-3-isopropyl-1H-indole (691); 2-(2,5-dimethylpyridin-4-yl)-3-isopropyl-5-(1-((1-methyl-1H-pyrazol-3-yl)methyl)piperidin-4-yl)-1H-indole (692); 5-(1-((4,6-dimethoxypyrimidin-2-yl)methyl)piperidin-4-yl)-2-(2,5-dimethylpyridin-4-yl)-3-isopropyl-1H-indole (693); 5-(1-((4,6-dimethoxypyrimidin-2-yl)methyl)piperidin-4-yl)-2-(5-fluoro-2-methylpyridin-4-yl)-3-isopropyl-1H-indole (694); 5-(1-((1H-tetrazol-5-yl)methyl)piperidin-4-yl)-2-(2,5-dimethylpyridin-4-yl)-3-isopropyl-1H-indole (695); 5-(1-((1H-tetrazol-5-yl)methyl) piperidin-4-yl)-2-(5-fluoro-2-methylpyridin-4-yl)-3-isopropyl-1H-indole (696); 2-cyclopropyl-5-((4-(2-(2,5-dimethylpyridin-4-yl)-3-isopropyl-1H-indol-5-yl)piperidin-1-yl)methyl)-1,3,4-oxadiazole (697); 2-cyclopropyl-5-((4-(2-(5-fluoro-2-methylpyridin-4-yl)-3-isopropyl-1H-indol-5-yl)piperidin-1-yl) methyl)-1,3,4-oxadiazole (698); 2-((4-(2-(2,5-dimethylpyridin-4-yl)-3-isopropyl-1H-indol-5-yl)piperidin-1-yl)methyl)oxazole (699); 2-((4-(2-(5-fluoro-2-methylpyridin-4-yl)-3-isopropyl-1H-indol-5-yl)piperidin-1-yl) methyl)oxazole (700); 3-isopropyl-5-(1'-isopropyl-[1,4'-bipiperidin]-4-yl)-2-(2-methylpyridin-4-yl)-1H-indole (701); 4-(3-isopropyl-2-(2-methylpyridin-4-yl)-1H-indol-5-yl)-[1,3'-bipiperidin]-2'-ol (702); 5-([1,3'-bipiperidin]-4-yl)-3-isopropyl-2-(2-methylpyridin-4-yl)-1H-indole (703); methyl 4-(3-isopropyl-2-(2-methylpyridin-4-yl)-1H-indol-5-yl)-[1,4'-bipiperidine]-2'-carboxylate (704); 5-(3'-fluoro-[1,4'-bipiperidin]-4-yl)-3-isopropyl-2-(2-methylpyridin-4-yl)-1H-indole (705); 5-(3'-fluoro-1'-isopropyl-[1,4'-bipiperidin]-4-yl)-3-isopropyl-2-(2-methylpyridin-4-yl)-1H-indole (706); 3-isopropyl-5-(1'-isopropyl-[1,3'-bipiperidin]-4-yl)-2-(2-methylpyridin-4-yl)-1H-indole (707); 3-isopropyl-5-(2'-methyl-[1,4'-bipiperidin]-4-yl)-2-(2-methylpyridin-4-yl)-1H-indole (708); 3-isopropyl-5-(3'-methyl-[1,4'-bipiperidin]-4-yl)-2-(2-methylpyridin-4-yl)-1H-indole (709); 3-isopropyl-2-(2-methylpyridin-4-yl)-5-(1-(tetrahydro-2H-pyran-4-yl)piperidin-4-yl)-1H-indole (710); 3-isopropyl-2-(2-methylpyridin-4-yl)-5-(1-(oxetan-3-yl)piperidin-4-yl)-1H-indole (711); 5-(1-(2,6-dimethyltetrahydro-2H-pyran-4-yl)piperidin-4-yl)-3-isopropyl-2-(2-methylpyridin-4-yl)-1H-indole (712); 5-(1-(2,6-dimethyltetrahydro-2H-pyran-4-yl)piperidin-4-yl)-3-isopropyl-2-(2-methylpyridin-4-yl)-1H-indole (713); 2-(2,5-dimethylpyridin-4-yl)-3-isopropyl-5-(1-(tetrahydro-2H-pyran-4-yl)piperidin-4-yl)-1H-indole (714); 2-(5-fluoro-2-methylpyridin-4-yl)-3-isopropyl-5-(1-(tetrahydro-2H-pyran-4-yl)piperidin-4-yl)-1H-indole (715); 2-(2,3-dimethylpyridin-4-yl)-3-isopropyl-5-(1-(tetrahydro-2H-pyran-4-yl)piperidin-4-yl)-1H-indole (716); 3-isopropyl-2-(2-methylpyridin-4-yl)-5-(1-(tetrahydrofuran-3-yl)piperidin-4-yl)-1H-indole (717); 3-isopropyl-2-(2-methylpyridin-4-yl)-5-(1-(tetrahydro-2H-pyran-3-yl)piperidin-4-yl)-1H-indole (718); 5-(1-(2,2-dimethyltetrahydro-2H-pyran-4-yl)piperidin-4-yl)-3-isopropyl-2-(2-methylpyridin-4-yl)-1H-indole (719); 3-isopropyl-2-(2-methoxypyridin-4-yl)-5-(1-(tetrahydro-2H-pyran-4-yl)piperidin-4-yl)-1H-indole (720); 2-(5-fluoro-2-methylpyridin-4-yl)-3-isopropyl-5-(1-(oxetan-3-yl)piperidin-4-yl)-1H-indole (721); 2-(2,5-dimethylpyridin-4-yl)-3-isopropyl-5-(1-(oxetan-3-yl)piperidin-4-yl)-1H-indole (722); 2-(2,5-dimethylpyridin-4-yl)-3-isopropyl-5-(1-((1-methyl-1H-1,2,4-triazol-3-yl)methyl) piperidin-4-yl)-1H-indole (723); 2-(5-fluoro-2-methylpyridin-4-yl)-3-isopropyl-5-(1-((1-methyl-1H-1,2,4-triazol-3-yl)methyl)piperidin-4-yl)-1H-indole (724); 2-(5-fluoro-2-methylpyridin-4-yl)-3-isopropyl-5-(1-(tetrahydrofuran-3-yl)piperidin-4-yl)-1H-indole (725); 2-(2,5-dimethylpyridin-4-yl)-3-isopropyl-5-(1-(tetrahydro-2H-pyran-3-yl) piperidin-4-yl)-1H-indole (726); 2-(5-fluoro-2-methylpyridin-4-yl)-3-isopropyl-5-(1-(tetrahydro-2H-pyran-3-yl)piperidin-4-yl)-1H-indole (727); 2-(2,5-dimethylpyridin-4-yl)-3-isopropyl-5-(1-(tetrahydrofuran-3-yl)piperidin-4-yl)-1H-indole (728); 2-(3-fluoro-2,6-dimethylpyridin-4-yl)-3-isopropyl-5-(1-(oxetan-3-yl)piperidin-4-yl)-1H-indole (729); 2-(3-fluoro-2-methylpyridin-4-yl)-3-isopropyl-5-(1-(oxetan-3-yl)piperidin-4-yl)-1H-indole (730); 2-(3-fluoro-2-methylpyridin-4-yl)-3-isopropyl-5-(1-((2-methoxypyrimidin-5-yl) methyl)piperidin-4-yl)-1H-indole (731); 2-(3-fluoro-2-methylpyridin-4-yl)-3-isopropyl-5-(1-((1-methyl-1H-1,2,4-triazol-3-yl)methyl)piperidin-4- yl)-1H-indole (732); 2-(5-fluoro-2-methylpyridin-4-yl)-3-isopropyl-5-(1-((2-methoxypyrimidin-5-yl)methyl)piperidin-4-yl)-1H-indole (733); 3-((4-(2-(2,5-dimethylpyridin-4-yl)-3-isopropyl-1H-indol-5-yl)piperidin-1-yl)methyl)-1,2,4-oxadiazole (734); 3-((4-(2-(5-fluoro-2-methylpyridin-4-yl)-3-isopropyl-1H-indol-5-yl)piperidin-1-yl)methyl)-1,2,4-oxadiazole (735); 2-(2,5-dimethylpyridin-4-yl)-3-isopropyl-5-(1-((4-methyl-4H-1,2,4-triazol-3-yl)methyl) piperidin-4-yl)-1H-indole (736); 2-(5-fluoro-2-methylpyridin-4-yl)-3-isopropyl-5-(1-((4-methyl-4H-1,2,4-triazol-3-yl)methyl)piperidin-4-yl)-1H-indole (737); (R)-3-isopropyl-2-(2-methylpyridin-4-yl)-5-(1-(pyrrolidin-3-ylmethyl)piperidin-4-yl)-1H-indole (738); (R)-3-ethyl-2-(2-methylpyridin-4-yl)-5-(1-(pyrrolidin-3-ylmethyl)piperidin-4-yl)-1H-indole (739); (S)-3-ethyl-2-(2-methylpyridin-4-yl)-5-(1-(pyrrolidin-2-ylmethyl)piperidin-4-yl)-1H-indole (740); (S)-3-ethyl-5-(1-((1-isopropylpyrrolidin-2-yl)methyl)piperidin-4-yl)-2-(2-methylpyridin-4-yl)-1H-indole (741); 3-isopropyl-5-(1-((1-isopropylpiperidin-4-yl) methyl)piperidin-4-yl)-2-(2-methylpyridin-4-yl)-1H-indole (742); 3-isopropyl-5-(1-((1-methylpiperidin-4-yl)methyl)piperidin-4-yl)-2-(2-methylpyridin-4-yl)-1H-indole (743); 3-isopropyl-5-(1-((4-methyl-1H-imidazol-5-yl)methyl)piperidin-4-yl)-2-(2-methylpyridin-4-yl)-1H-indole (744); 4-(5-(1-((1H-imidazol-5-yl)methyl)piperidin-4-yl)-3-isopropyl-1H-indol-2-yl)-2-methylpyridin-3-amine (745); N-methyl-2-(4-(3-methyl-2-(2-(4-methylpiperazin-1-yl)pyridin-4-yl)-1H-indol-5-yl)piperidin-1-yl)ethan-1-amine (746); N-methyl-2-(4-(3-methyl-2-(2-(trifluoromethyl)pyridin-4-yl)-1H-indol-5-yl) piperidin-1-yl)ethan-1-amine (747); 2-(4-(2-(2-ethylpyridin-4-yl)-3-methyl-1H-indol-5-yl)piperidin-1-yl)-N-methylethan-1-amine (748); 2-(4-(2-(5-fluoro-2-(2-methoxyethoxy) pyridin-4-yl)-3-methyl-1H-indol-5-yl) piperidin-1-yl)-N-methylethan-1-amine (749); 2-(4-(2-(2-fluoropyridin-4-yl)-3-methyl-1H-indol-5-yl)piperidin-1-yl)-N-methylethan-1-amine (750); 2-(4-(2-(2-chloropyridin-4-yl)-3-methyl-1H-indol-5-yl)piperidin-1-yl)-N-methylethan-1-amine (751); methyl 4-(3-methyl-5-(1-(2-(methylamino)ethyl)piperidin-4-yl)-1H-indol-2-yl)picolinate (752); N-(4-(3-methyl-5-(1-(2-(methylamino)ethyl) piperidin-4-yl)-1H-indol-2-yl)pyridin-2-yl)acetamide (753); 2-(4-(2-(3-methoxypyridin-4-yl)-3-methyl-1H-indol-5-yl)piperidin-1-yl)-N-methylethan-1-amine (754); 4-(3-methyl-5-(1-(2-(methylamino)ethyl)piperidin-4-yl)-1H-indol-2-yl)picolinonitrile (755); 2-(4-(2-(5-fluoro-2-methoxypyridin-4-yl)-3-methyl-1H-indol-5-yl)piperidin-1-yl)-N-methylethan-1-amine (756); 2-(4-(2-(2-chloro-5-methoxypyridin-4-yl)-3-methyl-1H-indol-5-yl)piperidin-1-yl)-N-methylethan-1-amine (757); 2-(2-chloropyridin-4-yl)-3-ethyl-5-(1'-isobutyl-[1,4'-bipiperidin]-4-yl)-1H-indole (758); 3-ethyl-2-(2-fluoropyridin-4-yl)-5-(1'-isobutyl-[1,4'-bipiperidin]-4-yl)-1H-indole (759); 2-(2-chloro-5-fluoropyridin-4-yl)-3-ethyl-5-(1'-isobutyl-[1,4'-bipiperidin]-4-yl)-1H-indole (760); 2-(2,6-difluoropyridin-4-yl)-3-ethyl-5-(1'-isobutyl-[1,4'-bipiperidin]-4-yl)-1H-indole (761); methyl 4-(3-ethyl-5-(1'-isobutyl-[1,4'-bipiperidin]-4-yl)-1H-indol-2-yl)picolinate (762); 2-(2-chloro-5-methoxypyridin-4-yl)-3-ethyl-5-(1'-isobutyl-[1,4'-bipiperidin]-4-yl)-1H-indole (763); ((1r,4r)-4-aminocyclohexyl)(4-(3-isopropyl-2-(2-methylpyridin-4-yl)-1H-indol-5-yl)piperidin-1-yl)methanone (764); 4-(3-ethyl-5-(1'-isobutyl-[1,4'-bipiperidin]-4-yl)-1H-indol-2-yl)pyridin-2-ol (765); N-(4-(3-ethyl-5-(1'-isobutyl-[1,4'-bipiperidin]-4-yl)-1H-indol-2-yl)pyridin-2-yl)acetamide (766); 4-(3-ethyl-5-(1'-isobutyl-[1,4'-bipiperidin]-4-yl)-1H-indol-2-yl)-N,N-dimethylpyridin-2-amine (767); 2-(2-ethoxypyridin-4-yl)-3-ethyl-5-(1'-isobutyl-[1,4'-bipiperidin]-4-yl)-1H-indole (768); 3-ethyl-5-(1'-isobutyl-[1,4'-bipiperidin]-4-yl)-2-(2-isopropoxypyridin-4-yl)-1H-indole (769); 2-((4-(3-ethyl-5-(1'-isobutyl-[1,4'-bipiperidin]-4-yl)-1H-indol-2-yl)pyridin-2-yl)oxy)-N,N-dimethylethan-1-amine (770); 4-(3-ethyl-5-(1'-isobutyl-[1,4'-bipiperidin]-4-yl)-1H-indol-2-yl)-N-methylpyridin-2-amine (771); N-ethyl-4-(3-ethyl-5-(1'-isobutyl-[1,4'-bipiperidin]-4-yl)-1H-indol-2-yl)pyridin-2-amine (772); 4-(3-ethyl-5-(1'-isobutyl-[1,4'-bipiperidin]-4-yl)-1H-indol-2-yl)pyridin-2-amine (773); 2-(2-(difluoromethoxy)pyridin-4-yl)-3-ethyl-5-(1'-isobutyl-[1,4'-bipiperidin]-4-yl)-1H-indole (774); 2-(2-(difluoromethoxy)pyridin-4-yl)-3-ethyl-5-(1'-isobutyl-[1,4'-bipiperidin]-4-yl)-1H-indole (775); N-methyl-2-(4-(3-methyl-2-(pyridin-4-yl)-1H-indol-5-yl)piperidin-1-yl)ethan-1-amine (776); 2-(4-(2-(2-methoxypyridin-4-yl)-3-methyl-1H-indol-5-yl)piperidin-1-yl)-N-methylethan-1-amine (777); 2-(4-(3-ethyl-2-(2-methoxypyridin-4-yl)-1H-indol-5-yl)piperidin-1-yl)-N-methylethan-1-amine (778); 3-ethyl-5-(1'-isobutyl-[1,4'-bipiperidin]-4-yl)-2-(pyridin-4-yl)-1H-indole (779); 3-ethyl-5-(1'-isobutyl-[1,4'-bipiperidin]-4-yl)-2-(2-methoxypyridin-4-yl)-1H-indole (780); 5-(1'-isobutyl-[1,4'-bipiperidin]-4-yl)-2-(2-methoxypyridin-4-yl)-3-methyl-1H-indole (781); 5-(1'-isobutyl-[1,4'-bipiperidin]-4-yl)-3-methyl-2-(pyridin-4-yl)-1H-indole (782); 2-(4-(3-isopropyl-2-(2-methoxypyridin-4-yl)-1H-indol-5-yl) piperidin-1-yl)-N-methylethan-1-amine (783); 2-(4-(3-(cyclopropylmethyl)-2-(2-methoxypyridin-4-yl)-1H-indol-5-yl)piperidin-1-yl)-N-methylethan-1-amine (784); 5-(1'-cyclopentyl-[1,4'-bipiperidin]-4-yl)-3-ethyl-2-(2-methoxypyridin-4-yl)-1H-indole (785); 3-ethyl-5-(1'-isopropyl-[1,4'-bipiperidin]-4-yl)-2-(2-methoxypyridin-4-yl)-1H-indole (786); 5-([1,4'-bipiperidin]-4-yl)-3-ethyl-2-(2-methoxypyridin-4-yl)-1H-indole (787); 5-(1'-cyclopropyl-[1,4'-bipiperidin]-4-yl)-3-ethyl-2-(2-methoxypyridin-4-yl)-1H-indole (788); 5-(1'-(cyclopropylmethyl)-[1,4'-bipiperidin]-4-yl)-3-ethyl-2-(2-methoxypyridin-4-yl)-1H-indole (789); 3-ethyl-2-(2-methoxypyridin-4-yl)-5-(1'-methyl-[1,4'-bipiperidin]-4-yl)-1H-indole (790); 3-ethyl-2-(2-methoxypyridin-4-yl)-5-(1-((1R,3s,5S)-8-methyl-8-azabicyclo[3.2.1]octan-3-yl)piperidin-4-yl)-1H-indole (791); 3-ethyl-5-(1'-ethyl-[1,4'-bipiperidin]-4-yl)-2-(2-methoxypyridin-4-yl)-1H-indole (792); 5-(1-(1-cyclopentylazepan-4-yl)piperidin-4-yl)-3-ethyl-2-(2-methoxypyridin-4-yl)-1H-indole (793); (S)-5-(1-(azepan-4-yl)piperidin-4-yl)-3-ethyl-2-(2-methoxypyridin-4-yl)-1H-indole (794); 3-isopropyl-2-(2-methoxypyridin-4-yl)-5-(1'-methyl-[1,4'-bipiperidin]-4-yl)-1H-indole (795); 5-(1'-(cyclopropylmethyl)-[1,4'-bipiperidin]-4-yl)-3-isopropyl-2-(2-methoxypyridin-4-yl)-1H-indole (796); 3-isopropyl-5-(1'-isopropyl-[1,4'-bipiperidin]-4-yl)-2-(2-methoxypyridin-4-yl)-1H-indole (797); 3-ethyl-2-(2-methoxypyridin-4-yl)-5-(1-((1R,3r,5S)-9-methyl-9-azabicyclo[3.3.1]nonan-3-yl)piperidin-4-yl)-1H-indole (798); 2-(2,3-dimethoxypyridin-4-yl)-5-(1'-isobutyl-[1,4'-bipiperidin]-4-yl)-3-methyl-1H-indole (799); 5-([1,4'-bipiperidin]-4-yl)-3-isopropyl-2-(2-methoxypyridin-4-yl)-1H-indole (800); 5-(1'-ethyl-[1,4'-bipiperidin]-4-yl)-3-isopropyl-2-(2-methoxypyridin-4-yl)-1H-indole (801); 5-(1'-cyclopentyl-[1,4'-bipiperidin]-4-yl)-3-isopropyl-2-(2-methoxypyridin-4-yl)-1H-indole (802); 5-(1'-isobutyl-[1,4'-bipiperidin]-4-yl)-3-isopropyl-2-(2-methoxypyridin-4-yl)-1H-indole (803); 3-ethyl-5-(1'-isopropyl-[1,4'-bipiperidin]-4-yl)-2-(pyridin-4-yl)-1H-indole (804); 3-ethyl-5-(1-((1-methyl-1H-pyrrol-2-yl)methyl)piperidin-4-yl)-2-(pyridin-4-yl)-1H-indole (805); 3-ethyl-5-(1'-methyl-[1,4'-bipiperidin]-4-yl)-2-(pyridin-4-yl)-1H-indole (806); 3-ethyl-2-(pyridin-4-yl)-5-(2',2',6',6'-tetramethyl-[1,4'-bipiperidin]-4-yl)-1H- indole (807); 2-(4-(3-ethyl-2-(pyridin-4-yl)-1H-indol-5-yl)piperidin-1-yl)-N-methylethan-1-amine (808); 3-ethyl-5-(1'-ethyl-[1,4'-bipiperidin]-4-yl)-2-(pyridin-4-yl)-1H-indole (809); 5-(1'-isobutyl-[1,4'-bipiperidin]-4-yl)-3-methyl-2-(2-methylpyridin-4-yl)-1H-indole (810); 5-(1'-isopropyl-[1,4'-bipiperidin]-4-yl)-3-methyl-2-(2-methylpyridin-4-yl)-1H-indole (811); 2-(2,3-dimethylpyridin-4-yl)-5-(1'-isopropyl-[1,4'-bipiperidin]-4-yl)-3-methyl-1H-indole (812); 2-(2,6-dimethylpyridin-4-yl)-5-(1'-isopropyl-[1,4'-bipiperidin]-4-yl)-3-methyl-1H-indole (813); 2-(2,5-dimethylpyridin-4-yl)-5-(1'-isopropyl-[1,4'-bipiperidin]-4-yl)-3-methyl-1H-indole (814); N-methyl-2-(4-(3-methyl-2-(2-methylpyridin-4-yl)-1H-indol-5-yl)piperidin-1-yl)ethan-1-amine (815); 4-(3-isopropyl-5-(1-((4-methyl-1H-imidazol-5-yl)methyl)piperidin-4-yl)-1H-indol-2-yl) pyridin-2-amine (816); 4-(5-(1-((1H-imidazol-5-yl)methyl)piperidin-4-yl)-3-isopropyl-1H-indol-2-yl)pyridin-2-amine (817); 4-(3-isopropyl-5-(1-((2-methyl-1H-imidazol-5-yl) methyl)piperidin-4-yl)-1H-indol-2-yl)pyridin-2-amine (818); (4-(2-(2-aminopyridin-4-yl)-3-isopropyl-1H-indol-5-yl)piperidin-1-yl)(piperidin-4-yl)methanone (819); 5-(1-((1H-imidazol-5-yl)methyl)piperidin-4-yl)-3-isopropyl-2-(2-methylpyridin-4-yl)-1H-indole (820); 3-isopropyl-5-(1-((2-methyl-1H-imidazol-5-yl)methyl)piperidin-4-yl)-2-(2-methylpyridin-4-yl)-1H-indole (821); 5-((4-(3-ethyl-2-(pyridin-4-yl)-1H-indol-5-yl)piperidin-1-yl)methyl)-N-(pyridin-2-yl)thiazol-2-amine (822); 4-(5-(1-((1H-imidazol-5-yl)methyl)piperidin-4-yl)-3-isopropyl-1H-indol-2-yl)-6-methylpyridin-3-amine (823); 5-(1-((1H-imidazol-5-yl)methyl)piperidin-4-yl)-2-(2,5-dimethylpyridin-4-yl)-3-isopropyl-1H-indole (824); 6-fluoro-3-isopropyl-5-(1'-isopropyl-[1,4'-bipiperidin]-4-yl)-2-(2-methylpyridin-4-yl)-1H-indole (825); 1-(4-(3-isopropyl-2-(2-methylpyridin-4-yl)-1H-indol-5-yl)piperidin-1-yl)ethan-1-one (826); 1-(4-(3-isopropyl-2-(2-methylpyridin-4-yl)-1H-indol-5-yl)-[1,4'-bipiperidin]-1'-yl)ethan-1-one (827); 2-(2,6-dimethylpyridin-4-yl)-6-fluoro-3-isopropyl-5-(1-methylpiperidin-4-yl)-1H-indole (828); 1-(4-(2-(2,6-dimethylpyridin-4-yl)-6-fluoro-3-isopropyl-1H-indol-5-yl)piperidin-1-yl)ethan-1-one (829); 2-(2,6-dimethylpyridin-4-yl)-5-(1-(2,6-dimethyltetrahydro-2H-pyran-4-yl) piperidin-4-yl)-6-fluoro-3-isopropyl-1H-indole (830); 2-(2,6-dimethylpyridin-4-yl)-6-fluoro-3-isopropyl-5-(1-(tetrahydro-2H-pyran-4-yl)piperidin-4-yl)-1H-indole (831); 2-(2,6-dimethylpyridin-4-yl)-6-fluoro-3-isopropyl-5-(1-((1-methyl-1H-1,2,4-triazol-3-yl) methyl)piperidin-4-yl)-1H-indole (832); 2-(2,6-dimethylpyridin-4-yl)-5-(1-(2,6-dimethyltetrahydro-2H-pyran-4-yl)piperidin-4-yl)-6-fluoro-3-isopropyl-1H-indole (833); 2-(2,6-dimethylpyridin-4-yl)-6-fluoro-3-isopropyl-5-(1-(oxetan-3-yl)piperidin-4-yl)-1H-indole (834); 2-(4-(2-(2,5-dimethylpyridin-4-yl)-6-fluoro-3-isopropyl-1H-indol-5-yl) piperidin-1-yl)-N,N-dimethylacetamide (835); 2-(4-(6-fluoro-2-(5-fluoro-2-methylpyridin-4-yl)-3-isopropyl-1H-indol-5-yl)piperidin-1-yl)-N,N-dimethylacetamide (836); 2-(4-(2-(2,6-dimethylpyridin-4-yl)-6-fluoro-3-isopropyl-1H-indol-5-yl)piperidin-1-yl)-N,N-dimethylacetamide (837); 2-(2-methoxypyridin-4-yl)-3-methyl-5-(1'-methyl-[1,4'-bipiperidin]-4-yl)-1H-indole (838); 5-(1'-ethyl-[1,4'-bipiperidin]-4-yl)-2-(2-methoxypyridin-4-yl)-3-methyl-1H-indole (839); 5-(1'-isopropyl-[1,4'-bipiperidin]-4-yl)-2-(2-methoxypyridin-4-yl)-3-methyl-1H-indole (840); 5-(1'-ethyl-[1,4'-bipiperidin]-4-yl)-3-methyl-2-(pyridin-4-yl)-1H-indole (841); 3-methyl-5-(1'-methyl-[1,4'-bipiperidin]-4-yl)-2-(pyridin-4-yl)-1H-indole (842); 5-(1'-isopropyl-[1,4'-bipiperidin]-4-yl)-3-methyl-2-(pyridin-4-yl)-1H-indole (843); 2-(4-(2-(1-hydroxy-2,6-dimethyl-1l4-pyridin-4-yl)-3-isopropyl-1H-indol-5-yl)piperidin-1-yl)-N,N-dimethylac-etamide (844); 4-(3-ethyl-2-(2-methylpyridin-4-yl)-1H-indol-5-yl)-N-(piperidin-4-yl)piperidine-1-carboxamide (845); 4-(3-ethyl-2-(2-methylpyridin-4-yl)-1H-indol-5-yl)-N-(1-(2,2,2-trifluoroacetyl)piperidin-4-yl)piperidine-1-carboxamide (846); 3-isopropyl-2-(2-methylpyridin-4-yl)-5-(1-(pyridin-3-yl)piperidin-4-yl)-1H-indole (847); 1-(4-(2-(2,6-dimethylpyridin-4-yl)-3-isopropyl-1H-indol-5-yl)piperidin-1-yl)-2-methylpropan-2-ol (848); 1-(4-(2-(2,6-dimethylpyridin-4-yl)-3-isopropyl-1H-indol-5-yl)piperidin-1-yl)-3-methylbutan-2-ol (849); 1-(4-(2-(2,6-dimethylpyridin-4-yl)-3-isopropyl-1H-indol-5-yl)piperidin-1-yl)-3,3-dimethylbutan-2-ol (850); 1-(4-(2-(2,5-dimethylpyridin-4-yl)-3-isopropyl-1H-indol-5-yl)piperidin-1-yl)-2-methylpropan-2-ol (851); (R)-1-(4-(2-(2,6-dimethylpyridin-4-yl)-3-isopropyl-1H-indol-5-yl)piperidin-1-yl)-3-methoxypropan-2-ol (852); 1-(4-(2-(2,6-dimethylpyridin-4-yl)-3-isopropyl-1H-indol-5-yl)piperidin-1-yl)-2-methylbut-3-en-2-ol (853); 3-(4-(2-(2,6-dimethylpyridin-4-yl)-3-isopropyl-1H-indol-5-yl)piperidin-1-yl)propane-1,2-diol (854); 1-(4-(2-(2,6-dimethylpyridin-4-yl)-3-isopropyl-1H-indol-5-yl)piperidin-1-yl)-3-methylbutan-2-ol (855); 1-(4-(2-(2,6-dimethylpyridin-4-yl)-3-isopropyl-1H-indol-5-yl) piperidin-1-yl)-2-(4-methylpiperazin-1-yl)ethane-1,2-dione (856); 1-(4-(2-(2,6-dimethylpyridin-4-yl)-3-isopropyl-1H-indol-5-yl)piperidin-1-yl)-2-(piperazin-1-yl) ethane-1,2-dione (857); N-(2-(dimethylamino)ethyl)-2-(4-(2-(2,6-dimethylpyridin-4-yl)-3-isopropyl-1H-indol-5-yl)piperidin-1-yl)-N-methyl-2-oxoacetamide (858); 2-(4-(2-(2,6-dimethylpyridin-4-yl)-3-isopropyl-1H-indol-5-yl)piperidin-1-yl)-2-oxoacetic acid (859); 2-(4-(2-(2,6-dimethylpyridin-4-yl)-3-isopropyl-1H-indol-5-yl)piperidin-1-yl)-2-oxo-N-(2-(pyridin-4-yl)ethyl) acetamide (860); 2-(4-(2-(2,6-dimethylpyridin-4-yl)-3-isopropyl-1H-indol-5-yl)piperidin-1-yl)-2-oxo-N-(piperidin-4-ylmethyl)acetamide (861); 4-(2-(2,6-dimethylpyridin-4-yl)-3-isopropyl-1H-indol-5-yl)piperidine-1-carbaldehyde (862); 3-ethyl-2-(2-methylpyridin-4-yl)-5-(1-(3,3,3-trifluoropropyl)piperidin-4-yl)-1H-indole (863); 5-(1-(1-fluoropropan-2-yl)piperidin-4-yl)-3-isopropyl-2-(2-methylpyridin-4-yl)-1H-indole (864); 5-(1-(1,3-difluoropropan-2-yl)piperidin-4-yl)-3-isopropyl-2-(2-methylpyridin-4-yl)-1H-indole (865); 5-(1-(cyclopropylmethyl)piperidin-4-yl)-3-isopropyl-2-(2-methylpyridin-4-yl)-1H-indole (866); 3-isopropyl-5-(1-((3-methyloxetan-3-yl)methyl)piperidin-4-yl)-2-(2-methylpyridin-4-yl)-1H-indole (867); 5-(1-(cyclohexylmethyl)piperidin-4-yl)-3-isopropyl-2-(2-methylpyridin-4-yl)-1H-indole (868); 3-isopropyl-5-(1-isopropylpiperidin-4-yl)-2-(2-methylpyridin-4-yl)-1H-indole (869); 2-(2,5-dimethylpyridin-4-yl)-5-(1-(1-fluoropropan-2-yl)piperidin-4-yl)-3-isopropyl-1H-indole (870); 5-(1-(cyclopropylmethyl)piperidin-4-yl)-2-(2,5-dimethylpyridin-4-yl)-3-isopropyl-1H-indole (871); 2-(2,5-dimethylpyridin-4-yl)-3-isopropyl-5-(1-((3-methyloxetan-3-yl)methyl)piperidin-4-yl)-1H-indole (872); 3-isopropyl-2-(2-methylpyridin-4-yl)-5-(1-(pyrrolidin-3-ylmethyl)piperidin-4-yl)-6-(trifluoromethyl)-1H-indole (873); 4-fluoro-3-isopropyl-5-(1-((1-isopropylpiperidin-4-yl)methyl) piperidin-4-yl)-2-(2-methylpyridin-4-yl)-1H-indole (874); 2-(4-(2-(2,6-dimethylpyridin-4-yl)-3-isopropyl-1H-indol-5-yl)piperidin-1-yl)acetic acid (875); 2-(4-(3-ethyl-2-(2-methylpyridin-4-yl)-1H-indol-5-yl)piperidin-1-yl)acetic acid (876); 1-(4-(3-ethyl-2-(2-methylpyridin-4-yl)-1H-indol-5-yl)piperidin-1-yl)-3-(isopropyl(methyl)amino) spropan-2-ol (877); 2-(4-(3-isopropyl-2-(2-methylpyridin-4-yl)-1H-indol-5-yl)piperidin-1-yl)-N,N-dimethyl-2-oxoacetamide (878); and 2-(4-(3-isopropyl-2-(2-methylpyridin-4-yl)-1H-indol-5-yl)piperidin-1-yl)-N-methyl-2-oxoacetamide (879).

8. A pharmaceutical composition comprising a compound according to claim 1 or a pharmaceutically-acceptable salt thereof; and a pharmaceutically acceptable carrier.

9. The compound according to claim 1, N-oxide, or salt thereof, wherein $R_1$ is $C_1$, —CN, $C_{1-4}$ alkyl, $C_{1-3}$ fluoroalkyl, $C_{1-3}$ hydroxy-fluoroalkyl, —$CR_2$=$CH_2$, $C_{3-6}$ cycloalkyl, —$CH_2(C_{3-6}$ cycloalkyl), —C(O)O($C_{1-3}$ alkyl), or tetrahydropyranyl.

10. The compound according to claim 1, N-oxide, or salt thereof, wherein $R_1$ is —$CH_3$, —$CH_2CH_3$, —$CH(CH_3)_2$, —$C(CH_3)_3$, —$CHF_2$, —$CH_2CHF_2$, —$CH(CH_3)CF_3$, —$C(CF_3)$=$CH_2$, —C(O)OCH$_3$, cyclopropyl, or —$CH_2$(cyclopropyl).

11. The compound according to claim 1, N-oxide, or salt thereof, wherein:
$R_3$ is -$L_1$-A;
$L_1$ is a bond, —$(CH_2)_{1-2}$—, —$CH_2CH(OH)$—, —$CH_2CH_2O$—, —$CH_2C(O)$—, —$CH_2C(O)NH$—, —$CH_2C(O)N(CH_3)$—, —$CH_2C(O)NHCH_2$—, —$CH_2C(O)NR_xCH_2CH_2$—, —$CH_2C(O)NHCH_2$—, —$CH_2C(O)N(CH_3)CH_2CH_2$—, —$CH_2C(O)N(CH_3)CH_2CH(OH)$—, —$CH_2C(O)NHCH_2C(CH_3)_2$—, —$CH_2C(O)N(CH_2CH_2OH)CH_2$—, —C(O)$(CH_2)_{0-2}$—, —C(O)CH$_2$C(O)NR$_x$—, —C(O)CH$_2$CH$_2$NR$_x$—, —C(O)NH—, —C(O)CH$_2$NR$_x$(CH$_2$)$_{0-2}$—, —C(O)CH$_2$NHCH$_2$C(CH$_3$)$_2$—, —C(O)CH$_2$N(CH$_3$)CH$_2$CH(OH)—, —C(O)CH$_2$N(CH$_2$CH$_2$OH)CH$_2$—, —C(O)CH$_2$CH$_2$NHS(O)$_2$—, —C(O)CH(NH$_2$)CH$_2$—, —C(O)O—, —C(O)C(O)—, —C(O)C(O)NH(CH$_2$)$_{1-2}$—, or —S(O)$_2$—; and
A is 2-oxa-6-azaspiro[3,3]heptanyl, 4-oxaspiro[2.5]octanyl, 7-azaspiro[3.5]nonanyl, 8-azabicyclo[3.2.1]octanyl, 8-oxa-3-azabicyclo[3.2.1]octanyl, 9-azabicyclo[3.3.1]nonanyl, adamantanyl, azepanyl, azetidinyl, $C_{3-6}$ cycloalkyl, dihydroinonyl, dihydropyrimidinonyl, dioxidoisothiazolidinyl, dioxidothiazinanyl, dioxotetrahydrothiophenyl, dioxotetrahydrothiopyranyl, dioxothiomorpholinyl, imidazolyl, imidazolidinonyl, isoxazolyl, morpholinyl, morpholinonyl, octahydrocyclopenta[b]pyranyl, oxazolidinonyl, oxadiazolyl, oxetanyl, oxazolyl, phenyl, piperidinyl, piperidinonyl, piperazinyl, piperazinonyl, pyrazolyl, pyridazinonyl, pyridinonyl, pyridinyl, pyrimidinyl, pyrrolidinonyl, pyrrolidinyl, pyrrolyl, quinolizinonyl, tetrahydrofuranyl, tetrahydropyranyl, tetrazolyl, thiazolyl, or triazolyl, each substituted with -$L_2$-$R_a$ and zero to 4 $R_b$.

12. The compound according to claim 1, N-oxide, or salt thereof:
$R_1$ is —$CH_3$, —$CH_2CH_3$, —$CH(CH_3)_2$, —$C(CH_3)_3$, —$CHF_2$, —$CH_2CHF_2$, —$CH(CH_3)CF_3$, —$C(CF_3)$=$CH_2$, —C(O)OCH$_3$, cyclopropyl, or —$CH_2$(cyclopropyl); and
$R_3$ is -$L_1$-A.

13. The compound according to claim 1, N-oxide, or salt thereof, wherein:
$R_1$ is —$CH_3$, —$CH_2CH_3$, —$CH(CH_3)_2$, —$C(CH_3)_3$, —$CHF_2$, —$CH_2CHF_2$, or —$CH(CH_3)CF_3$;
$R_3$ is -$L_1$-A;
$L_1$ is a bond, —$(CH_2)_{1-2}$—, —$CH_2CH(OH)$—, —$CH_2CH_2O$—, —$CH_2C(O)$—, —$CH_2C(O)NH$—, —$CH_2C(O)N(CH_3)$—, —$CH_2C(O)NHCH_2$—, —$CH_2C(O)NR_xCH_2CH_2$—, —$CH_2C(O)NHCH_2$—, —$CH_2C(O)N(CH_3)CH_2CH_2$—, —$CH_2C(O)N(CH_3)CH_2CH(OH)$—, —$CH_2C(O)NHCH_2C(CH_3)_2$—, —$CH_2C(O)N(CH_2CH_2OH)CH_2$—, —C(O)$(CH_2)_{0-2}$—, —C(O)CH$_2$C(O)NR$_x$—, —C(O)CH$_2$CH$_2$NR$_x$—, —C(O)NH—, —C(O)CH$_2$NR$_x$(CH$_2$)$_{0-2}$—, —C(O)CH$_2$NHCH$_2$C(CH$_3$)$_2$—, —C(O)CH$_2$N(CH$_3$)CH$_2$CH(OH)—, —C(O)CH$_2$N(CH$_2$CH$_2$OH)CH$_2$—, —C(O)CH$_2$CH$_2$NHS(O)$_2$—, —C(O)CH(NH$_2$)CH$_2$—, —C(O)O—, —C(O)C(O)—, —C(O)C(O)NH(CH$_2$)$_{1-2}$—, or —S(O)$_2$—; and
A is 2-oxa-6-azaspiro[3,3]heptanyl, 4-oxaspiro[2.5]octanyl, 7-azaspiro[3.5]nonanyl, 8-azabicyclo[3.2.1]octanyl, 8-oxa-3-azabicyclo[3.2.1]octanyl, 9-azabicyclo[3.3.1]nonanyl, adamantanyl, azepanyl, azetidinyl, $C_{3-6}$ cycloalkyl, dihydroinonyl, dihydropyrimidinonyl, dioxidoisothiazolidinyl, dioxidothiazinanyl, dioxotetrahydrothiophenyl, dioxotetrahydrothiopyranyl, dioxothiomorpholinyl, imidazolyl, imidazolidinonyl, isoxazolyl, morpholinyl, morpholinonyl, octahydrocyclopenta[b]pyranyl, oxazolidinonyl, oxadiazolyl, oxetanyl, oxazolyl, phenyl, piperidinyl, piperidinonyl, piperazinyl, piperazinonyl, pyrazolyl, pyridazinonyl, pyridinonyl, pyridinyl, pyrimidinyl, pyrrolidinonyl, pyrrolidinyl, pyrrolyl, quinolizinonyl, tetrahydrofuranyl, tetrahydropyranyl, tetrazolyl, thiazolyl, or triazolyl, each substituted with -$L_2$-$R_a$ and zero to 4 $R_b$.

14. The compound according to claim 1, N-oxide, or salt thereof, wherein:
$R_1$ is —$CH_2CH_3$ or —$CH(CH_3)_2$;
$R_3$ is -$L_1$-A;
$L_1$ is a bond, —$(CH_2)_{1-2}$—, —$CH_2CH(OH)$—, —$CH_2CH_2O$—, —$CH_2C(O)$—, —$CH_2C(O)NH$—, —$CH_2C(O)N(CH_3)$—, —$CH_2C(O)NHCH_2$—, —$CH_2C(O)NR_xCH_2CH_2$—, —$CH_2C(O)NHCH_2$—, —$CH_2C(O)N(CH_3)CH_2CH_2$—, —$CH_2C(O)N(CH_3)CH_2CH(OH)$—, —$CH_2C(O)NHCH_2C(CH_3)_2$—, —$CH_2C(O)N(CH_2CH_2OH)CH_2$—, —C(O)$(CH_2)_{0-2}$—, —C(O)CH$_2$C(O)NR$_x$—, —C(O)CH$_2$CH$_2$NR$_x$—, —C(O)NH—, —C(O)CH$_2$NR$_x$(CH$_2$)$_{0-2}$—, —C(O)CH$_2$NHCH$_2$C(CH$_3$)$_2$—, —C(O)CH$_2$N(CH$_3$)CH$_2$CH(OH)—, —C(O)CH$_2$N(CH$_2$CH$_2$OH)CH$_2$—, —C(O)CH$_2$CH$_2$NHS(O)$_2$—, —C(O)CH(NH$_2$)CH$_2$—, —C(O)O—, —C(O)C(O)—, —C(O)C(O)NH(CH$_2$)$_{1-2}$—, or —S(O)$_2$—; and
A is 2-oxa-6-azaspiro[3,3]heptanyl, 4-oxaspiro[2.5]octanyl, 7-azaspiro[3.5]nonanyl, 8-azabicyclo[3.2.1]octanyl, 8-oxa-3-azabicyclo[3.2.1]octanyl, 9-azabicyclo[3.3.1]nonanyl, adamantanyl, azepanyl, azetidinyl, $C_{3-6}$ cycloalkyl, dihydroinonyl, dihydropyrimidinonyl, dioxidoisothiazolidinyl, dioxidothiazinanyl, dioxotetrahydrothiophenyl, dioxotetrahydrothiopyranyl, dioxothiomorpholinyl, imidazolyl, imidazolidinonyl, isoxazolyl, morpholinyl, morpholinonyl, octahydrocyclopenta[b]pyranyl, oxazolidinonyl, oxadiazolyl, oxetanyl, oxazolyl, phenyl, piperidinyl, piperidinonyl, piperazinyl, piperazinonyl, pyrazolyl, pyridazinonyl, pyridinonyl, pyridinyl, pyrimidinyl, pyrrolidinonyl, pyrrolidinyl, pyrrolyl, quinolizinonyl, tetrahydrofuranyl, tetrahydropyranyl, tetrazolyl, thiazolyl, or triazolyl, each substituted with -$L_2$-$R_a$ and zero to 4 $R_b$.

15. The compound according to claim 14, N-oxide, or salt thereof, wherein A is 8-azabicyclo[3.2.1]octanyl, azepanyl, azetidinyl, $C_{3-6}$ cycloalkyl, dihydroinonyl, dioxotetrahydrothiopyranyl, isoxazolyl, oxetanyl, piperidinonyl, piperidinyl, pyrazolyl, pyridazinonyl, pyridinonyl, pyridinyl, pyrrolidinonyl, pyrrolidinyl, quinolizinonyl, tetrahydrofuranyl, tetrahydropyranyl, thiazolyl, or 7-azaspiro[3.5]nonanyl, each substituted with -$L_2$-$R_a$ and zero to 4 $R_b$.

16. The compound according to claim 1, N-oxide, or salt thereof, wherein:
   each $R_2$ is independently F, $C_1$, —CN, —$CH_3$, —$OCH_3$, —$NH_2$, or cyclopropyl; and
   p is 2.

17. The compound according to claim 1, N-oxide, or salt thereof, wherein:
   one $R_2$ is —$CH_3$; and the other $R_2$ is F, $C_1$, —CN, —$CH_3$, —$OCH_3$, —$NH_2$, or cyclopropyl; and
   p is 2.

18. A method of treating an autoimmune disease or a chronic inflammatory disease, comprising administering to a mammalian patent a compound according to claim 1 or a pharmaceutically acceptable salt thereof, wherein said autoimmune disease or chronic inflammatory disease is selected from systemic lupus erythematosus (SLE), rheumatoid arthritis, multiple sclerosis (MS), and Sjögren's syndrome.

* * * * *

UNITED STATES PATENT AND TRADEMARK OFFICE
CERTIFICATE OF CORRECTION

PATENT NO. : 10,660,877 B2
APPLICATION NO. : 16/330964
DATED : May 26, 2020
INVENTOR(S) : Alaric Dyckman et al.

It is certified that error appears in the above-identified patent and that said Letters Patent is hereby corrected as shown below:

In the Claims

In Claim 1, Column 356, Line 38, delete "($C_{1-2}$ alkyl))," and insert -- ($C_{1-2}$ alkyl)), --, therefor.

In Claim 1, Column 356, Line 64, delete "—$(CH_2)_{1-2}C(O)NR_x(CH_2)_{1-2}$ $S(O)_2OH$," and insert -- —$(CH_2)_{1-2}C(O)NR_x(CH_2)_{1-2}S(O)_2OH$, --, therefor.

In Claim 1, Column 356, Line 65, delete "$(CH_2)$ $1-2NR_xC$" and insert -- $(CH_2)_{1-2}NR_xC$ --, therefor.

In Claim 1, Column 357, Line 38, delete "$C_1$," and insert -- Cl, --, therefor.

In Claim 1, Column 358, Line 3, delete "$C_1$," and insert -- Cl, --, therefor.

In Claim 2, Column 358, Line 19, delete "$NO_2$," and insert -- $NO_2^+$, --, therefor.

In Claim 2, Column 359, Line 2, delete "$(CR_xR_x)$ $1-2N$" and insert -- $(CR_xR_x)_{1-2}N$ --, therefor.

In Claim 2, Column 359, Line 37, delete "$C_1$," and insert -- Cl, --, therefor.

In Claim 3, Column 360, Line 7, delete "$C_1$," and insert -- Cl, --, therefor.

In Claim 3, Column 361, Line 56, delete "$NR_x$," and insert -- $NR_x$—, --, therefor.

In Claim 3, Column 362, Line 14, delete "$C_1$," and insert -- Cl, --, therefor.

In Claim 6, Column 363, Lines 26-28, delete "—$C(O)CH(NH_{12})CH_2CH_2CH_2NH_2$, —$C(O)CH(NH_{12})CH_2CH_2CH_2CH_2NH_2$, —$C(O)CH(NH_{12})CH_2CH_2CH_2NHC(O)NH_{12}$," and insert -- —$C(O)CH(NH_2)CH_2CH_2CH_2NH_2$, —$C(O)CH(NH_2)CH_2CH_2CH_2CH_2NH_2$, —$C(O)CH(NH_2)CH_2CH_2CH_2NHC(O)NH_2$, --, therefor.

Signed and Sealed this
Second Day of February, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,660,877 B2

In Claim 7, Column 364, Lines 60-64, delete "2-(2,6-dimethyl-1-(l1-oxidanyl)-1l4-pyridin-4-yl)-3-isopropyl-5-(piperidin-4-yl)-1H-indole (56); --2-(2,6-dimethyl-1-(l1-oxidanyl)-1l4-pyridin-4-yl)-3-isopropyl-5-(piperidin-4-yl)-1H-indole (57);" and insert -- 2-(2,6-dimethyl-1-($\lambda^1$-oxidaneyl)-1$\lambda^4$-pyridin-4-yl)-3-isopropyl-5-(piperidin-4-yl)-1H-indole (56); 3-isopropyl-2-(3-methoxy-2-methyl-1-($\lambda^1$-oxidaneyl)-1$\lambda^4$-pyridin-4-yl)-5-(piperidin-4-yl)-1H-indole (57); --, therefor.

In Claim 7, Column 368, Line 37, delete "((2 S,4R)" and insert -- ((2S,4R) --, therefor.

In Claim 7, Column 369, Line 42, delete "((1r,3 s,5R,7S)" and insert -- ((1r,3s,5R,7S) --, therefor.

In Claim 9, Column 389, Line 5, delete "$C_1$," and insert -- Cl, --, therefor.

In Claim 11, Column 389, Line 24, delete "$NR_x$," and insert -- $NR_x$—, --, therefor.

In Claim 13, Column 389, Line 67, delete "$NR_x$," and insert -- $NR_x$—, --, therefor.

In Claim 14, Column 390, Line 36, delete "$NR_x$," and insert -- $NR_x$—, --, therefor.

In Claim 16, Column 391, Line 3, delete "$C_1$," and insert -- Cl, --, therefor.

In Claim 17, Column 391, Line 8, delete "$C_1$," and insert -- Cl, --, therefor.